US008067448B2

(12) United States Patent
Miller

(10) Patent No.: US 8,067,448 B2
(45) Date of Patent: Nov. 29, 2011

(54) SELECTIVE ANDROGEN RECEPTOR MODULATORS

(75) Inventor: Chris P. Miller, Hingham, MA (US)

(73) Assignee: Radius Health, Inc., Cambridge, MA (US)

( * ) Notice: Subject to any disclaimer, the term of this patent is extended or adjusted under 35 U.S.C. 154(b) by 218 days.

(21) Appl. No.: 12/378,812

(22) Filed: Feb. 19, 2009

(65) Prior Publication Data
US 2009/0253758 A1  Oct. 8, 2009

Related U.S. Application Data

(60) Provisional application No. 61/205,727, filed on Jan. 21, 2009, provisional application No. 61/132,353, filed on Jun. 18, 2008, provisional application No. 61/066,697, filed on Feb. 22, 2008.

(51) Int. Cl.
A61K 31/4245 (2006.01)
C07D 271/10 (2006.01)
(52) U.S. Cl. .............................. 514/364; 548/143
(58) Field of Classification Search .................. None
See application file for complete search history.

(56) References Cited

U.S. PATENT DOCUMENTS

| 5,411,981 | A | 5/1995 | Gaillard-Kelly et al. |
| 6,960,474 | B2 | 11/2005 | Salvati et al. |
| 2005/0182105 | A1 | 8/2005 | Nirschl et al. |
| 2005/0250749 | A1 | 11/2005 | Labrie et al. |
| 2005/0261303 | A1 | 11/2005 | Taniguchi et al. |
| 2006/0106067 | A1 | 5/2006 | Shiraishi et al. |
| 2006/0142387 | A1 | 6/2006 | Cadilla et al. |
| 2006/0148893 | A1 | 7/2006 | Blanc et al. |
| 2006/0211756 | A1 | 9/2006 | Zhang et al. |
| 2006/0287327 | A1 | 12/2006 | Labrie et al. |
| 2007/0088039 | A1 | 4/2007 | Balog et al. |
| 2007/0281906 | A1 | 12/2007 | Dalton et al. |
| 2008/0057068 | A1 | 3/2008 | Dalton et al. |
| 2009/0042967 | A1 | 2/2009 | Hasuoka |
| 2009/0264534 | A1 | 10/2009 | Dalton et al. |
| 2010/0041721 | A1 | 2/2010 | Miller |

FOREIGN PATENT DOCUMENTS

| EP | 0 580 459 B1 | 3/2001 |
| JP | 01-261381 A | 10/1989 |
| WO | WO 96/41793 A1 | 12/1996 |
| WO | WO 97/49709 A1 | 12/1997 |
| WO | WO 02/16310 A1 | 2/2002 |
| WO | WO 03/011824 A1 | 2/2003 |
| WO | WO 03/068217 A1 | 8/2003 |
| WO | WO 03/096980 A2 | 11/2003 |
| WO | WO 2004/041277 A1 | 5/2004 |
| WO | WO 2004/041782 A1 | 5/2004 |
| WO | WO 2004/045518 A2 | 6/2004 |
| WO | WO 2004/080377 A2 | 9/2004 |
| WO | WO 2004/110978 A2 | 12/2004 |
| WO | WO 2005/000309 A2 | 1/2005 |
| WO | WO 2005/000794 A1 | 1/2005 |
| WO | WO 2005/000795 A2 | 1/2005 |
| WO | WO 2005/040136 A1 | 5/2005 |
| WO | WO 2005/042464 A1 | 5/2005 |
| WO | WO 2005/049574 A1 | 6/2005 |
| WO | WO 2005/049580 A1 | 6/2005 |
| WO | WO 2005/060956 A1 | 7/2005 |
| WO | WO 2005/077925 A1 | 8/2005 |
| WO | WO 2005/085185 A1 | 9/2005 |
| WO | WO 2005/086735 A2 | 9/2005 |
| WO | WO 2005/087232 A1 | 9/2005 |
| WO | WO 2005/089118 A2 | 9/2005 |
| WO | WO 2005/090282 A1 | 9/2005 |
| WO | WO 2005/090328 A1 | 9/2005 |
| WO | WO 2005/094810 A2 | 10/2005 |
| WO | WO 2005/099707 A1 | 10/2005 |
| WO | WO 2005/102998 A1 | 11/2005 |
| WO | WO 2005/108351 A1 | 11/2005 |
| WO | WO 2005/111028 A1 | 11/2005 |
| WO | WO 2005/115361 A2 | 12/2005 |
| WO | WO 2005/116001 A1 | 12/2005 |
| WO | WO 2005/120483 A2 | 12/2005 |
| WO | WO 2006/039243 A1 | 4/2006 |
| WO | WO 2006/044707 A1 | 4/2006 |
| WO | WO 2006/055184 A2 | 5/2006 |
| WO | WO 2006/060108 A1 | 6/2006 |
| WO | WO 2006/076317 A2 | 7/2006 |
| WO | WO 2006/113552 A2 | 10/2006 |
| WO | WO 2006/124447 A2 | 11/2006 |
| WO | WO 2006/133216 A2 | 12/2006 |
| WO | WO 2007/002181 A2 | 1/2007 |

(Continued)

OTHER PUBLICATIONS

Acevedo, S., et al., "Selective Androgen Receptor Modulators Antagonize Apolipoprotein E4-Induced Cognitive Impairments," *Letters in Drug Design & Discovery*, 5: 271-276 (2008).

Allan G. F., et al., "A Selective Androgen Receptor Modulator with Minimal Prostate Hypertrophic Activity Enhances Lean Body Mass in Male Rats and Stimulates Sexual Behavior in Female Rats," *Endocr.*, 32: 41-51 (2007).

Allan, G., et al., "A Selective Androgen Receptor Modulator that Reduces Prostate Tumor Size and Prevents Orchidectomy-Induced Bone Loss in Rats," *Journal of Steroid Biochemistry & Molecular Biology*, 103: 76-83 (2007).

Bohl, C.E., et al., "Structural Basis for Accommodation of Nonsteroidal Ligands in the Androgen Receptors," *The Journal of Biological Chemistry*, 280 (45): 37747-37754 (Nov. 11, 2005).

(Continued)

Primary Examiner — Rebecca Anderson
Assistant Examiner — Alicia L Otton
(74) Attorney, Agent, or Firm — Hamilton, Brook, Smith & Reynolds, P.C.

(57) ABSTRACT

This invention provides compounds of formulas I, Ia, Ib, Ic, Id, Ie, and or salts thereof, pharmaceutical compositions comprising a compound of formulas I, Ia, Ib, Ic, Id, Ie, and a pharmaceutically acceptable excipient, methods of modulating the androgen receptor, methods of treating diseases beneficially treated by an androgen receptor modulator (e.g., sarcopenia, prostate cancer, contraception, type 2 diabetes related disorders or diseases, anemia, depression, and renal disease) and processes for making compounds of formulas I, Ia, Ib, Ic, Id, Ie, and intermediates useful in the preparation of same.

4 Claims, No Drawings

FOREIGN PATENT DOCUMENTS

| | | |
|---|---|---|
| WO | WO 2007/005887 A2 | 1/2007 |
| WO | WO 2007/015567 A1 | 2/2007 |
| WO | WO 2007/034846 A1 | 3/2007 |
| WO | WO 2007/067490 A1 | 6/2007 |
| WO | WO 2007/087518 A2 | 8/2007 |
| WO | WO 2007/099200 A1 | 9/2007 |
| WO | WO 2008/008433 A2 | 1/2008 |
| WO | WO 2008/011072 A2 | 1/2008 |
| WO | WO 2008/011073 A1 | 1/2008 |
| WO | WO 2008/024456 A2 | 2/2008 |
| WO | WO 2008/042571 A2 | 4/2008 |
| WO | WO 2008/044033 A1 | 4/2008 |
| WO | WO 2008/063867 A2 | 5/2008 |
| WO | WO 2008/121602 A1 | 10/2008 |
| WO | WO 2008/124000 A2 | 10/2008 |
| WO | WO 2008/124922 A1 | 10/2008 |
| WO | WO 2008/127717 A1 | 10/2008 |
| WO | WO 2008/128100 A1 | 10/2008 |
| WO | WO 2009/081197 A1 | 7/2009 |
| WO | WO 2009/082437 A2 | 7/2009 |
| WO | WO 2009/105214 A2 | 8/2009 |
| WO | WO 2009/133861 A1 | 11/2009 |
| WO | WO 2009/140448 A1 | 11/2009 |

OTHER PUBLICATIONS

Bohl, C. E., "Structural Basis for Antagonism and Resistance of Bicalutamide in Prostate Cancer," *PNAS*, 102 (17): 6201-6206 (2005).

Cantin, L., et al., "Structural Characterization of the Human Androgen Receptor Ligand-Binding Domain Complexed with EM5744, a Rationally Designed Steroidal Ligand Bearing a Bulky Chain Directed Toward Helix 12," *Journal of Biological Chemistry*, 282 (42): 30910-30919 (Oct. 19, 2007).

Gao, W., et al., "Ockham's Razor and Selective Androgen Receptor Modulators (SARMs): Are we Overlooking the Role of 5α-Reductase?", *Molecular Interventions*, 7: 10-13 (Feb. 2007).

Gao, W., et al., "Expanding the Therapeutic use of Androgens via Selective Androgen Receptor Modulators (SARMs)," *Drug Discovery Today*, 12: 241-248 (Mar. 2007).

Gao, W., et al., "Selective Androgen Receptor Modulator (SARM) Treatment Improves Muscle Strength," *Endocrinology*, doi:10.1210/en.2005-0572, pp. 1-37 (Aug. 11, 2005).

Gao, W., et al., "Comparison of the Pharmacological Effects of a Novel Selective Androgen Receptor Modulator, the 5α-Reductase Inhibitor Finasteride, and the Antiandrogen Hydroxyflutamide in Intact Rats: New Approach for Benign Prostate Hyperplasia,"*Endocrinology*, 145 (12): 5420-5428 (Dec. 2004).

Gao, W., et al., "Selective Androgen Receptor Modulator Treatment Improves Muscle Strength and Body Composition and Prevents Bone Loss in Orchidectomized Rats," *Endocrinology*, 146 (11): 4887-4897 (Nov. 2005).

Hamann, L G., "Discovery and Preclinical Profile of a Highly Potent and Muscle Selective Androgen Receptor Modulator (SARM)," 227th National Meeting of the American Chemical Society Medicinal Chemistry Division, Mar. 28, 2004, Anaheim, CA.

Hamann, L.G., et al., "Tandem Optimization of Target Activity and Elimination of Mutagenic Potential in a Potent Series of N-aryl Bicyclic Hydantoin-Based Selective Androgen Receptor Modulators," *Bioorganic & Medicinal Chemistry Letters*, 17: 1860-1864 (2007).

Hanada, K., et al. "Bone Anabolic Effects of S-40503, a Novel Nonsteroidal Selective Androgen Receptor Modulator (SARM), in Rat Models of Osteoporosis," *Biol. Pharm. Bull.*, 26(11): 1563- 1569 (Nov. 2003).

Higuchi, R. I., et al., "Novel Series of Potent, Nonsteroidal, Selective Androgen Receptor Modulators Based on 7 H-[1,4]Oxazino[3,2-g]quinolin-7-ones," *J. Med. Chem.*, 50(10): 2486-2496 (2007).

Higuchi, R. I., et al.,"Novel Series of Potent, Nonsteroidal, Selectve Androgen Receptor Modulators Based on 7H[1,4]Oxazino[3,2-g]quinolin-7-ones," *Journal of Medicinal Chemistry*, pp. A-K (Apr. 17, 2007).

Hwang, D. J., et al., "Arylisothiocyanato Selective Androgen Receptor Modulators (SARMs) for Prostate Cancer," *Bioorganic & Medicinal Chemistry*, 14: 6525-6538 (2006).

Kemppainen, J. A., et al., "Distinguishing Androgen Receptor Agonists and Antagonists: Distinct Mechanisms of Activation by Medroxyprogesterone Acetate and Dihydrotestosterone," *Molecular Endocrinology*, 13: 440-454 (1999).

Kilbourne, E. J., et al., "Selective Androgen Receptor Modulators for Frailty and Osteoporosis," *Current Opinion in Investigational Drugs*, 8(10): 821-829 (2007).

Kim, J., et al., "The 4-P*ara* Substituent of S-3-(phenoxy)-2-hydroxy-2-methyl-N-(4-nitro-3-trifluoromethyl-pheny1)-propionamides is a Major Structural Determinant of in Vivo Disposition and Activity of Selective Androgen Receptor Modulators," *JPET* #88344, DOI:10.1124/jpet.105.088344, 42 pages (Jun. 29, 2005).

Kinoyama, I., et al., "(+)-(2*R*,5*S*)-4-[4-Cyano-3-(tritluoromethyl)phenyl]-2,5-dimethyl-*N*-[6-(trifluoromethyl)pyridin-3-y1]piperazine-1-carboxamide (YM580) as an Orally Potent and Peripherally Selective Nonsteroidal Androgen Receptor Antagonist," *J. Med. Chem.* 49(2): 716-726 (2006).

Lanter, J. C., et al., "The Discovery of a Potent Orally Efficacious Indole Androgen Receptor Antagonist Through in vivo Screening," *Bioorganic & Medicinal Chemistry Letters*, 17: 123-126 (2007).

Martinborough, E., et al., "Substituted 6-(1-(Pyrrolidine)quinolin-2(1*H*)-ones as Novel Selective Androgen Receptor Modulators," *J. Med. Chem.* 50(21): 5049-5052 (Oct. 18, 2007).

McGinley, P. L., et al., "Circumventing Anti-Androgen Resistance by Molecular Design," *J. Am. Chem. Soc.*, 129: 3822-3823 (2007).

Miller, C. P., et al., "Design, Synthesis, and Preclinical Characterization of the Selective Androgen Receptor Modulator (SARM) RAD140," *ACS Med. Chem. Lett.*, XXXX, XXX, DOI: 10.1021/m11002508, pp. A-F (Dec. 2, 2010).

Mitchell, H. J., et al., Design, Synthesis, and Biological Evaluation of 16-Substituted 4-Azasteroids as Tissue-Selective Androgen Receptor Modulators (SARMs), *J. Med Chem.*, XXXX, vol. XXX, No. XX, pp. A-D (2009).

Mohler, M. L., et al., "Nonsteroidal Selective Androgen Receptor Modulators (SARMs): Dissociating the Anabolic and Androgenic Activities of the Androgen Receptor for Therapeutic Benefit,"*J. Med. Chem.*, XXXX, vol. XXX, No. XX, pp. A-T (May 11, 2009).

Morris, J. J., et al., "Non-steroidal Antiandrogens. Design of Novel Compounds Based on an Infrared Study of the Dominant Conformation and Hydrogen-Bonding Properties of a Series of Anilide Antiandrogens," *J. Med. Chem.*, 34: 447-455 (1991).

Ng, R. A., "Synthesis and SAR of Potent and Selective Androgen Receptor Antagonists: 5,6-Dicholoro-benzimidazole Derivatives," *Bioorganic & Medicinal Chemistry Letters*, 17: 784-788 (2007).

Ng, R. A., "Synthesis of Potent and Tissue-Selective Androgen Receptor Modulators (SARMs): 2-(2,2,2)-Trifluoroethyl-benzimidazole Scaffold," *Bioorganic & Medicinal Chemistry Letters*, 17: 1784-1787 (2007).

Ostrowski, J., et al., "Pharmacological and X-Ray Structural Characterization of a Novel Selective Androgen Receptor Modulator: Potent Hyperanabolic Stimulation of Skeletal Muscle with Hypostimulation of Prostate in Rats," *Endocrinology*, 148(1): 4-12 (Jan. 2007).

Piu, F., et al., "Pharmacological Characterization of AC-262536, A Novel Selective Androgen Receptor Modulator," *Journal of Steroid Biochemistry & Molecular Biology*, 109: 129-137 (2008).

Salvati, M. E., et al., "Identification and Optimization of a Novel Series of [2.2.1]-oxabicyclo imide-based Androgen Receptor Antagonists," *Bioorganic & Medicinal Chemistry Letters*, 18: 1910-1915 (2008).

Sun, C., et al. "Discovery of Potent, Orally-Active, and Muscle-Selective Androgen Receptor Modulators Based on an N-Aryl-hydroxybicyclohydantoin Scaffold," *J. Med. Chem.* 49(26): 7596-7599 (2006).

Tucker, H., et al., "Nonsterodial Antiandrogens, Synthesis and Structure-Activity Relationships of 3-Substituted Derivatives of 2-Hydroxypropionanilides," *J. Med. Chem.*, 31: 954-959 (1988).

Vajda, E. G., et al., Pharmacokinetics and Pharmacodynamics of LGD-3303 [9-Cholor-2-ethy1-1-methy1-3-(2,2,2-trifluoroethyl)-3*H*-pyrrolo-[3,2-*f*]quinolin-7(6*H*)-one], an Orally Available Nonsteroidal-Selective Androgen Receptor Modulator, *The Journal of Pharmacology and Experimental Therapeutics*, 328(2): 663-670 (2009).

Van Oeveren, A., et al., "Novel Selective Androgen Receptor Modulators: SAR Studies on 6-bisalkylamino-2-quinolinones," *Bioorganic & Medicinal Chemistry Letters*, 17: 1527-1531 (2007).

Zeng, C., et al., "Efficient Synthesis of (2R,3S)-2-amino-3-(benzyloxy)-4,4,4-trifluorobutanoic acid (4,4,4-trifluoro-OBn-D-allothreonine)," *Tetrahedron Letters*, 51: 5361-5363 (2010).

Zhang, X., et al., "Design, Synthesis, and in Vivo SAR of a Novel Series of Pyrazolines as Potent Selective Androgen Receptor Modulators," *J. Med. Chem*, 50(16): 3857-3869 (2007).

Zhang, X., et al., "Synthesis and SAR of Novel Hydantoin Derivatives as Selective Androgen Receptor Modulators," *Bioorganic & Medicinal Chemistry Letters*, 16: 5763-5766 (2006).

Notification of Transmittal of International Search Report and The Written Opinion of the International Searching Authority, or The Declaration, dated Aug. 7, 2009, International Application No. PCT/US2009/001035.

Notification Concerning Transmittal of International Preliminary Report on Patentability, dated Sep. 2, 2010, International Application No. PCT/US2009/001035.

Miller, C.P., et al., "Synthesis of Potent, Substituted Carbazoles as Selective Androgen Receptor Modulators (SARMs)," *Bioorg. Med. Chem. Lett.*, 20: 7516-7520 (2010).

SELECTIVE ANDROGEN RECEPTOR MODULATORS

RELATED APPLICATIONS

This application claims the benefit of U.S. Provisional Application No. 61/205,727, filed on Jan. 21, 2009, U.S. Provisional Application No. 61/132,353 filed on Jun. 18, 2008 and U.S. Provisional Application No. 61/066,697, filed on Feb. 22, 2008. The entire teachings of the above applications are incorporated herein by reference.

BACKGROUND OF THE INVENTION

Androgen signaling is mediated through the androgen receptor (AR) and is a nuclear signaling pathway of tremendous importance in mammals. In addition to its primary role in sexual development, maturation and maintenance of sexual function in both males and females, this critical hormone signaling pathway affects a large number of non-sexual tissues including, bone, muscle, CNS, liver, etc. In humans, testosterone and dihydrotestosterone are the primary ligands that mediate AR-signaling. Both are high affinity ligands for AR, with dihydrotestosterone having somewhat higher affinity. Testosterone is converted to dihydrotestosterone through the action of 5α-reductase enzymes and is converted to 17β-estradiol (potent endogenous estrogen) through the action of P-450 aromatase enzymes. AR signaling is mediated by binding of an AR ligand to AR in the cellular cytosol, homodimerization of two AR receptors and nuclear location of the ligand bound dimer to the cell nucleus where the complex associates with various coactivators as well as Androgen Response Elements (palindrome-like sequences of DNA) which serve as activation sites for certain AR-mediated genes. Due to the very large number of AR target tissues, both sexual and non-sexual, androgens such as testosterone and dihydrotestosterone have a number of potentially desirable actions as well as non-desirable actions depending on the particular individual's age, sex, therapeutic need, etc. In the adult male and female, certain positive consequences of AR-agonist signaling can be generalized as including increased bone mineral density and a corresponding reduction of risk of bone fractures. Accordingly, androgen supplementation can be very valuable in the prevention or treatment of osteoporosis where the osteoporosis might originate from any number of different causes, such as corticosteroid induced osteoporosis and age-related osteoporosis (e.g. post-menopausal). Likewise, males and females respond to agonist supplementation with an increase in muscle mass and very often a decrease in fat mass. This is beneficial in a very large number of treatment modalities. For example, there are many wasting syndromes associated with different disease states where the therapeutic goal is for a patient to maintain weight and function, such as the treatment of cancer associated cachexia, AIDs-related cachexia, anorexia and many more. Other muscle-wasting disorders such as muscular dystrophy in its many forms as well as related disorders can also be treated to advantage with androgens. The increase in muscle mass with concomitant reduction in fat mass associated with anabolic androgen action has additional health benefits for many men and women including potentially increased sensitivity to insulin. Androgen supplementation is also associated with reduction of high triglycerides, though there is a general correlation with androgen use and decreased HDL levels and in some cases, increased LDL levels. In the CNS, numerous laudatory benefits have been associated with androgen supplementation including improved sexual desire and functioning, increased cognition, memory, sense of well being and possible decrease in risk of Alzheimer's disease.

Androgen antagonists have been used in treating prostate cancer, where blockade of androgen signaling is desired whereas some androgens agonists (e.g. dihydrotestosterone) stimulate the hypertrophy of prostate tissue and may be a causative factor in prostate cancer. Androgen agonist activity is often associated with stimulation of benign prostate hyperplasia, a disease characterized by an enlarged prostate often accompanied by discomfort and difficulty in urination due to blockage of the urethra. As a result, androgen antagonists have efficacy in the reduction of the size of the prostate and the corresponding symptoms of benign prostate hyperplasia, though it is much more common to use a 5α-reductase inhibitor (e.g. finasteride) as such inhibitors do not decrease androgen signaling systemically to the same extent as a typical anti-androgen (e.g. bicalutamide), but rather reduce androgen drive more site specifically to where testosterone to DHT conversion occurs such as the prostate and scalp. Androgen antagonists also find utility in the treatment of hirsutism in women as well as the treatment of acne. Androgens are generally contraindicated in conditions that are treated with androgen antagonists since they can exacerbate the symptoms that are being treated.

Ideally, an androgen would retain the benefits of androgen agonists while minimizing the stimulatory effects on the prostate in males as well as some of the other untoward effects of androgens including masculinization of women and increase in acne in both sexes. Androgens that demonstrate tissue selective effects compared to the benchmarks testosterone and/or dihydrotestosterone are typically referred to as androgen receptor modulators or more often, selective androgen receptor modulators (SARMs). At the far end of potential selectivity, an ideal SARM would demonstrate no prostate stimulation while maintaining or growing muscle sufficient to effectively mimic the effects of testosterone or dihydrotestosterone. The growing appreciation of the positive contribution that SARMs can make in the many therapeutic areas where androgen activity is desirable has led to a large amount of research into this important area. Due to a compelling need for novel and effective androgen therapies with potentially reduced side effects, novel and effective SARM compounds are urgently needed.

SUMMARY OF THE INVENTION

In certain embodiments, this invention describes a compound of formula I

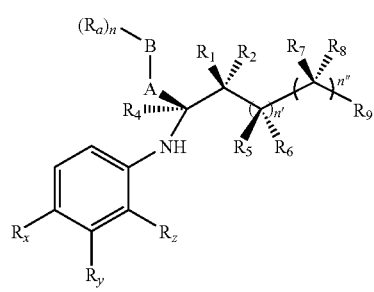

wherein $R_x$ is CN, Cl, Br, $NO_2$ or $R_{x1}$;
$R_y$ is $CH_3$, $CF_3$, or halogen;
$R_z$ is hydrogen or optionally $C_{1-3}$ alkyl, $C_{2-3}$ alkenyl, $C_{1-3}$ hydroxyalkyl, $C_{1-3}$ haloalkyl, $NO_2$, $NH_2$, OMe, halogen or OH; or $R_y$ and $R_z$ together form

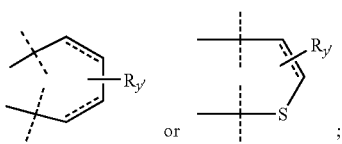

wherein $R_{y'}$ is hydrogen or optionally halogen, $C_{1-3}$ alkyl, $C_{1-3}$ haloalkyl or OH;

$R_{x1}$ is a 5 member heteroaryl, said heteroaryl selected from

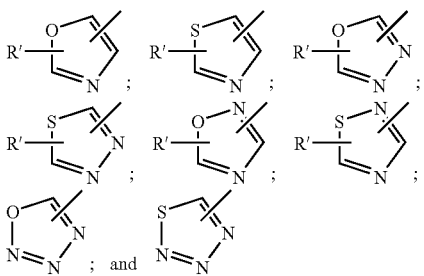

R' is hydrogen or optionally $C_1$-$C_2$ alkyl, $CF_3$, or halogen; or $R_x$ and $R_y$ together with the phenyl group to which they are attached form a 5 member aromatic ring selected from:

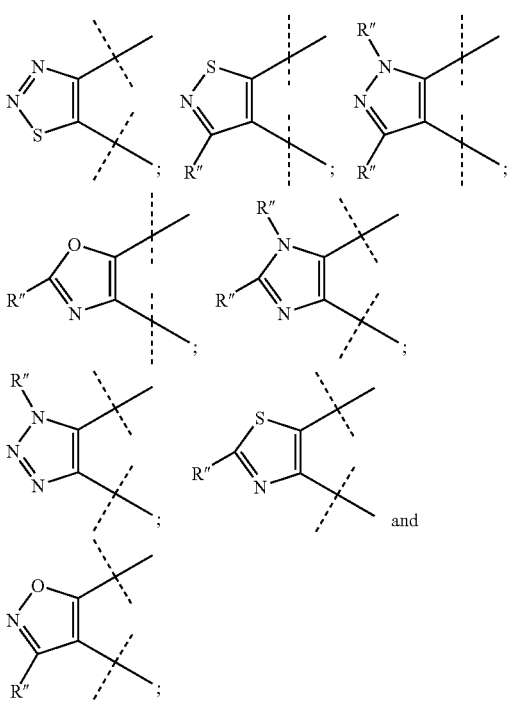

wherein each R" is independently hydrogen or optionally $CF_3$, or $C_1$-$C_2$ alkyl;

A is a 5- or 6-member heteroaryl group wherein said 5- or 6-member heteroaryl is substituted with hydrogen and optionally up to two substituents selected from $C_{1-3}$ alkyl, CN, $C_{1-3}$ haloalkyl or halogen;

B is a phenyl, $C_{1-6}$ alkyl, $C_{1-6}$ haloalkyl, 5- or 6-member heteroaryl or bicyclic heteroaryl;

each $R_a$ is independently selected from $C_{1-4}$ alkyl (wherein said $C_{1-4}$ alkyl is optionally substituted with from 1-2 substituents independently selected from CN, OH and 5 member heteroaryl), 5-member heteroaryl, CN, —N($R_b$)C(O)O$C_{1-6}$ alkyl, —N($R_b$)C(O)OPhenyl (wherein said phenyl is optionally substituted with from 1-3 substituents independently selected from CN, halogen, OH, $C_{1-3}$ alkyl, and O$C_{1-3}$ alkyl), N($R_b$)C(O)$C_{1-6}$ alkyl, —N($R_b$)C(O)phenyl (wherein said phenyl is optionally substituted with from 1-3 substituents independently selected from CN, halogen, OH, $C_{1-3}$ alkyl, and O$C_{1-3}$ alkyl), N$R_b R_{b'}$, $C_{1-4}$ haloalkyl, halogen, OH, O$C_{1-3}$ alkyl, O$C_{1-3}$ haloalkyl, OC(O)$C_{1-12}$alkyl, OC(O)phenyl (wherein said phenyl is optionally substituted with from 1-3 substituents independently selected from CN, halogen, OH, $C_{1-3}$ alkyl, and O$C_{1-3}$ alkyl), OC(O)O$C_{1-12}$ alkyl, OC(O)Ophenyl (wherein said phenyl is optionally substituted with from 1-3 substituents independently selected from CN, halogen, OH, $C_{1-3}$ alkyl, and O$C_{1-3}$ alkyl), OSO$_2$-phenyl, (wherein said phenyl is optionally substituted with halogen, $C_{1-3}$ alkyl or $C_{1-3}$ haloalkyl), OSO$_3$—, OPO$_3$—, OSO$_2$N$R_b R_{b'}$, S(O)$_{0-2}$-phenyl, and S(O)$_{0-2}$$C_{1-3}$ alkyl;

each $R_b$ and $R_{b'}$ is independently selected from hydrogen, $C_{1-3}$ alkyl and $C_{1-3}$ haloalkyl;

n is 0, 1, 2, or 3;

n' is 0 or 1;

n" is 0 or 1;

each $R_1$, $R_2$, $R_5$, $R_6$, $R_7$ and $R_8$ are independently selected from hydrogen, $C_{1-3}$ alkyl, $C_{1-3}$ haloalkyl, OR$_3$ and phenyl;

$R_9$ is hydrogen, $C_{1-3}$ alkyl or OR$_3$;

provided that at least one of $R_1$, $R_2$, $R_5$, $R_6$, $R_7$, $R_8$ or $R_9$ is OR$_3$;

each $R_3$ is independently selected from hydrogen, $C_{1-4}$ alkyl, $C_{1-4}$ haloalkyl, $C_{2-4}$ hydroxylalkyl, benzyl (wherein the phenyl group of said benzyl is optionally substituted with from 1-3 substituents independently selected from halogen, $C_{1-3}$ alkyl, S(O)$_{0-2}$$C_{1-3}$ alkyl, S(O)$_{0-2}$-phenyl, O—$C_{1-6}$ alkyl, and OCF$_3$), C(O)—$C_{1-10}$ alkyl, SO$_3$—, PO$_3$—, SO$_2$N$R_b R_{b'}$ and C(O)phenyl; and $R_4$ is H, $C_{1-4}$ alkyl or $C_{1-4}$ haloalkyl; or pharmaceutically acceptable salts thereof.

DETAILED DESCRIPTION OF THE INVENTION

In certain embodiments, this invention describes a compound of formula I

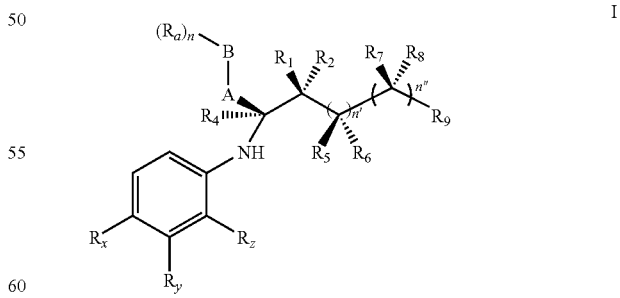

wherein $R_x$ is CN, Cl, Br, NO$_2$ or $R_{x1}$;

$R_y$ is CH$_3$, CF$_3$, or halogen;

$R_z$ is hydrogen or optionally $C_{1-3}$ alkyl, $C_{2-3}$ alkenyl, $C_{1-3}$ hydroxyalkyl, $C_{1-3}$ haloalkyl, NO$_2$, NH$_2$, OMe, halogen or OH; or $R_y$ and $R_z$ together form

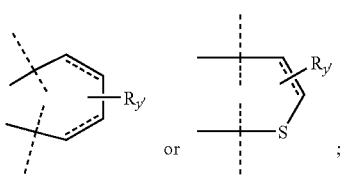

wherein $R_{y'}$ is hydrogen or optionally halogen, $C_{1-3}$ alkyl, $C_{1-3}$ haloalkyl or OH;

$R_{x1}$ is a 5 member heteroaryl, said heteroaryl selected from

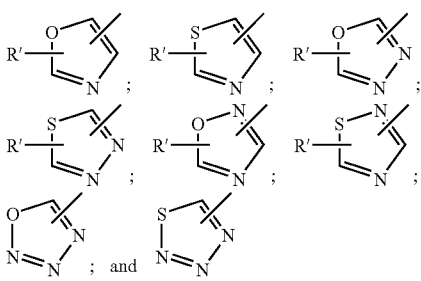

R' is hydrogen or optionally $C_1$-$C_2$ alkyl, $CF_3$, or halogen; or $R_x$ and $R_y$ together with the phenyl group to which they are attached form a 5 member aromatic ring selected from:

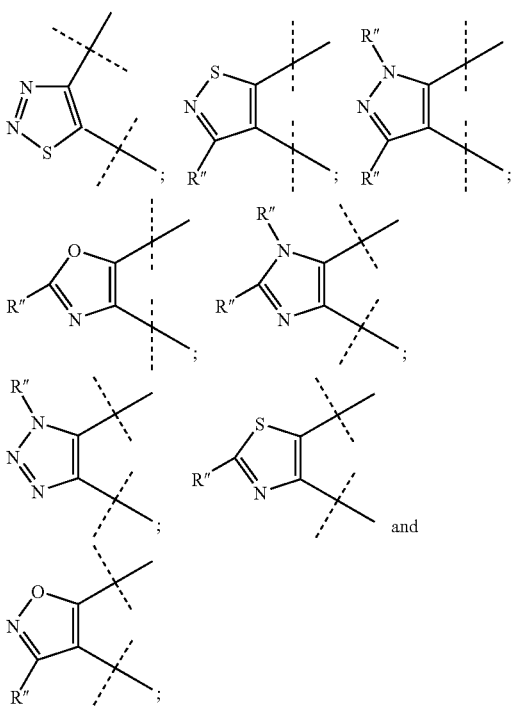

wherein each R" is independently hydrogen, $CF_3$ or $C_1$-$C_2$ alkyl;

A is a 5- or 6-member heteroaryl group wherein said 5- or 6-member heteroaryl is substituted with hydrogen and optionally up to two substituents selected from $C_{1-3}$ alkyl, CN, $C_{1-3}$ haloalkyl or halogen;

B is a phenyl, $C_{1-6}$ alkyl, $C_{1-6}$ haloalkyl, 5- or 6-member heteroaryl or bicyclic heteroaryl;

each $R_a$ is independently selected from $C_{11}$ alkyl (optionally substituted with from 1-2 substituents independently selected from CN, OH and 5 member heteroaryl), 5-member heteroaryl, CN, $N(R_b)C(O)OC_{1-6}$ alkyl, $N(R_b)C(O)OPhenyl$ (wherein said phenyl is optionally substituted with from 1-3 substituents independently selected from CN, halogen, OH, $C_{1-3}$ alkyl, and $OC_{1-3}$ alkyl), $N(R_b)C(O)C_{1-6}$ alkyl, $N(R_b)C(O)phenyl$ (wherein said phenyl is optionally substituted with from 1-3 substituents independently selected from CN, halogen, OH, $C_{1-3}$ alkyl, and $OC_{1-3}$ alkyl), $NR_bR_{b'}$, $C_{1-4}$ haloalkyl, halogen, OH, $OC_{1-3}$ alkyl, $OC_{1-3}$ haloalkyl, $OC(O)C_{1-12}$ alkyl, OC(O)phenyl (wherein said phenyl is optionally substituted with from 1-3 substituents independently selected from CN, halogen, OH, $C_{1-3}$ alkyl, and $OC_{1-3}$ alkyl), OC(O)OC_{1-12} alkyl, OC(O)Ophenyl (wherein said phenyl is optionally substituted with from 1-3 substituents independently selected from CN, halogen, OH, $C_{1-3}$ alkyl, and $OC_{1-3}$ alkyl), $OSO_2$-phenyl, (wherein said phenyl is optionally substituted with halogen, $C_{1-3}$ alkyl or $C_{1-3}$ haloalkyl), $OSO_3$—, $OPO_3$—, $OSO_2NR_bR_{b'}$, $S(O)_{0-2}$-phenyl, and $S(O)_{0-2}C_{1-3}$ alkyl;

each $R_b$ and $R_{b'}$ is independently selected from hydrogen, $C_{1-3}$ alkyl and $C_{1-3}$ haloalkyl;

n is 0, 1, 2, or 3;

n' is 0 or 1;

n" is 0 or 1;

each $R_1$, $R_2$, $R_5$, $R_6$, $R_7$ and $R_8$ are each independently selected from hydrogen, $C_{1-3}$ alkyl, $C_{1-3}$ haloalkyl, $OR_3$ and phenyl;

$R_9$ is hydrogen, $C_{1-3}$ alkyl or $OR_3$;

provided that at least one of $R_1$, $R_2$, $R_5$, $R_6$, $R_7$, $R_8$ or $R_9$ is $OR_3$;

each $R_3$ is independently selected from hydrogen, $C_{1-4}$ alkyl, $C_{1-4}$ haloalkyl, $C_{2-4}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl, and $OCF_3$), C(O)—$C_{1-10}$ alkyl, $SO_3$—, $PO_3$—, $SO_2NR_bR_{b'}$, and C(O)phenyl; and $R_4$ is H, $C_{1-4}$ alkyl or $C_{1-4}$ haloalkyl; or pharmaceutically acceptable salts thereof.

In certain embodiments of this invention, for the compound of formula I, $R_x$ is CN.

In certain embodiments of this invention, for the compound of formula I, $R_y$ is $CF_3$ or Cl.

In certain embodiments of this invention, for the compound of formula I, $R_z$ is $C_{1-3}$ alkyl, halogen, $C_{1-3}$ hydroxyalkyl or $C_2$ alkenyl.

In some embodiments of this invention, for the compound of formula I, $R_z$ is $CH_3$, $CH_2CH_3$ or Cl.

In certain embodiments of this invention, for the compound of formula I, $R_x$ is CN, $R_y$ is $CF_3$ or Cl and $R_z$ is $CH_3$, $CH_2CH_3$ or Cl.

In some embodiments of this invention, for the compound of formula I, $R_4$ is hydrogen or $CH_3$.

In certain embodiments of this invention, for the compound of formula I, $R_4$ is hydrogen.

In some embodiments of this invention, for the compound of formula I, $R_x$ is CN, $R_y$ is $CF_3$ or Cl, $R_z$ is $CH_3$, $CH_2CH_3$ or Cl and $R_4$ is hydrogen.

In certain aspects of this invention, for the compound of formula I, A is a 5 member heteroaryl.

In certain aspects of this invention, for the compound of formula I, A is a 5 member heteroaryl selected from the following group of 5 member heteroaryls:

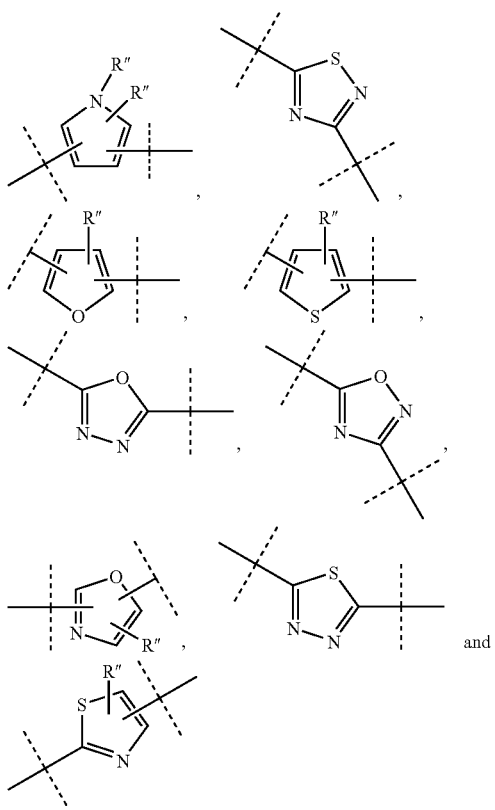

wherein each R" is independently hydrogen, CF$_3$, or C$_1$-C$_2$ alkyl;

In some embodiments of this invention, for the compound of formula I, A is

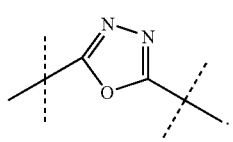

In certain embodiments of this invention, for the compound of formula I, R$_x$ is CN, R$_y$ is CF$_3$ or Cl, R$_z$ is CH$_3$, CH$_2$CH$_3$ or Cl, R$_4$ is hydrogen and A is

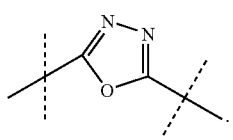

In some embodiments, for the compound of formula I, B is phenyl.

In certain embodiments of this invention, for the compound of formula I, R$_x$ is CN, R$_y$ is CF$_3$ or Cl, R$_z$ is CH$_3$, CH$_2$CH$_3$ or Cl, R$_4$ is hydrogen, A is

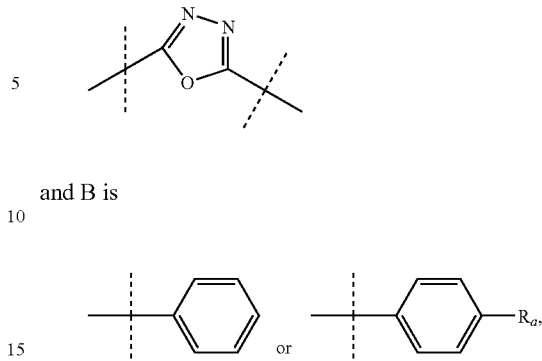

and B is wherein R$_a$ is as defined previously in I.

In some embodiments of this invention, for the compound of formula I, R$_x$ is CN, R$_y$ is CF$_3$ or Cl, R$_z$ is CH$_3$, CH$_2$CH$_3$ or Cl, R$_4$ is hydrogen, A is

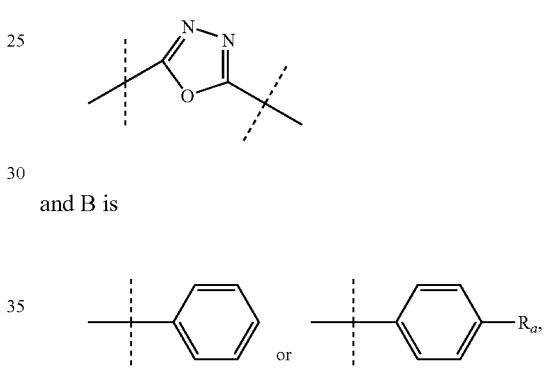

and B is wherein R$_a$ is CN, OH, F or Cl.

In some embodiments of this invention, for the compound of formula I, B is

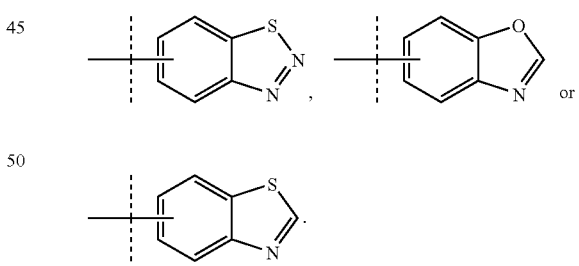

In some embodiments of this invention, for the compound of formula I, R$_x$ is CN, R$_y$ is CF$_3$ or Cl, R$_z$ is CH$_3$, CH$_2$CH$_3$ or Cl, R$_4$ is hydrogen, A is

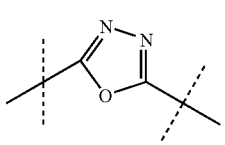

and B is

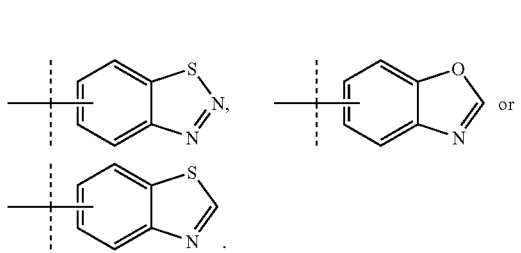

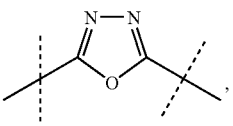

In some embodiments of this invention, for the compound of formula I, $R_x$ is CN, $R_y$ and $R_z$ together form

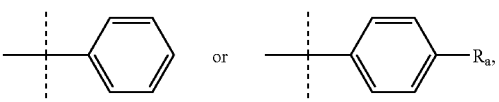

B is

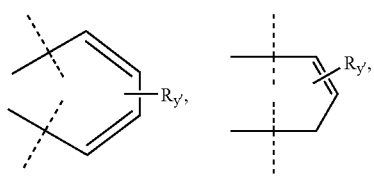

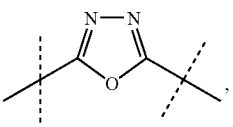

wherein $R_a$ is CN, OH, F or Cl and $R_1$ or $R_2$ is $OR_3$, either $R_1$ or $R_2$ is methyl, n' and n" are each 0 and $R_9$ is hydrogen or methyl.

In certain embodiments of this invention, for the compound of formula I, $R_x$ is CN, $R_y$ is $CF_3$ or Cl, $R_z$ is $CH_3$, $CH_2CH_3$ or Cl, $R_4$ is hydrogen, A is $R_4$ is hydrogen, A is

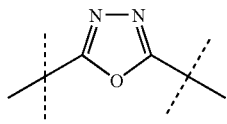

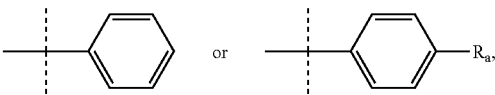

and B is

B is

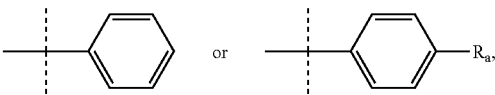

wherein $R_a$ is CN, OH, F or Cl.

In certain aspects of this invention, for the compound of formula I, either $R_1$ or $R_2$ is $OR_3$.

In certain aspects of this invention, for the compound of formula I, either $R_5$ or $R_6$ is $OR_3$.

In certain aspects of this invention, for the compound of formula I, either $R_7$ or $R_8$ is $OR_3$ and $R_9$ is hydrogen.

In certain aspects of this invention, for the compound of formula I, either $R_1$ or $R_2$ is $OR_3$, either $R_1$ or $R_2$ is methyl and n' and n" are each 0 and $R_9$ is hydrogen or methyl.

In certain aspects of this invention, for the compound of formula I, $R_1$ is $OR_3$, $R_2$ is hydrogen, n' is 0 and n" is 0 and $R_9$ is hydrogen.

In some embodiments of this invention, for the compound of formula I, $R_1$ and $R_2$ are each hydrogen, $R_5$ is $OR_3$ and $R_6$ is hydrogen, $R_9$ is hydrogen and n" is 0.

In certain embodiments of this invention, for the compound of formula I, $R_3$ is hydrogen.

In certain embodiments of this invention, for the compound of formula I, $R_x$ is CN, $R_y$ is $CF_3$ or Cl, $R_z$ is $CH_3$, $CH_2CH_3$ or Cl, $R_4$ is hydrogen, A is wherein $R_a$ is CN, OH, F or Cl and $R_1$ or $R_2$ is $OR_3$, either $R_1$ or $R_2$ is methyl, n' and n" are each 0 and $R_9$ is hydrogen or methyl and $R_3$ is hydrogen.

In some embodiments of this invention, for the compound of formula I, $R_x$ is CN, Ry and Rz together form

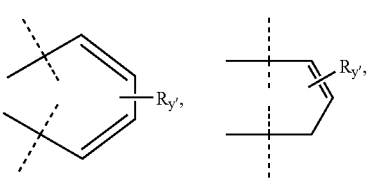

$R_y'$ is hydrogen, $R_4$ is hydrogen, A is

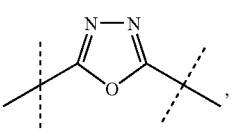

B is

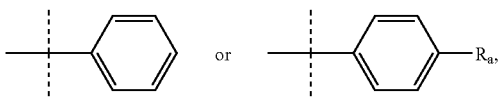

wherein $R_a$ is, CN, OH, F or Cl and $R_1$ or $R_2$ is $OR_3$, either $R_1$ or $R_2$ is methyl, n' and n'' are each 0, $R_9$ is hydrogen or methyl and $R_3$ is hydrogen.

The invention described herein relates to compounds of formula Ia:

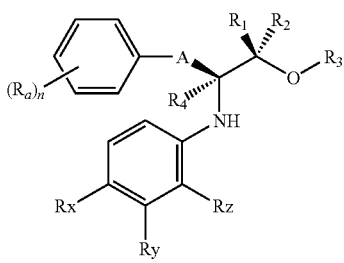

wherein:

$R_x$ is CN, Cl, Br, $NO_2$ or $R_{x1}$;

$R_y$ is $CH_3$, $CF_3$, or halogen;

$R_z$ is H, $C_{1-3}$ alkyl, $C_{1-3}$ haloalkyl, $NO_2$, $NH_2$, OMe, halogen or OH; or $R_y$ and $R_z$ form

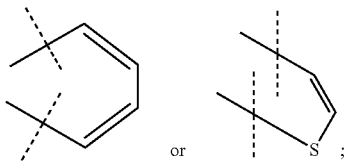

$R_{x1}$ is a 5 member heteroaryl, said heteroaryl selected from

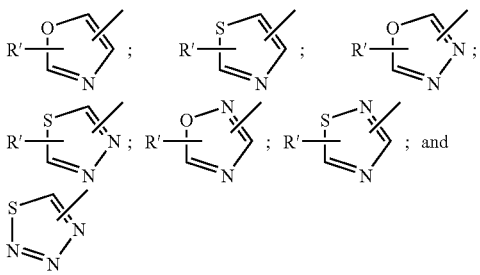

R' is hydrogen, $C_1$-$C_2$ alkyl, $CF_3$, or halogen; or $R_x$ and $R_y$ together with the phenyl group to which they are attached form a 5 member aromatic ring selected from:

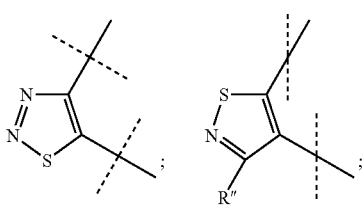

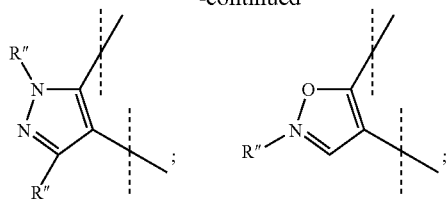

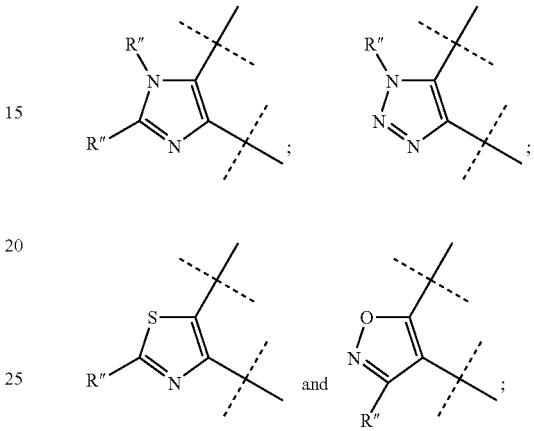

wherein each R'' is independently hydrogen, $CF_3$, or $C_1$-$C_2$ alkyl;

A is a 5- or 6-member heteroaryl group;

each $R_a$ is independently selected from $C_{1-4}$alkyl (optionally substituted with from 1-2 substituents independently selected from CN, OH and 5 member heteroaryl), 5-member heteroaryl, CN, —N($R_b$)C(O)O$C_{1-6}$ alkyl, —N($R_b$)C(O)OPhenyl (wherein said phenyl is optionally substituted with from 1-3 substituents independently selected from CN, halogen, OH, $C_{1-3}$ alkyl, and O$C_{1-3}$ alkyl), —N($R_b$)C(O)$C_{1-6}$ alkyl, —N($R_b$)C(O)Phenyl (wherein said phenyl is optionally substituted with from 1-3 substituents independently selected from CN, halogen, OH, $C_{1-3}$alkyl, and O$C_{1-3}$alkyl), $NR_bR_{b'}$, $C_{1-4}$haloalkyl, halogen, OH, O$C_{1-3}$ alkyl, O$C_{1-3}$ haloalkyl, $OSO_2$-phenyl, (wherein said phenyl is optionally substituted with halogen, $C_{1-3}$ alkyl or $C_{1-3}$ haloalkyl), $S(O)_{0-2}$phenyl, and $S(O)_{0-2}C_{1-3}$ alkyl;

$R_b$ and $R_{b'}$ are each independently selected from hydrogen, $C_{1-3}$ alkyl and $C_{1-3}$ haloalkyl;

n is 0, 1, 2, or 3;

$R_1$ and $R_2$ are each independently selected from hydrogen, $C_{1-3}$ alkyl, $C_{1-3}$ haloalkyl and phenyl;

$R_3$ is hydrogen, $C_{1-4}$ alkyl, $C_{1-4}$ haloalkyl, $C_{2-4}$ hydroxylalkyl, benzyl (wherein the phenyl group of said benzyl is optionally substituted with from 1-3 substituents selected from: halogen, $C_{1-3}$ alkyl, $S(O)_{0-2}C_{1-3}$ alkyl, $S(O)_{0-2}$phenyl, O—$C_{1-6}$ alkyl, $OCF_3$), C(O)—$C_{1-6}$ alkyl and C(O)Phenyl; and $R_4$ is H, $C_{1-4}$alkyl or $C_{1-4}$haloalkyl; or pharmaceutically acceptable salts thereof.

In certain embodiments of this invention, for the compound of formula Ia, A is a 5 member heteroaryl group.

In some embodiments of this invention, for the compound of formula Ia, A is a 5 member heteroaryl group selected from the group consisting of:

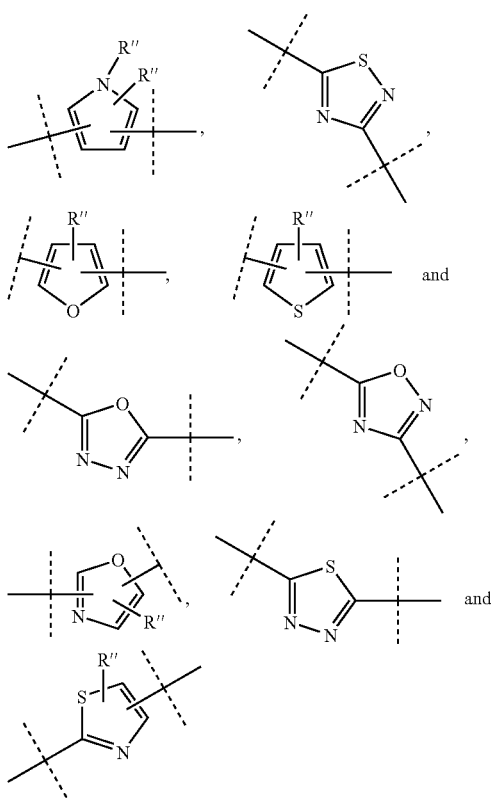

wherein each R'' is independently hydrogen, $CF_3$, or $C_1$-$C_2$ alkyl.

In certain embodiments of this invention, for the compound of formula Ia, $R_x$ is CN.

In some embodiments, for the compound of formula Ia, $R_y$ is $CF_3$ or Cl.

In certain embodiments, for the compound of formula Ia, $R_z$ is H, $CH_3$, $CF_3$ or Cl.

In some embodiments, for the compound of formula Ia, $R_x$ is CN, $R_y$ is Cl, $R_z$ is $CH_3$.

In certain embodiments of this invention, for the compound of formula Ia, A is

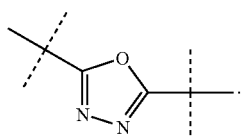

In some embodiments of this invention, for the compound of formula Ia, $R_a$ is OH, OMe, $OCF_3$, CN, $SO_2CH_3$, or halogen and n is 1.

In certain embodiments of this invention, for the compound of formula Ia, $R_a$ is 4'-Fl or 4'-Cl.

In certain embodiments of this invention, for the compound of formula Ia, $R_a$ is 4'-OH.

In certain embodiments of this invention, for the compound of formula Ia, $R_a$ is 4'-CN.

In certain embodiments of this invention, for the compound of formula Ia, n is 0.

In some embodiments, for the compound of formula Ia, $R_4$ is H, $CH_3$ or $CH_2CF_3$.

In some embodiments of this invention, for the compound of formula Ia, $R_4$ is H.

In certain embodiments of this invention, for the compound of formula Ia, $R_1$ and $R_2$ are each independently H, $CH_3$, or $CF_3$, and at least one of $R_1$ and $R_2$ is not H.

In other embodiments of this invention, for the compound of formula Ia, $R_1$ is H and $R_2$ is $CH_3$.

In some embodiments of this invention, for the compound of formula Ia, $R_1$ is $CH_3$ and $R_2$ is H.

In certain embodiments of this invention, for the compound of formula Ia, $R_1$ is H, $R_2$ is $CF_3$.

In some embodiments of this invention, for the compound of formula Ia, $R_1$ is $CF_3$ and $R_2$ is H.

In certain embodiments of this invention, for the compound of formula Ia, $R_3$ is H.

In some embodiments of this invention, for the compound of formula Ia, $R_1=R_2=CH_3$.

In some embodiments of this invention, for the compound of formula Ia, $R_x$ is CN, $R_y$ is $CF_3$ or Cl, $R_z$ is Cl, $CH_3$ or $CF_3$, A is

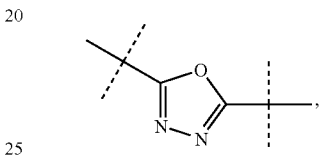

$R_a$ is selected from halogen, CN, $OCH_3$, $SO_2CH_3$ and OH, n is 0 or 1, $R_1$ is $CH_3$, $CF_3$ or H, $R_2$ is $CH_3$, $CF_3$ or H, $R_3$ is H, $R_4$ is H, $CH_3$, $CH_2CH_3$, or $CH_2CF_3$.

In certain embodiments of this invention, for the compound of formula Ia, $R_x$ is CN, $R_y$ is Cl, $R_z$ is $CH_3$, A is

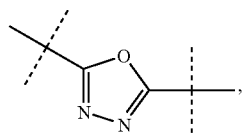

$R_a$ is selected from halogen, CN, $OCH_3$ and OH, n is 0 or 1, $R_1$ is H or $CH_3$, $R_2$ is H or $CH_3$, $R_3$ is H, $R_4$ is H, wherein at least one of $R_1$ and $R_2$ is not H.

In certain embodiments of this invention, for the compound of formula Ia, $R_x$ is CN, $R_y$ is Cl, $R_z$ is $CH_3$, A is

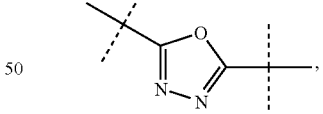

$R_a$ is 4'-Cl, $R_1$ is H or $CH_3$, $R_2$ is H or $CH_3$, $R_3$ is H, $R_4$ is H, wherein at least one of $R_1$ and $R_2$ is not H.

In certain embodiments of this invention, for the compound of formula Ia, $R_x$ is CN, $R_y$ is Cl, $R_z$ is $CH_3$, A is

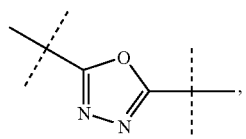

$R_a$ is 4'-CN, $R_1$ is H or $CH_3$, $R_2$ is H or $CH_3$, $R_3$ is H, $R_4$ is H, wherein at least one of $R_1$ and $R_2$ is not H.

In certain embodiments, this invention describes a compound of formula Ib

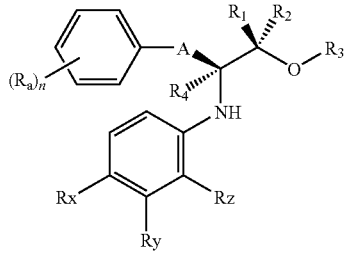

Ib wherein:

$R_x$ is CN, Cl, Br, NO$_2$ or $R_{x1}$;

$R_y$ is CH$_3$, CF$_3$ or Cl;

$R_z$ is H, C$_{1-3}$ alkyl, C$_{1-3}$ haloalkyl, NO$_2$, NH$_2$, OMe, Cl or OH; or $R_y$ and $R_z$ together with their intervening atoms form

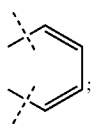

$R_{x1}$ is a 5 member heteroaryl, said heteroaryl selected from

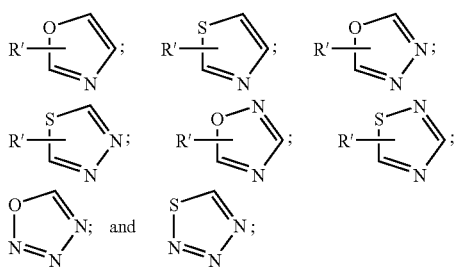

R' is hydrogen, C$_1$-C$_2$ alkyl, CF$_3$, or halogen; or $R_x$ and $R_y$ together with the phenyl group to which they are attached form a 5 member aromatic ring selected from:

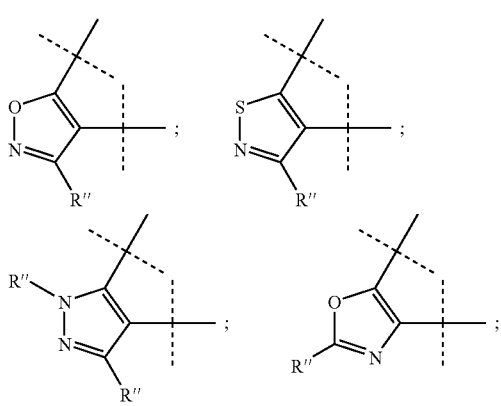

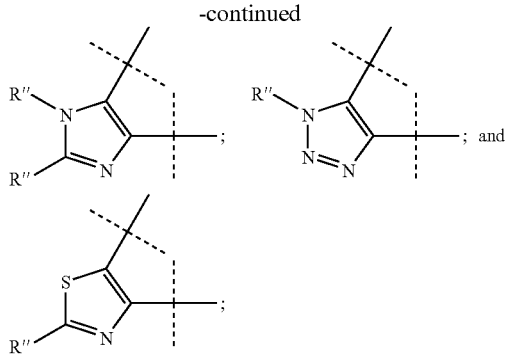

wherein each R'' is independently hydrogen, CF$_3$, or C$_1$-C$_2$ alkyl;

A is a five member heteroaryl selected from

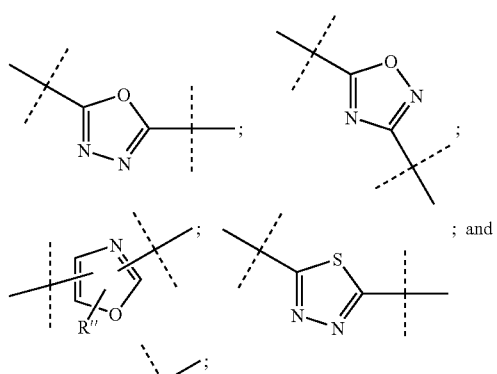

each $R_a$ is independently selected from C$_{1-4}$ alkyl, C$_{1-4}$ haloalkyl, halogen, OH, OC$_{1-3}$ alkyl, OC$_{1-3}$ haloalkyl, OSO$_2$-phenyl, (wherein said phenyl is optionally substituted with halogen, C$_{1-3}$ alkyl or C$_{1-3}$ haloalkyl), S(O)$_{0-2}$phenyl, and S(O)$_{0-2}$C$_{1-3}$ alkyl;

n is 0, 1, 2, or 3;

$R_1$ and $R_2$ are each independently selected from hydrogen, C$_{1-3}$ alkyl, C$_{1-3}$ haloalkyl and phenyl;

$R_3$ is hydrogen, C$_{1-4}$ alkyl, C$_{1-4}$ haloalkyl, C$_{2-4}$ hydroxylalkyl, benzyl (wherein the phenyl group of said benzyl is optionally substituted with from 1-3 substituents selected from: halogen, C$_{1-3}$ alkyl, S(O)$_{0-2}$C$_{1-3}$ alkyl, S(O)$_{0-2}$phenyl, O—C$_{1-6}$ alkyl, OCF$_3$), C$_{1-6}$ acyl, and benzoyl;

$R_4$ is H, C$_{1-4}$ alkyl or C$_{1-4}$ haloalkyl; or pharmaceutically acceptable salts thereof.

In certain embodiments of this invention, for the compound of formula Ib, $R_x$ is CN.

In some embodiments, for the compound of formula Ib, $R_y$ is CF$_3$ or Cl.

In other embodiments, for the compound of formula Ib, $R_z$ is H, CH$_3$, CF$_3$ or Cl.

In some embodiments, for the compound of formula Ib, $R_x$ is CN, $R_y$ is Cl, $R_z$ is CH$_3$.

In certain embodiments of this invention, for the compound of formula Ib, A is

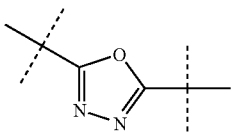

In some embodiments of this invention, for the compound of formula Ib, $R_a$ is OH, OMe, OCF$_3$, SO$_2$CH$_3$, or halogen and n is 1.

In certain embodiments of this invention, for the compound of formula Ib, $R_a$ is 4'-Fl or 4'-Cl.

In certain embodiments of this invention, for the compound of formula Ib, n is 0.

In some embodiments, for the compound of formula Ib, $R_4$ is H, CH$_3$ or CH$_2$CF$_3$.

In some embodiments of this invention, for the compound of formula Ib, $R_4$ is H.

In certain embodiments of this invention, for the compound of formula Ib, $R_1$ and $R_2$ are each independently H, CH$_3$, or CF$_3$, and at least one of $R_1$ and $R_2$ is not H.

In other embodiments of this invention, for the compound of formula Ib, $R_1$ is H and $R_2$ is CH$_3$.

In some embodiments of this invention, for the compound of formula Ib, $R_1$ is CH$_3$ and $R_2$ is H.

In certain embodiments of this invention, for the compound of formula Ib, $R_1$ is H, $R_2$ is CF$_3$.

In some embodiments of this invention, for the compound of formula Ib, $R_1$ is CF$_3$ and $R_2$ is H.

In certain embodiments of this invention, for the compound of formula Ib, $R_3$ is H. In some embodiments of this invention, for the compound of formula Ib, $R_1$=$R_2$=CH$_3$.

In some embodiments of this invention, for the compound of formula Ib, $R_x$ is CN, $R_y$ is CF$_3$ or Cl, $R_z$ is Cl, CH$_3$ or CF$_3$, A is

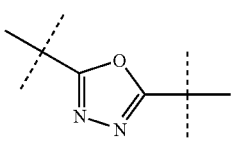

$R_a$ is selected from halogen, OCH$_3$, SO$_2$CH$_3$ and OH, n is 0 or 1, $R_1$ is CH$_3$, CF$_3$ or H, $R_2$ is CH$_3$, CF$_3$ or H, $R_3$ is H, $R_4$ is H, CH$_3$, CH$_2$CH$_3$, or CH$_2$CF$_3$.

In certain embodiments of this invention, for the compound of formula Ib, $R_x$ is CN, $R_y$ is Cl, $R_z$ is CH$_3$, A is

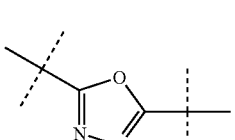

$R_a$ is selected from halogen, OCH$_3$ and OH, n is 0 or 1, $R_1$ is H or CH$_3$, $R_2$ is H or CH$_3$, $R_3$ is H, $R_4$ is H, wherein at least one of $R_1$ and $R_2$ is not H.

In certain embodiments of this invention, for the compound of formula Ib, $R_x$ is CN, $R_y$ is Cl, $R_z$ is CH$_3$, A is

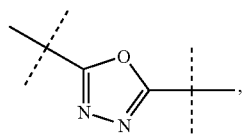

$R_a$ is 4'-Cl, $R_1$ is H or CH$_3$, $R_2$ is H or CH$_3$, $R_3$ is H, $R_4$ is H, wherein at least one of $R_1$ and $R_2$ is not H.

In some embodiments, this invention describes a compound of formula Ic:

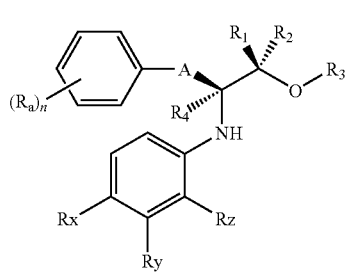

wherein:
$R_x$=CN, Cl, Br, or NO$_2$;
$R_y$=CH$_3$, CF$_3$ or Cl;
$R_z$=H, C$_{1-3}$ alkyl, C$_{1-3}$ haloalkyl, NO$_2$, NH$_2$, OMe, Cl or OH; or
$R_y$ and $R_z$ together form

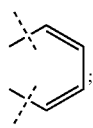

or
$R_x$ and $R_y$ together with the phenyl group they are attached form

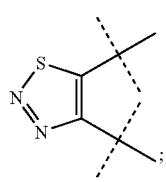

A is a five member heteroaryl selected from

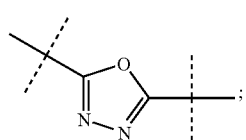 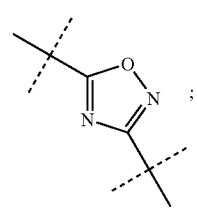

-continued

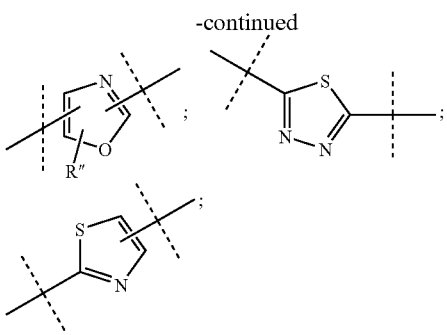

wherein each R" is independently hydrogen, CF$_3$, or C$_1$-C$_2$ alkyl;

R$_a$ is C$_{1-4}$ alkyl, C$_{1-4}$ haloalkyl, halogen, OH, OC$_{1-3}$ alkyl, OC$_{1-3}$ haloalkyl, OSO$_2$-phenyl (wherein said phenyl is optionally substituted with halogen, C$_{1-3}$ alkyl or C$_{1-3}$ haloalkyl) or S(O)$_{0-2}$C$_{1-3}$ alkyl;

n is 0, 1, 2, or 3;

R$_1$ and R$_2$ are each independently selected from hydrogen, C$_{1-3}$ alkyl, C$_{1-3}$ haloalkyl or phenyl;

R$_3$ is hydrogen, C$_{1-4}$ alkyl, C$_{1-4}$ haloalkyl, C$_{2-4}$ hydroxylalkyl, benzyl (wherein the phenyl group of said benzyl is optionally with from 1-3 substituents selected from halogen, C$_{1-3}$ alkyl, S(O)$_{0-2}$C$_{1-3}$ alkyl, O—C$_{1-6}$ alkyl and OCF$_3$), C$_{1-6}$ acyl; or benzoyl;

R$_4$ is H, C$_{1-4}$ alkyl or C$_{1-4}$ haloalkyl; and pharmaceutically acceptable salts thereof.

In certain embodiments of this invention, for the compound of formula Ic, R$_x$ may be CN.

In some embodiments, for the compound of formula Ic, R$_y$=CF$_3$ or Cl.

In other embodiments, for the compound of formula Ic, R$_z$=H, CH$_3$, CF$_3$ or Cl.

In some embodiments, for the compound of formula Ic, R$_x$=CN, R$_y$=Cl, R$_z$=CH$_3$.

In certain embodiments of this invention, for the compound of formula Ic, A is

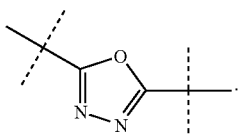

In some embodiments of this invention, for the compound of formula Ic, R$_a$ is OH, OMe, OCF$_3$, SO$_2$CH$_3$, or halogen and n is 1.

In certain embodiments of this invention, for the compound of formula Ic, R$_a$ is 4'-Fl or 4'-Cl.

In certain embodiments of this invention, for the compound of formula Ic, n is 0.

In some embodiments, for the compound of formula Ic, R$_4$ is H, CH$_3$ or CH$_2$CF$_3$.

In some embodiments of this invention, for the compound of formula Ic, R$_4$ is H.

In certain embodiments of this invention, for the compound of formula Ic, R$_1$ and R$_2$ are each independently H, CH$_3$, or CF$_3$, and at least one of R$_1$ and R$_2$ is not H.

In other embodiments of this invention, for the compound of formula Ic, R$_1$ is H and R$_2$ is CH$_3$.

In some embodiments of this invention, for the compound of formula Ic, R$_1$ is CH$_3$ and R$_2$ is H.

In certain embodiments of this invention, for the compound of formula Ic, R$_1$ is H, R$_2$ is CF$_3$.

In some embodiments of this invention, for the compound of formula Ic, R$_1$ is CF$_3$ and R$_2$ is H.

In certain embodiments of this invention, for the compound of formula Ic, R$_3$ is H.

In some embodiments of this invention, for the compound of formula Ic, R$_1$=R$_2$=CH$_3$.

In some embodiments of this invention, for the compound of formula Ic, R$_x$=CN, R$_y$=CF$_3$ or Cl, R$_z$=Cl, CH$_3$ or CF$_3$, A is

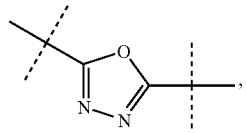

R$_a$ is selected from halogen, OCH$_3$, SO$_2$CH$_3$ or OH, n is 0 or 1, R$_1$ is CH$_3$, CF$_3$ or H, R$_2$ is CH$_3$, CF$_3$ or H, R$_3$ is H, R$_4$ is H, CH$_3$, CH$_2$CH$_3$, or CH$_2$CF$_3$.

In certain embodiments of this invention, for the compound of formula Ic, R$_x$=CN, R$_y$=Cl, R$_z$=CH$_3$, A is

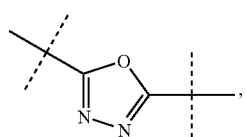

R$_a$ is selected from halogen, OCH$_3$ or OH, n is 0 or 1, R$_1$ is H or CH$_3$, R$_2$ is H or CH$_3$, R$_3$ is H, R$_4$ is H, wherein at least one of R$_1$ and R$_2$ is not H.

In certain embodiments of this invention, for the compound of formula Ic, R$_x$=CN, R$_y$=Cl, R$_z$=CH$_3$, A is

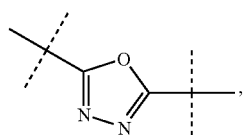

R$_a$ is selected from 4'-Cl, R$_1$ is H or CH$_3$, R$_2$ is H or CH$_3$, R$_3$ is H, R$_4$ is H, wherein at least one of R$_1$ and R$_2$ is not H.

The invention described herein also relates to compounds of formula Id:

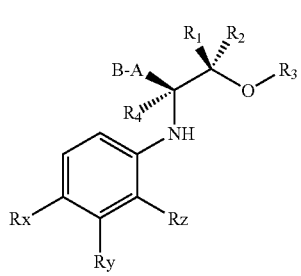

wherein:
R$_x$ is CN, Cl, Br, NO$_2$ or R$_{x1}$;
R$_y$ is CH$_3$, CF$_3$ or Cl;
R$_z$ is H, C$_{1-3}$ alkyl, C$_{1-3}$ haloalkyl, NO$_2$, NH$_2$, OMe, Cl or OH; or $R_y$ and $R_z$ together with their intervening atoms form

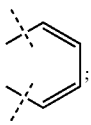

$R_{x1}$ is a 5 member heteroaryl, said heteroaryl selected from

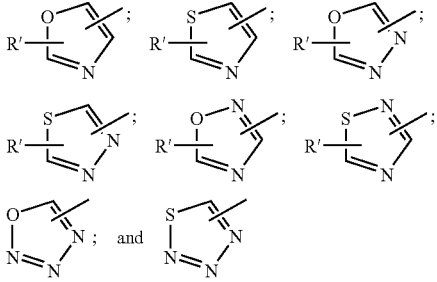

R' is hydrogen, $C_1$-$C_2$ alkyl, $CF_3$, or halogen; or $R_x$ and $R_y$ together with the phenyl group to which they are attached form a 5 member aromatic ring selected from:

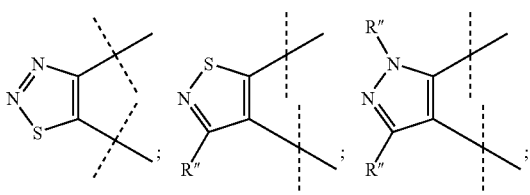

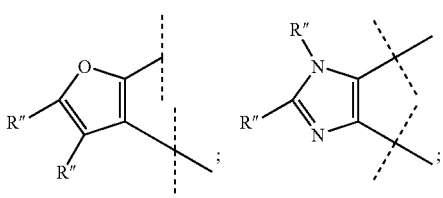

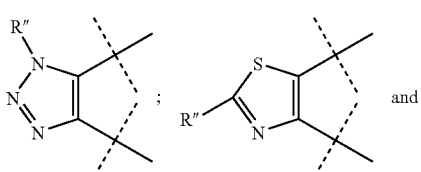

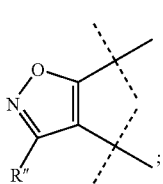

wherein each R" is independently hydrogen, $CF_3$, or $C_1$-$C_2$ alkyl;

A is a five member heteroaryl selected from

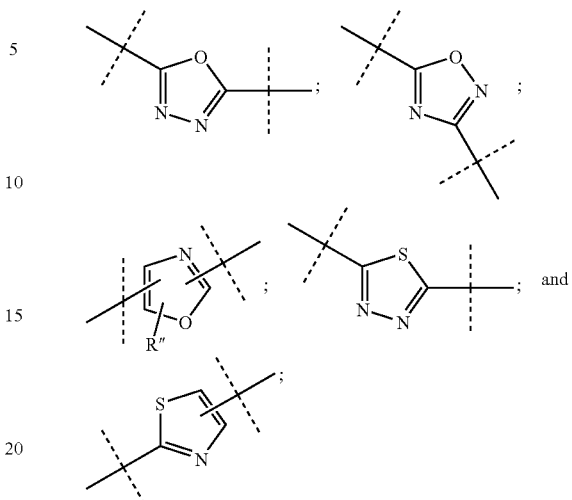

B is

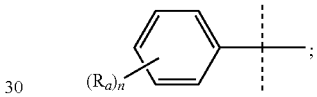

$C_{1-6}$ alkyl or $C_{1-6}$ haloalkyl;

each $R_a$ is independently selected from $C_{1-4}$ alkyl, $C_{1-4}$ haloalkyl, halogen, OH, $OC_{1-3}$ alkyl, $OC_{1-3}$ haloalkyl, $OSO_2$-phenyl, (wherein said phenyl is optionally substituted with halogen, $C_{1-3}$ alkyl or $C_{1-3}$ haloalkyl), $S(O)_{0-2}$phenyl, and $S(O)_{0-2}C_{1-3}$ alkyl;

n is 0, 1, 2, or 3;

$R_1$ and $R_2$ are each independently selected from hydrogen, $C_{1-3}$ alkyl, $C_{1-3}$ haloalkyl and phenyl;

$R_3$ is hydrogen, $C_{1-4}$ alkyl, $C_{1-4}$ haloalkyl, $C_{2-4}$ hydroxylalkyl, benzyl (wherein the phenyl group of said benzyl is optionally substituted with from 1-3 substituents selected from: halogen, $C_{1-3}$ alkyl, $S(O)_{0-2}C_{1-3}$ alkyl, $S(O)_{0-2}$phenyl, O—$C_{1-6}$ alkyl, $OCF_3$), $C_{1-6}$ acyl, and benzoyl;

$R_4$ is H, $C_{1-4}$ alkyl or $C_{1-4}$ haloalkyl; or pharmaceutically acceptable salts thereof.

In certain embodiments, this invention describes a compound of formula Ie

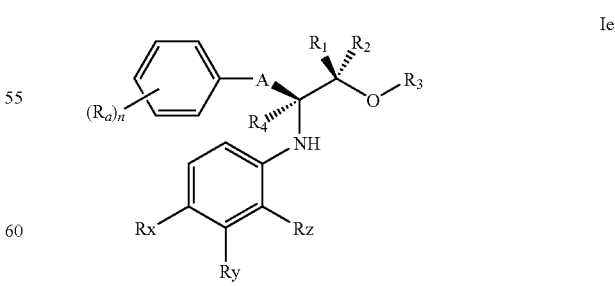

wherein:

$R_x$=CN or Cl;

$R_y$=$CH_3$, $CF_3$ or Cl;

$R_z$=$CH_3$, CH=$CH_2$, $CH_2CH_3$ or Cl;

or Ry and Rz together form:

A is a five member heteroaryl selected from or each $R_a$ is independently selected from $C_{1-4}$ alkyl, —$N(R_b)$ C(O)$C_{1-6}$ alkyl, $N(R_b)$C(O)OPhenyl, $C_{1-4}$ haloalkyl, halogen, CN, OH, $OSO_2NR_bR_{b'}$, $OSO_3$—, $OC_{1-3}$ alkyl, $OC_{1-3}$ haloalkyl, O(S)(O)$_2$-phenyl (wherein said phenyl is optionally substituted with halogen, $C_{1-3}$ alkyl or $C_{1-3}$ haloalkyl) and $S(O)_{0-2}C_{1-3}$ alkyl;
each $R_b$ and $R_{b'}$ are independently selected from hydrogen, $C_{1-3}$ alkyl and $C_{1-3}$ haloalkyl;
n is 0, 1, 2, or 3;
$R_1$ and $R_2$ are each independently selected from hydrogen, $C_{1-3}$ alkyl, $C_{1-3}$ haloalkyl or phenyl;
$R_3$ is hydrogen, $SO_2NR_bR_{b'}$, $SO_3$—, $C_{1-4}$ alkyl, $C_{1-4}$ haloalkyl, $C_{2-4}$ hydroxylalkyl, benzyl (wherein the phenyl group of said benzyl is optionally with from 1-3 substituents selected from halogen, $C_{1-3}$ alkyl, $S(O)_{0-2}C_{1-3}$ alkyl, O—$C_{1-6}$ alkyl, $OCF_3$), $C_{1-6}$ acyl; or benzoyl;
$R_4$ is H, $C_{1-4}$ alkyl or $C_{1-4}$ haloalkyl; and
pharmaceutically acceptable salts thereof.

In certain embodiments, this invention describes a compound of formula If:

If wherein:
$R_x$=CN;
$R_y$=$CF_3$ or Cl;
$R_z$=$CH_3$, $CH_2CH_3$ or Cl;
or Ry and Rz together form:

$R_{a'}$ is hydrogen, fluorine, chlorine, CN,

OH, or $OSO_3$—;
$R_1$ and $R_2$ are each independently selected from hydrogen and methyl; and
pharmaceutically acceptable salts thereof.

In some embodiments of this invention, the compound of formula I, Ia, Ib, Ic, Id, Ie or If is selected from the following list. (The compound names in the list were generated with the assistance of ChemDraw® versions 8.0, 9.0 and/or 11.0 (CambridgeSoft Corporation, 100 CambridgePark Drive, Cambridge, Mass. 02140 USA)). When the stereochemistry at a chiral center is not defined in the compound name this indicates that the sample prepared contained a mixture of isomers at this center.

2-Chloro-4-((1R,2S)-2-hydroxy-1-(5-phenyl-1,3,4-oxadiazol-2-yl)propylamino)-3-methylbenzonitrile,
2-Chloro-4-((1R,2S)-2-hydroxy-1-(5-(4-methoxyphenyl)-1,3,4-oxadiazol-2-yl)propylamino)-3-methylbenzonitrile,
2-Chloro-4-((1R,2R)-2-hydroxy-1-(5-phenyl-1,3,4-oxadiazol-2-yl)propylamino)-3-methylbenzonitrile,
2-Chloro-4-((1R,2S)-1-(5-(4-chlorophenyl)-1,3,4-oxadiazol-2-yl)-2-hydroxypropylamino)-3-methylbenzonitrile,
2-Chloro-4-((1R,2S)-1-(5-(4-fluorophenyl)-1,3,4-oxadiazol-2-yl)-2-hydroxypropylamino)-3-methylbenzonitrile,
2-Chloro-4-((1R,2S)-2-hydroxy-1-(5-(3-methoxyphenyl)-1,3,4-oxadiazol-2-yl)propylamino)-3-methylbenzonitrile,
2-Chloro-4-((1R,2S)-2-hydroxy-1-(5-(3-hydroxyphenyl)-1,3,4-oxadiazol-2-yl)propylamino)-3-methylbenzonitrile,
2-Chloro-4-((1R,2S)-2-hydroxy-1-(5-(4-hydroxyphenyl)-1,3,4-oxadiazol-2-yl)propylamino)-3-methylbenzonitrile,
2-Chloro-4-((1R,2R)-2-hydroxy-1-(5-(3-hydroxyphenyl)-1,3,4-oxadiazol-2-yl)propylamino)-3-methylbenzonitrile,
2-Chloro-4-((1R,2R)-2-hydroxy-1-(5-(4-hydroxyphenyl)-1,3,4-oxadiazol-2-yl)propylamino)-3-methylbenzonitrile,
2-Chloro-3-ethyl-4-((1R,2S)-2-hydroxy-1-(5-phenyl-1,3,4-oxadiazol-2-yl)propylamino)benzonitrile,
2-Chloro-4-((1R,2S)-2-hydroxy-1-(5-phenyl-1,3,4-oxadiazol-2-yl)propylamino)benzonitrile,
4-((1R,2S)-2-Hydroxy-1-(5-phenyl-1,3,4-oxadiazol-2-yl)propylamino)-1-naphthonitrile,
(R)-2-Chloro-4-(2-hydroxy-2-methyl-1-(5-phenyl-1,3,4-oxadiazol-2-yl)propylamino)-3-methylbenzonitrile,
(R)-2-Chloro-4-(1-(5-(4-chlorophenyl)-1,3,4-oxadiazol-2-yl)-2-hydroxy-2-methylpropylamino)-3-methylbenzonitrile, 4-((1R,2S)-2-Hydroxy-1-(5-phenyl-1,3,4-oxadiazol-2-yl)propylamino)-2-(trifluoromethyl)benzonitrile,
(R)-2-Chloro-4-(2-hydroxy-1-(5-phenyl-1,3,4-oxadiazol-2-yl)ethylamino)-3-methylbenzonitrile,
2-Chloro-4-((1R,2R)-2-hydroxy-1-(3-phenyl-1,2,4-oxadiazol-5-yl)propylamino)-3-methylbenzonitrile,
2-Chloro-4-((1R,2R)-1-(5-(4-fluorophenyl)-1,3,4-oxadiazol-2-yl)-2-hydroxypropylamino)-3-methylbenzonitrile,
2-Chloro-4-((1R,2R)-1-(5-(4-chlorophenyl)-1,3,4-oxadiazol-2-yl)-2-hydroxypropylamino)-3-methylbenzonitrile,
2-Chloro-4-((1R,2S)-1-(5-(3-chlorophenyl)-1,3,4-oxadiazol-2-yl)-2-hydroxypropylamino)-3-methylbenzonitrile,
2-Chloro-4-((1R,2S)-1-(5-(4-cyanophenyl)-1,3,4-oxadiazol-2-yl)-2-hydroxypropylamino)-3-methylbenzonitrile,
2-Chloro-4-((1R,2R)-1-(5-(4-cyanophenyl)-1,3,4-oxadiazol-2-yl)-2-hydroxypropylamino)-3-methylbenzonitrile,
2-Chloro-4-((1R,2S)-2-hydroxy-1-(5-(4-(methylsulfonyl)phenyl)-1,3,4-oxadiazol-2-yl)propylamino)-3-methylbenzonitrile,
2-Chloro-4-((1R,2R)-2-hydroxy-1-(5-(4-(methylsulfonyl)phenyl)-1,3,4-oxadiazol-2-yl)propylamino)-3-methylbenzonitrile,
2-Chloro-4-((1R,2R)-2-hydroxy-1-(5-phenyl-1,3,4-thiadiazol-2-yl)propylamino)-3-methylbenzonitrile,
2-Chloro-4-((1R,2S)-2-hydroxy-1-(5-phenyl-1,3,4-thiadiazol-2-yl)propylamino)-3-methylbenzonitrile,
2-Chloro-4-((1R,2R)-1-(5-(4-fluorophenyl)-1,3,4-thiadiazol-2-yl)-2-hydroxypropylamino)-3-methylbenzonitrile,
2-Chloro-4-((1R,2S)-1-(5-(3-fluoro-4-hydroxyphenyl)-1,3,4-oxadiazol-2-yl)-2-hydroxypropylamino)-3-methylbenzonitrile,
2-Chloro-4-((1R,2R)-1-(5-(3-chloro-4-hydroxyphenyl)-1,3,4-oxadiazol-2-yl)-2-hydroxypropylamino)-3-methylbenzonitrile,
4-((1R,2R)-1-(5-(4-Cyanophenyl)-1,3,4-oxadiazol-2-yl)-2-hydroxypropylamino)-3-methyl-2-(trifluoromethyl)benzonitrile,
2-Chloro-4-((1R,2R)-1-(5-(3,4-dichlorophenyl)-1,3,4-oxadiazol-2-yl)-2-hydroxypropylamino)-3-methylbenzonitrile,
2,3-Dichloro-4-((1R,2S)-2-hydroxy-1-(5-phenyl-1,3,4-oxadiazol-2-yl)propylamino)benzonitrile,
2,3-Dichloro-4-((1R,2S)-1-(5-(4-chlorophenyl)-1,3,4-oxadiazol-2-yl)-2-hydroxypropylamino)benzonitrile,
2-Chloro-4-((1R,2R)-1-(5-(2,4-difluorophenyl)-1,3,4-oxadiazol-2-yl)-2-hydroxypropylamino)-3-methylbenzonitrile,
2-Chloro-4-((1R,2S)-2-hydroxy-1-(5-phenyloxazol-2-yl)propylamino)-3-methylbenzonitrile,
2-Chloro-4-((1R,2S)-1-(5-(3-chloro-4-hydroxyphenyl)-1,3,4-oxadiazol-2-yl)-2-hydroxypropylamino)-3-methylbenzonitrile,
Threo-2-chloro-4-(2-hydroxy-2-phenyl-1-(5-phenyl-1,3,4-oxadiazol-2-yl)ethylamino)-3-methylbenzonitrile,
2-Chloro-4-((1R,2R)-1-(5-(3,4-difluorophenyl)-1,3,4-oxadiazol-2-yl)-2-hydroxypropylamino)-3-methylbenzonitrile,
2-Chloro-4-((1R,2S)-1-(5-(4-fluoro-3-hydroxyphenyl)-1,3,4-oxadiazol-2-yl)-2-hydroxypropylamino)-3-methylbenzonitrile,
2-Chloro-4-((1R,2R)-1-(5-(4-fluoro-3-hydroxyphenyl)-1,3,4-oxadiazol-2-yl)-2-hydroxypropylamino)-3-methylbenzonitrile,
4-((1R,2S)-1-(5-(4-Cyanophenyl)-1,3,4-oxadiazol-2-yl)-2-hydroxypropylamino)-3-methyl-2-(trifluoromethyl)benzonitrile,
2-Chloro-4-((1R,2S)-2-hydroxy-1-(5-methyl-1,3,4-oxadiazol-2-yl)propylamino)-3-methylbenzonitrile,
4-((1R,2R)-1-(5-(4-Cyanophenyl)-1,3,4-oxadiazol-2-yl)-2-hydroxypropylamino)-2-(trifluoro-methyl)benzonitrile,
4-((1R,2S)-1-(5-(4-Cyanophenyl)-1,3,4-oxadiazol-2-yl)-2-hydroxypropylamino)-2-(trifluoromethyl)benzonitrile,
2-Chloro-4-((1R,2R)-1-(5-(4-cyanophenyl)-1,3,4-oxadiazol-2-yl)-2-hydroxypropylamino)-benzonitrile,
2-Chloro-4-((1R,2S)-1-(5-(4-cyanophenyl)-1,3,4-oxadiazol-2-yl)-2-hydroxypropylamino)-3-ethylbenzonitrile,
2-Chloro-4-((1R,2S)-2-hydroxy-1-(5-(4-(methylsulfonyl)phenyl)-1,3,4-oxadiazol-2-yl)propylamino)benzonitrile,
2-Chloro-4-((1R,2S)-2-hydroxy-1-(5-(4-(hydroxymethyl)phenyl)-1,3,4-oxadiazol-2-yl)propylamino)-3-methylbenzonitrile,
2-Chloro-4-((1R,2S)-1-(5-(4-cyanophenyl)-1,3,4-oxadiazol-2-yl)-2-hydroxypropylamino)benzonitrile,
4-((1R,2R)-1-(5-(4-Cyanophenyl)-1,3,4-oxadiazol-2-yl)-2-hydroxypropylamino)-1-naphthonitrile,
4-((1R,2R)-2-Hydroxy-1-(5-phenyl-1,3,4-oxadiazol-2-yl)propylamino)-1-naphthonitrile,
4-((1R,2S)-1-(5-(4-(1H-Pyrazol-1-yl)phenyl)-1,3,4-oxadiazol-2-yl)-2-hydroxypropylamino)-2-chloro-3-methylbenzonitrile,
2-Chloro-4-((1R,2R)-1-(5-(4-cyanophenyl)-1,3,4-oxadiazol-2-yl)-2-hydroxypropylamino)-3-ethylbenzonitrile,
2-Chloro-4-((1R,2S)-1-(5-(3,4-dichlorophenyl)-1,3,4-oxadiazol-2-yl)-2-hydroxypropylamino)-3-methylbenzonitrile,
4-((1R,2S)-1-(5-(4-Bromophenyl)-1,3,4-oxadiazol-2-yl)-2-hydroxypropylamino)-2-chloro-3-methylbenzonitrile,
2-Chloro-4-((1R,2S)-2-hydroxy-1-(5-(4-iodophenyl)-1,3,4-oxadiazol-2-yl)propylamino)-3-methylbenzonitrile,
(R)-2-Chloro-4-(1-(5-(4-cyanophenyl)-1,3,4-oxadiazol-2-yl)-2-hydroxyethylamino)-3-methylbenzonitrile,
4-((1R,2R)-2-Hydroxy-1-(5-(4-(methylsulfonyl)phenyl)-1,3,4-oxadiazol-2-yl)propylamino)-2-(trifluoromethyl)benzonitrile;
4-((1R,2S)-1-(5-(4-Cyanophenyl)-1,3,4-oxadiazol-2-yl)-2-hydroxypropylamino)benzo[b]thiophene-7-carbonitrile,
4-((1R,2R)-1-(5-(4-Cyanophenyl)-1,3,4-oxadiazol-2-yl)-2-hydroxypropylamino)benzo[b]thiophene-7-carbonitrile,
4-((1R,2S)-1-(5-(4-Fluorophenyl)-1,3,4-oxadiazol-2-yl)-2-hydroxypropylamino)benzo[b]thiophene-7-carbonitrile,
4-((1R,2S)-2-Hydroxy-1-(5-phenyl-1,3,4-oxadiazol-2-yl)propylamino)benzo[b]thiophene-7-carbonitrile,
4-((1R,2R)-1-(5-(4-Fluorophenyl)-1,3,4-oxadiazol-2-yl)-2-hydroxypropylamino)benzo[b]thiophene-7-carbonitrile,
4-((1R,2R)-2-Hydroxy-1-(5-phenyl-1,3,4-oxadiazol-2-yl)propylamino)benzo[b]thiophene-7-carbonitrile,
5-(5-((1R,2R)-2-(Butyryloxy)-1-(3-chloro-4-cyano-2-methylphenylamino)propyl)-1,3,4-oxa-diazol-2-yl)-2-fluorophenyl butyrate,
4-(5-((1R,2S)-2-(Butyryloxy)-1-(3-chloro-4-cyano-2-methylphenylamino)propyl)-1,3,4-oxa-diazol-2-yl)-2-chlorophenyl butyrate,
2-Chloro-4-((1R,2S)-2-hydroxy-1-(5-(4-(trifluoromethyl)phenyl)-1,3,4-oxadiazol-2-yl)propylamino)-3-methylbenzonitrile,
N-(4-(5-((1R,2R)-1-(3-Chloro-4-cyano-2-methylphenylamino)-2-hydroxypropyl)-1,3,4-oxadiazol-2-yl)phenyl)benzamide,
N-(4-(5-((1R,2R)-1-(3-Chloro-4-cyano-2-methylphenylamino)-2-hydroxypropyl)-1,3,4-oxadiazol-2-yl)phenyl)acetamide, N-(4-(5-((1R,2R)-1-(3-Chloro-4-cyano-2-methylphenylamino)-2-hydroxypropyl)-1,3,4-oxadiazol-2-yl)phenyl) butyramide,
Sodium 4-(5-((1R,2S)-1-(3-chloro-4-cyano-2-methylphenylamino)-2-hydroxypropyl)-1,3,4-oxadiazol-2-yl)phenyl sulfate,
4-(5-((1R,2S)-2-Acetoxy-1-(3-chloro-4-cyano-2-methylphenylamino)propyl)-1,3,4-oxadiazol-2-yl)phenyl acetate,
4-(5-((1R,2S)-2-(Butyryloxy)-1-(3-chloro-4-cyano-2-methylphenylamino)propyl)-1,3,4-oxadiazol-2-yl)phenyl butyrate,
4-(5-((1R,2S)-2-(Benzoyloxy)-1-(3-chloro-4-cyano-2-methylphenylamino)propyl)-1,3,4-oxadiazol-2-yl)phenyl benzoate,
(1R,2S)-1-(3-Chloro-4-cyano-2-methylphenylamino)-1-(5-phenyl-1,3,4-oxadiazol-2-yl)propan-2-yl acetate,
N-(4-(5-((1R,2S)-1-(3-Chloro-4-cyano-2-methylphenylamino)-2-hydroxypropyl)-1,3,4-oxadiazol-2-yl)phenyl) benzamide,
N-(4-(5-((1R,2S)-1-(3-Chloro-4-cyano-2-methylphenylamino)-2-hydroxypropyl)-1,3,4-oxadiazol-2-yl)phenyl) acetamide,
(R)-2-Chloro-4-(1-(5-(4-cyanophenyl)-1,3,4-oxadiazol-2-yl)-3-hydroxypropylamino)-3-methylbenzonitrile,
2-Chloro-4-((1R,2S)-1-(5-(4-cyanophenyl)-1,3,4-oxadiazol-2-yl)-2-hydroxypropylamino)-3-vinylbenzonitrile,
2-Chloro-4-((1R,2S)-1-(5-(3-fluorophenyl)-1,3,4-oxadiazol-2-yl)-2-hydroxypropylamino)-3-methylbenzonitrile,
(1R,2S)-1-(3-Chloro-4-cyano-2-methylphenylamino)-1-(5-phenyl-1,3,4-oxadiazol-2-yl)propan-2-yl butyrate, and
(1R,2S)-1-(3-Chloro-4-cyano-2-methylphenylamino)-1-(5-phenyl-1,3,4-oxadiazol-2-yl)propan-2-yl benzoate,
or a pharmaceutically acceptable salt of any of the foregoing.

The invention also relates to pharmaceutical compositions comprising a compound of formula I, Ia, Ib, Ic, Id, Ie or If, or any of the structural embodiments described herein and at least one pharmaceutically acceptable excipient.

The invention also provides a method of modulating an androgen receptor in a cell, comprising the administration of a compound to said cell wherein said compound has structural formula I, Ia, Ib, Ic, Id, Ie or If, or any of the structural embodiments described herein, or a pharmaceutically acceptable salt thereof.

This invention provides a method of identifying a compound capable of modulating an androgen receptor comprising contacting a cell expressing an androgen receptor with a compound according to formula I, Ia, Ib, Ic, Id, Ie or If, and monitoring the effect of the compound on the cell.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient androgen levels in a mammal in need thereof, wherein said method comprises the administration to said mammal of an effective amount of a compound of formula I, Ia, Ib, Ic, Id, Ie or If, or any one of the structural embodiments described herein or a pharmaceutically acceptable salt thereof, or a pharmaceutical composition comprising a compound of formula I, Ia, Ib, Ic, Id, Ie or If, or one of the structural embodiments described herein, or a pharmaceutically acceptable salt thereof and a pharmaceutically acceptable excipient. In a particular embodiment, the mammal is a human.

In some embodiments, this invention provides a method of treating (e.g., preventing, or ameliorating the symptoms associated with, or reducing the incidence of, reducing the pathogenesis of, facilitating the recovery from or delaying the onset of) sarcopenia, frailty, multiple sclerosis, osteoporosis, anemia, cognitive impairment, cachexia, muscular dystrophy, weak appetite, low body weight, anorexia nervosa, acne, seborrhea, polycystic ovarian syndrome, hair loss, AIDs wasting, chronic fatigue syndrome, short stature, low testosterone levels, diminished libido, benign prostate hypertrophy, infertility, erectile dysfunction, vaginal dryness, premenstrual syndrome, postmenopausal symptoms, female hormone replacement therapy, male hormone replacement therapy, depression, Type II diabetes, mood disorders, sleep disorders, memory disorders, neurodegenerative disorders, Alzheimer's dementia, attention deficit disorder, senile dementia, coronary artery disease, hirsutism, pain, myalgia, myocardial infarction, stroke, clotting disorders, thromboembolisms, congestive heart disorder, low insulin sensitivity, low glucose utilization, high blood sugar, organ transplant, metabolic syndrome, diabetes, glucose intolerance, hyperinsulinemia, insulin resistance, tooth injury, tooth disease, periodontal disease, liver disease, thrombocytopenia, fatty liver conditions, endometriosis, hot flushes, hot flashes, vasomotor disturbance, stress disorders, dwarfism, dyslipidemia, cardiovascular disease, coronary artery disease, renal disease, thin skin disorders, lethargy, osteopenia, dialysis, irritable bowel syndrome, Crohn's disease, Paget's disease, osteoarthritis, connective tissue disease or disorders, injury, burns, trauma, wounds, bone fracture, atherosclerosis, cachexia, cancer cachexia, and obesity, in a mammal in need thereof comprising the administration to said mammal of an effective amount of a compound according to a structure of formula I, Ia, Ib, Ic, Id, Ie or If, or one of the structural embodiments described herein, or a pharmaceutically acceptable salt thereof, or a pharmaceutical composition comprising a compound of structural formula I, Ia, Ib, Ic, Id, Ie or If, or one of the structural embodiments described herein including pharmaceutically acceptable salts thereof and a pharmaceutically acceptable excipient. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound according to a structure of formula I, Ia, Ib, Ic, Id, Ie or If, or one of the structural embodiments described herein, or a pharmaceutically acceptable salt thereof, or a pharmaceutical composition comprising a compound of structural formula I, Ia, Ib, Ic, Id, Ie or If, or one of the structural embodiments described herein including pharmaceutically acceptable salts thereof and a pharmaceutically acceptable excipient. In a particular embodiment, the mammal is a human.

In some embodiments, this invention describes a process for the preparation of a compound of formula IV, comprising:
a) reacting a compound of formula II with a compound of formula III to produce a compound of formula IV:

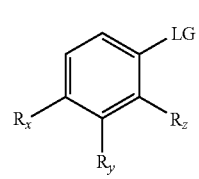

II

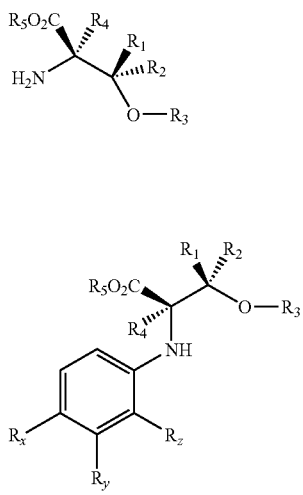

III

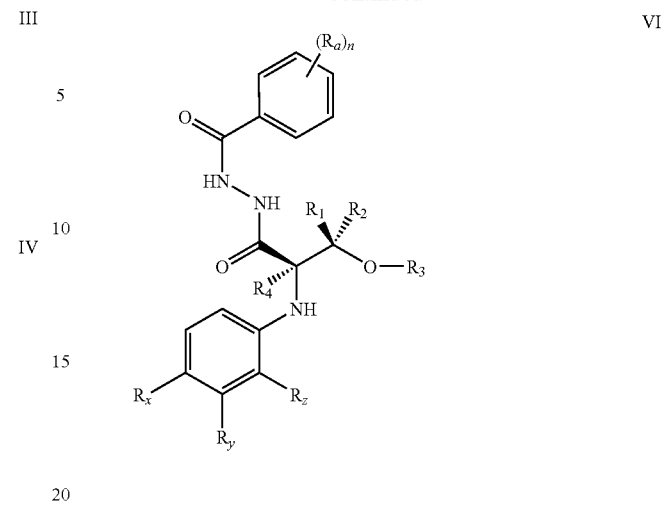

VI

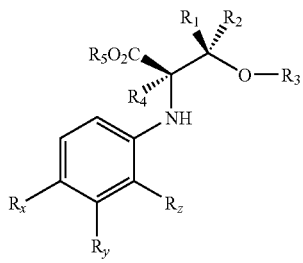

IV wherein: $R_x$, $R_y$, $R_z$, $R_1$, $R_2$, and $R_4$ are each independently as defined for formula Ia; LG is a leaving group;

$R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$-phenyl, O—$C_{1-6}$ alkyl and $OCF_3$), $C_{1-6}$ acyl, benzoyl, or $SiR_aR_bR_c$ (wherein $R_a$, $R_b$ and $R_c$ are each independently $C_{1-6}$ alkyl or phenyl); and $R_5$ is hydrogen, $C_{1-6}$ alkyl or benzyl;

or salts thereof.

In some embodiments, the reaction of II and III is done in the presence of a base.

In certain embodiments, LG is a leaving group selected from F, Cl, $N_2^+$, $OSO_2CF_3$ and $OSO_2Ph$ (wherein said Ph is optionally substituted with from 1 to 3 substituents selected from $C_{1-4}$ alkyl or halogen). In some embodiments, LG is F.

In some embodiments, this invention describes a process for preparing a compound of formula VI, said process comprising a) reacting a compound of formula IV with a compound of formula V to produce a compound of formula VI wherein:

$R_x$, $R_y$, $R_z$, $(R_a)$, n, $R_1$, $R_2$, and $R_4$ are each independently as defined for formula Ia, Ib, Ic, or Id, $R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl and $OCF_3$), $C_{1-6}$ acyl, benzoyl, or $SiR_aR_bR_c$ (wherein $R_a$, $R_b$ and $R_c$ are each independently $C_{1-6}$alkyl or phenyl);

$R_5$ is hydrogen, $C_{1-6}$ alkyl or benzyl;

or salts thereof.

In certain embodiments, $R_5$ is hydrogen and said reacting occurs in the presence of a coupling reagent.

In some embodiments, this invention describes a process for the preparation of a compound of formula VI, said process comprising:

a) reacting a compound of formula VII with a compound of formula VIII to produce a compound of formula VI

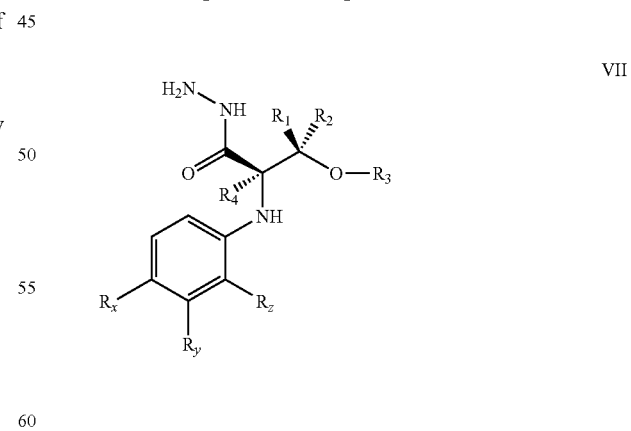

VII

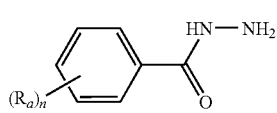

V

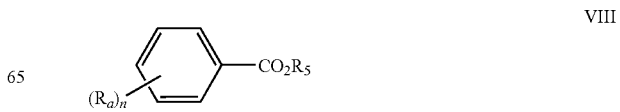

VIII

-continued

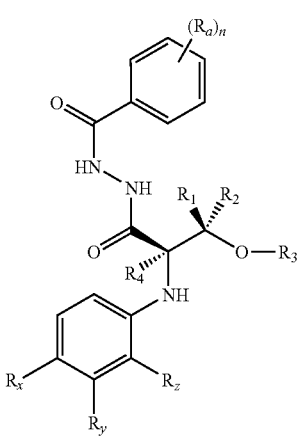

wherein:
$R_x$, $R_y$, $R_z$, $(R_a)$, n, $R_1$, $R_2$, and $R_4$ are each independently as for formula Ia, Ib, Ic, Id, Ie or If;
$R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl and OCF$_3$), $C_{1-6}$ acyl, benzoyl, or SiR$_a$R$_b$R$_c$ (wherein R$_a$, R$_b$ and R$_c$ are each independently $C_{1-6}$ alkyl or phenyl);
$R_5$ is hydrogen, $C_{1-6}$ alkyl or benzyl;
or salts thereof.

In certain embodiments, $R_5$ is hydrogen and said reacting is a coupling reaction.

In some embodiments, this invention describes the preparation of a compound of formula IX comprising the dehydration of a compound of formula VI

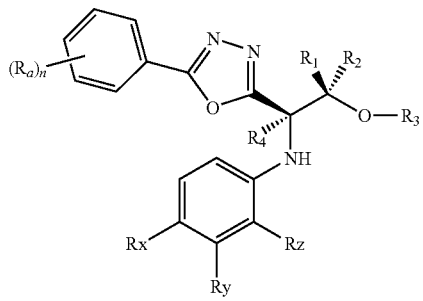

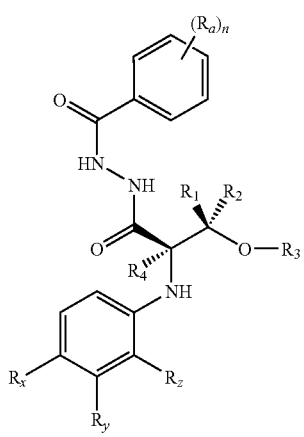

wherein:
$R_x$, $R_y$, $R_z$, $(R_a)$, n, $R_1$, $R_2$, and $R_4$ are each independently as defined for formula Ia, Ib, Ic, Id, Ie or If;
$R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl, OCF$_3$), $C_{1-6}$ acyl, benzoyl, or SiR$_a$R$_b$R$_c$ (wherein R$_a$, R$_b$ and R$_c$ are each independently $C_{1-6}$ alkyl or phenyl);
or salts thereof.

In certain embodiments, the dehydration reaction of compound VI to compound IX is conducted in the presence of a reagent comprising one or more of triphenylphosphine, polymer supported triphenylphosphine, $Cl_2$, $Br_2$, $I_2$, $CCl_3CN$; $ClCH_2CH_2Cl$, $BrCH_2CH_2Br$, $CCl_4$, $CBr_4$, $CI_4$, $Cl(CO)(CO)Cl$, $POCl_3$, $PCl_5$, $SOCl_2$, $H_2SO_4$, HCl, $H_3PO_4$, $O(SO_2CF_3)_2$, TMS-polyphosphate, MeOC(=O)N$^-$SO$_2$N$^+$Et$_3$ (Burgess reagent), diazophosphorene, toluenesulfonyl chloride, $CH_3SO_2Cl$, $CF_3SO_2Cl$, $P_2O_5$, Me$_2^+$N=CH—OPCl$_2$, Lawesson's reagent, 2-tert-Butylimino-2-diethylamino-1,3-dimethylperhydro-1,3,2-diazaphosphorine, polystyrene-supported 2-tert-Butylimino-2-diethylamino-1,3-dimethylperhydro-1,3,2-diazaphosphorine, and $(Me_3Si)_2NH$.

In certain embodiments, this invention describes a process for the preparation of a compound having the formula IX

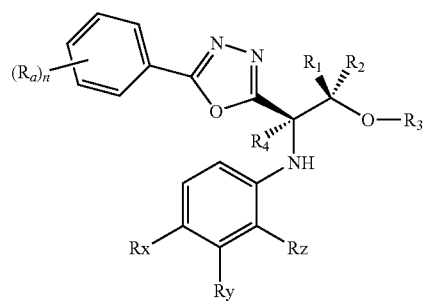

comprising,
a) reacting a compound of formula II with a compound of formula III to produce a compound of formula IV:

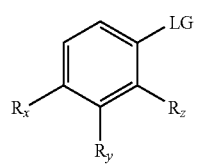

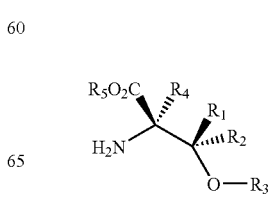

-continued

IV

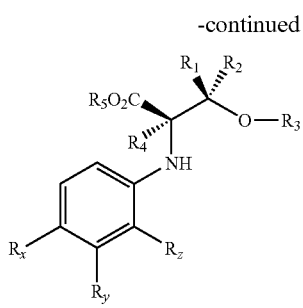

wherein:
$R_x$, $R_y$, $R_z$, $R_1$, $R_2$, and $R_4$ are each independently as defined for formula Ia, Ib, Ic, or Id; LG is a leaving group;
$R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl and $OCF_3$), $C_{1-6}$ acyl, benzoyl, or $SiR_aR_bR_c$ (wherein $R_a$, $R_b$ and $R_c$ are each independently $C_{1-6}$ alkyl or phenyl); and
$R_5$ is hydrogen, $C_{1-6}$ alkyl or benzyl;
or salts thereof; and
b) reacting a compound of formula IV with a compound of formula V to form a compound of formula VI

IV

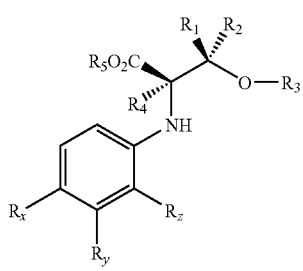

V

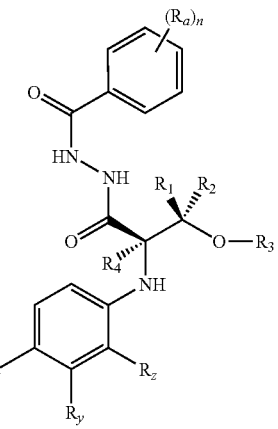

VI wherein:
$R_x$, $R_y$, $R_z$, $(R_a)$, n, $R_1$, $R_2$, and $R_4$ are each independently as defined for formula Ia, Ib, Ic, Id, Ie or If;
$R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl and $OCF_3$), $C_{1-6}$ acyl, benzoyl, or $SiR_aR_bR_c$ (wherein $R_a$, $R_b$ and $R_c$ are each independently $C_{1-6}$ alkyl or phenyl);
$R_5$ is hydrogen, $C_{1-6}$ alkyl or benzyl;
or salts thereof; and
c) dehydrating a compound of formula VI to form the compound of formula IX

IX

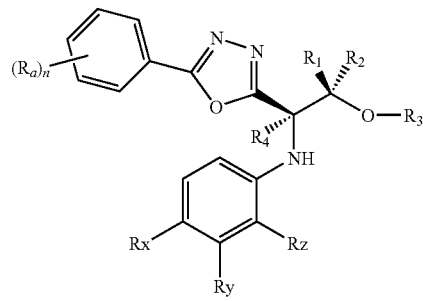

VI

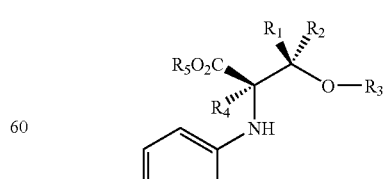

wherein:
$R_x$, $R_y$, $R_z$, $(R_a)$, n, $R_1$, $R_2$, and $R_4$ are each independently as defined for formula Ia, Ib, Ic, Id, Ie or If;
$R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl and $OCF_3$), $C_{1-6}$ acyl, benzoyl, or $SiR_aR_bR_c$ (wherein $R_a$, $R_b$ and $R_c$ are each independently $C_{1-6}$ alkyl or phenyl); or salts thereof.

In certain embodiments, this invention describes compounds useful for the production of an androgen receptor modulator, said compound having the formula IV

IV

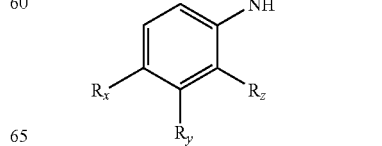

wherein:

$R_x$, $R_y$, $R_z$, $R_1$, $R_2$, and $R_4$ are as defined for formula Ia, Ib, Ic, Id, Ie or If;

$R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl and $OCF_3$), $C_{1-6}$ acyl, benzoyl, or $SiR_aR_bR_c$ (wherein $R_a$, $R_b$ and $R_c$ are each independently $C_{1-6}$ alkyl or phenyl);

$R_5$ is hydrogen, $C_{1-6}$ alkyl or benzyl;

or salts thereof.

In some embodiments, this invention describes compounds useful for the production of an androgen receptor modulator, said compound having the formula VI

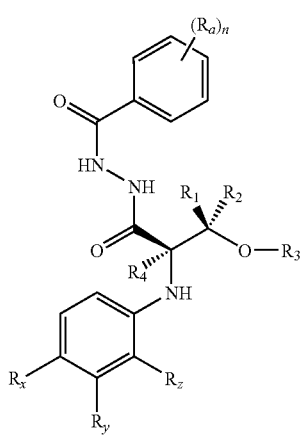

VI wherein:

$R_x$, $R_y$, $R_z$, $(R_a)$, n, $R_1$, $R_2$, and $R_4$ are as defined for formula Ia, Ib, Ic, Id, Ie or If; $R_3$ is hydrogen, $C_{1-3}$ alkyl, $C_{1-3}$ haloalkyl, $C_{2-3}$ hydroxylalkyl, benzyl (wherein the phenyl group of said benzyl is optionally substituted with from 1-3 substituents selected from halogen, $C_{1-3}$ alkyl, $S(O)_{0-2}C_{1-3}$ alkyl, $S(O)O_{0-2}$phenyl, O—$C_{1-6}$ alkyl and $OCF_3$), $C_{1-6}$ acyl, benzoyl, or $SiR_aR_bR_c$ (wherein $R_a$, $R_b$ and $R_c$ are each independently $C_{1-6}$ alkyl or phenyl);

or salts thereof.

In certain embodiments of this invention, the compounds of formula VI are useful as androgen receptor modulators and therefore useful in the methods of this invention.

The term "alkenyl" as used herein refers to a hydrocarbon backbone radical, having the number of carbon atoms falling within the specified range. For example, $C_{2-3}$ alkenyl means that a hydrocarbon radical is attached that may contain anywhere from 2 to 3 carbon atoms with the remaining valence filled in by hydrogen atoms unless specified otherwise. The term also includes each permutation as though it were separately listed. Thus, $C_{2-3}$ alkenyl includes ethenyl, 1-propenyl and 2-propenyl.

The term "alkyl" as used herein refers to both straight and branch chain hydrocarbon radicals, having the number of carbon atoms falling within the specified range. For example, $C_{1-4}$ alkyl means that a hydrocarbon radical is attached that may contain anywhere from 1 to 4 carbon atoms with the remaining valence filled in by hydrogen atoms. The definition also includes separately each permutation as though it were separately listed. Thus, $C_{1-2}$alkyl includes methyl and ethyl. The term $C_{1-3}$ alkyl includes methyl, ethyl, propyl and 2-propyl. The term $C_{1-4}$ alkyl includes methyl, ethyl, n-propyl, 2-propyl, n-butyl, 2-butyl, iso-butyl and tert-butyl. The term $C_{1-5}$ alkyl includes methyl, ethyl, 2-propyl, n-butyl, 2-methylbutyl, tert-butyl, n-pentyl, pentan-2-yl, pentan-3-yl, and tert-pentyl, iso-pentyl.

The term "halogen" as used herein refers to a fluorine, chlorine, bromine or iodine radical.

The term "haloalkyl" refers to an alkyl radical wherein said alkyl radical is the same as defined for the term "alkyl" except that the alkyl radical additionally has from 1 to 5 halogen atoms attached to the alkyl chain. For example, $C_1$ haloalkyl includes —$CH_2F$, —$CHF_2$, —$CF_3$ and the like, $C_2$ haloalkyl includes —$CH_2F$, $CHF_2$, $CF_3$, —$CH_2CH_2F$, —$CH_2CHF_2$, —$CH_2CF_3$, —$CF_2CHF_2$, —$CF_2CF_3$ and the like. $C_{1-3}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CF_3$, and the like. $C_{1-4}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CF_3$, —$CH_2CH_2CH_2CF_3$, $CHClCF_2CH_2CH_3$, $CF_2CH_2CH_2CHF_2$, $CH_2CH_2CH_2CH_2F$, $CH_2CH_2CH_2CH_2Cl$, and the like.

The term "hydroxyalkyl" refers to an alkyl radical wherein said alkyl radical is the same as defined for the term "alkyl" except that the alkyl radical additionally has from 1 or 2 hydroxyl groups attached to the alkyl chain. For example, $C_{2-4}$hydroxyalkyl includes 2-hydroxyethyl, 2-hydroxypropyl, 2,4-dihydroxybutyl and the like.

The term "5-member heteroaryl" refers to a heteroaryl ring system radical wherein said heteroaryl contains at least one heteroatom selected from the groups consisting of N, O and S and up to 3 additional heteroatoms selected from the group consisting of N, O and S. If not otherwise defined, the 5-member rings system is optionally substituted with 1-2 substituents selected from halogen, $C_{1-2}$ alkyl, $C_{1-2}$ haloalkyl, or CN. The points of attachment of the optional substituent(s) as well as the rest of the molecule maybe selected from any position wherein there is an open valence. Some examples of 5-member heteroaryls include:

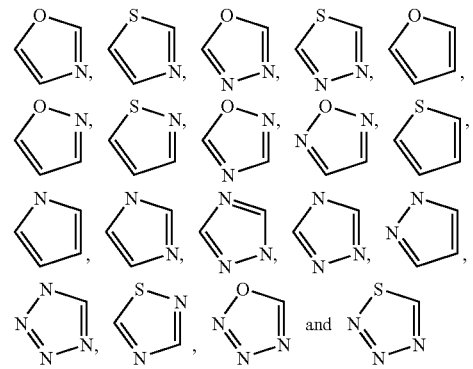

The term "6-member heteroaryl" refers to a heteroaryl ring system radical wherein said heteroaryl contains at least one heteroatom selected from N and up to two additional Ns. If not otherwise specified, the 6-member heteroaryl ring is optionally substituted with 1-2 substituents selected from halogen, $C_{1-2}$ alkyl, $C_{1-2}$ haloalkyl, or CN. The points of attachment of the optional substituent(s) as well as the rest of the molecule maybe selected from any position wherein there is an open valence. Some examples of 6-membered heteroaryls include:

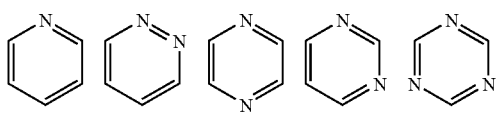

The term "bicyclic heteroaryl" as used herein refers to a bicyclic fused-ring system wherein at least one of the two rings is substituted with at least one heteroatom selected from N, O and S. The bicyclic heteroaryl ring system contains from 8 to 12 backbone atoms and may contain a total of up to 4 heteroatoms in the backbone. The bicyclic heteroaryl ring systems of this invention require that at least one of the two rings is aromatic but the two rings together may be aromatic as well (e.g. quinoline). Some non-limiting examples of bicyclic heteroaryl ring systems are provided below:

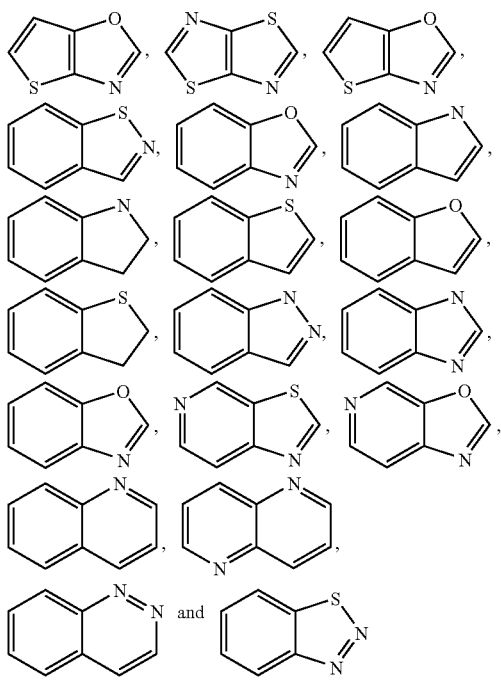

The compounds of this invention may be present as solids and when so present, may be in an amorphous form or they may be crystalline. When the compounds of this invention are in the crystalline form, they might be present as a single polymorph or a mixture of polymorphs or even as a mixture of amorphous material together with one or more distinct polymorphs—the invention is not limited according to any particular solid or liquid state form.

The compounds of this invention contain at least one stereocenter and therefore, exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. Thus, "R" and "S" denote the relative configurations of substituents around one or more chiral carbon atoms When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

The compounds of the invention may be prepared as individual isomers by incorporating or starting with a specific isomer, isomer-specific synthesis or resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Where compounds of this invention include one or more basic sites such as amines, acid addition salts can be made and this invention includes such acid addition salts. Some representative (non-limiting) acid addition salts include hydrochloride, hydrobromide, hydroiodide, acetate, benzenesulfonate, mesylate, besylate, benzoate, tosylate, citrate, tartrate, sulfate, bisulfate, lactate, maleate, mandelate, valerate, laurate, caprylate, propionate, succinate, phosphate, salicylate, napsylate, nitrate, tannate, resorcinate and the like, including multiprotic salts as well as mixtures of the acid addition salts. In cases where an amine is present, this invention also embraces quaternized ammonium salts of those amines. It should be appreciated that N-oxides of amines are also embraced within the definition of the compounds of this invention. Likewise, where compounds of this invention include one or more acid sites such as carboxylic acids, phenols and the like, basic addition salts can be made and this invention includes such basic addition salts. For example, some representative (non-limiting) acidic compounds of this invention may be present as their lithium, sodium, potassium, ammonium, trialkyammonium, calcium, magnesium, barium and the like.

The compounds of this invention can also be present as solvates and such solvates are embraced within the scope of this invention even where not explicitly described. Such solvates are preferably hydrates but can be solvates comprised of other solvents, preferably where those solvents are considered to be non-toxic or at least acceptable for administration to mammals, preferably humans. The solvates can be stoichiometric or non-stoichiometric, singular or in combination. Some exemplary solvates include water, ethanol, acetic acid and the like.

The therapeutic utility of these compounds includes "treating" a mammal, preferably a human where treating is understood to include treating, preventing, or ameliorating the symptoms associated with, or reducing the incidence of, reducing the pathogenesis of, facilitating the recovery from or delaying the onset of the syndrome, illness, malady or condition being considered. The compounds of this invention can also be useful in states or conditions where no clear deficit, illness or malady per se is perceived but rather, where a preferred condition, sensation, performance, capability or state is obtainable through therapeutic intervention with a compound of this invention.

The compounds of this invention, when used as therapeutics can be administered by any method known to one of skill in the art such as orally, bucally, intravenously, subcutaneously, intramuscularly, transdermally, intradermally, intravascularly, intranasally, sublingually, intracranially, rectally, intratumorally, intravaginally, intraperitonealy, pulmonary, ocularly and intratumorally.

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

When administered, the compounds and compositions of this invention maybe given once daily or with multiple daily doses such as twice per day, three times per day and four times per day.

In one embodiment of this invention, the compound is administered orally where it can be formulated for solid dosage administration or liquid dosage administration. Solid dosage administration can be in the form of a tablet, granule, capsule, pill, pellet, powder and the like. Liquid dosage formulations include syrups, solutions, gels, suspensions, elixirs, emulsions, colloids, oils, and the like.

As mentioned previously, the compounds of this invention may be solids and when present as solids, they maybe of defined particle size. Where the compound of this invention is not particularly water soluble, it is sometimes preferable to administer the compound with a certain particle size—a particle size with a preferred range where the average mean particle size diameter is under 100 microns, or 75 microns, or 50 microns, or 35 microns, or 10 microns or 5 microns.

Solid dosage formulations will comprise at least one compound of this invention together with one or more pharmaceutical excipients. Those excipients are known to one of skill in the art and include, by way of non-limiting example diluents (monosaccharides, disaccharides and polyhydric alcohols including starch, mannitol, dextrose, sucrose, microcrystalline cellulose, maltodextrin, sorbitol, xylitol, fructose and the like), binders (starch, gelatin, natural sugars, gums, waxes and the like), disintegrants (alginic acid, carboxymethylcellulose (calcium or sodium), cellulose, crocarmellose, crospovidone, microcrystalline cellulose, sodium starch glycolate, agar and the like), acidic or basic buffering agents (citrates, phoshphates, gluconates, acetates, carbonates, bicarbonates and the like), chelating agents (edetic acid, edetate calcium, edetate disodium and the like), preservatives (benzoic acid, chlorhexidine gluconate, potassium benzoate, potassium sorbate, sorbic acid, sodium benzoate and the like), glidants and lubricants (calcium stearate, oils, magnesium stearate, magnesium trisilicate, sodium fumarate, colloidal silica, zinc stearate, sodium oleate, stearic acid, and the like), antioxidants and/or preservatives (tocopherols, ascorabtes, phenols, and the like) and acidifying agents (citric acid, fumaric acid, malic acid, tartaric acid and the like) as well as coloring agents, coating agents, flavoring agents, suspending agents, dessicants, humectants and other excipients known to those of skill in the art.

The solid dosage formulations of this invention can be prepared in different forms including most commonly, tablets and capsules. The tablets can be formulated by a wide variety of methods known to one of skill in the art including, for example, preparing a dry powder mixture of the drug substance in combination with one or more of the excipients granulating the mixture and pressing to together into a tablet and optionally coating the tablet with an enteric or non-enteric coating. The final coat typically includes a light protective pigment such as titanium oxide and a shellac or wax to keep the tablet dry and stable. While not intending to be limited by theory or example, in some instances it might be preferred to prepare the tablets by wet granulating the drug with one or more of the excipients and then extruding the granulated material.

The solid dosage forms of this invention also include capsules wherein the drug is enclosed inside the capsule either as a powder together with optional excipients or as granules containing usually including one or more excipients together with the drug and wherein the granule in turn can be optionally coated, for example, enterically or non-enterically.

In certain embodiments of this invention, the solid dosage formulations of this invention are formulated in a sustained release formulation. Such formulations are known to those of skill in the art and generally rely on the co-formulation of the drug with one or more matrix forming substances that slow the release of the androgen receptor modulator thus extending the compound's lifetime in the digestive track and thereby extend the compounds half-life. Some non-limiting matrix forming substances include hydroxypropyl methylcellulose, carbopol, sodium carboxymethylcellulose and the like.

In some embodiments of this invention, the compounds are formulated for delivery other than via a solid oral dosage form. For example, in certain instances it might be preferable to deliver a compound of this invention by a pulmonary route. A pulmonary route of administration typically means that the compound of this invention is inhaled into the lung where it is absorbed into the circulation. Such a route of administration has the advantage of avoiding a first pass liver effect thereby possibly increasing bioavailability as well as decreasing or eliminating undesirable androgen agonist effects on the liver such as increasing liver enzymes and/or decreasing HDL. Formulating a compound of the invention for pulmonary delivery can be accomplished by micronizing the compound of the invention to a very fine size particle, typically with a mean average diameter of less than 20 microns, or less than 10 microns or between 2 and 5 microns. The powder may then be inhaled by itself or more likely mixed with one or more excipients such as lactose or maltose. The powder can then be inhaled in a dry powder inhaling device either once or multiple times per day depending on the particular compound and the patients need. Other types of pulmonary dosage forms are also embraced by this invention. In an alternative to the dry powder delivery, the compound of this invention may be suspended in an aerosolizing medium and inhaled as a suspension through a meter dosed inhaler or a nebulizer.

The compounds of this invention can be formulated for transdermal delivery. Effective advantage of these compounds can be taken through a wide variety of transdermal options. For example, the compounds of this invention maybe formulated for passive diffusion patches where they are preferably embedded in a matrix that allows for slow diffusion of the compound into the treated subject's circulation. For this purpose, the compound is preferably dissolved or suspended in solvents including by way of non-limiting examples one or more of ethanol, water, propylene glycol, and Klucel HF. In some instances, a polymer matrix (e.g. acrylate adhesive) will comprise the bulk of the transdermal formulation. In some instances, the transdermal formulations maybe designed to be compatible with alternate transdermal delivery technologies. For example, some transdermal technologies achieve greater and/or more consistent delivery by creating micropores in the skin using radio frequency, heat, ultrasound or electricity. In some cases, the compounds of this invention can be used with microneedle technology wherein the compound is loaded into very small needles which due not need to penetrate the dermis to be effective.

The compounds of this invention may be employed alone or in combination with other therapeutic agents. By way of non-limiting example, the compounds of this invention can be used in combination with anti-lipidemics (statins, fibrates, omega-3 oils, niacinates and the like), bone anti-resorptives (bisphosphonates, estrogens, selective estrogen receptor modulators (SERMs), calcitonin, and the like), bone anabolic agents (PTH and fragments e.g teriparatide, PTHRP and analogues e.g. BaO58), anti-diabetics (e.g. insulin sensitizers, glucose absorption and synthesis inhibitors (e.g. metformin)), anti-anxiety agents, antidepressants, anti-obesity agents, contraceptive agents, anti-cancer agents, PPARγ agonists (e.g. pioglitazone), and the like. When used in combination, the compounds of this invention may be co-formulated or co-administered wherein said co-administration does not require dosing at exactly the same time but rather indicates that the patient is undergoing treatment with one or more of the additional agents during the timeframe of treatment with the selective androgen modulators of this invention. Thus, the additional drug(s) for combination treatment can be administered concomitantly, sequentially or separately from the compounds of this invention.

The compounds of this invention may be administered according to different dosage scheduling and the dosage may be adjusted as deemed necessary by the subject or preferably by the subject in consultation with a qualified practitioner of medicine. Dosing of the compounds of this invention can take place by multiple routes and consequently, the dosing schedule and amounts are dependent not only on the particular subject's weight, sex, age, therapy contemplated, etc but also by the route of the drug chosen.

By way of non-limiting example, the compounds of this invention may be dosed by the oral route in a once daily, twice daily, three times daily or more than three times per day depending on the particular needs of that subject, the formulation of the drug, etc. The dosage will typically be from about 0.01 mg to 500 mg of drug per daily dosage, for example from about 0.1 mg to about 10 mg, such as from about 0.1 mg to about 3 mg, or from about 0.1 mg to about 250 mg of drug per daily dosage, or from about 1 mg to about 150 mg of drug per daily dosage, or from about 5 mg to about 100 mg of drug per daily dosage.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc. In one embodiment, a compound of this invention is dosed once every seven days.

The compounds of this invention can also be dosed on a monthly basis meaning that administration is done once per month. In addition, the compounds of this invention can be dosed on a weekly basis (once a week), every other week, every three weeks or every four weeks for a single day or multiple days.

The compounds of this invention can also be dosed on an as needed or "pro re nata" "prn" schedule, and "on demand". In this type of dosing, the compounds of this invention are administered in a therapeutically effective dose at some time prior to commencement of an activity wherein the therapeutic effect of the compounds of this invention is desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

The compounds of this invention can be prepared by a variety of synthetic routes and techniques known to those of skill in the art. The processes disclosed herein should not be construed as limiting the examples or scope of the invention in any way but rather are provided as just some of the representative ways that the compounds of this invention can be or were prepared.

In some cases, protective groups are employed in the synthesis of the compounds of this invention and it should be appreciated that there are a diverse array of protective groups and strategies that can be employed in organic synthesis (T. W. Green and P. G. M. Wuts (2006) Greene's Protective Groups in Organic Synthesis, herein incorporated by reference in its entirety) and that where a protective group is referred to generically, any appropriate protective group should be considered.

In some instances, leaving groups are employed in the synthesis of compounds of this invention. Where a specific leaving group is referred to, it should be appreciated that other leaving groups might also be used. Leaving groups typically include those groups that can stabilize an anion. In the case of nucleophilic aromatic substitutions, the leaving group may be an anion or a neutrally charged group. In some cases, the leaving group for nucleophilic aromatic substitution may be a group that is not typically considered to be a stabilized anion (e.g. fluoride or hydride). While not intending to be bound by theory or the examples, some typical nucleophilic leaving groups include halogens, sulfonates (O-mesylates, O-tosylates, etc), hydrides, quaternized amines, nitro, and the like. Additional discussion and examples can be found in leading textbooks on organic chemistry including, for example, March's Advanced Organic Chemistry: Reactions, Mechanisms, and Structure, $5^{th}$ Edition, which is herein incorporated in its entirety.

In scheme 1, a general method for preparing the compounds of this invention is set forth. Scheme 1 is useful for the synthesis of phenyl substituted 1,3,4-oxadiazoles. In scheme 1, the starting material used is a phenyl ring substituted with a leaving group where that leaving group is typically a halogen, preferably a fluorine but may also be additional leaving groups such as trialkylammonium salts and the like. The group displacing the leaving group is an amine compound of formula B. The amines can be prepared by different methods well-known by those of skill in the art and in many cases, the amines are commercially available hydroxyl-amino acids (e.g. D-threonine, D-serine, D-allo-threonine, etc). Normally, the reaction is done in the presence of a base to facilitate the displacement. Inorganic bases such as $K_2CO_3$, $Na_2CO_3$, NaH, etc can typically be used to good effect, or in some cases organic bases might be preferable ($Et_3N$, etc) depending on the solvent, reactants, etc. Normally, a solvent is chosen that can dissolve at least some of each of the components of the reaction. Polar solvents are generally preferred since they help facilitate the dissolution of one or more of the components as well as can accelerate nucleophilic substitution reactions. DMSO can be a very good solvent for these reactions but other solvents such as alcohols, DMF, HMPA, etc. should be considered as well. After the addition reaction, the product C is isolated and carried to the next step. Isolation techniques are well-known to those of skill in the art and include chromatography and/or crystallization. The product of the reaction C is then coupled to an acyl hydrazide of formula D. In cases where $R_5$ is not hydrogen, $R_5$ can be cleaved prior to the coupling reaction assuming standard coupling-type conditions are employed (EDCI, DCC, mixed anhydride, etc). In some instances, it might be preferable to react the acyl hydrazide 4 with the compound C even where $R_5$ is other than hydrogen (e.g. alkyl or benzyl) due to the nucleophilicity of the hydrazide. Also, in cases where $R_3$ is hydrogen, one can optionally protect the alcohol at this point prior to the hydrazide coupling if a free alcohol interferes substantially in the coupling. After the formation of the coupled product D, the bis-acyl hydrazide product can be dehydrated using a number of potential reagents well-known to those of skill in the art. Some possibly useful reagents include triphenylphosphine, polymer supported triphenylphosphine, $Cl_2$, $Br_2$, $I_2$, $CCl_3CN$; $ClCH_2CH_2Cl$, $BrCH_2CH_2Br$, $CCl_4$, $CBr_4$, $CI_4$, $Cl(CO)(CO)Cl$, $POCL_3$, $PCl_5$, $SOCl_2$, $H_2SO_4$, $HCl$, $H_3PO_4$, $O(SO_2CF_3)_2$, TMS-polyphosphate, $MeOC(=O)N^-SO_2N^+Et_3$ (Burgess reagent), diazophosphorene, toluenesulfonyl chloride, $CH_3SO_2Cl$, $CF_3SO_2Cl$, $P_2O_5$, $Me_2^+N=CH-OPCl_2$, Lawesson's reagent, 2-tert-Butylimino-2-diethylamino-1,3-dimethylperhydro-1,3,2-diazaphosphorine, polystyrene-supported 2-tert-Butylimino-2-diethylamino-1,3-dimethylperhydro-1,3,2-diazaphosphorine, and $(Me_3Si)_2NH$. If the alcohol is not protected at this point ($R_5$=hydrogen), it is often preferable to protect it prior to the dehydration. Some protection groups that have been found to be particularly useful include trialkyl silyl groups (e.g. TBDMS) but other groups such as esters, ethers, etc. could be useful as well. Protecting groups might also be considered at other positions of the molecule depending on the compound structure and likelihood of interference of that group during any point in the synthesis including in the cyclo-dehydration reaction. For example, where $R_a$ is a phenol, it might be advantageous to protect it as, for example, its corresponding tri-alkylsilyl ether. In such instances, it might be advantageous to simultaneously protect the phenol and alcohol at the same time, using the same protecting group, thus increasing synthetic efficiency.

After the dehydration to form the oxadiazole, additional manipulations can take place such as de-protecting, making a salt, or converting one of the variable groups to a different group falling under any of the Markush structure embodiments of the invention.

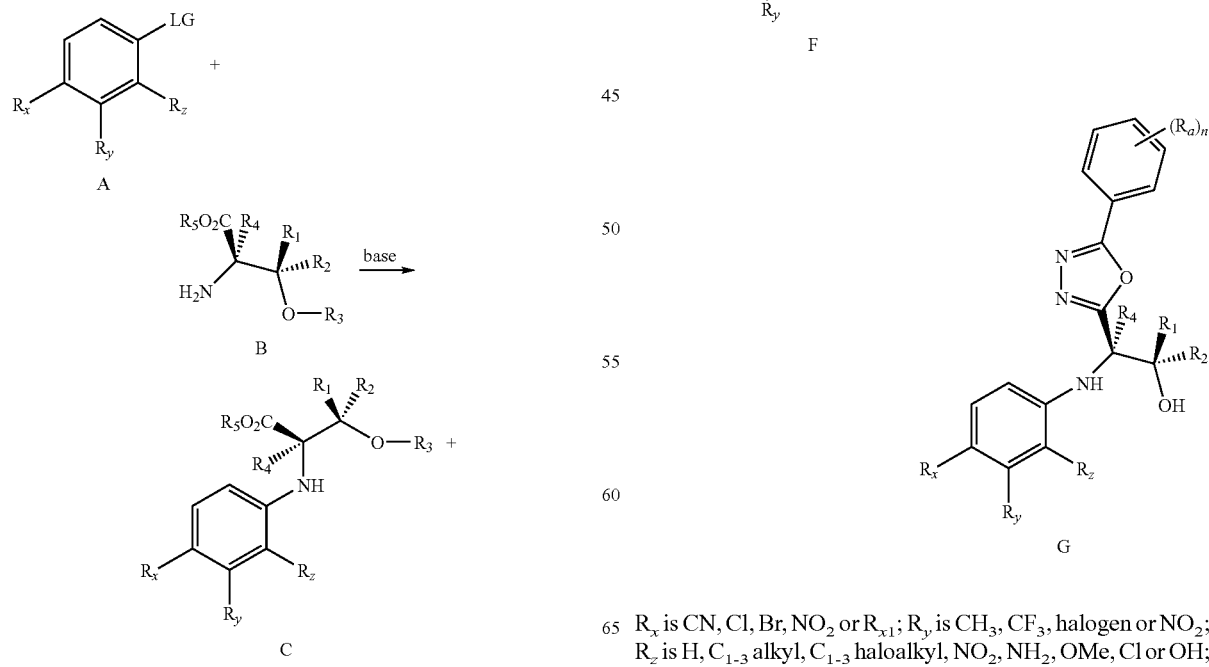

$R_x$ is CN, Cl, Br, $NO_2$ or $R_{x1}$; $R_y$ is $CH_3$, $CF_3$, halogen or $NO_2$; $R_z$ is H, $C_{1-3}$ alkyl, $C_{1-3}$ haloalkyl, $NO_2$, $NH_2$, OMe, Cl or OH; or $R_y$ and $R_z$ together form

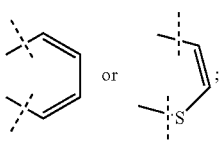 or ;

$R_{x1}$ is 5 member heteroaryl, said heteroaryl selected from

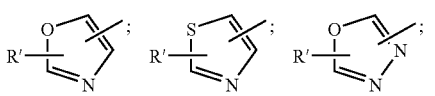

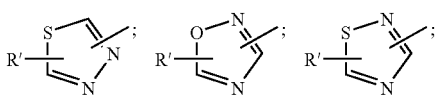

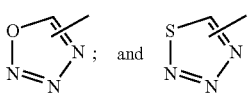 and ;

R' is hydrogen, $C_1$-$C_2$ alkyl, $CF_3$, or halogen; or $R_x$ and $R_y$ together with the phenyl group to which they are attached form a 5 member aromatic ring selected from:

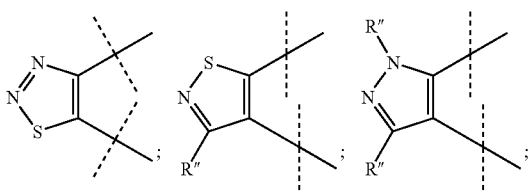

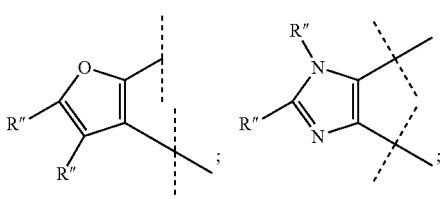

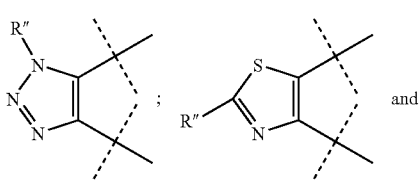 and ;

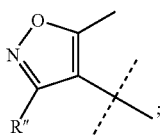 ;

wherein each R" is independently hydrogen, $CF_3$, or $C_1$-$C_2$ alkyl; $R_a$ is $C_{1-4}$alkyl (optionally substituted with from 1-2 CN, OH or 5 member heteroaryl), 5-member heteroaryl, CN, $C_{1-4}$ haloalkyl, halogen, OH, $OC_{1-3}$ alkyl, $OC_{1-3}$ haloalkyl, $OSO_2$-phenyl, (wherein said phenyl is optionally substituted with halogen, $C_{1-3}$ alkyl or $C_{1-3}$ haloalkyl), $S(O)_{0-2}$phenyl, and $S(O)_{0-2}C_{1-3}$ alkyl; n is 0, 1, 2, or 3; $R_1$ and $R_2$ are each independently selected from hydrogen, $C_{1-3}$ alkyl, or phenyl; $R_3$ is hydrogen, $C_{1-4}$ alkyl, $C_{1-4}$ haloalkyl, $C_{2-4}$ hydroxylalkyl, benzyl (wherein the phenyl group of said benzyl is optionally with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl, $OCF_3$), $C_{1-6}$ acyl; or benzoyl; $R_4$ is H, $C_{1-4}$ alkyl or $C_{1-4}$haloalkyl; $R_3$ is hydrogen, $C_{1-3}$ alkyl, $C_{1-3}$ haloalkyl, $C_{2-3}$ hydroxylalkyl, benzyl (wherein the phenyl group of said benzyl is optionally with from 1-3 substituents selected from halogen, $C_{1-3}$ alkyl, $S(O)_{0-2}C_{1-3}$ alkyl, $S(O)_{0-2}$phenyl, O—$C_{1-6}$ alkyl, $OCF_3$), $C_{1-6}$ acyl, benzoyl, or $SiR_aR_bR_c$ (wherein $R_a$, $R_b$ and $R_c$ are each independently $C_{1-6}$alkyl or phenyl); and $R_5$ is hydrogen, $C_{1-6}$ alkyl or benzyl.

Alternatively, compounds of formula G from scheme 1 might be prepared by the alternative route illustrated in scheme 1a. In the alternative route, the acyl hydrazide used in making the diacyl hydrazide precursor to the 1,3,4-oxadiazole is present on the core portion of the molecule rather than on the phenacyl portion. $R_5$ can be hydrogen, $C_{1-6}$ alkyl or benzyl. In the case where $R_5$ is hydrogen, the acyl hydrazide C' can be prepared by a coupling reaction between the carboxylic acid and hydrazine using standard coupling reaction conditions known to those of skill in the art. Where $R_5$ is $C_{1-6}$ alkyl or benzyl, the acyl hydrazide can be prepared by reacting the ester directly with hydrazine, heating the reaction and using base if necessary. The diacylhydrazide E can then be taken onto the final product G as demonstrated previously in scheme 1.

Scheme 1a

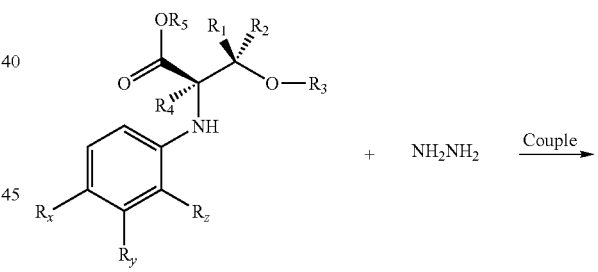

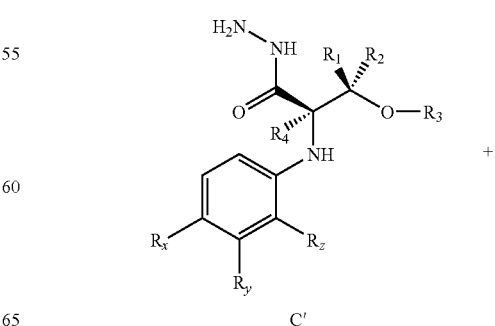

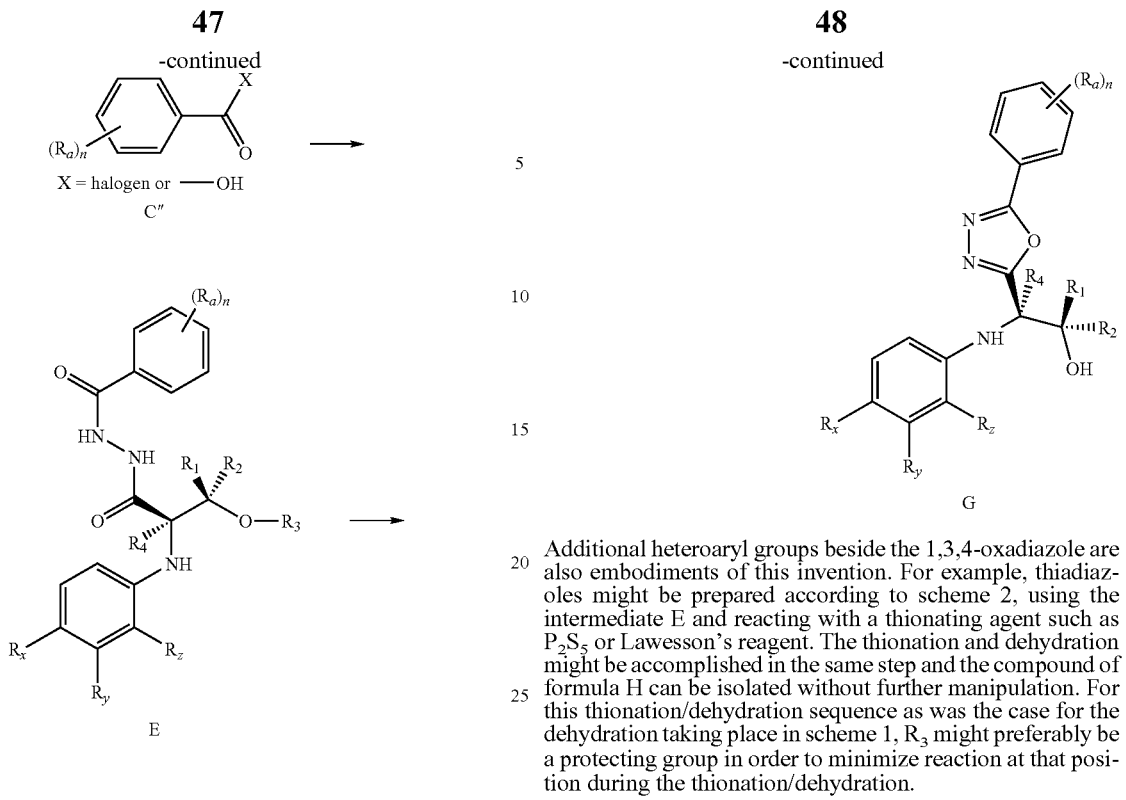

Additional heteroaryl groups beside the 1,3,4-oxadiazole are also embodiments of this invention. For example, thiadiazoles might be prepared according to scheme 2, using the intermediate E and reacting with a thionating agent such as $P_2S_5$ or Lawesson's reagent. The thionation and dehydration might be accomplished in the same step and the compound of formula H can be isolated without further manipulation. For this thionation/dehydration sequence as was the case for the dehydration taking place in scheme 1, $R_3$ might preferably be a protecting group in order to minimize reaction at that position during the thionation/dehydration.

Scheme 2

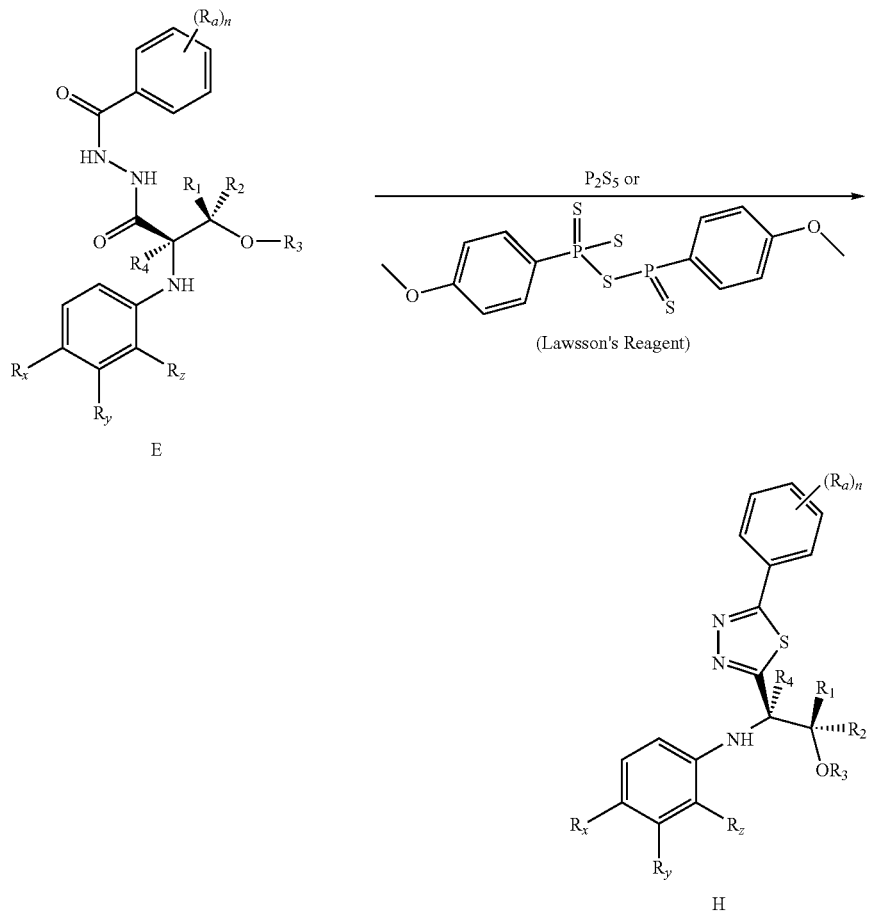

Additional oxadiazole isomers can also be prepared and are useful for the methods of this invention. For example, scheme 3 illustrates how a N'-hydroxybenzimidamide can be coupled to the carboxylic and then cyclized to yield the 1,2,4-oxadiazole derivative of structural formula J. The cyclization reaction can be performed under many mild conditions including, for example, HCl or heat and in some instances might occur during the coupling reaction between the hydrazide and the acid.

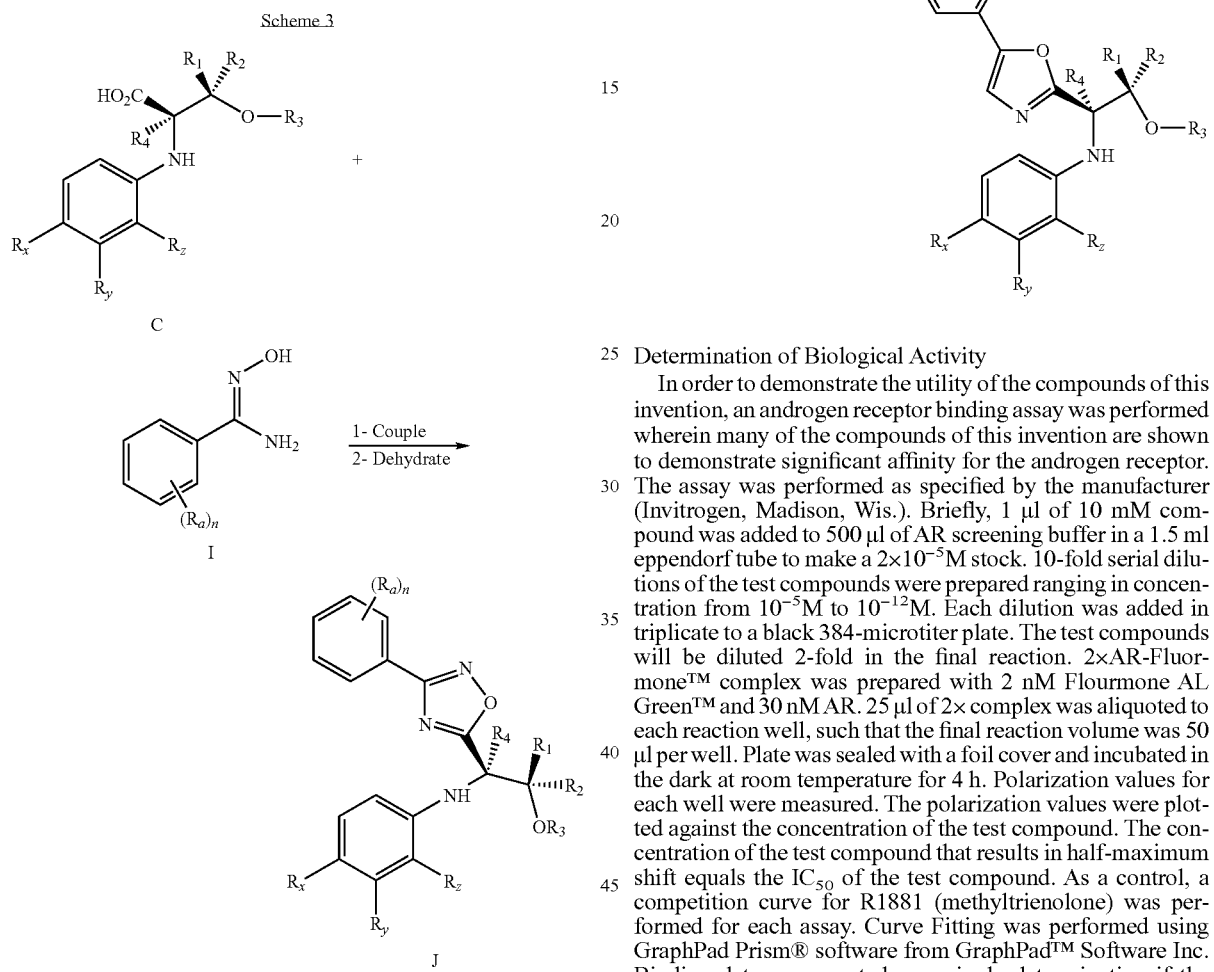

Other heteroaryl rings in place of variable A may also be prepared. For example, a 1,3 oxazole derivative maybe prepared by the method illustrated in scheme 4 shown below.

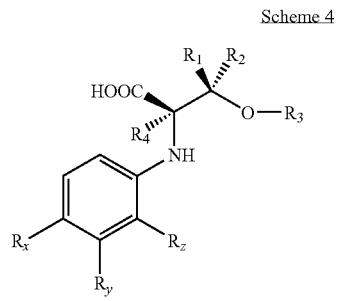

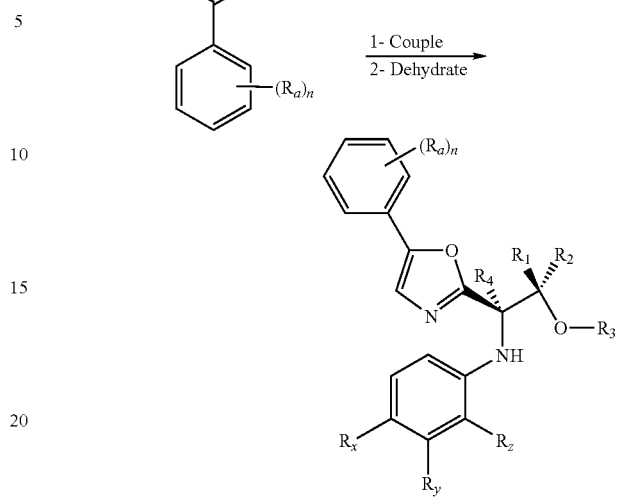

Determination of Biological Activity

In order to demonstrate the utility of the compounds of this invention, an androgen receptor binding assay was performed wherein many of the compounds of this invention are shown to demonstrate significant affinity for the androgen receptor. The assay was performed as specified by the manufacturer (Invitrogen, Madison, Wis.). Briefly, 1 µl of 10 mM compound was added to 500 µl of AR screening buffer in a 1.5 ml eppendorf tube to make a $2 \times 10^{-5}$M stock. 10-fold serial dilutions of the test compounds were prepared ranging in concentration from $10^{-5}$M to $10^{-12}$M. Each dilution was added in triplicate to a black 384-microtiter plate. The test compounds will be diluted 2-fold in the final reaction. 2×AR-Fluormone™ complex was prepared with 2 nM Flourmone AL Green™ and 30 nM AR. 25 µl of 2× complex was aliquoted to each reaction well, such that the final reaction volume was 50 µl per well. Plate was sealed with a foil cover and incubated in the dark at room temperature for 4 h. Polarization values for each well were measured. The polarization values were plotted against the concentration of the test compound. The concentration of the test compound that results in half-maximum shift equals the $IC_{50}$ of the test compound. As a control, a competition curve for R1881 (methyltrienolone) was performed for each assay. Curve Fitting was performed using GraphPad Prism® software from GraphPad™ Software Inc. Binding data are reported as a single determination if the experiment was run once only and as the average of experiments if the binding experiment was performed two or more times with that compound. Results are set forth in Table 1.

In Vivo Rat Model of Androgen and Anabolic Activity-Rat Herschberger Assay

The following is a typical procedure of the in vivo evaluation of the selective androgens of this invention. In particular, this assay looks primarily at the ability of the selective androgens of this invention to increase muscle size in an immature, castrated rat. In addition, androgenic effects are looked at primarily by weighing the prostate and seminal vesicles. Selective compounds will show a greater increase in the levator ani relative to the prostate and seminal vesicles when compared to testosterone treated, castrated animals or to intact animals that have not been treated. Immature Sprague Dawley male rats were obtained Charles River Laboratories (Stoneridge, N.Y.). All animals were maintained in a temperature and humidity controlled room with a 12 hr light: 12 hr dark cycle, with ad lib access to food (TD 291615, Teklad, Madison, Wis.) and water. Rats were anesthetized and orchidectomized (GDX) or sham surgery (SHAM) was performed. After a 7-day recovery period, the animals were randomized according to weight and assigned to treatment groups (n=5), SHAM, OVX+vehicle, OVX+Cpd treated. Testosterone propionate (TP 1 mg/kg in 5% DMSO/95% corn oil) was administered by once daily subcutaneous injections, while the compounds of the invention are dosed in vehicle (typically 20% cyclodextrin or 0.5% carboxymethylcellulose) was administered by once daily oral gavage. The rats were then dosed once daily for 4 days. All animals were euthanized via carbon dioxide inhalation 24 hs after the last dose. The prostate, seminal vesicle and levator ani and bulba cavernous (LABC) tissues were removed, weighed and recorded. Body weights were recorded for each animal at baseline and at sacrifice. Results are set forth in Table 2.

In Vivo Models of Bone Loss and Prevention

Compounds of this invention may also be assayed in vivo to determine their effect on preventing bone loss in animal models of bone loss. Animal models of bone loss are well-known to those of ordinary skill in the art. Examples of bone loss models include the rat and mouse ovariectomized models. Examples of such models are replete in the art, some non-limiting methods and examples are provided in Cesnjaj, et al *European Journal of Clinical Chemistry and Clinical Biochemistry* (1991), 29(4), 211-219; Y. L. Ma et al., *Japanese Journal of Bone and Mineral Research* 23 (Suppl.):62-68 (2005); Ornoy, et al, Osteoporosis: Animal Models for the Human Disease; *Animal Models of Human Related calcium Metabolic Disorders* (1995), 105-126.

Compound Characterization

All solvents were commercially available and used without further purification. Reactions were monitored by thin-layer chromatography (TLC) on silica gel plates (60 F254; EMD Chemicals) which were visualized using ultraviolet light, iodine vapor, or vanillin stain. Flash chromatography was performed on silica gel (230-400 mesh, Silicycle) using commercially available high purity solvents. $^1$H and $^{13}$C NMR spectra were determined in CDCl$_3$, MeOH-d$_6$, DMSO-d$_6$, or acetone-d$_6$ using either a Varian Unity 400 MHz spectrometer or a Varian Unity 500 MHz spectrometer. Proton chemical shifts (δ) are relative to the residual solvent peaks for each deuterated solvent and expressed in ppm. Coupling constants (J) are expressed in hertz. Mass spectra were obtained on a Waters HQH Quattro II mass spectrometer. All melting points were obtained on a Tottoli melting point apparatus manufactured by Büchi and are uncorrected. All hydrazides were either purchased or prepared according to procedures described in the literature. All chemical reagents are commercially available and were used without further purification unless stated otherwise.

Example 1

2-chloro-4-((1R,2S)-2-hydroxy-1-(5-phenyl-1,3,4-oxadiazol-2-yl)propylamino)-3-methylbenzonitrile

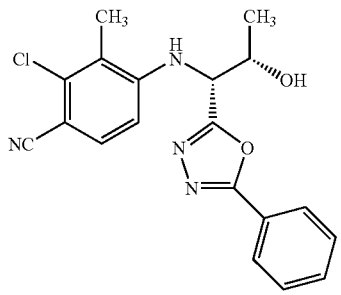

Intermediate 1a (2R,3S)-2-(3-chloro-4-cyano-2-methylphenylamino)-3-hydroxybutanoic acid

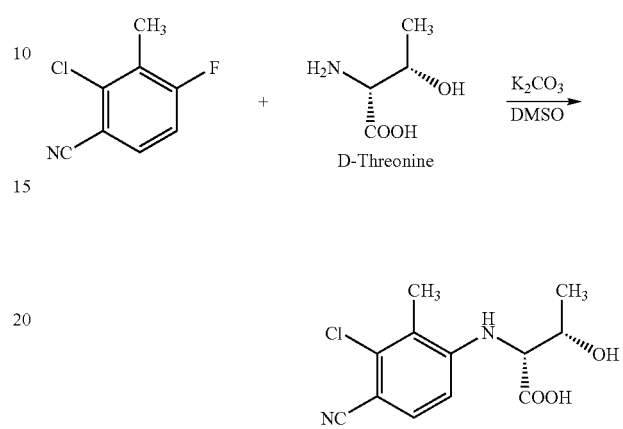

2-chloro-4-fluoro-3-methylbenzonitrile (CAS 796600-15-2, 45 g, 265.4 mmol) was mixed together with H-D-Thr-OH (37.92 g, 318.4 mmol) in DMSO (250 mL). K$_2$CO$_3$ (73.35 g, 530.7 mmol) was added to the reaction mixture and the reaction mixture stirred at 75° C. for 24 h. The reaction mixture was cooled to room temperature and poured slowly into a 10% citric acid solution and stirred for 10 min at room temperature. The solution was extracted with EtOAc several times to get the crude product. The crude product was chromatographed on silica gel with a gradient of hexanes/EtOAc and then with EtOAc, 100% to get the purified final product (39.0 g, 54%) $^1$H NMR (500 MHz, Acetone-d$_6$, δ in ppm) 7.49 (d, J=9 Hz, 1H), 6.70 (d, J=9 Hz, 1H), 5.38 (d, J=10 Hz, 1H), 4.47 (d, J=6 Hz, 1H), 4.25 (m, 1H), 2.34 (s, 3H), 1.33 (d, J=6 Hz, 3H).

Intermediate 1b

N'-((2R,3S)-2-(3-chloro-4-cyano-2-methylphenylamino)-3-hydroxybutanoyl)benzohydrazide

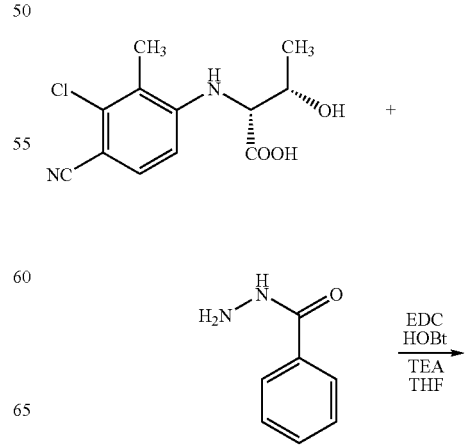

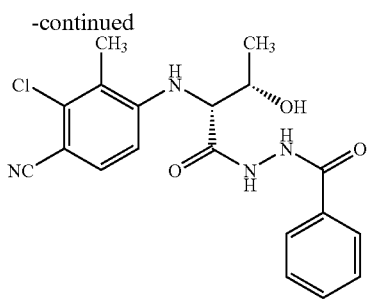

(2R,3S)-2-(3-chloro-4-cyano-2-methylphenylamino)-3-hydroxybutanoic acid (intermediate 1A) (18.66 g, 69.45 mmol) and benzoic hydrazide (9.45 g, 69.45 mmol) were mixed together in THF (500 ml) and cooled to −20° C. under N₂ atmosphere. To the pre-cooled reaction mixture were added hydroxybenzotriazole (HOBT) (9.38 g, 69.45 mmol), TEA (10.54 g, 104.17 mmol) followed by N-(3-Dimethylaminopropyl)-N'-ethylcarbodiimide hydrochloride (EDCI) (19.96 g, 104.17 mmol). The reaction mixture was allowed to stir at −20° C. for 1 h and then at room temperature overnight. After the reaction was complete based on TLC, the urea was filtered off and the solution was washed with water, 5% citric acid followed by 5% NaHCO₃ to provide the crude hydrazide product (20.5 g, 74%). ¹H NMR (500 MHz, Acetone-d₆, δ in ppm) 9.4-9.7 (br s, 2H), 7.94 (d, J=9 Hz, 2H), 7.59 (m, 1H), 7.52 (m, 3H), 6.68 (d, J=9 Hz, 1H), 5.57 (d, J=9 Hz, 1H), 4.39 (m, 1H), 4.08 (m, 1H), 2.37 (s, 3H), 1.36 (d, J=6 Hz, 3H).

Example 1

2-chloro-4-((1R,2S)-2-hydroxy-1-(5-phenyl-1,3,4-oxadiazol-2-yl)propylamino)-3-methylbenzonitrile

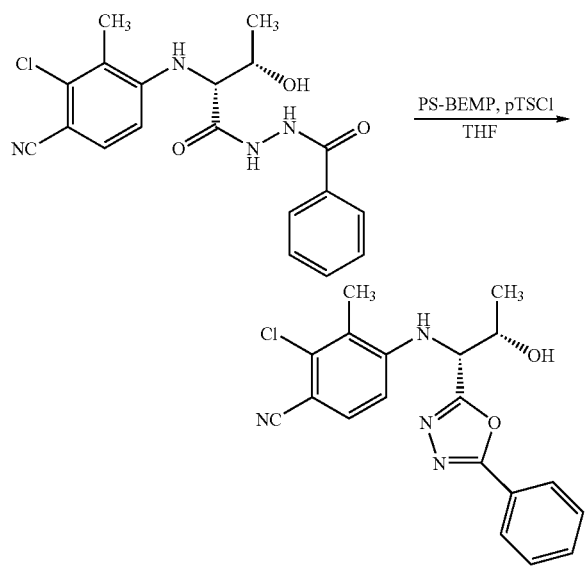

The crude material from the reaction above N'-((2R,3S)-2-(3-chloro-4-cyano-2-methylphenylamino)-3-hydroxybutanoyl)benzohydrazide (intermediate 1b) (20.46 g, 52.89 mmol) was added to THF (800 mL) stirred at room temperature. Polystyrene fixed (2-tert-butylamino-2-diethylamino-1,3-dimethylperhydro-1,3,2-diazophosphorine) PS-BEMP (72.12 g, 158.67 mmol base, 2.2 mmol loading per gram base, Aldrich Chemical Company) was added to the solution followed by slow addition of para-toluenesulfonyl chloride (p-TSCl) (12.10 g, 63.47 mmol). The reaction mixture was stirred for 3 h and the progress of the reaction was monitored by TLC. After the completion of the reaction, the BEMP reagent was filtered off and the solution concentrated to get the crude material. The crude material was chromatographed on silica gel with hexanes:EtOAc (6:4) to get the product (5.0 g). ¹H NMR (500 MHz, CDCl₃, δ in ppm) 7.94 (d, J=9 Hz, 2H), 7.54 (m, 1H), 7.48 (m, 2H), 7.42 (d, J=9 Hz, 1H), 6.67 (d, J=9 Hz, 1H), 5.26 (d, J=9 Hz, 1H), 4.74 (d, J=9 Hz, 1H), 4.64 (m, 1H), 3.16 (d, J=5 Hz, 1H), 2.35 (s, 3H), 1.43 (d, J=6 Hz, 3H).

Example 2

2-chloro-4-((1R,2S)-2-hydroxy-1-(5-(4-methoxyphenyl)-1,3,4-oxadiazol-2-yl)propylamino)-3-methylbenzonitrile

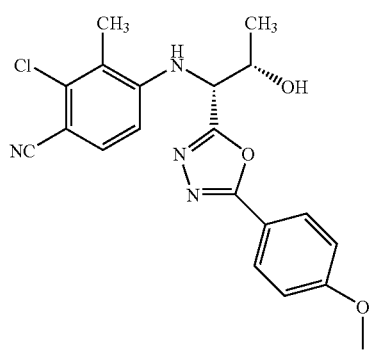

Intermediate 2a

N'-((2R,3S)-2-(3-chloro-4-cyano-2-methylphenylamino)-3-hydroxybutanoyl)-4-methoxybenzohydrazide

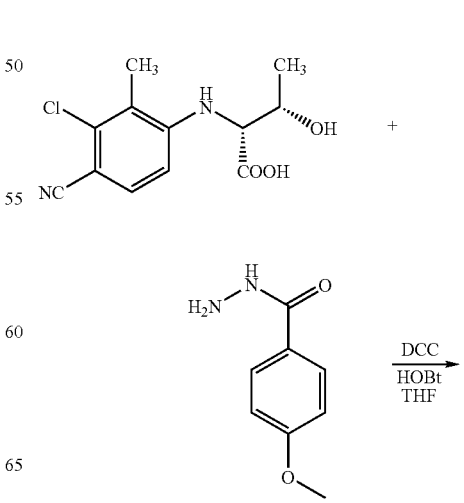

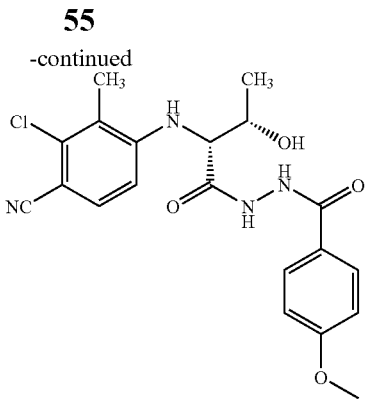

(2R,3S)-2-(3-chloro-4-cyano-2-methylphenylamino)-3-hydroxybutanoic acid (220 mg, 0.82 mmol) and 4-methoxybenzo-hydrazide (CAS 3290-99-1, 136 mg, 0.82 mmol) were mixed together in THF (20 mL) and cooled down to −20° C. under $N_2$ atmosphere. To the pre-cooled reaction mixture were added HOBt (111 mg, 0.82 mmol) followed by dicyclohexylcarbodiimide (DCC) (203 mg, 0.98 mmol). The reaction mixture were allowed to stir at −20° C. for 1 h and then at room temperature overnight. After the reaction is complete the urea was filtered off and the solution washed with 5% citric acid followed by 5% NaHCO$_3$ to get the crude hydrazide product (286 mg, 83%). $^1$H NMR (500 MHz, Acetone-d$_6$, δ in ppm) 7.96 (d, J=9 Hz, 2H), 7.54 (d, J=9 Hz, 1H), 7.01 (d, J=9 Hz, 2H), 6.62 (d, J=9 Hz, 1H), 5.58 (d, J=9 Hz, 1H), 4.38 (m, 1H), 4.12 (m, 1H), 3.83 (s, 3H), 2.38 (s, 3H), 1.37 (d, J=6 Hz, 3H).

Example 2

2-chloro-4-((1R,2S)-2-hydroxy-1-(5-(4-methoxyphenyl)-1,3,4-oxadiazol-2-yl)propylamino)-3-methylbenzonitrile

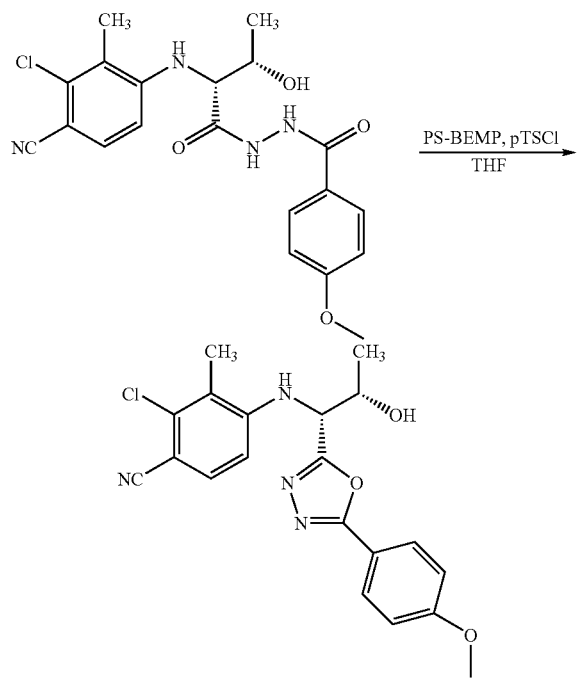

The crude material from the reaction immediately preceding (Intermediate 2a) N'-((2R,3S)-2-(3-chloro-4-cyano-2-methylphenylamino)-3-hydroxybutanoyl)-4-methoxy benzohydrazide (330 mg, 0.79 mmol) was added to THF (40 mL) and stirred at room temperature. PS-BEMP (1.08 g, 2.37 mmol base) was added to the solution followed by slow addition of p-TSCl (166 mg, 0.87 mmol). The reaction mixture was stirred for 3 h and the progress of the reaction was monitored by TLC. After the completion of the reaction the BEMP reagent was filtered off and the solution concentrated to get the crude material. The crude material was chromatographed on silica gel with Hex:EtOAc (6:4) to get the purified product (130 mg, 41%). $^1$H NMR (500 MHz, Acetone-d$_6$, δ in ppm) 7.93 (d, J=9 Hz, 2H), 7.50 (d, J=9 Hz, 1H), 7.11 (d, J=9 Hz, 2H), 6.87 (d, J=9 Hz, 1H), 5.68 (d, J=9 Hz, 1H), 5.07 (m, 1H), 4.79 (m, 1H), 4.60 (m, 1H), 3.89 (s, 3H), 2.40 (s, 3H), 1.40 (d, J=6 Hz, 3H).

Example 3

2-chloro-4-((1R,2R)-2-hydroxy-1-(5-phenyl-1,3,4-oxadiazol-2-yl)propylamino)-3-methylbenzonitrile

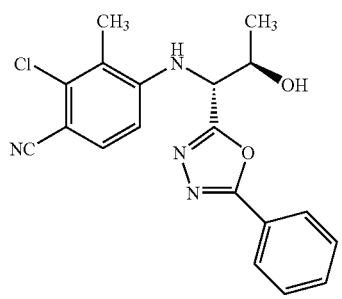

Intermediate 3a (2R,3R)-2-(3-Chloro-4-cyano-2-methylphenylamino)-3-hydroxybutanoic acid

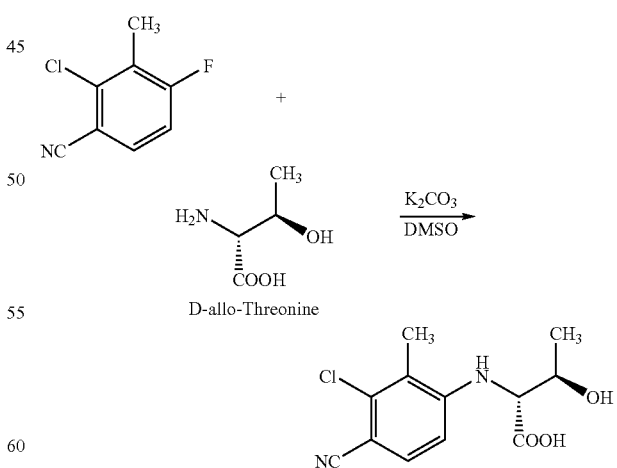

2-Chloro-4-fluoro-3-methylbenzonitrile (1.19 g, 7.00 mmol) was mixed together with H-D-allo-Thr-OH (1.0 g, 8.40 mmol) in DMSO (15 mL). K$_2$CO$_3$ (1.93 g, 13.99 mmol) was added to the reaction mixture and stirred at 75° C. for 24 h. Then the reaction mixture was cooled down to room temperature and poured slowly into a 10% citric acid solution and stirred for 10 min at room temperature. The solution was extracted with EtOAc several times to get the crude product. The crude product was chromatographed on silica gel with a gradient of hexanes/EtOAc and then with EtOAc, 100% to get the purified final product (1.20 g, 63%). $^1$H NMR (500 MHz, Acetone-$d_6$, δ in ppm) 7.47 (d, J=9 Hz, 1H), 6.73 (d, J=9 Hz, 1H), 5.48 (d, J=9 Hz, 1H), 4.26 (m, 2H), 2.28 (s, 3H), 1.32 (d, J=6 Hz, 3H).

A Scale-Up Reaction of Intermediate 3a was Performed as Follows:

To a three-necked, 500 mL, round-bottomed flask fitted with a nitrogen inlet, mechanical stirring apparatus, and septum was added D-allo-threonine (24.98 g, 210 mmol) followed by anhydrous DMSO (250 mL) and potassium carbonate (63.7 g, 460 mmol). This mixture was stirred under nitrogen at room temperature for a period of 30 min. To this mixture was then added 2-chloro-4-fluoro-3-methylbenzonitrile (35.51 g, 210 mmol) followed by heating of the reaction mixture to 70° C. in an oil bath for a period of 48 hs. The reaction was then allowed to cool to room temperature followed by subsequent cooling to 0° C. and a 5% citric acid/water solution (1.5 Liters) was slowly added followed by careful addition of solid citric acid until evolution of gas was no longer observed. This solution was then extracted with EtOAc (5×1 L). The combined organic extracts were then dried over $Na_2SO_4$ and decanted away from the drying agent. The solvent was then removed under reduced pressure using rotary evaporation to reveal a red oil that was purified by silica gel chromatography by first eluting with hexanes/EtOAc, 1/1 (2 L) followed by methanol/EtOAc 1/7 (5 L) to afford of (2R,3R)-2-(3-chloro-4-cyano-2-methylphenylamino)-3-hydroxybutanoic acid as a light red oil/solid (27.05 g, 48%). $^1$H NMR (500 MHz, $CD_3OD$, δ in ppm) 7.42 (d, J=8.7 Hz, 1H), 6.65 (d, J=8.7 Hz, 1H), 4.24 (m, 1H), 4.17 (m, 1H), 2.32 (s, 3H), 1.35 (d, J=6.6 Hz, 3H); $^{13}$C NMR (125.6 MHz, $CD_3OD$) δ 174.2, 151.9, 137.16, 134.0, 122.6, 119.1, 110.1, 101.2, 69.1, 63.2, 20.0, 14.0.

Intermediate 3b

N'-((2R,3R)-2-(3-chloro-4-cyano-2-methylphenylamino)-3-hydroxybutanoyl)benzohydrazide

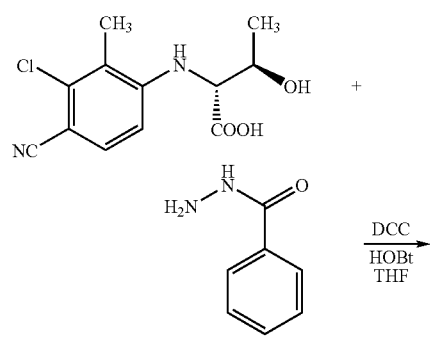

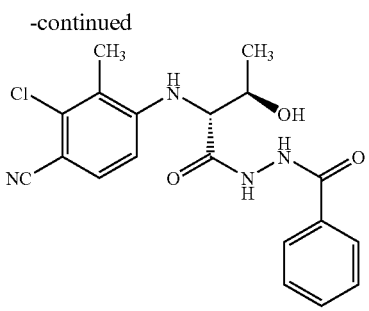

(2R,3R)-2-(3-chloro-4-cyano-2-methylphenylamino)-3-hydroxybutanoic acid (182 mg, 0.68 mmol) and benzoic hydrazide (92 mg, 0.68 mmol) were mixed together in THF (20 mL) and cooled down to −20° C. under $N_2$ atmosphere. To the pre-cooled reaction mixture were added HOBt (92 mg, 0.68 mmol) followed by DCC (168 mg, 0.81 mmol). The reaction mixture was allowed to stir at −20° C. for 1 h and then at room temperature overnight. After the reaction was complete, the urea was filtered off and the solution was washed with water, 5% citric acid followed by 5% $NaHCO_3$ to get the crude hydrazide product (210 mg, 80%). $^1$H NMR (500 MHz, acetone-$d_6$, δ in ppm) 9.4-9.7 (br s, 2H), 7.91 (d, J=9 Hz, 2H), 7.57 (m, 1H), 7.48 (m, 3H), 6.69 (d, J=9 Hz, 1H), 5.57 (d, J=9 Hz, 1H), 4.20 (m, 1H), 4.08 (m, 1H), 2.32 (s, 3H), 1.35 (d, J=6 Hz, 3H).

A Scale-Up Reaction of Intermediate 3b was Performed as Follows:

To a 100 mL, round-bottomed flask equipped with a magnetic stir bar and septum was added (2R,3R)-2-(3-chloro-4-cyano-2-methylphenylamino)-3-hydroxybutanoic acid (2.02 g, 7.5 mmol) followed by a addition of anhydrous THF (60 mL) under an atmosphere of nitrogen. Benzhydrazide (1.02 g, 7.5 mmol) was subsequently added and the mixture was cooled to −15° C. To this mixture was added HOBt (1.02 g, 7.5 mmol) followed by addition of EDC (2.88 g, 15.0 mmol) and lastly, TEA (3.2 mL, 23 mmol) was slowly added. The temperature of this reaction was maintained between −25° C. and −15° C. for a period of 1 h then allowed to warm to room temperature overnight. The solids were filtered off and washed with additional THF (20 mL) and EtOAc (20 mL). The mother liquor was then diluted with EtOAc (200 mL) and washed with 5% citric acid/water (2×50 mL), saturated sodium bicarbonate (1×25 mL), and brine (1×50 mL) then dried over sodium sulfate. The solution was then filtered and concentrated under reduced pressure using rotary evaporation to reveal a white solid. This was purified via silica gel chromatography eluted with 85% EtOAc/hexane to provide title compound as a white solid (1.49 g, 51%). $^1$H NMR (400 MHz, acetone-$d_6$, δ in ppm) 9.64 (br s, 2H), 7.94 (m, 2H), 7.60 (m, 1H), 7.51 (m, 3H), 6.73 (d, J=8.7 Hz, 1H), 5.59 (d, J=7.2 Hz, 1H), 4.71 (br s, 1H), 4.24 (m, 1H), 4.12 (dd, J=5.1, 7.3 Hz, 1H), 2.35 (s, 3H), 1.39 (d, J=6.3 Hz, 3H).

Example 3

2-Chloro-4-((1R,2R)-2-hydroxy-1-(5-phenyl-1,3,4-oxadiazol-2-yl)propylamino)-3-methylbenzonitrile

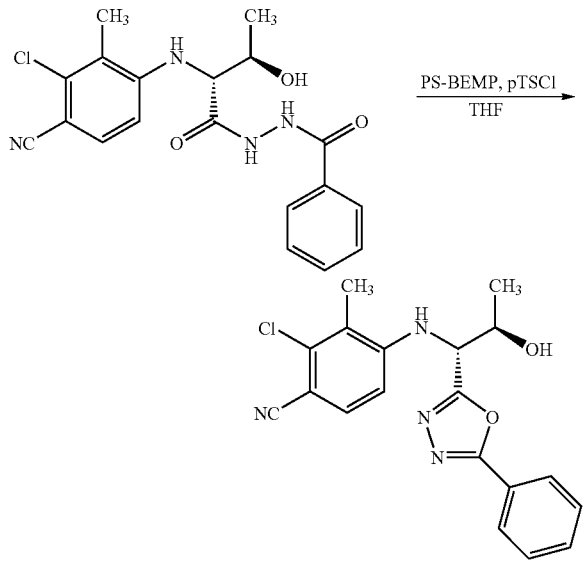

The crude material (intermediate 3b from the preceding reaction) N'-((2R,3R)-2-(3-chloro-4-cyano-2-methylphenylamino)-3-hydroxybutanoyl)benzohydrazide (183 mg, 0.47 mmol) was added to THF (30 mL) and stirred at room temperature. PS-BEMP (645 mg, 14.20 mmol base) was added to the solution followed by slow addition of p-TSCl (108 mg, 0.57 mmol). The reaction mixture was stirred for 3 h and the progress of the reaction was monitored by TLC. After the completion of the reaction the BEMP reagent was filtered off and the solution concentrated to get the crude material. The crude material was chromatographed with hexanes:EtOAc (6:4) to get the purified product (63 mg): $^1$H NMR (500 MHz, CDCl$_3$, δ in ppm) 7.99 (d, J=9 Hz, 2H), 7.56 (m, 1H), 7.51 (m, 2H), 7.40 (d, J=9 Hz, 1H), 6.68 (d, J=9 Hz, 1H), 5.32 (d, J=9 Hz, 1H), 4.85 (m, 1H), 4.42 (m, 1H), 2.34 (s, 3H), 1.38 (d, J=6 Hz, 3H).

Example 4

2-chloro-4-((1R,2S)-1-(5-(4-chlorophenyl)-1,3,4-oxadiazol-2-yl)-2-hydroxypropylamino)-3-methylbenzonitrile

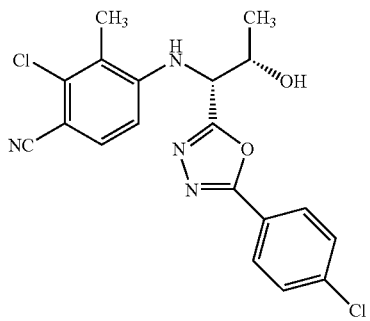

Intermediate 4a

N'-((2R,3S)-2-(3-Chloro-4-cyano-2-methylphenylamino)-3-hydroxybutanoyl)-4-chlorobenzohydride

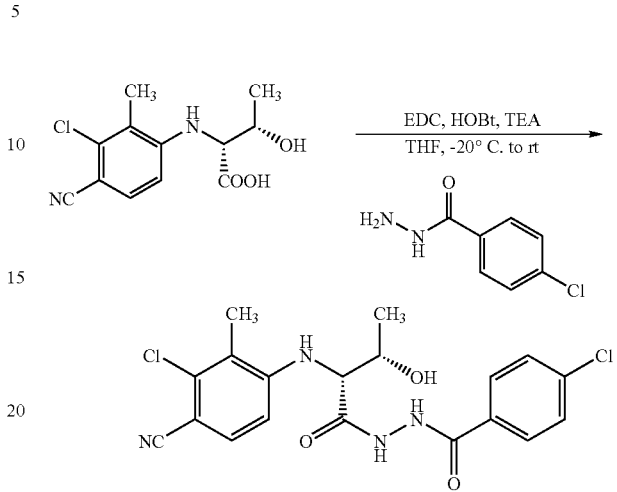

4-Chloro-N'-((2R,3S)-2-(3-chloro-4-cyano-2-methylphenylamino)-3-hydroxy butanoyl)benzohydrazide was prepared using 4-chlorobenzoic hydrazide (CAS 536-40-3) in an analogous fashion to the procedure described in the synthesis of intermediate 5a described below. The crude golden yellow solid was recrystallized using hot methylene chloride and hexanes to provide the desired product as a light yellow solid (890 mg, 46% yield). Other data: $^1$H NMR (400 MHz, acetone-d$_6$, δ in ppm) 9.89 (br. s., 1H), 9.47 (br. s., 1H), 7.94 (d, J=8.5 Hz, 2H), 7.55 (d, J=8.5 Hz, 2H), 7.54 (d, J=8.7 Hz, 1H), 6.68 (d, J=8.6 Hz, 1H), 5.55 (br. d, J=5.3 Hz, 1H), 4.39 (m, 1H), 4.11 (br. dd, J=5, 6 Hz, 1H), 2.36 (s, 3H), 1.36 (d, J=6.35 Hz, 3H); TLC R$_f$=0.41, 100% EtOAc, vanillin stain).

Example 4

2-Chloro-4-((1R,2S)-1-(5-(4-chlorophenyl)-1,3,4-oxadiazol-2-yl)-2-hydroxypropylamino)-3-methylbenzonitrile

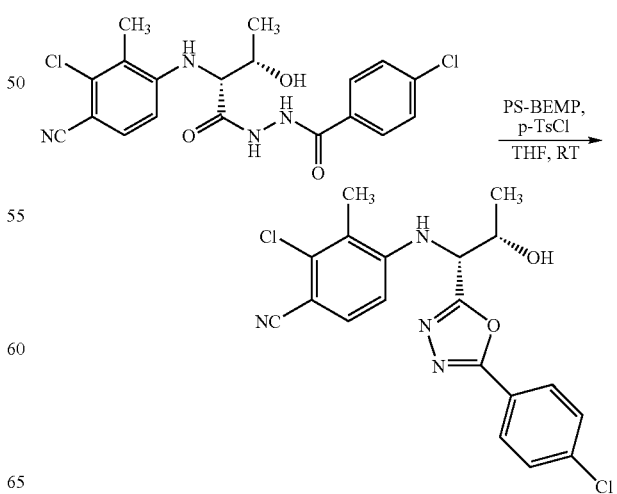

To a 500 mL round bottom flask was added 4-chloro-N'-((2R,3S)-2-(3-chloro-4-cyano-2-methylphenylamino)-3-hydroxybutanoyl)benzohydrazide (intermediate 4a) (880 mg, 2.09 mmol, 1.0 equiv.) and anhydrous THF (209 mL). After being flushed with nitrogen, p-toluenesulfonic acid (439 mg, 2.3 mmol, 1.1 equiv.) was added and the solution was stirred for 10 min at room temperature. Then PS-BEMP (2.85 g, 6.27 mmol, 3.0 equiv.) was added. The reaction was stirred at room temperature for 8 h. The contents of the flask were filtered over Celite® in a ground glass fritted funnel and the Celite® was rinsed with several portions of acetone. The solvent was removed in vacuo to yield a yellow solid. The product was purified via flash chromatography (0→50% EtOAc/hexanes, 110 g of silica gel; TLC $R_f$=0.51, 100% EtOAc, vanillin stain) to provide the desired product as an off-white solid (150 mg, 18%). Other data: $^1$H NMR (400 MHz, acetone-$d_6$, δ in ppm) 8.01 (d, J=8.79 Hz, 2H), 7.62 (d, J=8.79 Hz, 2H), 7.49 (d, J=8.54 Hz, 1H), 6.86 (d, J=8.54 Hz, 1H), 5.68 (br. d, J=8.31 Hz, 1H), 5.12 (dd, J=3.91, 8.55 Hz, 1H), 4.82 (br. d, J=5.29 Hz, 1H), 4.62 (m, 1H), 2.40 (s, 3H), 1.41 (d, J=6.35 Hz, 3H); LRMS (ESI+) exact mass calcd for $C_{19}H_{16}Cl_2N_4O_2$ [M]$^+$ 403.26. found 403.4.

Example 5

2-Chloro-4-((1R,2S)-1-(5-(4-fluorophenyl)-1,3,4-oxadiazol-2-yl)-2-hydroxypropylamino)-3-methylbenzonitrile

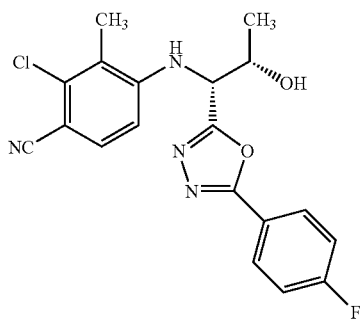

Intermediate 5a

N'-((2R,3S)-2-(3-Chloro-4-cyano-2-methylphenylamino)-3-hydroxybutanoyl)-4-fluorobenzohydride

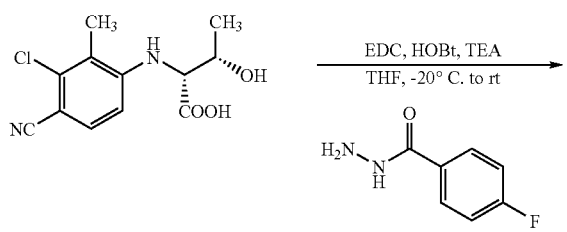

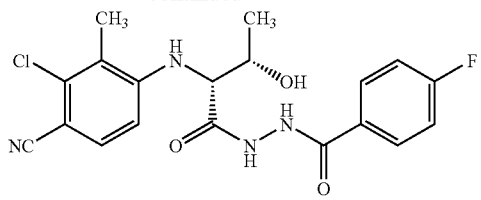

To a 50 mL round bottom flask was added (2R,3S)-2-(3-chloro-4-cyano-2-methylphenylamino)-3-hydroxybutanoic acid (intermediate 1a) (1.17 g, 4.35 mmol, 1.0 equiv.) and anhydrous THF (22 mL). After being flushed with nitrogen, 4-fluorobenzoic hydrazide (CAS-456-06-4) (865 mg, 5.07 mmol, 1.1 equiv.) was added. The stirring solution was cooled to −20° C., and 1-hydroxybenzotriazole (HOBt) (685 mg, 5.07 mmol, 1.1 equiv.) was added in one portion, followed by 1-ethyl-3-(3'-dimethylaminopropyl)carbodiimide (EDC) (1.67 g, 8.7 mmol, 2.0 equiv.) and then triethylamine (TEA) (2.42 mL, 17.4 mmol. 4.0 equiv.). The solution was stirred at −20° C. for 1 h and gradually warmed to room temperature overnight. The reaction was filtered over Celite® in a ground glass fritted funnel to remove the solid. The solution was then diluted with 50 mL of EtOAc. The EtOAc solution was washed with 5% citric acid solution (w/v) (2×50 mL), distilled water (2×50 mL), and brine (1×50 mL). The organic layer was dried over $Na_2SO_4$ and then concentrated in vacuo to yield a light yellow solid. The product was purified via flash chromatography (0→80% EtOAc/hexanes, 110 g of silica gel; TLC $R_f$=0.4, 100% EtOAc, vanillin stain) to provide the desired product as an off-white solid (0.4724 g, 27% yield). Other data: $^1$H NMR (500 MHz, acetone-$d_6$, δ in ppm) 9.81 (br. s., 1H), 9.56 (br.s., 1H), 8.01 (m, 2H), 7.535 (d, J=8.6 Hz, 1H), 7.27 (m, 2H), 6.67 (d, J=8.6 Hz, 1H), 5.55 (br. d, J=6.9 Hz, 1H), 4.825 (br. s., 1H), 4.39 (dq, J=3.2, 6.4 Hz, 1H), 4.10 (dd, J=3.4, 7.1 Hz, 1H), 2.36 (s, 3H), 1.355 (d, J=6.4 Hz, 3H); LRMS (ESI+) exact mass calcd for $C_{19}H_{18}ClFN_4O_3$ [M]$^+$ 404.82. found 405.4.

Example 5

2-Chloro-4-((1R,2S)-1-(5-(4-fluorophenyl)-1,3,4-oxadiazol-2-yl)-2-hydroxypropylamino)-3-methylbenzonitrile

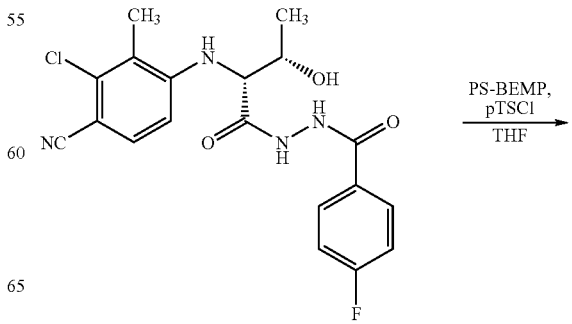

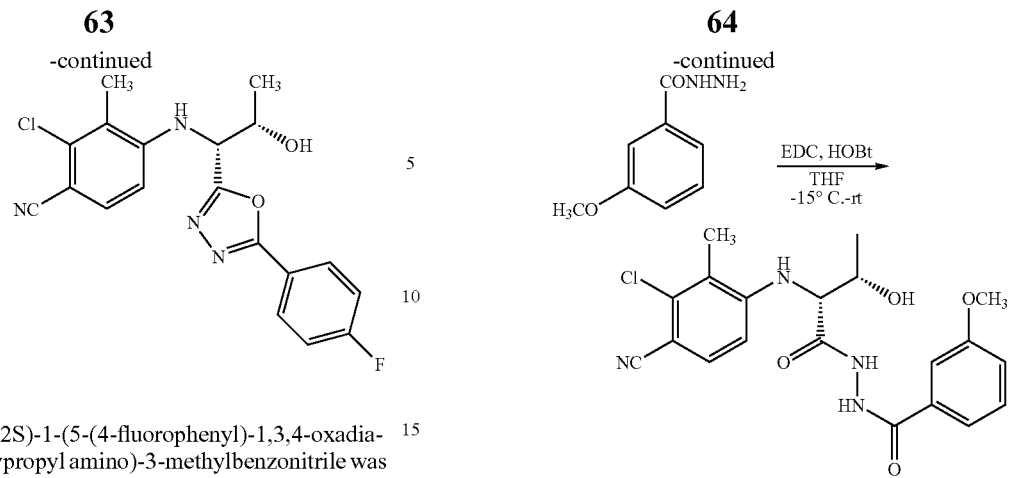

2-Chloro-4-((1R,2S)-1-(5-(4-fluorophenyl)-1,3,4-oxadiazol-2-yl)-2-hydroxypropylamino)-3-methylbenzonitrile was prepared as described in the preparation of example 4 using N'-((2R,3S)-2-(3-chloro-4-cyano-2-methylphenylamino)-3-hydroxybutanoyl)-4-fluorobenzohydrazide (1.15 mmol, 1.0 equiv.). The crude off-white solid was purified via column chromatography (0→50% EtOAc/hexanes then 100% EtOAc, 110 g of silica gel; TLC $R_f$=0.44, 100% EtOAc, vanillin stain) to provide the desired product as an off-white solid (153 mg, 35% yield). Other data: $^1$H NMR (400 MHz, acetone-$d_6$, δ in ppm) 9.63 (br. s, 1H), 8.02 (dd, J=5.4, 8.8 Hz, 2H), 7.54 (d, J=8.8 Hz, 1H), 7.28 (m, 2H), 6.67 (d, J=8.8 Hz, 1H), 5.55 (br. d, J=6.8 Hz, 1H), 4.39 (m, 1H), 4.10 (m, 1H), 2.37 (s, 3H), 1.35 (d, J=6.4 Hz, 3H).

Example 6

2-chloro-4-((1R,2S)-2-hydroxy-1-(5-(3-methoxyphenyl)-1,3,4-oxadiazol-2-yl)propylamino)-3-methylbenzonitrile

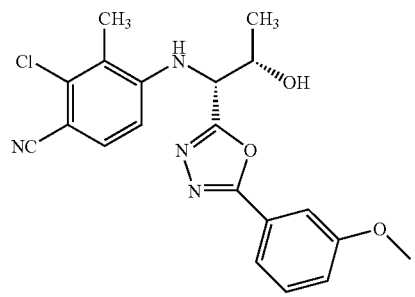

Intermediate 6a

N'-((2R,3S)-2-(3-Chloro-4-cyano-2-methylphenylamino)-3-hydroxybutanoyl)-3-methoxy-benzohydrazide

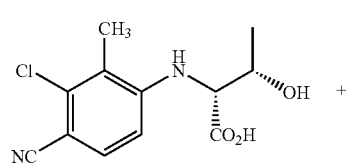

Intermediate 6a was synthesized similarly to the procedure outlined for intermediate 1b described above using (2R,3S)-2-(3-chloro-4-cyano-2-methylphenylamino)-3-hydroxybutanoic acid (intermediate 1a) (530 mg, 2.0 mmol) and 3-methoxy-benzohydrazide (329 mg, 2.0 mmol). After column chromatography (2% methanol/EtOAc) the title compound was isolated as a white solid (471 mg, 57%). $^1$H NMR (500 MHz, $d_6$-acetone, δ in ppm) 9.88 (br s, 1H), 9.53 (br s, 1H), 7.47 (m, 3H), 7.38 (at, J=8.0 Hz, 1H), 7.12 (m, 1H), 6.66 (d, J=8.7 Hz, 1H), 5.55 (d, J=7.0 Hz, 1H), 4.88 (br s, 1H), 4.40 (m, 1H), 4.12 (dd, J=3.3, 7.0 Hz, 1H), 3.83 (s, 3H), 2.34 (s, 3H), 1.35 (d, J=6.3 Hz, 3H).

Example 6

2-Chloro-4-((1R,2S)-2-hydroxy-1-(5-(3-methoxyphenyl)-1,3,4-oxadiazol-2-yl)propylamino)-3-methylbenzonitrile

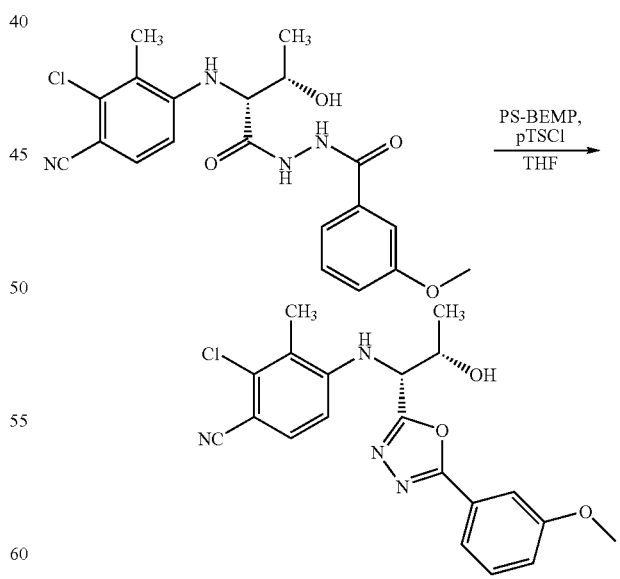

To a 100 mL round bottom flask was added N'-((2R,3S)-2-(3-chloro-4-cyano-2-methylphenylamino)-3-hydroxybutanoyl)-3-methoxybenzohydrazide (Intermediate 6a) (441 mg, 1.1 mmol) was added THF (90 mL) and stirred at room temperature. PS-BEMP (1.45 g, 3.2 mmol base) was added to the solution followed by slow addition of p-TSCl (208 mg, 1.1 mmol). The reaction mixture was stirred for 2 h and the progress of the reaction was monitored by TLC. After the completion of the reaction, the BEMP reagent was filtered off, washed with methanol (100 mL), and the resulting solution was concentrated to obtain the crude material. The crude material was chromatographed on silica gel with hexanes:EtOAc (2:8) to get the purified product (232 mg, 55%). $^1$H NMR (400 MHz, $d_6$-acetone, δ in ppm) 7.42 (m, 1H), 7.33 (m, 3H), 7.01 (m, 1H), 6.50 (d, J=8.7 Hz, 1H), 5.37 (d, J=8.5 Hz, 1H), 4.72 (m, 1H), 4.62 (m, 1H), 3.94 (br s, 1H), 3.80 (s, 3H), 2.37 (s, 3H), 1.43 (d, J=6.4 Hz, 3H).

Example 7

2-chloro-4-((1R,2S)-2-hydroxy-1-(5-(3-hydroxyphenyl)-1,3,4-oxadiazol-2-yl)propylamino)-3-methylbenzonitrile

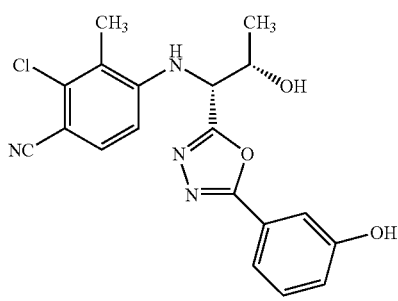

Intermediate 7a

N'-((2R,3S)-2-(3-chloro-4-cyano-2-methylphenylamino)-3-hydroxybutanoyl)-3-hydroxy-benzohydrazide

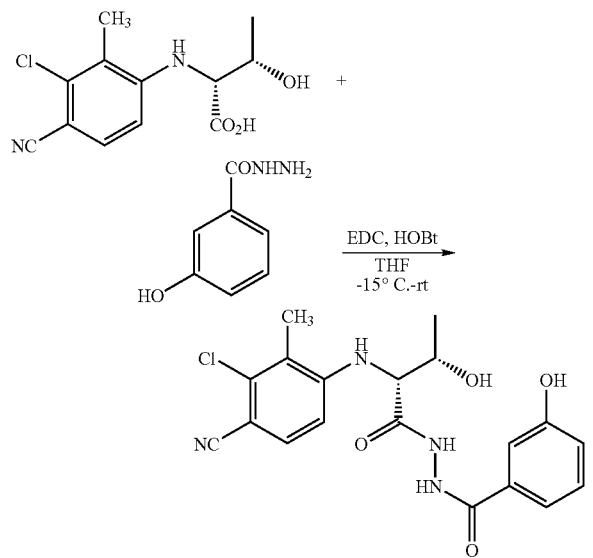

Intermediate 7a was synthesized similarly to the procedure outlined for intermediate 1b described above using (2R,3S)-2-(3-chloro-4-cyano-2-methylphenylamino)-3-hydroxybutanoic acid (intermediate 1a) (522 mg, 1.9 mmol) and 3-hydroxy-benzohydrazide (296 mg, 1.9 mmol). After column chromatography (EtOAc), the title compound was isolated as a white solid (407 mg, 52%). $^1$H NMR (400 MHz, acetone-$d_6$, δ in ppm) δ 9.80 (br s, 1H), 9.52 (br s, 1H), 8.76 (br s, 1H), 7.49 (d, J=8.7 Hz, 1H), 7.40 (m, 1H), 7.29 (at, J=8.1 Hz, 1H), 7.04 (m, 1H), 6.66 (d, J=8.7 Hz, 1H), 5.55 (d, J=7.1 Hz, 1H), 4.89 (br s, 1H), 4.39 (m, 1H), 4.11 (dd, J=3.3, 7.0 Hz, 1H), 2.35 (s, 3H), 1.34 (d, J=6.5 Hz, 3H).

Intermediate 7b 3-(tert-butyldimethylsilyloxy)-N'-((2R,3S)-3-(tert-butyldimethylsilyloxy)-2-(3-chloro-4-cyano-2-methylphenylamino)butanoyl)benzohydrazide

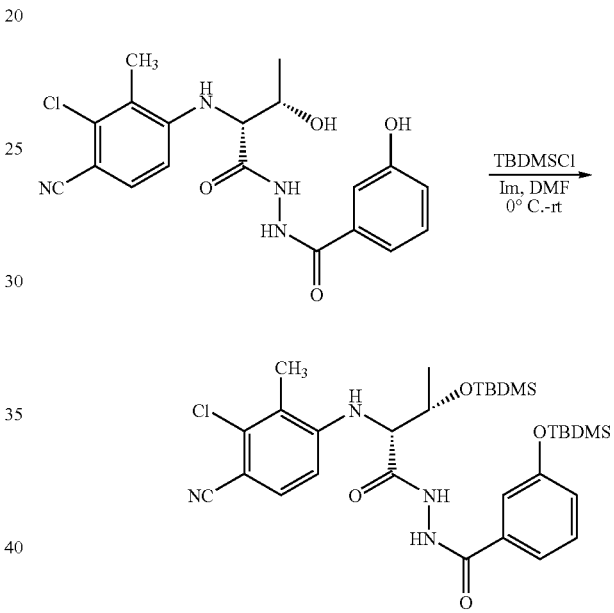

To a 25 mL round-bottomed flask equipped with a magnetic stir bar and a septum was added N'-((2R,3S)-2-(3-chloro-4-cyano-2-methylphenylamino)-3-hydroxybutanoyl)-3-hydroxybenzohydrazide (intermediate 7a) (105 mg, 0.26 mmol). This was dissolved in dry DMF (3 mL) under an atmosphere of nitrogen. This mixture was cooled to 0° C. followed by addition of imidazole (0.2303 g, 3.38 mmol) and TBDMSCl (278 mg, 1.84 mmol). The reaction was allowed to slowly warm to room temperature overnight quenched by slow addition of brine (10 mL). The solution was extracted with EtOAc (3×10 mL). The combined organic extracts were dried over $Na_2SO_4$, filtered, and concentrated under reduced pressure using rotary evaporation to reveal a brown oil. This was purified via silica gel chromatography eluted with 40% EtOAc/hexanes to yield the title compound as a white solid (100 mg, 61%). $^1$H NMR (400 MHz, $CDCl_3$, δ in ppm) 9.39 (d, J=6.2 Hz, 1H), 8.84 (d, J=6.1 Hz, 1H), 7.40 (d, J=8.5 Hz, 1H), 7.32 (m, 3H), 7.00 (m, 3H), 6.46 (d, J=8.7 Hz, 1H), 5.35 (d, J=6.2 Hz, 1H), 4.50 (m, 1H), 3.97 (dd, J=2.1, 6.1 Hz, 1H), 2.33 (s, 3H), 1.25 (d, J=6.2 Hz, 3H), 0.97 (s, 9H), 0.92 (s, 9H), 0.19 (s, 6H), 0.13 (s, 3H), 0.08 (s, 3H).

Intermediate 7c ((1R,2S)-2-(tert-butyldimethylsilyloxy)-1-(5-(3-(tert-butyldimethylsilyloxy)phenyl)-1,3,4-oxadiazol-2-yl)propylamino)-2-chloro-3-methylbenzonitrile

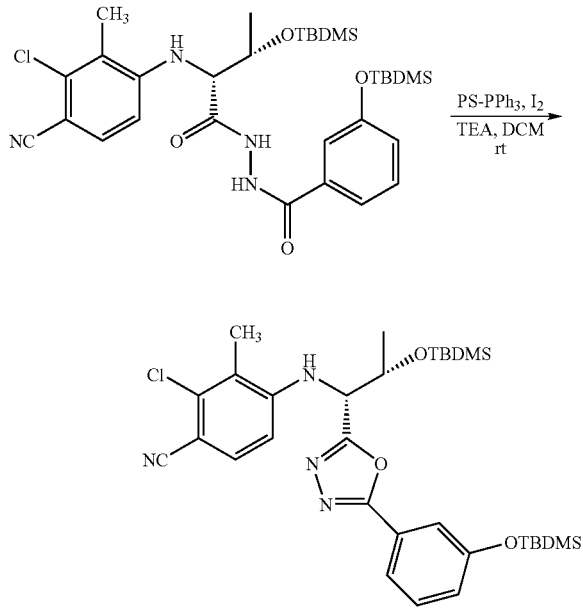

To a 25 mL round bottom flask equipped with a magnetic stir bar and septum was added triphenylphosphine (polymer bound, 3.0 mmol/g loading) (100 mg, 0.3 mmol) under an atmosphere of nitrogen. To this was added methylene chloride (3 mL) followed by addition of solid iodine (76 mg, 0.30 mmol). This was allowed to stir at room temperature for a period of 10 min followed by slow addition of triethylamine (0.17 mL, 1.2 mmol). This mixture was allowed to stir at room temperature for an additional ten min. 3-(tert-butyldimethylsilyloxy)-N'-((2R,3S)-3-(tert-butyldimethylsilyloxy)-2-(3-chloro-4-cyano-2-methylphenylamino)butanoyl)benzohydrazide (95 mg, 0.15 mmol) was taken up in methylene chloride (5 mL) and slowly added to the heavily stirred reaction mixture. After a period of 20 min, the solid polymer was filtered out and washed with additional methylene chloride (20 mL). The organic filtrate was then washed with 10% sodium thiosulfate/water (2×10 mL), brine (1×20 mL) and dried (Na$_2$SO$_4$). The solution was then filtered and concentrated under reduced to reveal a brown oil/solid, which was purified via silica gel chromatography eluted with 20% EtOAc/hexanes to provide the title compound as a white solid (63 mg, 68%): $^1$H NMR (400 MHz, CDCl$_3$, δ in ppm) 7.52 (m, 1H), 7.38 (m, 1H), 7.33 (m, 2H), 6.99 (m, 1H), 6.46 (d, J=8.6 Hz, 1H), 5.37 (d, J=8.8 Hz, 1H), 4.80 (dd, J=1.8, 8.8 Hz, 1H), 4.54 (m, 1H), 2.37 (s, 3H), 1.42 (d, J=6.2 Hz, 3H), 0.98 (s, 9H), 0.86 (s, 9H), 0.19 (s, 6H), 0.06 (s, 3H), −0.20 (s, 3H).

Example 7

2-chloro-4-((1R,2S)-2-hydroxy-1-(5-(3-hydroxyphenyl)-1,3,4-oxadiazol-2-yl)propylamino)-3-methylbenzonitrile

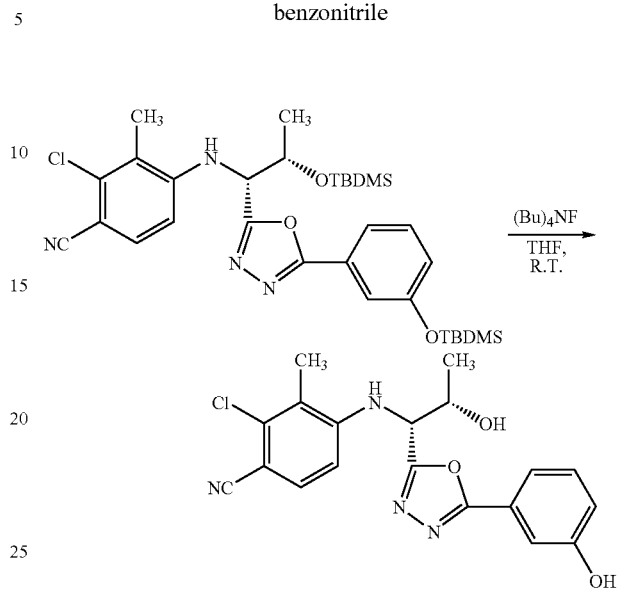

To a 25 mL round bottom flask equipped with a magnetic stirrer and a septum was added 4-((1R,2S)-2-(tert-butyldimethylsilyloxy)-1-(5-(3-(tert-butyldimethyl-silyloxy)phenyl)-1,3,4-oxadiazol-2-yl)propylamino)-2-chloro-3-methylbenzonitrile (intermediate 7c) (62 mg, 0.1 mmol), which was then dissolved in anhydrous THF (3 mL) under an atmosphere of nitrogen. To this was added the tetrabutylammonium fluoride as a 1M solution in THF (0.4 mL, 0.4 mmol) producing an instant color change to yellow. This was allowed to stir at room temperature for a period of 4 h. The solvent was then removed under reduced pressure to yield a black residue. This residue was taken up in EtOAc (20 mL) and washed with water (2×10 mL), brine (1×10 mL) and dried over Na$_2$SO$_4$. The solution was then filtered and concentrated under reduced pressure using rotary evaporation to reveal a yellow solid. This was purified via silica gel chromatography eluted with 70% EtOAc/hexanes to provide the title compound as a white solid (31 mg, 81%). $^1$H NMR (500 MHz, acetone-d$_6$, δ in ppm) 8.88 (br s, 1H), 7.48 (m, 3H), 7.38 (m, 1H), 7.06 (m, 1H), 6.86 (d, J=8.8 Hz, 1H), 5.68 (d, J=8.5 Hz, 1H), 5.10 (dd, J=3.6, 8.5 Hz, 1H), 4.83 (br s, 1H), 4.62 (m, 1H), 2.40 (s, 3H), 1.41 (d, J=6.3 Hz, 3H).

Example 8

2-chloro-4-((1R,2S)-2-hydroxy-1-(5-(4-hydroxyphenyl)-1,3,4-oxadiazol-2-yl)propylamino)-3-methylbenzonitrile

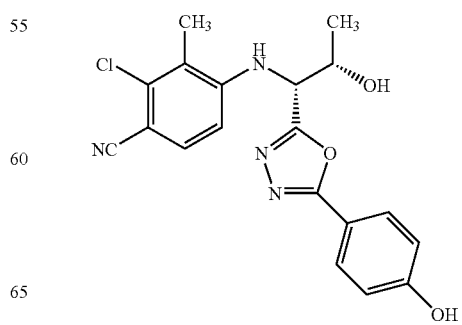

Intermediate 8a

N'-((2R,3S)-2-(3-chloro-4-cyano-2-methylphenylamino)-3-hydroxybutanoyl)-4-hydroxy-benzohydrazide

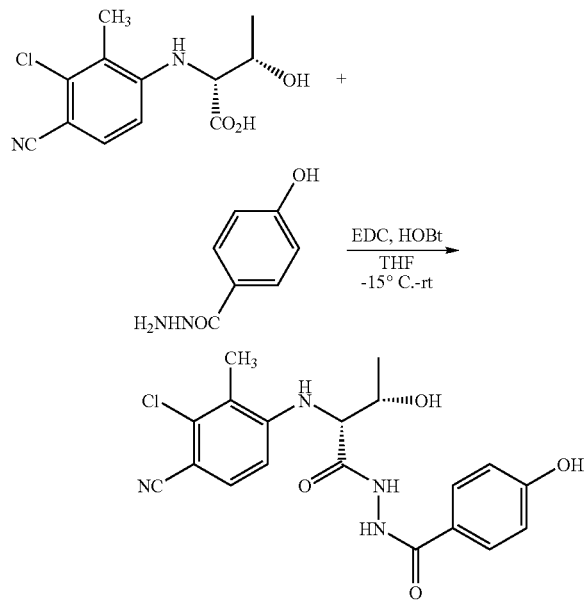

(2R,3S)-2-(3-chloro-4-cyano-2-methylphenylamino)-3-hydroxybutanoic acid (intermediate 1a) (534 mg, 1.9 mmol) and 4-hydroxy-benzohydrazide (304 mg, 2.0 mmol) were coupled similarly to the procedure described for the preparation of intermediate 1b. After column chromatography (3% methanol/EtOAc) the title compound was isolated as a white solid (490 mg, 61%). $^1$H NMR (500 MHz, acetone-d$_6$, δ in ppm) 9.76 (br s, 1H), 9.49 (br s, 1H), 9.15 (br s, 1H), 7.83 (AA'XX', J=8.8 Hz, 2H), 7.46 (d, J=8.6 Hz, 1H), 6.89 (AA'XX', J=8.8 Hz, 2H), 6.64 (d, J=8.7 Hz, 1H), 5.53 (d, J=7.2 Hz, 1H), 5.01 (br s, 1H), 4.39 (m, 1H), 4.11 (dd, J=3.0, 6.4 Hz, 1H), 2.33 (s, 3H), 1.33 (d, J=6.5 Hz, 3H).

Intermediate 8b 4-(tert-butyldimethylsilyloxy)-N'-((2R,3S)-3-(tert-butyldimethylsilyloxy)-2-(3-chloro-4-cyano-2-methylphenylamino)butanoyl)benzohydrazide

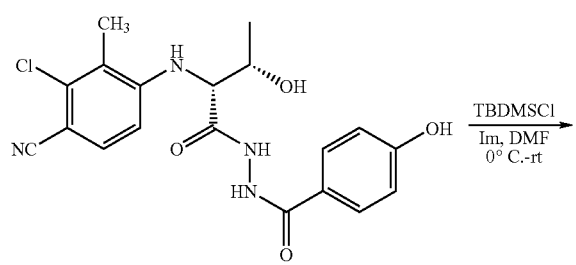

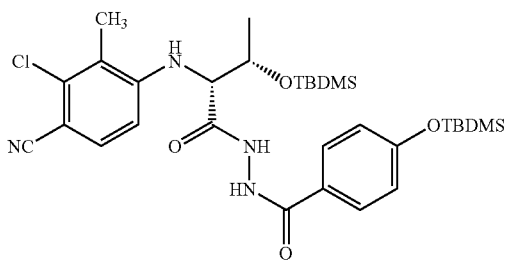

N'-((2R,3S)-2-(3-chloro-4-cyano-2-methylphenylamino)-3-hydroxybutanoyl)-4-hydroxy benzohydrazide (intermediate 8a) (490 mg, 1.2 mmol) was silyated using TBDMSCl (1.28 g, 8.5 mmol) and imidazole (1.57 g, 23 mmol) as described previously for intermediate 7b. After column chromatography (30% EtOAc/hexanes) the title compound was isolated as a white solid (453 mg, 59%). $^1$H NMR (500 MHz, CDCl$_3$, δ in ppm) 9.46 (d, J=5.9 Hz, 1H), 9.05 (d, J=5.7 Hz, 1H), 7.71 (AA'XX', J=8.6 Hz, 2H), 7.37 (d, J=8.6 Hz, 1H), 6.84 (AA'XX', J=8.7 Hz, 2H), 6.45 (d, J=8.7 Hz, 1H), 5.34 (d, J=6.5 Hz, 1H), 4.48 (m, 1H), 3.97 (m, 1H), 2.32 (s, 3H), 1.25 (d, J=6.2 Hz, 3H), 0.97 (s, 9H), 0.91 (s, 9H), 0.21 (s, 6H), 0.12 (s, 3H), 0.07 (s, 3H).

Intermediate 8c 4-((1R,2S)-2-(tert-butyldimethylsilyloxy)-1-(5-(4-(tert-butyldimethylsilyloxy)phenyl)-1,3,4-oxadiazol-2-yl)propylamino)-2-chloro-3-methylbenzonitrile

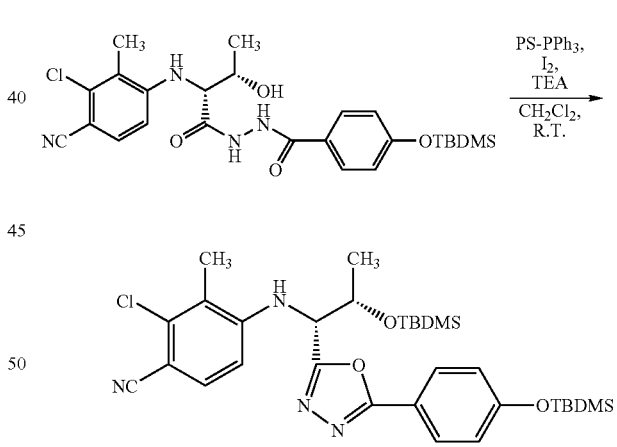

Dehydrative cyclization of 4-(tert-butyldimethylsilyloxy)-N'-((2R,3S)-3-(tert-butyldimethylsilyloxy)-2-(3-chloro-4-cyano-2-methylphenylamino)butanoyl)benzohydrazide (intermediate 8b) (453 mg, 0.72 mmol) with performed with polystyrene supported triphenylphosphine (PS-PPh$_3$) (3.0 mmol/g, 575 mg, 1.72 mmol), I$_2$ (435 mg, 1.71 mmol), and TEA (0.8 mL, 5.7 mmol) as described in the preparation of intermediate 7c. After column chromatography (30% EtOAc/hexanes) the title compound was isolated as a white solid (329 mg, 75%). $^1$H NMR (500 MHz, CDCl$_3$, δ in ppm) 7.81 (AA'XX', J=8.7 Hz, 2H), 7.32 (d, J=8.6 Hz, 1H), 6.91 (AA'XX', J=8.8 Hz, 2H), 6.47 (d, J=8.7 Hz, 1H), 5.35 (d, J=8.7 Hz, 1H), 4.77 (m, 1H), 4.52 (m, 1H), 2.36 (s, 3H), 1.40 (d, J=6.2 Hz, 3H), 0.98 (s, 9H), 0.86 (s, 9H), 0.22 (s, 6H), 0.06 (s, 3H), −0.18 (s, 3H).

Example 8

2-chloro-4-((1R,2S)-2-hydroxy-1-(5-(4-hydroxyphenyl)-1,3,4-oxadiazol-2-yl)propylamino)-3-methylbenzonitrile

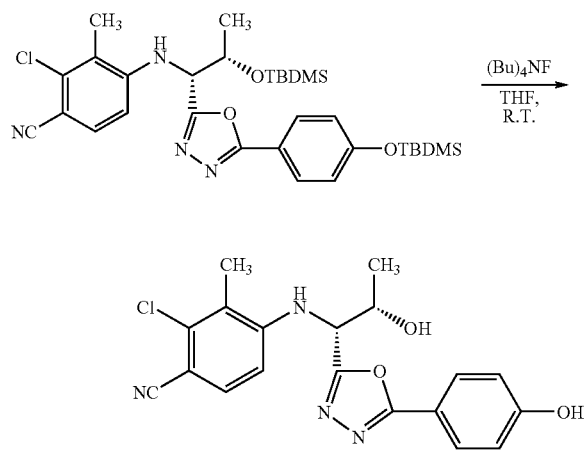

Deprotection of 4-((1R,2S)-2-(tert-butyldimethylsilyloxy)-1-(5-(4-(tert-butyldimethyl silyloxy)phenyl)-1,3,4-oxadiazol-2-yl)propylamino)-2-chloro-3-methylbenzonitrile (intermediate 8c) (327 mg, 0.5 mmol) was performed as described for the preparation of example 7 using tetrabutylammonium fluoride (1.0 M solution in THF, 2.1 mL, 2.1 mmol). After column chromatography (80% EtOAc/hexanes) the title compound was isolated as a white solid (176 mg, 86%). $^1$H NMR (500 MHz, acetone-$d_6$, δ in ppm) 7.84 (AA'XX', J=9.0 Hz, 2H), 7.49 (d, J=8.7 Hz, 1H), 6.99 (AA'XX', J=9 Hz, 2H), 6.86 (d, J=8.7 Hz, 1H), 5.67 (d, J=8.4 Hz, 1H), 5.06 (dd, J=3.8, 8.3 Hz, 1H), 4.60 (dd, J=3.6, 6.3 Hz, 1H), 2.39 (s, 3H), 1.40 (d, J=6.3 Hz, 3H).

Example 9

2-chloro-4-((1R,2R)-2-hydroxy-1-(5-(3-hydroxyphenyl)-1,3,4-oxadiazol-2-yl)propylamino)-3-methylbenzonitrile

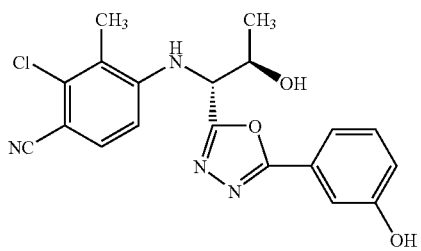

Intermediate 9a

N'-((2R,3R)-2-(3-chloro-1-cyano-2-methylphenylamino)-3-hydroxybutanoyl)-3-hydroxy-benzohydrazide

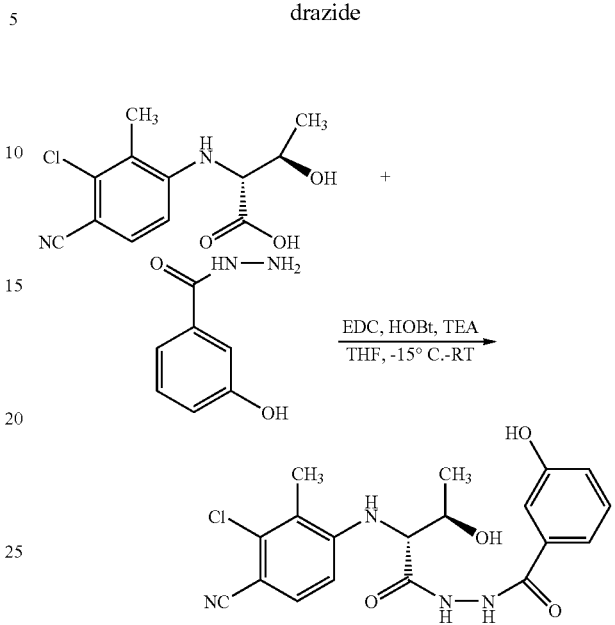

(2R,3R)-2-(3-chloro-4-cyano-2-methylphenylamino)-3-hydroxybutanoic acid (663 mg, 2.5 mmol) (intermediate 3a) and 3-hydroxy-benzohydrazide (376 mg, 2.5 mmol) were coupled similarly to the procedure used for intermediate 1b. After column chromatography (5% methanol/EtOAc) the title compound was isolated as a white solid (615 mg, 62%). $^1$H NMR (500 MHz, acetone-$d_6$, δ in ppm) 9.79 (br s, 1H), 8.81 (br s, 1H), 7.45 (ad, J=8.7 Hz, 1H), 7.38 (m, 2H), 7.27 (t, J=7.87 Hz, 1H), 7.02 (m, 1H), 6.71 (d, J=8.7 Hz, 1H), 5.61 (m, 1H), 4.23 (m, 1H), 4.14 (m, 1H), 2.29 (s, 3H), 1.37 (d, J=6.5 Hz, 3H).

Intermediate 9b 3-(tert-butyldimethylsilyloxy)-N'-((2R,3R)-3-(tert-butyldimethylsilyloxy)-2-(3-chloro-4-cyano-2-methylphenylamino)butanoyl)benzohydrazide

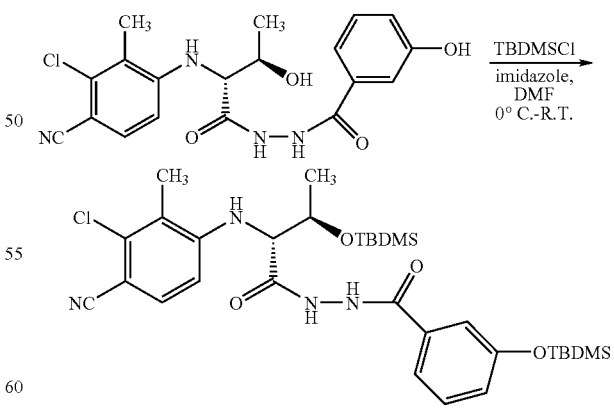

N'-((2R,3R)-2-(3-chloro-4-cyano-2-methylphenylamino)-3-hydroxybutanoyl)-3-hydroxybenzohydrazide (intermediate 9a) (564 mg, 1.4 mmol) was protected using TBDMSCl (1.47 g, 10 mmol) and imidazole (1.81 g, 27 mmol) as described previously for intermediate 7b. After column chromatography (40% EtOAc/hexanes) the title compound was isolated as a white solid (397 mg, 45%). ¹H NMR (500 MHz, CDCl₃, δ in ppm) 9.65 (d, J=5.4 Hz, 1H), 9.35 (d, J=5.4 Hz, 1H), 7.35 (m, 1H), 7.25 (m, 3H), 6.98 (m, 1H), 6.53 (d, J=8.7 Hz, 1H), 4.95 (d, J=6.1 Hz, 1H), 4.33 (m, 1H), 4.04 (at, J=5.6 Hz, 1H), 2.36 (br s, 1H), 2.26 (s, 3H), 1.33 (d, J=6.3 Hz, 3H), 0.95 (s, 9H), 0.87 (s, 9H), 0.17 (s, 6H), 0.11 (s, 3H), 0.06 (s, 3H).

Intermediate 9c 4-((1R,2R)-2-(tert-butyldimethylsilyloxy)-1-(5-(3-(tert-butyldimethylsilyloxy)phenyl)-1,3,4-oxadiazol-2-yl)propylamino)-2-chloro-3-methylbenzonitrile

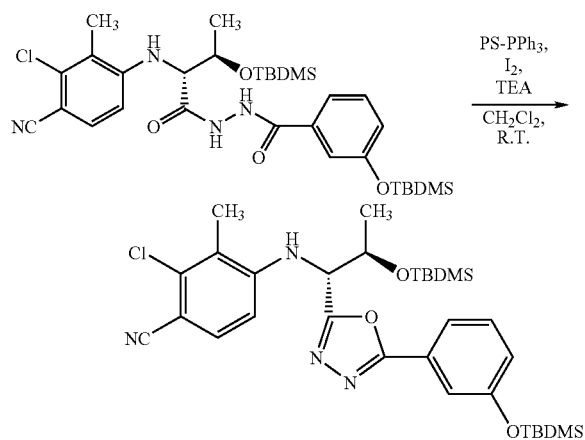

3-(tert-butyldimethylsilyloxy)-N'-((2R,3R)-3-(tert-butyldimethylsilyloxy)-2-(3-chloro-4-cyano-2-methylphenylamino)butanoyl)benzohydrazide (intermediate 9b) (362 mg, 0.57 mmol) was cyclized with PS-PPh₃ (3.0 mmol/g, 389 mg, 1.2 mmol), I₂ (289 mg, 1.1 mmol), and TEA (0.65 mL, 4.7 mmol) as described for the preparation of intermediate 7c. After column chromatography (20% EtOAc/hexanes) the title compound was isolated as a white solid (229 mg, 65%). ¹H NMR (500 MHz, CDCl₃, δ in ppm) 7.56 (m, 1H), 7.44 (m, 1H), 7.33 (m, 2H), 6.98 (m, 1H), 6.62 (d, J=8.8 Hz, 1H), 5.13 (ad, J=9 Hz, 1H), 4.83 (m, 1H), 4.44 (m, 1H), 2.32 (s, 3H), 1.30 (d, J=6.4 Hz, 3H), 0.99 (s, 9H), 0.93 (s, 9H), 0.21 (s, 6H), 0.13 (s, 3H), 0.11 (s, 3H).

Example 9

2-chloro-4-((1R,2R)-2-hydroxy-1-(5-(3-hydroxyphenyl)-1,3,4-oxadiazol-2-yl)propylamino)-3-methylbenzonitrile

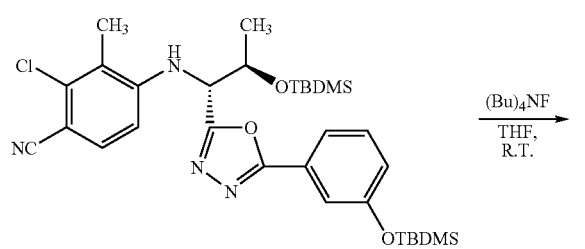

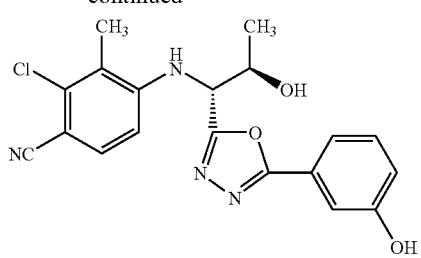

4-((1R,2R)-2-(tert-butyldimethylsilyloxy)-1-(5-(3-(tert-butyldimethylsilyloxy)phenyl)-1,3,4-oxadiazol-2-yl)propylamino)-2-chloro-3-methylbenzonitrile (intermediate 9c) (226 mg, 0.37 mmol) was deprotected using tetrabutylammonium fluoride (1.0 M solution in THF, 1.5 mL, 1.5 mmol) as described in the preparation of example 7. After column chromatography (80% EtOAc/hexanes) the title compound was isolated as a white solid (140 mg, quant.). ¹H NMR (500 MHz, acetone-d₆, δ in ppm) 8.87 (br s, 1H), 7.46 (m, 3H), 7.37 (at, J=8.1 Hz, 1H), 7.05 (m, 1H), 6.87 (d, J=8.7 Hz, 1H), 5.86 (d, J=8.8 Hz, 1H), 5.06 (dd, J=5.5, 8.8 Hz, 1H), 4.73 (br s, 1H), 4.53 (m, 1H), 2.35 (s, 3H), 1.42 (d, J=6.3 Hz, 3H).

Example 10

2-chloro-4-((1R,2R)-2-hydroxy-1-(5-(4-hydroxyphenyl)-1,3,4-oxadiazol-2-yl)propylamino)-3-methylbenzonitrile

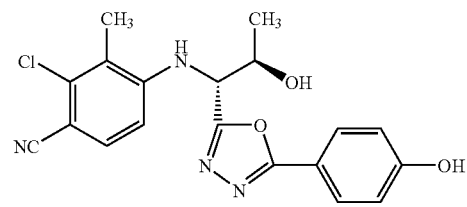

Intermediate 10a

N'-((2R,3R)-2-(3-chloro-4-cyano-2-methylphenylamino)-3-hydroxybutanoyl)-4-hydroxybenzohydrazide

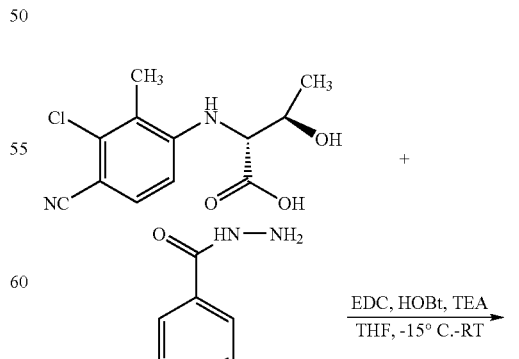

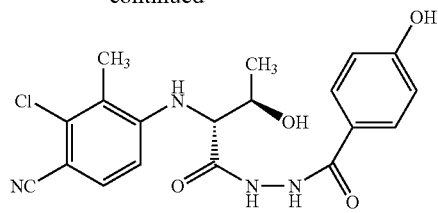

(2R,3R)-2-(3-chloro-4-cyano-2-methylphenylamino)-3-hydroxybutanoic acid (intermediate 3a) (503 mg, 1.9 mmol) was coupled with 4-hydroxy-benzohydrazide (285 mg, 1.9 mmol) similarly to the procedure described for the preparation of intermediate 1b. Trituration with hot methylene chloride provided the title compound as a white solid (380 mg, 62%). $^1$H NMR (500 MHz, acetone-$d_6$, δ in ppm) 9.68 (br s, 1H), 9.30 (br s, 1H), 7.85 (AA'XX', J=8.7 Hz, 2H), 7.52 (d, J=8.7 Hz, 1H), 6.91 (AA'XX', J=8.8 Hz, 2H), 6.71 (d, J=8.6 Hz, 1H), 5.59 (d, J=7.1 Hz, 1H), 4.84 (br s, 1H), 4.20 (m, 1H), 4.09 (m, 1H), 2.34 (s, 3H), 1.37 (d, J=6.3 Hz, 3H).

Intermediate 10b 4-(tert-butyldimethylsilyloxy)-N'-((2R,3R)-3-(tert-butyldimethylsilyloxy)-2-(3-chloro-4-cyano-2-methylphenylamino)butanoyl)benzohydrazide

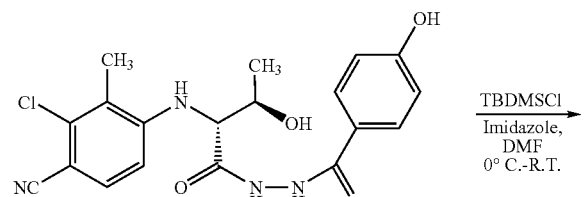

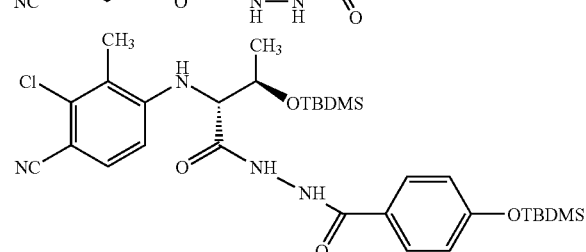

N'-((2R,3R)-2-(3-chloro-4-cyano-2-methylphenylamino)-3-hydroxybutanoyl)-4-hydroxybenzohydrazide (intermediate 10a) (380 mg, 0.9 mmol) was protected using TBDMSCl (854 mg, 5.7 mmol) and imidazole (772 mg, 11.3 mmol) as described for the preparation of intermediate 7b. After column chromatography (30% EtOAc/hexanes) the title compound was isolated as a white solid (203 mg, 34%). $^1$H NMR (500 MHz, CDCl$_3$, δ in ppm) 9.47 (d, J=5.5 Hz, 1H), 9.08 (d, J=5.5 Hz, 1H), 7.69 (AA'XX', J=8.6 Hz, 2H), 7.32 (d, J=8.6 Hz, 1H), 6.83 (AA'XX', J=8.6 Hz, 2H), 6.55 (d, J=8.7 Hz, 1H), 5.94 (d, J=6.0 Hz, 1H), 4.35 (m, 1H), 4.02 (at, J=5.4 Hz, 1H), 2.27 (s, 3H), 1.35 (d, J=6.3 Hz, 3H), 0.97 (s, 9H), 0.90 (s, 9H), 0.20 (s, 6H), 0.13 (s, 3H), 0.08 (s, 3H).

Intermediate 10c 4-((1R,2R)-2-(tert-butyldimethylsilyloxy)-1-(5-(4-(tert-butyldimethylsilyloxy)phenyl)-1,3,4-oxadiazol-2-yl)propylamino)-2-chloro-3-methylbenzonitrile

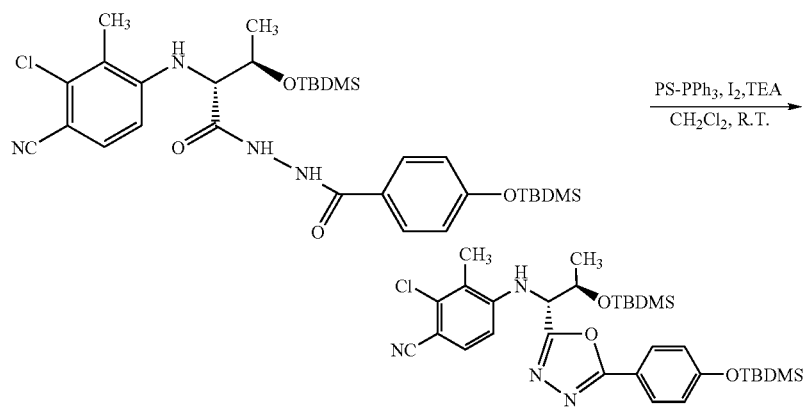

4-(tert-butyldimethylsilyloxy)-N'-((2R,3R)-3-(tert-butyldimethylsilyloxy)-2-(3-chloro-4-cyano-2-methylphenylamino)butanoyl)benzohydrazide (intermediate 10b) (202 mg, 0.3 mmol) was cyclized with PS-PPh$_3$ (3.0 mmol/g, 209 mg, 0.63 mmol), I$_2$ (152 mg, 0.6 mmol), and TEA (0.33 mL, 2.4 mmol) as described for the preparation of intermediate 7c. After column chromatography (20% EtOAc/hexanes) the title compound was isolated as a white solid (147 mg, 75%). $^1$H NMR (500 MHz, CDCl$_3$, δ in ppm) 7.86 (AA'XX', J=8.7 Hz, 2H), 7.34 (d, J=8.6 Hz, 1H), 6.91 (AA'XX', J=8.7 Hz, 2H), 6.62 (d, J=8.7 Hz, 1H), 5.11 (d, J=8.8 Hz, 1H), 4.81 (dd, J=3.9, 8.8 Hz, 1H), 4.43 (m, 1H), 2.32 (s, 3H), 1.28 (d, J=6.3 Hz, 3H), 0.98 (s, 9H), 0.93 (s, 9H), 0.22 (s, 6H), 0.13 (s, 3H), 0.10 (s, 3H).

Example 10

2-chloro-4-((1R,2R)-2-hydroxy-1-(5-(4-hydroxyphenyl)-1,3,4-oxadiazol-2-yl)propylamino)-3-methylbenzonitrile

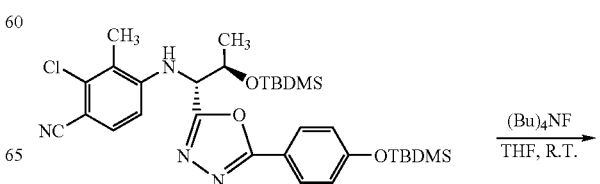

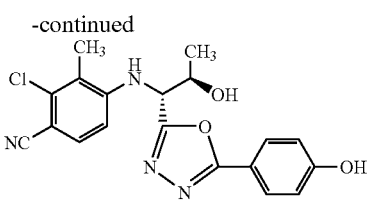

4-((1R,2R)-2-(tert-butyldimethylsilyloxy)-1-(5-(4-(tert-butyldimethylsilyloxy)phenyl)-1,3,4-oxadiazol-2-yl)propylamino)-2-chloro-3-methylbenzonitrile (intermediate 10c) (146 mg, 0.24 mmol) was deprotected in a similar manner to that for example 7 using tetrabutylammonium fluoride (1.0 M solution in THF, 0.95 mL, 0.95 mmol). After column chromatography (80% EtOAc/hexanes) the title compound was isolated as a white solid (90 mg, 98%). $^1$H NMR (500 MHz, acetone-$d_6$, δ in ppm) 8.01 (s, 1H), 7.84 (AA'XX', J=8.9 Hz, 2H), 7.48 (d, J=8.7 Hz, 1H), 6.97 (AA'XX', J=8.8 Hz, 2H), 6.88 (d, J=8.8 Hz, 1H), 5.85 (d, J=8.8 Hz, 1H), 5.0 (dd, J=5.5, 8.7 Hz, 1H), 4.50 (m, 1H), 2.35 (s, 3H), 1.41 (d, J=6.4 Hz, 3H).

Example 11

2-chloro-3-ethyl-4-((1R,2S)-2-hydroxy-1-(5-phenyl-1,3,4-oxadiazol-2-yl)propylamino)benzonitrile

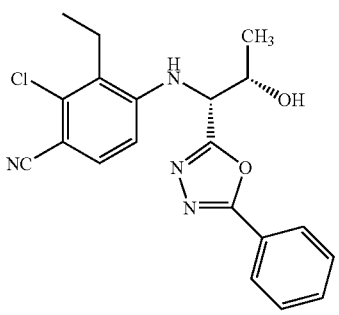

Intermediate 11a

2-Chloro-3-ethyl-4-fluorobenzonitrile

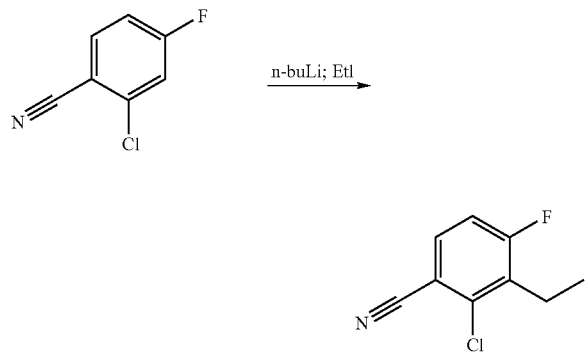

A 500 mL round bottomed flask was charged with diisopropylamine (11.81 mL, 83.60 mmol), anhydrous THF (30 mL) and a magnetic stir bar while being maintained under at atmosphere of $N_2$. The mixture was stirred and cooled to −5° C. with the aid of an ice/methanol bath whereupon a 2.5M solution of n-BuLi (30.87 mL, 77.17 mmol) was added dropwise and the mixture stirred for a further hour. The LDA was then added via cannula to a 500 mL three-necked round bottomed flask containing a pre-cooled solution of 2-chloro-4-fluoro-benzonitrile (10.0 g, 64.31 mmol) in anhydrous THF at −78° C. The reaction mixture was stirred and maintained at this temperature for 4.5 h whereupon iodoethane was added slowly. When the addition was complete the mixture was stirred overnight and allowed to gradually warm to room temperature. After 18 h a saturated aqueous solution of ammonium chloride (60 mL) was added to the mixture, followed by EtOAc (50 mL). The phases were partitioned and the aqueous phase was extracted with EtOAc. The combined organics were dried ($Na_2SO_4$) and concentrated to furnish a yellow solid (12 g). A sample of the mixture was taken and $^1$H NMR analysis revealed that a trace of starting material remained. The crude mixture was then subjected to flash column chromatography on silica gel [hexanes-EtOAc (95:5) as eluent] to furnish the title compound (5 g, 42%). $^1$H NMR (500 MHz, CDCl$_3$, δ in ppm) 7.56 (dd, J=1.0, 8.0 Hz, 1H), 7.07 (t, J=8 Hz, 1H), 2.82 (q, J=7 Hz, 2H), 1.19 (t, J=7 Hz, 3H).

Intermediate 11b (2R,3S)-2-(3-chloro-4-cyano-2-ethylphenylamino)-3-hydroxybutanoic acid

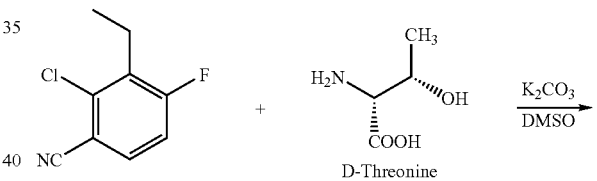

4-Fluoro-2-chloro-3-ethyl benzonitrile (1.0 g, 5.45 mmol), D-threonine (779 mg, 6.54 mmol), potassium carbonate (1.51 g, 10.9 mmol) and DMSO (6 mL) were heated at 85° C. for 17.5 h. The reaction mixture was allowed to cool to room temperature whereupon water (20 mL) was added followed by citric acid monohydrate (2 g). After stirring for 10 min the mixture was partitioned between EtOAc (40 mL) and water. The organic phase was then washed with water (15 mL), brine (15 mL), dried ($Na_2SO_4$) and concentrated to furnish a pale yellow solid (7.2 g). This crude product was then passed through a silica-plug [hexanes-EtOAc (95:5) as eluent] to furnish a white solid (928 mg), which was used directly in the next step.

Intermediate 11c

N'-((2R,3S)-2-(3-chloro-4-cyano-2-ethylphenylamino)-3-hydroxybutanoyl)benzohydrazide

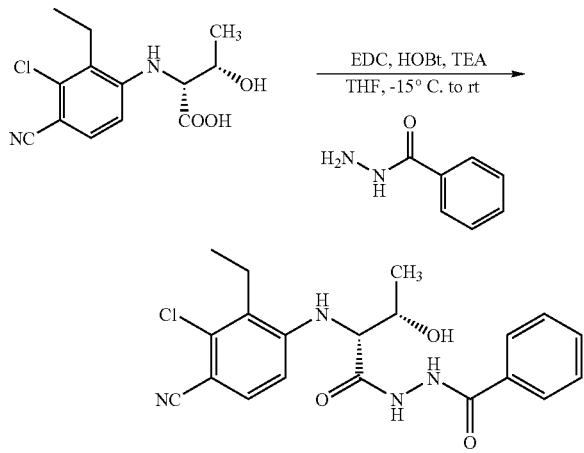

(2R,3S)-2-(3-chloro-4-cyano-2-ethylphenylamino)-3-hydroxybutanoic acid (850 mg, 3 mmol) (intermediate 11b), benzoic hydrazide (408 mg, 3 mmol) and anhydrous THF (20 mL) were placed in a 50 mL round bottomed flask and the mixture was cooled to −15° C. 1-Hydroxybenzotriazole hydrate (405 mg, 3 mmol) was added to the mixture together with N-(3-Dimethylaminopropyl)-N'-ethylcarbodiimide HCl (864 mg, 4.51 mmol) at −15° C. followed by triethylamine (0.628 mL, 4.51 mmol). The reaction mixture was maintained at −15° C. and stirred for 1 h, after which stirring continued overnight while the mixture slowly warmed to room temperature. After 18 h the mixture was filtered under vacuum and the residue washed with THF (30 mL). The THF solution was concentrated to ca. 10 mL, whereupon EtOAc (40 mL) was added followed by water (30 mL). The phases were partitioned and the organic phase washed with water (15 mL), brine (15 mL) dried (Na₂SO₄) and concentrated to furnish a light brown solid (1.05 g). Purification by flash column chromatography on silica gel [EtOAc-hexanes (4:1) as eluent] afforded the title compound as a white solid (62% yield). $^1$H NMR (500 MHz, acetone d₆, δ in ppm) 9.7 (br s, 2H), 7.97 (d, J=8 Hz, 2H), 7.44-7.62 (m, 4H), 6.7 (d, J=8 Hz, 1H), 5.64 (d, J=7 Hz, 1H), 4.38-4.41 (m, 1H), 4.1-4.17 (m, 1H), 2.81-2.87 (q, J=7 Hz, 2H), 1.38 (d, J=6 Hz, 3H), 1.2 (t, J=7 Hz, 3H).

Example 11

2-chloro-3-ethyl-4-((1R,2S)-2-hydroxy-1-(5-phenyl-1,3,4-oxadiazol-2-yl)propylamino)benzonitrile

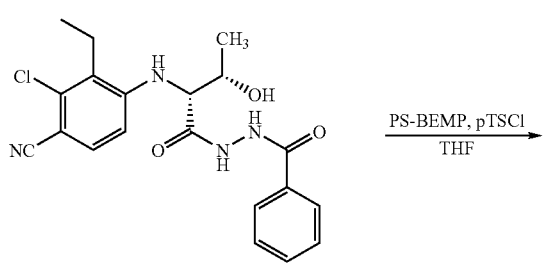

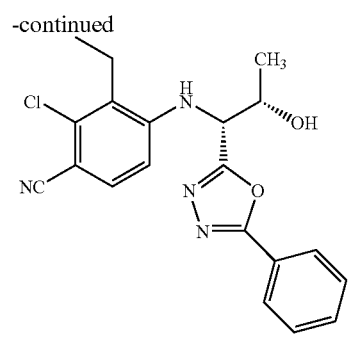

To a solution of N'-((2R,3S)-2-(3-chloro-4-cyano-2-ethylphenylamino)-3-hydroxybutanoyl)benzohydrazide (intermediate 11c) (195 mg, 0.486 mmol) in anhydrous THF (20 mL) at room temperature was added 2-tert-butylamino-2-diethylamino-1,3-dimethyl perhydro-1,3,2-diazaphosphorine on polystyrene (667 mg, 2.2 mmol base/g) followed by para-toluene sulfonyl chloride (p-TSCl) (111 mg, 0.583 mmol) and the mixture was stirred for 1 h. The mixture was filtered under suction and the residue washed with acetone (200 mL) followed by methanol (200 mL). The filtrate was then concentrated and subjected to flash column chromatography [EtOAc-hexanes (3:2)] to give two fractions. The first-eluted material was identified by $^1$H NMR spectroscopy as (Z)-2-chloro-3-ethyl-4-(1-(5-phenyl-1,3,4-oxadiazol-2-yl)prop-1-enylamino)benzonitrile (34 mg, 20%) $^1$H NMR (500 MHz, CDCl₃, δ in ppm) 8.04 (d, J=8 Hz, 2H), 7.57-7.6 (m, 4H), 7.39 (d, J=8 Hz, 1H), 6.79 (q, J=7 Hz, 1H), 6.5 (d, J=7 Hz, 1H), 5.82 (s, 1H), 2.93 (q, J=7 Hz, 2H), 1.83 (d, J=6 Hz, 3H), 1.38 (t, J=7 Hz, 3H).

The second-eluted material was the desired 2-chloro-3-ethyl-4-((1R,2S)-2-hydroxy-1-(5-phenyl-1,3,4-oxadiazol-2-yl)propylamino)benzonitrile (69 mg, 37%). $^1$H NMR (500 MHz, CDCl₃, δ in ppm) 7.82 (d, J=8 Hz, 2H), 7.47-7.50 (m, 1H), 7.39-7.41 (m, 2H) 7.32-7.37 (m, 1H), 6.58 (d, J=8 Hz, 1H), 5.44 (d, J=8 Hz, 1H), 4.78 (d, J=8 Hz, 1H), 4.60-4.62 (m, 1H), 3.94 (m, 1H), 2.83 (q, J=7 Hz, 2H), 1.42 (d, J=6 Hz, 3H), 1.22 (t, J=7 Hz, 3H).

Example 12

2-chloro-4-((1R,2S)-2-hydroxy-1-(5-phenyl-1,3,4-oxadiazol-2-yl)propylamino)benzonitrile

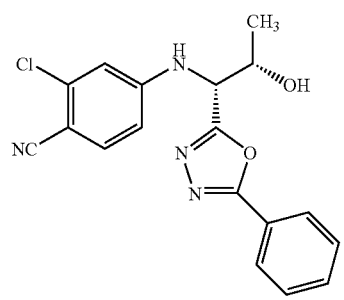

Intermediate 12a

(2R,3S)-2-(3-chloro-4-cyanophenylamino)-3-hydroxybutanoic acid

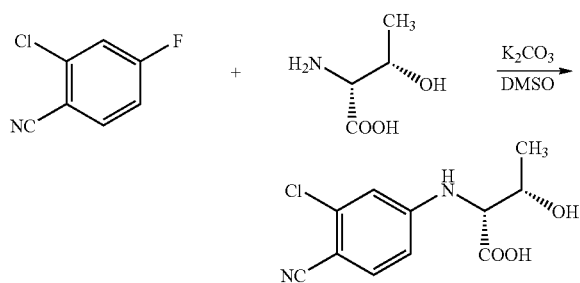

2-chloro-4-fluorobenzonitrile (60702-69-4) (2.0 g, 12.86 mmol) was mixed together with H-D-Thr-OH (1.84 g, 15.43 mmol) in DMSO (30 mL). $K_2CO_3$ (3.73 g, 27.0 mmol) was added to the reaction mixture and stirred at 75° C. for 24 h. The reaction mixture was cooled down to room temperature and poured slowly into a 10% citric acid solution and stirred for 10 min at room temperature. The solution was extracted with EtOAc several times to get the crude product. The crude product was chromatographed with a gradient of hexane EtOAc and then with EtOAc, 100% to get the pure final product 1.8 g): $^1$H NMR (500 MHz, acetone-$d_6$, δ in ppm) 7.51 (d, J=9 Hz, 1H), 6.95 (s, 1H), 6.82 (d, J=9 Hz, 1H), 5.17 (d, J=9 Hz, 1H), 4.42 (m, 1H), 4.22 (d, J=6 Hz, 1H), 2.34 (s, 3H), 1.28 (d, J=6 Hz, 3H).

Intermediate 12b

((2R,3S)-2-(3-chloro-4-cyanophenylamino)-3-hydroxybutanoyl)benzohydrazide

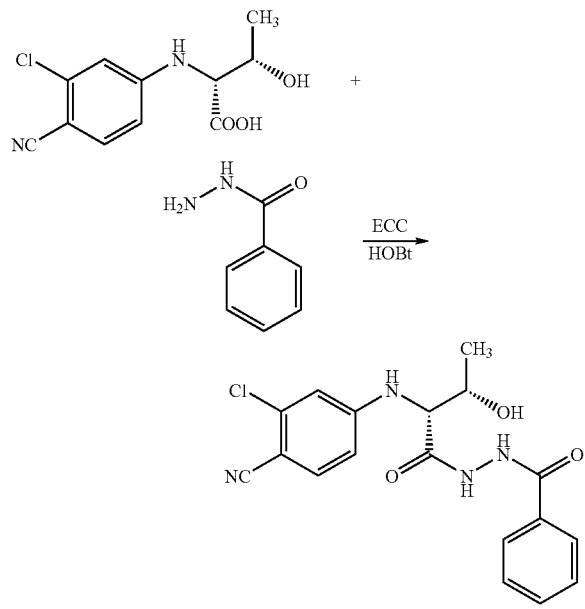

(2R,3S)-2-(3-chloro-4-cyanophenylamino)-3-hydroxybutanoic acid (intermediate 12a) (400 mg, 1.57 mmol) and benzoic hydrazide (214 mg, 1.57 mmol) were mixed together in THF (60 mL) and cooled to −20° C. under $N_2$ atmosphere. To the pre-cooled reaction mixture were added HOBt (212 mg, 1.57 mmol), TEA (238 mg, 2.36 mmol) followed by EDC (452 mg, 2.36 mmol). The reaction mixture was allowed to stir at −20° C. for 1 h and then at room temperature overnight. After the reaction was complete, the urea was filtered off and the solution was washed with water, 5% citric acid followed by 5% $NaHCO_3$ to get the crude hydrazide product 450 mg). $^1$H NMR (500 MHz, acetone-$d_6$, δ in ppm) 9.83 (br s, 1H), 9.42 (br s, 1H), 7.95 (d, J=9 Hz, 2H), 7.54 (m, 4H), 6.97 (s, 1H), 6.82 (d, J=9 Hz, 1H), 6.28 (d, J=9 Hz, 1H), 4.31 (m, 1H), 4.04 (m, 1H), 1.30 (d, J=6 Hz, 3H).

Example 12

2-chloro-4-((1R,2S)-2-hydroxy-1-(5-phenyl-1,3,4-oxadiazol-2-yl)propylamino)benzonitrile

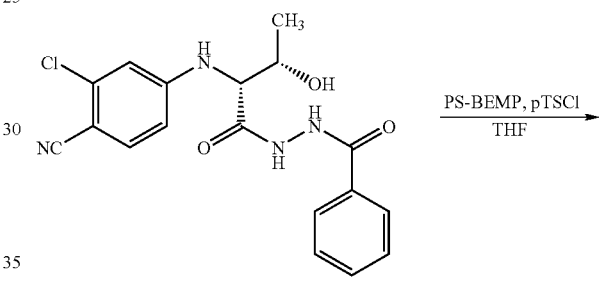

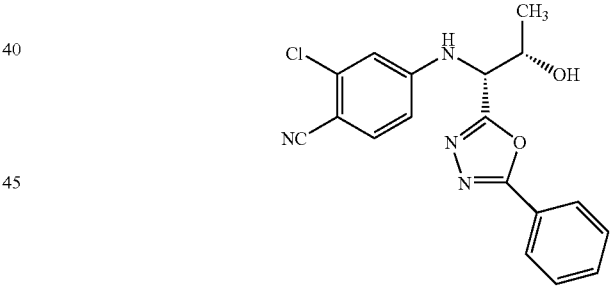

The crude material of N'-((2R,3S)-2-(3-chloro-4-cyanophenylamino)-3-hydroxybutanoyl)benzohydrazide (intermediate 12b) (509 mg, 1.36 mmol) was added to THF (100 mL) stirred at room temperature. PS-BEMP (1.86 g, 4.09 mmol base) was added to the solution followed by slow addition of p-TSCl (286 mg, 1.50 mmol). The reaction mixture was stirred for 2 h and the progress of the reaction was monitored by TLC. After the completion of the reaction, the BEMP reagent was filtered off and the solution concentrated to get the crude material. The crude material was chromatographed with hexanes:EtOAc (6:4) to provide the title compound (140 mg). $^1$H NMR (500 MHz, $CDCl_3$, δ in ppm) 7.93 (d, J=9 Hz, 2H), 7.54 (m, 1H), 7.46 (m, 3H), 6.83 (s, 1H), 6.65 (d, J=9 Hz, 1H), 5.35 (d, J=9 Hz, 1H), 4.70 (d, J=9 Hz, 1H), 4.62 (m, 1H), 3.30 (d, J=5 Hz, 1H), 1.42 (d, J=6 Hz, 3H).

Example 13

4-((1R,2S)-2-hydroxy-1-(5-phenyl-1,3,4-oxadiazol-2-yl)propylamino)-1-naphthonitrile

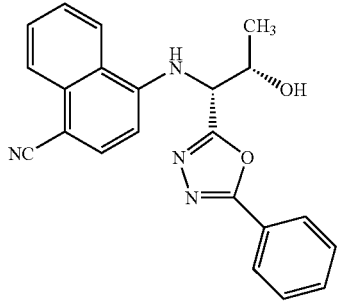

Intermediate 13a (2R,3S)-2-(4-cyanonaphthalen-1-ylamino)-3-hydroxybutanoic acid

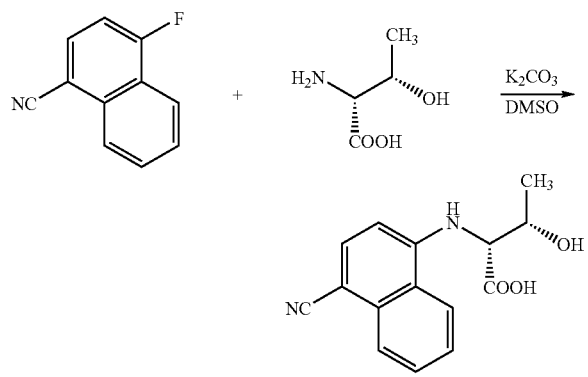

4-fluoro-1-naphthonitrile (13916-99-9) (1.0 g, 5.84 mmol) was mixed together with H-D-Thr-OH (835 mg, 7.01 mmol) in DMSO (20 mL). $K_2CO_3$ (1.61 g, 11.68 mmol) was added to the reaction mixture and stirred at 75° C. for 24 h. The reaction mixture was cooled to room temperature and poured slowly into a 10% citric acid solution and stirred for 10 min at room temperature. The solution was extracted with EtOAc several times to get the crude product. The crude product was chromatographed with a gradient of hexane/EtOAc and then with EtOAc, 100% to get the pure final product (1.1 g): $^1$H NMR (500 MHz, acetone-$d_6$, δ in ppm) 8.25 (d, J=9 Hz, 1H), 8.09 (d, J=9 Hz, 1H), 7.84 (d, J=9 Hz, 1H), 7.75 (t, J=9 Hz, 1H), 7.65 (t, J=9 Hz, 1H), 6.70 (d, J=9 Hz, 1H), 6.32 (d, J=9 Hz, 1H), 4.53 (m, 1H), 4.38 (m, 1H), 1.40 (d, J=6 Hz, 3H).

Intermediate 13b

N'-((2R,3S)-2-(4-cyanonaphthalen-1-ylamino)-3-hydroxybutanoyl)benzohydrazide

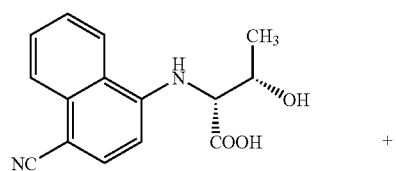

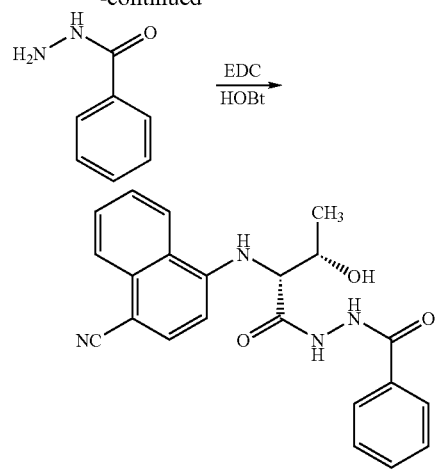

(2R,3S)-2-(4-cyanonaphthalen-1-ylamino)-3-hydroxybutanoic acid (intermediate 13a) (500 mg, 1.85 mmol) and benzoic hydrazide (252 mg, 1.85 mmol) were mixed together in THF (70 mL) and cooled to −20° C. under $N_2$ atmosphere. To the pre-cooled reaction mixture were added HOBt (250 mg, 1.85 mmol), TEA (275 mg, 2.77 mmol) followed by EDC (532 mg, 2.77 mmol). The reaction mixture was allowed to stir at −20° C. for an hour and then at room temperature overnight. After the reaction was complete, the urea was filtered and the solution was washed with water, 5% citric acid followed by 5% $NaHCO_3$ to get the crude hydrazide product (610 mg, 85%), which was used without further purification.

Example 13

4-((1R,2S)-2-hydroxy-1-(5-phenyl-1,3,4-oxadiazol-2-yl)propylamino)-1-naphthonitrile

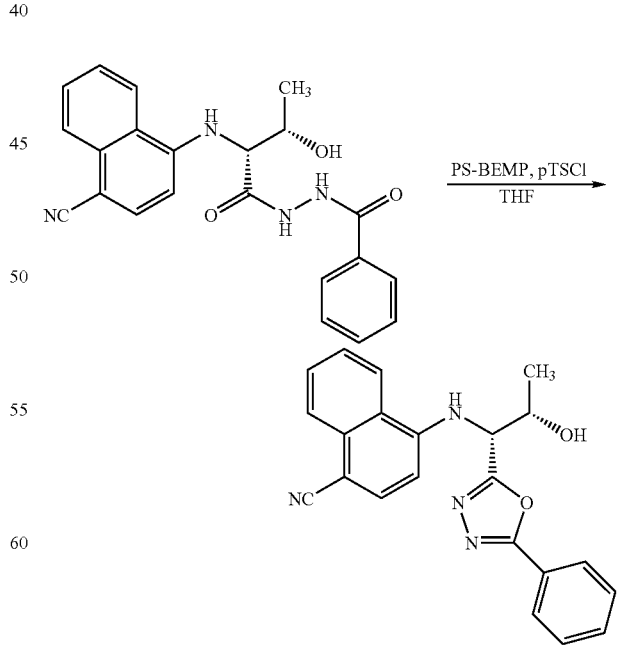

The crude material of N'-((2R,3S)-2-(4-cyanonaphthalen-1-ylamino)-3-hydroxybutanoyl)benzohydrazide (intermediate 13b) (602 mg, 1.5501 mmol) was added to THF (100 mL) stirred at room temperature. PS-BEMP (2.11 g, 4.65 mol base) was added to the solution followed by slow addition of p-TSCl (355 mg, 1.8601 mmol). The reaction mixture was stirred for 2 h and the progress of the reaction was monitored by TLC. After the completion of the reaction the BEMP reagent was filtered off and the solution concentrated to get the crude material. The crude material was chromatographed with hexanes:EtOAc (6:4) to give the product (160 mg, 28%). $^1$H NMR (500 MHz, CDCl$_3$, δ in ppm) 8.11 (d, J=9 Hz, 1H), 8.01 (d, J=9 Hz, 1H), 7.83 (d, J=9 Hz, 2H), 7.69 (d, J=9 Hz, 1H), 7.62 (t, J=9 Hz, 1H), 7.52 (t, J=9 Hz, 1H), 7.45 (t, J=9 Hz, 1H), 7.36 (t, J=9 Hz, 2H), 6.64 (d, J=9 Hz, 1H), 6.20 (d, J=9 Hz, 1H), 4.93 (dd, J=5.0, 9.0 Hz, 1H), 4.70 (m, 1H), 4.06 (d, J=5 Hz, 1H), 1.47 (d, J=6 Hz, 3H).

Example 14

(R)-2-chloro-4-(2-hydroxy-2-methyl-1-(5-phenyl-1,3,4-oxadiazol-2-yl)propylamino)-3-methylbenzonitrile

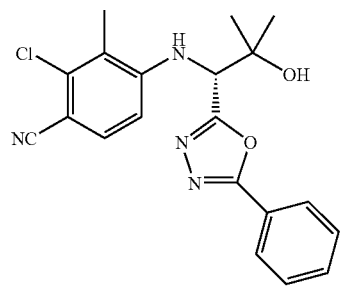

Intermediate 14a (R)-2-(3-chloro-4-cyano-2-methylphenylamino)-3-hydroxy-3-methylbutanoic acid

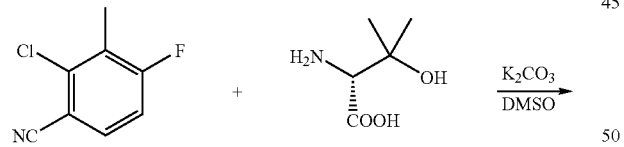

2-chloro-4-fluoro-3-methylbenzonitrile (1.06 g, 6.26 mmol) was mixed together with (R)-2-amino-3-hydroxy-3-methylbutanoic acid (1.00 g, 7.51 mmol) in DMSO (25 mL). K$_2$CO$_3$ (1.73 g, 12.52 mmol) was added to the reaction mixture and stirred at 75° C. for 24 h. Then the reaction mixture was cool down to room temperature and poured slowly in to a 10% citric acid solution and stirred for 10 min at room temperature. The solution was extracted with EtOAc several times to get the crude product. The crude product was chromatographed with a gradient of hexane/EtOAc (4:6) and then with EtOAc, 100% to get the title compound (1.40 g). $^1$H NMR (500 MHz, acetone-d$_6$, δ in ppm) 7.51 (d, J=9 Hz, 1H), 6.72 (d, J=9 Hz, 1H), 5.48 (d, J=9 Hz, 1H), 4.16 (d, J=9 Hz, 1H), 2.34 (s, 3H), 1.43 (s, 3H), 1.41 (s, 3H).

Intermediate 14b (R)—N'-(2-(3-chloro-4-cyano-2-methylphenylamino)-3-hydroxy-3-methylbutanoyl)benzohydrazide

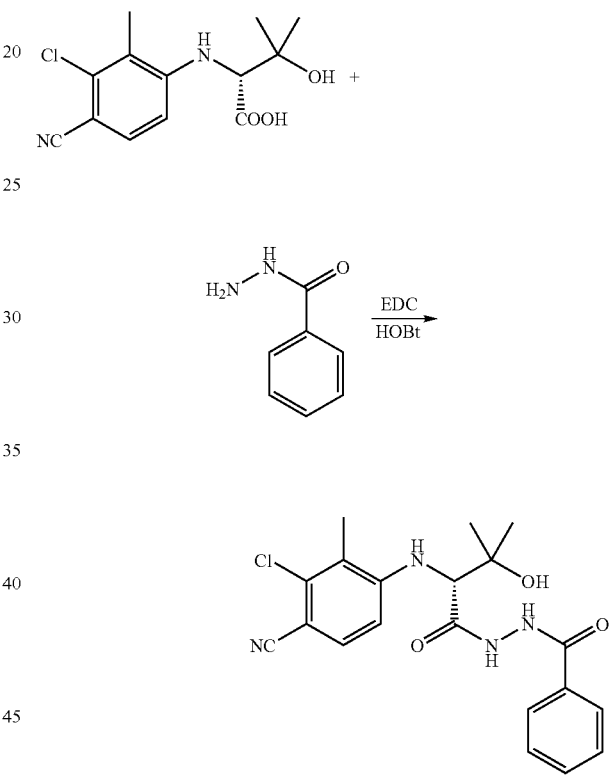

(R)-2-(3-chloro-4-cyano-2-methylphenylamino)-3-hydroxy-3-methylbutanoic acid (intermediate 14a) (200 mg, 0.71 mmol) and benzoic hydrazide (96 mg, 0.71 mmol) were mixed together in THF (40 mL) and cool down to −20° C. under N$_2$ atmosphere. To the pre-cooled reaction mixture were added HOBt (96 mg, 0.71 mmol), TEA (107 mg, 1.06 mmol) followed by EDC (203 mg, 1.06 mmol). The reaction mixture was allowed to stir at −20° C. for 1 h and then at room temperature overnight. After the reaction is complete, the urea was filtered and the solution was washed with water, 5% citric acid followed by 5% NaHCO$_3$ to give the crude hydrazide product (243 mg): $^1$H NMR (500 MHz, acetone-d$_6$, δ in ppm) 9.4-9.7 (br s, 2H), 7.94 (d, J=9 Hz, 2H), 7.59 (m, 1H), 7.52 (m, 3H), 6.73 (d, J=9 Hz, 1H), 5.56 (d, J=9 Hz, 1H), 4.08 (d, J=9 Hz, 1H), 2.38 (s, 3H), 1.47 (s, 3H), 1.42 (s, 3H).

Example 14

(R)-2-chloro-4-(2-hydroxy-2-methyl-1-(5-phenyl-1,3,4-oxadiazol-2-yl)propylamino)-3-methylbenzonitrile

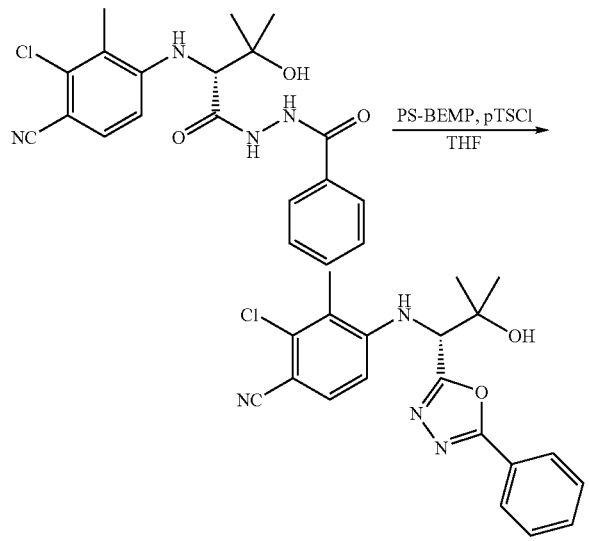

The crude material of (R)—N'-(2-(3-chloro-4-cyano-2-methylphenylamino)-3-hydroxy-3-methylbutanoyl)benzohydrazide (intermediate 14b) (218 mg, 0.54 mmol) was added to THF (50 mL) stirred at room temperature. PS-BEMP (742 mg, 1.63 mmol base) was added to the solution, followed by slow addition of p-TSCl (114 mg, 0.60 mmol). The reaction mixture was stirred for 1.5 h and the progress of the reaction was monitored by TLC. After the completion of the reaction, the BEMP reagent was filtered off and the solution concentrated to give the crude material. The crude material was chromatographed with hexanes:EtOAc (6:4) to give the title compound (75 mg, 28%): $^1$H NMR (500 MHz, CDCl$_3$, δ in ppm) 7.94 (d, J=9 Hz, 2H), 7.54 (m, 1H), 7.46 (m, 2H), 7.34 (d, J=9 Hz, 1H), 6.56 (d, J=9 Hz, 1H), 5.45 (d, J=9 Hz, 1H), 4.71 (d, J=9 Hz, 1H), 3.12 (s, 1H), 2.37 (s, 3H), 1.50 (s, 3H), 1.37 (s, 3H).

Example 15

(R)-2-chloro-4-(1-(5-(4-chlorophenyl)-1,3,4-oxadiazol-2-yl)-2-hydroxy-2-methylpropylamino)-3-methylbenzonitrile

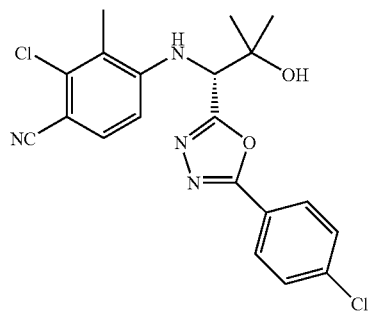

Intermediate 15a (R)-4-chloro-N'-(2-(3-chloro-4-cyano-2-methylphenylamino)-3-hydroxy-3-methylbutanoyl)benzohydrazide

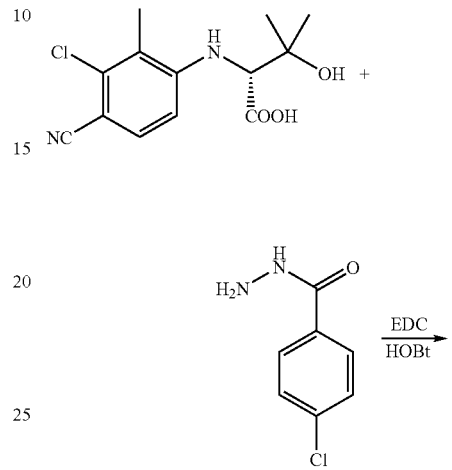

((R)-2-(3-chloro-4-cyano-2-methylphenylamino)-3-hydroxy-3-methylbutanoic acid (intermediate 14a) (200 mg, 0.71 mmol) and 4-chloro benzoic hydrazide (121 mg, 0.71 mmol) were mixed together in THF (40 mL) and cooled to −20° C. under N$_2$ atmosphere. To the pre-cooled reaction mixture were added HOBt (96 mg, 0.71 mmol), TEA (107 mg, 1.1 mmol) followed by EDC (203 mg, 1.1 mmol). The reaction mixture was allowed to stir at −20° C. for 1 h and then at room temperature overnight. After the reaction was complete, the urea was filtered off and the solution was washed with water, 5% citric acid followed by 5% NaHCO$_3$ to get the crude hydrazide product (243 mg): $^1$H NMR (500 MHz, acetone-d$_6$, δ in ppm) 9.4-9.7 (br s, 2H), 7.96 (d, J=9 Hz, 2H), 7.56 (m, 3H), 6.74 (d, J=9 Hz, 1H), 5.57 (d, J=9 Hz, 1H), 4.08 (d, J=9 Hz, 1H), 2.38 (s, 3H), 1.48 (s, 3H), 1.43 (s, 3H).

Example 15

(R)-2-chloro-4-(1-(5-(4-chlorophenyl)-1,3,4-oxadiazol-2-yl)-2-hydroxy-2-methylpropylamino)-3-methylbenzonitrile

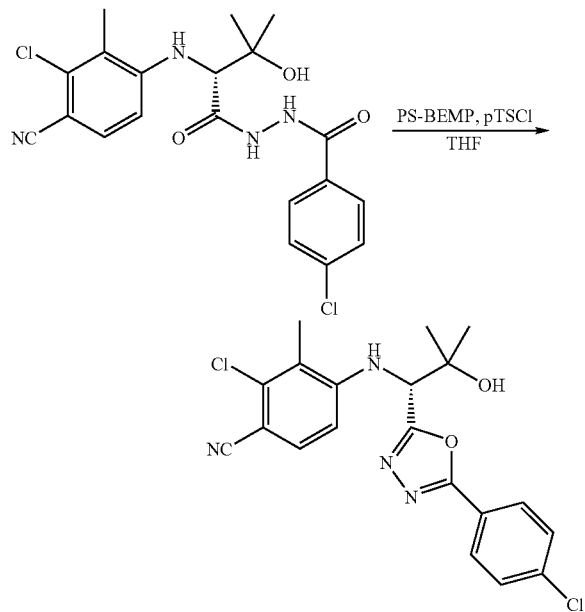

The crude material of (R)-4-chloro-N'-(2-(3-chloro-4-cyano-2-methylphenylamino)-3-hydroxy-3-methylbutanoyl)benzohydrazide (intermediate 15a) (230 mg, 0.53 mmol) was added to THF (50 mL) stirred at room temperature. PS-BEMP (721 mg, 1.59 mmol base) was added to the solution followed by slow addition of p-TSCl (111 mg, 0.58 mmol). The reaction mixture was stirred for 1 h and the progress of the reaction was monitored by TLC. After the completion of the reaction the BEMP reagent was filtered off and the solution concentrated to get the crude material. The crude material was chromatographed with hexanes:EtOAc (6:4) to provide the product (740 mg): $^1$H NMR (500 MHz; CDCl$_3$, δ in ppm) 7.95 (d, J=9 Hz, 2H), 7.50 (d, J=9 Hz, 2H), 39 (d, J=9 Hz, 1H), 6.63 (d, J=9 Hz, 1H), 5.37 (d, J=9 Hz, 1H), 4.74 (d, J=9 Hz, 1H), 2.36 (s, 3H), 1.52 (s, 3H), 1.36 (s, 3H).

Example 16

4-((1R,2S)-2-hydroxy-1-(5-phenyl-1,3,4-oxadiazol-2-yl)propylamino)-2-(trifluoromethyl)benzonitrile

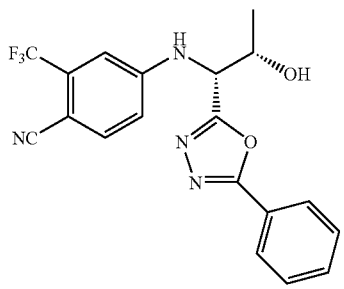

7.

Intermediate 16a (2R,3S)-2-(4-cyano-3-(trifluoromethyl)phenylamino)-3-hydroxybutanoic acid

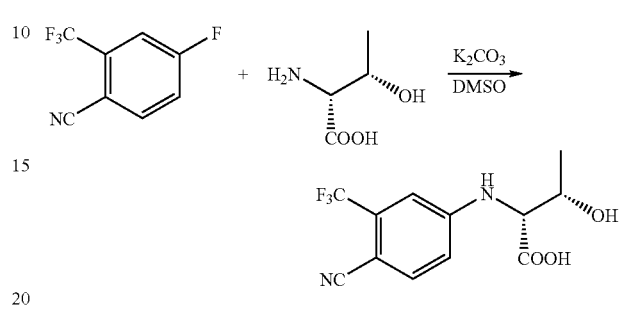

4-fluoro-2-(trifluoromethyl)benzonitrile (194853-86-6) (2.0 g, 10.6 mmol) was mixed together with H-D-Thr-OH (1.51 g, 12.69 mmol) in DMSO (30 mL). K$_2$CO$_3$ (3.06 g, 22.21 mmol) was added to the reaction mixture and stirred at 75° C. for 24 h. The reaction mixture was cooled to room temperature and poured slowly into a 10% citric acid solution and stirred for 10 min at room temperature. The solution was extracted with EtOAc several times to get the crude product. The crude product was chromatographed with a gradient of hexanes/EtOAc and then with EtOAc, 100% to get the pure final product (1.7 g): $^1$H NMR (500 MHz, CDCl$_3$, δ in ppm) 9.02 (br s, 1H), 7.76 (d, J=9 Hz, 1H), 7.52 (s, 1H), 7.39 (d, J=9 Hz, 1H), 6.41 d, J=9 Hz, 1H), 4.42 (m, 1H), 4.01 (m, 1H), 1.24 (d, J=6 Hz, 3H).

Intermediate 16b

N'N'-((2R,3S)-2-(4-cyano-3-(trifluoromethyl)phenylamino)-3-hydroxybutanoyl)benzohydrazide

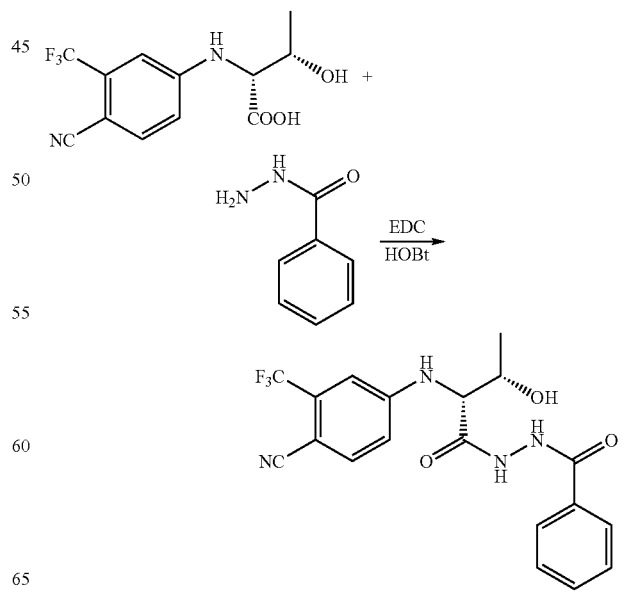

(2R,3S)-2-(4-cyano-3-(trifluoromethyl)phenylamino)-3-hydroxybutanoic acid (intermediate 16a) (400 mg, 1.39 mmol) and benzoic hydrazide (189 gm, 1.39 mmol) were mixed together in THF (60 mL) and cooled to −20° C. under $N_2$ atmosphere. To the pre-cooled reaction mixture were added HOBt (188 mg, 1.39 mmol), TEA (211 mg, 2.08 mmol) followed by EDC (399 mg, 2.08 mmol). The reaction mixture was allowed to stir at −20° C. for 1 h and then at room temperature overnight. After the reaction was complete, the urea was filtered off and the solution was washed with water, 5% citric acid followed by 5% $NaHCO_3$ to get the crude hydrazide product (470 mg). $^1$H NMR (500 MHz, acetone-$d_6$, δ in ppm) 9.43 (br s, 1H), 9.82 (br s, 1H), 7.92 (2H, d, J=9 Hz), 7.77 (1H, d, J=9 Hz), 7.45 (3H, m), 7.31 (1H, s), 7.02 (1H, d, J=9 Hz), 6.53 (d, 1H, J=9 Hz), 4.32 (1H, m), 4.17 (1H, m), 1.28 (3H, d, J=6 Hz).

Example 16

4-((1R,2S)-2-hydroxy-1-(5-phenyl-1,3,4-oxadiazol-2-yl)propylamino)-2-(trifluoromethyl)benzonitrile

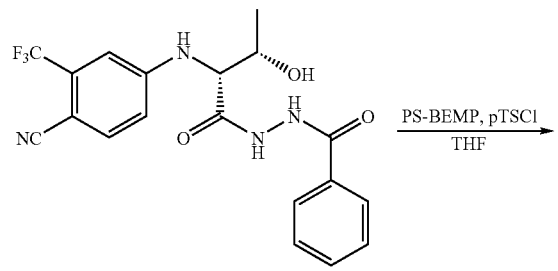

The crude material of N'N'-((2R,3S)-2-(4-cyano-3-(trifluoromethyl)phenylamino)-3-hydroxybutanoyl)benzohydrazide (intermediate 16b) (510 mg, 1.25 mmol) was added to THF (100 mL) stirred at room temperature. PS-BEMP (1.71 g, 3.76 mmol base) was added to the solution followed by slow addition of p-TSCl (263 mg, 1.38 mmol). The reaction mixture was stirred for 1 h and the progress of the reaction was monitored by TLC. After the completion of the reaction, the BEMP reagent was filtered off and the solution concentrated to get the crude material. The crude material was chromatographed with hexanes:EtOAc (6:4) to give the product (220 mg): $^1$H NMR (500 MHz, $CDCl_3$, δ in ppm) 7.95 (d, J=9 Hz, 2H), 7.63 (d, J=9 Hz, 1H), 7.55 (m, 1H), 7.49 (m, 2H), 7.11 (s, 1H), 6.90 (d, J=9 Hz, 1H), 5.45 (d, J=9 Hz, 1H), 4.76 (d, J=9 Hz, 1H), 4.66 (m, 1H), 3.06 (d, J=5H, 1 Hz), 1.44 (d, J=6 Hz, 3H).

Example 17

(R)-2-chloro-4-(2-hydroxy-1-(5-phenyl-1,3,4-oxadiazol-2-yl)ethylamino)-3-methylbenzonitrile

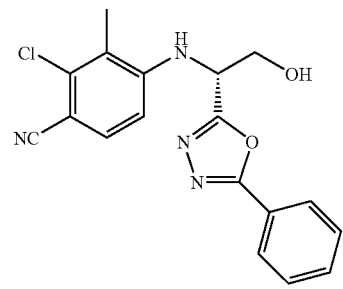

Intermediate 17a (R)-2-(3-chloro-4-cyano-2-methylphenylamino)-3-hydroxypropanoic acid 2-chloro-4-fluoro-3-methylbenzonitrile (500 mg, 2.95 mmol) was mixed together with H-D-Ser-OH (682 mg, 6.49 mmol) in DMSO (20 mL). $K_2CO_3$ (856 mg, 6.19 mmol) was added to the reaction mixture and stirred at 75° C. for 24 h. The reaction mixture was cooled to room temperature and poured slowly in to a 10% citric acid solution and stirred for 10 min at room temperature. The solution was extracted with EtOAc several times to get the crude product. The crude product was chromatographed with a gradient of hexanes/EtOAc and then with EtOAc, 100% to give the final product (220 mg): $^1$H NMR (500 MHz, DMSO-$d_6$, δ in ppm) 7.47 (d, J=9 Hz, 1H), 6.57 (d, J=9 Hz, 1H), 6.13 (br s, 1H), 3.62 (m, 2H), 2.18 (s, 3H).

Intermediate 17b (R)—N'-(2-(3-chloro-4-cyano-2-methylphenylamino)-3-hydroxypropanoyl)benzohydrazide

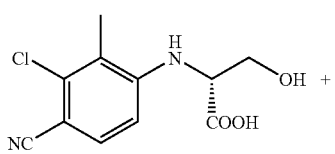

-continued

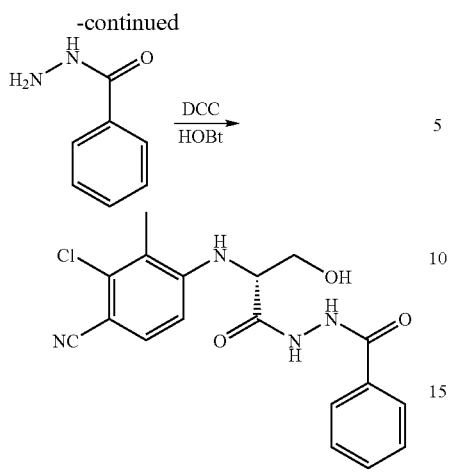

(R)-2-(3-chloro-4-cyano-2-methylphenylamino)-3-hydroxypropanoic acid (intermediate 17a) (500 mg, 1.96 mmol) and benzoic hydrazide (321 mg, 2.36 mmol) were mixed together in THF (60 mL) and cooled to −20° C. under $N_2$ atmosphere. To the pre-cooled reaction mixture was added HOBt (265 mg, 1.96 mmol) followed by DCC (486 mg, 2.36 mmol). The reaction mixture was allowed to stir at −20° C. for 1 h and then at room temperature overnight. After the reaction was complete, the urea was filtered off and the solution was washed with water, 5% citric acid followed by 5% $NaHCO_3$ to get the crude hydrazide product (364 mg). $^1$H NMR (500 MHz, acetone-$d_6$, δ in ppm) 7.95 (d, J=9 Hz, 2H), 7.60 (m, 1H), 7.52 (m, 3H), 6.70 (d, J=9 Hz, 1H), 5.69 (d, J=9 Hz, 1H), 4.29 (m, 1H), 4.08 (m, 1H), 3.99 (m, 1H), 2.36 (s, 3H).

Example 17

(R)-2-chloro-4-(2-hydroxy-1-(5-phenyl-1,3,4-oxadiazol-2-yl)ethylamino)-3-methylbenzonitrile

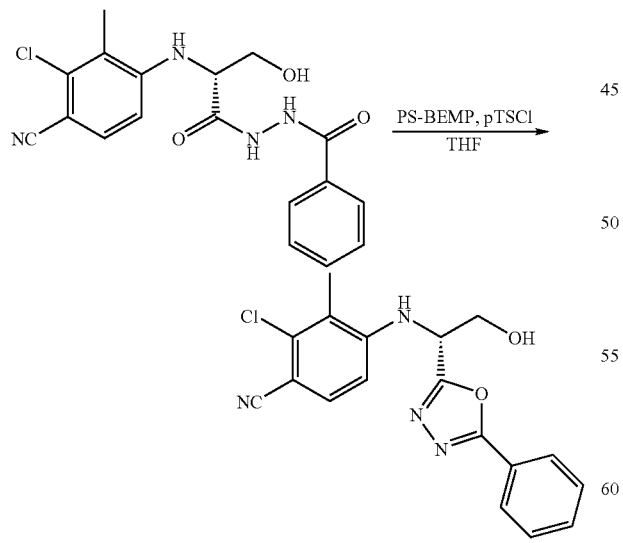

The crude material of N'(R)—N'-(2-(3-chloro-4-cyano-2-methylphenylamino)-3-hydroxypropanoyl)benzohydrazide (intermediate 17b) (700 mg, 1.88 mmol) was added to THF (90 mL) and stirred at room temperature. PS-BEMP (2.56 g, 5.63 mmol base) was added to the solution followed by slow addition of p-TSCl (394 mg, 2.07 mmol). The reaction mixture was stirred for 1 h and the progress of the reaction was monitored by TLC. After the completion of the reaction, the BEMP reagent was filtered off and the solution concentrated to give the crude material. The crude material was chromatographed with hexanes:EtOAc (6:4) to give the product (110 mg): $^1$H NMR (500 MHz, $CDCl_3$, δ in ppm) 7.97 (d, J=9 Hz, 2H), 7.56 (m, 1H), 7.50 (m, 3H), 7.45 (d, J=9 Hz, 1H), 6.73 (d, J=9 Hz, 1H), 5.24 (d, J=9 Hz, 1H), 4.98 (m, 1H), 4.38 (dd, J=3, 8 Hz, 1H), 4.20 (dd, J=3, 8 Hz, 1H), 2.34 (s, 3H).

Example 18

2-chloro-4-((1R,2R)-2-hydroxy-1-(3-phenyl-1,2,4-oxadiazol-5-yl)propylamino)-3-methylbenzonitrile

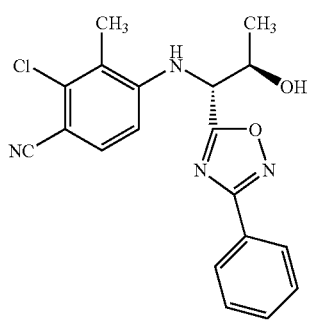

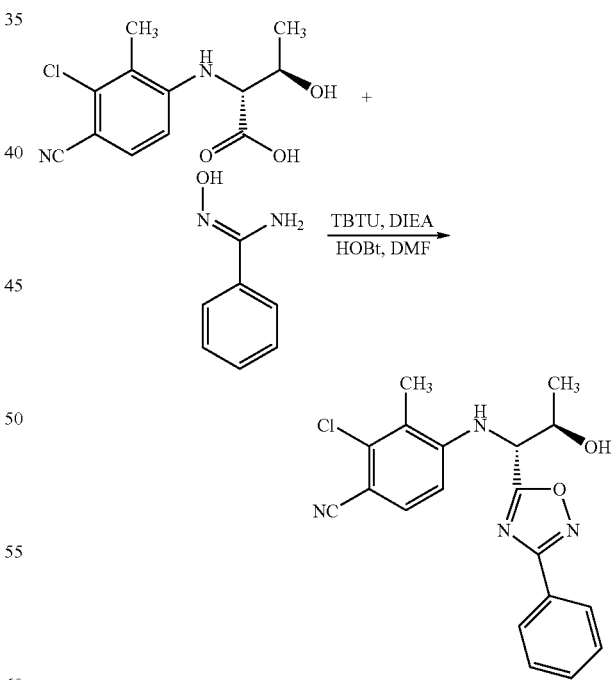

To a 25 mL round bottom flask charged with (2R,3R)-2-(3-chloro-4-cyano-2-methylphenylamino)-3-hydroxybutanoic acid (413 mg, 1.5 mmol) (intermediate 3a) and anhydrous DMF (15 mL) was added O-(benztriazol-1-yl)N,N,N',N'-tetramethyluronium tetrafluorborate (743 mg, 2.3 mmol), diisopropylethylamine (1.3 mL, 7.5 mmol), and HOBt (42 mg, 0.31 mmol). This mixture was let stir for a period of 10 min, to this mixture was added benzamidoxime (312 mg, 2.3 mmol). This mixture was allowed to stir for a period of 16 h. The reaction was then heated to 100° C. for a period of 5 h then cooled to room temperature. To the reaction was added brine (25 mL) and this was extracted with EtOAc (2×25 mL). The combined organic extracts were then washed with water (20 mL) and brine (25 mL) then dried over sodium sulphate. Filtration and concentration gave a dark oil. This was purified via silica gel chromatography eluted with 50% EtOAc/hexanes. A second column was run, eluting with 30% EtOAc/hexanes to provide product (21 mg, 4%). $^1$H NMR (500 MHz, CDCl$_3$, δ in ppm) 8.04 (m, 2H), 7.49 (m, 3H), 7.34 (d, J=8.6 Hz, 1H), 6.60 (d, J=8.7 Hz, 1H), 5.40 (d, J=8.7 Hz, 1H), 4.87 (dd, J=3.9, 8.7 Hz, 1H), 4.42 (br s, 1H), 2.77 (br s, 1H), 2.33 (s, 3H), 1.33 (d, J=6.5 Hz, 3H).

Example 19

2-chloro-4-((1R,2R)-1-(5-(4-fluorophenyl)-1,3,4-oxadiazol-2-yl)-2-hydroxypropylamino)-3-methyl-benzonitrile

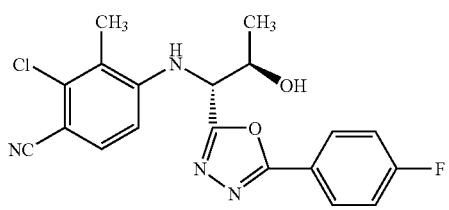

Intermediate 19a

N'-((2R,3R)-2-(3-chloro-4-cyano-2-methylphenylamino)-3-hydroxybutanoyl)-4-fluorobenzohydrazide

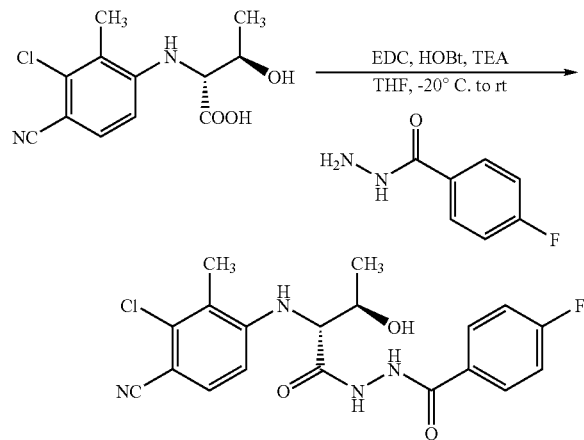

N'-((2R,3R)-2-(3-chloro-4-cyano-2-methylphenylamino)-3-hydroxybutanoyl)-4-fluoro benzohydrazide was prepared using 4-fluorobenzoic hydrazide (4.4 mmol, 1.1 equiv.) and (2R,3R)-2-(3-chloro-4-cyano-2-methylphenylamino)-3-hydroxybutanoic acid (4.0 mmol, 1.0 equiv.) as described previously in the preparation of intermediate 5a. The crude golden yellow solid was recrystallized using hot methylene chloride to provide the desired product as a light yellow solid (870 mg, 54% yield). Other data: $^1$H NMR (400 MHz, acetone-d$_6$, δ in ppm) 9.85 (br. s., 1H), 9.5 (br. s., 1H), 8.02 (dd, J=5.4, 8.8 Hz, 2H), 7.53 (d, J=8.8 Hz, 1H), 7.27 (d, J=8.8 Hz, 2H), 6.73 (d, J=8.5 Hz, 1H), 5.59 (br. d, J=6.8 Hz, 1H), 4.70 (br. s., 1H), 4.24 (m, 1H), 4.12 (dd, J=4.9, 7.3 Hz, 1H), 2.35 (s, 3H), 1.38 (d, J=6.3 Hz, 3H); LRMS (ESI+) exact mass calcd for C$_{19}$H$_{18}$ClFN$_4$O$_3$ [M]$^+$ 404.82. found 405.4; TLC R$_f$=0.38, 100% EtOAc, vanillin stain.

Example 19

2-chloro-4-((1R,2R)-1-(5-(4-fluorophenyl)-1,3,4-oxadiazol-2-yl)-2-hydroxypropylamino)-3-methyl-benzonitrile

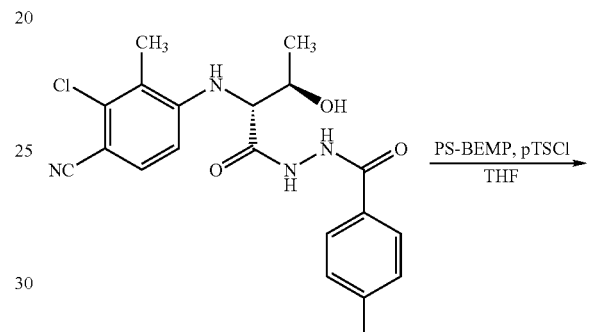

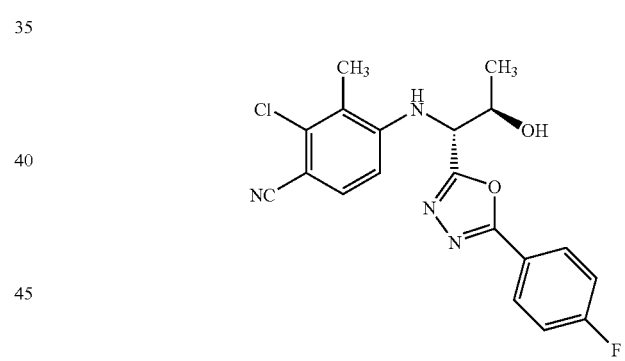

2-Chloro-4-((1R,2R)-1-(5-(4-fluorophenyl)-1,3,4-oxadiazol-2-yl)-2-hydroxypropyl amino)-3-methylbenzonitrile was prepared using N'-((2R,3R)-2-(3-chloro-4-cyano-2-methylphenylamino)-3-hydroxybutanoyl)-4-fluorobenzohydrazide (2.14 mmol, 1.0 equiv.) as described in the preparation of example 4. The crude off-white solid was recrystallized using hot methylene chloride to provide the desired product as a white solid (357 mg, 43% yield). Other data: $^1$H NMR (400 MHz, acetone-d$_6$, δ in ppm) 8.04 (dd, J=5.4, 9.0 Hz, 2H), 7.46 (d, J=8.6 Hz, 1H), 7.31 (m, 2H), 6.87 (d, J=8.6 Hz, 1H), 5.89 (br. d, J=8.8 Hz, 1H), 5.06 (m, 1H), 4.78 (br. s, 1H), 4.53 (m, 1H), 2.34 (s, 3H), 1.42 (d, J=6.4 Hz, 3H); LRMS (ESI+) exact mass calcd for C$_{19}$H$_{16}$ClFN$_4$O$_2$ [M]$^+$ 386.81. found 387.4; TLC R$_f$=0.6, 100% EtOAc, vanillin stain.

Example 20

2-Chloro-4-((1R,2R)-1-(5-(4-chlorophenyl)-1,3,4-oxadiazol-2-yl)-2-hydroxypropylamino)-3-methyl-benzonitrile

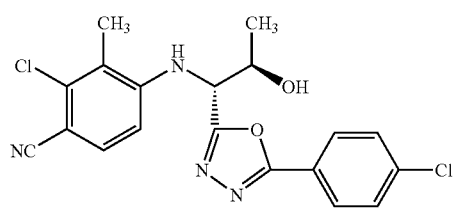

Intermediate 20a

4-Chloro-N'-((2R,3R)-2-(3-chloro-4-cyano-2-methylphenylamino)-3-hydroxybutanoyl)benzohydrazide

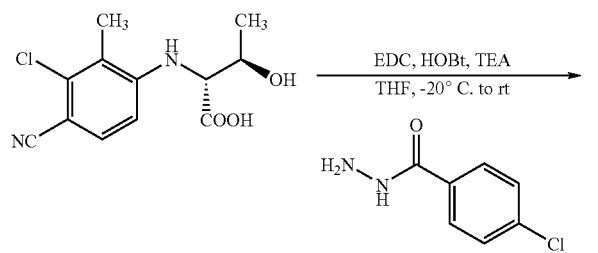

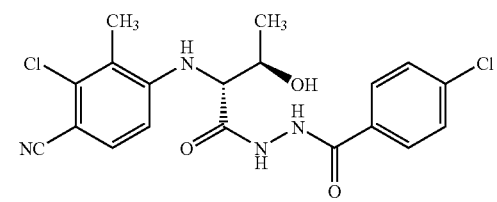

4-Chloro-N'-((2R,3R)-2-(3-chloro-4-cyano-2-methylphenylamino)-3-hydroxybutanoyl)benzohydrazide was prepared using 4-chlorobenzoic hydrazide (4.42 mmol, 1.1 equiv.) and (2R,3R)-2-(3-chloro-4-cyano-2-methylphenylamino)-3-hydroxybutanoic acid (4.02 mmol, 1.0 equiv.) according to the procedure as described for intermediate 5a. The crude off-white solid was recrystallized using hot methylene chloride to provide the desired product as a white solid (1.57 g, 93% yield). Other data: $^1$H NMR (400 MHz, acetone-$d_6$, δ in ppm) 9.94 (br. s, 1H), 9.48 (br. s, 1H), 7.95 (d, J=8.5 Hz, 2H), 7.55 (m, 3H), 6.73 (d, J=8.5 Hz, 1H), 5.59 (br. d., J=7.1 Hz, 1H), 4.25 (m, 1H), 4.13 (m, 1H), 2.35 (s, 3H), 1.37 (d, J=6.4 Hz, 3H); LRMS (ESI+) exact mass calcd for $C_{19}H_{18}Cl_2N_4O_3$ [M]$^+$ 421.28. found 421.3; TLC R$_f$=0.32, 100% EtOAc, vanillin stain.

Example 20

2-Chloro-4-((1R,2R)-1-(5-(4-chlorophenyl)-1,3,4-oxadiazol-2-yl)-2-hydroxypropylamino)-3-methyl-benzonitrile

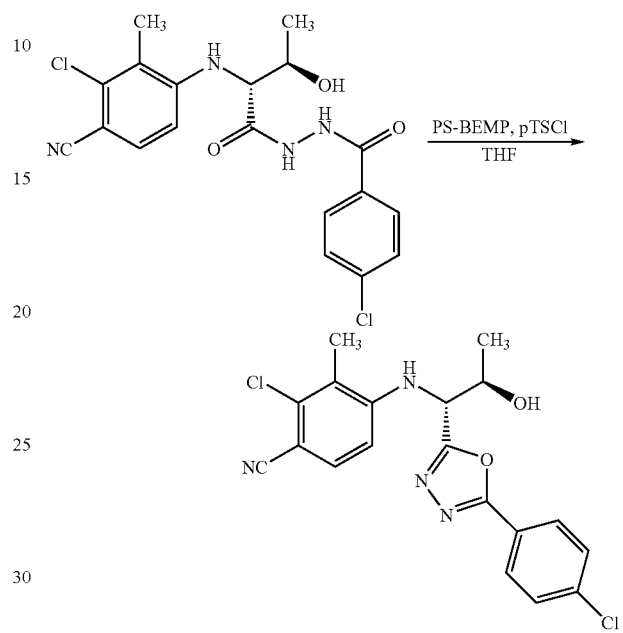

2-Chloro-4-((1R,2R)-1-(5-(4-chlorophenyl)-1,3,4-oxadiazol-2-yl)-2-hydroxypropyl amino)-3-methylbenzonitrile was prepared using 4-chloro-N'-((2R,3R)-2-(3-chloro-4-cyano-2-methylphenylamino)-3-hydroxybutanoyl)benzohydrazide (intermediate 20a) (4.5 mmol, 1.0 equiv.) as described for the preparation of example 5. The crude off-white solid was recrystallized using hot methylene chloride to provide the desired product as a white solid (1.28 g, 71% yield). Other data: $^1$H NMR (400 MHz, acetone-$d_6$, δ in ppm) 9.78 (br. s, 1H), 7.95 (d, J=8.6 Hz, 2H), 7.54 (d, J=8.6 Hz, 2H), 7.51 (d, J=8.5 Hz, 1H), 6.74 (d, J=8.8 Hz, 1H), 5.62 (br. d, J=7.0 Hz, 1H), 4.26 (m, 1H), 4.16 (m, 1H), 2.34 (s, 3H), 1.37 (d, J=6.4 Hz, 3H); TLC R$_f$=0.52, 100% EtOAc, vanillin stain.

Example 21

2-chloro-4-((1R,2S)-1-(5-(3-chlorophenyl)-1,3,4-oxadiazol-2-yl)-2-hydroxypropylamino)-3-methyl-benzonitrile

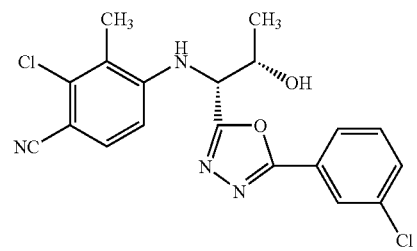

Intermediate 21a 3-chloro-N'-((2R,3S)-2-(3-chloro-4-cyano-2-methylphenylamino)-3-hydroxybutanoyl)benzohydrazide

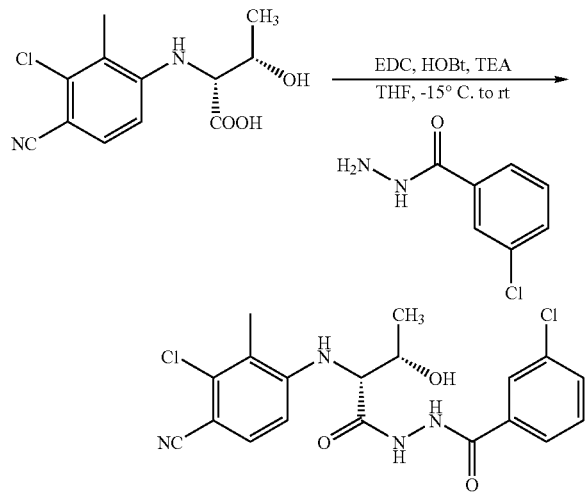

(2R,3S)-2-(3-chloro-4-cyano-2-ethylphenylamino)-3-hydroxybutanoic acid (800 mg, 2.98 mmol), 3-Chlorobenzhydrazide (508 mg, 2.98 mmol) and anhydrous THF (40 mL) were placed in a 100 mL round bottomed flask and the mixture was cooled to −15° C. 1-Hydroxybenzotriazole hydrate (403 mg, 2.98 mmol) was added to the mixture together with N-(3-Dimethylaminopropyl)-N-ethylcarbodimide HCl (857 mg, 4.47 mmol) at −15° C. followed by triethylamine (0.62 mL, 4.47 mmol). The reaction mixture was maintained at −15° C. and stirred for 1 h after which, stirring continued overnight while the mixture slowly warmed to room temperature. Water (40 mL) was added to the reaction mixture followed by citric acid (4 g) while stirring. EtOAc (60 mL) was then added to the mixture and the phases were partitioned. The organic phase was then washed with saturated aqueous sodium bicarbonate (40 mL) and the organic phase dried (Na$_2$SO$_4$). EtOAc was removed under vacuum and replaced by chloroform (60 mL). The insoluble hydrazide was then separated from the mixture by filtration and dried under reduced pressure to furnish a white solid (855 mg, 68%). $^1$H NMR (500 MHz, acetone-d$_6$, δ in ppm) 9.7 (br s, 2H), 7.96 (s, 1H), 7.83 (d, J=8.5 Hz, 1H), 7.46-7.7 (m, 2H), 6.64 (d, J=8.6 Hz, 1H), 5.3 (d, J=7 Hz, 1H), 4.19-4.03 (m, 1H), 3.98-3.87 (m, 1H), 2.35 (s, 3H) and 1.26 (d, J=6.35 Hz, 3H).

Example 21

2-chloro-4-((1R,2S)-1-(5-(3-chlorophenyl)-1,3,4-oxadiazol-2-yl)-2-hydroxypropylamino)-3-methylbenzonitrile

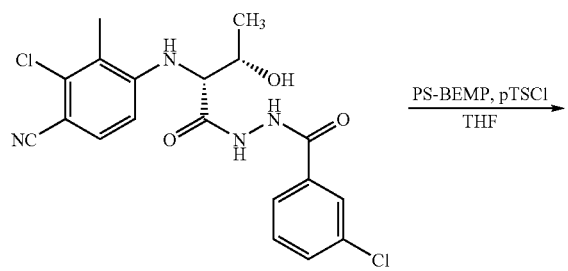

-continued

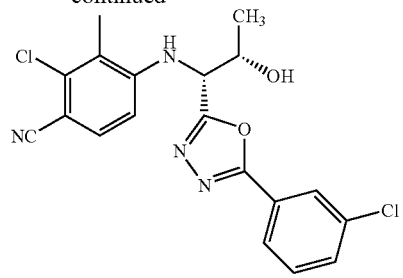

To a solution of 3-chloro-N'-((2R,3S)-2-(3-chloro-4-cyano-2-methylphenylamino)-3-hydroxybutanoyl)benzohydrazide (800 mg, 1.9 mmol) in anhydrous THF (20 mL) at room temperature was added 2-tert-butylamino-2-diethylamino-1,3-dimethyl perhydro-1,3,2-diazaphosphorine on polystyrene (2.2 mmol base/g) (2.59 g) followed by p-TSCl (435 mg, 2.28 mmol) and the mixture was stirred for 1 h. The mixture was filtered and the residue washed with acetone (800 mL) followed by Methanol (200 mL). The filtrate was then concentrated and subjected to flash column chromatography [EtOAc-Hexanes (1:2)] to give two fractions. The first-eluted material was identified by $^1$H NMR spectroscopy as (Z)-2-chloro-4-(1-(5-(3-chlorophenyl)-1,3,4-oxadiazol-2-yl)prop-1-enylamino)-3-methylbenzonitrile (140 mg, 33%) $^1$H NMR (500 MHz, CDCl$_3$, δ in ppm) 8.03 (s, 1H), 8.01 (d, J=8.5 Hz, 1H), 7.42 (d, J=9 Hz, 1H), 7.03 (q, J=7 Hz, 1H), 6.61 (d, J=8.5 Hz, 1H), 2.44 (s, 3H), 1.92 (d, J=6 Hz, 3H).

The second-eluted material was the desired 2-chloro-4-((1R,2S)-1-(5-(3-chlorophenyl)-1,3,4-oxadiazol-2-yl)-2-hydroxypropylamino)-3-methylbenzonitrile (145 mg, 20%). $^1$H NMR (500 MHz, CDCl$_3$, δ in ppm) 8.01 (s, 1H), 7.99 (d, J=8.5 Hz, 1H), 7.60-7.63 (m, 2H) 7.45 (d, J=8.5 Hz, 1H), 6.89 (d, J=8.6 Hz, 1H), 5.70 (d, J=9 Hz, 1H), 5.18 (m, 1H), 4.60-4.64 (m, 1H), 2.40 (s, 3H), 1.41 (d, J=6 Hz, 3H).

Example 22

2-chloro-4-((1R,2S)-1-(5-(4-cyanophenyl)-1,3,4-oxadiazol-2-yl)-2-hydroxypropylamino)-3-methylbenzonitrile

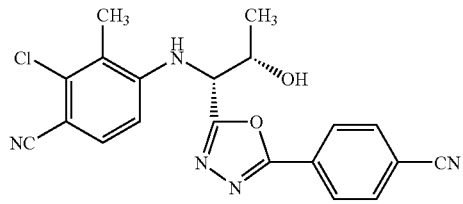

Intermediate 22a

Ethyl 4-cyanobenzoate

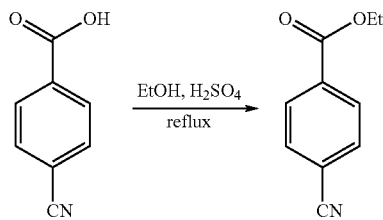

To a 250 mL round bottom flask charged with 4-cyanobenzoic acid (19.36 g, 0.13 mol) in abs. ethanol (100 mL) was added concentrated sulfuric acid (3 mL). This mixture was heated to reflux for a period of 28 h, then allowed to cool to room temperature overnight. The solvent was removed via rotary evaporation and the resulting off-white residue was taken up in diethyl ether (500 mL). This was then washed with saturated sodium bicarbonate/water solution (5×100 mL), then brine (1×100 mL), and dried over magnesium sulfate. Filtration and concentration yielded an off-white solid. Recrystallization from 95% ethanol (50 mL) yielded product as white crystals (16.85 g, 73%). $^1$H NMR (400 MHz, CDCl$_3$, δ in ppm) 8.14 (AA'XX', J=8.6 Hz, 2H), 7.74 (AA'XX', J=8.6 Hz, 2H), 4.42 (q, J=7.1 Hz, 2H), 1.41 (t, J=7.1 Hz, 3H).

Intermediate 22b

4-Cyanobenzohydrazide

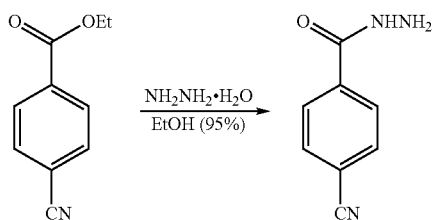

To a 250 mL round bottom flask charged with ethyl 4-cyanobenzoate (16.85 g, 96.2 mmol) in 95% ethanol (75 mL) was added hydrazine mono-hydrate (18.2 mL, 64% solution, 240 mmol). This mixture was heated to reflux for a period of 4.5 h, then allowed to cool to room temperature over a 16 h period. The solvent was removed under reduced pressure and the yellow residue was taken up in ice-cold water (150 mL). The light yellow solid was filtered off and washed with additional cold water (50 mL). The solid was then dried under high vacuum to yield the title compound as a light yellow solid (13.98 g, 90%). $^1$H NMR (400 MHz, DMSO-d$_6$, δ in ppm) 10.05 (br s, 1H), 7.95 (AA'XX', J=8.5 Hz, 4H), 4.61 (br s, 2H).

Intermediate 22c

N'-((2R,3S)-2-(3-chloro-4-cyano-2-methylphenylamino)-3-hydroxybutanoyl)-4-cyanobenzohydrazide

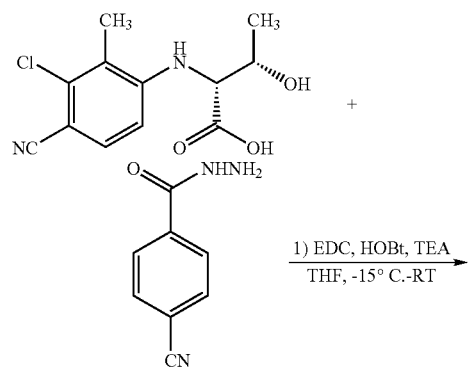

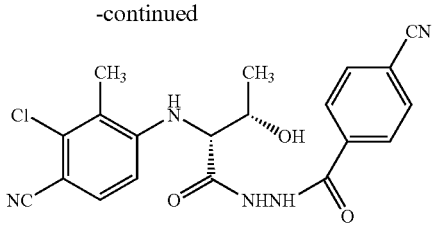

(2R,3S)-2-(3-chloro-4-cyano-2-methylphenylamino)-3-hydroxybutanoic acid (intermediate 1a) (10.03 g, 37.3 mmol) and 4-cyano-benzohydrazide (6.02 g, 37.3 mmol) were coupled in an analogous procedure as described for the preparation of intermediate 3b. The crude product was purified by boiling in chloroform (100 mL) followed by cooling to 0° C. and filtration to yield product as a light yellow solid (12.05 g, 78%). $^1$H NMR (400 MHz, acetone-d$_6$, δ in ppm) 9.81 (br s, 2H), 8.08 (AA'XX', J=8.6 Hz, 2H), 7.91 (AA'XX', J=8.7 Hz, 2H), 7.51 (d, J=8.7 Hz, 1H), 6.69 (d, J=8.8 Hz, 1H), 5.57 (d, J=7.0 Hz, 1H), 4.40 (m, 1H), 2.34 (dd, J=3.6, 6.9 Hz, 1H), 2.34 (s, 3H), 1.35 (d, J=6.4 Hz, 3H).

Intermediate 22d

N'-((2R,3S)-3-(tert-butyldimethylsilyloxy)-2-(3-chloro-4-cyano-2-methylphenyl-amino)butanoyl)-4-cyanobenzohydrazide

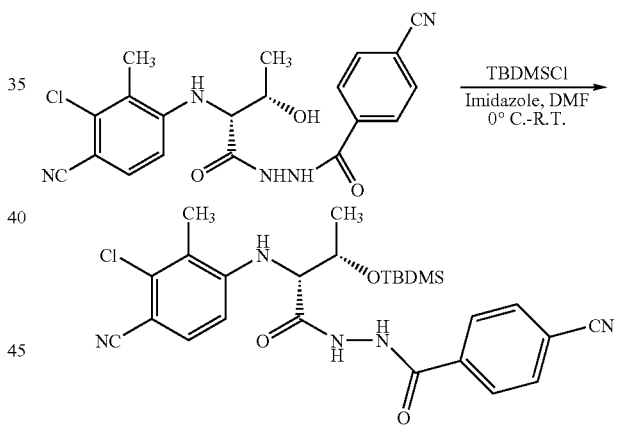

N'-((2R,3S)-2-(3-chloro-4-cyano-2-methylphenylamino)-3-hydroxybutanoyl)-4-cyano benzohydrazide (12.1 g, 29.3 mmol) was reacted with TBDMSCl (13.2 g, 88.0 mmol) and imidazole (68.1 g, 146.0 mmol) in a manner analogous to that described for the preparation of intermediate 7b. Purification of the compound was accomplished by pouring the reaction mixture into ice-cold water and filtering off the solid precipitate. This was taken up in methylene chloride (400 mL) and sequentially washed with water (2×100 mL) and brine (100 mL). This was dried over sodium sulfate, filtered and concentrated down to roughly 100 mL. Hexanes were then added producing a white solid. This was filtered out and washed with hexanes to give the product as a white solid (12.92 g, 84%). $^1$H NMR (400 MHz, CDCl$_3$, δ in ppm) 9.32 (m, 2H), 7.89 (AA'XX', J=8.4 Hz, 2H), 7.71 (AA'XX', J=8.6 Hz, 2H), 7.37 (d, J=8.4 Hz, 1H), 6.47 (d, J=8.8 Hz, 1H), 5.37 (d, J=6.2 Hz, 1H), 4.49 (m, 1H), 3.99 (m, 1H), 2.33 (s, 3H), 1.25 (d, J=6.2 Hz, 3H), 0.92 (s, 9H), 0.14 (s, 3H), 0.09 (s, 3H).

103

Intermediate 22e 4-((1R,2S)-2-(tert-butyldimethylsilyloxy)-1-(5-(4-cyanophenyl)-1,3,4-oxadiazol-2-yl)propylamino)-2-chloro-3-methylbenzonitrile

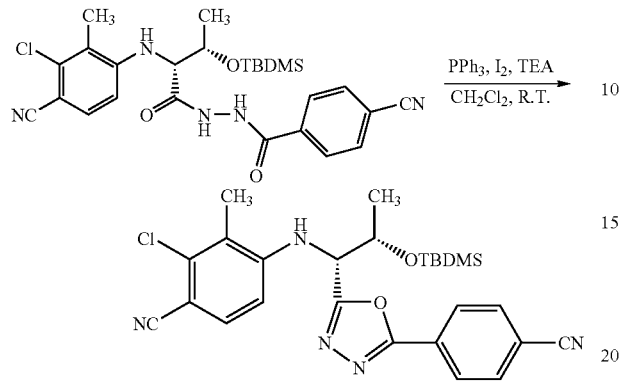

To a 1 L round bottom flask equipped with a magnetic stir bar and septum was added triphenylphosphine (12.3 g, 47.0 mmol) under an atmosphere of nitrogen. To this was added methylene chloride (500 mL) followed by addition of solid iodine (11.91 g, 47.0 mmol). This was allowed to stir at room temperature for a period of 10 min. then cooled to 0° C. Triethylamine (13.1 mL, 94 mmol) was then slowly added to this reaction (CAUTION: Exotherm). This mixture was allowed to stir at room temperature for an additional ten min., during which the reaction became a thick slurry. N'-((2R,3S)-3-(tert-butyldimethylsilyloxy)-2-(3-chloro-4-cyano-2-methylphenyl-amino) butanoyl)-4-cyanobenzohydrazide (12.35 g, 23.5 mmol) was taken up in methylene chloride (200 mL) and slowly added to the heavily stirred reaction mixture. After a period of 10 min, TLC (1:1 EtOAc:hexanes) showed product formation and no starting material. The reaction was then quenched by slow addition of 10% Na$_2$S$_2$O$_3$/H$_2$O (500 mL). The organic layer was then isolated and washed with additional 10% sodium thiosulfate/water (1×200 mL), brine (1×200 mL), then dried (Na$_2$SO$_4$). The solution was then filtered and concentrated under reduced pressure to reveal a brown oil/solid. This was purified via silica gel chromatography eluted with 25% EtOAc/hexanes to provide the title compound as a white solid (9.98 g, 84%). $^1$H NMR (400 MHz, CDCl$_3$, δ in ppm) (AA'XX', J=8.8 Hz, 2H), 7.79 (AA'XX', J=8.8 Hz, 2H), 7.33 (d, J=8.7 Hz, 1H), 6.44 (d, J=8.7 Hz, 1H), 5.35 (d, J=8.8 Hz, 1H), 4.82 (dd, J=2.0, 8.7 Hz, 1H), 3.54 (m, 1H), 2.37 (s, 3H), 1.42 (d, J=6.2 Hz, 3H), 0.85 (s, 9H), 0.07 (s, 3H), −0.22 (s, 3H).

Example 22

2-chloro-4-((1R,2S)-1-(5-(4-cyanophenyl)-1,3,4-oxadiazol-2-yl)-2-hydroxypropylamino)-3-methylbenzonitrile

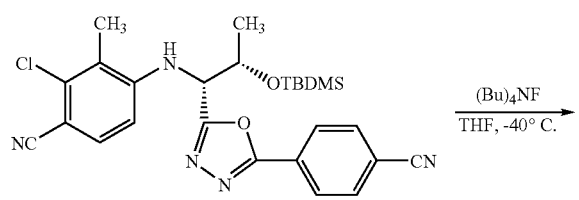

104

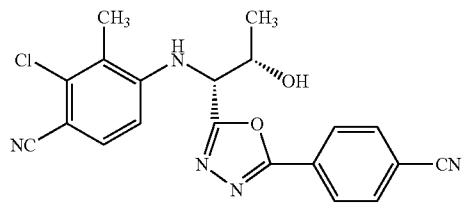

To a 25 mL round bottom flask equipped with a magnetic stirrer and a septum was added 4-((1R,2S)-2-(tert-butyldimethylsilyloxy)-1-(5-(4-cyanophenyl)-1,3,4-oxadiazol-2-yl) propylamino)-2-chloro-3-methylbenzonitrile (9.98 g, 19.6 mmol), followed by anhydrous THF (245 mL) under an atmosphere of nitrogen. The reaction mixture was cooled to −40° C. via a CO$_2$/acetone bath. To this was added tetrabutylammonium fluoride as a 1M solution in THF (22.54 mL, 22.54 mmol) producing an instant color change to yellow. This was allowed to warm to room temperature for a period of 4 h. The solvent was then removed under reduced pressure to yield a black residue. This residue was taken up in EtOAc (200 mL) and washed with water (2×250 mL), brine (1×200 mL) and dried over Na$_2$SO$_4$. The solution was then filtered and concentrated under reduced pressure using rotary evaporation to reveal a yellow solid. This was purified via silica gel chromatography eluted with hexanes-EtOAc (20:80) the title compound as a white solid (5.23 g, 68%). $^1$H NMR (500 MHz, CDCl$_3$, δ in ppm) 8.10 (d, J=8.4 Hz, 2H), 7.80 (d, J=8.4 Hz, 2H), 7.40 (d, J=8.4 Hz, 1H), 6.65 (d, J=8.4 Hz, 1H), 5.27 (d, J=8.0 Hz, 1H), 4.80 (dd, J=2.8, 8.4 Hz, 1H), 4.62-4.65 (m, 1H), 2.91 (br s, 1H), 2.37 (s, 3H), 1.46 (d, J=6.4 Hz, 3H).

It is noted here that additional methods may be used for the preparation of the desilyated material. For example, ammonium fluoride in refluxing methanol can also be used for deprotection though the reaction can take significantly longer (e.g. 48 h) but in some cases may yield less byproducts (such as β-elimination of the alcohol).

Example 23

2-chloro-4-((1R,2R)-1-(5-(4-cyanophenyl)-1,3,4-oxadiazol-2-yl)-2-hydroxypropylamino)-3-methylbenzonitrile

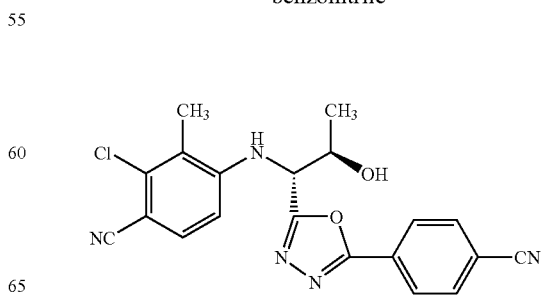

Intermediate 23a

N'-((2R,3R)-2-(3-chloro-4-cyano-2-methylphenylamino)-3-hydroxybutanoyl)-4-cyanobenzohydrazide

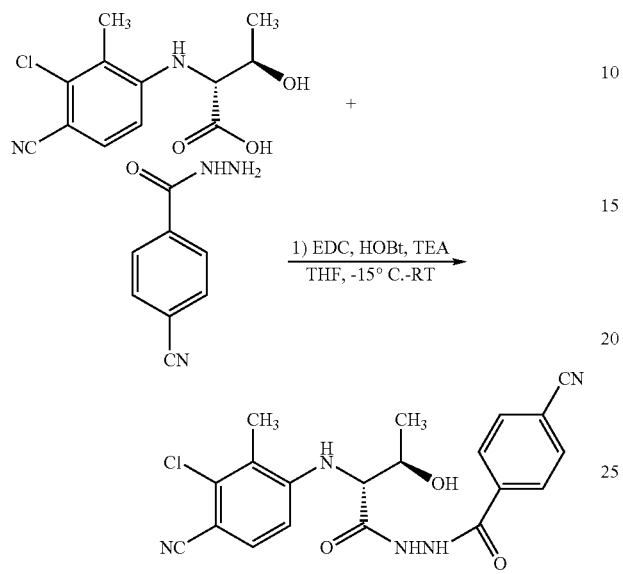

(2R,3R)-2-(3-chloro-4-cyano-2-methylphenylamino)-3-hydroxybutanoic acid (805 mg, 3.0 mmol) and 4-cyano-benzohydrazide (483 mg, 3.0 mmol) were coupled in a procedure analogous to that used for the preparation of intermediate 3b. The crude product was purified by boiling in chloroform (10 mL) followed by cooling to 0° C. and filtration to yield product as a light yellow solid (718 mg, 50%). $^1$H NMR (500 MHz, acetone-$d_6$, δ in ppm) 9.85 (br s, 2H), 8.09 (AA'XX', J=8.2 Hz, 2H), 7.92 (AA'XX', J=8.6 Hz, 2H), 7.52 (d, J=8.6 Hz, 1H), 6.74 (d, J=8.7 Hz, 1H), 5.60 (d, J=7.3 Hz, 1H), 4.27 (m, 1H), 4.16 (dd, J=5.0, 7.3 Hz, 1H), 2.88 (br s, 1H), 2.34 (s, 3H), 1.39 (d, J=6.4 Hz, 3H).

Example 23

2-chloro-4-((1R,2R)-1-(5-(4-cyanophenyl)-1,3,4-oxadiazol-2-yl)-2-hydroxypropylamino)-3-methylbenzonitrile

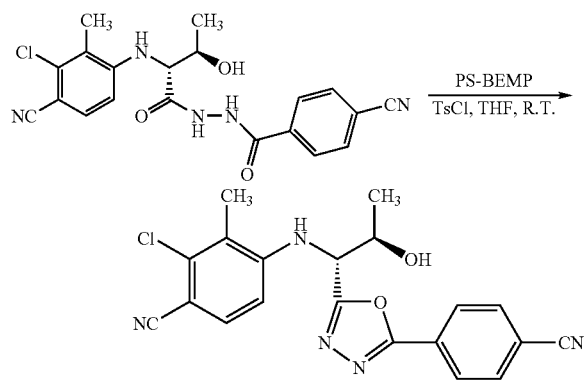

To a 250 mL, round-bottomed flask equipped with a magnetic stir bar and septum was added N'-((2R,3R)-2-(3-chloro-4-cyano-2-methylphenylamino)-3-hydroxybutanoyl)-4-cyanobenzohydrazide (0.6871 g, 2.4 mmol) followed by addition of anhydrous THF (200 mL) under an atmosphere of nitrogen. To this was then added tosyl chloride (318 mg, 1.7 mmol) followed by addition of polystyrene bound (2-tert-butylimino-2-diethylamino-1,3-dimethylperhydro-1,3,2-diazaphosphorine (PS-BEMP) (2.2 mmol/g loading, 2.29 g, 5.0 mmol). This mixture was allowed to stir at room temperature for a period of 16 h. The solids were then filtered off and washed with additional THF (100 mL). The filtrate was then concentrated under reduced pressure to reveal a yellow solid. This was purified via silica gel chromatography eluted with 50% EtOAc/hexanes to provide product as a white solid (138 mg, 21%). $^1$H NMR (500 MHz, acetone-$d_6$, δ in ppm) 8.19 (AA'XX', J=8.4 Hz, 2H), 7.98 (AA'XX', J=8.5 Hz, 2H), 7.48 (d, J=8.6 Hz, 1H), 6.89 (d, J=8.7 Hz, 1H), 5.89 (d, J=8.8 Hz, 1H), 5.11 (dd, J=5.6, 8.8 Hz, 1H), 4.71 (d, J=5.9 Hz, 1H), 4.55 (m, 1H), 2.36 (s, 3H), 1.43 (d, J=6.3 Hz, 3H).

Example 24

2-chloro-4-((1R,2S)-2-hydroxy-1-(5-(4-(methylsulfonyl)phenyl)-1,3,4-oxadiazol-2-yl)propylamino)-3-methylbenzonitrile

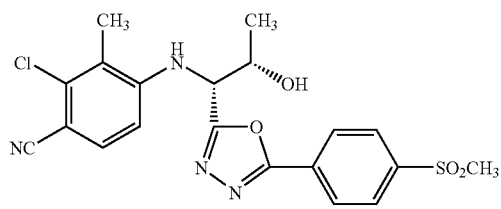

Intermediate 24a

Ethyl 4-(methylsulfonyl)benzoate

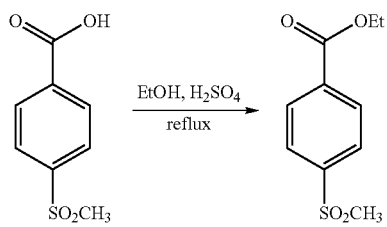

The ethyl ester of 4-(methylsulfonyl)benzoic acid (5.05 g, 25 mmol) was prepared analogously to intermediate 22a and isolated as white crystals (4.72 g, 82%). No recrystallization was needed. $^1$H NMR (500 MHz, CDCl$_3$, δ in ppm) 8.22

(AA'XX', J=8.7 Hz, 2H), 8.01 (AA'XX', J=8.7 Hz, 2H), 4.41 (q, J=7.2 Hz, 2H), 3.07 (s, 3H), 1.41 (t, J=7.1 Hz, 3H).

Intermediate 24b 4-(Methylsulfonyl)benzohydrazide

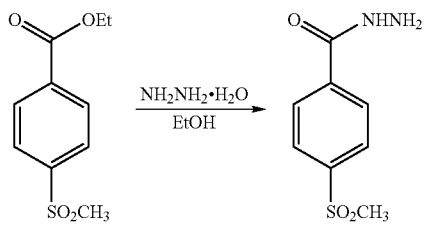

The title compound was prepared from Ethyl 4-(methylsulfonyl)benzoate (4.68 g, 21 mmol) according to the procedure described for 22b and isolated as white crystals (3.79 g, 86%). ¹H NMR (500 MHz, DMSO-d$_6$, δ in ppm) 10.06 (br s, 1H), 8.03 (AA'XX', J=8.7 Hz, 4H), 4.62 (s, 2H), 3.27 (s, 3H).

Intermediate 24c

N-((2R,3S)-2-(3-Chloro-4-cyano-2-methylphenylamino)-3-hydroxybutanoyl)-4-(methylsulphonyl)benzohydrazide

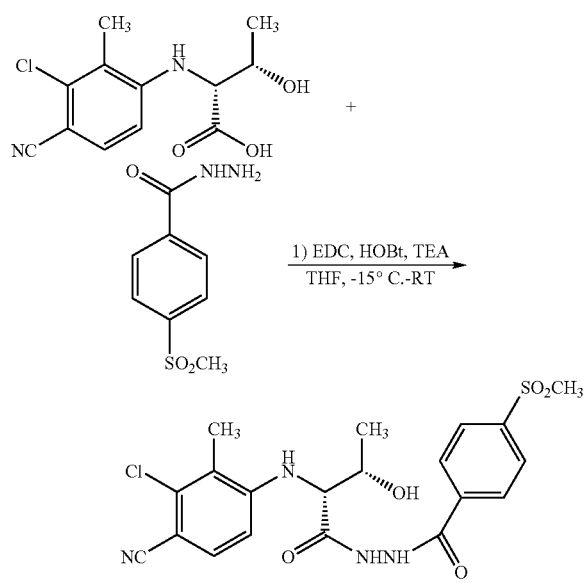

(2R,3S)-2-(3-chloro-4-cyano-2-methylphenylamino)-3-hydroxybutanoic acid (813 mg, 3.0 mmol) and 4-(methylsulfonyl)benzohydrazide (648 mg, 3.0 mmol) were coupled in a procedure analogous to that described for the preparation of intermediate 3b. The crude product was recrystallized from hot chloroform (100 mL) to yield product as a white solid (1.16 g, 82%). ¹H NMR (500 MHz, acetone-d$_6$, δ in ppm) 9.83 (br s, 2H), 8.14 (AA'XX', J=8.5 Hz, 2H), 8.06 (AA'XX', J=8.5 Hz, 2H), 7.53 (d, J=8.6 Hz, 1H), 6.70 (d, J=8.7 Hz, 1H), 5.57 (d, J=7.0 Hz, 1H), 4.40 (m, 1H), 4.14 (dd, J=3.4, 6.9 Hz, 1H), 3.19 (s, 3H), 2.90 (br s, 1H), 2.36 (s, 3H), 1.36 (d, J=6.4 Hz, 3H).

Example 24

2-chloro-4-((1R,2S)-2-hydroxy-1-(5-(4-(methylsulfonyl)phenyl)-1,3,4-oxadiazol-2-yl)propylamino)-3-methylbenzonitrile

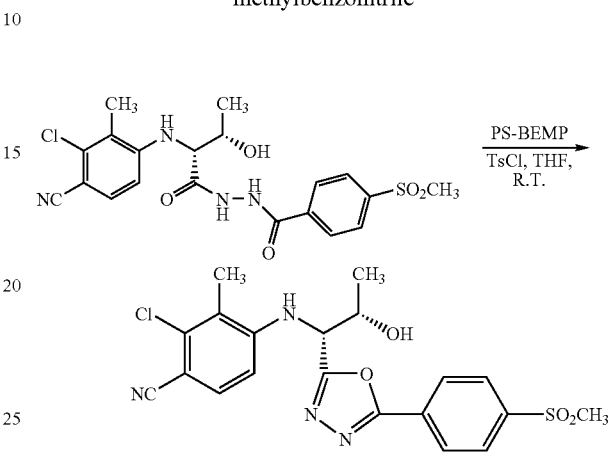

To a 500 mL, round-bottomed flask equipped with a magnetic stir bar and septum was added N'-((2R,3S)-2-(3-chloro-4-cyano-2-methylphenyl-amino)-3-hydroxybutanoyl)-4-(methylsulphonyl)benzohydrazide (1.12 mg, 2.4 mmol) followed by a addition of anhydrous THF (250 mL) under an atmosphere of nitrogen. To this was then added tosyl chloride (461 mg, 2.4 mmol) followed by addition of polystyrene bound (2-tert-butylimino-2-diethylamino-1,3-dimethylperhydro-1,3,2-diazaphosphorine (PS-BEMP) (2.2 mmol/g loading, 3.30 g, 7.3 mmol). This mixture was allowed to stir at room temperature for a period of 16 h. The solids were then filtered off and washed with additional THF (100 mL). The filtrate was then concentrated under reduced pressure to reveal a red solid. This was purified via silica gel chromatography eluted with 80% EtOAc/hexanes to yield product as a white solid (247 mg, 23%). ¹H NMR (500 MHz, acetone-d$_6$, δ in ppm) 8.23 (AA'XX', J=8.7 Hz, 2H), 8.12 (AA'XX', J=8.6 Hz, 2H), 7.47 (d, J=8.7 Hz, 1H), 6.87 (d, J=8.8 Hz, 1H), 5.70 (d, J=8.7 Hz, 1H), 5.17 (dd, J=3.6, 8.5 Hz, 1H), 4.86 (br s, 1H), 4.66 (m, 1H), 3.20 (s, 3H), 2.40 (s, 3H), 1.43 (d, J=6.3 Hz, 3H).

Example 25

2-chloro-4-((1R,2R)-2-hydroxy-1-(5-(4-(methylsulfonyl)phenyl)-1,3,4-oxadiazol-2-yl)propylamino)-3-methylbenzonitrile

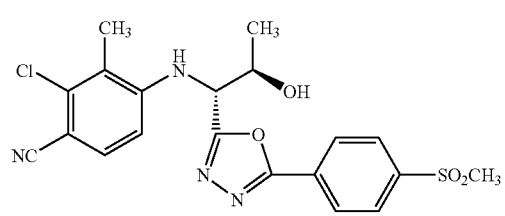

Intermediate 25a

N'-((2R,3R)-2-(3-chloro-4-cyano-2-methylphenyl-amino)-3-hydroxybutanoyl)-4-(methylsulphonyl) benzohydrazide

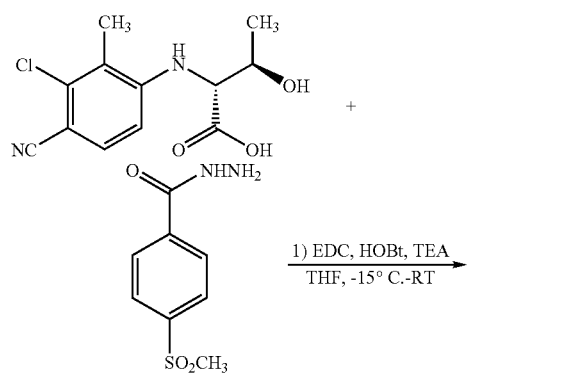

(2R,3R)-2-(3-chloro-4-cyano-2-methylphenylamino)-3-hydroxybutanoic acid (802 mg, 3.0 mmol) and 4-(methylsulfonyl)benzohydrazide (638 mg, 3.0 mmol) were coupled together in a procedure analogous to that described for the preparation of intermediate 3b. The crude product was purified by boiling in chloroform (100 mL) followed by cooling to 0° C. and filtration to yield product as a red solid (900 mg, 65%). $^1$H NMR (500 MHz, acetone-$d_6$, δ in ppm) 8.15 (AA'XX', J=8.6 Hz, 2H), 8.06 (AA'XX', J=8.7 Hz, 2H), 7.51 (d, J=8.7 Hz, 1H), 6.75 (d, J=8.7 Hz, 1H), 5.61 (d, J=7.5 Hz, 1H), 4.28 (m, 1H), 4.18 (dd, J=5.0, 7.2 Hz, 1H), 3.18 (s, 3H), 2.34 (s, 3H), 1.39 (d, J=6.3 Hz, 3H).

Example 25

2-chloro-4-((1R,2R)-2-hydroxy-1-(5-(4-(methylsulfonyl)phenyl)-1,3,4-oxadiazol-2-yl)propylamino)-3-methylbenzonitrile

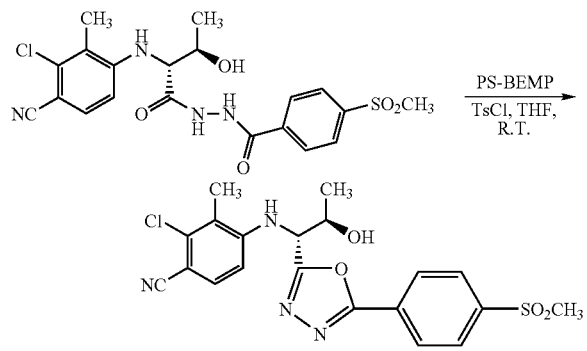

To a 250 mL, round-bottomed flask equipped with a magnetic stir bar and septum was added N'-((2R,3R)-2-(3-chloro-4-cyano-2-methylphenyl-amino)-3-hydroxybutanoyl)-4-(methylsulphonyl)benzohydrazide (855 mg, 1.8 mmol) followed by a addition of anhydrous THF (200 mL) under an atmosphere of nitrogen. To this was then added tosyl chloride (350 mg, 1.8 mmol) followed by addition of polystyrene bound (2-tert-butylimino-2-diethylamino-1,3-dimethylperhydro-1,3,2-diazaphosphorine (PS-BEMP) (2.2 mmol/g loading, 2.51 g, 5.5 mmol). This mixture was allowed to stir at room temperature for 6.5 h. The solids were then filtered off and washed with additional THF (100 mL). The filtrate was then concentrated under reduced pressure to reveal a red solid. This was purified via silica gel chromatography eluted with 70% EtOAc/hexanes to yield product as a white solid (209 mg, 25%). $^1$H NMR (400 MHz, acetone-$d_6$, δ in ppm) 8.25 (AA'XX', J=8.4 Hz, 2H), 8.13 (AA'XX', J=8.8 Hz, 2H), 7.49 (d, J=8.8 Hz, 1H), 6.90 (d, J=8.8 Hz, 1H), 5.90 (d, J=9.0 Hz, 1H), 5.11 (dd, J=5.6, 8.9 Hz, 1H), 4.70 (d, J=6.0 Hz, 1H), 4.55 (m, 1H), 3.19 (s, 3H), 2.37 (s, 3H), 1.43 (d, J=6.2 Hz, 3H).

Example 26

2-chloro-4-((1R,2R)-2-hydroxy-1-(5-phenyl-1,3,4-thiadiazol-2-yl)propylamino)-3-methylbenzonitrile

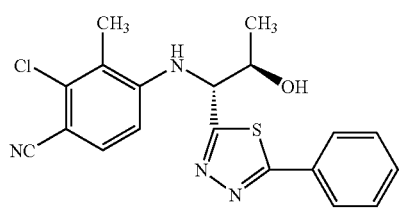

Intermediate 26a 4-((1R,2R)-2-(tert-butyldimethylsilyloxy)-1-(5-phenyl-1,3,4-thiadiazol-2-yl)propylamino)-2-chloro-3-methylbenzonitrile

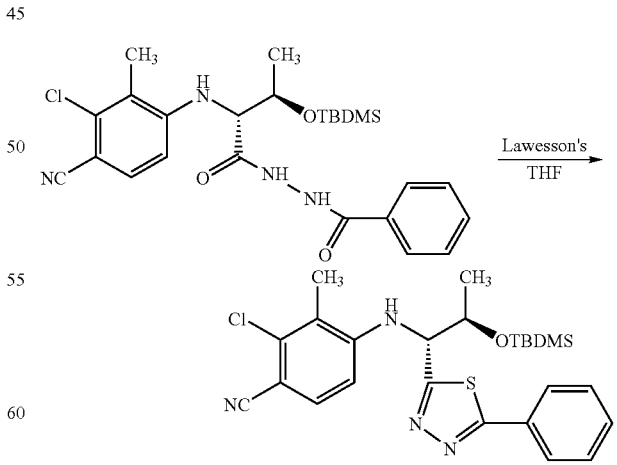

To a 25-mL round bottom flask charged with a solution of N'-((2R,3R)-3-(tert-butyldimethylsilyloxy)-2-(3-chloro-4-cyano-2-methylphenylamino)butanoyl)-benzohydrazide (326 mg, 0.65 mmol) in dry THF (10 mL) and equipped with a magnetic stirbar and septum was added Lawesson's reagent (527 mg, 1.3 mmol) under an atmosphere of nitrogen. This was stirred at room temperature for a period of 20 h. The solvent was then blown off under a gentle stream of nitrogen and the residue was directly purified via silica gel chromatography eluted with 30% EtOAc/hexanes to yield the product as a white solid (246 mg, 76%). $^1$H NMR (500 MHz, CDCl$_3$, δ in ppm) 7.90 (m, 2H), 7.46 (m, 3H), 7.31 (d, J=8.8 Hz, 1H), 6.75 (d, J=8.8 Hz, 1H), 5.19 (d, J=7.9 Hz, 1H), 5.00 (dd, J=3.1, 7.9 Hz, 1H), 4.50 (m, 1H), 2.27 (s, 3H), 1.21 (d, J=6.3 Hz, 3H), 1.02 (s, 9H), 0.24 (s, 3H), 0.17 (s, 3H).

Example 26

2-Chloro-4-((1R,2R)-2-hydroxy-1-(5-phenyl-1,3,4-thiadiazol-2-yl)propylamino)-3-methylbenzonitrile

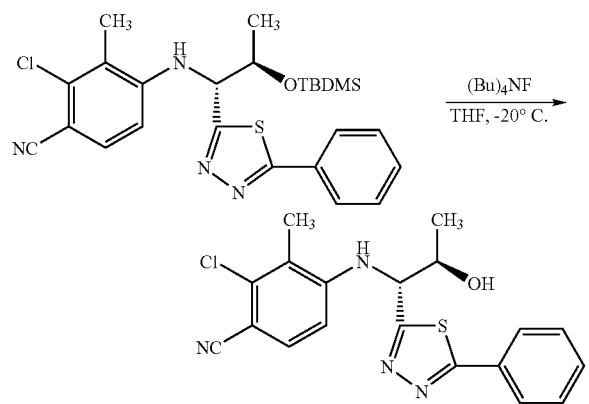

4-((1R,2R)-2-(tert-butyldimethylsilyloxy)-1-(5-phenyl-1,3,4-thiadiazol-2-yl)propyl amino)-2-chloro-3-methylbenzonitrile (242 mg, 0.49 mmol) was deprotected using tetrabutylammonium fluoride (1.0 M solution in THF, 0.97 mL, 0.97 mmol) in a procedure analogous to that used for the preparation of example 7. After column chromatography (50% EtOAc/hexanes) the title compound was isolated as a white solid (182 mg, 97%). $^1$H NMR (400 MHz, acetone-d$_6$, δ in ppm) 7.96 (m, 2H), 7.51 (m, 4H), 6.85 (d, J=8.8 Hz, 1H), 5.89 (d, J=7.7 Hz, 1H), 5.15 (dd, J=7.6 Hz, 3.91H), 5.03 (d, J=4.4 Hz, 1H), 4.53 (m, 1H), 2.35 (s, 3H), 1.28 (d, J=6.4 Hz, 3H).

Example 27

2-chloro-4-((1R,2S)-2-hydroxy-1-(5-phenyl-1,3,4-thiadiazol-2-yl)propylamino)-3-methylbenzonitrile

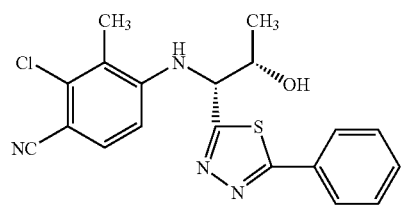

Intermediate 27a 4-((1R,2S)-2-(tert-butyldimethylsilyloxy)-1-(5-phenyl-1,3,4-thiadiazol-2-yl)propylamino)-2-chloro-3-methylbenzonitrile

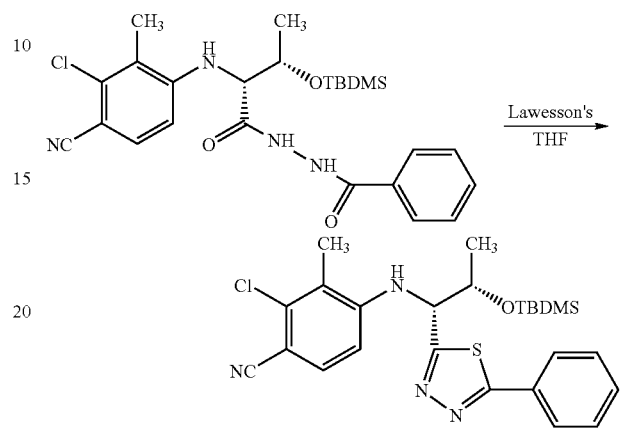

Intermediate 27a was prepared by a procedure analogous to that used for the preparation of intermediate 26a by cyclization of N'-((2R,3S)-3-(tert-butyldimethylsilyloxy)-2-(3-chloro-4-cyano-2-methylphenylamino)butanoyl)benzo-hydrazide (505 mg, 1.0 mmol) to form the title compound as a white solid (458 mg, 91%). $^1$H NMR (500 MHz, CDCl$_3$, δ in ppm) 7.88 (m, 2H), 7.46 (m, 3H), 7.34 (d, J=8.6 Hz, 1H), 6.47 (d, J=8.7 Hz, 1H), 5.65 (d, J=7.3 Hz, 1H), 4.88 (dd, J=1.8, 7.2 Hz, 1H), 4.57 (m, 1H), 2.36 (s, 3H), 1.38 (d, J=6.2 Hz, 3H), 0.90 (s, 9H), 0.09 (s, 3H), −0.18 (s, 3H).

Example 27

2-chloro-4-((1R,2S)-2-hydroxy-1-(5-phenyl-1,3,4-thiadiazol-2-yl)propylamino)-3-methylbenzonitrile

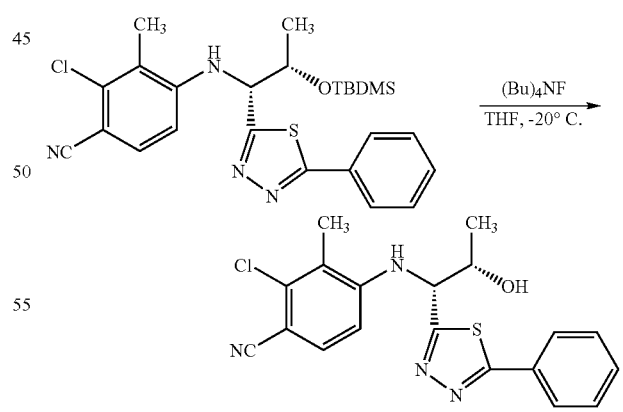

4-((1R,2S)-2-(tert-butyldimethylsilyloxy)-1-(5-phenyl-1,3,4-thiadiazol-2-yl)propyl amino)-2-chloro-3-methylbenzonitrile (425 mg, 0.85 mmol) was deprotected using tetrabutylammonium fluoride (1.0 M solution in THF, 1.7 mL, 1.7 mmol) in a procedure analogous to that used for the preparation of example 7. After column chromatography (50% EtOAc/hexanes) the title compound was isolated as a white solid (225 mg, 69%). ¹H NMR (500 MHz, acetone-d₆, δ in ppm) 7.94 (m, 2H), 7.51 (m, 4H), 6.81 (d, J=8.7 Hz, 1H), 5.88 (d, J=7.1 Hz, 1H), 5.13 (dd, J=3.5, 7.2 Hz, 1H), 5.02 (br s, 1H), 4.48 (m, 1H), 2.39 (s, 3H), 1.41 (d, J=6.3 Hz, 3H).

Example 28

2-chloro-4-((1R,2R)-1-(5-(4-fluorophenyl)-1,3,4-thiadiazol-2-yl)-2-hydroxypropylamino)-3-methylbenzonitrile

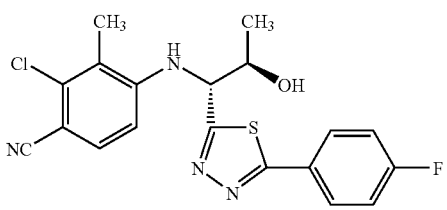

Intermediate 28a

N'-((2R,3S)-3-(tert-butyldimethylsilyloxy)-2-(3-chloro-4-cyano-2-methylphenylamino)-butanoyl)-4-fluorobenzohydrazide

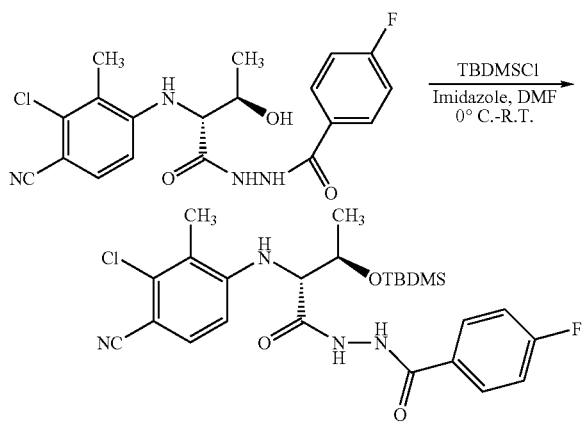

N'-((2R,3S)-2-(3-chloro-4-cyano-2-methylphenylamino)-3-hydroxybutanoyl)-4-fluoro benzohydrazide (15.2 g, 38.0 mmol) was protected using TBDMSCl (11.32 g, 75.0 mmol) and imidazole (10.23 g, 150 mmol) in a manner analogous to that described for the preparation of intermediate 7b. Purification of the compound was accomplished by pouring the reaction mixture into ice-cold water (1.6 L) and filtering off the solid precipitate. This was taken up in methylene chloride (700 mL) and sequentially washed with water (2×200 mL) and brine (1×200 mL). This was then dried over sodium sulfate, filtered and concentrated down to give a yellow solid. After column chromatography (50% EtOAc/hexanes) the title compound was isolated as a white solid (20 g, quant.). ¹H NMR (400 MHz, CDCl₃, δ in ppm) 9.32 (m, 2H), 7.77 (dd, J=5.3, 8.8 Hz, 2H), 7.27 (d, J=8.7 Hz, 1H), 7.05 (t, J=8.6 Hz, 2H), 6.54 (d, J=8.7 Hz, 1H), 4.94 (d, J=6.0 Hz, 1H), 4.36 (m, 1H), 4.01 (t, J=5.3 Hz, 1H), 2.26 (s, 3H), 1.35 (d, J=6.4 Hz, 3H), 0.89 (s, 9H), 0.14 (s, 3H), 0.09 (s, 3H).

Intermediate 28b 4-((1R,2R)-2-(tert-butyldimethylsilyloxy)-1-(5-(4-fluorophenyl)-1,3,4-thiadiazol-2-yl)propylamino)-2-chloro-3-methylbenzonitrile

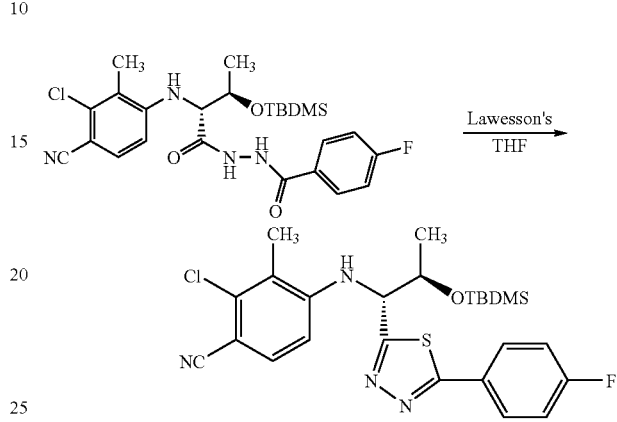

Intermediate 28b was prepared by a procedure analogous to that used for the preparation of intermediate 26a by cyclization of N'-((2R,3R)-3-(tert-butyldimethylsilyloxy)-2-(3-chloro-4-cyano-2-methylphenylamino)butanoyl)-4-fluoro benzohydrazide (503 mg, 1.0 mmol) provided the title compound as a white solid (349 mg, 70%). ¹H NMR (400 MHz, CDCl₃, δ in ppm) 7.89 (m, 2H), 7.28 (d, J=8.7 Hz, 1H), 7.13 (m, 2H), 6.73 (d, J=8.8 Hz, 1H), 5.17 (d, J=7.9 Hz, 1H), 4.99 (dd, J=2.9, 7.9 Hz, 1H), 4.50 (m, 1H), 2.24 (s, 3H), 1.19 (d, J=6.4 Hz, 3H), 1.00 (s, 9H), 0.23 (s, 3H), 0.16 (s, 3H).

Example 28

2-chloro-4-((1R,2R)-1-(5-(4-fluorophenyl)-1,3,4-thiadiazol-2-yl)-2-hydroxypropylamino)-3-methylbenzonitrile

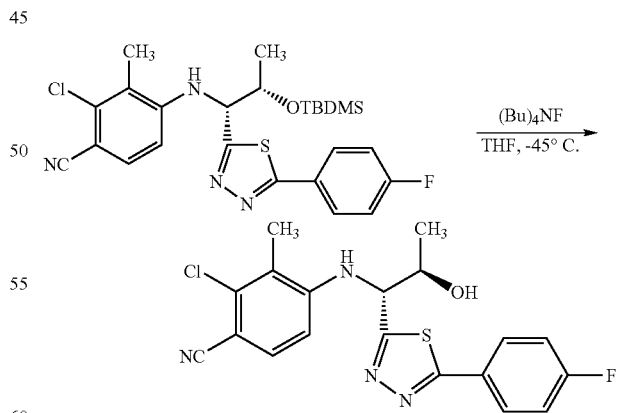

4-((1R,2R)-2-(tert-butyldimethylsilyloxy)-1-(5-(4-fluorophenyl)-1,3,4-thiadiazol-2-yl)propylamino)-2-chloro-3-methylbenzonitrile (347 mg, 0.67 mmol) was deprotected using tetrabutylammonium fluoride (1.0 M solution in THF, 0.8 mL, 0.8 mmol) in a procedure analogous to that used for the preparation of example 7. After column chromatography (50% EtOAc/hexanes) the title compound was isolated as a white solid (269 mg, quant). ¹H NMR (500 MHz, CDCl₃, δ in ppm) 7.88 (m, 2H), 7.29 (d, J=8.5 Hz, 1H), 7.13 (m, 2H), 6.63 (d, J=8.7 Hz, 1H), 5.47 (d, J=7.6 Hz, 1H), 4.99 (dd, J=3.4, 7.5 Hz, 1H), 4.49 (m, 1H), 3.09 (br s, 1H), 2.30 (s, 3H), 1.31 (d, J=6.4 Hz, 3H).

Example 29

2-chloro-4-((1R,2S)-1-(5-(3-fluoro-4-hydroxyphenyl)-1,3,4-oxadiazol-2-yl)-2-hydroxypropylamino)-3-methylbenzonitrile

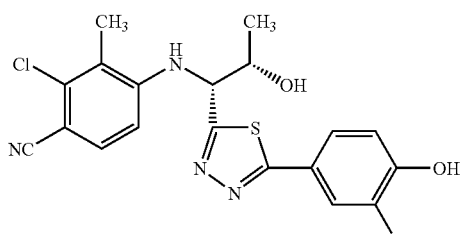

Intermediate 29a

Ethyl-3-fluoro-4-hydroxybenzoate

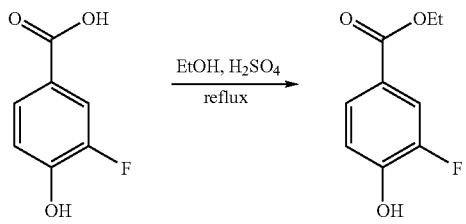

Intermediate 29a was prepared by a procedure analogous to that used for the preparation of intermediate 24a by esterification of 3-fluoro-4-hydroxybenzoic acid (5.06 g, 32.4 mmol) provided the title compound as white crystals (5.27 g, 88%). ¹H NMR (500 MHz, CDCl₃, δ in ppm) 7.76 (m, 2H), 7.03 (m, 1H), 6.51 (br s, 1H), 4.35 (q, J=7.1 Hz, 2H), 1.38 (t, J=7.1 Hz, 3H).

Example 29b 3-fluoro-4-hydroxybenzohydrazide

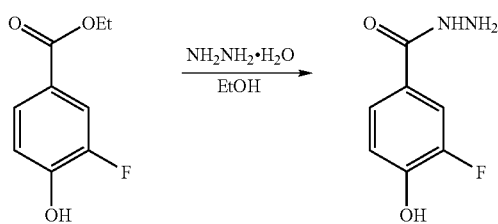

Intermediate 29b was prepared by a procedure analogous to that used for the preparation of intermediate 24b by hydrazide formation of ethyl-3-fluoro-4-hydroxybenzoate (5.19 g, 28 mmol) to provide the title compound as white crystals (1.65 g, 34%). ¹H NMR (500 MHz, DMSO-d₆, δ in ppm) 9.61 (br s, 1H), 7.56 (m, 3H), 6.97 (t, J=8.7 Hz, 1H), 4.43 (br s, 2H).

Example 29c

N'-((2R,3S)-2-(3-chloro-4-cyano-2-methylphenylamino)-3-hydroxybutanoyl)-3-fluoro-4-hydroxybenzohydrazide

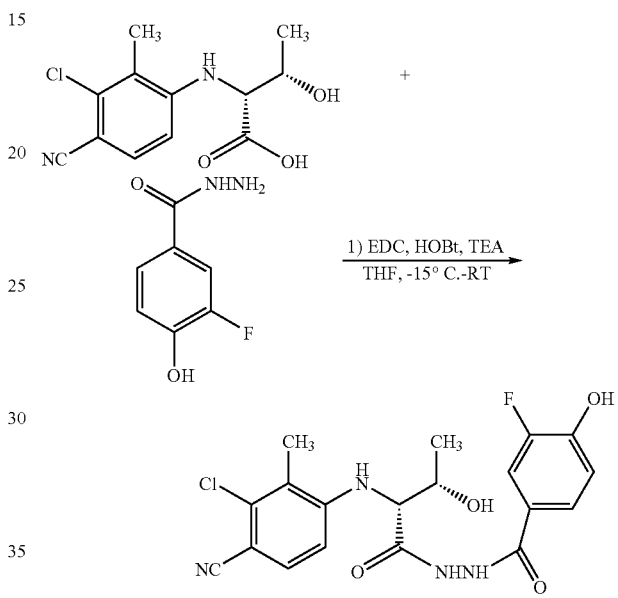

(2R,3S)-2-(3-chloro-4-cyano-2-methylphenylamino)-3-hydroxybutanoic acid (1.00 g, 3.7 mmol) and 4-(methylsulfonyl)benzohydrazide (636 mg, 3.7 mmol) were coupled together in a procedure analogous to that described for the preparation of intermediate 3b. The crude product was purified by boiling in chloroform (50 mL) followed by cooling to 0° C. and filtration to yield product as a red solid (900 mg, 65%). ¹H NMR (400 MHz, acetone-d₆, δ in ppm) 7.67 (m, 1H), 7.50 (m, 1H), 7.08 (m, 1H), 6.66 (d, J=8.6 Hz, 1H), 5.54 (d, J=7.0 Hz, 1H), 4.37 (dd, J=3.1, 6.2 Hz, 1H), 4.09 (dd, J=3.4, 7.1 Hz, 1H), 2.36 (s, 3H), 1.34 (d, J=6.3 Hz, 3H).

Example 29d 4-(tert-Butyldimethylsilyloxy)-N'-((2R,3S)-3-(tert-butyldimethylsilyloxy)-2-(3-chloro-4-cyano-2-methylphenylamino)butanoyl)-3-fluorobenzohydrazide

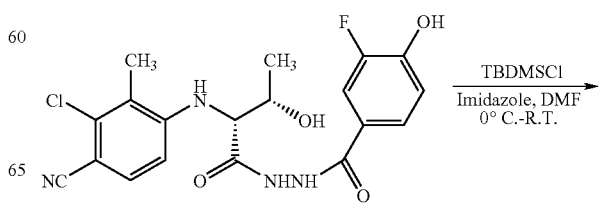

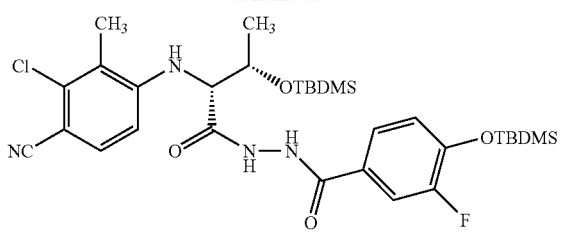

N'-((2R,3S)-2-(3-chloro-4-cyano-2-methylphenylamino)-3-hydroxybutanoyl)-3-fluoro-4-hydroxybenzohydrazide (1.14 g, 2.7 mmol) was protected using TBDMSCl (2.85 g, 19 mmol) and imidazole (2.57 g, 38 mmol) in a manner analogous to that described for the preparation of intermediate 7b. After column chromatography (30% EtOAc/hexanes) the title compound was isolated as a white solid (640 mg, 37%). $^1$H NMR (400 MHz, CDCl$_3$, δ in ppm) 9.36 (m, 1H), 8.86 (s, 1H), 7.55 (m, 1H), 7.48 (m, 1H), 7.31 (t, J=9.2 Hz, 1H), 6.89 (t, J=8.3 Hz, 1H), 6.44 (m, 1H), 5.35 (d, J=6.1 Hz, 1H), 4.46 (m, 1H), 4.41 (m, 1H), 3.95 (m, 1H), 2.29 (s, 3H), 1.25 (d, J=6.3 Hz, 3H), 0.97 (s, 9H), 0.90 (s, 9H), 0.19 (s, 6H), 0.11 (s, 3H), 0.06 (s, 3H).

Example 29e 4-((1R,2S)-2-(tert-butyldimethylsilyloxy)-1-(5-(4-(tert-butyldimethylsilyloxy)-3-fluoro-phenyl)-1,3,4-oxadiazol-2-yl)propylamino)-2-chloro-3-methylbenzonitrile

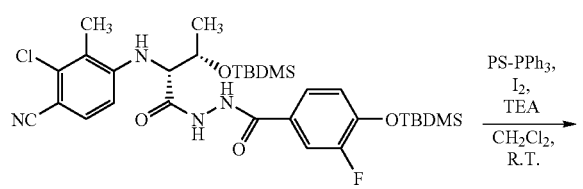

Intermediate 29e was prepared by a procedure analogous to that used for the preparation of intermediate 10c by cyclization of 4-(tert-butyldimethylsilyloxy)-N'-((2R,3S)-3-(tert-butyldimethylsilyloxy)-2-(3-chloro-4-cyano-2-methylphenylamino)butanoyl)-3-fluoro benzohydrazide (640 mg, 0.99 mmol) with PS-PPh$_3$ (3.0 mmol/g, 661 mg, 1.98 mmol), I$_2$ (502 mg, 1.98 mmol), and TEA (1.4 mL, 10 mmol). After column chromatography (25% EtOAc/hexanes) the title compound was isolated as a white solid (131 mg, 21%). $^1$H NMR (400 MHz, CDCl$_3$, δ in ppm) 7.65 (m, 1H), 7.59 (m, 1H), 7.32 (d, J=8.6 Hz, 1H), 6.9 (t, J=8.3 Hz, 1H), 6.45 (d, J=8.8 Hz, 1H), 5.35 (d, J=8.6 Hz, 1H), 4.77 (dd, J=1.9, 8.7 Hz, 1H), 4.51 (m, 1H), 2.36 (s, 3H), 1.40 (d, J=6.1 Hz, 3H), 0.99 (s, 9H), 0.86 (s, 9H), 0.21 (s, 6H), 0.06 (s, 3H), −0.20 (s, 3H).

Example 29

2-chloro-4-((1R,2S)-1-(5-(3-fluoro-4-hydroxyphenyl)-1,3,4-oxadiazol-2-yl)-2-hydroxypropylamino)-3-methylbenzonitrile

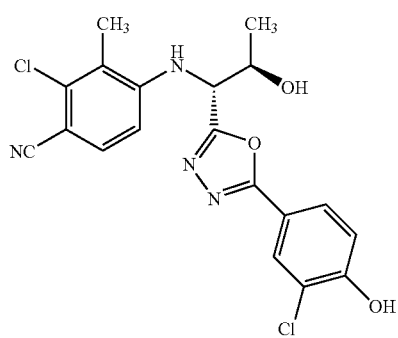

4-((1R,2S)-2-(tert-butyldimethylsilyloxy)-1-(5-(4-(tert-butyldimethylsilyloxy)-3-fluoro-phenyl)-1,3,4-oxadiazol-2-yl)propylamino)-2-chloro-3-methylbenzonitrile (130 mg, 0.21 mmol) using tetrabutylammonium fluoride (1.0 M solution in THF, 0.62 mL, 0.62 mmol) in a procedure analogous to that used for the preparation of example 7. After column chromatography (50% EtOAc/hexanes) the title compound was isolated as a white solid (743 mg, 88%). $^1$H NMR (400 MHz, CDCl$_3$, δ in ppm) 7.49 (m, 2H), 7.16 (m, 1H), 6.89 (d, J=8.6 Hz, 1H), 5.67 (d, J=8.6 Hz, 1H), 5.08 (dd, J=3.7, 8.4 Hz, 1H), 4.61 (m, 1H), 2.98 (br s, 1H), 2.40 (s, 3H), 1.40 (d, J=6.3 Hz, 3H).

Example 30

2-Chloro-4-((1R,2R)-1-(5-(3-chloro-4-hydroxyphenyl)-1,3,4-oxadiazol-2-yl)-2-hydroxypropylamino)-3-methylbenzonitrile

Intermediate 30a 3-chloro-N'-((2R,3R)-2-(3-chloro-4-cyano-2-methylphenylamino)-3-hydroxybutanoyl)-4-hydroxybenzohydrazide

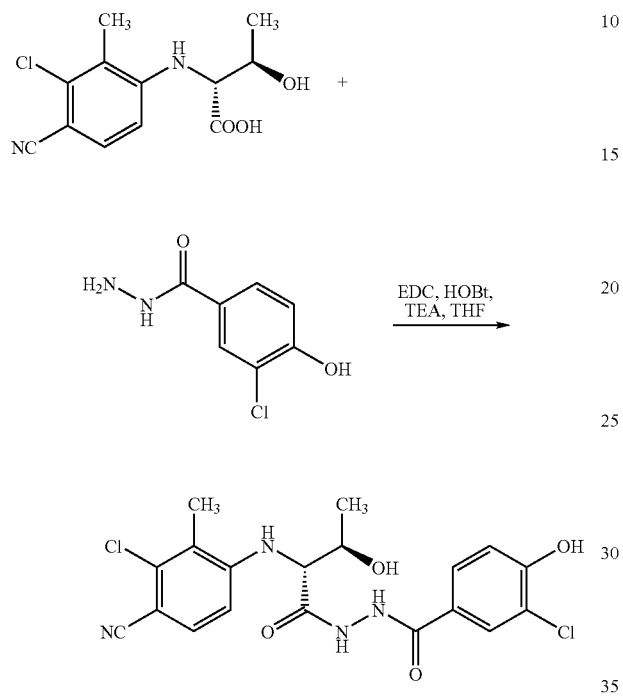

To a 50 mL round bottom flask was added (2R,3R)-2-(3-chloro-4-cyano-2-methylphenylamino)-3-hydroxybutanoic acid (1.00 g, 3.73 mmol, 1.0 equiv.) and anhydrous THF (18.7 mL). After the flask was flushed with nitrogen, 3-chloro-4-hydroxybenzoic hydrazide (766 mg, 4.11 mmol, 1.1 equiv.) was added. The stirring solution was cooled to −20° C., and 1-hydroxybenzotriazole (HOBt) (555 mg, 4.11 mmol, 1.1 equiv.) was added in one portion, followed by 1-ethyl-3-(3'-dimethylaminopropyl)carbodiimide (EDC) (1.79 g, 9.33 mmol, 2.5 equiv.) and then triethylamine (TEA) (2.08 mL, 14.9 mmol. 4.0 equiv.). The solution was stirred at −20° C. for 1 h and gradually warmed to room temperature overnight. The contents of the flask were filtered over Celite® in a ground glass fritted funnel to remove solids formed during the reaction. The solution was diluted with 50 mL of EtOAc. The EtOAc solution was washed with 5% citric acid solution (w/v) (2×50 mL), distilled water (2×50 mL), and brine (1×50 mL). The organic layer was dried over $Na_2SO_4$ and then concentrated in vacuo to yield a light yellow solid. The product was purified via automated flash chromatography (0→50% EtOAc/hexanes→100% EtOAc, 24 g of silica gel; TLC $R_f$=0.38, 100% EtOAc, vanillin stain) to provide the desired product as an off-white solid (870 mg, 53% yield). Other data: $^1$H NMR (400 MHz, acetone-$d_6$, δ in ppm) 7.96 (d, J=2.2 Hz, 1H), 7.79 (dd, J=2.19, 8.49 Hz, 1H), 7.53 (d, J=8.65 Hz, 1H), 7.105 (d, J=8.5 Hz, 1H), 6.72 (d, J=8.65 Hz, 1H), 5.58 (d, J=7.18 Hz, 1H), 4.22 (m, 1H), 4.11 (dd, J=5.13, 7.18 Hz, 1H), 2.35 (s, 3H), 1.37 (d, J=6.45 Hz, 3H); LRMS (ESI−) exact mass calcd for $C_{19}H_{18}Cl_2N_4O_4$ [M]$^+$ 437.28. found 438.1.

Intermediate 30b 4-(tert-Butyldimethylsilyloxy)-N'-((2R,3R)-3-(tert-butyldimethylsilyloxy)-2-(3-chloro-4-cyano-2-methylphenylamino)butanoyl)-3-chlorobenzohydrazide

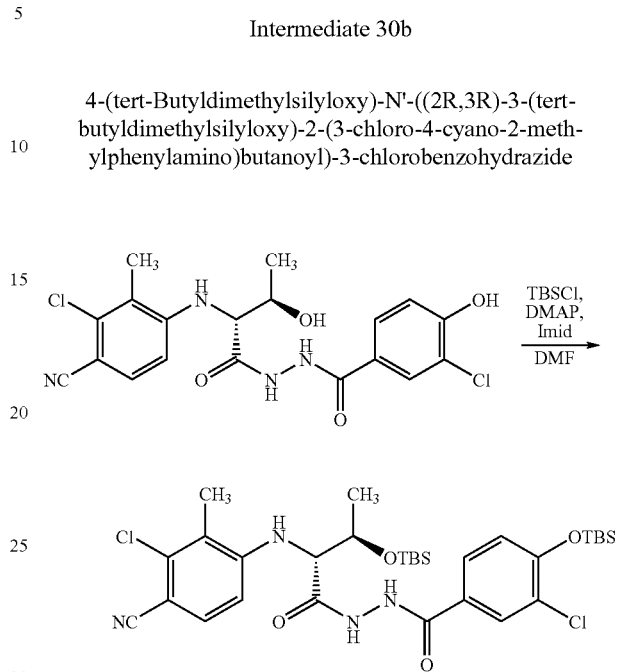

To a 50 mL round bottom flask was added 3-chloro-N'-((2R,3R)-2-(3-chloro-4-cyano-2-methylphenylamino)-3-hydroxybutanoyl)-4-hydroxybenzohydrazide (870 mg, 1.99 mmol, 1.0 equiv.) and 10 mL of anhydrous DMF. The flask was cooled to 0° C. using an ice-water bath and then DMAP (49 mg, 0.398 mmol, 0.2 equiv.) was added in one portion followed by imidazole (677 mg, 9.95 mmol, 5.0 equiv.). The solution was stirred at 0° C. for 15 min, then TBSCl was added (1.50 g, 9.95 mmol, 5.0 equiv.). The reaction was allowed to warm to room temperature slowly and stirred for 7 h until the reaction appeared to be complete by TLC. The solution was dumped into a beaker of ice water and the ice was allowed to melt. The solid that precipitated was filtered and washed with distilled water. The yellow solid was dissolved in 10 mL of dichloromethane and washed with distilled water (1×10 mL) and brine (1×10 mL). The organic layer was dried over $Na_2SO_4$ and then concentrated in vacuo to yield a light yellow solid. The product was purified via automated flash chromatography (0→30% EtOAc/hexanes→100% EtOAc, 24 g of silica gel; TLC $R_f$=0.8, 100% EtOAc, vanillin stain) to provide the desired product as an off-white solid (689 mg, 52% yield). Other data: $^1$H NMR (400 MHz, acetone-$d_6$, δ in ppm) 9.82 (br. s., 2H), 7.94 (d, J=2.15 Hz, 1H), 7.77 (dd, J=2.15, 8.4 Hz, 1H), 7.47 (d, J=8.79 Hz, 1H), 7.07 (d, J=8.59 Hz, 1H), 6.79 (d, J=8.59 Hz, 1H), 5.37 (d, J=6.84 Hz, 1H), 4.47 (m, 1H), 4.26 (dd, J=5.08, 6.84 Hz, 1H), 2.32 (s, 3H), 1.40 (d, J=6.25 Hz, 3H), 1.04 (s, 9H), 0.88 (s, 9H), 0.29 (s, 6H), 0.13 (s, 3H), 0.10 (s, 3H); LRMS (ESI−) exact mass calcd for $C_{31}H_{46}Cl_2N_4O_4Si_2$ [M]$^+$ 665.8. found 666.2.

Intermediate 30c 4-((1R,2R)-2-(tert-Butyldimethylsilyloxy)-1-(5-(3-chloro-4-hydroxyphenyl)-1,3,4-oxadiazol-2-yl)propylamino)-2-chloro-3-methylbenzonitrile

Example 30

2-chloro-4-((1R,2R)-1-(5-(3-chloro-4-hydroxyphenyl)-1,3,4-oxadiazol-2-yl)-2-hydroxypropylamino)-3-methylbenzonitrile

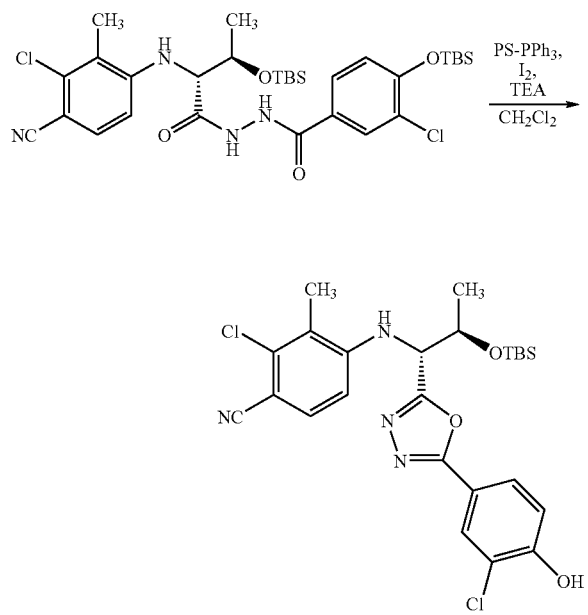

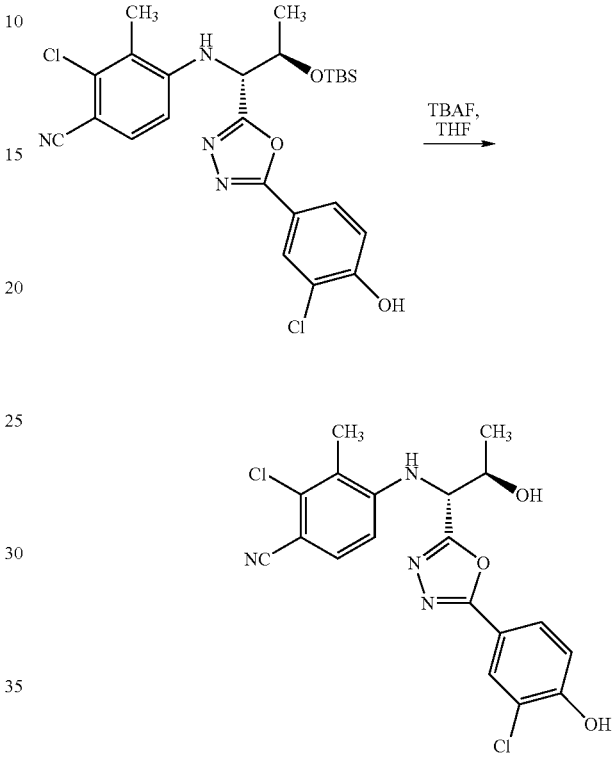

To a 25 mL round bottom flask was added polymer supported triphenylphosphine (687 mg, 2.06 mmol, 2.0 equiv., approx. 3 mmol/g) and 10.3 mL of methylene chloride. The reaction was cooled to 0° C. using an ice-water bath and then iodine (523 mg, 2.06 mmol, 2.0 equiv.) was added followed by TEA (0.57 mL, 4.12 mmol, 4.0 equiv.). After stirring for 5 min, 4-(tert-butyldimethylsilyloxy)-N-((2R,3R)-3-(tert-butyldimethylsilyloxy)-2-(3-chloro-4-cyano-2-methylphenylamino)butanoyl)-3-chloro benzohydrazide (688 mg, 1.03 mmol, 1.0 equiv.) was added. The reaction was allowed to stir at room temperature for 2 h. The mixture was filtered over Celite® in a ground glass fritted funnel and the solids rinsed with methylene chloride several times. The organics were washed with 10% $Na_2S_2O_3$ (3×10 mL) followed by a wash with brine (1×10 mL). The solution was dried over $Na_2SO_4$ and was concentrated in vacuo to yield a brown oil. The product was purified via automated flash chromatography (0→30% EtOAc/hexanes→100% EtOAc, 40 g of silica gel) to provide the desired product as a yellow oil (586 mg, 88% yield). Other data: $^1$H NMR (400 MHz, acetone-$d_6$, δ in ppm) 7.92 (d, J=2.14 Hz, 1H), 7.80 (dd, J=1.95, 8.4 Hz, 1H), 7.50 (d, J=8.79 Hz, 1H), 7.18 (d, J=8.6 Hz, 1H), 6.93 (d, J=8.79 Hz, 1H), 5.79 (d, J=9.18 Hz, 1H), 5.02 (dd, J=6.65, 9.19 Hz, 1H), 4.65 (m, 1H), 2.34 (s, 3H), 1.41 (d, J=6.05 Hz, 3H), 0.81 (s, 9H), 0.09 (s, 3H), 0.03 (s, 3H); LRMS (ESI−) exact mass calcd for $C_{25}H_{30}Cl_2N_4O_3Si$ [M]$^+$ 533.5. found 534.2.

To a 100 mL round bottom flask was added 4-((1R,2R)-2-(tert-butyldimethylsilyloxy)-1-(5-(3-chloro-4-hydroxyphenyl)-1,3,4-oxadiazol-2-yl)propylamino)-2-chloro-3-methyl benzonitrile (586 mg, 0.9 mmol, 1.0 equiv.) and 60 mL of anhydrous THF. The solution was cooled to −78° C. and TBAF (1 mL, 0.99 mmol, 1.1 equiv., 1M in THF) was added dropwise via a syringe. The solution was stirred for 3 h while the temperature was kept below −30° C. The reaction was quenched with 25 mL of saturated ammonium chloride and diluted with 25 mL of EtOAc. The layers were separated and the organic layer was washed with distilled water (1×25 mL) and brine (1×25 mL). The organic layer was dried over $Na_2SO_4$ and was concentrated in vacuo to yield an off-white solid. The product was purified via automated flash chromatography (0→50% EtOAc/hexanes→100% EtOAc, 24 g of silica gel; TLC $R_f$=0.43, 100% EtOAc, vanillin stain) to provide the desired product as a white solid (239 mg, 63% yield). Other data: $^1$H NMR (400 MHz, acetone-$d_6$, δ in ppm) 7.92 (d, J=2.15 Hz, 1H), 7.80 (dd, J=2.15, 8.6 Hz, 1H), 7.49 (d, J=8.6 Hz, 1H), 7.17 (d, J=8.6 Hz, 1H), 6.89 (d, J=8.79 Hz, 1H), 5.87 (d, J=8.79 Hz, 1H), 5.02 (dd, J=5.66, 8.79 Hz, 1H), 4.51 (m, 1H), 2.36 (s, 3H), 1.41 (d, J=6.45 Hz, 3H); LRMS (ESI+) exact mass calcd for $C_{19}H_{16}Cl_2N_4O_3$ [M]$^+$ 419.26. found 419.2.

Example 31

4-((1R,2R)-1-(5-(4-cyanophenyl)-1,3,4-oxadiazol-2-yl)-2-hydroxypropylamino)-3-methyl-2-(trifluoromethyl)benzonitrile

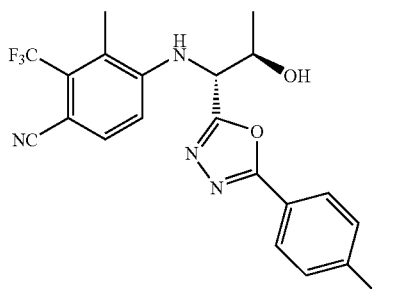

Intermediate 31a 4-fluoro-3-methyl-2-(trifluoromethyl)benzonitrile

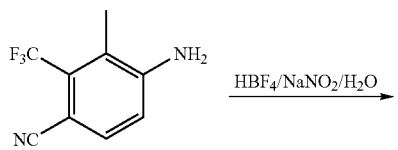

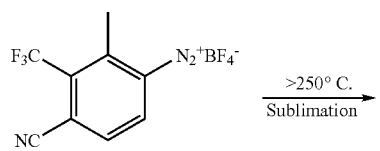

4-amino-3-methyl-2-(trifluoromethyl)benzonitrile (CAS 573764-86-0, 2.0 g, 9.99 mmol) was dissolved in fluoroboric acid, HBF$_4$ solution (15 mL) at −10° C. (ice/MeOH). To the pre-cooled solution was added NaNO$_2$ (689 mg, 9.992 mmol) in 2 mL H$_2$O drop by drop under constant stirring. The reaction mixture was allowed to stir for 15 min at −10° C. and filtered off. The white residue was washed with cold EtOH and cold ether to get the diazosalt as a white crystalline solid. The salt is dried over high vacuum for 4-5 h. to provide 1.9 g. The salt was heated up (>250° C.) and sublimed under reduced pressure to get the crude fluoro compound as an oil. The oil is chromatographed to get the pure 4-fluoro-3-methyl-2-(trifluoromethyl)benzonitrile as a clear oil (700 mg):

$^1$H NMR (400 MHz, CDCl3, δ in ppm) 7.68 (dd, J=5.0, 9.0 Hz, 1H), 7.33 (t, J=9 Hz, 1H), 2.43 (quin, J=2 Hz, 3H).

Intermediate 31b (2R,3R)-2-(4-Cyano-2-methyl-3-(trifluoromethyl)phenylamino)-3-hydroxybutanoic acid

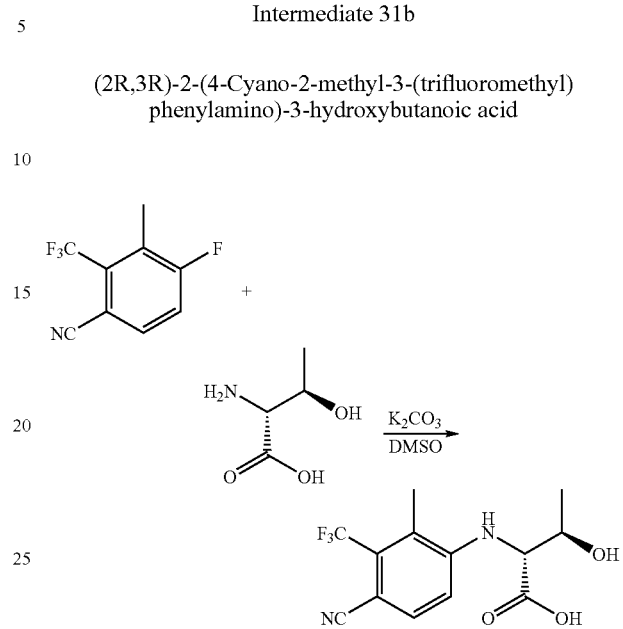

4-fluoro-3-methyl-2-(trifluoromethyl)benzonitrile (1.16 g, 5.74 mmol) and D-allo-theronine (1.03 g, 8.6104 mmol) was added to DMSO (15 mL). K$_2$CO$_3$ (1.98 g) was added to the reaction mixture and stirred at 75° C. for 24 h. The reaction mixture was cooled to room temperature and poured slowly into a 10% citric acid solution and stirred for 10 min at room temperature. The solution was extracted with EtOAc several times to get the crude product. The crude product was chromatographed with a gradient of hexanes/EtOAc and then with EtOAc, 100% to give the final product (700 mg). $^1$H NMR (400 MHz, acetone-d$_6$, δ in ppm) 7.60 (d, J=9 Hz, 1H), 7.02 (d, J=9 Hz, 1H), 5.62 (d, J=9 Hz, 1H), 4.30 (m, 2H), 2.31 (m, 3H), 1.33 (d, J=6 Hz, 3H).

Intermediate 31c

4-Cyano-N'-((2R,3R)-2-(4-cyano-2-methyl-3-(trifluoromethyl)phenylamino)-3-hydroxybutanoyl)benzohydrazide

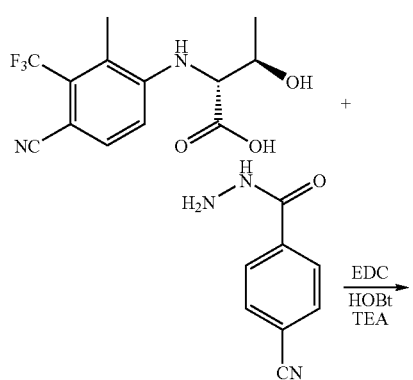

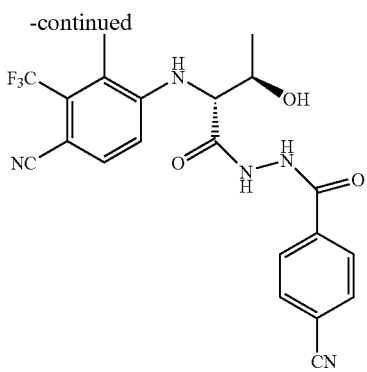

(2R,3R)-2-(4-cyano-2-methyl-3-(trifluoromethyl)phenylamino)-3-hydroxybutanoic acid (703 mg, 2.33 mmol) and 4-cyanobenzohydrazide (375 mg, 2.33 mmol) were mixed together in THF (50 mL) and cooled to −20° C. under N₂ atmosphere. To the pre-cooled reaction mixture was added HOBt (314 mg, 2.33 mmol), TEA (471 mg, 4.65 mmol) followed by EDC (891 mg, 4.65 mmol). The reaction mixture was allowed to stir at −20° C. for 1 h and then at room temperature overnight. After the reaction was complete, the urea was filtered off and the solution was washed with water, 5% citric acid followed by 5% NaHCO₃ to give the crude hydrazide product (800 mg).

Intermediate 31d

N'-((2R,3R)-3-(tert-butyldimethylsilyloxy)-2-(4-cyano-2-methyl-3-(trifluoromethyl)phenylamino)butanoyl)-4-cyanobenzohydrazide

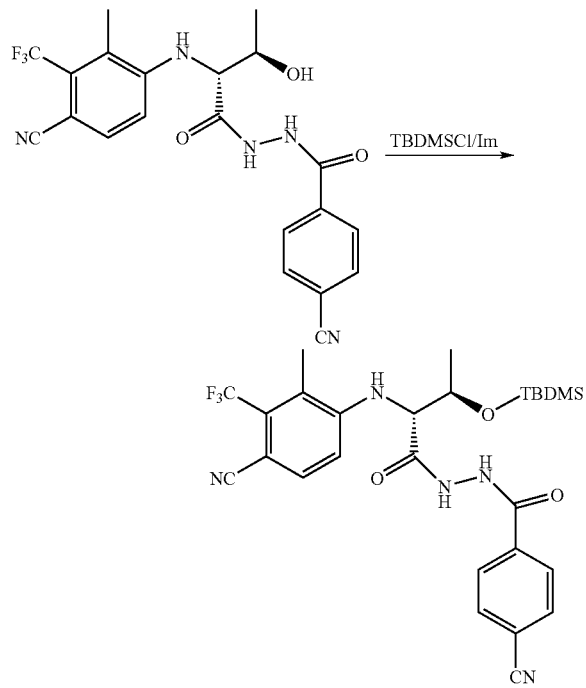

The crude material 4-cyano-N'-((2R,3R)-2-(4-cyano-2-methyl-3-(trifluoromethyl)phenylamino)-3-hydroxybutanoyl)benzohydrazide (800 mg, 1.75 mmol) was added to DMF (40 mL), followed by addition of TBDMS-Cl (1.06 g, 7.00 mmol) and imidazole (954 mg, 14.01 mmol) at 0° C. The solution was allowed to stir at 0° C. for 30 min and then at room temperature for overnight. The reaction was quenched with the addition of 200 mL brine and extract with EtOAc. The resulting crude material was chromatographed to get the desired product (640 mg) ¹H NMR (400 MHz, acetone-d₆, δ in ppm): 9.62 (br s), 7.93 (d, J=9 Hz, 2H), 7.79 (d, J=9 Hz, 2H), 7.55 (d, J=9 Hz, 1H), 6.98 (d, J=9 Hz, 1H), 5.38 (d, J=9 Hz, 1H), 4.41 (m, 1H), 4.18 (m, 1H), 2.25 (m, 3H), 1.31 (d, J=6 Hz, 3H), 0.77 (s, 9H), 0.03 (s, 6H), 0.00 (s, 3H).

Intermediate 31e 4-(((1R,2R)-2-(tert-Butyldimethylsilyloxy)-1-(5-(4-cyanophenyl)-1,3,4-oxadiazol-2-yl)propylamino)-3-methyl-2-(trifluoromethyl)benzonitrile

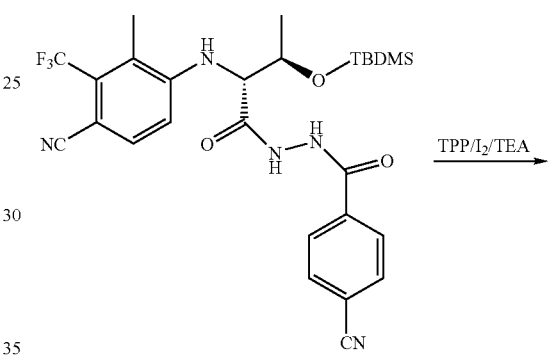

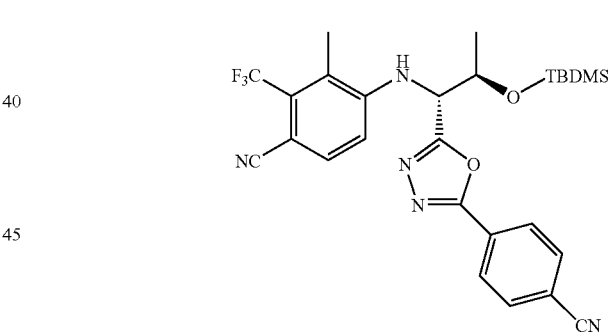

Triphenylphosphine (590 mg, 2.25 mmol) was dissolved in 25 mL of DCM followed by addition of I₂ (571 mg, 2.25 mmol) and TEA (456 mg, 4.50 mmol) at 0° C. N'-((2R,3R)-3-(tert-butyldimethylsilyloxy)-2-(4-cyano-2-methyl-3-(trifluoromethyl)phenylamino)butanoyl)-4-cyanobenzohydrazide (630 mg, 1.13 mmol) in 25 mL DCM was added to the pre-cooled solution mixture of PPh₃/I₂/TEA system and stirred. The temperature was allowed to rise to room temperature and stirred for additional 10 min. The reaction was quenched with 50 mL saturated sodium thiosulfate and extract with EtOAc. The crude mixture was chromatographed to give the product (510 mg, 84%) ¹H NMR (400 MHz, acetone-d₆, δ in ppm): 8.23 (d, J=9 Hz, 2H), 8.04 (d, J=9 Hz, 2H), 7.67 (d, J=9 Hz, 1H), 7.27 (d, J=9 Hz, 1H), 5.94 (d, J=9 Hz, 1H), 5.19 (m, 1H), 4.74 (m, 1H), 2.39 (m, 3H), 1.48 (d, J=6 Hz, 3H), 0.81 (s, 9H), 0.12 (s, 3H), 0.00 (s, 3H).

Example 31

4-((1R,2R)-1-(5-(4-Cyanophenyl)-1,3,4-oxadiazol-2-yl)-2-hydroxypropylamino)-3-methyl-2-(trifluoromethyl)benzonitrile

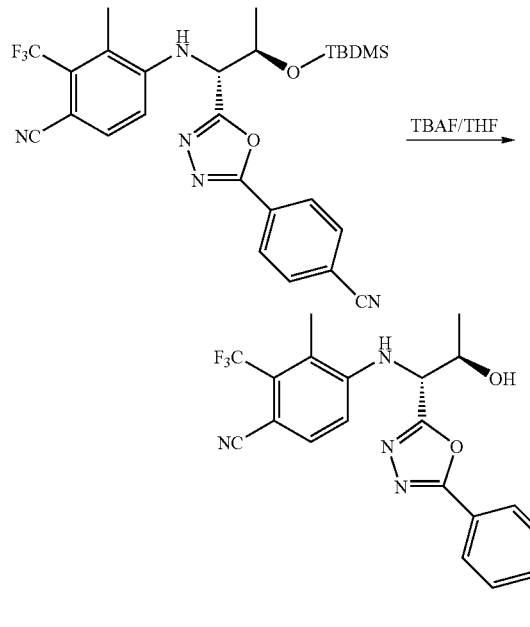

4-((1R,2R)-2-(tert-butyldimethylsilyloxy)-1-(5-(4-cyanophenyl)-1,3,4-oxadiazol-2-yl)propylamino)-3-methyl-2-(trifluoromethyl)benzonitrile (500 mg, 0.92 mmol) was dissolved in THF and cooled to −55° C. under N$_2$ atmosphere. TBAF (11.0M solution in THF, 1.10 mL, 1.11 mmol) was added to the precooled solution slowly and the temperature was allowed to rise. The progress of the reaction was monitored by TLC. After the reaction was complete, it was quenched with a saturated solution of NH$_4$Cl and extracted with EtOAc. Purification with column chromatography provided the desired product (270 mg, 68%). $^1$H NMR (400 MHz, acetone-d$_6$, δ in ppm): 8.17 (d, J=9 Hz, 2H), 7.96 (d, J=9 Hz, 2H), 7.60 (d, J=9 Hz, 1H), 7.15 (d, J=9 Hz, 1H), 6.01 (d, J=9 Hz, 1H), 5.13 (m, 1H), 4.69 (d, J=6 Hz, 1H), 4.53 (m, 1H), 2.35 (m, 3H), 1.39 (d, J=6 Hz, 3H).

Example 32

2-Chloro-4-((1R,2R)-1-(5-(3,4-dichlorophenyl)-1,3,4-oxadiazol-2-yl)-2-hydroxypropylamino)-3-methyl-benzonitrile

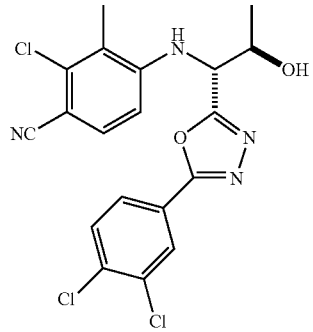

Intermediate 32a

3,4-dichloro-N'-((2R,3R)-2-(3-chloro-4-cyano-2-methylphenylamino)-3-hydroxybutanoyl)benzohydrazide

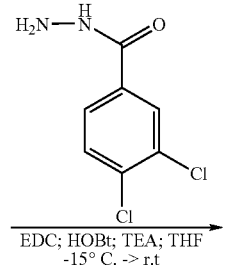

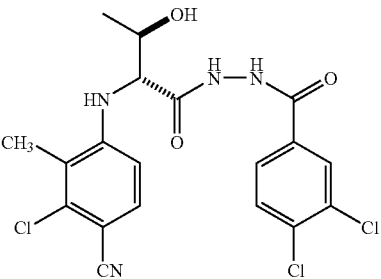

(2R,3R)-2-(3-chloro-4-cyano-2-methylphenylamino)-3-hydroxybutanoic acid (800 mg, 2.98 mmol) and 3,4-dichlorobenzohydrazide (615 mg, 2.98 mmol) were coupled together in a procedure analogous to that described for the preparation of intermediate 11c to furnish the title compound (1.10 g, 81%). $^1$H NMR (500 MHz, acetone d$_6$, δ in ppm) 10.0 (br s, 2H), 8.17 (s, 1H), 7.87 (d, J=8 Hz, 1H), 7.68 (d, J=8 Hz, 1H), 7.47 (d, J=8 Hz, 1H), 6.79 (d, J=8 Hz, 1H), 5.61 (d, J=7 Hz, 1H), 4.29-4.22 (m, 1H), 4.17-4.19 (m, 1H), 2.39 (s, 3H), 1.40 (d, J=6 Hz, 3H).

Example 32

2-chloro-4-((1R,2R)-1-(5-(3,4-dichlorophenyl)-1,3,4-oxadiazol-2-yl)-2-hydroxypropylamino)-3-methyl-benzonitrile

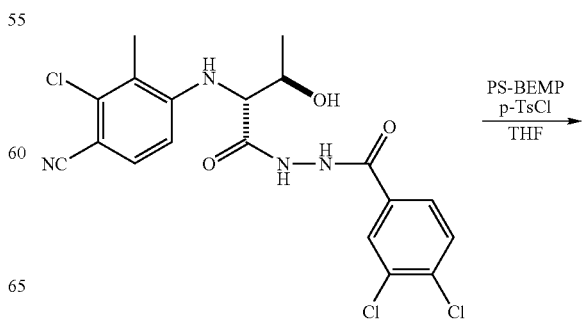

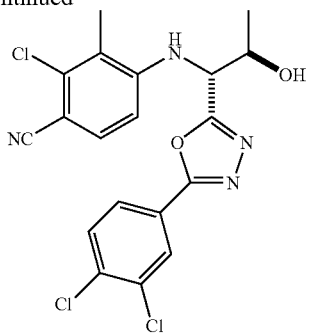

The title compound was prepared from 3,4-dichloro-N'-((2R,3R)-2-(3-chloro-4-cyano-2-methylphenylamino)-3-hydroxybutanoyl)benzohydrazide (800 mg, 1.89 mmol) utilizing the techniques described for the preparation of example 11 (210 mg, 25%). $^1$H NMR (500 MHz, CDCl$_3$, δ in ppm) 8.1 (d, J=8 Hz, 1H), 7.98 (d, J=8 Hz, 1H), 7.78 (d, J=8 Hz, 1H), 7.42 (d, J=8 Hz, 1H), 6.9 (d, J=8 Hz, 1H), 5.90 (d, J=8 Hz, 1H), 5.07-5.10 (m, 1H), 4.72 (d, J=6 Hz, 1H), 4.52-4.61 (m, 1H), 2.39 (s, 3H), 1.42 (d, J=6 Hz, 3H).

Example 33

2,3-dichloro-4-((1R,2S)-2-hydroxy-1-(5-phenyl-1,3,4-oxadiazol-2-yl)propylamino)benzonitrile

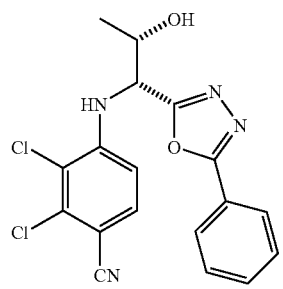

Intermediate 33a (2R,3S)-2-(2,3-Dichloro-4-cyanophenylamino)-3-hydroxybutanoic acid

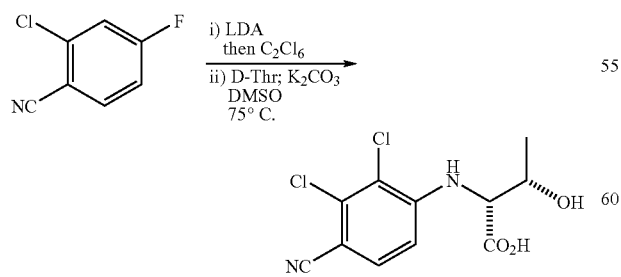

A 500 mL round bottomed flask was charged with diisopropylamine (11.81 mL, 83.60 mmol) and dry THF (100 mL) then the flask was cooled to −5° C. A 2.5M hexane solution of n-butyllithium (30.87 mL, 77.17 mmol) was then added and the mixture was stirred for 1 h at 0° C. This pre-formed LDA solution was then added via cannula to a −78° C. solution of 2-chloro-4-fluorobenzonitrile (10 g, 64.31 mmol) in THF (100 mL) and the mixture was stirred for 2 h. To this was added a solution of hexachloroethane (16 g, 67.58 mmol) in dry THF (50 mL), and the mixture was allowed to warm to room temperature and stirred for 17 h before being concentrated to furnish a yellow solid (12.15 g) which was used directly in the next step without further purification. K$_2$CO$_3$ (17.8 g, 128.62 mol) was added to a solution of 2,3-dichloro-4-fluorobenzonitrile (12.15 g, 64.31 mol) and (2R,3S)-2-amino-3-hydroxybutanoic acid (11.43 g, 0.096 mol) in DMSO (150 mL) at room temperature. The reaction mixture was heated to 75° C. and stirred for 16.5 h, then was allowed to cool to room temperature whereupon water (150 mL) and ethyl acetate (150 mL) was added to the mixture which was then partitioned. The aqueous phase was then washed with EtOAc (70 mL) and the acidified with citric acid monohydrate (19 g). The aqueous phase was then extracted with EtOAc (180 mL) (×2) and the combined organics were washed with water (80 mL), dried (Na$_2$SO$_4$), filtered and concentrated to furnish the title compound as a brown solid (9 g, 48%). $^1$H NMR (500 MHz, acetone d$_6$, δ in ppm) 7.61 (d, J=8 Hz, 1H), 6.84 (d, J=8 Hz, 1H), 6.02 (d, J=7 Hz, 1H), 4.60-4.57 (m, 1H), 4.39-4.37 (m, 1H) and 1.38 (d, J=7 Hz, 3H).

Intermediate 33b

N'-((2R,3S)-2-(2,3-Dichloro-4-cyanophenylamino)-3-hydroxybutanoyl)benzohydrazide

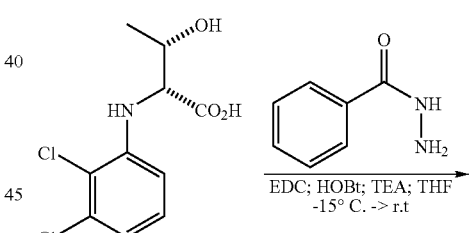

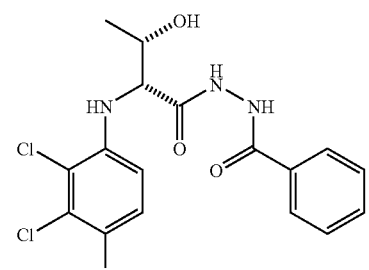

(2R,3S)-2-(2,3-dichloro-4-cyanophenylamino)-3-hydroxybutanoic acid (1.0 g, 3.46 mmol) and benzohydrazide (471 mg, 3.46 mmol) were reacted using the techniques described for the preparation of intermediate 11c to furnish the title compound (700 mg, 50%). $^1$H NMR (500 MHz, acetone-d$_6$, δ in ppm) 9.7 (br s, 2H), 7.91 (d, J=8 Hz, 2H), 7.41-7.62 (m, 4H), 6.82 (d, J=8 Hz, 1H), 6.18 (d, J=7 Hz, 1H), 4.90 (br s, 1H), 4.38-4.41 (m, 1H), 4.19-4.21 (m, 1H) and 1.32 (d, J=6 Hz, 3H).

Example 33

2,3-Dichloro-4-((1R,2S)-2-hydroxy-1-(5-phenyl-1,3,4-oxadiazol-2-yl)propylamino)benzonitrile

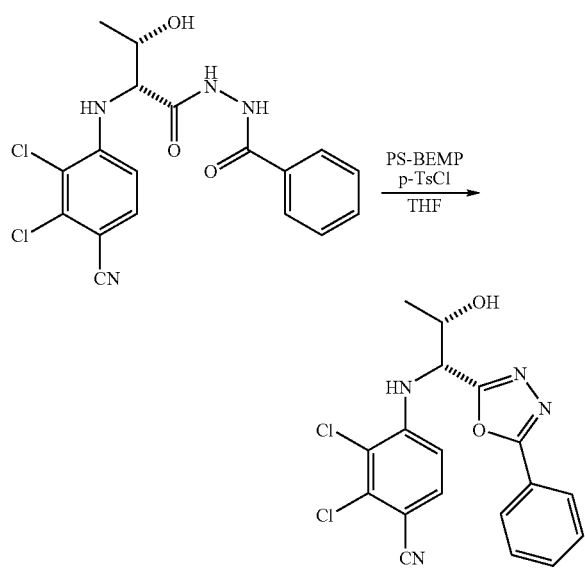

The title compound was prepared from N'-((2R,3S)-2-(2,3-dichloro-4-cyanophenyl amino)-3-hydroxybutanoyl)benzohydrazide (690 mg, 1.7 mmol) utilizing the techniques described for the preparation of example 11 (31 mg, 5%). Mp 156° C. $^1$H NMR (500 MHz, CDCl$_3$, δ in ppm) 7.85 (d, J=8 Hz, 1H), 7.40-7.52 (m, 4H), 6.72 (d, J=8 Hz, 1H), 4.72-4.74 (m, 1H), 4.60-4.67 (m, 1H), 3.09 (br s, 1H), 1.40 (d, J=6 Hz, 3H).

Example 34

2,3-Dichloro-4-((1R,2S)-1-(5-(4-chlorophenyl)-1,3,4-oxadiazol-2-yl)-2-hydroxypropylamino)benzonitrile

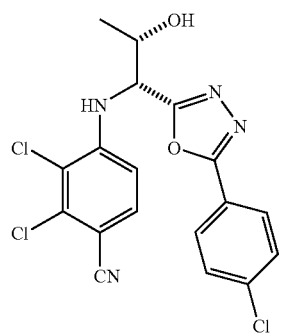

Intermediate 34a

4-Chloro-N'-((2R,3S)-2-(2,3-dichloro-4-cyanophenylamino)-3-hydroxybutanoyl)benzohydrazide

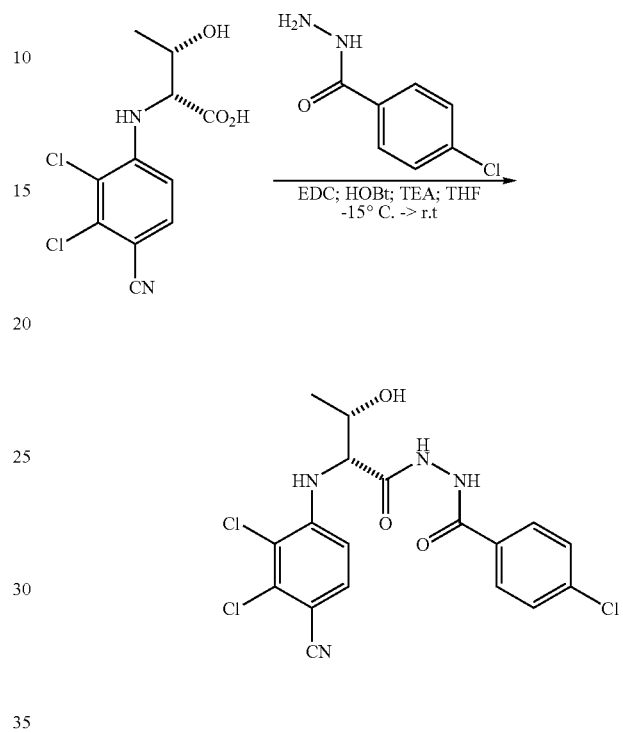

(2R,3S)-2-(2,3-dichloro-4-cyanophenylamino)-3-hydroxybutanoic acid (1.0 g, 3.46 mmol) and 4-chlorobenzohydrazide (590 mg, 3.46 mmol) were reacted using the techniques described for the preparation of intermediate 11c to furnish the title compound (800 mg, 52%). $^1$H NMR (500 MHz, acetone-d$_6$, δ in ppm) 10.4 (br s, 2H), 7.98 (d, J=8 Hz, 2H), 7.61 (d, J=8 Hz, 1H), 7.43 (d, J=8 Hz, 2H), 6.84 (d, J=8 Hz, 1H), 6.18 (d, J=6 Hz, 1H), 5.0 (br s, 1H), 4.31-4.38 (m, 1H), 4.18-4.2 (m, 1H), 1.36 (d, J=6 Hz, 3H).

Example 34

2,3-Dichloro-4-((1R,2S)-1-(5-(4-chlorophenyl)-1,3,4-oxadiazol-2-yl)-2-hydroxypropylamino)benzonitrile

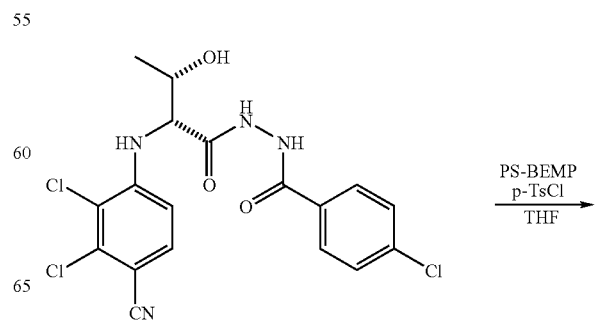

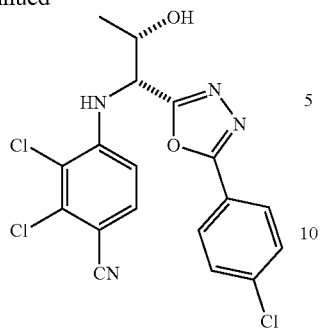

The title compound was prepared from 4-chloro-N'-((2R, 3S)-2-(2,3-dichloro-4-cyanophenylamino)-3-hydroxybutanoyl)benzohydrazide (796 mg, 1.8 mmol) utilizing the techniques described for the preparation of example 11 (40 mg, 5%). $^1$H NMR (500 MHz, CDCl$_3$, δ in ppm) 7.82 (d, J=8 Hz, 2H), 7.39-7.41 (m, 3H), 6.69 (d, J=8 Hz, 1H), 6.00 (d, J=6 Hz, 1H), 4.70-4.73 (m, 1H), 4.59-4.62 (m, 1H), 3.10 (br s, 1H) and 1.40 (d, J=6 Hz, 3H).

Example 35

2-Chloro-4-((1R,2R)-1-(5-(2,4-difluorophenyl)-1,3,4-oxadiazol-2-yl)-2-hydroxypropylamino)-3-methyl-benzonitrile

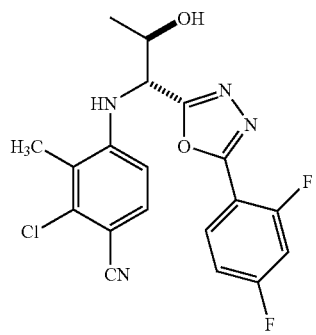

Intermediate 35a

N'-((2R,3R)-2-(3-Chloro-4-cyano-2-methylphenylamino)-3-hydroxybutanoyl)-2,4-difluorobenzohydrazide

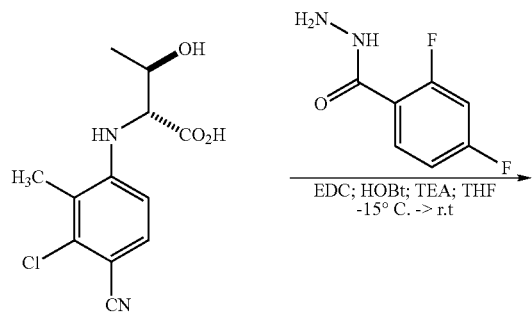

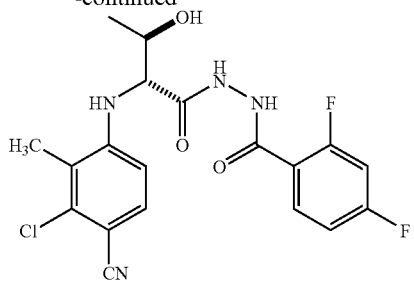

(2R,3R)-2-(3-chloro-4-cyano-2-methylphenylamino)-3-hydroxybutanoic acid (1.0 g, 3.72 mmol) and 2,4-difluorobenzohydrazide (704 mg, 4.09 mmol) were reacted using the techniques described for the preparation of intermediate 11c to furnish the title compound (1.5 g, 96%). $^1$H NMR (500 MHz, acetone-d$_6$, δ in ppm) 9.6 (br s, 2H), 7.85-7.97 (m, 1H), 7.46 (d, J=8 Hz, 1H), 7.10-7.19 (m, 2H), 6.73 (d, J=8 Hz, 1H), 5.58 (d, J=7 Hz, 1H), 4.20-4.28 (m, 1H), 4.15-4.18 (m, 1H), 2.32 (s, 3H) and 1.38 (d, J=6 Hz, 3H).

Example 35

2-Chloro-4-((1R,2R)-1-(5-(2,4-difluorophenyl)-1,3,4-oxadiazol-2-yl)-2-hydroxypropylamino)-3-methyl-benzonitrile

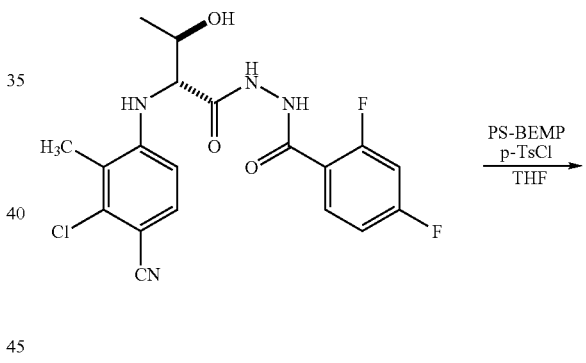

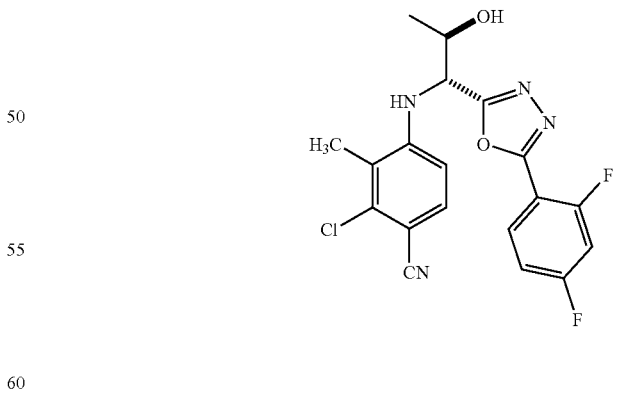

The title compound was prepared from N'-((2R,3R)-2-(3-chloro-4-cyano-2-methylphenylamino)-3-hydroxybutanoyl)-2,4-difluorobenzohydrazide (1.46 g, 3.47 mmol) utilizing the techniques described for the preparation of example 11 (98 mg, 6%). $^1$H NMR (500 MHz, CDCl$_3$, δ in ppm) 7.87-7.98 (m, 1H), 7.30 (d, J=8 Hz, 1H), 6.88-7.01 (m, 2H), 6.58 (d, J=8 Hz, 1H), 5.39 (d, J=7 Hz, 1H), 4.81-4.83 (m, 1H), 4.36-4.42 (br s, 1H), 2.33 (s, 3H), 1.39 (d, J=6 Hz, 3H).

Example 36

2-Chloro-4-((1R,2S)-2-hydroxy-1-(5-phenyloxazol-2-yl)propylamino)-3-methylbenzonitrile

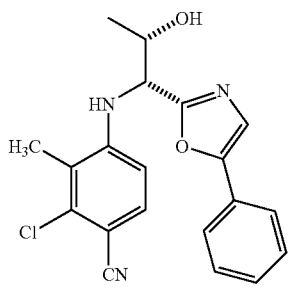

Intermediate 36a (2R,3S)-2-(3-Chloro-4-cyano-2-methylphenylamino)-3-hydroxy-N-(2-oxo-2-phenylethyl)butanamide

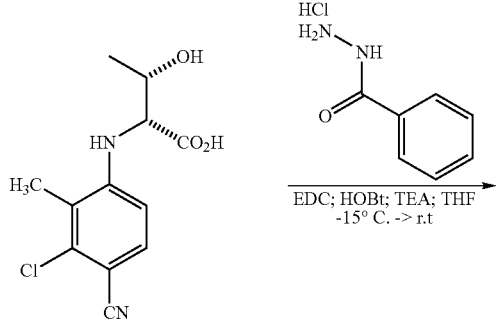

(2R,3S)-2-(3-chloro-4-cyano-2-methylphenylamino)-3-hydroxybutanoic acid (6.0 g, 22.33 mmol) and 2-amino-1-phenylethanone hydrochloride (3.83 g, 22.33 mmol) were reacted using the techniques described in for the preparation of intermediate 11c to furnish the title compound (7.9 g, 92%). $^1$H NMR (500 MHz, acetone-d$_6$, δ in ppm) 8.03 (d, J=8 Hz, 2H), 7.92 (br s, 1H), 7.68 (t, J=8 Hz, 1H), 7.54-7.58 (m, 3H), 6.70 (d, J=8 Hz, 1H), 5.63 (d, J=6 Hz, 1H), 4.79-4.81 (m, 2H), 4.70 (d, J=4 Hz, 1H), 4.38-4.42 (m, 1H), 4.08-4.12 (m, 1H), 2.38 (s, 3H), 1.33 (d, J=6 Hz, 3H).

Intermediate 36b (2R,3S)-3-(tert-Butyldimethylsilyloxy)-2-(3-chloro-4-cyano-2-methylphenylamino)-N-(2-oxo-2-phenylethyl)butanamide

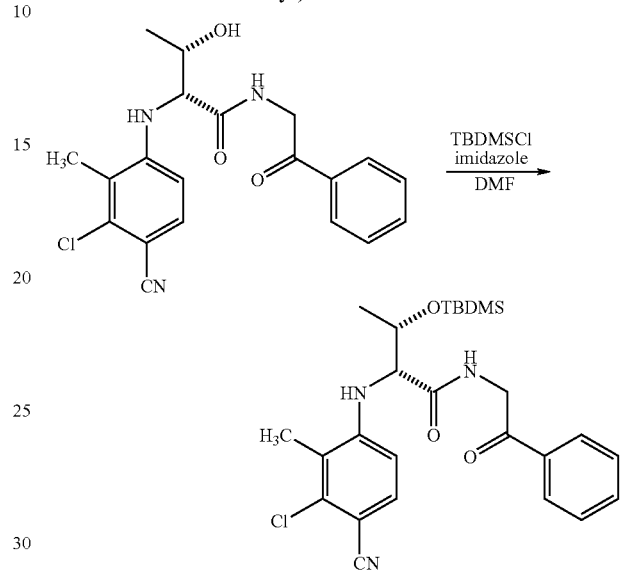

A 500 mL round bottomed flask was charged with (2R,3S)-2-(3-chloro-4-cyano-2-methylphenylamino)-3-hydroxy-N-(2-oxo-2-phenylethyl)butanamide (7.87 g, 20.4 mmol) and DMF (200 mL) then cooled to 0° C. Imidazole (6.94 g, 102 mmol) and tert-butylchlorodimethylsilane (9.22 g, 61.2 mmol) were added and the mixture was stirred and warmed to room temperature overnight. Water (200 mL) was added to the mixture followed by EtOAc (200 mL) and the phases partitioned. The organic phase was washed with water (2×100 mL), brine (100 mL), dried (Na$_2$SO$_4$) and concentrated to furnish the title compound as a white solid (8.2 g, 80%). $^1$H NMR (500 MHz, acetone-d$_6$, δ in ppm) 7.97 (d, J=8 Hz, 2H), 7.44-7.66 (m, 1H), 7.40 (d, J=8 Hz, 1H), 6.42 (d, J=8 Hz, 1H), 5.43 (d, J=6 Hz, 1H), 4.77 (dd, J=6, 8 Hz, 2H), 4.79 (dd, J=5, 15 Hz, 2H), 4.70 (d, J=5, 15 Hz, 1H), 4.52-4.58 (m, 1H), 3.85-4.89 (m, 1H), 2.39 (s, 3H), 1.24 (d, J=6 Hz, 3H).

Example 36

2-Chloro-4-((1R,2S)-2-hydroxy-1-(5-phenyloxazol-2-yl)propylamino)-3-methylbenzonitrile

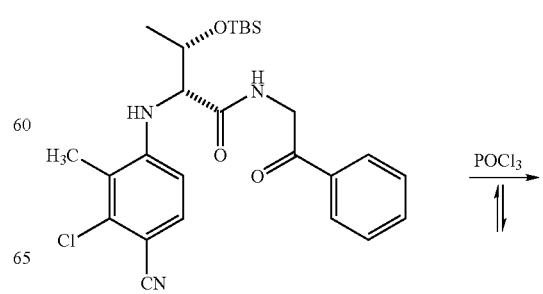

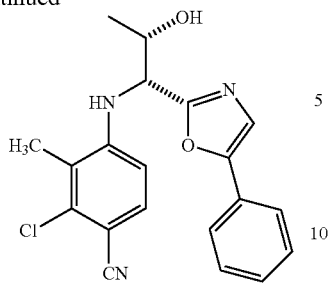

A 100 mL round bottomed flask was charged with phosphorous oxychloride (0.5 mL, 5.24 mmol) and benzene (20 mL). (2R,3S)-3-(tert-butyldimethylsilyloxy)-2-(3-chloro-4-cyano-2-methylphenylamino)-N-(2-oxo-2-phenylethyl)butanamide (1.14 g, 2.28 mmol) was then added to the mixture which was then placed under reflux for 4 h. The mixture was then concentrated en vacuo, then partitioned between EtOAc (40 mL) and a saturated solution of sodium bicarbonate (30 mL). The organic layer was washed with water (20 mL), dried (Na$_2$SO$_4$). Purification by flash column chromatography [hexanes/Et$_2$O (3:2) as eluent] afforded the title compound as a white solid (30 mg, 4% yield). $^1$H NMR (500 MHz, CDCl$_3$, δ in ppm) 7.59 (d, J=8 Hz, 2H), 7.32-7.42 (m, 4H), 7.28 (s, 1H), 6.58 (d, J=8 Hz, 1H), 5.17 (d, J=7 Hz, 1H), 4.93-4.95 (m, 1H), 4.66-4.75 (m, 1H), 2.40 (s, 3H) and 1.63 (d, J=6 Hz, 3H).

Example 37

2-Chloro-4-((1R,2S)-1-(5-(3-chloro-4-hydroxyphenyl)-1,3,4-oxadiazol-2-yl)-2-hydroxypropylamino)-3-methylbenzonitrile

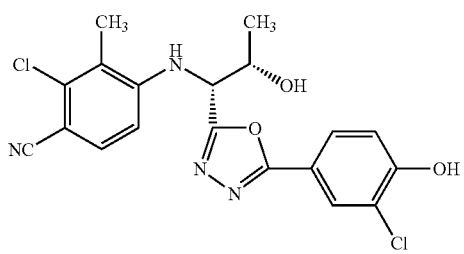

Intermediate 37a

Ethyl 3-chloro-4-hydroxybenzoate

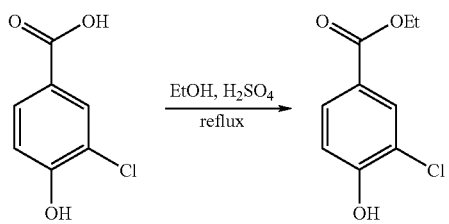

3-chloro-4-hydroxybenzoic acid (5.00 g, 27.5 mmol) was esterified to the ethyl ester as described previously in the preparation of intermediate 22a to afford the product as white crystals (5.02 g, 86%). $^1$H NMR (500 MHz, CDCl$_3$, δ in ppm) 8.04 (d, J=2.1 Hz, 1H), 7.88 (dd, J=8.5, 2.1 Hz, 1H), 7.05 (d, J=8.6 Hz, 1H), 6.22 (br s, 1H), 4.35 (q, J=7.1 Hz, 2H), 1.38 (t, J=7.1 Hz, 3H).

Intermediate 37b

3-Chloro-4-hydroxybenzohydrazide

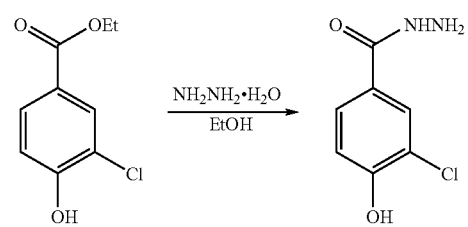

Ethyl-3-chloro-4-hydroxybenzoate (4.95 g, 25 mmol) was reacted with hydrazine as described for the preparation of intermediate 22b to afford the product as white crystals (3.15 g, 69%). $^1$H NMR (400 MHz, DMSO-d$_6$, δ in ppm) 10.71 (br s, 1H), 9.64 (br s, 1H), 7.83 (d, J=2.1 Hz, 1H), 7.65 (dd, J=2.1, 8.4 Hz, 1H), 6.99 (d, J=8.4 Hz, 1H), 4.43 (br s, 2H).

Intermediate 37c

N'-((2R,3S)-2-(3-Chloro-4-cyano-2-methylphenylamino)-3-hydroxybutanoyl)-3-chloro-4-hydroxybenzohydrazide

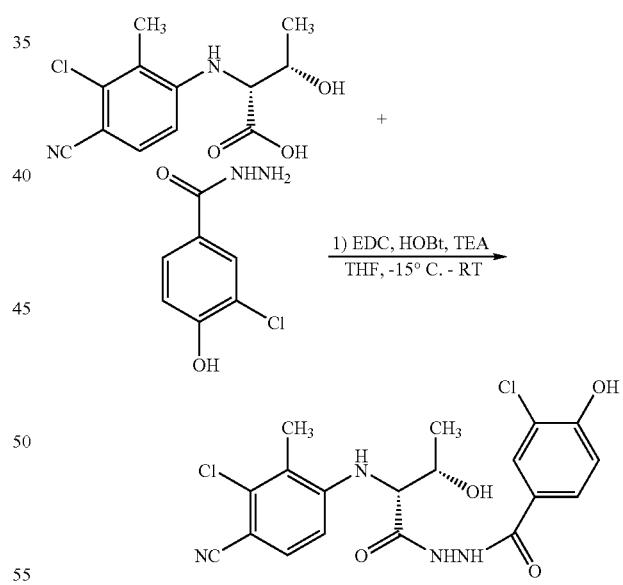

(2R,3S)-2-(3-chloro-4-cyano-2-methylphenylamino)-3-hydroxybutanoic acid (1.02 g, 3.8 mmol) and 3-chloro-4-hydroxybenzohydrazide (711 mg, 3.8 mmol) were coupled in an analogous fashion as the procedure used for the preparation of intermediate 3b. The crude product was purified by boiling in chloroform (50 mL) followed by cooling to 0° C. and filtration to yield product as a white solid (1.36 g, 82%). $^1$H NMR (400 MHz, acetone-d$_6$, δ in ppm) 7.93 (d, J=2.2 Hz, 1H), 7.75 (dd, J=2.2, 8.4 Hz, 1H), 7.52 (d, J=8.8 Hz, 1H), 7.08 (d, J=8.6 Hz, 1H), 6.67 (m, 1H), 5.55 (d, J=6.8 Hz, 1H), 4.38 (m, 1H), 4.10 (dd, J=3.1, 7.0 Hz, 1H), 2.36 (s, 3H), 1.34 (d, J=6.5 Hz, 3H).

Intermediate 37d 4-(tert-Butyldimethylsilyloxy)-N'-((2R,3S)-3-(tert-butyldimethylsilyloxy)-2-(3-chloro-4-cyano-2-methylphenylamino)butanoyl)-3-chlorobenzohydrazide

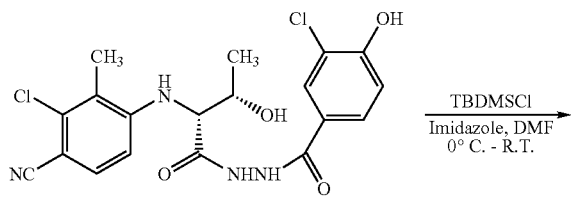

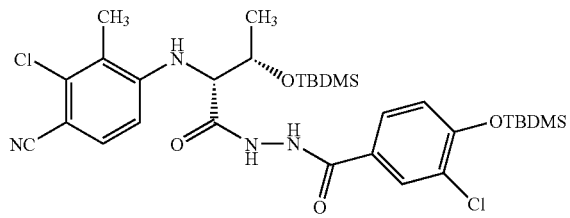

N'-((2R,3S)-2-(3-chloro-4-cyano-2-methylphenylamino)-3-hydroxybutanoyl)-3-chloro-4-hydroxybenzohydrazide (1.27 g, 2.9 mmol) was protected using TBDMSCl (3.06 g, 20 mmol) and imidazole (2.77 g, 41 mmol) in a manner analogous to that described for the preparation of intermediate 7b. After column chromatography (30% EtOAc/hexanes) the title compound was isolated as a white solid (629 mg, 33%). $^1$H NMR (400 MHz, CDCl$_3$, δ in ppm) 7.85 (d, J=2.2 Hz, 1H), 7.60 (dd, J=2.3, 8.5 Hz, 1H), 7.36 (d, J=8.6 Hz, 1H), 6.86 (d, J=8.4 Hz, 1H), 6.44 (d, J=8.6 Hz, 1H), 5.34 (d, J=6.5 Hz, 1H), 4.46 (m, 1H), 3.97 (dd, J=2.2, 6.3 Hz, 1H), 2.30 (s, 3H), 1.24 (d, J=6.3 Hz, 3H), 1.01 (s, 9H), 0.90 (s, 9H), 0.23 (s, 6H), 0.11 (s, 3H), 0.06 (s, 3H).

Intermediate 37e 4-((1R,2S)-2-(tert-Butyldimethylsilyloxy)-1-(5-(4-(tert-butyldimethylsilyloxy)-3-chloro-phenyl)-1,3,4-oxadiazol-2-yl)propylamino)-2-chloro-3-methylbenzonitrile

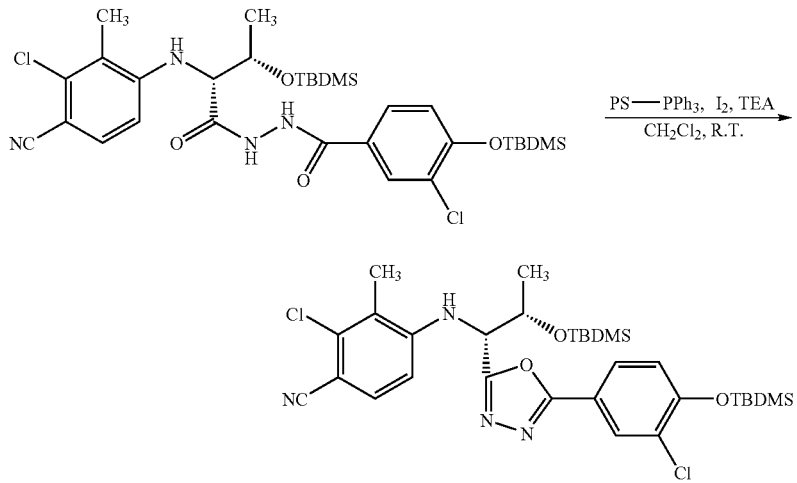

4-(tert-butyldimethylsilyloxy)-N'-((2R,3S)-3-(tert-butyldimethylsilyloxy)-2-(3-chloro-4-cyano-2-methylphenylamino)butanoyl)-3-chlorobenzohydrazide (629 mg, 0.95 mmol) was cyclized with PS-PPh$_3$ (3.0 mmol/g, 630 mg, 1.89 mmol), I$_2$ (480 mg, 1.89 mmol), and TEA (1.3 mL, 9.3 mmol) in an analogous fashion to the procedure described for the preparation of example 11. After column chromatography (25% EtOAc/hexanes) the title compound was isolated as a white solid (422 mg, 69%). $^1$H NMR (400 MHz, CDCl$_3$, δ in ppm) 7.95 (d, J=2.2 Hz, 1H), 7.72 (dd, J=2.2, 8.4 Hz, 1H), 7.32 (d, J=8.6 Hz, 1H), 6.95 (d, J=8.4 Hz, 1H), 6.45 (d, J=8.6 Hz, 1H), 5.35 (d, J=8.6 Hz, 1H), 4.77 (dd, J=2.0, 8.6 Hz, 1H), 4.50 (m, 1H), 2.36 (s, 3H), 1.40 (d, J=6.1 Hz, 3H), 1.02 (s, 9H), 0.87 (s, 9H), 0.25 (s, 6H), 0.06 (s, 3H), −0.20 (s, 3H).

Example 37

2-Chloro-4-((1R,2S)-1-(5-(3-chloro-4-hydroxyphenyl)-1,3,4-oxadiazol-2-yl)-2-hydroxypropylamino)-3-methylbenzonitrile

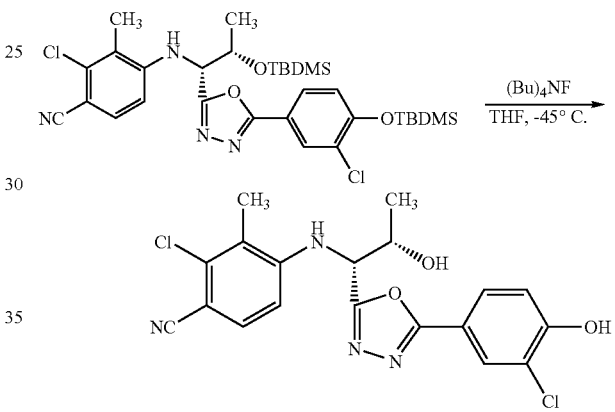

4-((1R,2S)-2-(tert-butyldimethylsilyloxy)-1-(5-(4-(tert-butyldimethylsilyloxy)-3-chloro-phenyl)-1,3,4-oxadiazol-2-yl)propylamino)-2-chloro-3-methylbenzonitrile (377 mg, 0.58 mmol) was deprotected using tetrabutylammonium fluoride (1.0 M solution in THF, 1.2 mL, 1.2 mmol) in a manner analogous used for the preparation of Example 22.

After column chromatography (80% EtOAc/hexanes) the title compound was isolated as an off-white solid (23 mg). $^1$H NMR (400 MHz, CDCl$_3$, δ in ppm) 7.91 (d, J=2.2 Hz, 1H), 7.77 (dd, J=2.2, 8.4 Hz, 1H), 7.46 (d, J=8.6 Hz, 1H), 7.15 (d, J=8.4 Hz, 1H), 6.84 (d, J=8.8 Hz, 1H), 5.68 (d, J=8.4 Hz, 1H), 5.08 (dd, J=3.7, 8.4 Hz, 1H), 4.62 (m, 1H), 2.39 (s, 3H), 1.40 (d, J=6.3 Hz, 3H).

Example 38

DL-Threo-2-chloro-4-(2-hydroxy-2-phenyl-1-(5-phenyl-1,3,4-oxadiazol-2-yl)ethylamino)-3-methyl-benzonitrile

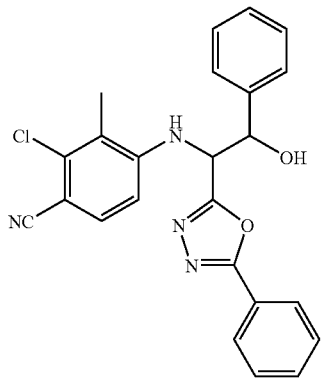

Intermediate 38a

DL-Threo-2-(3-chloro-4-cyano-2-methylphenylamino)-3-hydroxy-3-phenylpropanoic acid

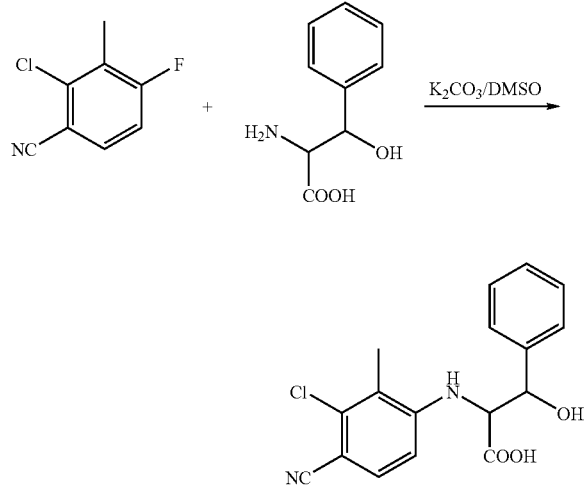

2-chloro-4-fluoro-3-methylbenzonitrile (2.0 g, 11.79 mmol) was mixed together with DL-Threo-3-phenylserine hydrate (2.82 g, 14.15 mmol) in DMSO (15 mL). K$_2$CO$_3$ (3.26 g) was added to the reaction mixture and stirred at 75° C. for 24 h. The reaction mixture was cooled to room temperature and poured slowly into a 10% citric acid solution and stirred for 10 min at room temperature. The solution was extracted with EtOAc several times to get the crude product. The crude product was chromatographed with a gradient of hexanes/EtOAc and then with EtOAc, 100% to get the pure final product (800 mg). $^1$H NMR (500 MHz, acetone-d$_6$, δ in ppm) 7.52 (m, 3H), 7.37 (d, J=9 Hz, 1H), 7.2-7.30 (m, 2H), 6.81 (d, J=9 Hz, 1H), 6.44 (d, J=6 Hz, 1H), 5.42 (m, 1H), 4.5 (br s, 1H), 4.17 (m, 1H) 2.24 (s, 3H)

Intermediate 38b

Synthesis of DL-Threo-N'-(2-(3-chloro-4-cyano-2-methylphenylamino)-3-hydroxy-3-phenylpropanoyl)benzohydrazide

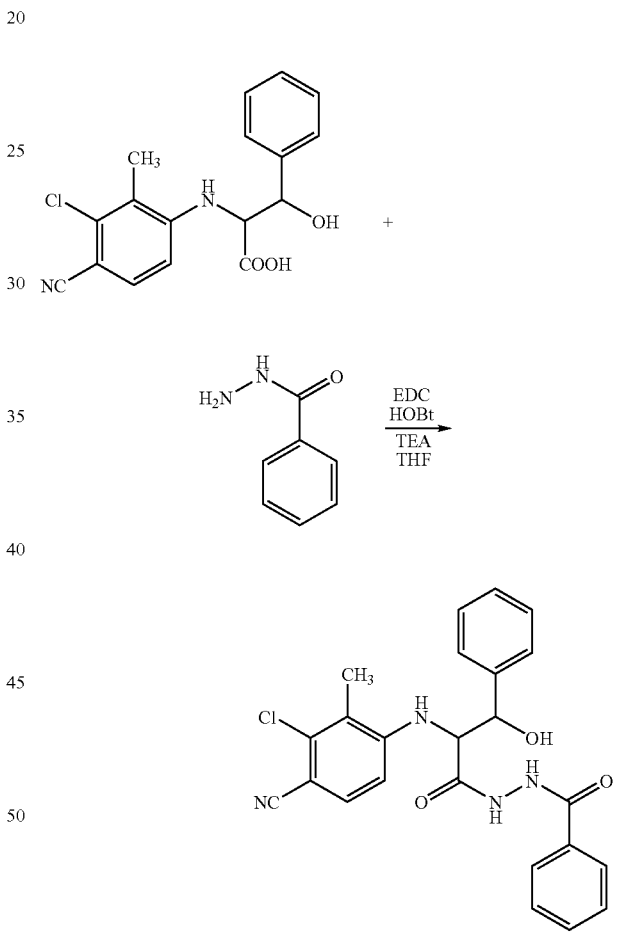

DL-Threo-2-(3-chloro-4-cyano-2-methylphenylamino)-3-hydroxy-3-phenylpropanoic acid (442 mg, 1.34 mmol) and benzoic hydrazide (182 mg, 1.34 mmol) were mixed together in THF (40 mL) and cooled to −20° C. under N$_2$ atmosphere. To the pre-cooled reaction mixture were added HOBt (181 mg, 1.34 mmol), TEA (203 mg, 2.01 mmol) followed by EDC (384 mg, 2.01 mmol). The reaction mixture was allowed to stir at −20° C. for 1 h and then allowed to warm to room temperature and stirred overnight. After the reaction was complete, the urea was filtered off and the solution was washed with water, 5% citric acid followed by 5% NaHCO$_3$ to get the crude hydrazide product (520 mg).

Example 38

DL-Threo-2-chloro-4-(2-hydroxy-2-phenyl-1-(5-phenyl-1,3,4-oxadiazol-2-yl)ethylamino)-3-methylbenzonitrile

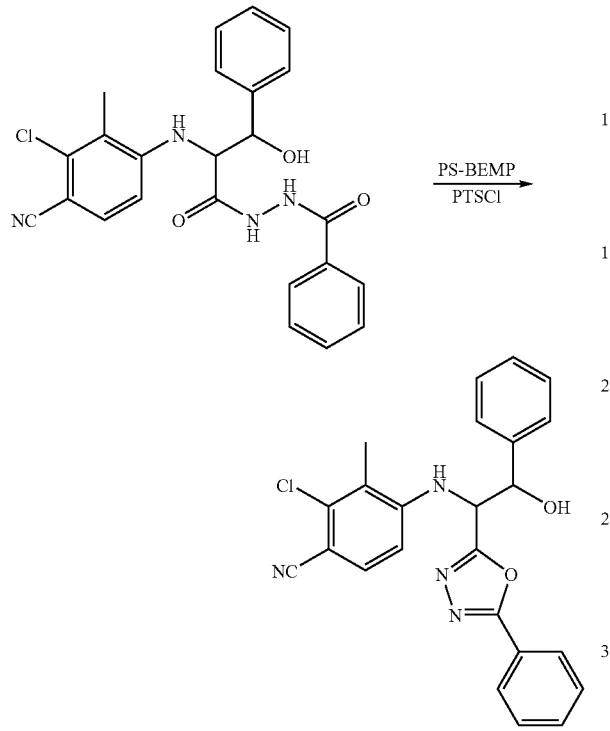

The crude material of DL-Threo-N'-(2-(3-chloro-4-cyano-2-methylphenylamino)-3-hydroxy-3-phenylpropanoyl)benzohydrazide (100 mg, 0.22 mmol) was added to THF (20 mL) stirred at room temperature. PS-BEMP (304 mg, 0.67 mmol base) was added to the solution, followed by slow addition of p-TSCl (114 mg, 0.60 mmol). The reaction mixture was stirred for 3 h and the progress of the reaction was monitored by TLC. After the completion of the reaction the BEMP reagent was filtered off and the solution concentrated to give the crude material. The crude material was chromatographed with hexanes:EtOAc (6:4) to give the product (9 mg) $^1$H NMR (500 MHz, CDCl$_3$, δ in ppm) 7.95 (m, 2H), 7.52 (m, 3H), 7.44 (m, 2H), 7.34 (m, 3H), 6.51 (d, J=9 Hz, 1H), 5.54 (br s, 1H), 5.27 (d, J=6 Hz, 1H), 5.06 (m, 1H), 3.28 (br s, 1H), 2.29 (s, 3H).

Example 39

2-Chloro-4-((1R,2R)-1-(5-(3,4-difluorophenyl)-1,3,4-oxadiazol-2-yl)-2-hydroxypropylamino)-3-methylbenzonitrile

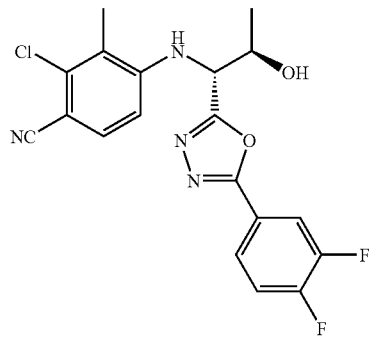

Intermediate 39a

N'-((2R,3R)-2-(3-Chloro-4-cyano-2-methylphenylamino)-3-hydroxybutanoyl)-3,4-difluorobenzohydrazide

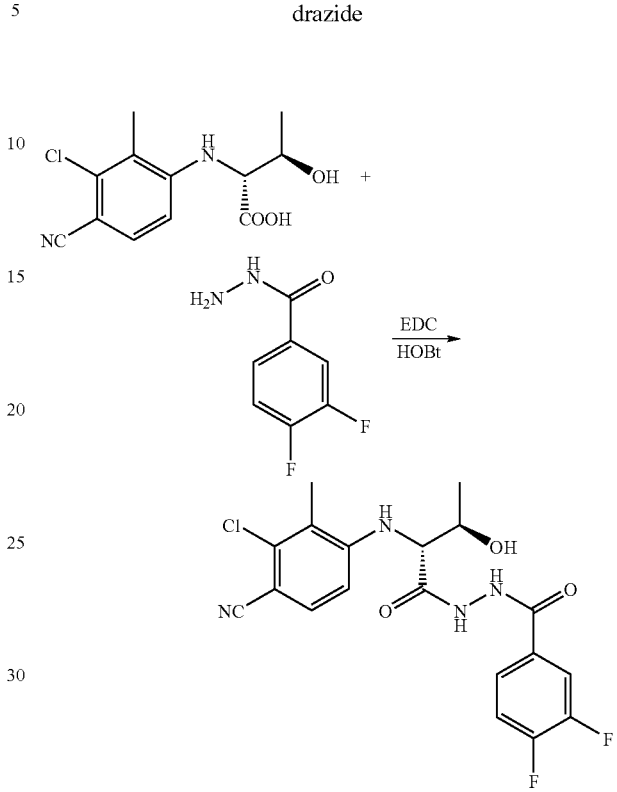

((2R,3R)-2-(3-chloro-4-cyano-2-methylphenylamino)-3-hydroxybutanoic acid (1.0 g, 3.72 mmol) and 3,4-difluorobenzohydrazide (641 mg, 3.72 mmol) were mixed together in THF (100 mL) and cool down to −20° C. under N$_2$ atmosphere. To the pre-cooled reaction mixture were added HOBt (503 mg, 3.72 mmol) followed by EDC (1.43 g, 7.44 mmol) and TEA (753 mg, 7.44 mmol). The reaction mixture was allowed to stir at −20° C. for 1 h and then at room temperature overnight. After the reaction was complete, the urea was filtered off and the solution was washed with 5% citric acid followed by 5% NaHCO$_3$ to give the crude hydrazide product (1.28 g).

Example 39

2-Chloro-4-((1R,2R)-1-(5-(3,4-difluorophenyl)-1,3,4-oxadiazol-2-yl)-2-hydroxypropylamino)-3-methylbenzonitrile

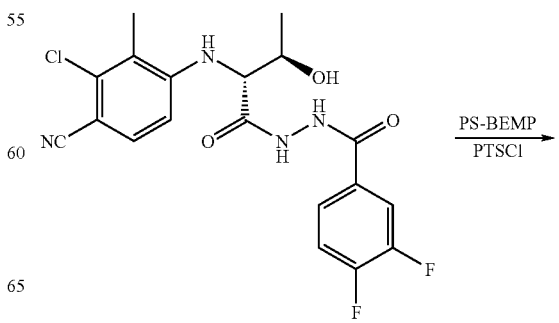

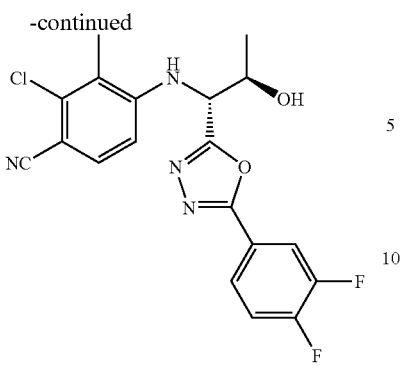

The crude material of N'-((2R,3R)-2-(3-chloro-4-cyano-2-methylphenylamino)-3-hydroxybutanoyl)-3,4-difluorobenzohydrazide (1.0 g, 2.37 mmol) was added to THF (120 mL) and stirred at room temperature. PS-BEMP (3.22 g, 7.10 mmol base) was added to the solution followed by slow addition of p-TSCl (496 mg, 2.60 mmol). The reaction mixture was stirred for 2 h and the progress of the reaction was monitored by TLC. After the completion of the reaction the BEMP reagent was filtered off and the solution concentrated to get the crude material. The crude material was chromatographed with hexanes:EtOAc (6:4) to give the product (330 mg). $^1$H NMR (500 MHz, acetone-$d_6$, δ in ppm) 7.81 (m, 2H), 7.37 (d, J=9 Hz, 1H), 7.23 (m, 1H), 6.59 (d, J=9 Hz, 1H), 5.28 (d, J=8 Hz, 1H), 4.8 (m, 1H), 4.39 (m, 1H), 2.39 (s, 3H), 1.38 (d, J=6 Hz, 3H).

Example 40

2-Chloro-4-((1R,2S)-1-(5-(4-fluoro-3-hydroxyphenyl)-1,3,4-oxadiazol-2-yl)-2-hydroxypropylamino)-3-methylbenzonitrile

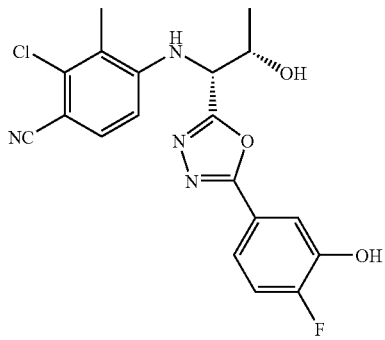

Intermediate 40a

4-Fluoro-3-hydroxybenzohydrazide

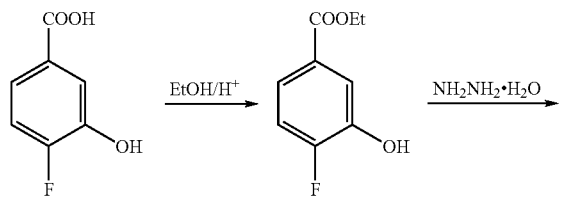

4-Fluoro-3-hydroxybenzoic acid (3.0 g, 19.22 mmol) was dissolved in 50 mL of ethanol and 0.3 mL of conc. $H_2SO_4$ was added into it. The reaction mixture was refluxed overnight. The solvent was removed under reduced pressure and the crude product was washed with sat $NaHCO_3$ solution to get the desired ester in quantitative yield. To the ester in 95% ethanol (60 mL) was added hydrazine hydrate (65% solution, 4 equivalents) and refluxed overnight. Evaporation of the solvent, addition of water, filtration and drying in the vac oven provided the product (3.0 g, 92%). $^1$H NMR (500 MHz, DMSO-$d_6$, δ in ppm) 10.16 (br s, 1H), 9.62 (br s, 1H), 7.41 (d, J=9 Hz, 1H), 7.22 (s, 1H), 7.18 (t, J=9 Hz, 1H), 4.62 (br s, 2H).

Intermediate 40b

N'-((2R,3S)-2-(3-Chloro-4-cyano-2-methylphenylamino)-3-hydroxybutanoyl)-4-fluoro-3-hydroxybenzohydrazide

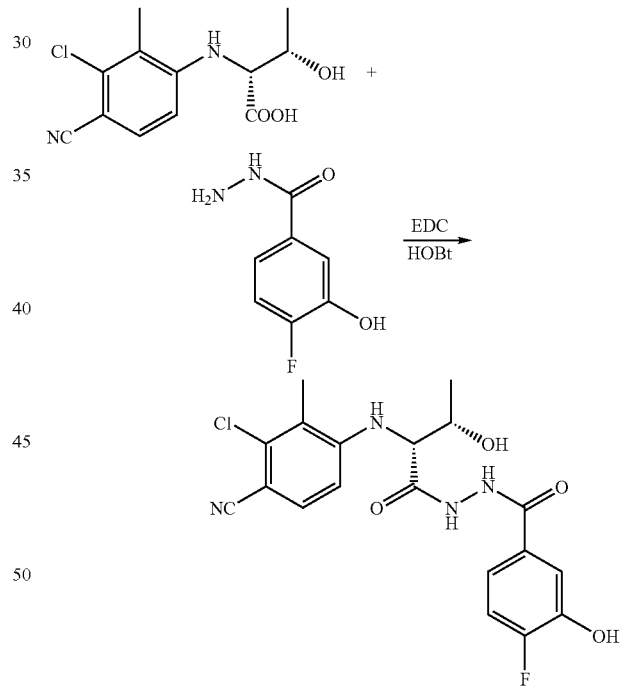

(2R,3S)-2-(3-chloro-4-cyano-2-methylphenylamino)-3-hydroxybutanoic acid (553 mg, 2.06 mmol) and 4-fluoro-3-hydroxybenzohydrazide (350 mg, 2.06 mmol) were mixed together in THF (40 mL) and cooled to −20° C. under $N_2$ atmosphere. To the pre-cooled reaction mixture were added HOBt (278 mg, 2.06 mmol) followed by EDC (7909 mg, 4.11 mmol) and TEA (416 mg, 4.11 mmol). The reaction mixture was allowed to stir at −20° C. for 1 h and then at room temperature overnight. After the reaction was complete the urea was filtered off and the solution was washed with water, 5% citric acid and followed by 5% $NaHCO_3$ to give the crude hydrazide product (420 mg), which was used without further purification.

Intermediate 40c 3-(tert-Butyldimethylsilyloxy)-N'-((2R,3S)-3-(tert-butyldimethylsilyloxy)-2-(3-chloro-4-cyano-2-methylphenylamino)butanoyl)-4-fluorobenzohydrazide

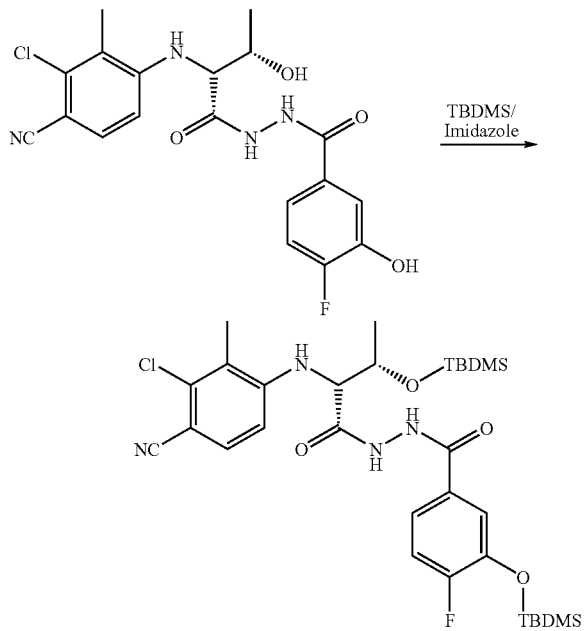

The crude material of N'-((2R,3S)-2-(3-chloro-4-cyano-2-methylphenylamino)-3-hydroxybutanoyl)-4-fluoro-3-hydroxybenzohydrazide (550 mg, 1.31 mmol) was added to DMF (30 mL), followed by addition of TBDMS-Cl (591 mg, 3.92 mmol) and imidazole (534 mg, 7.85 mmol) at 0° C. The solution was allowed to stir at 0° C. for 30 min and then at room temperature overnight. The reaction was quenched with the addition of 200 mL brine and extracted with EtOAc. The resulting crude material was chromatogrphaed to give the desired product (410 mg): ¹H NMR (500 MHz, acetone-d₆, δ in ppm): 9.36 (br s, 2H), 7.42 (m, 3H), 7.13 (t, J=9 Hz, 1H), 6.63 (d, J=9 Hz, 1H), 5.36 (d, J=9 Hz, 1H), 4.46 (m, 1H), 4.07 (m, 1H), 2.23 (s, 3H), 1.23 (d, J=6 Hz, 3H), 0.89 (s, 9H), 0.81 (s, 9H), 0.10 (s, 6H), 0.04 (s, 3H), 0.00 (s, 3H).

Intermediate 40d 4-((1R,2S)-2-(tert-Butyldimethylsilyloxy)-1-(5-(3-(tert-butyldimethylsilyloxy)-4-fluorophenyl)-1,3,4-oxadiazol-2-yl)propylamino)-2-chloro-3-methylbenzonitrile

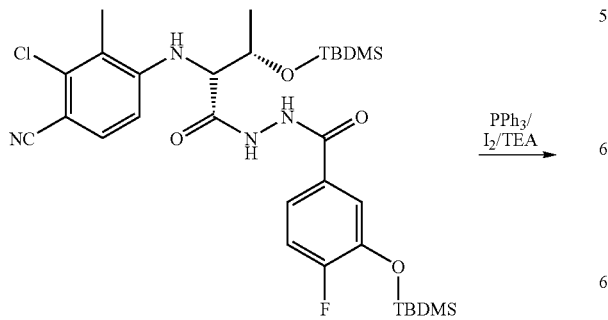

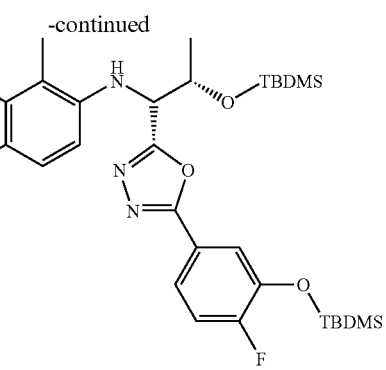

Triphenylphosphine (331 mg, 1.26 mmol) was dissolved in 25 mL of DCM followed by addition of I₂ (321 mg, 1.26 mmol) and TEA (256 mg, 2.53 mmol) at 0° C. 3-(tert-butyldimethylsilyloxy)-N'-((2R,3S)-3-(tert-butyldimethylsilyloxy)-2-(3-chloro-4-cyano-2-methylphenylamino)butanoyl)-4-fluorobenzohydrazide (410 mg, 0.631 mmol) in 15 mL DCM was added to the pre-cooled solution mixture of PPh₃/I₂/TEA system and stirred. The temperature was allowed to rise to room temperature and stirred for additional 10 min. The reaction was quenched with 50 mL saturated sodium thiosulfate and extracted with EtOAc. The crude mixture was chromatographed to give the product (400 mg). ¹H NMR (500 MHz, CDCl₃, δ in ppm): 7.69 (m, 3H), 7.54 (d, J=9 Hz, 1H), 7.35 (t, J=9 Hz, 1H), 6.65 (d, J=9 Hz, 1H), 5.56 (d, J=9 Hz, 1H), 4.99 (m, 1H), 4.74 (m, 1H), 2.37 (s, 3H), 1.62 (d, J=6 Hz, 3H), 1.20 (s, 9H), 1.06 (s, 9H), 0.40 (s, 6H), 0.27 (s, 3H), 0.00 (s, 3H).

Example 40

2-Chloro-4-((1R,2S)-1-(5-(4-fluoro-3-hydroxyphenyl)-1,3,4-oxadiazol-2-yl)-2-hydroxypropylamino)-3-methylbenzonitrile

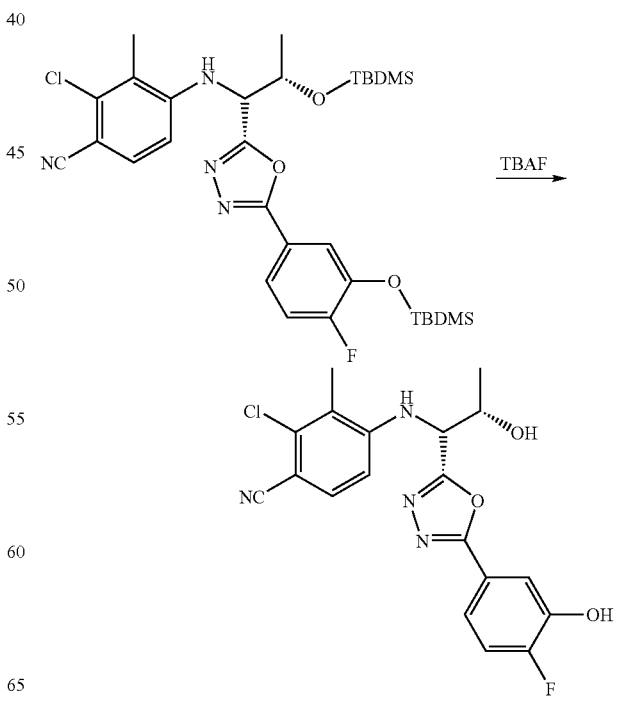

4-((1R,2S)-2-(tert-butyldimethylsilyloxy)-1-(5-(3-(tert-butyldimethylsilyloxy)-4-fluorophenyl)-1,3,4-oxadiazol-2-yl)propylamino)-2-chloro-3-methylbenzonitrile (400 mg, 0.63 mmol) was dissolved in THF (10 mL) and cooled to −55° C. under N₂ atmosphere. TBAF (1.0M solution in THF, 1.52 mL, 1.52 mmol) was added to the pre-cooled solution slowly and the temperature allowed to rise gradually. After the reaction was complete, sat. NH₄Cl (200 mL) was added and the mixture was extracted with EtOAc (3×100 mL). Purification by flash chromatography over silica gel provided the desired product (230 mg). Mp 103-108° C., ¹H NMR (500 MHz, acetone-d₆, δ in ppm): 7.64 (d, J=9 Hz, 1H), 7.49 (m, 1H), 7.30 (t, J=9 Hz, 1H), 6.86 (d, J=9 Hz, 1H), 5.69 (d, J=9 Hz, 1H), 5.09 (m, 1H), 4.60 (m, 1H), 2.40 (s, 3H), 1.40 (d, J=6 Hz, 3H).

Example 41

2-Chloro-4-((1R,2R)-1-(5-(4-fluoro-3-hydroxyphenyl)-1,3,4-oxadiazol-2-yl)-2-hydroxypropylamino)-3-methylbenzonitrile

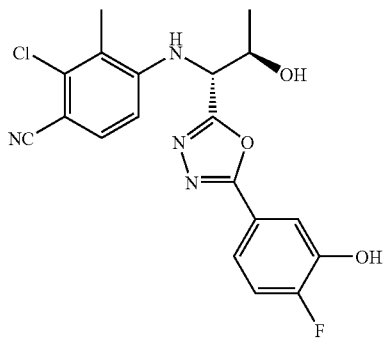

Intermediate 41a

N'-((2R,3R)-2-(3-Chloro-4-cyano-2-methylphenylamino)-3-hydroxybutanoyl)-4-fluoro-3-hydroxybenzohydrazide

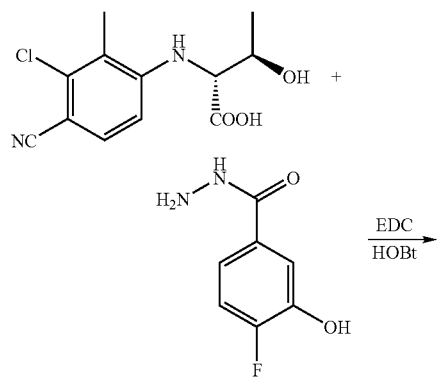

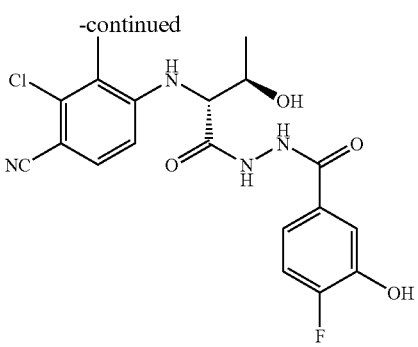

((2R,3R)-2-(3-chloro-4-cyano-2-methylphenylamino)-3-hydroxybutanoic acid (1.76 g, 6.58 mmol) and 4-fluoro-3-hydroxybenzohydrazide (1.12 g, 6.58 mmol) were mixed together in THF (100 mL) and cooled to −20° C. under N₂ atmosphere. To the pre-cooled reaction mixture was added HOBt (880 g, 6.58 mmol) followed by EDC (2.52 g, 13.17 mmol) and TEA (1.33 g, 13.17 mmol). The reaction mixture was allowed to stir at −20° C. for 1 h and then at room temperature overnight. After the reaction was complete, the urea was filtered off and the solution was washed with water, 5% citric acid and followed by 5% NaHCO₃ to give the crude hydrazide product (1.7 g), which was used without further purification.

Intermediate 41b 3-(tert-Butyldimethylsilyloxy)-N'-((2R,3S)-3-(tert-butyldimethylsilyloxy)-2-(3-chloro-4-cyano-2-methylphenylamino)butanoyl)-4-fluorobenzohydrazide

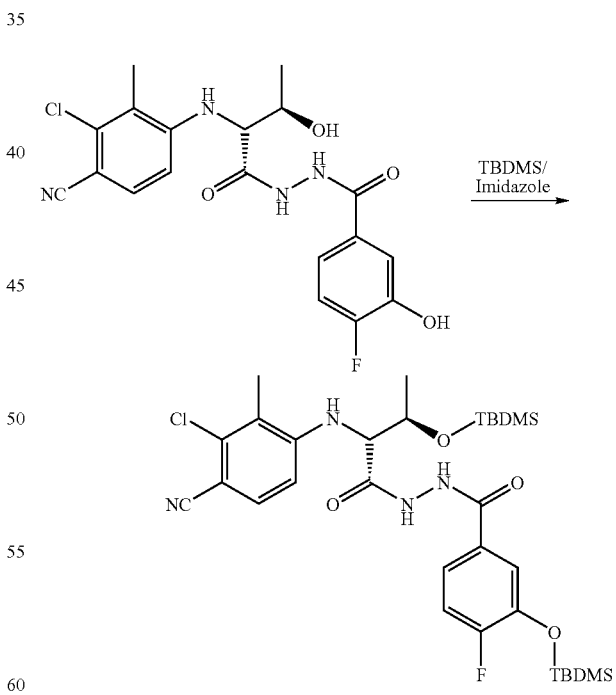

The crude material of N'-((2R,3R)-2-(3-chloro-4-cyano-2-methylphenylamino)-3-hydroxybutanoyl)-4-fluoro-3-hydroxybenzohydrazide (1.7 g, 4.04 mmol) was added to DMF (60 mL), followed by addition of TBDMS-Cl (2.43 g, 16.16 mmol) and imidazole (2.20 g, 32.32 mmol) at 0° C. The solution was allowed to stir at 0° C. for 30 min and then at room temperature for overnight. The reaction was quenched with the addition of 200 mL brine and extract with EtOAc. The resulting crude material was chromatogrphaed via flash chromatography over silica gel (EtOAc) to provide the desired product (1.25 g): ¹H NMR (400 MHz, DMSO-d$_6$, δ in ppm) 10.53 (br s, 1H), 10.39 (br s, 3H), 7.59 (d, J=8.6 Hz, 1H), 7.55-7.46 (m, 2H), 7.35 (dd, J=8.4, 10.6 Hz, 1H), 6.81 (d, J=9.0 Hz, 1H), 5.61 (d, J=8.2 Hz, 1H), 4.37 (pentet, J=6.1 Hz, 1H), 4.15 (dd, J=5.9, 8.0 Hz, 1H), 2.26 (s, 3H), 1.27 (d, J=6.1 Hz, 3H), 0.97 (s, 9H), 0.84 (s, 9H), 0.19 (s, 6H), 0.08 (s, 3H), 0.04 (s, 3H).

Intermediate 41c 4-((1R,2R)-2-(tert-Butyldimethylsilyloxy)-1-(5-(3-(tert-butyldimethylsilyloxy)-4-fluorophenyl)-1,3,4-oxadiazol-2-yl)propylamino)-2-chloro-3-methylbenzonitrile

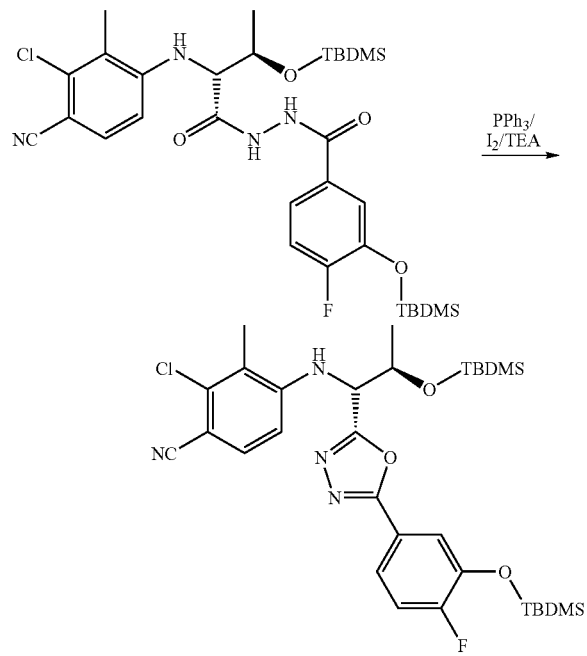

Triphenylphosphine (1.0 g, 3.85 mmol) was dissolved in 25 mL of DCM followed by addition of I$_2$ (977 mg, 3.85 mmol) and TEA (779 mg, 7.70 mmol) at 0° C. 3-(tert-butyldimethylsilyloxy)-N'-((2R,3S)-3-(tert-butyldimethylsilyloxy)-2-(3-chloro-4-cyano-2-methylphenylamino)butanoyl)-4-fluorobenzohydrazide (1.25 g, 1.93 mmol) in 35 mL DCM was added to the pre-cooled solution mixture of PPh$_3$/I$_2$/TEA system and stir. The temperature was allowed to rise to room temperature and stirred for additional 10 min. The reaction was quenched with 100 mL saturated sodium thiosulfate and extracted with EtOAc. The crude mixture was chromatographed to give the product (1.10 g). ¹H NMR (400 MHz, DMSO-d$_6$, δ in ppm): 7.71 (m, 1H), 7.70 (d, J=9 Hz, 1H), 7.65 (m, 1H), 7.03 (d, J=9 Hz, 1H), 6.53 (d, J=9 Hz, 1H), 5.15 (d, J=9 Hz, 1H), 4.80 (m, 1H), 2.44 (s, 3H), 1.51 (d, J=6 Hz, 3H), 1.13 (s, 9H), 0.83 (s, 9H), 0.36 (s, 6H), 0.19 (s, 3H), 0.00 (s, 3H).

Example 41

2-Chloro-4-((1R,2R)-1-(5-(4-fluoro-3-hydroxyphenyl)-1,3,4-oxadiazol-2-yl)-2-hydroxypropylamino)-3-methylbenzonitrile

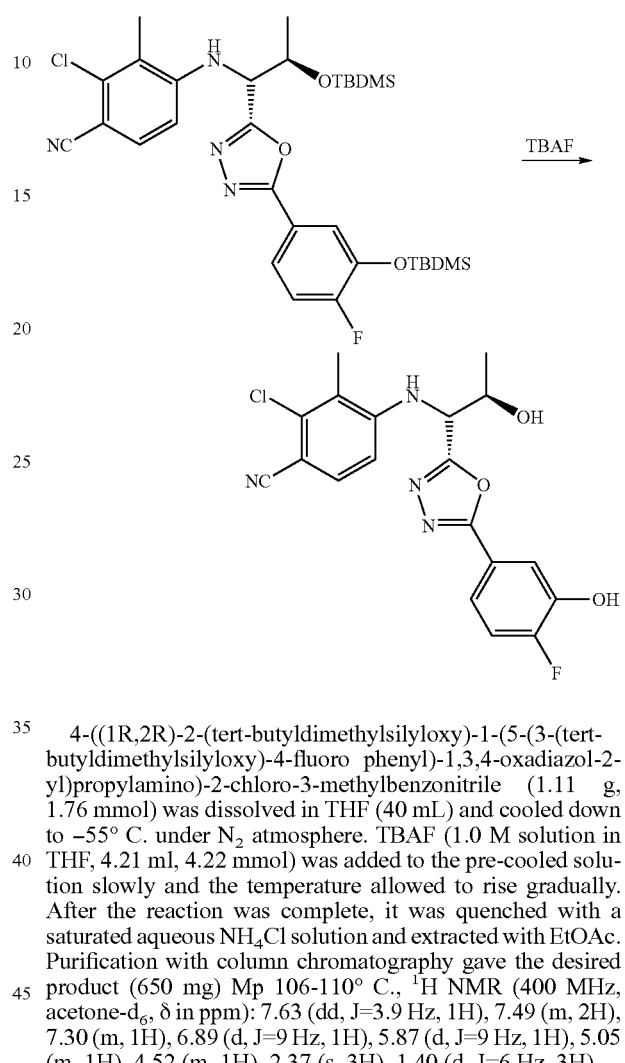

4-((1R,2R)-2-(tert-butyldimethylsilyloxy)-1-(5-(3-(tert-butyldimethylsilyloxy)-4-fluoro phenyl)-1,3,4-oxadiazol-2-yl)propylamino)-2-chloro-3-methylbenzonitrile (1.11 g, 1.76 mmol) was dissolved in THF (40 mL) and cooled down to −55° C. under N$_2$ atmosphere. TBAF (1.0 M solution in THF, 4.21 ml, 4.22 mmol) was added to the pre-cooled solution slowly and the temperature allowed to rise gradually. After the reaction was complete, it was quenched with a saturated aqueous NH$_4$Cl solution and extracted with EtOAc. Purification with column chromatography gave the desired product (650 mg) Mp 106-110° C., ¹H NMR (400 MHz, acetone-d$_6$, δ in ppm): 7.63 (dd, J=3.9 Hz, 1H), 7.49 (m, 2H), 7.30 (m, 1H), 6.89 (d, J=9 Hz, 1H), 5.87 (d, J=9 Hz, 1H), 5.05 (m, 1H), 4.52 (m, 1H), 2.37 (s, 3H), 1.40 (d, J=6 Hz, 3H).

Example 42

4-((1R,2S)-1-(5-(4-Cyanophenyl)-1,3,4-oxadiazol-2-yl)-2-hydroxypropylamino)-3-methyl-2-(trifluoromethyl)benzonitrile

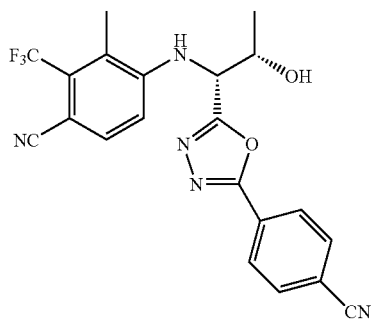

Intermediate 42a (2R,3S)-2-(4-Cyano-2-methyl-3-(trifluoromethyl) phenylamino)-3-hydroxybutanoic acid

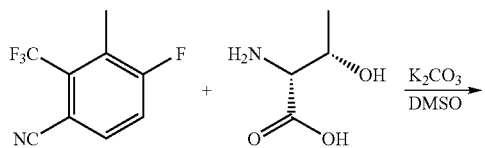

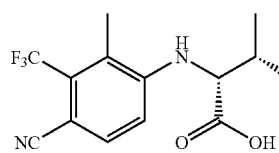

4-fluoro-3-methyl-2-(trifluoromethyl)benzonitrile (1.0 g, 4.92 mmol) and D-theronine (703 mg, 90 mmol) were added to DMSO (15 mL). $K_2CO_3$ (3.26 g) was added to the reaction mixture and stirred at 75° C. for 24 h. The reaction mixture was cooled to room temperature and poured slowly in to a 10% citric acid solution and stirred for 10 min at room temperature. The solution was extracted with EtOAc several times to give the crude product. The crude product was chromatographed with a gradient of hexanes/EtOAc and then with EtOAc, 100% to give the final product (400 mg). $^1$H NMR (500 MHz, acetone-$d_6$, δ in ppm) 7.62 (d, J=9 Hz, 1H), 6.98 (d, J=9 Hz, 1H), 5.52 (d, J=9 Hz, 1H), 4.52 (m, 1H), 4.32 (m, 1H), 2.35 (s, 3H), 1.35 (d, J=6 Hz, 3H).

Intermediate 42b

4-Cyano-N'-((2R,3S)-2-(4-cyano-2-methyl-3-(trifluoromethyl)phenylamino)-3-hydroxybutanoyl)benzohydrazide

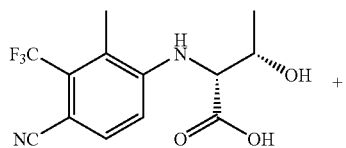

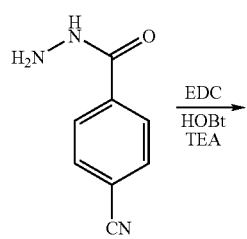

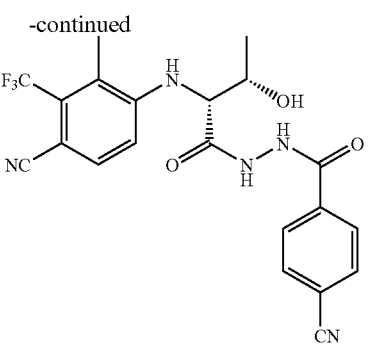

(2R,3S)-2-(4-cyano-2-methyl-3-(trifluoromethyl)phenylamino)-3-hydroxybutanoic acid (410 mg, 1.36 mmol) and 4-cyanobenzohydrazide (219 mg, 1.36 mmol) were mixed together in THF (40 mL) and cooled to −20° C. under $N_2$ atmosphere. To the pre-cooled reaction mixture were added HOBt (183 mg, 1.36 mmol), TEA (275 mg, 2.71 mmol) followed by EDC (520 g, 2.71 mmol). The reaction mixture was allowed to stir at −20° C. for 1 h and then at room temperature overnight. After the reaction was complete, the urea was filtered off and the solution was washed with water, 5% citric acid followed by 5% $NaHCO_3$ to give the crude hydrazide product (500 mg), which was used immediately without further purification.

Intermediate 42c

N'-((2R,3S)-3-(tert-Butyldimethylsilyloxy)-2-(4-cyano-2-methyl-3-(trifluoromethyl)phenylamino)butanoyl)-4-cyanobenzohydrazide

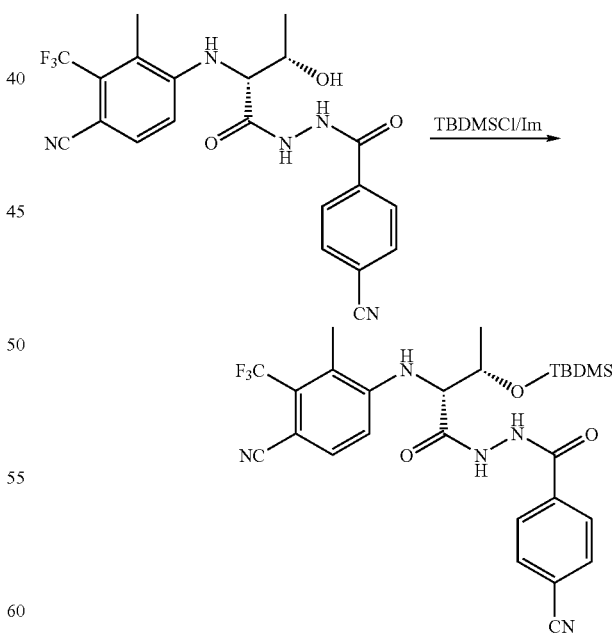

The crude material 4-cyano-N'-((2R,3S)-2-(4-cyano-2-methyl-3-(trifluoromethyl)phenylamino)-3-hydroxybutanoyl)benzohydrazide (507 mg, 1.14 mmol) was added to DMF (30 mL), followed by addition of TBDMS-Cl (686 mg, 4.55 mmol) and imidazole (619 mg, 9.10 mmol) at 0° C. The solution was allowed to stir at 0° C. for 30 min and then at room temperature for overnight. The reaction was quenched with the addition of 200 mL brine and extracted with EtOAc. The resulting crude material was chromatographed to give the desired product (390 mg) $^1$H NMR (400 MHz, acetone-$d_6$, δ in ppm): 9.6 (br s), 7.92 (d, J=9 Hz, 2H), 7.8 (d, J=9 Hz, 2H), 7.56 (d, J=9 Hz, 1H), 6.92 (d, J=9 Hz, 1H), 5.55 (d, J=9 Hz, 1H), 4.51 (m, 1H), 4.16 (m, 1H), 2.25 (m, 3H), 1.24 (d, J=6 Hz, 3H), 0.82 (s, 9H), 0.05 (s, 6H), 0.00 (s, 3H).

Intermediate 42d 4-((1R,2S)-2-(tert-Butyldimethylsilyloxy)-1-(5-(4-cyanophenyl)-1,3,4-oxadiazol-2-yl)propylamino)-3-methyl-2-(trifluoromethyl)benzonitrile

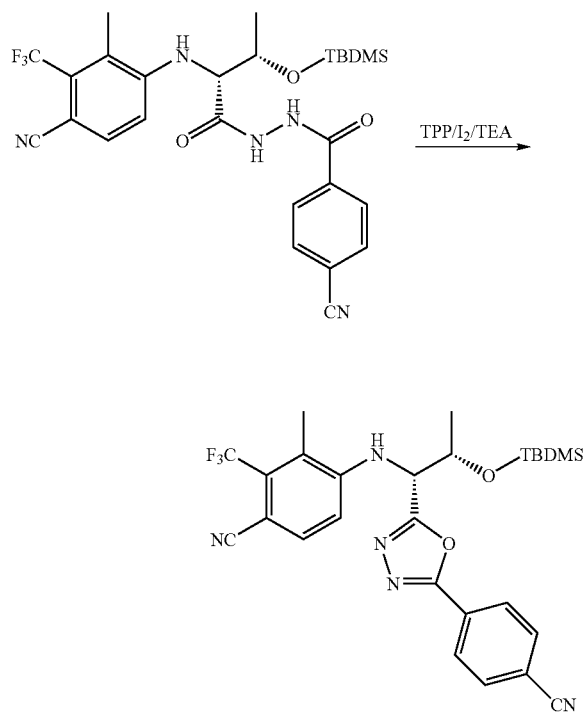

Triphenylphosphine (374 mg, 1.43 mmol) was dissolved in 25 mL of DCM followed by addition of I$_2$ (362 mg, 1.43 mmol) and TEA (289 mg, 2.85 mmol) at 0° C. N'-((2R,3S)-3-(tert-butyldimethylsilyloxy)-2-(4-cyano-2-methyl-3-(trifluoromethyl)phenylamino)butanoyl)-4-cyanobenzohydrazide (400 mg, 0.71 mmol) in 15 mL DCM was added to the precooled solution mixture of PPh$_3$/I$_2$/TEA system and stirred. The temperature was allowed to rise to room temperature and stirred for an additional 10 min. The reaction was quenched with 50 mL saturated sodium thiosulfate and extracted with EtOAc. The crude mixture was chromatographed to give the product (380 mg) $^1$H NMR (400 MHz, acetone-$d_6$, δ in ppm): 8.39 (d, J=9 Hz, 2H), 8.19 (d, J=9 Hz, 2H), 7.79 (d, J=9 Hz, 1H), 7.32 (d, J=9 Hz, 1H), 5.88 (d, J=9 Hz, 1H), 5.53 (m, 1H), 4.99 (m, 1H), 2.61 (m, 3H), 1.67 (d, J=6 Hz, 3H), 1.02 (s, 9H), 0.29 (s, 3H), 0.00 (s, 3H).

Example 42

4-((1R,2S)-1-(5-(4-Cyanophenyl)-1,3,4-oxadiazol-2-yl)-2-hydroxypropylamino)-3-methyl-2-(trifluoromethyl)benzonitrile

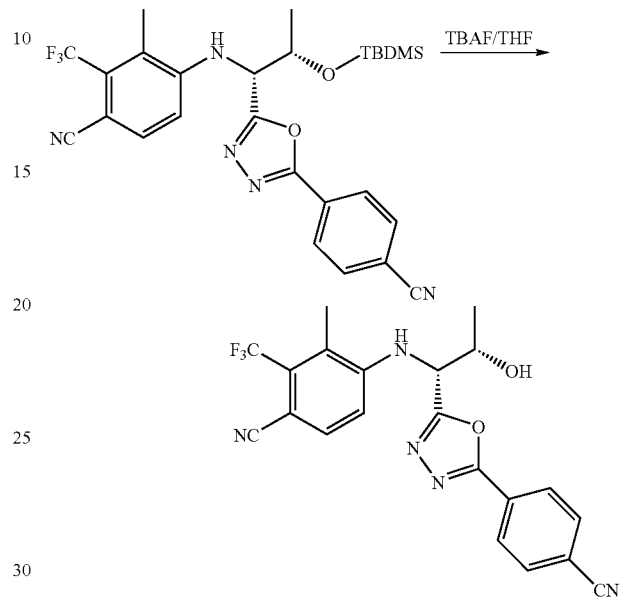

4-((1R,2S)-2-(tert-butyldimethylsilyloxy)-1-(5-(4-cyanophenyl)-1,3,4-oxadiazol-2-yl)propylamino)-3-methyl-2-(trifluoromethyl)benzonitrile (380 mg, 0.70 mmol) was dissolved in THF (20 mL) and cooled to −55° C. under N$_2$ atmosphere. TBAF (1.0 M solution in THF, 0.84 mL, 0.84 mmol) was added to the pre-cooled solution slowly and the temperature was allowed to rise gradually. After the reaction was complete, saturated aqueous NH$_4$Cl (100 mL) was added and the solution was extracted with EtOAc (3×100 mL). Purification by column chromatography on silica gel provided the desired product (180 mg): $^1$H NMR (500 MHz, acetone-$d_6$, δ in ppm): 8.18 (d, J=9 Hz, 2H), 7.97 (d, J=9 Hz, 2H), 7.59 (d, J=9 Hz, 1H), 7.13 (d, J=9 Hz, 1H), 5.82 (d, J=9 Hz, 1H), 5.18 (m, 1H), 4.83 (d, J=6 Hz, 1H), 4.64 (m, 1H), 2.40 (m, 3H), 1.40 (d, J=6 Hz, 3H).

Example 43

2-Chloro-4-((1R,2S)-2-hydroxy-1-(5-methyl-1,3,4-oxadiazol-2-yl)propylamino)-3-methylbenzonitrile hydrochloride

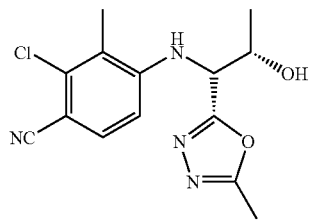

Intermediate 43a (2R,3S)—N'-Acetyl-2-(3-chloro-4-cyano-2-methylphenylamino)-3-hydroxybutanehydrazide

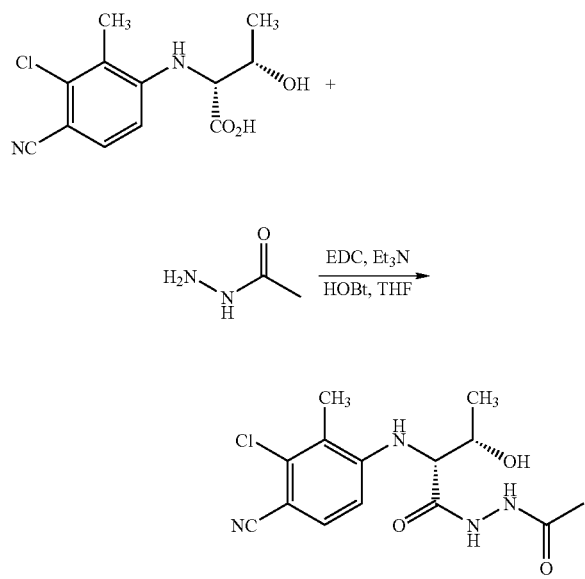

((2R,3S)-2-(3-chloro-4-cyano-2-methylphenylamino)-3-hydroxybutanoic acid (6.33 g, 23.56 mmol) and acetylhydrazide (1.92 g, 25.91 mmol) were mixed together in THF (168 mL) and cooled to −20° C. under N₂ atmosphere. To the pre-cooled reaction mixture were added HOBt (3.18 g, 23.56 mmol), TEA (4.14 mL, 29.45 mmol) followed by EDC (5.65 g, 29.45 mmol). The reaction mixture was allowed to stir at −20° C. for 1 h and then at room temperature overnight. After the reaction was complete, the urea was filtered off and the solution was washed with water, 5% citric acid followed by 5% NaHCO₃ to give the crude hydrazide (2.40 g, crude): ¹H NMR (400 MHz, DMSO-d₆, δ in ppm) 10.01 (br s, 1H), 9.95 (br s, 1H), 7.55 (d, J=8.8 Hz, 1H), 6.64 (d, J=8.8 Hz, 1H), 5.71 (d, J=8.4 Hz, 1H), 5.17 (d, J=5.2 Hz, 1H), 4.12-4.07 (m, 1H), 3.95 (dd, J=6.0, 8.0 Hz, 1H), 2.26 (s, 3H), 1.84 (s, 3H), 1.19 (d, J=6.4 Hz, 3H).

Intermediate 43b 4-((1R,2S)-2-(tert-Butyldimethylsilyloxy)-1-(5-methyl-1,3,4-oxadiazol-2-yl)propylamino)-2-chloro-3-methylbenzonitrile

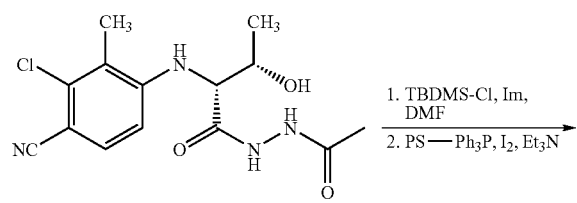

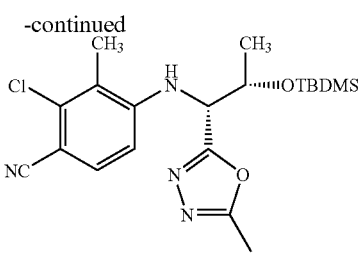

Step 1: TBDMS-Cl (3.20 g, 21.25 mmol) was added to a pre-cooled (0° C.) solution of (2R,3S)—N'-acetyl-2-(3-chloro-4-cyano-2-methylphenylamino)-3-hydroxybutane hydrazide (2.30 g, 7.08 mmol) and imidazole (2.41 g, 35.41 mmol) in DMF (47 mL). The reaction mixture was allowed to warm to room temperature and stirred overnight, whereupon it was poured into H₂O (300 mL) and diluted with EtOAc (50 mL). The organic layer was separated and the aqueous layer extracted with EtOAc (3×50 mL). The combined organic layers were dried (Na₂SO₄), filtered and concentrated under reduced pressure to provide crude title compound. Step 2: In a separate flask, I₂ (2.70 g, 10.63 mmol) and Et₃N (3.98 mL, 28.34 mmol) were added sequentially to a solution of PS-Ph₃P (3.54 g, 3.0 mmol/g loading) in CH₂Cl₂ (25 mL) at 0° C. To this solution was added crude hydrazide in CH₂Cl₂ (51 mL). After 30 min, the reaction mixture was filtered and the mother liquid washed with 10% Na₂S₂O₃ (200 mL), separated and the aqueous layer extracted with CH₂Cl₂ (3×50 mL). The combined organic extracts were dried (Na₂SO₄), filtered and concentrated to provide a yellow oil, which was purified by flash chromatography over SiO₂ (30% EtOAc in hexanes) yielding the title compound (2.9 g, 97%): ¹H NMR (400 MHz, DMSO-d₆, δ in ppm) 7.49 (d, J=8.8 Hz, 1H), 6.86 (d, J=8.8 Hz, 1H), 5.66-5.63 (m, 1H), 4.98 (dd, J=6.8, 8.8 Hz, 1H), 4.58-4.52 (m, 1H), 2.46 (s, 3H), 2.32 (s, 3H), 1.38 (d, J=6.0 Hz, 3H), 0.83 (s, 9H), 0.09 (s, 3H), 0.01 (s, 3H).

Example 43

2-Chloro-4-((1R,2S)-2-hydroxy-1-(5-methyl-1,3,4-oxadiazol-2-yl)propylamino)-3-methylbenzonitrile

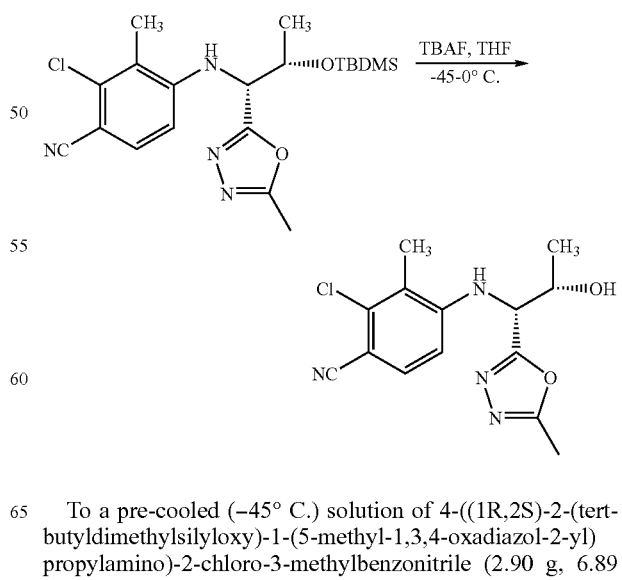

To a pre-cooled (−45° C.) solution of 4-((1R,2S)-2-(tert-butyldimethylsilyloxy)-1-(5-methyl-1,3,4-oxadiazol-2-yl)propylamino)-2-chloro-3-methylbenzonitrile (2.90 g, 6.89 mmol) in THF (28 mL) was added TBAF (8.27 mL, 1 M solution in THF) over 1 minute. Upon complete addition, the reaction mixture was allowed to warm to 0° C. and concentrated under reduced pressure. The resulting orange residue was taken up in EtOAc (100 mL) and washed with H₂O (400 mL). The biphasic mixture was separated and the aqueous layer extracted with EtOAc (2×50 mL). The combined organic layers were washed with brine (1×300 mL), dried (Na₂SO₄), filtered and concentrated under reduced pressure to provide a yellow/orange oil, which was purified by flash chromatography over silica gel (50% EtOAc in hexanes) to provide the title compound as a yellow solid (2.0 g, 95%): mp: 181-183° C.; ¹H NMR (400 MHz, DMSO-d₆, δ in ppm) 7.48 (d, J=8.0 Hz, 1H), 6.80 (d, J=8.0 Hz, 1H), 5.75 (d, J=8.8 Hz, 1H), 4.92 (dd, J=6.0, 8.8 Hz, 1H), 4.42 (m, 1H), 2.44 (s, 3H), 2.33 (s, 3H), 1.33 (d, J=6.4 Hz).

Example 44

4-((1R,2R)-1-(5-(4-Cyanophenyl)-1,3,4-oxadiazol-2-yl)-2-hydroxypropylamino)-2-(trifluoro-methyl)benzonitrile

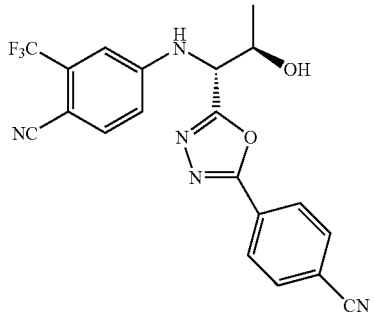

Intermediate 44a (2R,3R)-2-(4-Cyano-3-(trifluoromethyl)phenylamino)-3-hydroxybutanoic acid

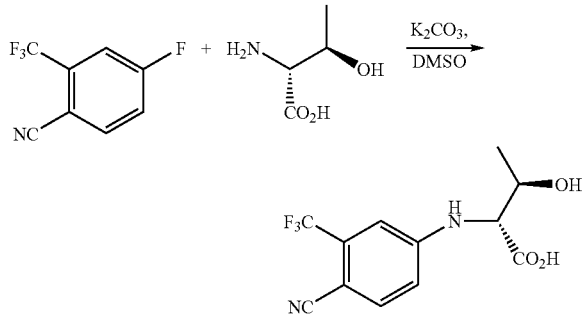

To a suspension of D-allo-threonine (4.30 g, 36.1 mmol) and K₂CO₃ (8.73 g, 63.2 mmol) in DMSO (50 mL) was added 4-fluoro-2-(trifluoromethyl)benzonitrile (5.69 g, 30.1 mmol) at room temperature. The reaction mixture was heated to 75° C. and stirred for 39 h. The reaction mixture was allowed to cool to room temperature and quenched with H₂O (400 mL) and extracted with EtOAc (3×200 mL). The aqueous layer was then acidified with solid citric acid and extracted with EtOAc (2×100 mL). The later organic extracts were combined, washed with H₂O (3×100 mL), dried (Na₂SO₄), filtered and concentrated under reduced pressure to provided the title compound as a brown oil (8.67 g, 100%): ¹H NMR (400 MHz, acetone-d₆, δ in ppm) 7.69 (d, J=8.6 Hz, 1H), 7.30 (d, J=2.5 Hz, 1H), 7.07 (dd, J=2.5, 8.4 Hz, 1H), 6.54 (d, J=8.4 Hz, 1H), 4.35 (dd, J=4.9, 8.4 Hz, 1H), 4.29 (dq, J=4.9, 6.5 Hz, 1H), 1.32 (d, J=6.4 Hz, 3H).

Intermediate 44b

4-Cyano-N'-((2R,3R)-2-(4-cyano-3-(trifluoromethyl)phenylamino)-3-hydroxybutanoyl)benz-ohydrazide

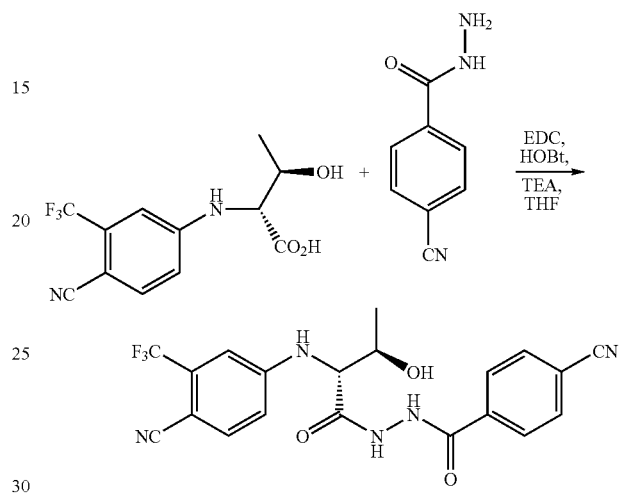

To a pre-cooled (−30° C.) solution of (2R,3R)-2-(4-cyano-3-(trifluoromethyl)-phenylamino)-3-hydroxybutanoic acid (1.05 g, 3.64 mmol) and 4-cyanobenzohydrazide (587 mg, 3.64 mmol) in anhydrous THF (60 mL) was added 1-Hydroxybenzotriazole monohydrate (563 mg, 3.64 mmol) and N-(3-Dimethylaminopropyl)-N'-ethylcarbodimide-HCl (1.40 g, 7.29 mmol) at −30° C. followed by triethylamine (1.02 mL, 7.29 mmol). The reaction mixture warmed to room temperature and stirred for 17 h, then quenched with 5% aq. citric acid (150 mL). The solution was extracted with EtOAc (150 mL). The organic extract was washed with 5% aq. citric acid (2×80 mL), sat. aq. NaHCO₃ (3×80 mL), H₂O (2×100 mL), dried (Na₂SO₄), filtered and concentrated under reduced pressure to provide the title compound as an off white solid (1.57 g, 100%): ¹H NMR (400 MHz, acetone-d₆, δ in ppm) 8.10 (dm, J=8.8 Hz, 2H), 7.94 (dm, J=8.8 Hz, 2H), 7.73 (d, J=8.6 Hz, 1H), 7.31 (d, J=2.3 Hz, 1H), 7.07 (dd, J=2.3, 8.6 Hz, 1H), 6.66 (d, J=7.2 Hz, 1H), 4.26-4.18 (m, 2H), 1.35 (d, J=6.3 Hz, 3H).

Intermediate 44c

N'-((2R,3R)-3-(tert-Butyldimethylsilyloxy)-2-(4-cyano-3-(trifluoromethyl)phenylamino)but-anoyl)-4-cyanobenzohydrazide

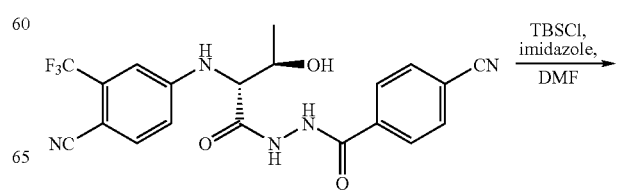

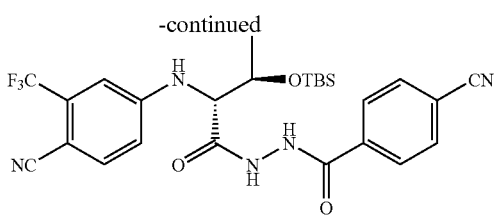

To a pre-cooled (0° C.) solution of 4-cyano-N'-((2R,3R)-2-(4-cyano-3-(trifluoromethyl)phenylamino)-3-hydroxybutanoyl)benzohydrazide (1.57 g, 3.64 mmol) in DMF (100 mL) was added imidazole (1.98 g, 29.4 mmol) then TBSCl (2.20 g, 14.58 mmol). The reaction was warmed slowly to room temperature, stirred for 19 h, cooled to 0° C. and quenched with $H_2O$ (300 mL). The solution was extracted with EtOAc (250 mL). The organic extract was washed with $H_2O$ (2×100 mL) and 5% aq. citric acid (3×80 mL), dried ($Na_2SO_4$), filtered and concentrated under reduced pressure to provide a brown oil, which was purified by flash chromatography over silica gel (20-30% EtOAc in hexanes) to provide the title compound as a colourless solid (1.57 g, 79%): $^1$H NMR (400 MHz, acetone-$d_6$, δ in ppm) 8.06 (dm, J=8.6 Hz, 2H), 7.91 (dm, J=8.6 Hz, 2H), 7.73 (d, J=8.8 Hz, 1H), 7.36 (d, J=2.2 Hz, 1H), 7.14 (dd, J=2.4, 8.6 Hz, 1H), 6.52 (d, J=7.6 Hz, 1H), 4.49-4.39 (m, 2H), 1.36 (d, J=6.1 Hz, 3H), 0.85 (s, 9H), 0.12 (s, 3H), 0.09 (s, 3H).

Intermediate 44d 4-((1R,2R)-2-(tert-Butyldimethylsilyloxy)-1-(5-(4-cyanophenyl)-1,3,4-oxadiazol-2-yl)propyl-amino)-2-(trifluoromethyl)benzonitrile

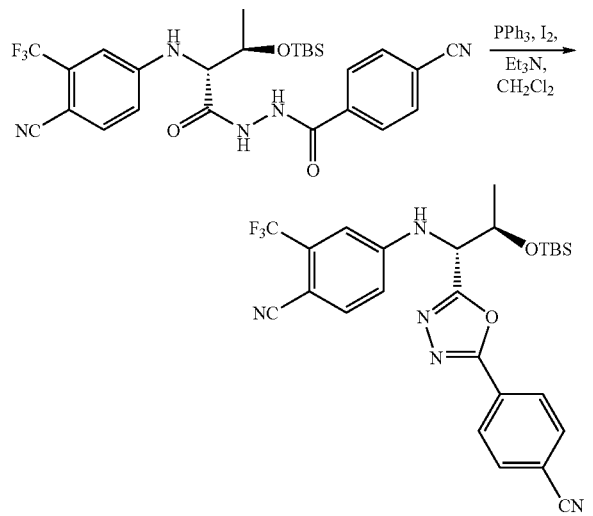

A solution of N'-((2R,3R)-3-(tert-butyldimethylsilyloxy)-2-(4-cyano-3-(trifluoromethyl)phenylamino)butanoyl)-4-cyanobenzohydrazide (944 mg, 1.73 mmol) in $CH_2Cl_2$ (30 mL) was added to a pre-cooled (0° C.) mixture of $PPh_3$ (907 mg, 3.46 mmol), iodine (878 mg, 3.46 mmol) and $Et_3N$ (0.96 mL, 6.92 mmol). The reaction mixture was warmed to room temperature, stirred for 30 min and quenched with sat. aq. sodium thiosulfate (200 mL). The solution was extracted with $CH_2Cl_2$ (200 mL). The organic extract was washed with sat. aq. sodium thiosulfate (150 mL), dried ($Na_2SO_4$), filtered and concentrated under reduced pressure to provide a brown oil, which was purified by flash chromatography over silica gel (20-30% EtOAc in hexanes) to provide the title compound as a light yellow oil (790 mg, 87%): $^1$H NMR (400 MHz, acetone-$d_6$, δ in ppm) 8.20 (dm, J=8.6 Hz, 2H), 8.03 (dm, J=8.8 Hz, 2H), 7.74 (d, J=8.8 Hz, 1H), 7.34 (d, J=2.4 Hz, 1H), 7.19 (dd, J=2.5, 8.8 Hz, 1H), 6.89 (d, J=9.0 Hz, 1H), 5.19 (dd, J=7.2, 9.0 Hz, 1H), 4.55 (dq, J=6.1, 7.2 Hz, 1H), 1.47 (d, J=6.1 Hz, 3H), 0.74 (s, 9H), 0.09 (s, 3H), −0.07 (s, 3H).

Example 44

4-((1R,2R)-1-(5-(4-Cyanophenyl)-1,3,4-oxadiazol-2-yl)-2-hydroxypropylamino)-2-(trifluoro-methyl)benzonitrile

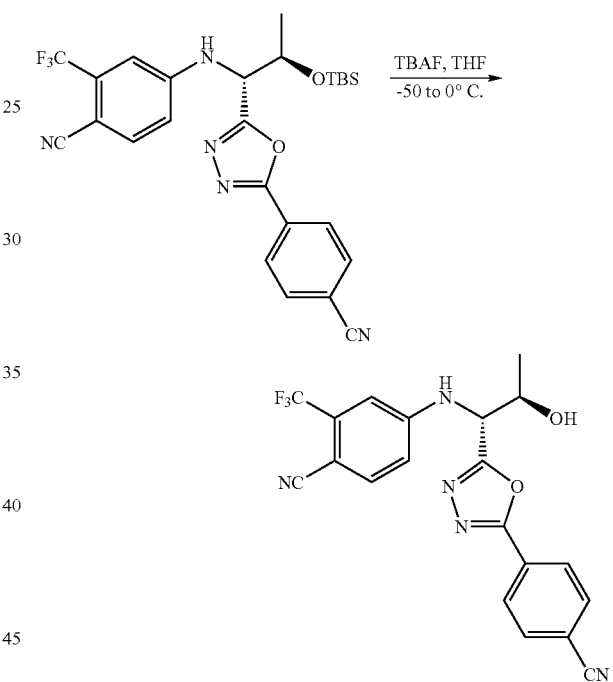

To a pre-cooled (−55° C.) solution of 4-((1R,2R)-2-(tert-butyldimethyl-silyloxy)-1-(5-(4-cyanophenyl)-1,3,4-oxadiazol-2-yl)propylamino)-2-(trifluoromethyl)benzonitrile (790 mg, 1.50 mmol) in THF (100 mL) was added TBAF (1.80 mL, 1.80 mmol, 1 M solution in THF) over 10 min. Upon complete addition the reaction mixture was allowed to warm to 0° C. over 1 h, then stirred at 0° C. for a further 30 min and quenched with sat. aq. $NH_4Cl$ (100 mL). The resulting mixture was partitioned between $H_2O$ (50 mL) and EtOAc (200 mL). The aqueous layer was extracted with EtOAc (150 mL). The combined organic extracts were dried ($Na_2SO_4$), filtered and concentrated under reduced pressure to provide a yellow oil, which was purified by flash chromatography over silica gel (50-80% EtOAc in hexanes) to provided the title compound as a colourless amorphous solid (610 mg, 98%): $^1$H NMR (400 MHz, acetone-$d_6$, δ in ppm) 8.20 (dm, J=8.8 Hz, 2H), 8.00 (dm, J=8.8 Hz, 2H), 7.73 (d, J=8.6 Hz, 1H), 7.38 (d, J=2.4 Hz, 1H), 7.17 (dd, J=2.5, 8.8 Hz, 1H), 7.01 (d, J=8.8 Hz, 1H), 5.17 (dd, J=5.7, 8.8 Hz, 1H), 4.45 (pentet, J=6.1 Hz, 1H), 1.42 (d, J=6.4 Hz, 3H).

Example 45

4-((1R,2S)-1-(5-(4-Cyanophenyl)-1,3,4-oxadiazol-2-yl)-2-hydroxypropylamino)-2-(trifluoromethyl)benzonitrile

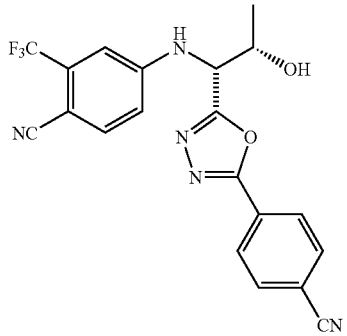

Intermediate 45a (2R,3S)-2-(4-Cyano-3-(trifluoromethyl)phenylamino)-3-hydroxybutanoic acid

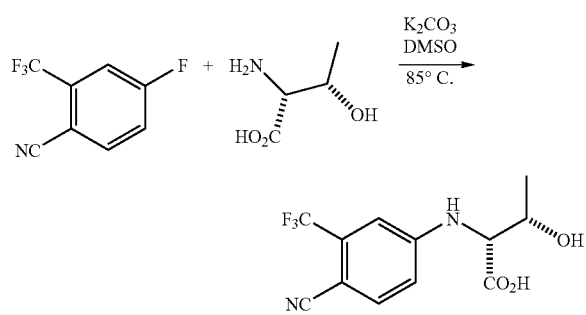

K$_2$CO$_3$ (7.31 g, 52.92 mmol) was added to a solution of 4-fluoro-2-(trifluoromethyl)benzonitrile (5 g, 26.46 mmol) and (2R,3S)-2-amino-3-hydroxybutanoic acid (3.47 g, 29.10 mol) in DMSO (100 mL) at room temperature. The reaction mixture was heated to 85° C. and stirred for 48 h, then was allowed to cool to room temperature whereupon water (20 mL) was added followed by citric acid monohydrate (2 g). After stirring for 10 min, the mixture was partitioned between EtOAc (40 mL) and water. The organic phase was then washed with water (15 mL), brine (15 mL), dried (Na$_2$SO$_4$) and concentrated to furnish a pale yellow solid (8.91 g). This crude product was then passed through a silica-plug [hexanes-EtOAc (5:95) as eluent] to furnish the title compound as a white solid (6.2 g, 81%) $^1$H NMR (500 MHz, acetone-d$_6$, δ in ppm) 7.69 (d, J=9 Hz, 1H), 7.31 (s, 1H), 7.03 (d, J=8 Hz, 1H), 6.42 (d, J=8 Hz, 1H), 4.46-4.40 (m, 1H), 4.29-4.24 (m, 1H), and 1.24 (d, J=7 Hz, 3H).

Intermediate 45b

4-Cyano-N'-((2R,3S)-2-(4-cyano-3-(trifluoromethyl)phenylamino)-3-hydroxybutanoyl)benzohydrazide

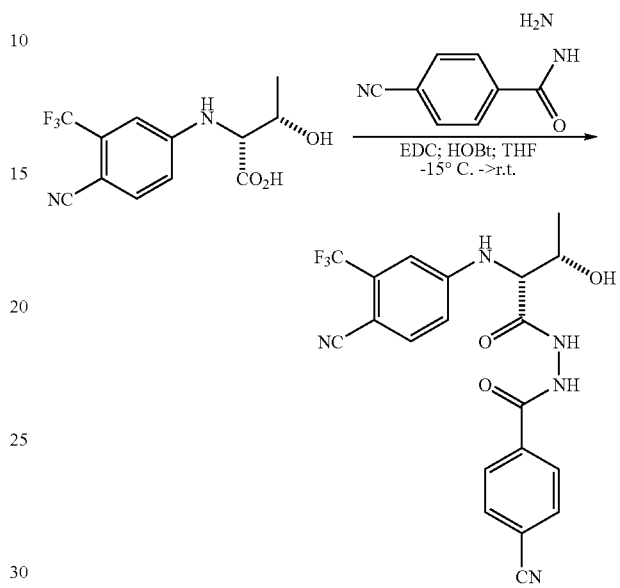

(2R,3S)-2-(4-cyano-3-(trifluoromethyl)phenylamino)-3-hydroxybutanoic acid (8.91 g, 30.91 mmol), 4-cyanobenzohydrazide (5.48 g, 34 mmol) and anhydrous THF (200 mL) were placed in a 500 mL round bottomed flask and the mixture was cooled to −15° C. 1-Hydroxybenzotriazole hydrate (4.18 g, 30.91 mmol) was added to the mixture together with N-(3-Dimethylaminopropyl)-N'-ethylcarbodimide HCl (8.89 g, 46.37 mmol) at −15° C. followed by triethylamine (6.46 mL, 46.37 mmol). The reaction mixture was maintained at −15° C. and stirred for 1 h, after which stirring continued overnight while the mixture slowly warmed to room temperature. After 18 h, the mixture was filtered under vacuum and the residue washed with THF (90 mL). The THF solution was concentrated to ca. 30 mL, whereupon EtOAc (100 mL) was added followed by water (60 mL). The phases were partitioned and the organic phase washed with water (30 mL), brine (30 mL) dried (Na$_2$SO$_4$) and concentrated to furnish a light brown solid (31 g). Purification by flash column chromatography [EtOAc-hexanes (1:1), then 100% EtOAc as eluent] afforded the title compound as a white solid (6.28 g, 59% yield).

Intermediate 45c

N'-((2R,3S)-3-(tert-Butyldimethylsilyloxy)-2-(4-cyano-3-(trifluoromethyl)phenylamino)but-anoyl)-4-cyanobenzohydrazide

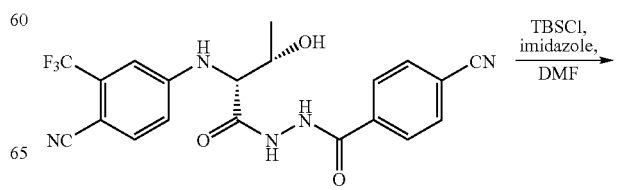

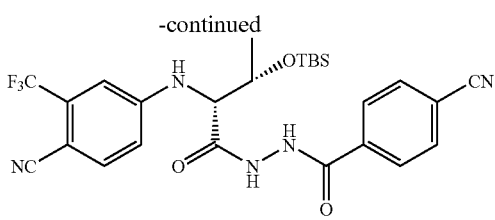

To a pre-cooled (0° C.) solution of 4-cyano-N'-((2R,3S)-2-(4-cyano-3-(trifluoromethyl)phenylamino)-3-hydroxybutanoyl)benzohydrazide (1.49 g, 3.45 mmol) in DMF (100 mL) was added imidazole (1.88 g, 27.63 mmol) then TBSCl (2.08 g, 13.82 mmol). The reaction was warmed slowly to room temperature, stirred for 18 h, cooled to 0° C. and quenched with H$_2$O (300 mL). The solution was extracted with EtOAc (250 mL). The organic extract was washed with H$_2$O (2×100 mL) and 5% aq. citric acid (3×80 mL), dried (Na$_2$SO$_4$), filtered and concentrated under reduced pressure to provide a yellow oil, which was purified by flash chromatography over silica gel (20-30% EtOAc in hexanes) to provide the title compound as a colourless solid (1.05 g, 56%): $^1$H NMR (400 MHz, acetone-d$_6$, δ in ppm) 8.06 (dm, J=8.4 Hz, 2H), 7.92 (dm, J=8.4 Hz, 2H), 7.72 (d, J=8.6 Hz, 1H), 7.31 (d, J=2.4 Hz, 1H), 7.11 (dd, J=2.3, 8.6 Hz, 1H), 6.48 (d, J=8.6 Hz, 1H), 4.43 (dq, J=4.5, 6.1 Hz, 1H), 4.35 (dd, J=4.5, 8.4 Hz, 1H), 1.37 (d, J=6.3 Hz, 3H), 0.87 (s, 9H), 0.12 (s, 3H), −0.04 (s, 3H).

Intermediate 45d 4-((1R,2S)-2-(tert-Butyldimethylsilyloxy)-1-(5-(4-cyanophenyl)-1,3,4-oxadiazol-2-yl)propyl-amino)-2-(trifluoromethyl)benzonitrile

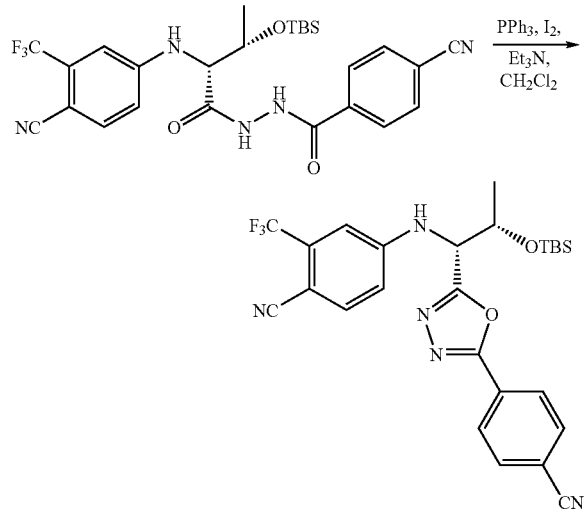

A solution of N'-((2R,3S)-3-(tert-butyldimethyl-silyloxy)-2-(4-cyano-3-(trifluoromethyl)phenylamino)butanoyl)-4-cyanobenzohydrazide (1.05 g, 1.92 mmol) in CH$_2$Cl$_2$ (40 mL) was added to a pre-cooled (0° C.) mixture of PPh$_3$ (1.01 g, 3.85 mmol), iodine (980 mg, 3.85 mmol) and Et$_3$N (1.1 mL, 7.70 mmol). The reaction mixture was warmed to room temperature, stirred for 30 min and quenched with sat. aq. sodium thiosulfate (200 mL). The solution was extracted with CH$_2$Cl$_2$ (150 mL). The organic extract was washed with sat. aq. sodium thiosulfate (100 mL), dried (Na$_2$SO$_4$), filtered and concentrated under reduced pressure to provide a light brown solid, which was purified by flash chromatography over silica gel (50% EtOAc in hexanes) to provide the title compound as a light yellow oil (900 mg, 89%): $^1$H NMR (400 MHz, acetone-d$_6$, δ in ppm) 8.22 (dm, J=8.8 Hz, 2H), 8.02 (dm, J=8.8 Hz, 2H), 7.72 (d, J=8.8 Hz, 1H), 7.41 (d, J=2.5 Hz, 1H), 7.17 (dd, J=2.3, 8.6 Hz, 1H), 6.75 (d, J=9.2 Hz, 1H), 5.36 (dd, J=3.3, 9.4 Hz, 1H), 4.73 (dq, J=3.1, 6.1 Hz, 1H), 1.45 (d, J=6.3 Hz, 3H), 0.78 (s, 9H), 0.07 (s, 3H), −0.13 (s, 3H Example 45

4-((1R,2S)-1-(5-(4-Cyanophenyl)-1,3,4-oxadiazol-2-yl)-2-hydroxypropylamino)-2-(trifluoro-methyl)benzonitrile

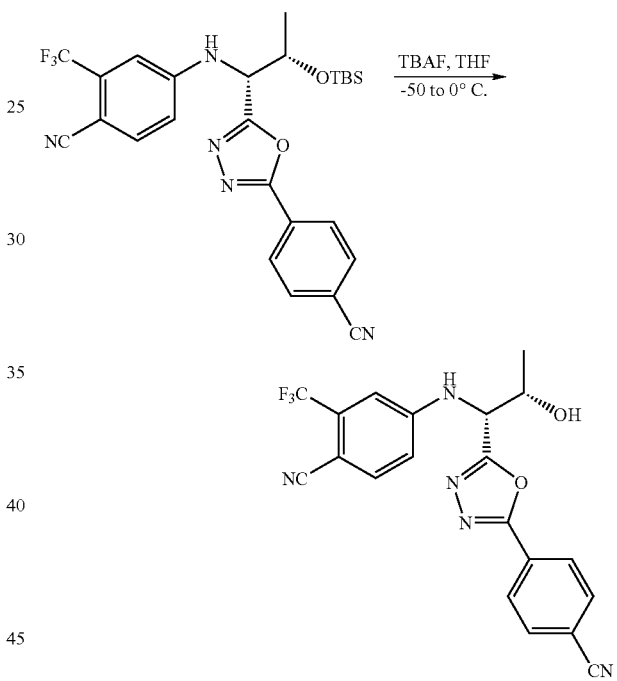

To a pre-cooled (−55° C.) solution of 4-((1R,2S)-2-(tert-butyldimethyl-silyloxy)-1-(5-(4-cyanophenyl)-1,3,4-oxadiazol-2-yl)propylamino)-2-(trifluoromethyl)benzonitrile (900 mg, 1.17 mmol) in THF (120 mL) was added TBAF (2.05 mL, 2.05 mmol, 1 M solution in THF) over 10 min. Upon complete addition the reaction mixture was allowed to warm to 0° C. over 1 h, then stirred at 0° C. for a further 30 min and quenched with sat. aq. NH$_4$Cl (150 mL). The resulting mixture was partitioned between H$_2$O (150 mL) and EtOAc (250 mL). The aqueous layer was extracted with EtOAc (100 mL). The combined organic extracts were dried (Na$_2$SO$_4$), filtered and concentrated under reduced pressure to provide a yellow oil, which was purified by flash chromatography over silica gel (30-50% EtOAc in hexanes) to provided the title compound as a colourless oil (420 mg, 66%): $^1$H NMR (400 MHz, acetone-d$_6$, δ in ppm) 8.20 (dm, J=8.8 Hz, 2H), 8.01 (dm, J=8.8 Hz, 2H), 7.73 (d, J=8.6 Hz, 1H), 7.46 (d, J=2.4 Hz, 1H), 7.20 (dd, J=2.5, 8.8 Hz, 1H), 6.84 (d, J=8.8 Hz, 1H), 5.23 (dd, J=3.5, 8.8 Hz, 1H), 4.62 (dq, J=3.5, 6.5 Hz, 1H), 1.40 (d, J=6.3 Hz, 3H).

Example 46

2-Chloro-4-((1R,2R)-1-(5-(4-cyanophenyl)-1,3,4-oxadiazol-2-yl)-2-hydroxypropylamino)-benzonitrile

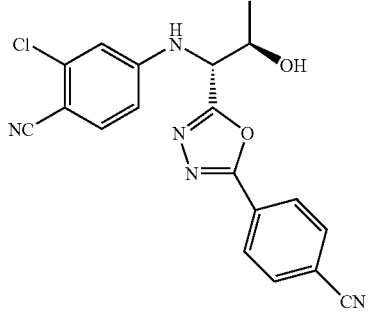

Intermediate 46a (2R,3R)-2-(3-Chloro-4-cyanophenylamino)-3-hydroxybutanoic acid

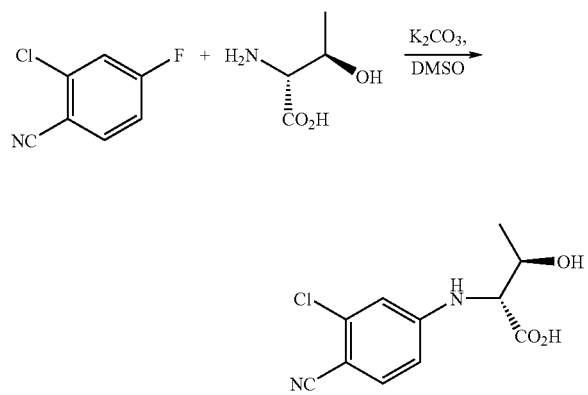

To a suspension of D-allo-threonine (5.08 g, 42.7 mmol) and K$_2$CO$_3$ (10.32 g, 74.7 mmol) in DMSO (50 mL) was added 2-chloro-4-fluorobenzonitrile (5.53 g, 35.5 mmol) at room temperature. The reaction mixture was heated to 75° C. and stirred for 39 h. The reaction mixture was allowed to cool to room temperature and quenched with H$_2$O (400 mL) and extracted with EtOAc (3×200 mL). The aqueous layer was then acidified with solid citric acid and extracted with EtOAc (2×100 mL). The later organic extracts were combined, washed with H$_2$O (3×150 mL), dried (Na$_2$SO$_4$), filtered and concentrated under reduced pressure to provided the title compound as a brown solid (9.04 g, 100%): $^1$H NMR (400 MHz, acetone-d$_6$, δ in ppm) 7.51 (d, J=8.8 Hz, 1H), 6.97 (d, J=2.3 Hz, 1H), 6.83 (dd, J=2.4, 8.8 Hz, 1H), 6.31 (br d, J=7.6 Hz, 1H), 4.28-4.20 (m, 2H), 1.31 (d, J=6.5 Hz, 3H).

Intermediate 46b

N'-((2R,3R)-2-(3-Chloro-4-cyanophenylamino)-3-hydroxybutanoyl)-4-cyanobenzohydrazide

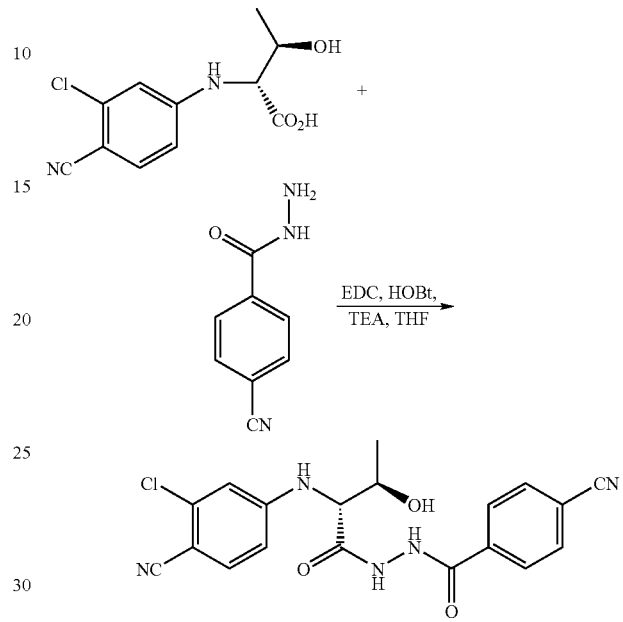

To a pre-cooled (−30° C.) solution of (2R,3R)-2-(3-chloro-4-cyanophenylamino)-3-hydroxybutanoic acid (1.06 g, 4.16 mmol) and 4-cyanobenzohydrazide (671 mg, 4.16 mmol) in anhydrous THF (60 mL) was added 1-Hydroxybenzotriazole monohydrate (637 mg, 4.16 mmol) and N-(3-Dimethylaminopropyl)-N'-ethylcarbodimide-HCl (1.60 g, 8.32 mmol) at −30° C. followed by triethylamine (1.16 mL, 8.32 mmol). The reaction mixture warmed to room temperature and stirred for 16 h, then quenched with 5% aq. citric acid (150 mL). The solution was extracted with EtOAc (150 mL). The organic extract was washed with 5% aq. citric acid (2×75 mL), sat. aq. NaHCO$_3$ (3×80 mL), H$_2$O (2×100 mL), dried (Na$_2$SO$_4$), filtered and concentrated under reduced pressure to provide the title compound as an off white solid (1.65 g, 100%): $^1$H NMR (400 MHz, acetone-d$_6$, δ in ppm) 8.11 (dm, J=8.8 Hz, 2H), 7.94 (dm, J=8.6 Hz, 2H), 7.54 (d, J=8.6 Hz, 1H), 6.96 (d, J=2.3 Hz, 1H), 6.85 (dd, J=2.3, 8.8 Hz, 1H), 6.44 (d, J=7.4 Hz, 1H), 4.21-4.11 (m, 2H), 1.35 (d, J=6.3 Hz, 3H).

Intermediate 46c

N'-((2R,3R)-3-(tert-Butyldimethylsilyloxy)-2-(3-chloro-4-cyanophenylamino)butanoyl)-4-cyanobenzohydrazide

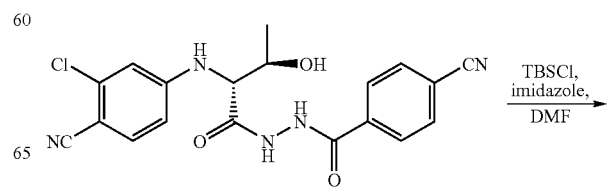

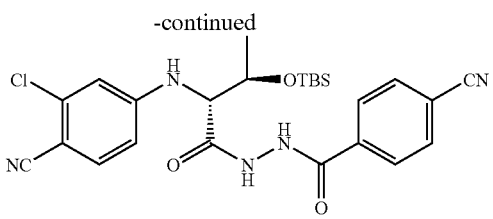

To a pre-cooled (0° C.) solution of N'-((2R,3R)-2-(3-chloro-4-cyanophenylamino)-3-hydroxybutanoyl)-4-cyanobenzohydrazide (1.65 g, 4.15 mmol) in DMF (100 mL) was added imidazole (2.26 g, 33.4 mmol) then TBSCl (2.50 g, 16.60 mmol). The reaction was warmed slowly to room temperature, stirred for 19 h, cooled to 0° C. and quenched with H$_2$O (300 mL). The solution was extracted with EtOAc (250 mL). The organic extract was washed with H$_2$O (2×100 mL) and 5% aq. citric acid (3×80 mL), dried (Na$_2$SO$_4$), filtered and concentrated under reduced pressure to provide a brown oil, which was purified by flash chromatography over silica gel (10-30% EtOAc in hexanes) to provide the title compound as a colourless amorphous solid (2.09 g, 98%): $^1$H NMR (400 MHz, acetone-d$_6$, δ in ppm) 8.06 (dm, J=8.6 Hz, 2H), 7.92 (dm, J=8.6 Hz, 2H), 7.53 (d, J=8.8 Hz, 1H), 7.04 (d, J=2.2 Hz, 1H), 6.91 (dd, J=2.4, 8.8 Hz, 1H), 6.26 (d, J=7.6 Hz, 1H), 4.42 (pentet, J=5.5 Hz, 1H), 4.31 (dd, J=5.5, 7.8 Hz, 1H), 1.35 (d, J=6.3 Hz, 3H), 0.87 (s, 9H), 0.12 (s, 3H), 0.10 (s, 3H).

Intermediate 46d 4-((1R,2R)-2-(tert-Butyldimethylsilyloxy)-1-(5-(4-cyanophenyl)-1,3,4-oxadiazol-2-yl)propyl-amino)-2-chlorobenzonitrile

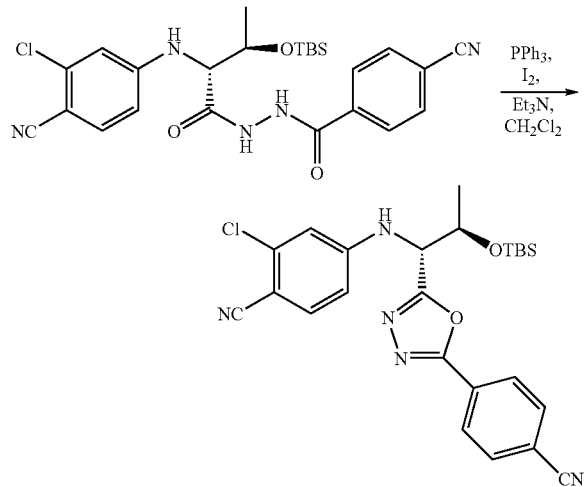

A solution of N'-((2R,3R)-3-(tert-butyldimethylsilyloxy)-2-(3-chloro-4-cyanophenylamino)butanoyl)-4-cyanobenzohydrazide (1.02 g, 1.98 mmol) in CH$_2$Cl$_2$ (30 mL) was added to a pre-cooled (0° C.) mixture of PPh$_3$ (1.04 g, 3.97 mmol), iodine (1.01 g, 3.97 mmol) and Et$_3$N (1.11 mL, 7.94 mmol). The reaction mixture was warmed to room temperature, stirred for 25 min and quenched with sat. aq. sodium thiosulfate (300 mL). The solution was extracted with CH$_2$Cl$_2$ (200 mL). The organic extract was washed with sat. aq. sodium thiosulfate (2×150 mL), dried (Na$_2$SO$_4$), filtered and concentrated under reduced pressure to provide a brown oil, which was purified by flash chromatography over silica gel (20% EtOAc in hexanes) to provide the title compound as a light yellow oil (984 mg, 100%): $^1$H NMR (400 MHz, acetone-d$_6$, δ in ppm) 8.22 (dm, J=8.6 Hz, 2H), 8.03 (dm, J=8.8 Hz, 2H), 7.55 (d, J=8.8 Hz, 1H), 7.07 (d, J=2.4 Hz, 1H), 6.92 (dd, J=2.3, 8.8 Hz, 1H), 6.67 (d, J=9.0 Hz, 1H), 5.10 (dd, J=7.2, 9.2 Hz, 1H), 4.52 (dq, J=6.1, 7.2 Hz, 1H), 1.45 (d, J=6.1 Hz, 3H), 0.75 (s, 9H), 0.09 (s, 3H), −0.07 (s, 3H).

Example 46

2-Chloro-4-((1R,2R)-1-(5-(4-cyanophenyl)-1,3,4-oxadiazol-2-yl)-2-hydroxypropylamino)-benzonitrile

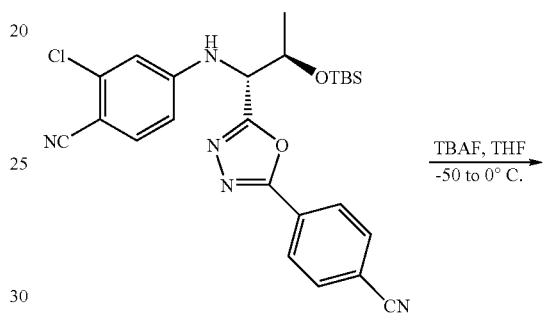

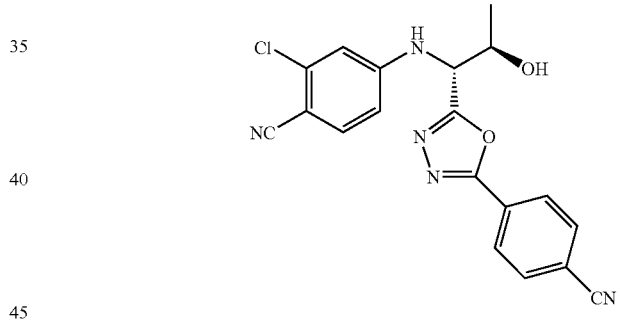

To a pre-cooled (−55° C.) solution of 4-((1R,2R)-2-(tert-butyldimethylsilyloxy)-1-(5-(4-cyanophenyl)-1,3,4-oxadiazol-2-yl)propylamino)-2-chlorobenzonitrile (860 mg, 1.74 mmol) in THF (100 mL) was added TBAF (2.09 mL, 2.09 mmol, 1 M solution in THF) over 10 min. Upon complete addition the reaction mixture was allowed to warm to 0° C. over 1 h, then stirred at 0° C. for a further 30 min and quenched with sat. aq. NH$_4$Cl (100 mL). The resulting mixture was partitioned between H$_2$O (50 mL) and EtOAc (200 mL). The aqueous layer was extracted with EtOAc (150 mL). The combined organic extracts were dried (Na$_2$SO$_4$), filtered and concentrated under reduced pressure to provide a yellow oil, which was purified by flash chromatography over silica gel (20-80% EtOAc in hexanes) to provided the title compound as a colourless amorphous solid (660 mg, 100%): $^1$H NMR (400 MHz, acetone-d$_6$, δ in ppm) 8.20 (dm, J=8.8 Hz, 2H), 8.00 (dm, J=8.8 Hz, 2H), 7.53 (d, J=8.6 Hz, 1H), 7.06 (d, J=2.4 Hz, 1H), 6.92 (dd, J=2.4, 8.6 Hz, 1H), 6.79 (d, J=8.8 Hz, 1H), 5.08 (dd, J=5.7, 8.8 Hz, 1H), 4.42 (pentet, J=6.1 Hz, 1H), 1.41 (d, J=6.5 Hz, 3H).

Example 47

2-Chloro-4-((1R,2S)-1-(5-(4-cyanophenyl)-1,3,4-oxadiazol-2-yl)-2-hydroxypropylamino)-3-ethylbenzonitrile

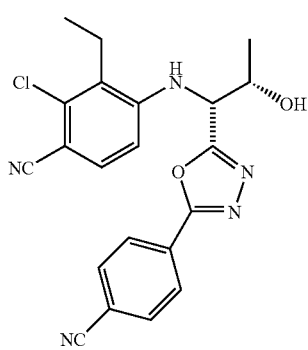

Intermediate 47a

N'-((2R,3S)-2-(3-Chloro-4-cyano-2-ethylphenylamino)-3-hydroxybutanoyl)-4-cyanobenzohydrazide

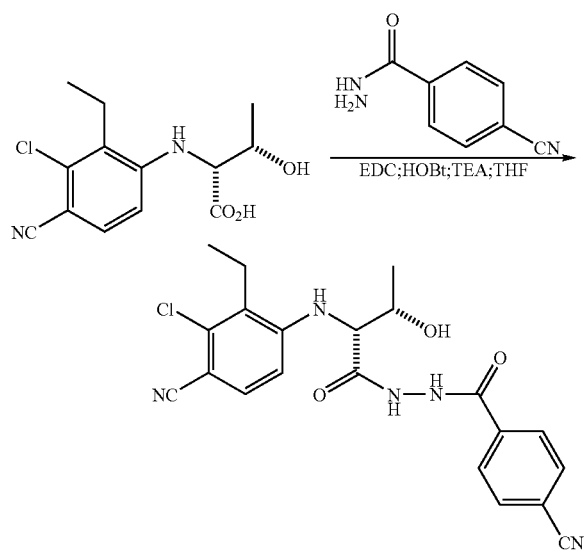

(2R,3S)-2-(3-chloro-4-cyano-2-ethylphenylamino)-3-hydroxybutanoic acid (700 mg, 2.48 mmol), 4-cyanobenzohydrazide (439 mg, 2.73 mmol) and anhydrous THF (20 mL) were placed in a 50 mL round bottomed flask and the mixture was cooled to −15° C. 1-Hydroxybenzotriazole hydrate (335 mg, 2.48 mmol) was added to the mixture together with N-(3-Dimethylaminopropyl)-N'-ethylcarbodiimide HCl (589 mg, 3.07 mmol) at −15° C. followed by triethylamine (0.43 mL, 3.07 mmol). The reaction mixture was maintained −15° C. and stirred for 1 h, after which stirring continued overnight while the mixture slowly warmed to room temperature. After 18 h, the mixture was filtered under vacuum and the residue washed with THF (30 mL). The THF solution was concentrated to ca. 10 mL, whereupon EtOAc (200 mL) was added followed by extraction with 5% citric acid (3×100 mL). The phases were partitioned and the organic phase washed with water (100 mL), brine (100 mL), dried ($Na_2SO_4$), filtered and concentrated to furnish a light yellow solid (920 mg, 87% yield). $^1$H NMR (500 MHz, acetone-$d_6$, δ in ppm) 9.80 (br s, 2H), 8.09 (d, J=8.6 Hz, 2H), 7.94 (d, J=8.6 Hz, 2H), 7.53 (d, J=8.6 Hz, 1H), 6.72 (d, J=8.6 Hz, 1H), 5.65 (d, J=6.7 Hz, 1H), 4.76 (br s, 1H), 4.43-4.35 (m, 1H), 4.15 (dd, J=3.7 Hz, 6.7 Hz, 1H), 2.94-2.79 (m, 2H) 1.38 (d, J=6.8 Hz, 3H) and 1.18 (t, J=7.6 Hz, 3H).

Example 47

2-Chloro-4-((1R,2S)-1-(5-(4-cyanophenyl)-1,3,4-oxadiazol-2-yl)-2-hydroxypropylamino)-3-ethylbenzonitrile

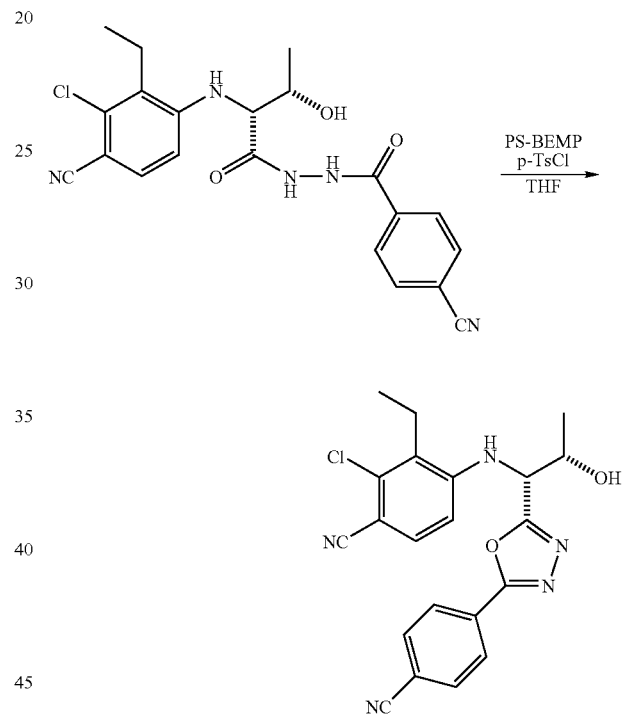

To a solution of N'-((2R,3S)-2-(3-chloro-4-cyano-2-ethylphenylamino)-3-hydroxybutanoyl)-4-cyanobenzohydrazide (310 mg, 0.73 mmol) in anhydrous THF (20 mL) at room temperature was added 2-tert-butylamino-2-diethylamino-1,3-dimethyl perhydro-1,3,2-diazaphosphorine on polystyrene (2.2 mmol base/g) (1.0 g) followed by p-TSCl (167 mg, 0.88 mmol) and the mixture was stirred for 1 h. The mixture was filtered under suction and the residue washed with acetone (200 mL) followed by MeOH (200 mL). The filtrate was concentrated and subjected to flash column chromatography [EtOAc-hexanes (2:1)]. The fourth fraction was the desired 2-chloro-4-((1R,2S)-1-(5-(4-cyanophenyl)-1,3,4-oxadiazol-2-yl)-2-hydroxypropylamino)-3-ethylbenzonitrile (45 mg, 15%).). $^1$H NMR (500 MHz, acetone-$d_6$, δ in ppm) 8.20 (d, J=8.6 Hz, 2H), 7.99 (d, J=8.6 Hz, 2H), 7.48 (d, J=8.6 Hz, 1H), 6.86 (d, J=8.6 Hz, 1H), 5.79 (d, J=8.3 Hz, 1H), 5.18 (dd, J=3.3 Hz, 8.3 Hz, 1H), 4.85 (d, J=5.1 Hz, 1H), 4.68-4.60 (m, 1H), 2.98-2.88 (m, 2H), 1.43 (d, J=6.4 Hz, 3H) and 1.2 (t, J=7.6 Hz, 3H).

Example 48

2-Chloro-4-((1R,2S)-2-hydroxy-1-(5-(4-(methylsulfonyl)phenyl)-1,3,4-oxadiazol-2-yl)propylamino)benzonitrile

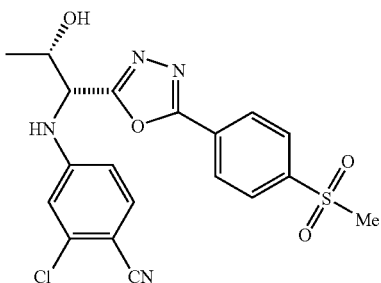

Intermediate 48a

N'-((2R,3S)-2-(3-Chloro-4-cyanophenylamino)-3-hydroxybutanoyl)-4-(methylsulfonyl)benzohydrazide

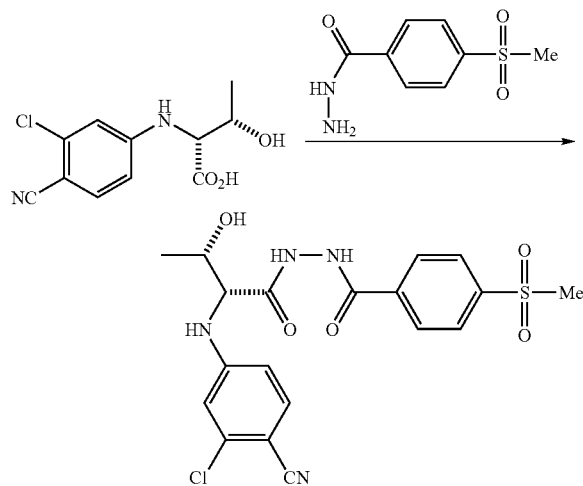

(2R,3S)-2-(3-chloro-4-cyanophenylamino)-3-hydroxybutanoic acid (3.33 g, 13.07 mmol), 4-(methylsulfonyl)benzohydrazide (3.08 g, 14.38 mmol) and anhydrous THF (200 mL) were placed in a 500 mL round bottomed flask and the mixture was cooled to −15° C. 1-Hydroxybenzotriazole hydrate (1.77 g, 13.07 mmol) was added to the mixture together with N-(3-Dimethylaminopropyl)-N'-ethylcarbodiimide HCl (3.76 g, 19.61 mmol) at −15° C. followed by triethylamine (2.73 mL, 19.61 mmol). The reaction mixture was maintained at −15° C. and stirred for 1 h after which, stirring continued overnight while the mixture slowly warmed to room temperature. After 17 h, the mixture was filtered under vacuum and the residue washed with THF (50 mL). The THF solution was concentrated to ca. 20 mL, whereupon EtOAc (100 mL) was added followed by water (50 mL). The phases were partitioned and the organic phase washed with water (30 mL), brine (30 mL) dried ($Na_2SO_4$) and concentrated to furnish a light brown solid (5.82 g). This crude product was chromatographed [100% EtOAc as eluent] to afford a pale yellow solid (5 g). The crude product was used directly in the next step.

Intermediate 48b

N'-((2R,3S)-3-(tert-Butyldimethylsilyloxy)-2-(3-chloro-4-cyanophenylamino)butanoyl)-4-(methylsulfonyl)benzohydrazide

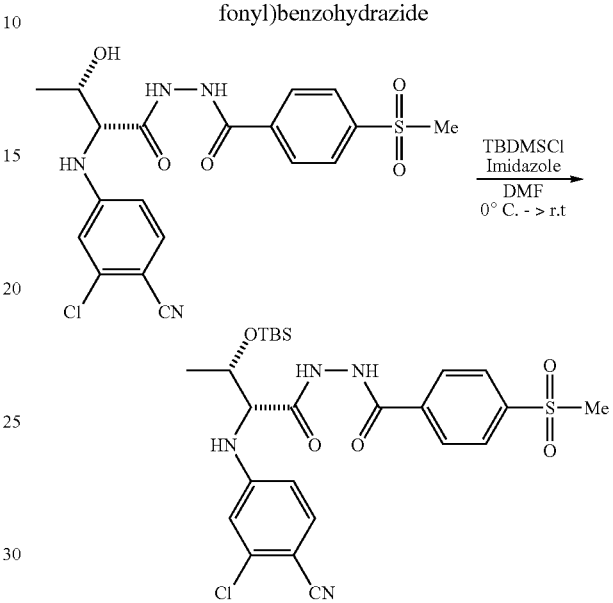

Imidazole (3.77 g, 55.44 mol) and TBDMS-Cl (5.01 g, 33.24 mmol) were added sequentially to a pre-cooled (0° C.) solution of N'-((2R,3S)-2-(3-chloro-4-cyanophenylamino)-3-hydroxybutanoyl)-4-(methylsulfonyl)benzohydrazide (5 g, 11.08 mmol) in DMF (350 mL). The reaction mixture was allowed to warm to room temperature and stirred for 17 h, whereupon the solution was poured into $H_2O$ (90 mL). The white precipitate was filtered, washed with $H_2O$ (30 mL) and taken up in $CH_2Cl_2$ (170 mL). This organic layer was washed with brine (1×50 mL), dried ($Na_2SO_4$), filtered and concentrated to provide the title compound (4.3 g, 69%). $^1$H NMR (400 MHz, acetone-$d_6$, δ in ppm) 9.8 (br s, 1H), 8.08 (d, J=8.0 Hz, 2H), 8.04 (d, J=9 Hz, 2H), 7.53 (d, J=8 Hz, 1H), 6.99 (s, 1H), 6.85 (d, J=8 Hz, 1H), 6.22 (d, J=8 Hz, 1H), 4.43-4.38 (m, 1H), 4.27-4.22 (m, 1H), 1.37 (d, J=7 Hz, 3H), 0.86 (s, 9H), 0.11 (s, 3H) and 0.05 (s, 3H).

Intermediate 48c 4-((1R,2S)-2-(tert-Butyldimethylsilyloxy)-1-(5-(4-(methylsulfonyl)phenyl)-1,3,4-oxadiazol-2-yl)propylamino)-2-chlorobenzonitrile

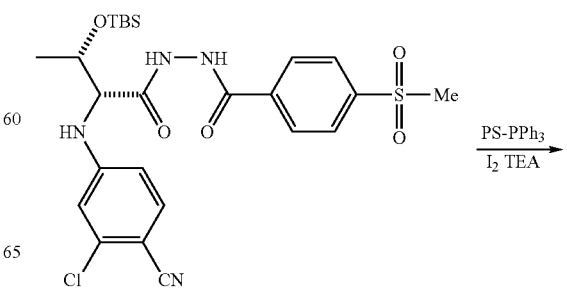

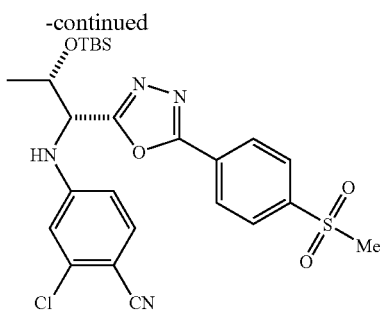

Polymer supported triphenylphosphine (2.08 g, 6.24 mmol) was dilluted in 200 ml of DCM followed by addition of I₂ (1.58 g, 6.24 mmol) and TEA (2.31 mL, 16.64 mmol) at 0° C. N'-((2R,3S)-3-(tert-butyldimethylsilyloxy)-2-(3-chloro-4-cyanophenylamino)butanoyl)-4-(methylsulfonyl)benzohydrazide (2.35 g, 4.16 mmol) in 200 mL DCM was added to the pre-cooled solution mixture of PPh₃/I₂/TEA system and stirred. The temperature was allowed to warm to room temperature and stirred for an additional 10 min. The reaction was quenched with 55 mL saturated sodium thiosulfate and the biphasic mixture was separated. The aqueous layer was extracted with EtOAc (3×70 mL) and the combined organic extracts were dried (Na₂SO₄), filtered and concentrated under reduced pressure. The resulting crude oil was purified by flash chromatography (SiO₂) [EtOAc-hexanes (1:2), then (1:1) as eluent] to provide the title compound (2.16 g, 95%). The crude material was used directly in the next step.

Example 48

2-Chloro-4-((1R,2S)-2-hydroxy-1-(5-(4-(methylsulfonyl)phenyl)-1,3,4-oxadiazol-2-yl)propylamino)benzonitrile

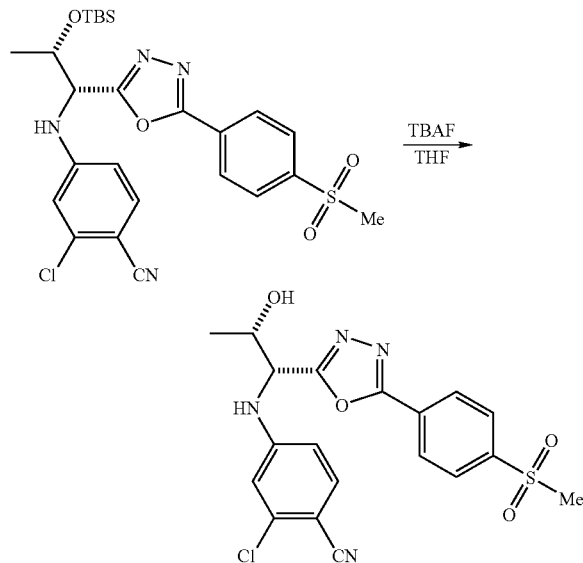

To a pre-cooled (−50° C.) solution of 4-((1R,2S)-2-(tert-butyldimethylsilyloxy)-1-(5-(4-(methylsulfonyl)phenyl)-1,3,4-oxadiazol-2-yl)propylamino)-2-chlorobenzonitrile (2.55 g, 4.66 mmol) in THF (600 mL) was added TBAF (4.66 mL, 4.66 mmol, 1 M solution in THF) dropwise over 10 min. Upon complete addition, the reaction mixture was concentrated under reduced pressure. The resulting residue was taken up in EtOAc (100 mL) and washed with H₂O (80 mL). The biphasic mixture was separated and the aqueous layer extracted with EtOAc (2×100 mL). The combined organic layers were washed with brine (1×70 mL), dried (Na₂SO₄), filtered and concentrated under reduced pressure to provide a yellow oil, which was purified by flash chromatography over silica gel (60% EtOAc in hexanes then 100% EtOAc) to provide the title compound as an off-white solid. The resulting solid was diluted with CH₂Cl₂ (45 mL) and hexanes (90 mL) was added. Upon concentration of the suspension a white solid was provided (0.5 g, 24%). ¹H NMR (400 MHz, acetone-d₆, δ in ppm) 8.26 (d, J=8.8 Hz, 2H), 8.17 (d, J=9 Hz, 2H), 7.57 (d, J=9 Hz, 1H), 7.14 (s, 1H), 6.98 (d, J=8 Hz, 1H), 6.61 (d, J=9 Hz, 1H), 5.17-5.15 (m, 1H), 4.63-5.53 (m, 2H), 3.2 (s, 3H), and 1.39 (d, J=7 Hz, 3H).

Example 49

2-Chloro-4-((1R,2S)-2-hydroxy-1-(5-(4-(hydroxymethyl)phenyl)-1,3,4-oxadiazol-2-yl)propylamino)-3-methylbenzonitrile

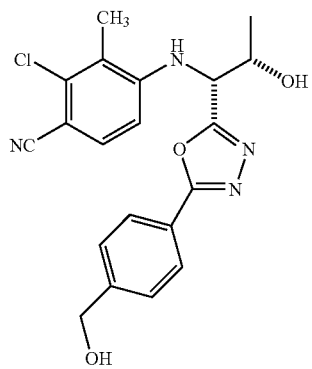

Intermediate 49a 4-((tert-Butyldimethylsilyloxy)methyl)benzohydrazide

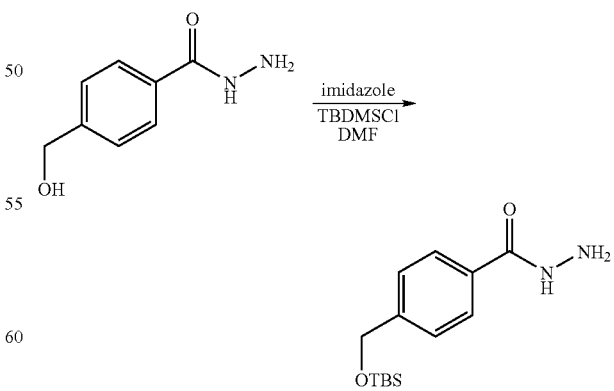

A 250 mL round bottomed flask was charged with 4-(hydroxymethyl)benzohydrazide (CAS 58855-42-8, 1 g, 6.02 mmol) and DMF (60 mL). Imidazole (2.05 g, 30.1 mmol) and tert-butyldimethyl silyl chloride (2.72 g, 18.06 mmol) were then added to the mixture, which was stirred at room temperature for 18 h. A sat. aq. NH₄Cl (40 mL) solution was then added to the mixture followed by EtOAc (80 mL). The phases were partitioned and the organic phase washed with water (4×60 mL), brine (60 mL), dried (Na₂SO₄), filtered and concentrated to furnish an off-white solid (3.1 g). Purification by passing through a silica-plug (1 inch) [EtOAc-hexanes (1:1) as eluent] afforded the title compound as a white solid (1.13 g, 67% yield). ¹H NMR (400 MHz, acetone-d₆, δ in ppm) δ 7.77 (d, J=8 Hz, 2H), 7.32 (d, J=8 Hz, 1H), 4.73 (s, 2H), 0.82 (s, 9H), and 0.01 (s, 6H).

Intermediate 49b 4-((tert-Butyldimethylsilyloxy)methyl)-1-((2R,3S)-2-(3-chloro-4-cyano-2-methylphenylamino)-3-hydroxybutanoyl)benzohydrazide

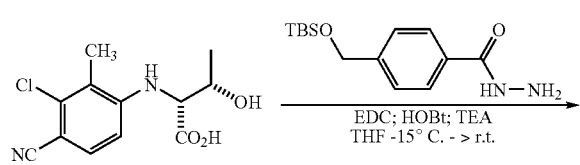
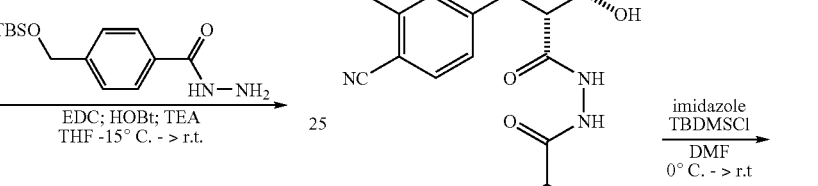
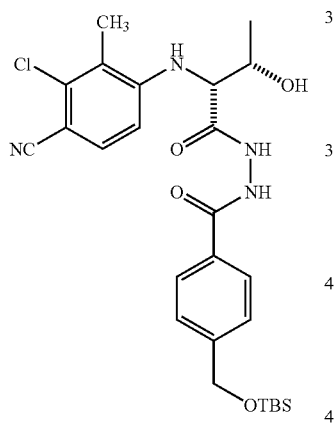

(2R,3S)-2-(3-chloro-4-cyano-2-methylphenylamino)-3-hydroxybutanoic acid (3 g, 11.16 mmol), 4-((tert-butyldimethylsilyloxy)methyl)benzohydrazide (3.44 g, 12.28 mmol) and anhydrous THF (250 mL) were placed in a 500 mL round bottomed flask and the mixture was cooled to −15° C. 1-Hydroxybenzotriazole hydrate (1.51 g, 11.16 mmol) was added to the mixture together with N-(3-Dimethylaminopropyl)-N'-ethylcarbodimide HCl (3.21 g, 16.74 mmol) at −15° C. followed by triethylamine (2.33 mL, 16.74 mmol). The reaction mixture was maintained at −15° C. and stirred for 1 h after which, stirring continued overnight while the mixture slowly warmed to room temperature. After 19 h, the mixture was filtered under vacuum and the residue washed with THF (70 mL). The THF solution was concentrated to ca. 20 mL, whereupon EtOAc (100 mL) was added followed by water (50 mL). The phases were partitioned and the organic phase washed with water (30 mL), brine (30 mL) dried (Na₂SO₄), filtered and concentrated to furnish a light brown solid (5.82 g). This crude product was not chromatographed. ¹H NMR (400 MHz, acetone-d₆, δ in ppm) 7.82 (d, J=9 Hz, 2H), 7.42 (d, J=8 Hz, 1H), 7.38 (d, J=8 Hz, 2H), 6.58 (d, J=8 Hz, 1H), 5.42 (d, J=8 Hz, 1H), 4.75 (s, 3H), 4.31-4.22 (m, 1H), 3.99-3.97 (m, 1H), 2.24 (s, 3H), 0.82 (s, 9H) and 0.01 (s, 6H).

Intermediate 49c

N'-((2R,3S)-3-(tert-Butyldimethylsilyloxy)-2-(3-chloro-4-cyano-2-methylphenylamino)butanoyl)-4-((tert-butyldimethylsilyloxy)methyl)benzohydrazide

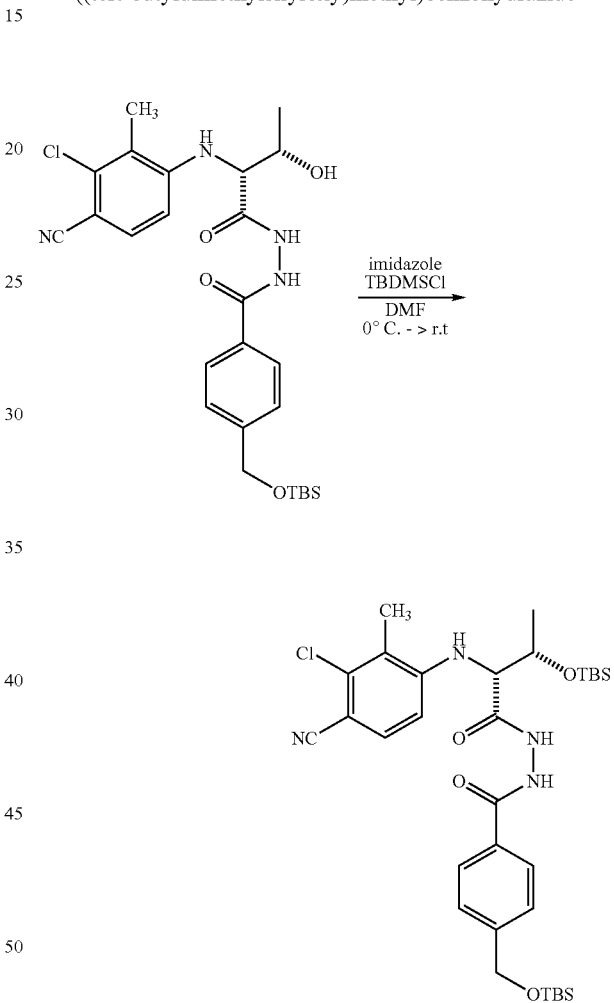

Imidazole (3.99 g, 58.55 mol) and TBDMS-Cl (5.29 g, 35 mmol) were added sequentially to a pre-cooled (0° C.) solution of 4-((tert-butyldimethylsilyloxy)methyl)-N'-((2R,3S)-2-(3-chloro-4-cyano-2-methylphenylamino)-3-hydroxybutanoyl)benzohydrazide (6.22 g, 11.71 mmol) in DMF (300 mL). The reaction mixture was allowed to warm to room temperature and stirred for 18 h, whereupon the solution was poured into H₂O (120 mL). The white precipitate was filtered, washed with H₂O (30 mL) and taken up in CH₂Cl₂ (200 mL). This organic layer was washed with brine (1×100 mL), dried (Na₂SO₄), filtered and concentrated to provide the title compound (10.2 g). This crude product was used directly in the next step.

Intermediate 49d 4-((1R,2S)-2-(tert-Butyldimethylsilyloxy)-1-(5-(4-((tert-butyldimethylsilyloxy)methyl)phenyl)-1,3,4-oxadiazol-2-yl)propylamino)-2-chloro-3-methylbenzonitrile

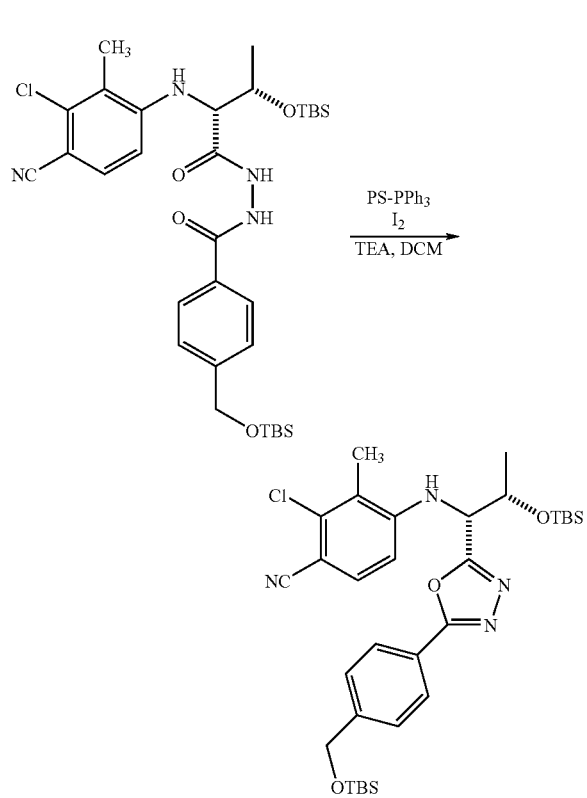

Polymer supported triphenylphosphine (6.22 g, 23.7 mmol) was dilluted in 200 mL of DCM followed by addition of I₂ (6.02 g, 23.7 mmol) and TEA (8.81 mL, 63.2 mmol) at 0° C. N'-((2R,3S)-3-(tert-butyldimethylsilyloxy)-2-(3-chloro-4-cyano-2-methylphenylamino)butanoyl)-4-((tert-butyldimethylsilyloxy)methyl)benzohydrazide (10.2 g, 15.8 mmol) in 200 mL DCM was added to the pre-cooled solution mixture of PPh₃/I₂/TEA system and stirred. The temperature was allowed to warm to room temperature and stirred for additional 10 min. The reaction was quenched with 50 mL saturated sodium thiosulfate and the biphasic mixture was separated. The aqueous layer was extracted with EtOAc (3×40 mL) and the combined organic extracts were dried (Na₂SO₄), filtered and concentrated under reduced pressure. The resulting crude oil was purified by flash chromatography (SiO₂) [EtOAc-hexanes (1:2), then 100% EtOAc as eluent] to provide the title compound (4.35 g, 44%). ¹H NMR (500 MHz, acetone d₆, δ in ppm): 8.16 (d, J=8 Hz, 2H), 7.75 (d, J=9 Hz, 2H), 7.64 (d, J=9 Hz, 1H), 7.01 (d, J=9 Hz, 1H), 5.73 (d, J=9 Hz, 1H), 5.41 (d, J=9 Hz, 1H), 5.03 (s, 2H), 4.97-4.88 (m, 1H), 2.22 (s, 3H), 1.63 (d, J=6 Hz, 3H), 1.11 (s, 9H), 1.06 (s, 9H), 0.30 (s, 3H), 0.28 (s, 3H).

Example 49

2-Chloro-4-((1R,2S)-2-hydroxy-1-(5-(4-(hydroxymethyl)phenyl)-1,3,4-oxadiazol-2-yl)propylamino)-3-methylbenzonitrile

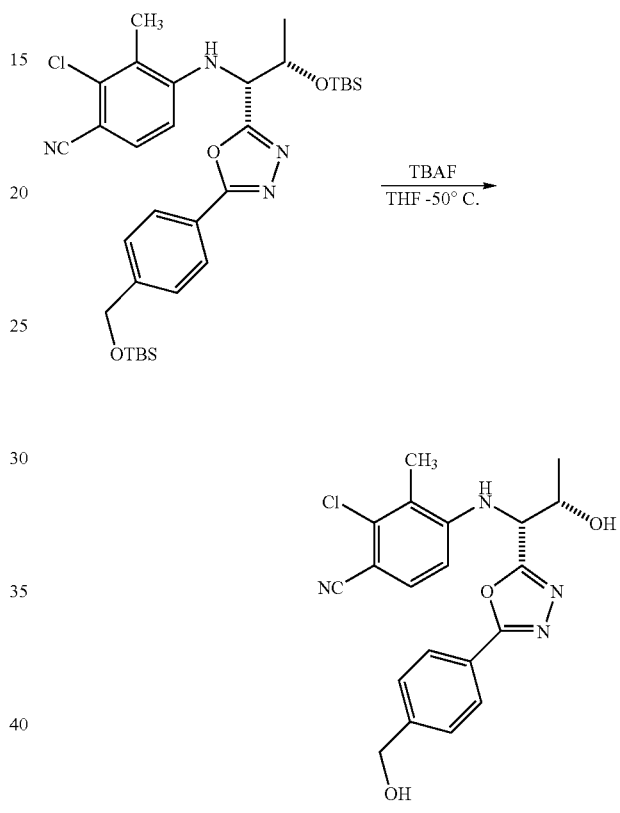

To a pre-cooled (−50° C.) solution of 4-((1R,2S)-2-(tert-butyldimethylsilyloxy)-1-(5-(4-((tert-butyldimethylsilyloxy)methyl)phenyl)-1,3,4-oxadiazol-2-yl)propylamino)-2-chloro-3-methylbenzonitrile (4.35 g, 6.93 mmol) in THF (600 mL) was added TBAF (13.87 mL, 13.87 mmol, 1 M solution in THF) dropwise over 10 min. Upon complete addition, the reaction mixture was concentrated under reduced pressure. The resulting residue was taken up in EtOAc (100 mL) and washed with H₂O (80 mL). The biphasic mixture was separated and the aqueous layer extracted with EtOAc (2×100 mL). The combined organic layers were washed with brine (1×70 mL), dried (Na₂SO₄), filtered and concentrated under reduced pressure to provide a yellow oil, which was purified by flash chromatography over silica gel (65% EtOAc in hexanes then EtOAc to provide the title compound as an off-white solid. The resulting solid was diluted with CH₂Cl₂ (30 mL) and hexanes (70 mL) was added. Upon concentration of the suspension a white solid was provided (2.4 g, 87%). ¹H NMR (400 MHz, acetone-d₆, δ in ppm) 7.98 (d, J=8.8 Hz, 2H), 7.57 (d, J=9 Hz, 2H), 7.47 (d, J=9 Hz, 1H), 6.84 (d, J=9

Hz, 1H), 5.69 (d, J=8 Hz, 1H), 5.11-5.05 (m, 1H), 4.74-4.71 (m, 2H), 2.40 (s, 3H) and 1.40 (d, J=7 Hz, 3H).

Example 50

2-Chloro-4-((1R,2S)-1-(5-(4-cyanophenyl)-1,3,4-oxadiazol-2-yl)-2-hydroxypropylamino)benzonitrile

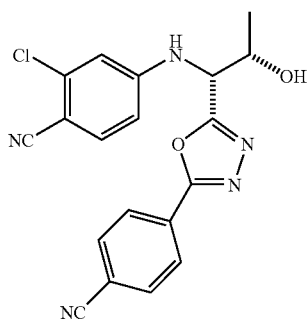

Intermediate 50a

N'-((2R,3S)-2-(3-Chloro-4-cyanophenylamino)-3-hydroxybutanoyl)-4-cyanobenzohydrazide

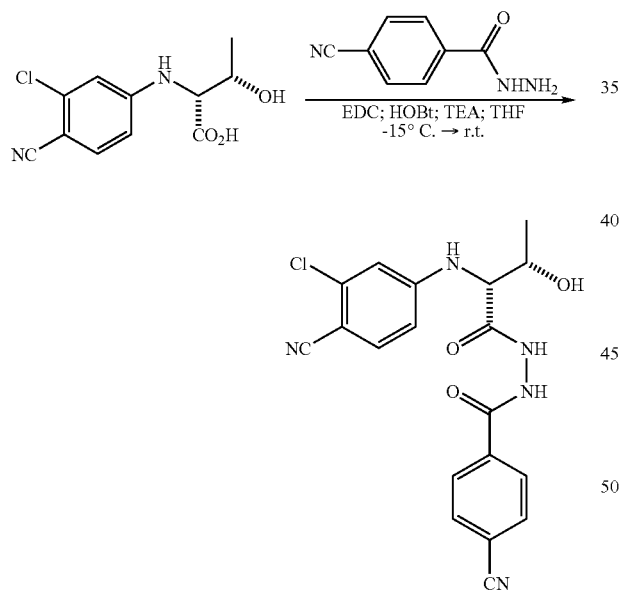

(2R,3S)-2-(3-chloro-4-cyanophenylamino)-3-hydroxybutanoic acid (6.3 g, 24.74 mmol), 4-cyanobenzohydrazide (4.38 g, 27.21 mmol) and anhydrous THF (200 mL) were placed in a 500 mL round bottomed flask and the mixture was cooled to −15° C. 1-Hydroxybenzotriazole hydrate (3.34 g, 24.74 mmol) was added to the mixture along with N-(3-Dimethylaminopropyl)-N'-ethylcarbodimide HCl (7.11 g, 37.11 mmol) at −15° C. followed by Et₃N (5.17 mL, 37.11 mmol). The reaction mixture was maintained at −15° C. and stirred for 1 hour after which stirring continued overnight while the mixture slowly warmed to room temperature. After 17.5 h, the mixture was filtered under vacuum and the residue washed with THF (100 mL). The THF solution was concentrated to ca. 30 mL, whereupon EtOAc (100 mL) was added followed by water (60 mL). The phases were partitioned and the organic phase washed with water (30 mL), brine (30 mL) dried (Na₂SO₄), filtered and concentrated to furnish a light brown solid (9.34 g). Purification by flash column chromatography [EtOAc-hexanes (1:1), then 100% EtOAc as eluent] afforded the title compound as a white solid (7.4 g, 69% yield) to be used directly in the next step.

Example 50

2-Chloro-4-((1R,2S)-1-(5-(4-cyanophenyl)-1,3,4-oxadiazol-2-yl)-2-hydroxypropylamino)benzonitrile

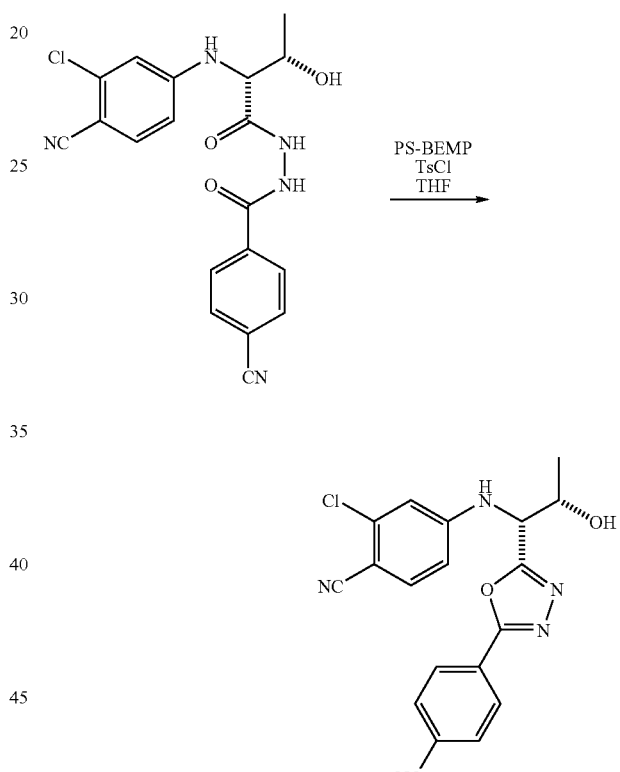

To a solution of N'-((2R,3S)-2-(3-chloro-4-cyanophenylamino)-3-hydroxybutanoyl)-4-cyanobenzohydrazide (2 g, 5.03 mmol) in anhydrous THF (300 mL) at room temperature was added 2-tert-butylamino-2-diethylamino-1,3-dimethylperhydro-1,3,2-diazaphosphorine on polystyrene (2.2 mmol base/g) (6.86 g) followed by p-TSCl (959 mg, 5.03 mmol) and the mixture was stirred for 1 h. The mixture was filtered and the residue washed with acetone (200 mL) followed by MeOH (200 mL). The filtrate was then concentrated and subjected to flash column chromatography [EtOAc-Hexanes (3:2)] to give two fractions. The second-eluted material was the desired 2-chloro-3-ethyl-4-((1R,2S)-2-hydroxy-1-(5-phenyl-1,3,4-oxadiazol-2-yl)propylamino)benzonitrile (231 mg, 12%). ¹H NMR (500 MHz, CDCl₃, δ in ppm) 8.2 (d, J=8 Hz, 2H), 7.99 (d, J=8 Hz, 2H), 7.57 (d, J=8 Hz, 1H), 7.14 (s, 1H), 6.97 (d, J=8 Hz, 1H), 6.61 (d, J=8 Hz, 1H), 5.17-5.13 (m, 1H), 4.64-4.54 (m, 2H), 1.40 (d, J=6 Hz, 3H).

Example 51

4-((1R,2R)-1-(5-(4-Cyanophenyl)-1,3,4-oxadiazol-2-yl)-2-hydroxypropylamino) 1-naphthonitrile

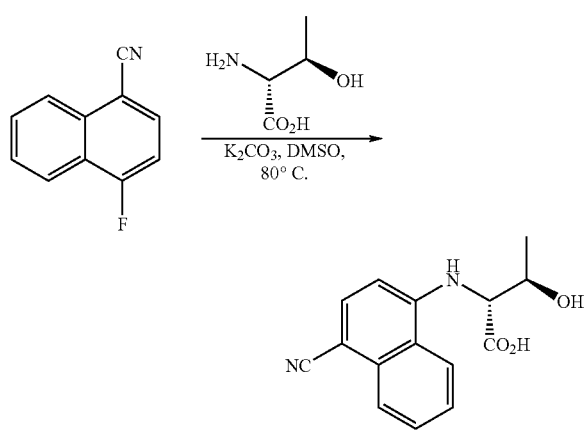

Intermediate 51a (2R,3R)-2-(4-Cyanonaphthalen-1-ylamino)-3-hydroxybutanoic acid

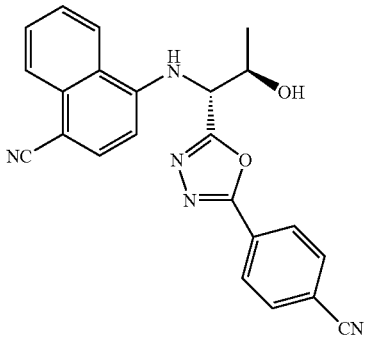

To a suspension of D-allo-threonine (2.09 g, 17.53 mmol) and K$_2$CO$_3$ (4.04 g, 29.21 mmol) in DMSO (40 mL) was added 4-fluoro-1-naphthonitrile (CAS 13916-99-9, 2.50 g, 14.61 mmol) at room temperature. The reaction mixture was heated to 80° C. and stirred for 89 h. The reaction mixture was allowed to cool to room temperature, quenched with H$_2$O (150 mL) and extracted with EtOAc (3×100 mL). The aqueous layer was then acidified with solid citric acid and extracted with EtOAc (2×100 mL). The later organic extracts were combined, washed with H$_2$O (3×100 mL), dried (Na$_2$SO$_4$), filtered and concentrated under reduced pressure to provided the title compound as a light brown solid (3.0 g, 76%): $^1$H NMR (400 MHz, DMSO-d$_6$, δ in ppm) 8.46 (d, J=8.8 Hz, 1H), 7.97 (d, J=8.2 Hz, 1H), 7.90 (d, J=8.6 Hz, 1H), 7.74 (t, J=7.0 Hz, 1H), 7.62 (t, J=7.6 Hz, 1H), 6.98 (d, J=8.0 Hz, 1H), 6.57 (d, J=8.4 Hz, 1H), 4.29-4.20 (m, 1H), 4.08-3.99 (m, 1H), 1.28 (d, J=6.1 Hz, 3H).

Intermediate 51b

4-Cyano-N'-((2R,3R)-2-(4-cyanonaphthalen-1-ylamino)-3-hydroxybutanoyl)benzohydrazide

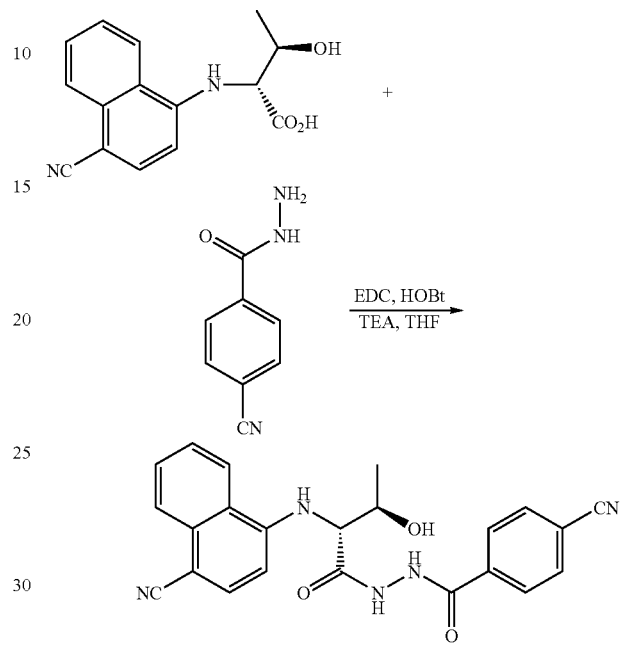

To a pre-cooled (−45° C.) solution of (2R,3R)-2-(4-cyanonaphthalen-1-ylamino)-3-hydroxybutanoic acid (1.50 g, 5.55 mmol) and 4-cyanobenzohydrazide (894 mg, 5.55 mmol) in anhydrous THF (80 mL) was added 1-Hydroxybenzotriazole monohydrate (850 mg, 5.55 mmol) and N-(3-Dimethylaminopropyl)-N'-ethylcarbodiimide-HCl (2.13 g, 11.1 mmol) at −45° C. followed by triethylamine (1.55 mL, 11.1 mmol). The reaction mixture warmed to room temperature and stirred for 24 h, then quenched with 5% aq. citric acid (300 mL). The solution was extracted with EtOAc (300 mL). The organic extract was washed with 5% aq. citric acid (2×150 mL), sat. aq. NaHCO$_3$ (3×150 mL), H$_2$O (2×150 mL), dried (Na$_2$SO$_4$), filtered and concentrated under reduced pressure to provide the title compound as a light brown solid (2.12 g, 92%): $^1$H NMR (400 MHz, DMSO-d$_6$, δ in ppm) 10.84 (s, 1H), 10.44 (s, 1H), 8.48 (d, J=8.8 Hz, 2H), 8.04-7.93 (m, 4H), 7.91 (d, J=8.2 Hz, 1H), 7.74 (t, J=6.8 Hz, 1H), 7.62 (t, J=7.2 Hz, 1H), 6.92 (d, J=8.2 Hz, 1H), 6.75 (d, J=8.2 Hz, 1H), 5.25 (d, J=4.5 Hz, 1H), 4.32-3.97 (m, 3H), 1.32 (d, J=6.1 Hz, 3H).

Example 51

4-((1R,2R)-1-(5-(4-Cyanophenyl)-1,3,4-oxadiazol-2-yl)-2-hydroxypropylamino)-1-naphthonitrile

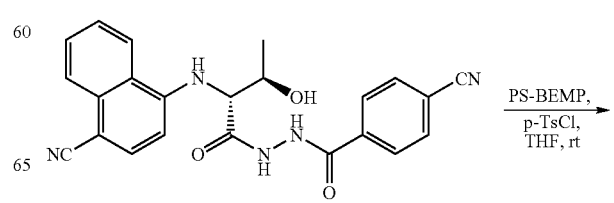

-continued

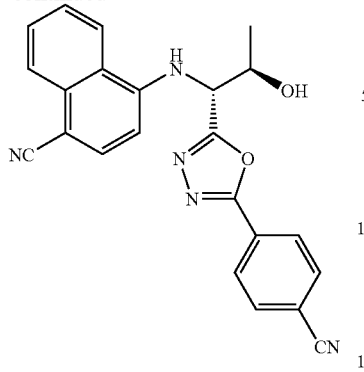

To a solution of 4-cyano-N'-((2R,3R)-2-(4-cyanonaphthalen-1-ylamino)-3-hydroxybutanoyl)benzohydrazide (900 mg, 2.18 mmol) in anhydrous THF (90 mL) at room temperature was added 2-tert-butylamino-2-diethylamino-1,3-dimethyl perhydro-1,3,2-diazaphosphorine on polystyrene (2.2 mmol base/g) (2.97 g, 6.53 mmol) followed by p-TSCl (498 mg, 2.60 mmol) and the mixture was stirred for 75 minutes. The mixture was filtered and the residue washed with acetone (3×100 mL) followed by MeOH (3×150 mL). The filtrate was concentrated under reduced pressure to provide an off white solid, which was purified by flash chromatography over silica gel (30-50% EtOAc in hexanes) to provided the title compound as a brown oil (25 mg, 3%): $^1$H NMR (400 MHz, CDCl$_3$, δ in ppm) 8.19 (d, J=8.4 Hz, 2H), 8.18 (d, J=8.4 Hz, 1H), 7.92 (d, J=8.4 Hz, 1H), 7.84 (d, J=8.6 Hz, 2H), 7.77 (d, J=8.2 Hz, 1H), 7.68 (t, J=7.4 Hz, 1H), 7.59 (t, J=7.2 Hz, 1H), 6.67 (d, J=8.2 Hz, 1H), 5.69 (d, J=9.6 Hz, 1H), 5.47 (d, J=3.7 Hz, 1H), 4.71 (dqd, J=3.7, 6.5, 9.9 Hz, 1H), 1.65 (d, J=6.4 Hz, 3H).

Example 52

4-((1R,2R)-2-Hydroxy-1-(5-phenyl-1,3,4-oxadiazol-2-yl)propylamino)-1-naphthonitrile

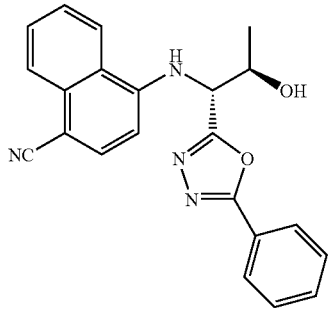

Intermediate 52a

N'-((2R,3R)-2-(4-Cyanonaphthalen-1-ylamino)-3-hydroxybutanoyl)benzohydrazide

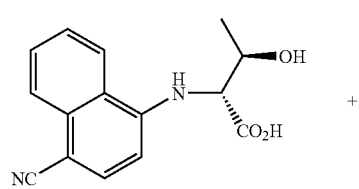

+

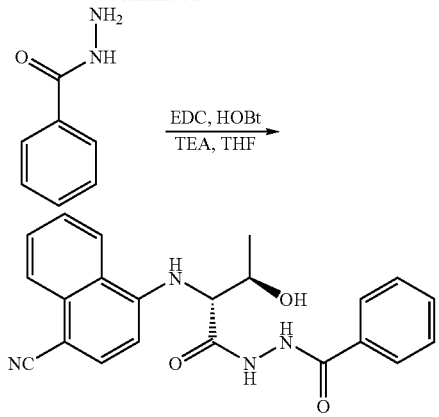

$\xrightarrow{\text{EDC, HOBt}}{\text{TEA, THF}}$

To a pre-cooled (−45° C.) solution of (2R,3R)-2-(4-cyanonaphthalen-1-ylamino)-3-hydroxybutanoic acid (1.50 g, 5.55 mmol) and benzohydrazide (756 mg, 5.55 mmol) in anhydrous THF (80 mL) was added 1-hydroxybenzotriazole monohydrate (850 mg, 5.55 mmol) and N-(3-Dimethylaminopropyl)-N'-ethylcarbodimide-HCl (2.13 g, 11.1 mmol) at −45° C. followed by triethylamine (1.55 mL, 11.1 mmol). The reaction mixture warmed to room temperature and stirred for 24 h, then quenched with 5% aq. citric acid (300 mL). The solution was extracted with EtOAc (300 mL). The organic extract was washed with 5% aq. citric acid (2×150 mL), sat. aq. NaHCO$_3$ (3×150 mL), H$_2$O (2×150 mL), dried (Na$_2$SO$_4$), filtered and concentrated under reduced pressure to provide the title compound as a off white solid (1.80 g, 83%): $^1$H NMR (400 MHz, CDCl$_3$, δ in ppm) 10.58 (br s, 1H), 10.34 (br s, 1H), 8.48 (d, J=9.0 Hz, 1H), 7.98 (d, J=8.0 Hz, 1H), 7.91 (d, J=8.4 Hz, 1H), 7.88 (d, J=7.2 Hz, 1H), 7.74 (t, J=7.4 Hz, 1H), 7.62 (t, J=8.0 Hz, 1H), 7.57 (t, J=8.6 Hz, 1H), 7.48 (t, J=8.0 Hz, 2H), 6.93 (d, J=8.6 Hz, 1H), 6.74 (d, J=8.4 Hz, 1H), 5.26 (d, J=4.9 Hz, 1H), 4.32-4.22 (m, 1H), 4.16 (t, J=7.8 Hz, 1H), 1.33 (d, J=6.3 Hz, 3H).

Example 52

4-((1R,2R)-2-Hydroxy-1-(5-phenyl-1,3,4-oxadiazol-2-yl)propylamino)-1-naphthonitrile

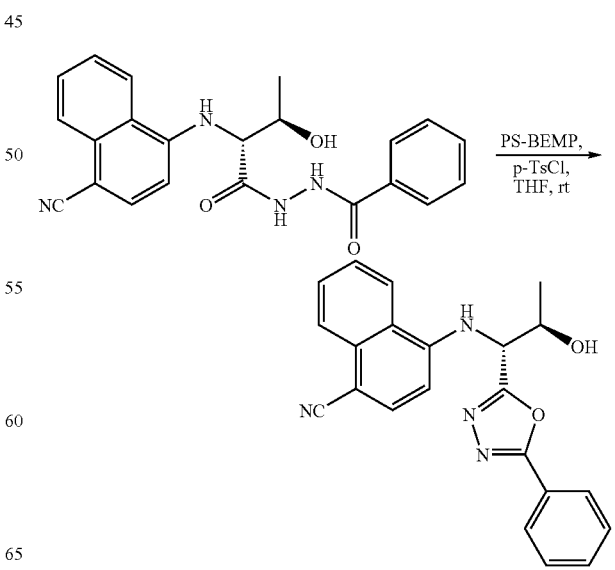

To a solution of N'-((2R,3R)-2-(4-cyanonaphthalen-1-ylamino)-3-hydroxybutanoyl)benzohydrazide (846 mg, 2.18 mmol) in anhydrous THF (90 mL) at room temperature was added 2-tert-butylamino-2-diethylamino-1,3-dimethyl perhydro-1,3,2-diazaphosphorine on polystyrene (2.2 mmol base/g) (2.97 g, 6.53 mmol) followed by p-TSCl (498 mg, 2.60 mmol) and the mixture was stirred for 75 min. The mixture was filtered under suction and the residue washed with acetone (3×100 mL) followed by MeOH (3×150 mL). The filtrate was concentrated under reduced pressure to provide a off white solid, which was purified by flash chromatography over silica gel (25-40% EtOAc in hexanes) to provided the title compound as a yellow solid (2.1 mg, 0.3%): $^1$H NMR (400 MHz, CDCl$_3$, δ in ppm) 8.19 (d, J=8.2 Hz, 1H), 7.92 (d, J=8.4 Hz, 1H), 7.84 (d, J=7.0 Hz, 2H), 7.80 (d, J=8.0 Hz, 1H), 7.67 (t, J=7.0 Hz, 1H), 7.63-7.53 (m, 2H), 7.49 (t, J=7.4 Hz, 2H), 6.74 (d, J=8.4 Hz, 1H), 5.41 (d, J=9.4 Hz, 1H), 4.95 (d, J=2.9 Hz, 1H), 4.75-4.64 (m, 1H), 1.50 (d, J=6.4 Hz, 3H).

Example 53

4-((1R,2S)-1-(5-(4-(1H-Pyrazol-1-yl)phenyl)-1,3,4-oxadiazol-2-yl)-2-hydroxypropylamino)-2-chloro-3-methylbenzonitrile

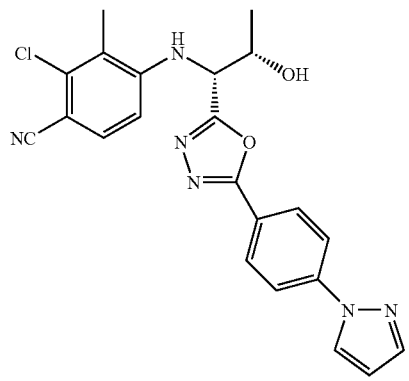

Intermediate 53a

Ethyl 4-(1H-pyrazol-1-yl)benzoate

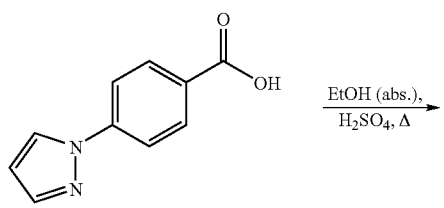

To a solution of 4-(1H-pyrazol-1-yl)benzoic acid (CAS 160209-00-0, 678 mg, 3.60 mmol) in absolute EtOH (10 mL) was added sulfuric acid (0.1 mL) at room temperature. The reaction mixture was heated to reflux and stirred for 71 h, then concentrated under reduced pressure. The residue was partitioned between sat. aq. NaHCO$_3$ (60 mL) and EtOAc (50 mL). The aqueous layer was extracted with EtOAc (50 mL). The combined organic extracts were dried (Na$_2$SO$_4$), filtered and concentrated under reduced pressure to provide the title compound as an off white solid (711 mg, 91%): $^1$H NMR (400 MHz, CDCl$_3$, δ in ppm) 8.14 (d, J=8.6 Hz, 2H), 8.01 (d, J=2.5 Hz, 1H), 7.78 (d, J=8.8 Hz, 2H), 7.78-7.75 (m, 1H), 6.51 (t, J=1.8 Hz, 1H), 4.39 (q, J=7.2 Hz, 2H), 1.41 (t, J=7.0 Hz, 3H).

Intermediate 53b 4-(1H-Pyrazol-1-yl)benzohydrazide

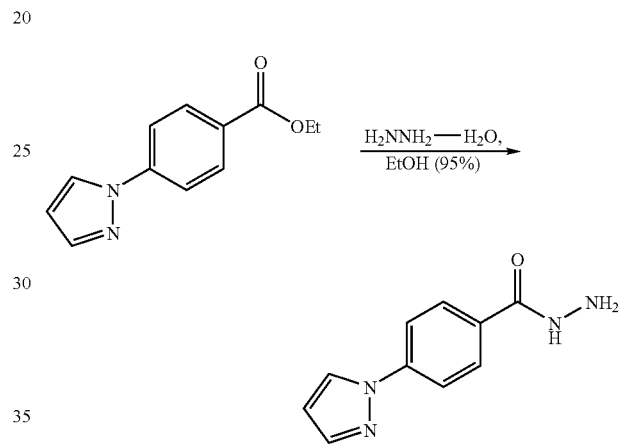

To a solution of ethyl 4-(1H-pyrazol-1-yl)benzoate (711 mg, 3.29 mmol) in absolute EtOH (50 mL) was added hydrazine monohydrate (1.6 mL, 32.9 mmol) at room temperature. The reaction mixture was heated to reflux and stirred for 6 d, then concentrated under reduced pressure. The residue was suspended in H$_2$O (30 mL), filtered, washed with H$_2$O (2×20 mL) and EtOH (2×20 mL) to provide the title compound as an off white solid (101 mg, 15%): $^1$H NMR (400 MHz, CDCl$_3$, δ in ppm) 9.84 (s, 1H), 8.62-8.59 (m, 1H), 7.98-7.90 (m, 4H), 7.81-7.78 (m, 1H), 6.61-6.57 (m, 1H), 4.51 (br d, J=3.3 Hz, 2H).

Intermediate 53c

N'-((2R,3S)-2-(3-Chloro-4-cyano-2-methylphenylamino)-3-hydroxybutanoyl)-4-(1H-pyrazol-1-yl)benzohydrazide

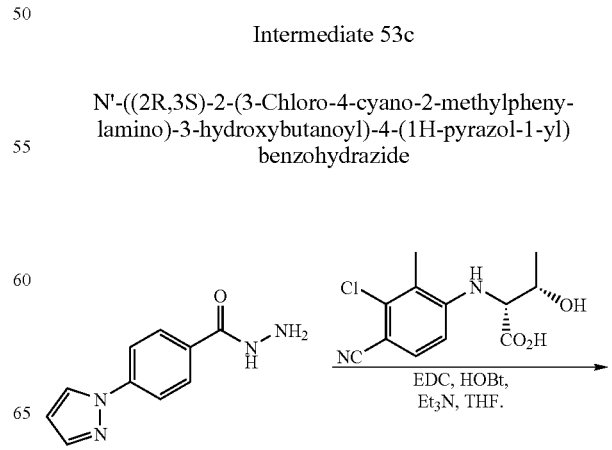

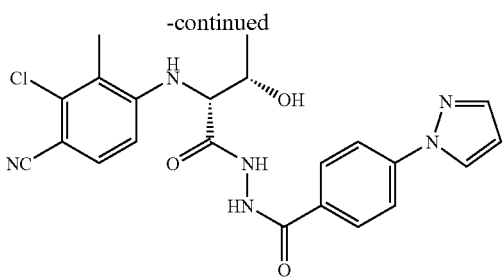

To a pre-cooled (−45° C.) solution of (2R,3S)-2-(3-chloro-4-cyano-2-methylphenylamino)-3-hydroxybutanoic acid (134 mg, 0.50 mmol) and 4-(1H-pyrazol-1-yl)benzohydrazide (101 mg, 0.50 mmol) in anhydrous THF (10 mL) was added 1-Hydroxybenzotriazole monohydrate (77 mg, 0.50 mmol) and N-(3-Dimethylaminopropyl)-N'-ethylcarbodimide-HCl (192 mg, 1.00 mmol) at −45° C. followed by triethylamine (0.14 mL, 1.00 mmol). The reaction mixture warmed to room temperature and stirred for 48 h, then quenched with 5% aq. citric acid (30 mL). The solution was extracted with EtOAc (30 mL). The organic extract was washed with 5% aq. Citric acid (2×20 mL), sat. aq. NaHCO$_3$ (3×20 mL), H$_2$O (2×20 mL), dried (Na$_2$SO$_4$), filtered and concentrated under reduced pressure to provide the title compound as an off white solid (164 mg, 73%): $^1$H NMR (400 MHz, CDCl$_3$, δ in ppm) 8.85 (br s, 1H), 7.99 (d, J=2.5 Hz, 1H), 7.89 (d, J=8.6 Hz, 2H), 7.80-7.72 (m, 3H), 7.37 (dd, J=3.7, 8.2 Hz, 1H), 6.54-6.50 (m, 1H), 6.45 (dd, J=5.7, 8.6 Hz, 1H), 5.25 (d, J=6.3 Hz, 1H), 4.71 (br s, 1H), 4.53-4.45 (m, 1H), 2.32 (s, 3H), 1.36 (d, J=6.3 Hz, 3H).

Example 53

4-((1R,2S)-1-(5-(4-(1H-Pyrazol-1-yl)phenyl)-1,3,4-oxadiazol-2-yl)-2-hydroxypropylamino)-2-chloro-3-methylbenzonitrile

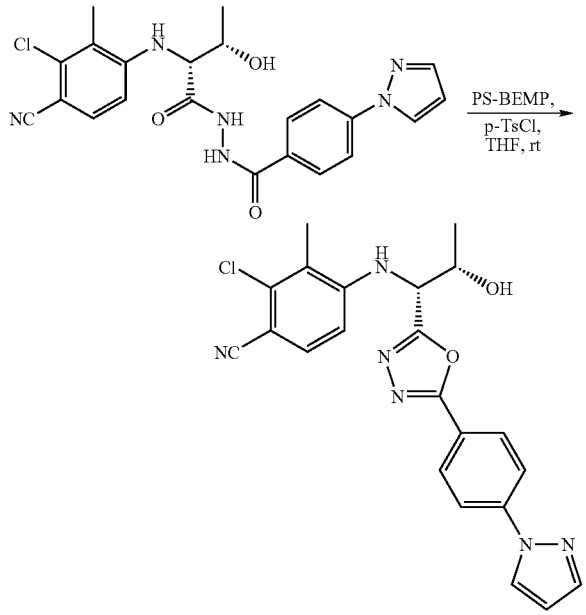

To a solution of N'-((2R,3S)-2-(3-chloro-4-cyano-2-methylphenylamino)-3-hydroxybutanoyl)-4-(1H-pyrazol-1-yl)benzohydrazide (164 mg, 0.36 mmol) in anhydrous THF (12 mL) at room temperature was added 2-tert-butylamino-2-diethylamino-1,3-dimethyl perhydro-1,3,2-diazaphosphorine on polystyrene (2.2 mmol base/g) (495 mg, 1.09 mmol) followed by p-TSCl (83 mg, 0.44 mmol) and the mixture was stirred for 70 min. The mixture was filtered under suction and the residue washed with acetone (2×50 mL) followed by MeOH (2×50 mL). The filtrate was concentrated under reduced pressure to provide a off white solid, which was purified by flash chromatography over silica gel (25-50% EtOAc in hexanes) to provided 4-((1R,2S)-1-(5-(4-(1H-pyrazol-1-yl)phenyl)-1,3,4-oxadiazol-2-yl)-2-hydroxypropylamino)-2-chloro-3-methylbenzonitrile as a yellow oil (24 mg, 15%): $^1$H NMR (400 MHz, acetone-d$_6$, δ in ppm) 8.46 (d, J=2.5 Hz, 1H), 8.11 (dm, J=9.2 Hz, 2H), 8.06 (dm, J=9.0 Hz, 2H), 7.77 (d, J=1.8 Hz, 1H), 7.50 (d, J=8.8 Hz, 1H), 6.88 (d, J=8.8 Hz, 1H), 6.57 (dd, J=1.8, 2.5 Hz, 1H), 5.70 (d, J=8.6 Hz, 1H), 5.12 (dd, J=3.5, 8.6 Hz, 1H), 4.86 (br s, 1H), 4.69-4.60 (m, 1H), 2.41 (s, 3H), 1.42 (d, J=6.5 Hz, 3H).

Example 54

2-Chloro-4-((1R,2R)-1-(5-(4-cyanophenyl)-1,3,4-oxadiazol-2-yl)-2-hydroxypropylamino)-3-ethylbenzonitrile

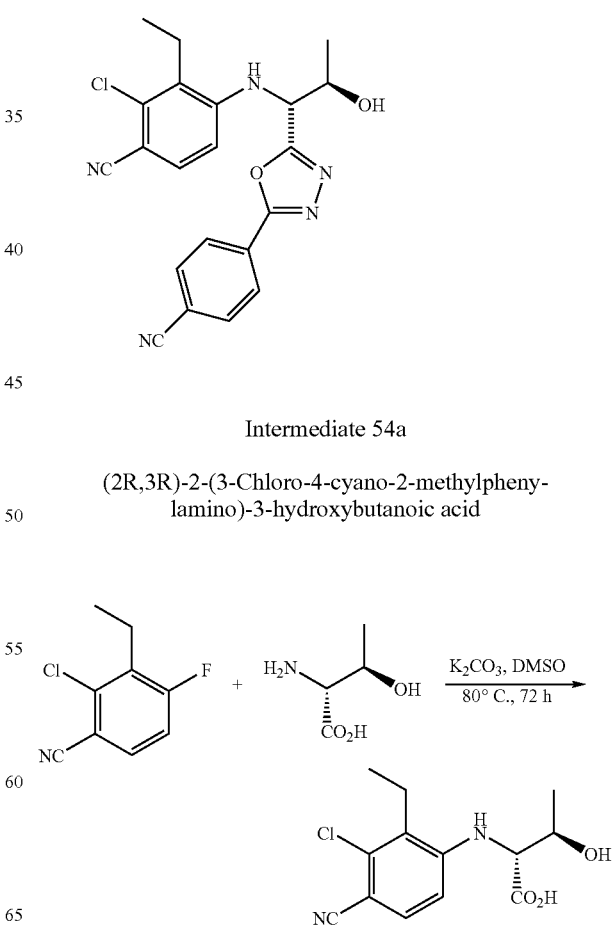

Intermediate 54a (2R,3R)-2-(3-Chloro-4-cyano-2-methylphenylamino)-3-hydroxybutanoic acid K$_2$CO$_3$ (3.15 g, 22.8 mmol) was added to a solution of 2-chloro-3-ethyl-4-fluorobenzonitrile (2.1 g, 11.4 mmol) and D-allo-threonine (2.04 g, 17.1 mmol) in DMSO (25 mL) at room temperature The reaction mixture was heated to 80° C. and stirred for 72 h then allowed to cool to room temperature. H$_2$O (200 mL) was added and the brown solution was extracted with MTBE (200 mL). The aqueous layer was cooled to 0° C. and solid citric acid monohydrate was added in 200 mg portions until the evolution of gas ceased. The aqueous layer was then extracted with EtOAc (3×200 mL). The combined organic layers were washed with brine (2×300 mL), dried with Na$_2$SO$_4$, filtered and concentrated to provide the title compound (1.44 g, 32%): $^1$H NMR (500 MHz, acetone-d$_6$, δ in ppm) 7.47 (d, J=8.6 Hz, 2H), 6.70 (d, J=8.6 Hz, 2H), 5.46 (d, J=8.7 Hz, 1H), 4.55-4.43 (m, 1H), 4.27 (dd, J=5.9 Hz, 8.7 Hz, 1H), 2.90-2.81 (m, 2H), 1.33 (d, J=6.3 Hz, 3H), 1.21 (t, J=7.6 Hz, 3H).

Intermediate 54b

N'-((2R,3R)-2-(3-Chloro-4-cyano-2-ethylphenylamino)-3-hydroxybutanoyl)-4-cyanobenzohydrazide

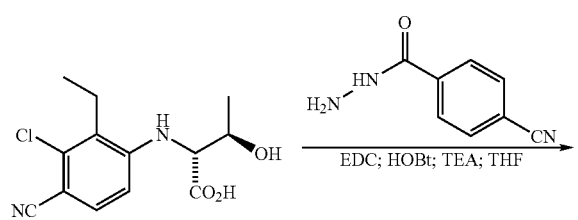

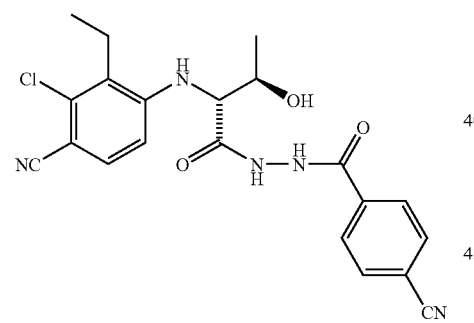

(2R,3R)-2-(3-chloro-4-cyano-2-ethylphenylamino)-3-hydroxybutanoic acid (700 mg, 2.48 mmol), 4-cyanobenzohydrazide (439 mg, 2.73 mmol) and anhydrous THF (20 mL) were placed in a 50 mL round bottomed flask and the mixture was cooled to −15° C. 1-Hydroxybenzotriazole hydrate (335 mg, 2.48 mmol) was added to the mixture together with N-(3-Dimethylaminopropyl)-N'-ethylcarbodiimide HCl (589 mg, 3.07 mmol) at −15° C. followed by triethylamine (0.43 mL, 3.07 mmol). The reaction mixture was maintained at −15° C. and stirred for 1 h after which, stirring continued overnight while the mixture slowly warmed to room temperature. After 18 h, the mixture was filtered under vacuum and the residue washed with THF (30 mL). The THF solution was concentrated to ca. 10 mL, whereupon EtOAc (40 mL) was added followed by water (30 mL). The phases were partitioned and the organic phase washed with water (15 mL), brine (15 mL), dried (Na$_2$SO$_4$), filtered and concentrated to furnish a light brown solid. Purification by flash column chromatography [EtOAc-hexanes (4:1) as eluent] afforded the title compound as a white solid (890 mg, 62%). $^1$H NMR (500 MHz, acetone-d$_6$, δ in ppm) δ 9.67 (br s, 2H), 8.11 (d, J=8.8 Hz, 2H), 7.96 (d, J=8.8 Hz, 2H), 7.52 (d, J=8.8 Hz, 1H), 6.79 (d, J=8.8 Hz, 1H), 5.66 (d, J=7.03 Hz, 1H), 4.62 (br s, 1H), 4.32-4.22 (m, 1H), 4.18 (dd, J=1.7 Hz, 7.4 Hz, 1H), 2.94-2.77 (m, 2H) 1.39 (d, J=6.2 Hz, 3H), 1.17 (t, J=7.6 Hz, 3H).

Example 54

2-Chloro-4-((1R,2R)-1-(5-(4-cyanophenyl)-1,3,4-oxadiazol-2-yl)-2-hydroxypropylamino)-3-ethylbenzonitrile

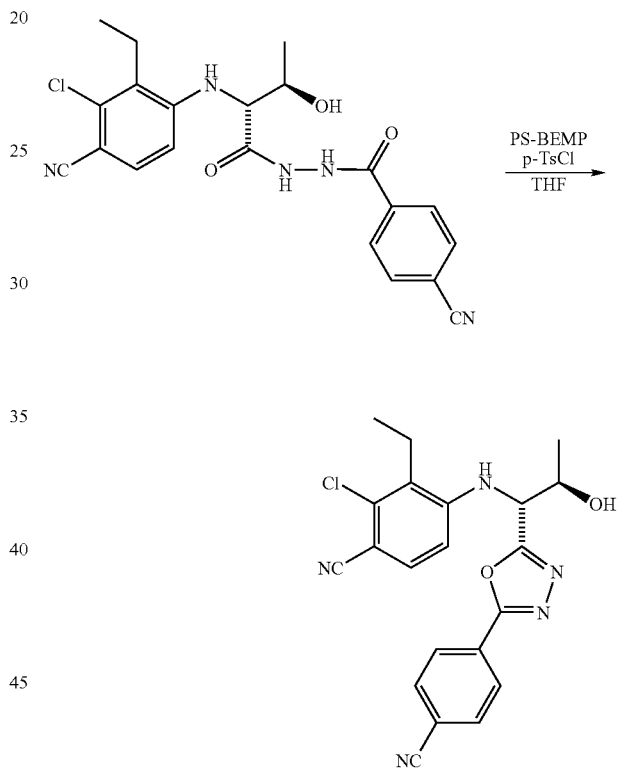

To a solution of N'-((2R,3S)-2-(3-chloro-4-cyano-2-ethylphenylamino)-3-hydroxybutanoyl)-4-cyanobenzohydrazide (310 mg, 0.73 mmol) in anhydrous THF (20 mL) at room temperature was added 2-tert-butylamino-2-diethylamino-1,3-dimethyl perhydro-1,3,2-diazaphosphorine on polystyrene (2.2 mmol base/g) (1.0 g) followed by p-TSCl (167 mg, 0.88 mmol) and the mixture was stirred for 1 h. The mixture was filtered and the residue washed with acetone (200 mL) followed by MeOH (200 mL). The filtrate was then concentrated and subjected to flash column chromatography [EtOAc-Hexanes (1:12)] to give two fractions. The second-eluted material was the desired product (50 mg, 17%): $^1$H NMR (500 MHz, acetone-d$_6$, δ in ppm) 8.20 (d, J=8.6 Hz, 2H), 7.99 (d, J=8.6 Hz, 2H), 7.48 (d, J=8.6 Hz, 1H), 6.86 (d, J=8.6 Hz, 1H), 5.99 (d, J=8.7 Hz, 1H), 5.12 (dd, J=4.5 Hz, 8.7

Hz, 1H), 4.71 (d, J=6.4 Hz, 1H), 4.57-4.49 (m, 1H), 2.97-2.82 (m, 2H), 1.41 (d, J=6.4 Hz, 3H), 1.20 (t, J=7.6 Hz, 3H).

Example 55

2-Chloro-4-((1R,2S)-1-(5-(3,4-dichlorophenyl)-1,3,4-oxadiazol-2-yl)-2-hydroxypropylamino)-3-methyl-benzonitrile

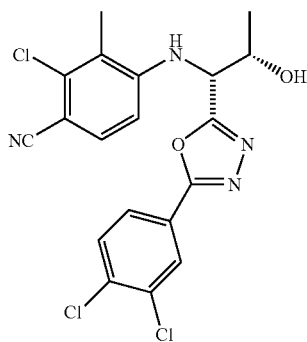

Intermediate 55a 3,4-Dichloro-N'-((2R,3S)-2-(3-chloro-4-cyano-2-methylphenylamino)-3-hydroxybutanoyl)benzo-hydrazide

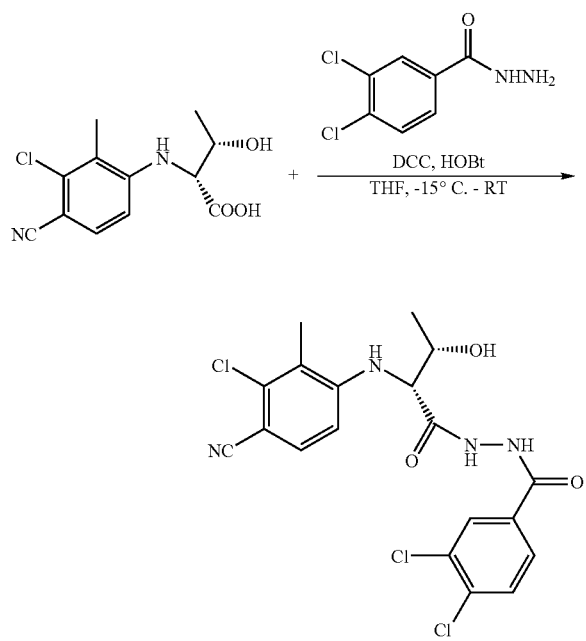

(2R,3S)-2-(3-chloro-4-cyano-2-methylphenylamino)-3-hydroxybutanoic acid (1.0 g, 3.7 mmol), 3,4-dichlorobenzo-hydrazide (CAS 28036-91-1, 763 mg, 3.7 mmol) and anhydrous THF (100 mL) were placed in a 500 mL round bottomed flask and the mixture was cooled to −15° C. 1-Hydroxybenzotriazole hydrate (502.8 mg, 3.7 mmol) was added to the mixture together with N-(3-Dimethylaminopropyl)-N'-ethylcarbodimide HCl (1.4 g, 7.4 mmol) and triethylamine (1.03 mL, 7.4 mmol) at −15° C. The reaction mixture was maintained at −15° C. and stirred for 1 h after which stirring continued overnight while the mixture slowly warmed to room temperature. After 18 h, the mixture was filtered under vacuum and the residue washed with THF (50 mL). The THF solution was concentrated to ca. 10 mL, whereupon ethyl acetate (200 mL) was added followed by water (100 mL). The phases were partitioned and the organic phase washed with water (50 mL), brine (50 mL), dried (Na$_2$SO$_4$), filtered and concentrated to furnish a light brown solid. $^1$H NMR (500 MHz, acetone-d$_6$, δ in ppm) 8.10 (d, J=2.1 Hz, 1H), 7.90 (dd, J=2.2 Hz, 8.3 Hz, 1H), 7.74 (d, J=8.3 Hz, 1H), 7.55 (d, J=8.5 Hz, 1H), 6.71 (d, J=8.5 Hz, 1H), 5.57 (d, J=6.8 Hz, 1H), 4.44-4.36 (m, 1H), 4.16-4.10 (m, 1H), 2.88-2.80 (m, 1H), 2.37 (s, 3H), 1.37 (d, J=6.3 Hz, 3H).

Example 55

2-Chloro-4-((1R,2S)-1-(5-(3,4-dichlorophenyl)-1,3,4-oxadiazol-2-yl)-2-hydroxypropylamino)-3-methyl-benzonitrile

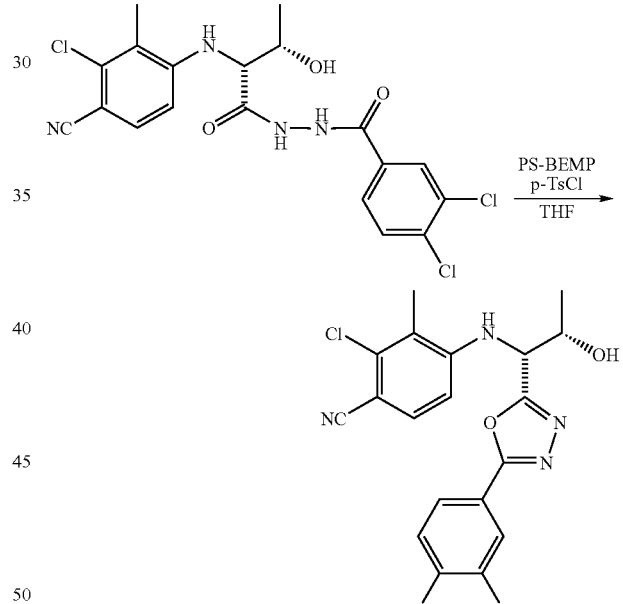

To a solution of 3,4-dichloro-N'-((2R,3S)-2-(3-chloro-4-cyano-2-methylphenyl-amino)-3-hydroxybutanoyl)benzo-hydrazide (1.35 g, 2.9 mmol) in anhydrous THF (100 mL) at room temperature was added 2-tert-butylamino-2-diethylamino-1,3-dimethyl perhydro-1,3,2-diazaphosphorine on polystyrene (2.2 mmol base/g) (4.0 g) followed by p-TSCl (621 mg, 3.2 mmol) and the mixture was stirred for 1 h. The mixture was filtered under suction and the residue washed with acetone (50 mL) followed by MeOH (50 mL). The filtrate was then concentrated and subjected to flash column chromatography [EtOAc-Hexanes (1:12)] to give the desired product (324 mg, 25%). $^1$H NMR (500 MHz, acetone-d$_6$, δ in ppm) 8.07 (d, J=2.1 Hz, 1H), 7.81 (dd, J=2.1 Hz, 8.3 Hz, 1H), 7.59 (d, J=8.3 Hz, 1H), 7.43 (d, J=8.6 Hz, 1H), 6.65 (d, J=8.6

Hz, 1H), 5.22 (d, J=8.3 Hz, 1H), 4.75 (dd, J=2.8 Hz, 8.2 Hz, 1H), 4.66-4.59 (m, 1H), 2.77 (d, J=3.6 Hz, 1H), 2.35 (s, 3H), 1.43 (d, J=6.3 Hz, 3H).

Example 56

4-((1R,2S)-1-(5-(4-Bromophenyl)-1,3,4-oxadiazol-2-yl)-2-hydroxypropylamino)-2-chloro-3-methylbenzonitrile

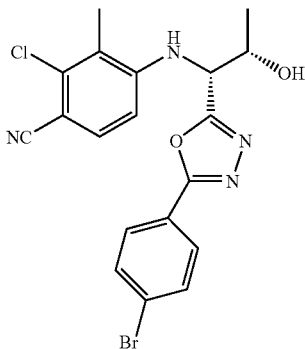

Intermediate 56a

4-Bromo-N'-((2R,3S)-2-(3-chloro-4-cyano-2-methylphenylamino)-3-hydroxybutanoyl)benzohydrazide

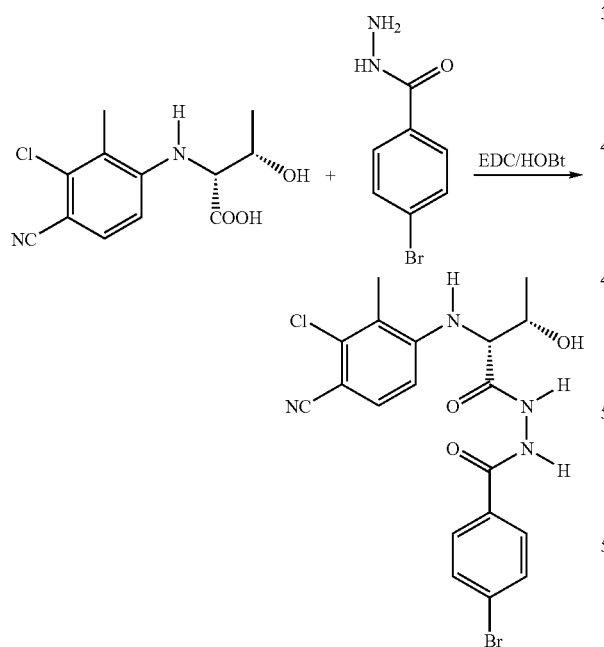

(2R,3S)-2-(3-chloro-4-cyano-2-methylphenylamino)-3-hydroxybutanoic acid (5.0 g, 18.6 mmol), 4-bromobenzhydrazide (CAS 5933-32-4, 4.0 g, 18.6 mmol) and 1-Hydroxybenzotriazole hydrate (2.52 g, 18.6 mmol) were placed in a 250 mL round bottomed flask. Anhydrous THF (120 mL) was added and the mixture was cooled to −20° C. N-(3-Dimethylaminopropyl)-N'-ethylcarbodiimide HCl (5.35 g, 27.9 mmol) was added, followed by Et$_3$N (3.9 mL, 28.0 mmol). The reaction mixture was stirred at −20° C. for 1 h and room temperature for overnight. The reaction was quenched by adding water and extracted with EtOAc, which was washed with 5% aqueous NaOH, water, brine and dried over Na$_2$SO$_4$. The extracts were filtered and the filtrate was concentrated to provide a brown solid, which was purified by flash chromatography washed with 80% EtOAc in hexanes to afford the title compound (6.6 g, 76%). $^1$H NMR (400 MHz, acetone-d$_6$, δ in ppm) 7.87 (d, J=8.6 Hz, 2H), 7.71 (d, J=8.6 Hz, 2H), 7.54 (d, J=8.6 Hz, 1H), 6.67 (d, J=8.6 Hz, 1H), 5.55 (d, J=7.4 Hz, 1H), 4.39 (m, 1H), 4.10 (dd, J=3.3, 7.4 Hz, 1H), 2.36 (s, 3H), 1.35 (d, J=6.4 Hz, 3H).

Intermediate 56b

4-Bromo-N'-((2R,3S)-3-(tert-butyldimethylsilyloxy)-2-(3-chloro-4-cyano-2-methylphenylamino)butanoyl)benzohydrazide To a solution of 4-bromo-N'-((2R,3S)-2-(3-chloro-4-cyano-2-methylphenylamino)-3-hydroxybutanoyl)benzohydrazide (4.0 g, 8.6 mmol) in DMF (60 mL) were added imidazole (2.3 g, 33.8 mmol) and TBSCl (2.6 g, 17.2 mmol) at 0° C. After addition, the mixture was allowed to warm to room temperature gradually and stirred overnight. The reaction was quenched by adding ice-water and extracted with EtOAc. The EtOAc extracts were washed with water, brine and dried over Na$_2$SO$_4$. Removal of the solvent gave a residue, which was purified by SiO$_2$ column to give the title compound (4.68 g, 94%), which was used directly in the next step.

Intermediate 56c 4-((1R,2S)-1-(5-(4-Bromophenyl)-1,3,4-oxadiazol-2-yl)-2-(tert-butyldimethylsilyloxy)propylamino)-2-chloro-3-methylbenzonitrile

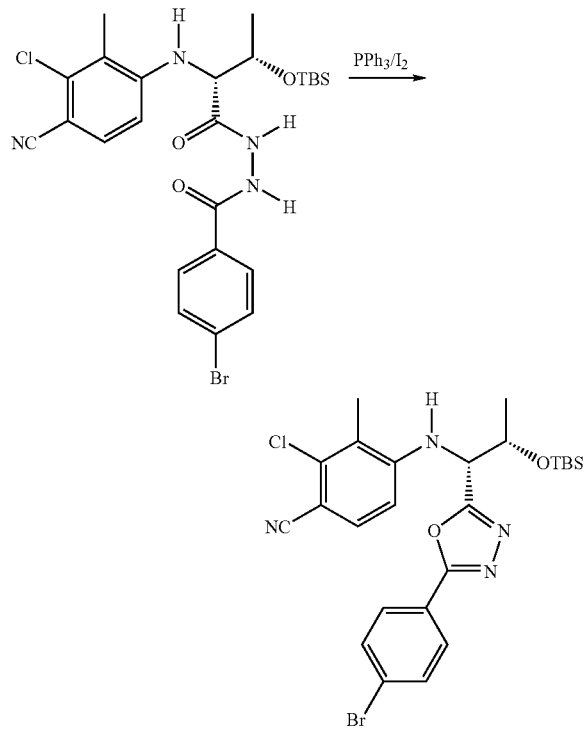

To a solution of triphenylphosphine (4.23 g, 16.1 mmol) in DCM (200 mL) was added I$_2$ (4.1 g, 16.2 mmol) at 0° C. After I$_2$ was dissolved completely, Et$_3$N (4.5 mL, 32.3 mmol) was added, followed by a solution of 4-bromo-N'-((2R,3S)-3-(tert-butyldimethylsilyloxy)-2-(3-chloro-4-cyano-2-methylphenylamino)butanoyl)-benzohydrazide (4.68 g, 8.1 mmol) in DCM (100 mL). The reaction mixture was allowed to warm to room temperature and stirred for additional 15 min. The reaction was quenched with saturated sodium thiosulfate (50 mL) and diluted with DCM (400 mL). The organic layer was separated and washed with water, brine, dried over Na$_2$SO$_4$, filtered and concentrated. The resulting residue was purified by flash chromatography to provide the title compound (4.03 g, 89%), which was used directly in the next step Example 56

4-((1R,2S)-1-(5-(4-Bromophenyl)-1,3,4-oxadiazol-2-yl)-2-hydroxypropylamino)-2-chloro-3-methylbenzonitrile

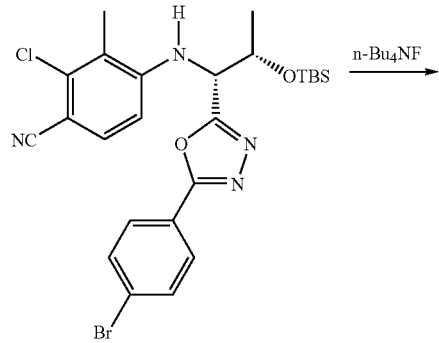

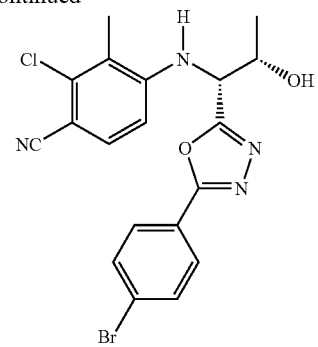

To a solution of 4-((1R,2S)-1-(5-(4-bromophenyl)-1,3,4-oxadiazol-2-yl)-2-(tert-butyldimethylsilyloxy)propylamino)-2-chloro-3-methylbenzonitrile (1.63 g, 2.9 mmol) in THF (60 mL) was added TBAF (3.2 mL, 3.2 mmol, 1 M solution in THF) at −50° C. After addition, the reaction mixture was allowed to warm to −20° C. gradually (about 1 h), then quenched by adding saturated aqueous NH$_4$Cl solution (20 mL) and extracted with EtOAc. The EtOAc extracts were washed with water, brine, dried over Na$_2$SO$_4$ and filtered. Concentration provided a residue, which was purified by flash chromatography over silica gel to provide the title compound 4-((1R,2S)-1-(5-(4-bromophenyl)-1,3,4-oxadiazol-2-yl)-2-hydroxypropylamino)-2-chloro-3-methylbenzonitrile (1.10 g, 85%). $^1$H NMR (400 MHz, CDCl$_3$, δ in ppm) 7.79 (d, J=8.4 Hz, 2H), 7.61 (d, J=8.4 Hz, 2H), 7.40 (d, J=8.8 Hz, 1H), 6.63 (d, J=8.8 Hz, 1H), 5.23 (d, J=8.6 Hz, 1H), 4.72 (dd, J=2.5, 8.6 Hz, 1H), 4.62 (m, 1H), 3.01 (d, J=3.5 Hz, 1H), 2.34 (s, 3H), 1.42 (d, J=6.3 Hz, 3H).

Example 57

2-Chloro-4-((1R,2S)-2-hydroxy-1-(5-(4-iodophenyl)-1,3,4-oxadiazol-2-yl)propylamino)-3-methylbenzonitrile

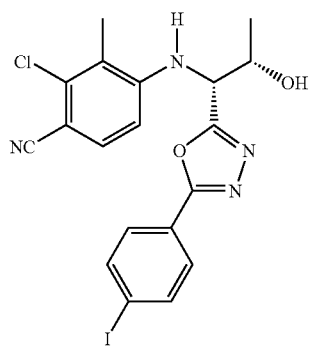

Intermediate 57a

N'-((2R,3S)-2-(3-Chloro-4-cyano-2-methylphenylamino)-3-hydroxybutanoyl)-4-iodobenzohydrazide

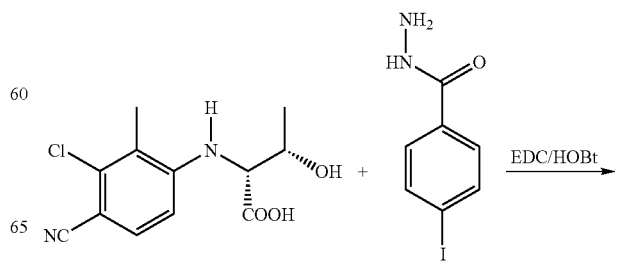

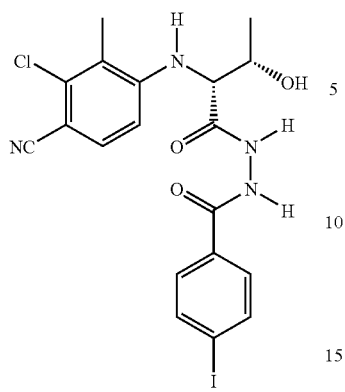

(2R,3S)-2-(3-chloro-4-cyano-2-methylphenylamino)-3-hydroxybutanoic acid (5.0 g, 18.6 mmol), 4-iodobenzhydrazide (CAS 39115-95-2, 4.88 g, 18.6 mmol) and 1-hydroxybenzotriazole hydrate (2.85 g, 18.6 mmol) were placed in a 250 mL round bottomed flask. Anhydrous THF (120 mL) was added and the mixture was cooled to −20° C. N-(3-Dimethylaminopropyl)-N'-ethylcarbodimide HCl (5.35 g, 27.9 mmol) was added, followed by Et₃N (3.9 mL, 28.0 mmol). The reaction mixture was stirred at −20° C. for 1 h and room temperature for overnight. The reaction was quenched by adding water and extracted with EtOAc, which was washed with 5% aqueous NaOH, water, brine and dried over Na₂SO₄. The extracts were filtered and the filtrate was concentrated to provide a brown solid, which was purified by flash chromatography (80% EtOAc in hexanes) to afford the title compound (7.3 g, 77%), which was used directly in the next step.

Intermediate 57b

N'-((2R,3S)-3-(tert-Butyldimethylsilyloxy)-2-(3-chloro-4-cyano-2-methylphenylamino)butanoyl)-4-iodobenzohydrazide

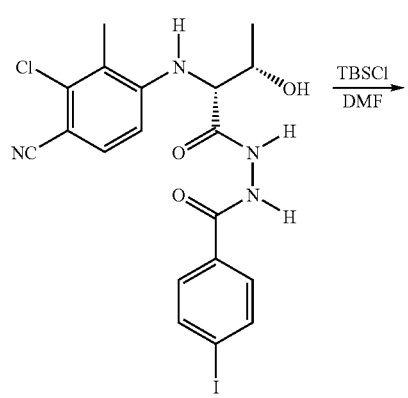

To a solution of N'-((2R,3S)-2-(3-chloro-4-cyano-2-methylphenylamino)-3-hydroxybutanoyl)-4-iodobenzohydrazide (7.3 g, 14.2 mmol) in DMF (60 mL) were added imidazole (3.9 g, 57.3 mmol) and TBSCl (4.3 g, 28.5 mmol) at 0° C. After addition, the mixture was allowed to warm to room temperature gradually and stirred overnight. The reaction was quenched by adding ice-water and extracted with EtOAc. The EtOAc extracts were washed with water, brine and dried over Na₂SO₄. Removal of the solvent gave a residue, which was purified by SiO₂ column to give the title compound (8.6 g, 97%), which was used directly in the next step.

Intermediate 57c 4-((1R,2S)-2-(tert-Butyldimethylsilyloxy)-1-(5-(4-iodophenyl)-1,3,4-oxadiazol-2-yl)propylamino)-2-chloro-3-methylbenzonitrile

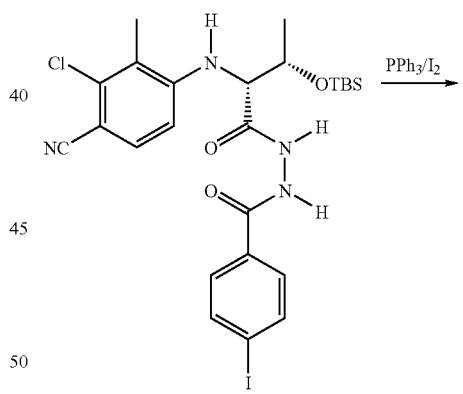

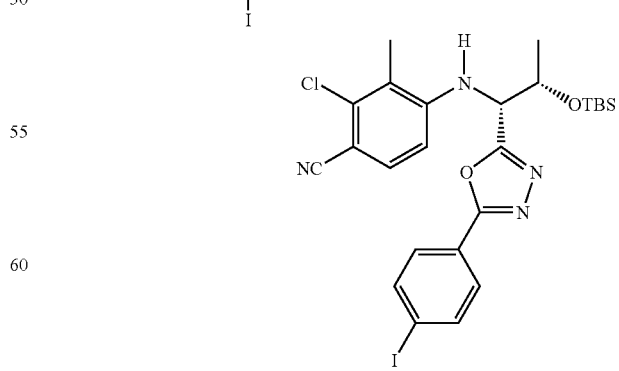

To a solution of triphenylphosphine (7.2 g, 27.5 mmol) in DCM (300 mL) was added I₂ (7.0 g, 27.5 mmol) at 0° C. After I$_2$ was dissolved completely, Et$_3$N (7.7 mL, 55.2 mmol) was added, followed by a solution of N'-((2R,3S)-3-(tert-butyldimethylsilyloxy)-2-(3-chloro-4-cyano-2-methylphenylamino)butanoyl)-4-iodobenzohydrazide (8.6 g, 13.7 mmol) in DCM (100 mL). The reaction mixture was allowed to warm to room temperature and stirred for an additional 60 min. The reaction was quenched with saturated sodium thiosulfate (50 mL) and diluted with DCM (500 mL). The organic layer was separated and washed with water, brine, dried over Na$_2$SO$_4$ and filtered. After the solvent was removed, the residue was purified by flash chromatography to provide the title compound (7.3 g, 88%). $^1$H NMR (400 MHz, CDCl$_3$, δ in ppm) 8.06 (d, J=8.6 Hz, 2H), 7.88 (d, J=8.6 Hz, 2H), 7.55 (d, J=8.4 Hz, 1H), 6.66 (d, J=8.4 Hz, 1H), 5.56 (d, J=8.8 Hz, 1H), 5.00 (dd, J=2.0, 8.8 Hz, 1H), 4.74 (m, 1H), 2.59 (s, 3H), 1.62 (d, J=6.3 Hz, 3H), 1.07 (s, 9H), 0.28 (s, 3H), 0.00 (s, 3H).

Example 57

2-Chloro-4-((1R,2S)-2-hydroxy-1-(5-(4-iodophenyl)-1,3,4-oxadiazol-2-yl)propylamino)-3-methylbenzonitrile

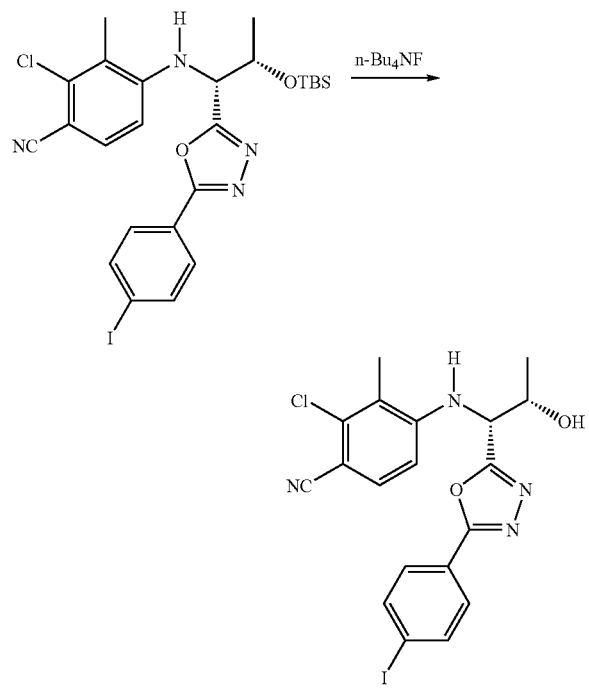

To a solution of 4-((1R,2S)-2-(tert-butyldimethylsilyloxy)-1-(5-(4-iodophenyl)-1,3,4-oxadiazol-2-yl)propylamino)-2-chloro-3-methylbenzonitrile (2.0 g, 3.3 mmol) in THF (60 mL) was added TBAF (3.7 mL, 3.7 mmol, 1 M solution in THF) at −50° C. After addition, the reaction mixture was allowed to warm to −30° C. gradually (about 1 h), then quenched by adding saturated aqueous NH$_4$Cl solution (20 mL) and extracted with EtOAc. The EtOAc extracts were washed with water, brine, dried over Na$_2$SO$_4$. Concentration provided a residue, which was purified by flash chromatography over silica gel to provide the title compound 2-chloro-4-((1R,2S)-2-hydroxy-1-(5-(4-iodophenyl)-1,3,4-oxadiazol-2-yl)propylamino)-3-methylbenzonitrile (1.54 g, 94%). $^1$H NMR (400 MHz, CDCl$_3$, δ in ppm) 7.83 (d, J=8.6 Hz, 2H), 7.64 (d, J=8.6 Hz, 2H), 7.40 (d, J=8.6 Hz, 1H), 6.63 (d, J=8.6 Hz, 1H), 5.24 (d, J=8.6 Hz, 1H), 4.72 (dd, J=2.6, 8.6 Hz, 1H), 4.62 (m, 1H), 3.07 (d, J=4.1 Hz, 1H), 2.35 (s, 3H), 1.42 (d, J=6.5 Hz, 3H).

Example 58

(R)-2-Chloro-4-(1-(5-(4-cyanophenyl)-1,3,4-oxadiazol-2-yl)-2-hydroxyethylamino)-3-methylbenzonitrile

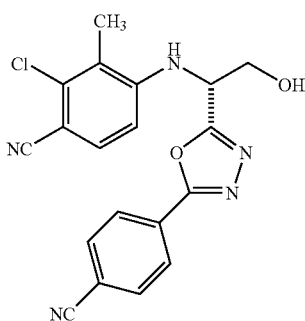

Intermediate 58a (R)-2-(3-Chloro-4-cyano-2-methylphenylamino)-3-hydroxypropanoic acid

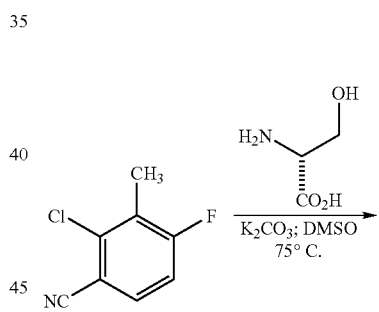

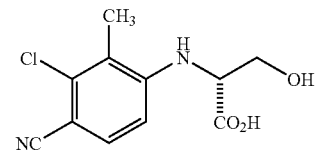

K$_2$CO$_3$ (5.71 g, 41.28 mol) was added to a solution of 2-chloro-4-fluoro-3-methylbenzonitrile (3.5 g, 20.64 mmol) and D-Serine (2.17 g, 20.096 mol) in DMSO (100 mL) at room temperature. The reaction mixture was heated to 75° C. and stirred for 19 h, then was allowed to cool to room temperature whereupon water (30 mL) was added followed by citric acid monohydrate (5 g). After stirring for 10 min the mixture was partitioned between EtOAc (50 mL) and water. The organic phase was then washed with water (20 mL), brine (20 mL), dried (Na$_2$SO$_4$), filtered and concentrated to furnish a pale yellow solid (4.2 g). This crude product was then passed through a silica-plug [hexanes-EtOAc (95:5) as eluent] to furnish the title compound as a white solid (1.5 g, 29%) $^1$H NMR (500 MHz, acetone-$d_6$, δ in ppm) 7.49 (d, J=9 Hz, 1H), 6.72 (d, J=9 Hz, 1H), 5.56 (d, J=8 Hz, 1H), 4.43-4.40 (m, 1H), 4.06 (dd, J=11, 18 Hz, 1H), 4.05 (dd, J=11, 18 Hz, 1H) and 2.31 (s, 3H).

Intermediate 58b (R)—N'-(2-(3-Chloro-4-cyano-2-methylphenylamino)-3-hydroxypropanoyl)-4-cyanobenzohydrazide

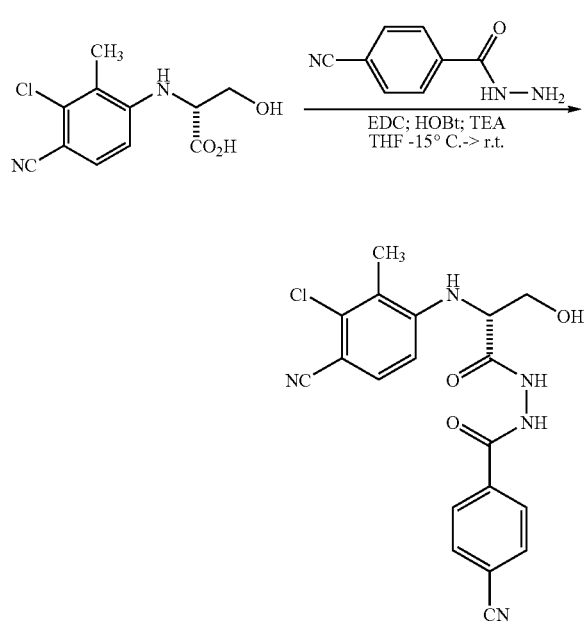

(R)-2-(3-chloro-4-cyano-2-methylphenylamino)-3-hydroxypropanoic acid (1.22 g, 4.79 mmol), 4-cyanobenzohydrazide (1.48 g, 5.28 mmol) and anhydrous THF (100 mL) were placed in a 250 mL round bottomed flask and the mixture was cooled to −15° C. 1-Hydroxybenzotriazole hydrate (647 mg, 4.79 mmol) was added to the mixture together with N-(3-Dimethylaminopropyl)-N'-ethylcarbodimide HCl (1.38 g, 7.19 mmol) at −15° C. followed by triethylamine (1.00 mL, 7.19 mmol). The reaction mixture was maintained at −15° C. and stirred for 1 h after which, stirring continued overnight while the mixture slowly warmed to room temperature. After 18 h, the mixture was filtered under vacuum and the residue washed with THF (65 mL). The THF solution was concentrated to ca. 20 mL, whereupon EtOAc (100 mL) was added followed by water (50 mL). The phases were partitioned and the organic phase washed with water (30 mL), brine (30 mL) dried ($Na_2SO_4$) and concentrated to furnish a light brown solid (31 g). Purification by flash column chromatography [EtOAc-hexanes (1:1), then 100% EtOAc as eluent] afforded the title compound as a white solid (1.78 g, 93% yield). $^1$H NMR (400 MHz, acetone-$d_6$, δ in ppm) 8.09 (d, J=8.0 Hz, 2H), 7.95 (d, J=9 Hz, 2H), 7.54 (d, J=8 Hz, 1H), 6.70 (d, J=8 Hz, 3H), 5.63 (d, J=8 Hz, 1H), 4.31-4.26 (m, 1H), 4.06 (dd, J=11, 18 Hz, 1H), 4.05 (dd, J=11, 18 Hz, 1H), 2.36 (s, 3H).

Intermediate 58c (R)—N'-(3-(tert-Butyldimethylsilyloxy)-2-(3-chloro-4-cyano-2-methylphenylamino)propanoyl)-4-cyanobenzohydrazide

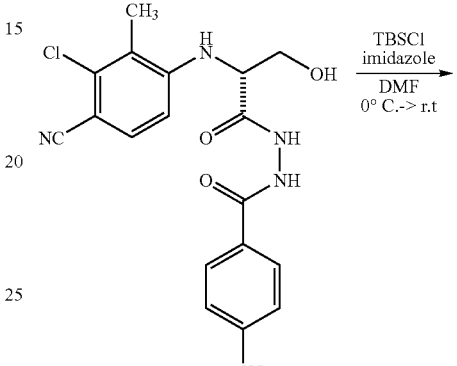

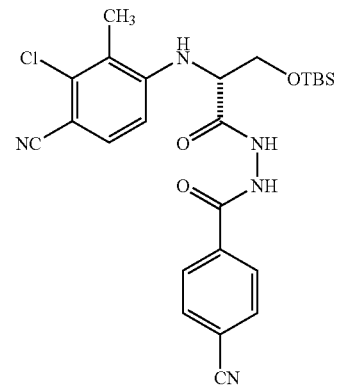

Imidazole (1.3 g, 19.1 mol) and TBDMS-Cl (1.73 g, 11.46 mmol) were added sequentially to a pre-cooled (0° C.) solution of (R)—N'-(2-(3-chloro-4-cyano-2-methylphenylamino)-3-hydroxypropanoyl)-4-cyanobenzohydrazide (1.52 g, 3.82 mmol) in DMF (145 mL). The reaction mixture was allowed to warm to room temperature and stirred for 20 h, whereupon the solution was poured into $H_2O$ (200 mL). The white precipitate was filtered, washed with $H_2O$ (35 mL) and taken up in $CH_2Cl_2$ (300 mL). This organic layer was washed with brine (1×160 mL), dried ($Na_2SO_4$), filtered and concentrated to provide the title compound (1.52 g, 78%). $^1$H NMR (400 MHz, acetone-$d_6$, δ in ppm) 9.6 (br s, 1H), 7.97 (d, J=8.0 Hz, 2H), 7.80 (d, J=9 Hz, 2H), 7.41 (d, J=8 Hz, 1H), 6.63 (d, J=8 Hz, 3H), 5.45 (d, J=8 Hz, 1H), 4.29-4.23 (m, 1H), 4.05-4.02 (m, 2H), 2.21 (s, 3H), 0.79 (s, 9H), 0.01 (s, 6H).

Intermediate 58d (R)-4-(2-(tert-Butyldimethylsilyloxy)-1-(5-(4-cyanophenyl)-1,3,4-oxadiazol-2-yl)ethylamino)-2-chloro-3-methylbenzonitrile

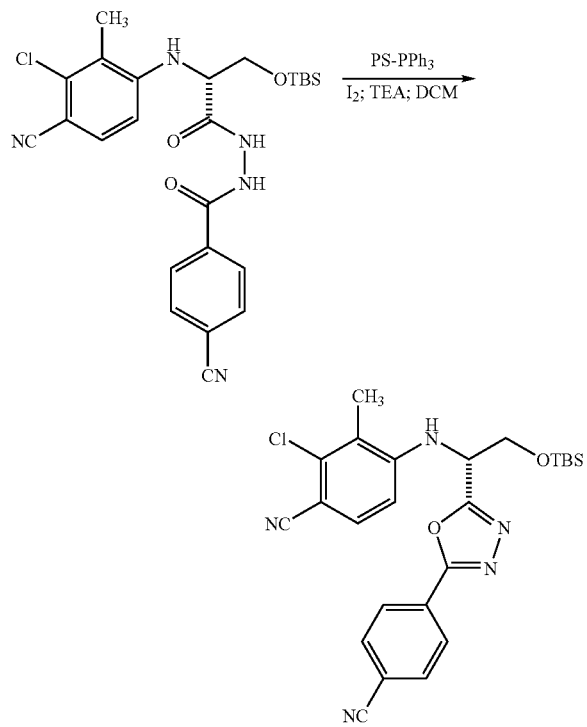

Polymer supported triphenylphosphine (1.5 g, 4.46 mmol) was dilluted in 200 mL of DCM followed by addition of I₂ (1.13 g, 4.46 mmol) and TEA (1.67 mL, 18.8 mmol) at 0° C. (R)—N-(3-(tert-butyldimethylsilyloxy)-2-(3-chloro-4-cyano-2-methylphenylamino) propanoyl)-4-cyanobenzohydrazide (1.52 g, 2.97 mmol) in 200 ml DCM was added to the pre-cooled solution mixture of PPh₃/I₂/TEA system and stirred. The temperature was allowed to come to room temperature and stirred for additional 10 min. The reaction was quenched with 50 mL saturated sodium thiosulfate and the biphasic mixture was separated. The aqueous layer was extracted with EtOAc (3×40 mL) and the combined organic extracts were dried (Na₂SO₄), filtered and concentrated under reduced pressure. The resulting crude oil was purified by flash chromatography (SiO₂) to provide the title compound (0.860 g, 59%). The crude material was used directly in the next step.

Example 58

(R)-2-Chloro-4-(1-(5-(4-cyanophenyl)-1,3,4-oxadiazol-2-yl)-2-hydroxyethylamino)-3-methylbenzonitrile

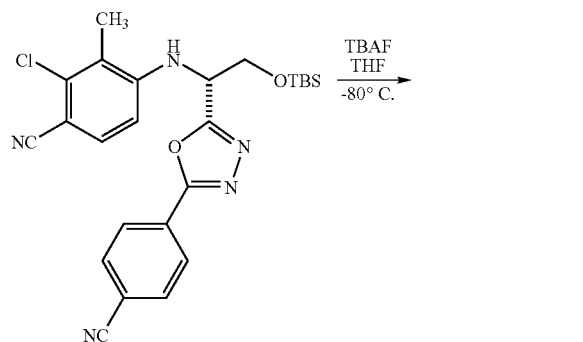

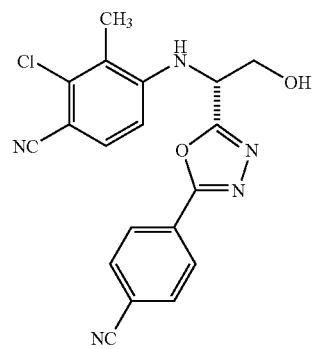

To a pre-cooled (−78° C.) solution of (R)—N'-(3-(tert-butyldimethylsilyloxy)-2-(3-chloro-4-cyano-2-methylphenylamino)propanoyl)-4-cyanobenzohydrazide (0.810 g, 1.64 mmol) in THF (160 mL) was added TBAF (1.64 mL, 1.64 mmol, 1 M solution in THF) dropwise over 10 min. Upon complete addition, the reaction mixture was concentrated under reduced pressure. The resulting residue was taken up in EtOAc (100 mL) and washed with H₂O (80 mL). The biphasic mixture was separated and the aqueous layer extracted with EtOAc (2×100 mL). The combined organic layers were washed with brine (1×70 mL), dried (Na₂SO₄), filtered and concentrated under reduced pressure to provide a yellow oil, which was purified by flash chromatography over silica gel (50% EtOAc in hexanes then 100% EtOAc) to provide the title compound as an off-white solid. The resulting solid was diluted with CH₂Cl₂ (90 mL) and hexanes (70 mL) was added. Upon concentration of the suspension a white solid was provided (460 mg, 74%). $^1$H NMR (400 MHz, acetone-d₆, δ in ppm) 8.21 (d, J=8.8 Hz, 2H), 8.00 (d, J=9 Hz, 2H), 7.53 (d, J=9 Hz, 1H), 6.95 (d, J=9 Hz, 1H), 5.85 (d, J=8 Hz, 1H), 5.34-5.27 (m, 1H), 4.29 (br s, 2H) and 2.38 (s, 3H).

Example 59

4-((1R,2R)-2-hydroxy-1-(5-(4-(methylsulfonyl)phenyl)-1,3,4-oxadiazol-2-yl)propylamino)-2-(trifluoromethyl)benzonitrile

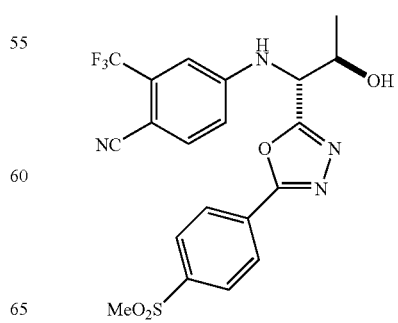

Intermediate 59a

N'-((2R,3R)-2-(4-Cyano-3-(trifluoromethyl)phenylamino)-3-hydroxybutanoyl)-4-(methylsulfonyl)benzohydrazidem

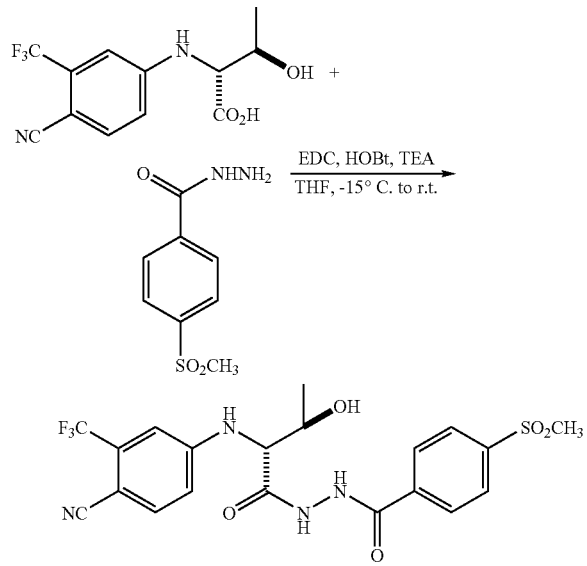

To a pre-cooled (−15° C.) solution of (2R,3R)-2-(4-cyano-3-(trifluoromethyl)phenylamino)-3-hydroxybutanoic acid (3.08 g, 10.7 mmol) and 4-(methylsulfonyl)benzohydrazide (2.29 g, 10.7 mmol) in anhydrous THF (75 mL) was added 1-hydroxybenzotriazole monohydrate (1.64 g, 11.0 mmol) and N-(3-dimethylaminopropyl)-N'-ethylcarbodiimide-HCl (4.10 g, 21.0 mmol) at −20° C. followed by triethylamine (5.9 mL, 42.0 mmol). The reaction mixture was stirred at −20° C. for 1 h, then warmed to room temperature and stirred for 16 h, then quenched with 5% aq. citric acid (150 mL). The organic extract was washed with 5% aq. citric acid (150 mL), sat. aq. NaHCO₃ (150 mL), H₂O (100 mL), brine (100 mL), dried (Na₂SO₄), filtered and concentrated under reduced pressure to provide the title compound as an off white solid (4.88 g, 94%): $^1$H NMR (400 MHz, acetone-$d_6$, δ in ppm) 10.30 (s, 1H), 9.89 (s, 1H), 8.10 (d, J=8.4 Hz, 2H), 8.01 (d, J=8.4 Hz, 2H), 7.66 (d, J=8.6 Hz, 1H), 7.28 (d, J=2.0 Hz, 1H), 7.05 (dd, J=2.0, 8.6 Hz, 1H), 6.76 (d, J=7.6 Hz, 1H), 4.40-4.20 (m, 2H), 3.18 (s, 3H), 1.39 (d, J=6.3 Hz, 3H).

Intermediate 59b

N'-((2R,3R)-3-(tert-Butyldimethylsilyloxy)-2-(4-cyano-3-(trifluoromethyl)phenylamino)butanoyl)-4-(methylsulfonyl)benzohydrazide

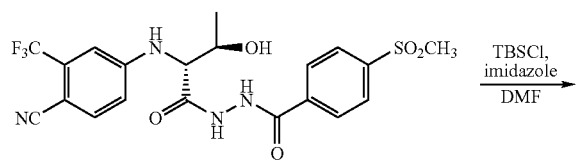

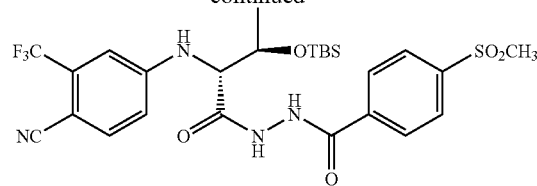

To a pre-cooled (0° C.) solution of N'-((2R,3R)-2-(4-cyano-3-(trifluoromethyl)phenylamino)-3-hydroxybutanoyl)-4-(methylsulfonyl)benzohydrazide (5.16 g, 10.7 mmol) in DMF (150 mL) was added imidazole (4.36 g, 64.0 mmol) then TBSCl (4.81 g, 32.0 mmol). The reaction was warmed slowly to room temperature, stirred for 17 h, cooled to 0° C. and quenched with H₂O (300 mL). The solution was extracted with EtOAc (250 mL). The organic extract was washed with brine (2×200 mL), dried (Na₂SO₄), filtered and concentrated under reduced pressure to provide a brown oil, which was purified by flash chromatography over silica gel (50% EtOAc in hexanes) to provide the title compound (5.29 g, 83%): $^1$H NMR (400 MHz, acetone-$d_6$, δ in ppm) 10.06 (s, 2H), 8.10 (dm, J=8.6 Hz, 2H), 8.03 (dm, J=8.6 Hz, 2H), 7.70 (d, J=8.6 Hz, 1H), 7.35 (d, J=2.4 Hz, 1H), 7.14 (dd, J=2.4, 8.6 Hz, 1H), 6.57 (d, J=7.4 Hz, 1H), 4.50-4.41 (m, 2H), 3.17 (s, 3H), 1.36 (d, J=5.9 Hz, 3H), 0.85 (s, 9H), 0.11 (s, 3H), 0.09 (s, 3H).

Intermediate 59c 4-((1R,2R)-2-(tert-Butyldimethylsilyloxy)-1-(5-(4-(methylsulfonyl)phenyl)-1,3,4-oxadiazol-2-yl)propylamino)-2-(trifluoromethyl)benzonitrile

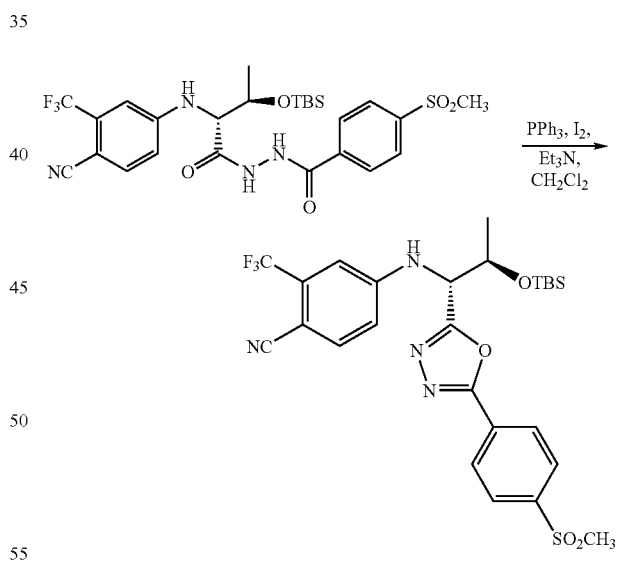

A solution of N'-((2R,3R)-3-(tert-butyldimethylsilyloxy)-2-(4-cyano-3-(trifluoromethyl)phenylamino)butanoyl)-4-(methylsulfonyl)benzohydrazide (5.29 g, 8.80 mmol) in CH₂Cl₂ (250 mL) was added to a pre-cooled (0° C.) mixture of PPh₃ (4.64 g, 17.7 mmol), iodine (4.48 g, 17.6 mmol) and Et₃N (4.9 mL, 35.2 mmol). The reaction mixture was warmed to room temperature, stirred for 20 minutes and quenched with 10% sodium thiosulfate (100 mL). The organic extract was washed with 10% sodium thiosulfate (100 mL), H₂O (100 mL), brine (50 mL), dried (Na₂SO₄), filtered and concentrated under reduced pressure to provide a pink foam, which was purified by flash chromatography over silica gel (50% EtOAc in hexanes) to provide the title compound (4.81 g, 94%), which was used directly in the next step.

Example 59

4-((1R,2R)-2-hydroxy-1-(5-(4-(methylsulfonyl)phenyl)-1,3,4-oxadiazol-2-yl)propylamino)-2-(trifluoromethyl)benzonitrile

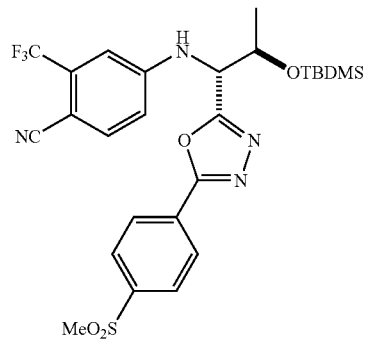

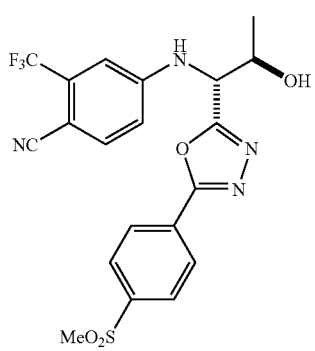

To a pre-cooled (−70° C.) solution of 4-((1R,2R)-2-(tert-butyldimethylsilyloxy)-1-(5-(4-(methylsulfonyl)phenyl)-1,3,4-oxadiazol-2-yl)propylamino)-2-(trifluoromethyl)benzonitrile (1 g, 1.83 mmol) in THF (200 mL) was added TBAF (1.83 mL, 1.83 mmol, 1 M solution in THF) dropwise over 10 minutes. Upon complete addition the reaction mixture was concentrated under reduced pressure. The resulting residue was taken up in EtOAc (100 mL) and washed with $H_2O$ (80 mL). The biphasic mixture was separated and the aqueous layer extracted with EtOAc (2×100 mL). The combined organic layers were washed with brine (1×70 mL), dried ($Na_2SO_4$), filtered and concentrated under reduced pressure to provide a yellow oil, which was purified by flash chromatography over silica gel (50% EtOAc in hexanes then 100% EtOAc) to provide the title compound as an off-white solid. The resulting solid was diluted with $CH_2Cl_2$ (90 mL) and hexanes (70 mL) was added. Upon concentration of the suspension a white solid was provided (329 mg, 39%). $^1H$ NMR (400 MHz, acetone-$d_6$, δ in ppm) 8.24 (d, J=8.8 Hz, 2H), 8.16 (d, J=9 Hz, 2H), 7.74 (d, J=9 Hz, 1H), 7.38 (s, 1H), 7.19 (d, J=9 Hz, 1H), 7.01 (d, J=8 Hz, 1H), 5.19 (dd, J=6, 8 Hz, 1H), 4.59 (d, J=6 Hz, 1H), 4.49-4.42 (m, 1H), 3.2 (s, 3H) and 1.42 (d, J=7 Hz, 3H).

Example 60

4-((1R,2S)-1-(5-(4-cyanophenyl)-1,3,4-oxadiazol-2-yl)-2-hydroxypropylamino)benzo[b]thiophene-7-carbonitrile

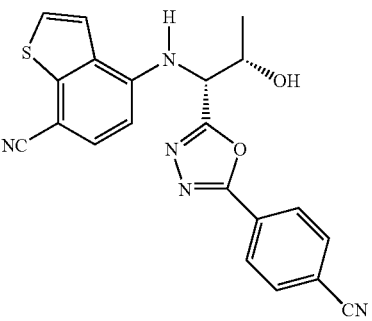

Intermediate 60a (2R,3S)-2-(7-cyanobenzo[b]thiophen-4-ylamino)-3-hydroxybutanoic acid

$K_2CO_3$ (1.97 g, 14.3 mmol) was added to a mixture of 4-fluorobenzo[b]thiophene-7-carbonitrile [(1.01 g, 5.70 mmol), which was prepared according to the procedures reported in WO 2004016576] and D-threonine (815 mg, 6.84 mmol) in DMSO (15 mL) at room temperature. The resulting mixture was heated to 80° C. and stirred for 15 h. After cooling to room temperature, the reaction mixture was poured into ice-water (150 mL) and extracted with 10% EtOAc in hexanes (2×50 mL). The aqueous phase was acidified to pH=2~3 with 2N HCl and extracted with EtOAc (2×100 mL). The EtOAc extracts were washed with water, brine and dried with $Na_2SO_4$. Removal of the solvent gave the crude (2R,3S)-2-(7-cyanobenzo[b]thiophen-4-ylamino)-3-hydroxybutanoic acid (1.20 g, 76%). $^1H$ NMR (400 MHz, Acetone-$d_6$, δ in ppm) 7.81 (d, J=5.7 Hz, 1H), 7.73 (d, J=5.7 Hz, 1H), 7.63

(d, J=8.4 Hz, 1H), 6.66 (d, J=8.4 Hz, 1H), 6.12 (d, J=8.0 Hz, 1H), 4.46 (m, 1H), 4.33 (m, 1H), 1.34 (d, J=6.2 Hz, 3H).

J=5.7 Hz, 1H), 7.67 (d, J=8.2 Hz, 1H), 6.68 (d, J=8.2 Hz, 1H), 6.21 (d, J=7.2 Hz, 1H), 4.42 (m, 1H), 4.25 (dd, J=3.9, 7.2 Hz, 1H), 1.39 (d, J=6.4 Hz, 3H).

Intermediate 60b 4-cyano-N'-((2R,3S)-2-(7-cyanobenzo[b]thiophen-4-ylamino)-3-hydroxybutanoyl)benzohydrazide Intermediate 60c N'-((2R,3S)-3-(tert-butyldimethylsilyloxy)-2-(7-cyanobenzo[b]thiophen-4-ylamino)butanoyl)-4-cyanobenzohydrazide

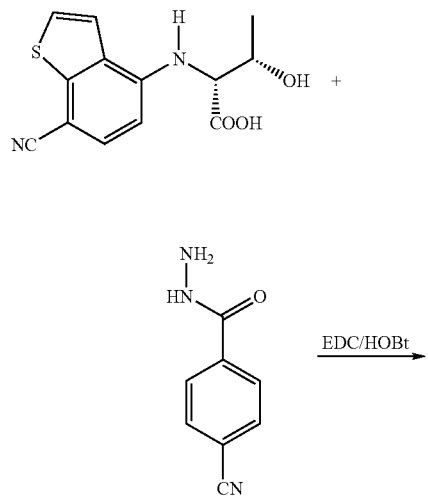

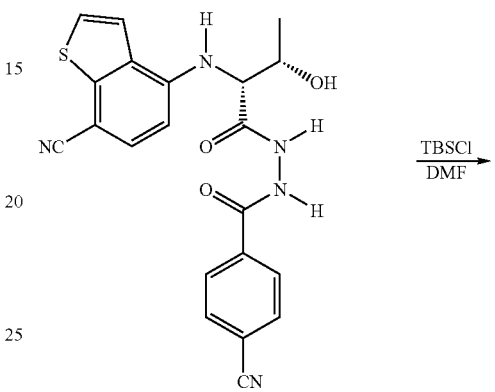

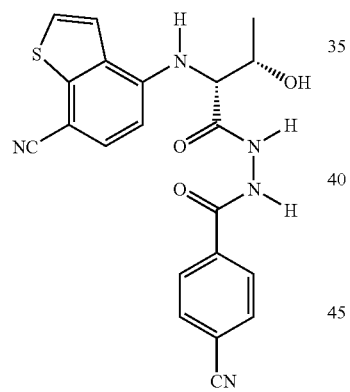

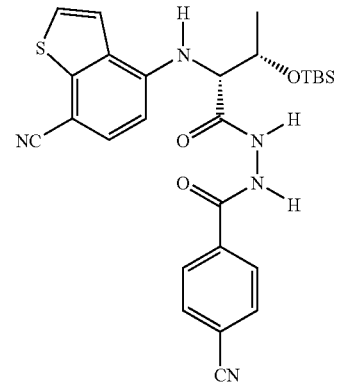

To a mixture of (2R,3S)-2-(7-cyanobenzo[b]thiophen-4-ylamino)-3-hydroxybutanoic acid (0.66 g, 2.39 mmol), 4-cyanobenzhydrazide (390 mg, 2.42 mmol), HOBt (327 mg, 2.42 mmol) in THF (40 mL) was added EDC (696 mg, 3.63 mmol) and Et$_3$N (0.56 mL, 4.02 mmol) at 0° C. The mixture was stirred at 0° C. for 30 min., then at room temperature overnight. The reaction was quenched by adding water and extracted with EtOAc (400 mL). The EtOAc extracts were washed with water, brine and dried over Na$_2$SO$_4$. Removal of the solvent and purification of the residue gave the title compound 4-cyano-N'-((2R,3S)-2-(7-cyanobenzo[b]thiophen-4-ylamino)-3-hydroxybutanoyl)benzohydrazide (0.68 g, 68%). $^1$H NMR (400 MHz, Acetone-d$_6$, δ in ppm) 8.09 (d, J=8.6 Hz, 2H), 7.93 (d, J=8.6 Hz, 2H), 7.81 (d, J=5.7 Hz, 1H), 7.73 (d, To a solution of 4-cyano-N'-((2R,3S)-2-(7-cyanobenzo[b]thiophen-4-ylamino)-3-hydroxybutanoyl)benzohydrazide (320 mg, 0.76 mmol) in DMF (10 mL) was added imidazole (208 mg, 3.06 mmol) and TBSCl (230 mg, 1.53 mmol) at 0° C. After addition, the mixture was allowed to warm to room temperature and stirred overnight. The reaction was quenched by adding ice-water and extracted with EtOAc. The EtOAc extracts were washed with water, brine and dried over Na$_2$SO$_4$. Removal of the solvent gave a residue, which was purified by SiO$_2$ column to afford N'-((2R,3S)-3-(tert-butyldimethylsilyloxy)-2-(7-cyanobenzo[b]thiophen-4-ylamino)butanoyl)-4-cyanobenzohydrazide (380 mg, 93%). $^1$H NMR (400 MHz, CDCl$_3$, δ in ppm) 9.28 (b, 1H), 8.63 (b, 1H), 7.77 (d, J=8.4 Hz, 2H), 7.63 (d, J=8.4 Hz, 2H), 7.45 (d, J=8.2 Hz, 1H), 7.42 (d, J=5.6 Hz, 1H), 7.23 (d, J=5.6 Hz, 1H), 6.35 (d, J=8.2 Hz, 1H), 5.59 (d, J=5.9 Hz, 1H), 4.44 (m, 1H), 4.01 (m, 1H), 1.14 (d, J=6.3 Hz, 3H), 0.83 (s, 9H), 0.03 (s, 3H), 0.00 (s, 3H).

Intermediate 60d 4-((1R,2S)-2-(tert-butyldimethylsilyloxy)-1-(5-(4-cyanophenyl)-1,3,4-oxadiazol-2-yl)propylamino)benzo[b]thiophene-7-carbonitrile

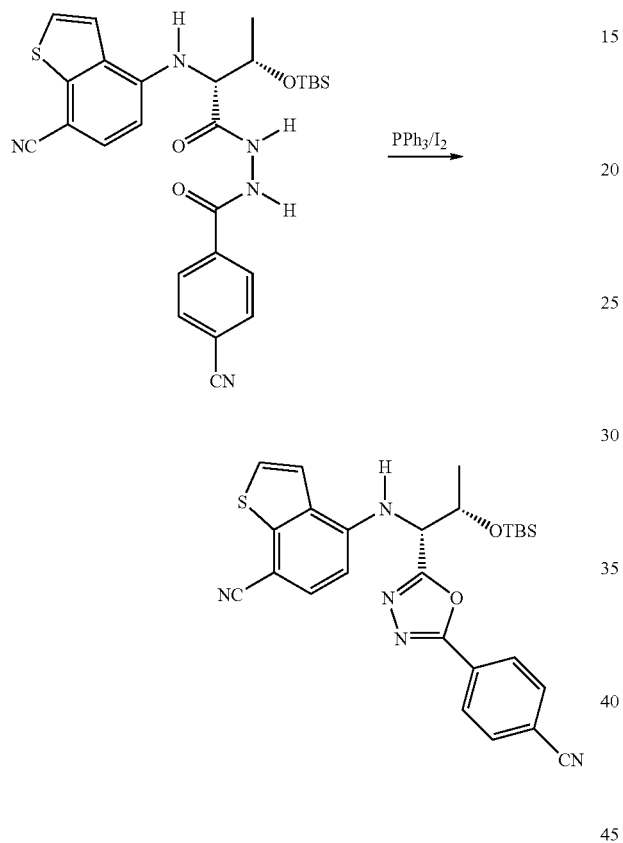

To a solution of triphenylphosphine (275 mg, 1.43 mmol) in DCM (24 mL) was added I₂ (363 mg, 1.43 mmol) at 0° C. After I₂ was dissolved completely, Et₃N (0.40 mL, 2.87 mmol) was added, followed by a solution of N'-((2R,3S)-3-(tert-butyldimethylsilyloxy)-2-(7-cyanobenzo[b]thiophen-4-ylamino)butanoyl)-4-cyanobenzohydrazide (380 mg, 0.71 mmol) in DCM (12 mL). After addition, the reaction mixture was allowed to warm to room temperature and stirred for additional 10 min. The reaction was quenched with saturated sodium thiosulfate (3 mL) and diluted with DCM (100 mL). The organic layer was separated and washed with water, brine and dried over Na₂SO₄. Removal of the solvent gave a residue, which was purified by flash chromatography to provide the title compound 4-((1R,2S)-2-(tert-butyldimethylsilyloxy)-1-(5-(4-cyanophenyl)-1,3,4-oxadiazol-2-yl)propylamino)benzo[b]thiophene-7-carbonitrile (360 mg, 98%). ¹H NMR (400 MHz, CDCl₃, δ in ppm) 8.22 (d, J=8.4 Hz, 2H), 7.93 (d, J=8.4 Hz, 2H), 7.73 (d, J=5.5 Hz, 1H), 7.68 (d, J=8.2 Hz, 1H), 7.55 (d, J=5.5 Hz, 1H), 6.63 (d, J=8.2 Hz, 1H), 5.89 (d, J=8.6 Hz, 1H), 5.12 (m, 1H), 4.74 (m, 1H), 1.61 (d, J=6.2 Hz, 3H), 1.05 (s, 9H), 0.26 (s, 3H), 0.00 (s, 3H).

Example 60

4-((1R,2S)-1-(5-(4-cyanophenyl)-1,3,4-oxadiazol-2-yl)-2-hydroxypropylamino)benzo[b]thiophene-7-carbonitrile

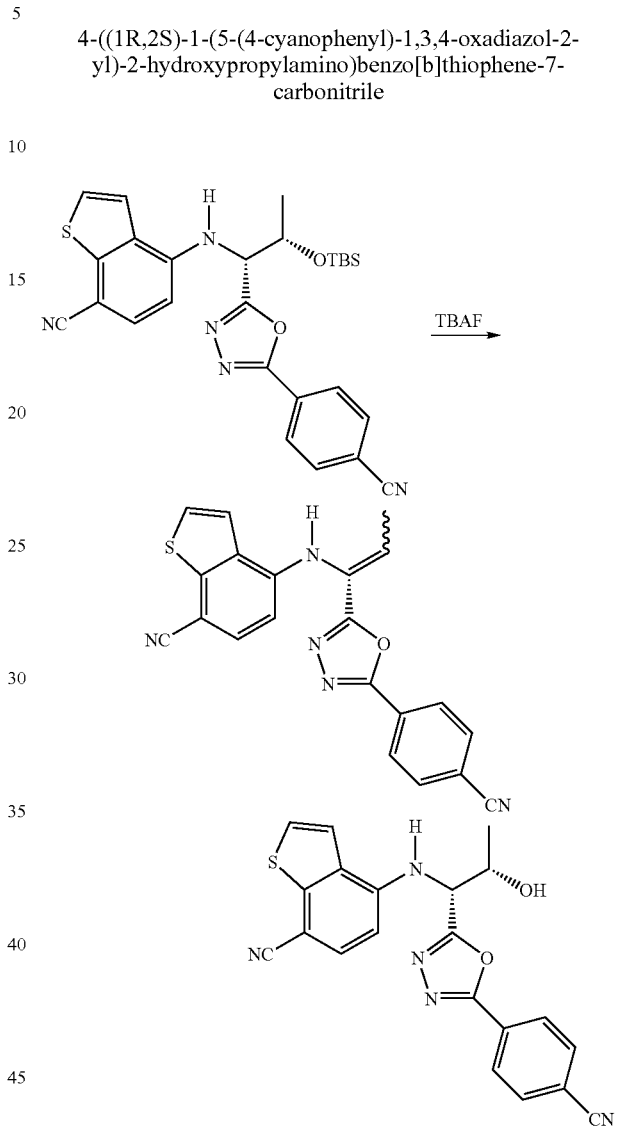

To a solution of 4-((1R,2S)-2-(tert-butyldimethylsilyloxy)-1-(5-(4-cyanophenyl)-1,3,4-oxadiazol-2-yl)propylamino)benzo[b]thiophene-7-carbonitrile (355 mg, 0.69 mmol) in THF (33 mL) was added TBAF (0.70 mL, 0.70 mmol, 1 M solution in THF) at −50° C. After addition, the reaction mixture was stirred between −30° C. to −50° C. for 2 h, then quenched by adding saturated aqueous NH₄Cl solution (10 mL) and extracted with EtOAc. The EtOAc extracts were washed with water, brine, dried over Na₂SO₄. The solvent was removed to provide a residue, which was subjected to flash chromatography purification to give the title compound 4-((1R,2S)-1-(5-(4-cyanophenyl)-1,3,4-oxadiazol-2-yl)-2-hydroxypropylamino)benzo[b]thiophene-7-carbonitrile (173 mg, 63%) and some dehydration product 4-(1-(5-(4-cyanophenyl)-1,3,4-oxadiazol-2-yl)prop-1-enylamino)benzo[b]thiophene-7-carbonitrile (70 mg, 27%). Title compound: ¹H NMR (400 MHz, Acetone-d₆, δ in ppm) 8.16 (d, J=8.8 Hz, 2H), 7.95 (d, J=8.8 Hz, 2H), 7.87 (d, J=5.7 Hz, 1H), 7.72 (d, J=5.7 Hz, 1H), 7.62 (d, J=8.2 Hz, 1H), 6.83 (d, J=8.2 Hz, 1H), 6.48 (d, J=8.6 Hz, 1H), 5.25 (dd, J=4.3, 8.6 Hz, 1H), 4.79 (b, 1H), 4.66 (m, 1H), 1.42 (d, J=6.3 Hz, 3H). Dehydration product: ¹H NMR (400 MHz, Acetone-d₆, δ in ppm) 8.25 (d, J=8.2 Hz, 2H), 8.01 (d, J=8.2 Hz, 2H), 7.96 (d, J=5.5 Hz, 1H), 7.81 (d, J=5.5 Hz, 1H), 7.61 (d, J=8.2 Hz, 1H), 7.09 (q, J=7.0 Hz, 1H), 6.58 (d, J=8.2 Hz, 1H), 1.95 (d, J=7.0 Hz, 3H).

Example 61

4-((1R,2R)-1-(5-(4-cyanophenyl)-1,3,4-oxadiazol-2-yl)-2-hydroxypropylamino)benzo[b]thiophene-7-carbonitrile

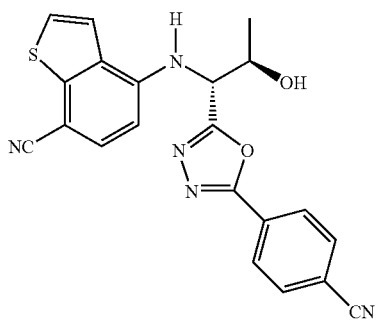

Intermediate 61a (2R,3R)-2-(7-cyanobenzo[b]thiophen-4-ylamino)-3-hydroxybutanoic acid

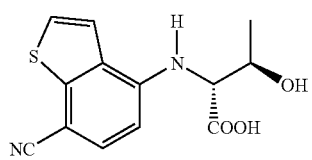

K₂CO₃ (1.50 g, 10.9 mmol) was added to a mixture of 4-fluorobenzo[b]thiophene-7-carbonitrile (770 mg, 4.35 mmol) and D-Allo-threonine (620 mg, 5.20 mmol) in DMSO (10 mL) at room temperature. The resulting mixture was heated to 80° C. and stirred for 15 h. After cooling to room temperature, the reaction mixture was poured into ice-water (150 mL) and extracted with 10% EtOAc in hexanes (2×50 mL). The aqueous phase was acidified to pH=2~3 with 2N HCl and extracted with EtOAc (2×100 mL). The EtOAc extracts were washed with water, brine and dried with Na₂SO₄. Removal of the solvent gave the crude (2R,3R)-2-(7-cyanobenzo[b]thiophen-4-ylamino)-3-hydroxybutanoic acid (1.20 g, ~100%). ¹H NMR (400 MHz, Acetone-d₆, δ in ppm) 7.81 (d, J=5.7 Hz, 1H), 7.70 (d, J=5.7 Hz, 1H), 7.64 (d, J=8.2 Hz, 1H), 6.72 (d, J=8.2 Hz, 1H), 6.28 (d, J=8.2 Hz, 1H), 4.33 (m, 2H), 1.39 (d, J=6.4 Hz, 3H).

Intermediate 61b 4-cyano-N'-((2R,3R)-2-(7-cyanobenzo[b]thiophen-4-ylamino)-3-hydroxybutanoyl)benzohydrazide

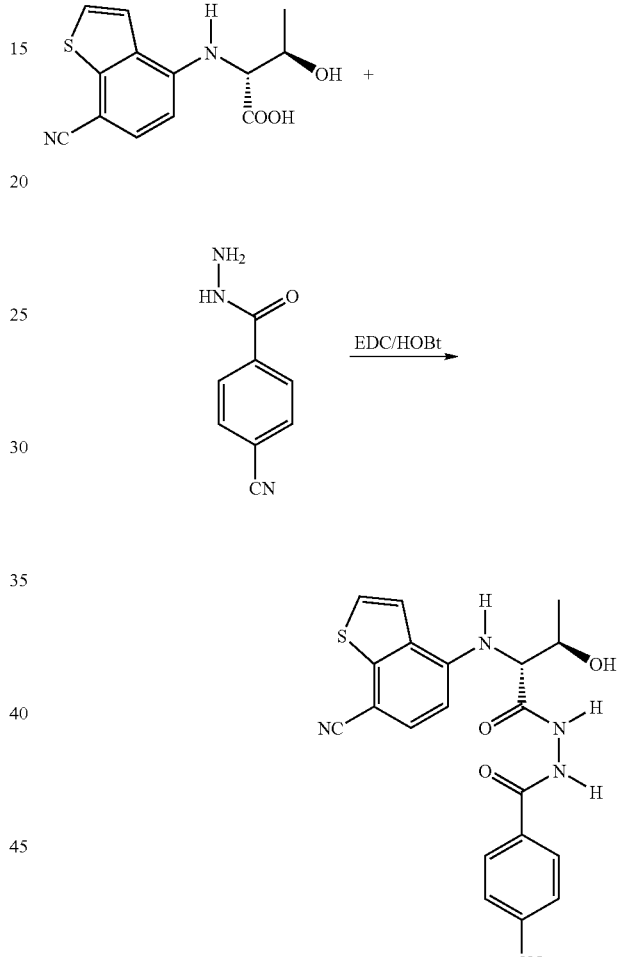

To a mixture of (2R,3R)-2-(7-cyanobenzo[b]thiophen-4-ylamino)-3-hydroxybutanoic acid (1.0 g, 3.62 mmol), 4-cyanobenzhydrazide (590 mg, 3.66 mmol), HOBt (495 mg, 3.66 mmol) in THF:DMF (1:1) (40 mL) was added EDC (1.05 g, 5.48 mmol) and Et₃N (0.80 mL, 5.74 mmol) at 0° C. The mixture was stirred at 0° C. for 30 min., then at room temperature overnight. The reaction was quenched by adding water and extracted with EtOAc (500 mL). The EtOAc extracts were washed with water, brine and dried over Na₂SO₄. Removal of the solvent and purification of the residue gave the title compound 4-cyano-N'-((2R,3R)-2-(7-cyanobenzo[b]thiophen-4-ylamino)-3-hydroxybutanoyl)benzohydrazide (1.25 g, 82%). ¹H NMR (400 MHz, Acetone-d₆, δ in ppm) 8.10 (d, J=8.6 Hz, 2H), 7.93 (d, J=8.6 Hz, 2H), 7.83

(d, J=5.5 Hz, 1H), 7.71 (d, J=5.5 Hz, 1H), 7.67 (d, J=8.4 Hz, 1H), 6.71 (d, J=8.4 Hz, 1H), 6.35 (d, J=7.8 Hz, 1H), 4.26 (m, 2H), 1.42 (d, J=6.3 Hz, 3H).

Example 61

4-((1R,2R)-1-(5-(4-cyanophenyl)-1,3,4-oxadiazol-2-yl)-2-hydroxypropylamino)benzo[b]thiophene-7-carbonitrile

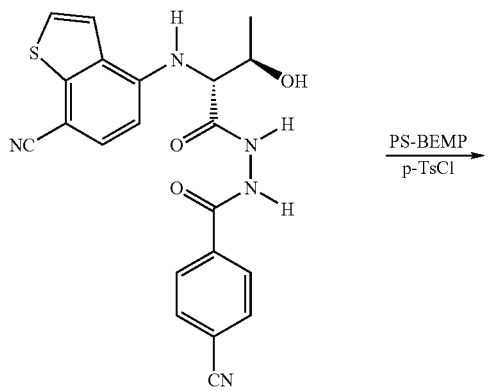

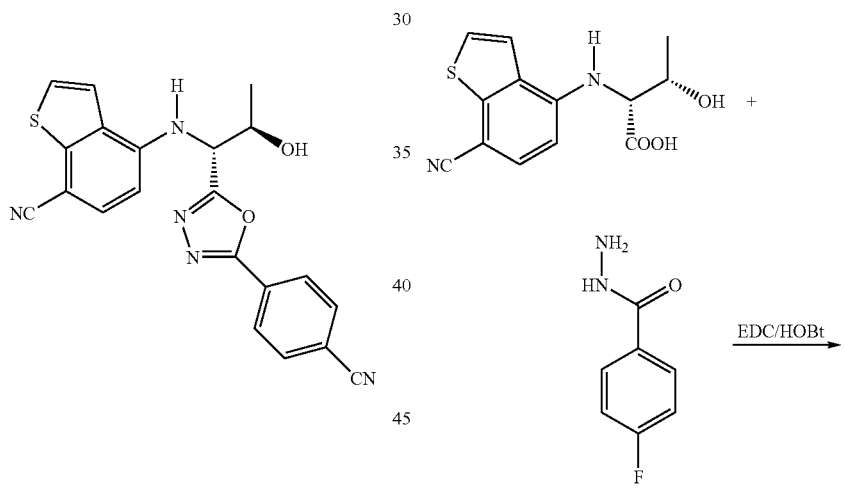

To a solution of 4-cyano-N'-((2R,3R)-2-(7-cyanobenzo[b]thiophen-4-ylamino)-3-hydroxybutanoyl)benzohydrazide (0.95 g, 2.26 mmol) in THF (150 mL) was added PS-BEMP (3.1 g, 6.82 mmol, ~2.2 mmol/g) and p-TsCl (470 mg, 2.46 mmol) at room temperature. The mixture was stirred at room temperature for 2 h, then methanol (5 mL) was added to quench the reaction. The resin was filtered and washed with MeOH (400 mL). The combined filtrate was concentrated to give a residue, which was purified by flash chromatography to afford the title compound 4-((1R,2R)-1-(5-(4-cyanophenyl)-1,3,4-oxadiazol-2-yl)-2-hydroxypropylamino)benzo[b]thiophene-7-carbonitrile (401 mg, 44%). $^1$H NMR (400 MHz, Acetone-$d_6$, δ in ppm) 8.14 (d, J=8.4 Hz, 2H), 7.92 (d, J=8.4 Hz, 2H), 7.83 (d, J=5.6 Hz, 1H), 7.68 (d, J=5.6 Hz, 1H), 7.61 (d, J=8.4 Hz, 1H), 6.85 (d, J=8.4 Hz, 1H), 6.72 (d, J=8.8 Hz, 1H), 5.18 (dd, J=6.5, 8.8 Hz, 1H), 4.72 (b, 1H), 4.61 (m, 1H), 1.50 (d, J=6.2 Hz, 3H).

Example 62

4-((1R,2S)-1-(5-(4-fluorophenyl)-1,3,4-oxadiazol-2-yl)-2-hydroxypropylamino)benzo[b]thiophene-7-carbonitrile

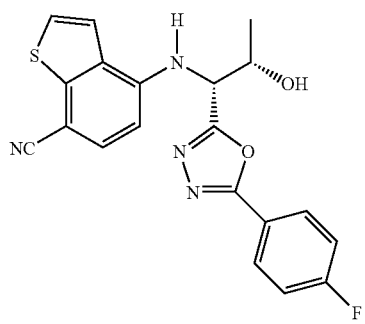

Intermediate 62a

N'-((2R,3S)-2-(7-cyanobenzo[b]thiophen-4-ylamino)-3-hydroxybutanoyl)-4-fluorobenzohydrazide

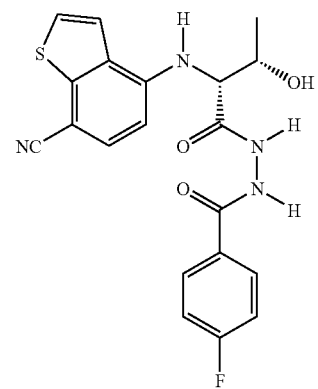

To a mixture of (2R,3S)-2-(7-cyanobenzo[b]thiophen-4-ylamino)-3-hydroxybutanoic acid (intermediate 60a) (0.52 g, 1.88 mmol), 4-fluorobenzoic hydrazide (295 mg, 1.91 mmol), HOBt (259 mg, 1.92 mmol) in THF:DMF (1:1) (30 mL) was added EDC (550 mg, 2.87 mmol) and Et$_3$N (0.40 mL, 2.87 mmol) at 0° C. The mixture was stirred at 0° C. for 30 min., then at room temperature overnight. The reaction was quenched by adding water and extracted with EtOAc. The EtOAc extracts were washed with water, brine and dried over Na$_2$SO$_4$. Removal of the solvent and purification of the residue gave the title compound N'-((2R,3S)-2-(7-cyanobenzo[b]thiophen-4-ylamino)-3-hydroxybutanoyl)-4-fluorobenzohydrazide (0.55 g, 71%). $^1$H NMR (400 MHz, Acetone-d$_6$, δ in ppm) 8.02 (dd, J=5.7, 8.6 Hz, 2H), 7.82 (d, J=5.5 Hz, 1H), 7.74 (d, J=5.5 Hz, 1H), 7.68 (d, J=8.0 Hz, 1H), 7.27 (t, J=8.6 Hz, 2H), 6.66 (d, J=8.0 Hz, 1H), 6.20 (d, J=7.2 Hz, 1H), 4.41 (m, 1H), 4.22 (dd, J=3.6, 7.2 Hz, 1H), 1.39 (d, J=6.4 Hz, 3H).

Example 62

4-((1R,2S)-1-(5-(4-fluorophenyl)-1,3,4-oxadiazol-2-yl)-2-hydroxypropylamino)benzo[b]thiophene-7-carbonitrile

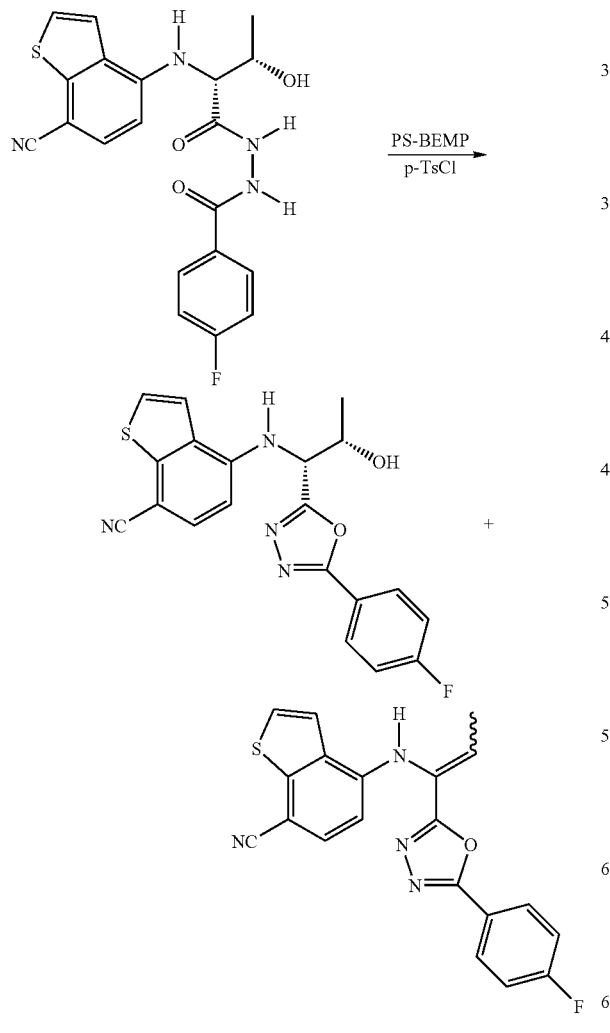

To a solution of N'-((2R,3S)-2-(7-cyanobenzo[b]thiophen-4-ylamino)-3-hydroxybutanoyl)-4-fluorobenzohydrazide (0.53 g, 1.29 mmol) in THF (90 mL) was added PS-BEMP (1.76 g, 3.87 mmol, ~2.2 mmol/g) and p-TsCl (265 mg, 1.39 mmol) at room temperature. The mixture was stirred at room temperature for 8 h, then methanol (5 mL) was added to quench the reaction. The resin was filtered and washed with MeOH. The combined filtrate was concentrated to give a residue, which was purified by flash chromatography to afford the title compound 4-((1R,2S)-1-(5-(4-fluorophenyl)-1,3,4-oxadiazol-2-yl)-2-hydroxypropylamino)benzo[b]thiophene-7-carbonitrile (139 mg, 27%) and the dehydration product 4-(1-(5-(4-fluorophenyl)-1,3,4-oxadiazol-2-yl)prop-1-enylamino)benzo[b]thiophene-7-carbonitrile (8 mg, 2%). Title compound: $^1$H NMR (400 MHz, Acetone-d$_6$, δ in ppm) 8.03 (dd, J=5.3, 8.8 Hz, 2H), 7.88 (d, J=5.7 Hz, 1H), 7.73 (d, J=5.7 Hz, 1H), 7.63 (d, J=8.2 Hz, 1H), 7.32 (t, J=8.8 Hz, 2H), 6.83 (d, J=8.2 Hz, 1H), 6.48 (d, J=8.4 Hz, 1H), 5.20 (dd, J=4.7, 8.4 Hz, 1H), 4.78 (b, 1H), 4.63 (m, 1H), 1.41 (d, J=6.4 Hz, 3H). Dehydration product: $^1$H NMR (400 MHz, Acetone-d$_6$, δ in ppm) 8.11 (dd, J=5.3, 8.6 Hz, 2H), 7.96 (d, J=5.6 Hz, 1H), 7.80 (d, J=5.6 Hz, 1H), 7.62 (d, J=8.2 Hz, 1H), 7.37 (t, J=8.6 Hz, 2H), 7.01 (q, J=7.1 Hz, 1H), 6.57 (d, J=8.2 Hz, 1H), 1.93 (d, J=7.1 Hz, 3H).

Example 63

4-((1R,2S)-2-hydroxy-1-(5-phenyl-1,3,4-oxadiazol-2-yl)propylamino)benzo[b]thiophene-7-carbonitrile

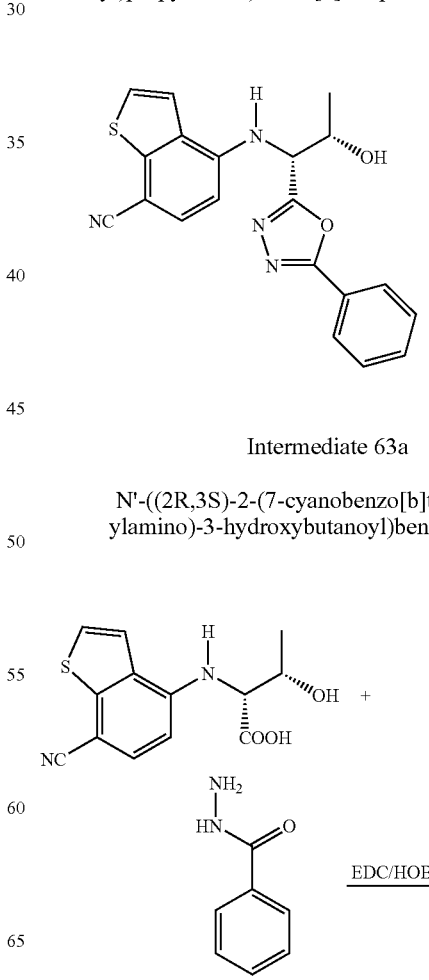

Intermediate 63a

N'-((2R,3S)-2-(7-cyanobenzo[b]thiophen-4-ylamino)-3-hydroxybutanoyl)benzohydrazide -continued

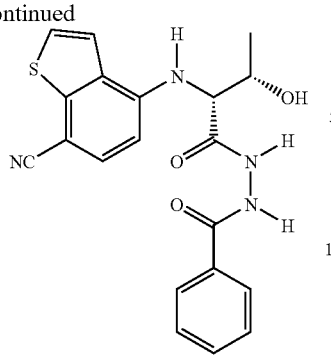

To a mixture of (2R,3S)-2-(7-cyanobenzo[b]thiophen-4-ylamino)-3-hydroxybutanoic acid (intermediate 60a) (0.66 g, 2.39 mmol), benzoic hydrazide (330 mg, 2.42 mmol), HOBt (328 mg, 2.42 mmol) in THF:DMF (1:1) (30 mL) was added EDC (698 mg, 3.64 mmol) and Et$_3$N (0.51 mL, 3.66 mmol) at 0° C. The mixture was stirred at 0° C. for 30 min., then at room temperature overnight. The reaction was quenched by adding water and extracted with EtOAc. The EtOAc extracts were washed with water, brine and dried over Na$_2$SO$_4$. Removal of the solvent and purification of the residue gave the title compound N'-((2R,3S)-2-(7-cyanobenzo[b]thiophen-4-ylamino)-3-hydroxybutanoyl)benzohydrazide (0.72 g, 76%). $^1$H NMR (400 MHz, Acetone-d$_6$, δ in ppm) 7.94 (m, 2H), 7.82 (d, J=5.7 Hz, 1H), 7.73 (d, J=5.7 Hz, 1H), 7.68 (d, J=8.2 Hz, 1H), 7.59 (m, 1H), 7.50 (m, 2H), 6.66 (d, J=8.2 Hz, 1H), 6.20 (d, J=7.4 Hz, 1H), 4.41 (m, 1H), 4.22 (dd, J=3.5, 7.4 Hz, 1H), 1.39 (d, J=6.4 Hz, 3H).

Example 63

4-((1R,2S)-2-hydroxy-1-(5-phenyl-1,3,4-oxadiazol-2-yl)propylamino)benzo[b]thiophene-7-carbonitrile

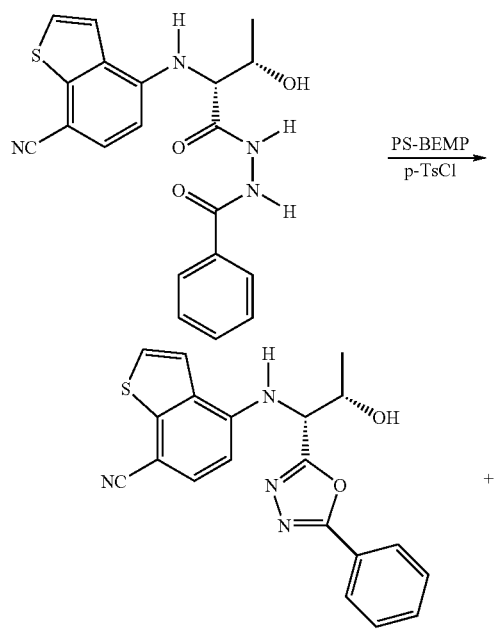

-continued

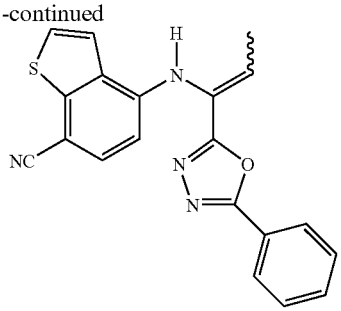

To a solution of N'-((2R,3S)-2-(7-cyanobenzo[b]thiophen-4-ylamino)-3-hydroxybutanoyl)benzohydrazide (0.69 g, 1.75 mmol) in THF (100 mL) were added PS-BEMP (2.39 g, 5.27 mmol, ~2.2 mmol/g) and p-TsCl (353 mg, 1.85 mmol) at room temperature. The mixture was stirred at room temperature for 14 h, then methanol (5 mL) was added to quench the reaction. The resin was filtered and washed with MeOH. The combined filtrate was concentrated to give a residue, which was purified by flash chromatography to afford the title compound 4-((1R,2S)-2-hydroxy-1-(5-phenyl-1,3,4-oxadiazol-2-yl)propylamino)benzo[b]thiophene-7-carbonitrile (167 mg, 25%) as a foam and the dehydration product 4-(1-(5-phenyl-1,3,4-oxadiazol-2-yl)prop-1-enylamino)benzo[b]thiophene-7-carbonitrile (33 mg, 5%). Title compound: $^1$H NMR (400 MHz, Acetone-d$_6$, δ in ppm) 7.98 (m, 2H), 7.88 (d, J=5.7 Hz, 1H), 7.72 (d, J=5.7 Hz, 1H), 7.63 (d, J=8.2 Hz, 1H), 7.51~7.57 (m, 3H), 6.85 (d, J=8.2 Hz, 1H), 6.50 (d, J=8.4 Hz, 1H), 5.22 (dd, J=4.7, 8.4 Hz, 1H), 4.80 (b, 1H), 4.65 (m, 1H), 1.42 (d, J=6.4 Hz, 3H). Dehydration product: $^1$H NMR (400 MHz, Acetone-d$_6$, δ in ppm) 8.05 (m, 2H), 7.95 (d, J=5.6 Hz, 1H), 7.78 (d, J=5.6 Hz, 1H), 7.55~7.62 (m, 4H), 7.01 (q, J=7.1 Hz, 1H), 6.57 (d, J=8.4 Hz, 1H), 1.93 (d, J=7.1 Hz, 3H).

Example 64

4-((1R,2R)-1-(5-(4-fluorophenyl)-1,3,4-oxadiazol-2-yl)-2-hydroxypropylamino)benzo[b]thiophene-7-carbonitrile

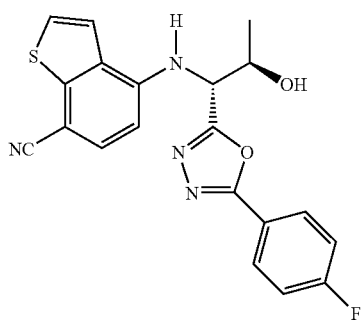

Intermediate 64a

N'-((2R,3R)-2-(7-cyanobenzo[b]thiophen-4-ylamino)-3-hydroxybutanoyl)-4-fluorobenzohydrazide

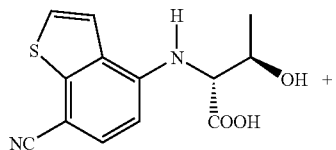

+

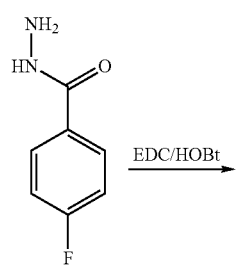

EDC/HOBt →

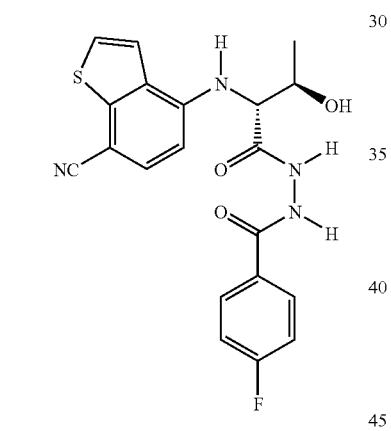

To a mixture of (2R,3R)-2-(7-cyanobenzo[b]thiophen-4-ylamino)-3-hydroxybutanoic acid (intermediate 61a) (0.56 g, 2.02 mmol), 4-fluorobenzoic hydrazide (316 mg, 2.05 mmol), HOBt (277 mg, 2.05 mmol) in THF:DMF (1:1) (30 mL) was added EDC (583 mg, 3.04 mmol) and Et$_3$N (0.43 mL, 3.08 mmol) at 0° C. The mixture was stirred at 0° C. for 30 min., then at room temperature overnight. The reaction was quenched by adding water and extracted with EtOAc. The EtOAc extracts were washed with water, brine and dried over Na$_2$SO$_4$. Removal of the solvent and purification of the residue gave two fractions. The first fraction (282 mg) contained mainly the title compound and some impurities. The second fraction was the pure desired compound N'-((2R,3R)-2-(7-cyanobenzo[b]thiophen-4-ylamino)-3-hydroxybutanoyl)-4-fluorobenzohydrazide (0.42 g, 50%). $^1$H NMR (400 MHz, Acetone-d$_6$, δ in ppm) 8.01 (dd, J=5.3, 8.8 Hz, 2H), 7.81 (d, J=5.7 Hz, 1H), 7.68 (d, J=5.7 Hz, 1H), 7.65 (d, J=8.2 Hz, 1H), 7.25 (t, J=8.8 Hz, 2H), 6.68 (d, J=8.2 Hz, 1H), 6.39 (d, J=7.4 Hz, 1H), 4.19~4.26 (m, 2H), 1.39 (d, J=6.2 Hz, 3H).

Example 64

4-((1R,2R)-1-(5-(4-fluorophenyl)-1,3,4-oxadiazol-2-yl)-2-hydroxypropylamino)benzo[b]thiophene-7-carbonitrile

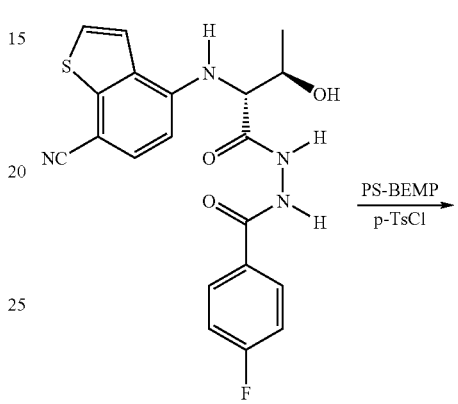

PS-BEMP
p-TsCl →

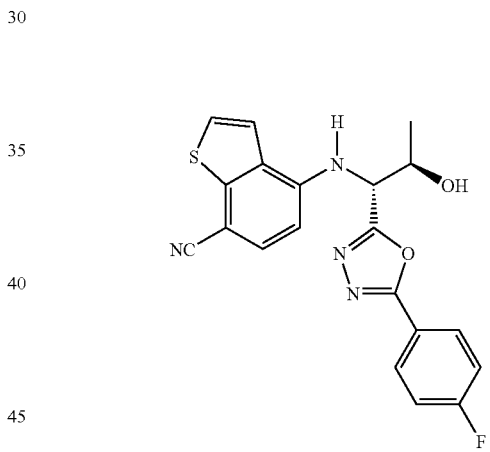

To a solution of N'-((2R,3R)-2-(7-cyanobenzo[b]thiophen-4-ylamino)-3-hydroxybutanoyl)-4-fluorobenzohydrazide (0.41 g, 0.99 mmol) in THF (80 mL) was added PS-BEMP (1.36 g, 2.99 mmol, ~2.2 mmol/g) and p-TsCl (191 mg, 1.0 mmol) at room temperature. The mixture was stirred at room temperature for 15 h, then methanol (5 mL) was added to quench the reaction. The resin was filtered and washed with MeOH. The combined filtrate was concentrated to give a residue, which was purified by flash chromatography to afford the title compound 4-((1R,2R)-1-(5-(4-fluorophenyl)-1,3,4-oxadiazol-2-yl)-2-hydroxypropylamino)benzo[b]thiophene-7-carbonitrile (170 mg, 43%). $^1$H NMR (400 MHz, Acetone-d$_6$, δ in ppm) 8.03 (dd, J=5.3, 8.8 Hz, 2H), 7.84 (d, J=5.6 Hz, 1H), 7.71 (d, J=5.6 Hz, 1H), 7.64 (d, J=8.2 Hz, 1H), 7.32 (t, J=8.8 Hz, 2H), 6.86 (d, J=8.2 Hz, 1H), 6.69

(d, J=8.8 Hz, 1H), 5.13 (dd, J=6.4, 8.8 Hz, 1H), 4.66 (d, J=6.1 Hz, 1H), 4.57 (m, 1H), 1.48 (d, J=6.2 Hz, 3H).

Example 65

4-((1R,2R)-2-hydroxy-1-(5-phenyl-1,3,4-oxadiazol-2-yl)propylamino)benzo[b]thiophene-7-carbonitrile

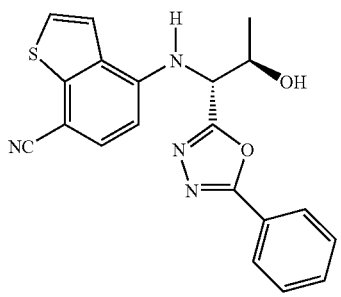

Intermediate 65a

N'-((2R,3R)-2-(7-cyanobenzo[b]thiophen-4-ylamino)-3-hydroxybutanoyl)benzohydrazide

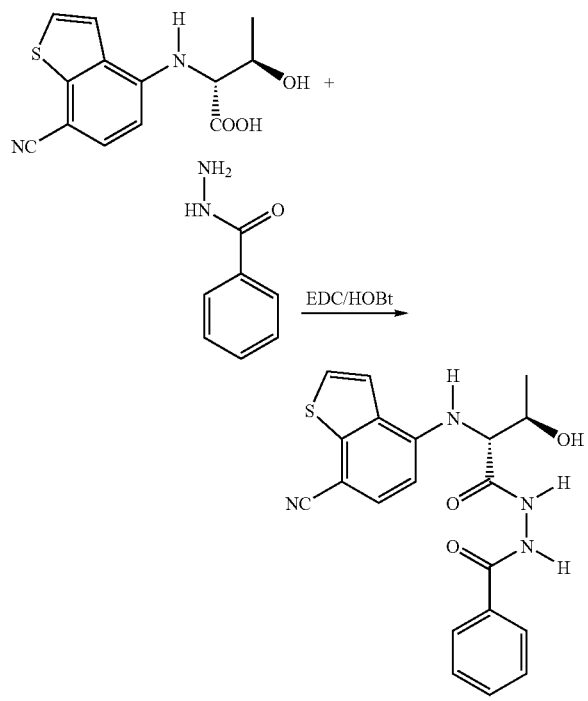

To a mixture of (2R,3R)-2-(7-cyanobenzo[b]thiophen-4-ylamino)-3-hydroxybutanoic acid (intermediate 61a) (0.62 g, 2.24 mmol), benzoic hydrazide (310 mg, 2.28 mmol), HOBt (308 mg, 2.28 mmol) in THF:DMF (1:1) (30 mL) was added EDC (645 mg, 3.36 mmol) and Et₃N (0.47 mL, 3.37 mmol) at 0° C. The mixture was stirred at 0° C. for 30 min., then at room temperature overnight. The reaction was quenched by adding water and extracted with EtOAc. The EtOAc extracts were washed with water, brine and dried over Na₂SO₄. After concentration, the residue was purified by flash chromatography to give two fractions. The first fraction (208 mg) contained mainly the title compound and some impurities. The second fraction was the pure desired compound N'-((2R,3R)-2-(7-cyanobenzo[b]thiophen-4-ylamino)-3-hydroxybutanoyl)benzohydrazide (0.58 g, 66%). ¹H NMR (400 MHz, Acetone-d₆, δ in ppm) 7.95 (m, 2H), 7.84 (d, J=5.7 Hz, 1H), 7.71 (d, J=5.7 Hz, 1H), 7.67 (d, J=8.2 Hz, 1H), 7.60 (m, 1H), 7.50 (m, 2H), 6.69 (d, J=8.2 Hz, 1H), 6.37 (d, J=6.9 Hz, 1H), 4.18~4.26 (m, 2H), 1.41 (d, J=6.3 Hz, 3H).

Example 65

4-((1R,2R)-2-hydroxy-1-(5-phenyl-1,3,4-oxadiazol-2-yl)propylamino)benzo[b]thiophene-7-carbonitrile

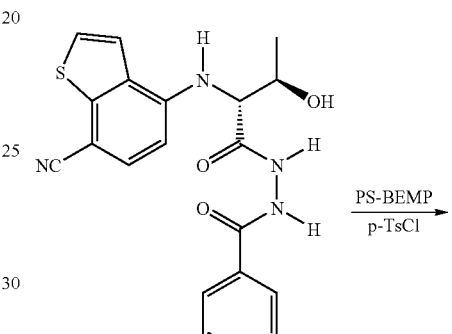

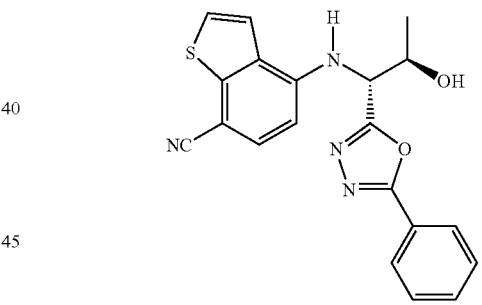

To a solution of N'-((2R,3R)-2-(7-cyanobenzo[b]thiophen-4-ylamino)-3-hydroxybutanoyl)benzohydrazide (0.56 g, 1.42 mmol) in THF (120 mL) was added PS-BEMP (1.94 g, 4.27 mmol, ~2.2 mmol/g) and p-TsCl (275 mg, 1.44 mmol) at room temperature. The mixture was stirred at room temperature for 18 h, then methanol (5 mL) was added to quench the reaction. The resin was filtered and washed with MeOH. The combined filtrate was concentrated to give a residue, which was purified by flash chromatography to afford the title compound 4-((1R,2R)-2-hydroxy-1-(5-phenyl-1,3,4-oxadiazol-2-yl)propylamino)benzo[b]thiophene-7-carbonitrile (229 mg, 43%). ¹H NMR (400 MHz, Acetone-d₆, δ in ppm) 7.98 (m, 2H), 7.85 (d, J=5.5 Hz, 1H), 7.71 (d, J=5.5 Hz, 1H), 7.64 (d, J=8.4 Hz, 1H), 7.51~7.57 (m, 3H), 6.87 (d, J=8.4 Hz, 1H), 6.71 (d, J=8.8 Hz, 1H), 5.14 (dd, J=6.5, 8.8 Hz, 1H), 4.66 (d, J=6.0 Hz, 1H), 4.58 (m, 1H), 1.49 (d, J=6.2 Hz, 3H).

Example 66

5-(5-((1R,2R)-2-(Butyryloxy)-1-(3-chloro-4-cyano-2-methylphenylamino)propyl)-1,3,4-oxa-diazol-2-yl)-2-fluorophenyl butyrate

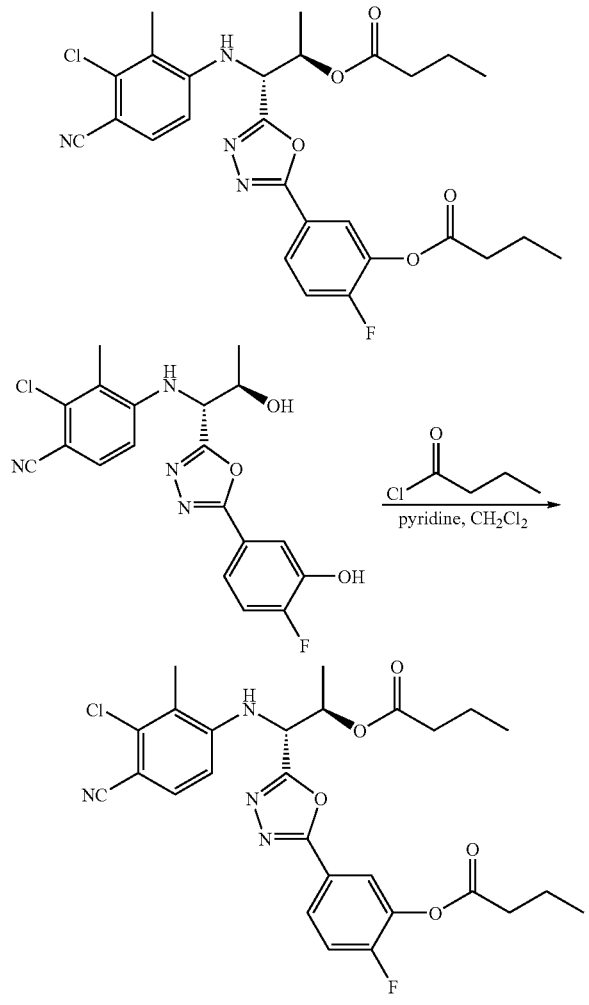

To a solution of 2-chloro-4-((1R,2R)-1-(5-(4-fluoro-3-hydroxyphenyl)-1,3,4-oxadiazol-2-yl)-2-hydroxypropylamino)-3-methylbenzonitrile (Example 41) (135.5 mg, 0.34 mmol) in pyridine (0.6 mL) and CH$_2$Cl$_2$ (4 mL) was added n-butyryl chloride (0.17 mL, 1.68 mmol). Upon complete addition the reaction mixture was stirred for 23 h, then quenched with 10% aqueous HCl (6 mL). The mixture was partitioned between H$_2$O (40 mL) and CH$_2$Cl$_2$ (40 mL). The aqueous layer was extracted with CH$_2$Cl$_2$ (40 mL). The combined organic extracts were washed with NaHCO$_3$ (45 mL), dried (Na$_2$SO$_4$), filtered and concentrated under reduced pressure to provide a yellow oil, which was purified by flash chromatography over silica gel (20-25% EtOAc in hexanes) to provide the title compound as an off white solid (137.3 mg, 74%): $^1$H NMR (400 MHz, d$_6$-acetone, δ in ppm) 7.94 (ddd, J=2.2, 4.5, 8.6 Hz, 1H), 7.86 (dd, J=2.0, 7.0 Hz, 1H), 7.52 (d, J=8.6 Hz, 1H), 7.52 (dd, J=8.8, 10.0 Hz, 1H), 6.95 (d, J=8.8 Hz, 1H), 6.13 (d, J=8.8 Hz, 1H), 5.68 (pentet, J=6.5 Hz, 1H), 5.36 (dd, J=6.5, 8.4 Hz, 1H), 2.67 (t, J=7.2 Hz, 2H), 2.28-2.22 (m, 2H), 2.07-2.03 (m, 2H), 1.82-1.71 (m, 2H), 1.53 (d, J=6.5 Hz, 3H), 1.03 (t, J=7.2 Hz, 3H), 0.82 (t, J=7.4 Hz, 3H).

Example 67

4-(5-((1R,2S)-2-(Butyryloxy)-1-(3-chloro-4-cyano-2-methylphenylamino)propyl)-1,3,4-oxa-diazol-2-yl)-2-chlorophenyl butyrate

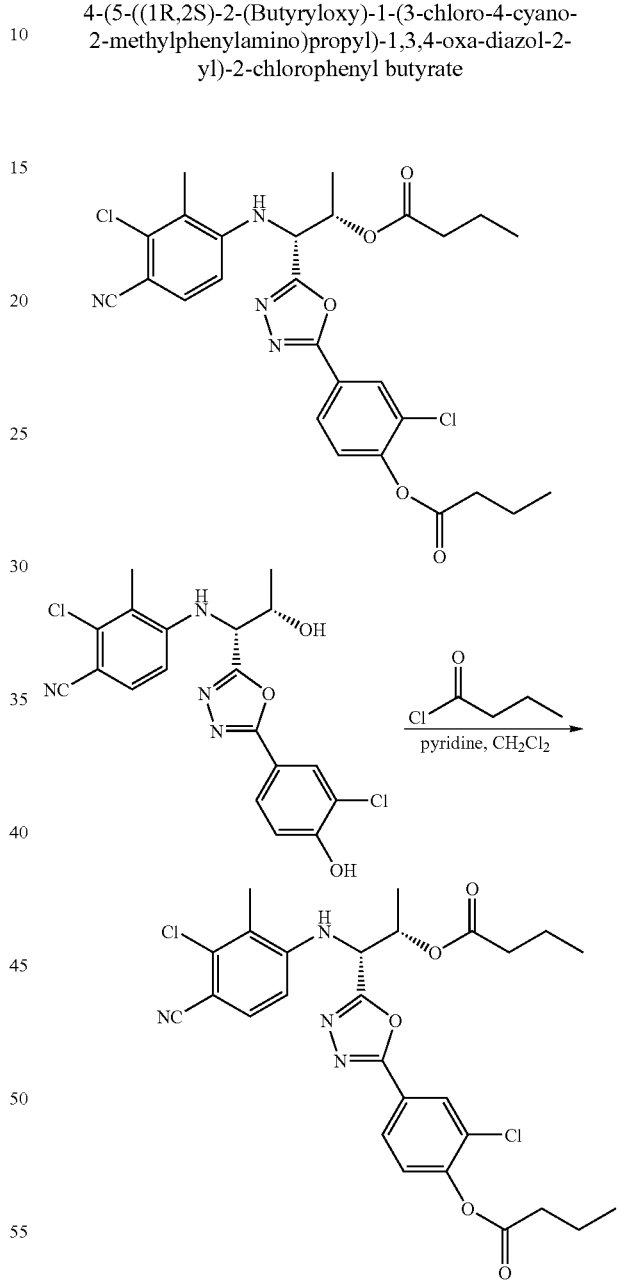

To a solution of 2-chloro-4-((1R,2S)-1-(5-(3-chloro-4-hydroxyphenyl)-1,3,4-oxadiazol-2-yl)-2-hydroxypropylamino)-3-methylbenzonitrile (example 37) (96.5 mg, 0.23 mmol) in pyridine (0.6 mL) and CH$_2$Cl$_2$ (4 mL) was added n-butyryl chloride (0.12 mL, 1.15 mmol). Upon complete addition the reaction mixture was stirred for 23 h, then quenched with 10% aqueous HCl (10 mL). The mixture was partitioned between H$_2$O (25 mL) and CH$_2$Cl$_2$ (30 mL). The aqueous layer was extracted with CH$_2$Cl$_2$ (20 mL). The combined organic extracts were washed with NaHCO₃ (30 mL), dried (Na₂SO₄), filtered and concentrated under reduced pressure to provide an orange/brown viscous oil, which was purified by flash chromatography over silica gel (20-25% EtOAc in hexanes) to provide the title compound as an off white solid (116 mg, 90%): ¹H NMR (400 MHz, d₆-acetone, δ in ppm) 8.11 (d, J=2.0 Hz, 1H), 8.03 (dd, J=2.2, 8.4 Hz, 1H), 7.54 (d, J=8.6 Hz, 1H), 7.49 (d, J=8.4 Hz, 1H), 7.01 (d, J=8.8 Hz, 1H), 5.74 (d, J=9.0 Hz, 1H), 5.67 (dq, J=5.7, 6.5 Hz, 1H), 5.45 (dd, J=5.7, 8.6 Hz, 1H), 2.67 (t, J=7.4 Hz, 2H), 2.33-2.28 (m, 2H), 1.83-1.72 (m, 2H), 1.66-1.52 (m, 2H), 1.47 (d, J=6.5 Hz, 3H), 1.04 (t, J=7.4 Hz, 3H), 0.86 (t, J=7.4 Hz, 3H).

Example 68

2-chloro-4-((1R,2S)-2-hydroxy-1-(5-(4-(trifluoromethyl)phenyl)-1,3,4-oxadiazol-2-yl)propylamino)-3-methylbenzonitrile

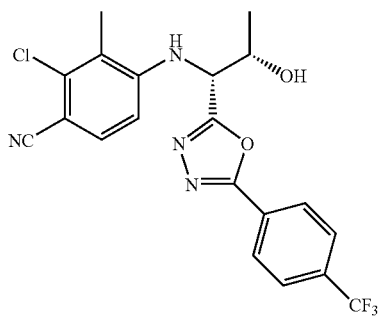

Intermediate 68a

N'-((2R,3S)-2-(3-Chloro-4-cyano-2-methylphenylamino)-3-hydroxybutanoyl)-4-(trifluoromethyl)benzohydrazide

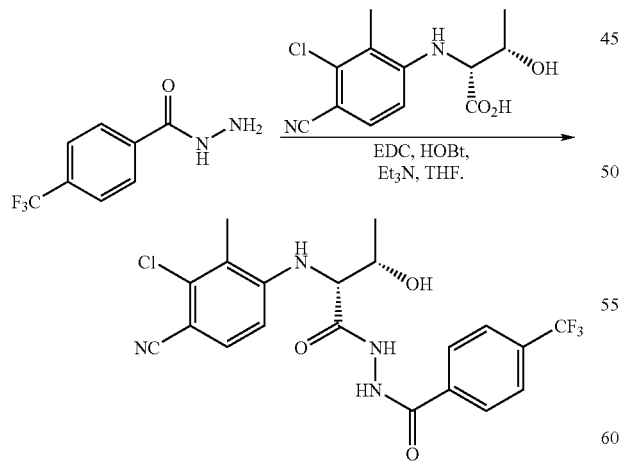

To a pre-cooled (−45° C.) solution of (2R,3S)-2-(3-chloro-4-cyano-2-methylphenylamino)-3-hydroxybutanoic acid (intermediate 1a) (1.97 g, 7.35 mmol) and 4-(trifluoromethyl)benzohydrazide (1.50 g, 7.35 mmol) in anhydrous THF (80 mL) was added 1-Hydroxybenzotriazole monohydrate (1.13 g, 7.35 mmol) and N-(3-Dimethylaminopropyl)-N'-ethylcarbodimide-HCl (2.82 g, 14.7 mmol) at −45° C. followed by triethylamine (2.0 mL, 14.7 mmol). The reaction mixture warmed to room temperature and stirred for 23 h, then quenched with 5% aq. citric acid (300 mL). The solution was extracted with EtOAc (300 mL). The organic extract was washed with 5% aq. citric acid (2×150 mL), sat. aq. NaHCO₃ (3×150 mL), H₂O (2×150 mL), dried (Na₂SO₄), filtered and concentrated under reduced pressure to provide the title compound as a off white solid (3.09 g, 92%): ¹H NMR (400 MHz, d₆-DMSO, δ in ppm) 10.71 (s, 1H), 10.31 (s, 1H), 8.05 (d, J=8.2 Hz, 2H), 7.89 (d, J=8.2 Hz, 2H), 7.61 (d, J=8.6 Hz, 1H), 6.66 (d, J=8.8 Hz, 1H), 5.67 (d, J=7.6 Hz, 1H), 5.31 (d, J=5.7 Hz, 1H), 4.14 (sextet, J=6.1 Hz, 1H), 3.94 (dd, J=5.7, 7.2 Hz, 1H), 2.30 (s, 3H), 1.28 (d, J=6.3 Hz, 3H).

Example 68

2-chloro-4-((1R,2S)-2-hydroxy-1-(5-(4-(trifluoromethyl)phenyl)-1,3,4-oxadiazol-2-yl)propylamino)-3-methylbenzonitrile

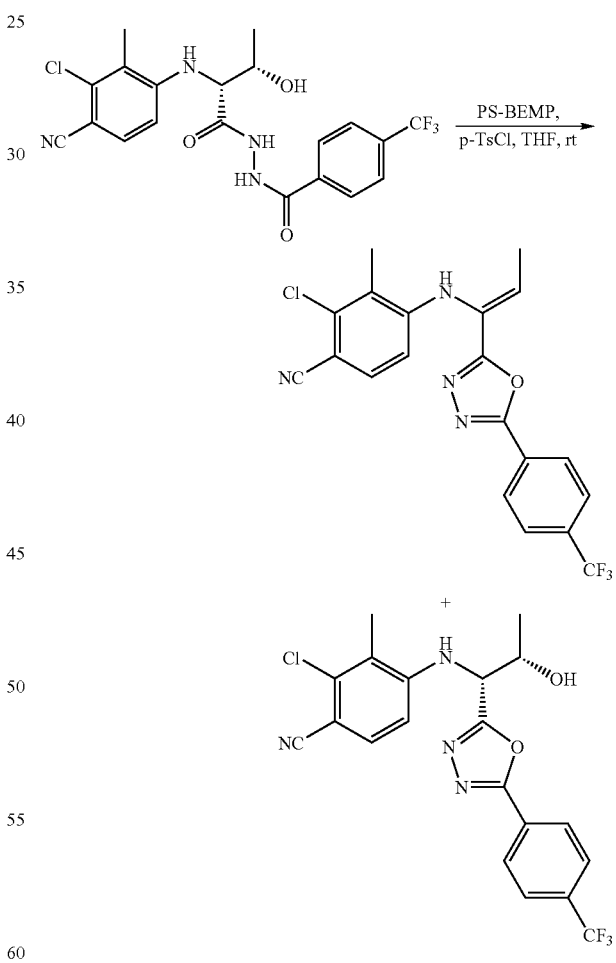

To a solution of N'-((2R,3S)-2-(3-chloro-4-cyano-2-methylphenylamino)-3-hydroxybutanoyl)-4-(trifluoromethyl)benzohydrazide (1.0 g, 2.20 mmol) in anhydrous THF (90 mL) at room temperature was added 2-tert-butylamino-2-diethylamino-1,3-dimethyl perhydro-1,3,2-diazaphosphorine on polystyrene (2.2 mmol base/g) (3.0 g, 6.60 mmol)

followed by para-toluenesulfonyl chloride (419 mg, 2.20 mmol) and the mixture was stirred for one hour. The mixture was filtered under suction and the residue washed with acetone (2×100 mL) followed by Methanol (2×150 mL). The filtrate was concentrated under reduced pressure to provide a yellow oil, which was purified by flash chromatography over silica gel (20-40% EtOAc in hexanes) to provided (Z)-2-chloro-3-methyl-4-(1-(5-(4-(trifluoromethyl)phenyl)-1,3,4-oxadiazol-2-yl)prop-1-enylamino)benzonitrile, the less polar component as a colourless solid (122 mg, 13%) and 2-chloro-4-((1R,2S)-2-hydroxy-1-(5-(4-(trifluoromethyl)phenyl)-1,3,4-oxadiazol-2-yl)propylamino)-3-methylbenzonitrile, the more polar component as a yellow oil (336 mg, 35%): Less polar compound; $^1$H NMR (400 MHz, d$_6$-acetone, δ in ppm) 8.27 (d, J=8.0 Hz, 2H), 7.93 (d, J=8.0 Hz, 2H), 7.44 (d, J=8.6 Hz, 1H), 7.13 (br s, 1H), 7.04 (q, J=7.2 Hz, 1H), 6.62 (d, J=8.8 Hz, 1H), 2.47 (s, 3H), 1.91 (d, J=7.0 Hz, 3H): More polar compound; $^1$H NMR (400 MHz, d$_6$-acetone, δ in ppm) 8.22 (d, J=8.0 Hz, 2H), 7.92 (d, J=8.2 Hz, 2H), 7.48 (d, J=8.6 Hz, 1H), 6.87 (d, J=8.8 Hz, 1H), 5.70 (d, J=8.6 Hz, 1H), 5.16 (dd, J=3.5, 8.6 Hz, 1H), 4.86 (br d, J=4.3 Hz, 1H), 4.70-4.61 (m, 1H), 2.40 (s, 3H), 1.43 (d, J=6.4 Hz, 3H).

Example 69

N'-(4-(5-((1R,2R)-1-(3-Chloro-4-cyano-2-methylphenylamino)-2-hydroxypropyl)-1,3,4-oxadiazol-2-yl)phenyl)benzamide

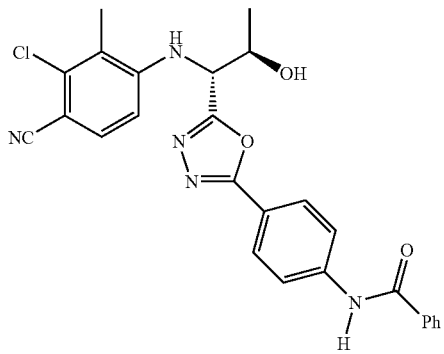

Intermediate 69a

N'-((2R,3R)-2-(3-Chloro-4-cyano-2-methylphenylamino)-3-hydroxybutanoyl)-4-nitrobenzohydrazide

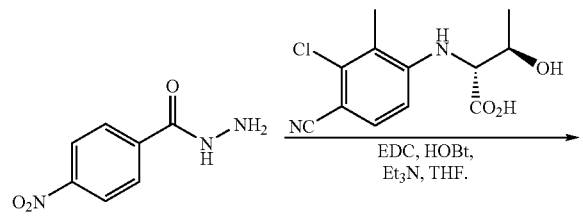

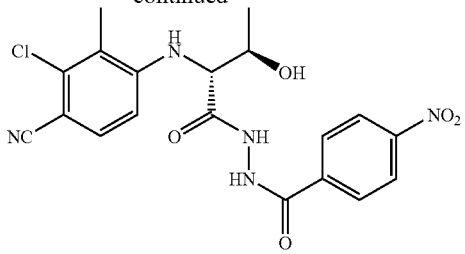

To a pre-cooled (−45° C.) solution of (2R,3R)-2-(3-chloro-4-cyano-2-methylphenylamino)-3-hydroxybutanoic acid (intermediate 3a) (18.54 g, 69.0 mmol) and 4-nitrobenzohydrazide (12.5 g, 69.0 mmol) in anhydrous THF (400 mL) was added 1-Hydroxybenzotriazole monohydrate (10.57 g, 69.0 mmol) and N-(3-Dimethylaminopropyl)-N'-ethylcarbodiimide-HCl (26.46 g, 138.0 mmol) at −45° C. followed by triethylamine (19.2 mL, 138.0 mmol). The reaction mixture warmed to room temperature and stirred for 66 h, then quenched with 5% aq. citric acid (350 mL). The solution was extracted with EtOAc (300 mL). The organic extract was washed with 5% aq. citric acid (2×300 mL), sat. aq. NaHCO$_3$ (3×300 mL), H$_2$O (2×300 mL), dried (Na$_2$SO$_4$), filtered and concentrated under reduced pressure to provide the title compound as a yellow solid (26.4 g, 89%): $^1$H NMR (400 MHz, d$_6$-acetone, δ in ppm) 8.37 (dm, J=9.0 Hz, 2H), 8.18 (dm, J=9.0 Hz, 2H), 7.54 (d, J=8.6 Hz, 1H), 6.75 (d, J=8.4 Hz, 1H), 5.59 (d, J=7.2 Hz, 1H), 4.29 (pentet, J=5.3 Hz, 1H), 4.17 (dd, J=5.1, 7.2 Hz, 1H), 2.36 (s, 3H), 1.40 (d, J=6.5 Hz, 3H).

Intermediate 69b

N'-((2R,3R)-3-(tert-Butyldimethylsilyloxy)-2-(3-chloro-4-cyano-2-methylphenylamino)butanoyl)-4-nitrobenzohydrazide

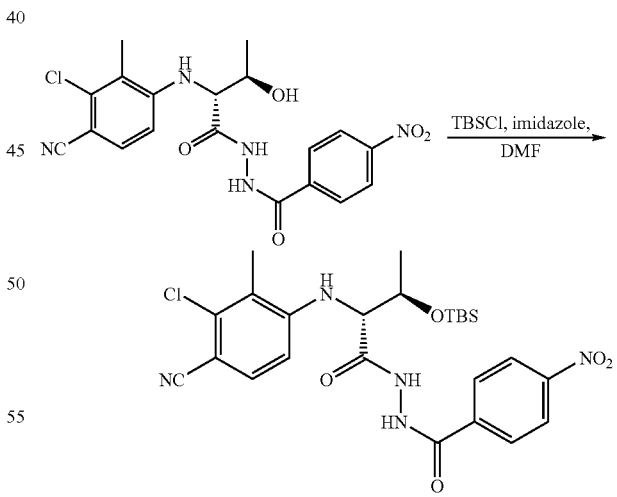

To a pre-cooled (0° C.) solution of N'-((2R,3R)-2-(3-chloro-4-cyano-2-methylphenylamino)-3-hydroxybutanoyl)-4-nitrobenzohydrazide (12.0 g, 27.79 mmol) in DMF (650 mL) was added imidazole (15.13 g, 222.31 mmol) then TBSCl (16.75 g, 111.15 mmol). The reaction was warmed slowly to room temperature, stirred for 72 h, cooled to 0° C. and quenched with H$_2$O (600 mL). The solution was extracted with EtOAc (700 mL). The organic extract was washed with H₂O (2×300 mL) and 5% aq. citric acid (3×250 mL), dried (Na₂SO₄), filtered and concentrated under reduced pressure to provide a light yellow oil, which was purified by flash chromatography over silica gel (30-40% EtOAc in hexanes) to provide the title compound as a colourless solid (8.50 g, 56%): ¹H NMR (400 MHz, d₆-DMSO, δ in ppm) 10.93 (s, 1H), 10.57 (s, 1H), 8.34 (dm, J=8.8 Hz, 2H), 8.07 (dm, J=9.0 Hz, 2H), 7.59 (d, J=8.6 Hz, 1H), 6.84 (d, J=9.0 Hz, 1H), 5.69 (d, J=8.4 Hz, 1H), 5.28 (s, 1H), 4.38 (pentet, J=6.3 Hz, 1H), 4.16 (dd, J=6.5, 8.0 Hz, 1H), 2.26 (s, 3H), 1.27 (d, J=6.3 Hz, 3H), 0.85 (s, 9H), 0.08 (s, 3H), 0.05 (s, 3H).

Intermediate 69c 4-((1R,2R)-2-(tert-Butyldimethylsilyloxy)-1-(5-(4-nitrophenyl)-1,3,4-oxadiazol-2-yl)propylamino)-2-chloro-3-methylbenzonitrile

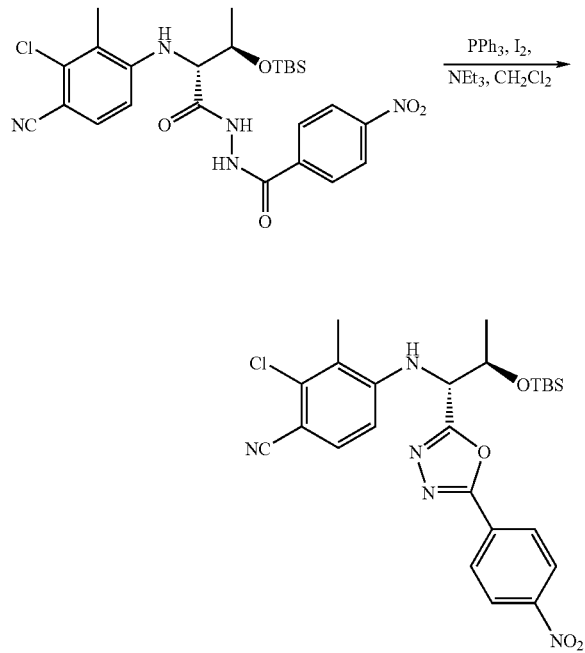

A solution of N'-((2R,3R)-3-(tert-butyldimethylsilyloxy)-2-(3-chloro-4-cyano-2-methylphenylamino)butanoyl)-4-nitrobenzohydrazide (8.5 g, 15.57 mmol) in CH₂Cl₂ (250 mL) was added to a pre-cooled (0° C.) mixture of PPh₃ (8.17 g, 31.13 mmol), iodine (7.90 g, 31.13 mmol) and Et₃N (1.11 mL, 7.94 mmol). The reaction mixture was warmed to room temperature, stirred for 50 minutes and quenched with sat. aq. sodium thiosulfate (400 mL). The solution was extracted with CH₂Cl₂ (250 mL). The organic extract was washed with sat. aq. sodium thiosulfate (300 mL), dried (Na₂SO₄), filtered and concentrated under reduced pressure to provide a brown oil, which was purified by flash chromatography over silica gel (20-40% EtOAc in hexanes) to provide the title compound as a light yellow solid (5.5 g, 67%): ¹H NMR (400 MHz, CDCl₃, δ in ppm) 8.37 (dm, J=9.0 Hz, 2H), 8.18 (dm, J=9.0 Hz, 2H), 7.36 (d, J=8.6 Hz, 1H), 6.61 (d, J=8.6 Hz, 1H), 5.11 (d, J=9.2 Hz, 1H), 4.87 (dd, J=3.9, 8.8 Hz, 1H), 4.46 (dq, J=3.7, 6.3 Hz, 1H), 2.34 (s, 3H), 1.31 (d, J=6.3 Hz, 3H), 0.93 (s, 9H), 0.15 (s, 3H), 0.12 (s, 3H).

Intermediate 69d 4-((1R,2R)-1-(5-(4-Aminophenyl)-1,3,4-oxadiazol-2-yl)-2-(tert-butyldimethylsilyloxy)propylamino)-2-chloro-3-methylbenzonitrile

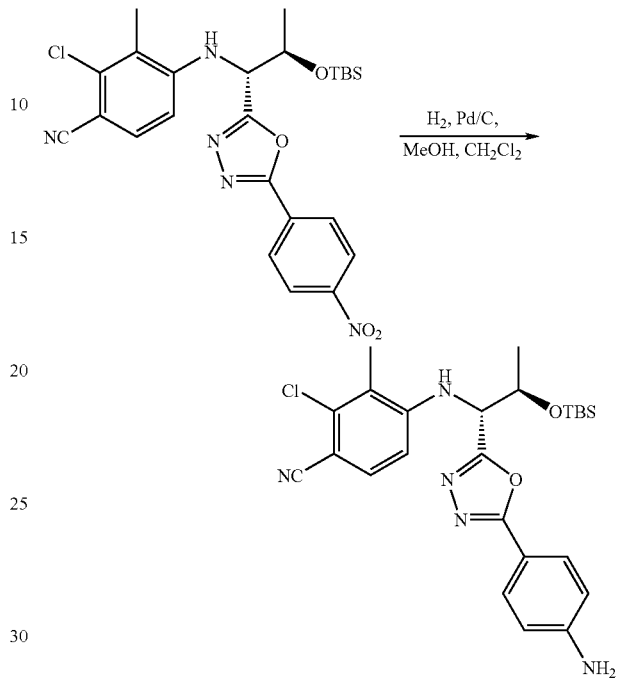

A suspension of 4-((1R,2R)-2-(tert-butyldimethylsilyloxy)-1-(5-(4-nitrophenyl)-1,3,4-oxadiazol-2-yl)propylamino)-2-chloro-3-methylbenzonitrile (1.6 g, 3.03 mmol), 5 wt. % Pd on activated carbon (700 mg) in CH₂Cl₂ (50 mL) was pressurized with 30 psi of H₂ and reacted on a Parr shaker for 5 h. The reaction was filtered through Celite® under N₂ and rinsed with CH₂Cl₂ (3×40 mL). The filtrate was concentrated under reduced pressure to provide a colourless solid (1.40 g, 93%): ¹H NMR (400 MHz, CDCl₃, δ in ppm) 7.76 (dm, J=8.8 Hz, 2H), 7.34 (d, J=8.6 Hz, 1H), 6.70 (dm, J=8.8 Hz, 2H), 6.62 (d, J=8.6 Hz, 1H), 5.11 (d, J=9.0 Hz, 1H), 4.79 (dd, J=3.9, 8.8 Hz, 1H), 4.41 (dq, J=3.9, 6.3 Hz, 1H), 4.05 (s, 2H), 2.32 (s, 3H), 1.28 (d, J=6.3 Hz, 3H), 0.93 (s, 9H), 0.13 (s, 3H), 0.10 (s, 3H).

Intermediate 69e

N-(4-(5-((1R,2R)-2-(tert-Butyldimethylsilyloxy)-1-(3-chloro-4-cyano-2-methylphenylamino)propyl)-1,3,4-oxadiazol-2-yl)phenyl)benzamide

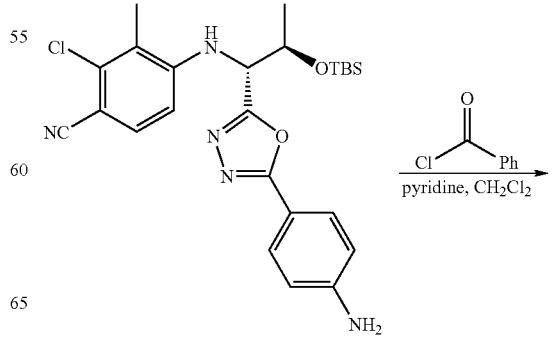

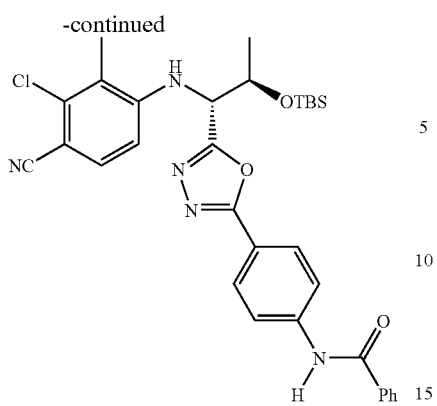

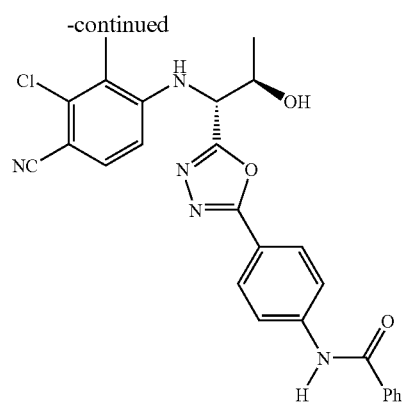

To a solution of 4-((1R,2R)-1-(5-(4-aminophenyl)-1,3,4-oxadiazol-2-yl)-2-(tert-butyldimethylsilyloxy)propylamino)-2-chloro-3-methylbenzonitrile (306 mg, 0.61 mmol) in CH$_2$Cl$_2$ (10 mL) and pyridine (1.5 mL) was added benzoylchloride (0.10 mL, 0.86 mmol) at room temperature. The resultant solution stirred for 24 hours and quenched with 2N aq. HCl (15 mL). The mixture was further partitioned between H$_2$O (40 mL) and CH$_2$Cl$_2$ (40 mL). The aqueous layer was extracted with CH$_2$Cl$_2$ (30 mL). The combined organic extracts were washed with sat. aq. NaHCO$_3$ (2×40 mL), dried (Na$_2$SO$_4$), filtered and concentrated under reduced pressure to provide a colourless oil (367 mg, 100%): $^1$H NMR (400 MHz, d$_6$-acetone, δ in ppm) 9.84 (s 1H), 8.10-7.98 (m, 6H), 7.67-7.48 (m, 4H), 6.96 (d, J=8.6 Hz, 1H), 5.76 (d, J=9.0 Hz, 1H), 5.05 (dd, J=6.5, 9.0 Hz, 1H), 4.67 (pentet, J=6.3 Hz, 1H), 2.36 (s, 3H), 1.45 (d, J=6.3 Hz, 3H), 0.83 (s, 9H), 0.11 (s, 3H), 0.00 (s, 3H).

Example 69

N-(4-(5-((1R,2R)-1-(3-Chloro-4-cyano-2-methylphenylamino)-2-hydroxypropyl)-1,3,4-oxadiazol-2-yl)phenyl)benzamide To a pre-cooled (−55° C.) solution of N-(4-(5-((1R,2R)-2-(tert-butyldimethylsilyloxy)-1-(3-chloro-4-cyano-2-methylphenylamino)propyl)-1,3,4-oxadiazol-2-yl)phenyl)benzamide (367 mg, 0.61 mmol) in THF (25 mL) was added TBAF (0.73 mL, 0.73 mmol, 1 M solution in THF) over 5 minutes. Upon complete addition the reaction mixture was allowed to warm to 13° C. over 3.5 h and quenched with sat. aq. NH$_4$Cl (30 mL). The resulting mixture was partitioned between H$_2$O (30 mL) and EtOAc (40 mL). The aqueous layer was extracted with EtOAc (30 mL). The combined organic extracts were dried (Na$_2$SO$_4$), filtered and concentrated under reduced pressure to provide a yellow oil, which was purified by flash chromatography over silica gel (20-60% EtOAc in hexanes) to provided the title compound as a colourless solid (270 mg, 91%): $^1$H NMR (400 MHz, d$_6$-acetone, δ in ppm) 9.83 (s 1H), 8.08-7.95 (m, 6H), 7.63-7.47 (m, 4H), 6.90 (d, J=8.6 Hz, 1H), 5.88 (d, J=8.8 Hz, 1H), 5.06 (dd, J=5.5, 8.8 Hz, 1H), 4.68 (br s, 1H), 4.53 (pentet, J=6.1 Hz, 1H), 2.37 (s, 3H), 1.43 (d, J=6.5 Hz, 3H).

Example 70

N-(4-(5-((1R,2R)-1-(3-Chloro-4-cyano-2-methylphenylamino)-2-hydroxypropyl)-1,3,4-oxadiazol-2-yl)phenyl)acetamide

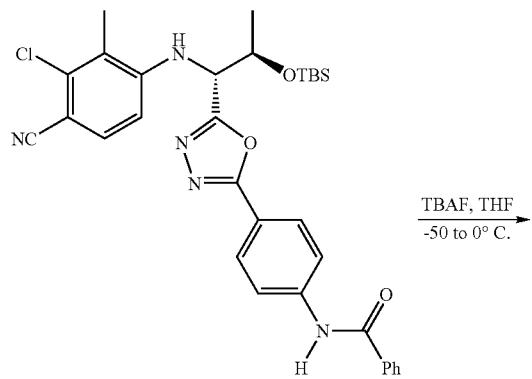

TBAF, THF
−50 to 0° C.

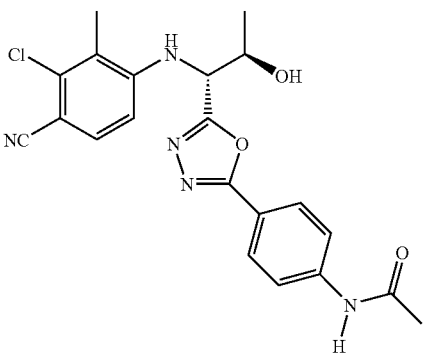

Intermediate 70a

N-(4-(5-((1R,2R)-2-(tert-Butyldimethylsilyloxy)-1-(3-chloro-4-cyano-2-methylphenylamino)propyl)-1,3,4-oxadiazol-2-yl)phenyl)acetamide

Example 70

N-(4-(5-((1R,2R)-1-(3-Chloro-4-cyano-2-methylphenylamino)-2-hydroxypropyl)-1,3,4-oxadiazol-2-yl)phenyl)acetamide

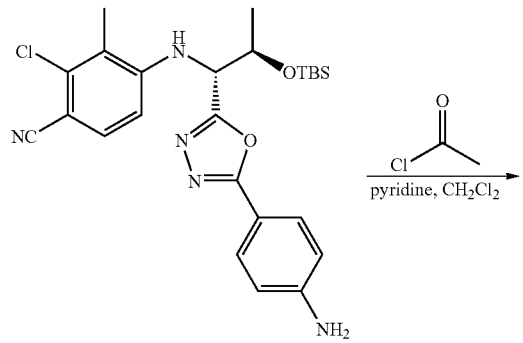

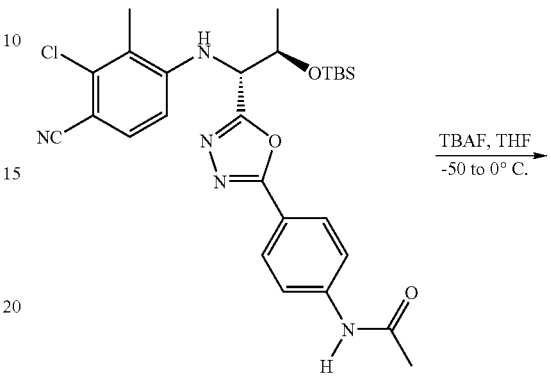

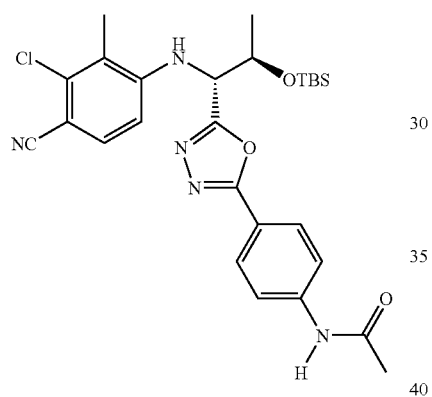

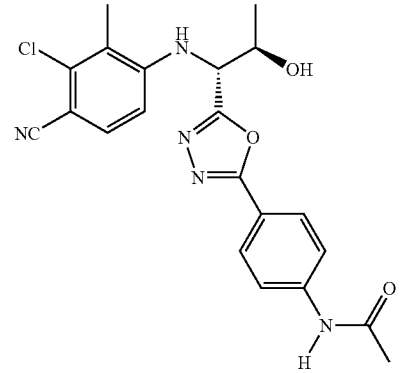

To a solution of 4-((1R,2R)-1-(5-(4-aminophenyl)-1,3,4-oxadiazol-2-yl)-2-(tert-butyldimethylsilyloxy)propylamino)-2-chloro-3-methylbenzonitrile (intermediate 69d) (311 mg, 0.62 mmol) in $CH_2Cl_2$ (10 mL) and pyridine (1.5 mL) was added acetylchloride (62 µL, 0.87 mmol) at room temperature. The resultant solution stirred for 89 hours and quenched with 2N aq. HCl (15 mL). The mixture was further partitioned between $H_2O$ (40 mL) and $CH_2Cl_2$ (40 mL). The aqueous layer was extracted with $CH_2Cl_2$ (35 mL). The combined organic extracts were washed with sat. aq. $NaHCO_3$ (2×45 mL), dried ($Na_2SO_4$), filtered and concentrated under reduced pressure to provide a colourless oil (335 mg, 100%): $^1$H NMR (400 MHz, $d_6$-acetone, δ in ppm) 9.49 (s 1H), 7.93 (dm, J=8.8 Hz, 2H), 7.83 (dm, J=8.8 Hz, 2H), 7.50 (d, J=8.6 Hz, 1H), 6.94 (d, J=8.8 Hz, 1H), 5.74 (d, J=9.0 Hz, 1H), 5.03 (dd, J=6.4, 9.0 Hz, 1H), 4.65 (pentet, J=6.4 Hz, 1H), 2.34 (s, 3H), 2.12 (s, 3H), 1.44 (d, J=6.1 Hz, 3H), 0.81 (s, 9H), 0.09 (s, 3H), −0.02 (s, 3H).

To a pre-cooled (−55° C.) solution of N-(4-(5-((1R,2R)-2-(tert-butyldimethylsilyloxy)-1-(3-chloro-4-cyano-2-methylphenylamino)propyl)-1,3,4-oxadiazol-2-yl)phenyl)acetamide (246 mg, 0.45 mmol) in THF (20 mL) was added TBAF (0.55 mL, 0.55 mmol, 1 M solution in THF) over 5 minutes. Upon complete addition the reaction mixture was allowed to warm to 10° C. over 2.5 h and quenched with sat. aq. $NH_4Cl$ (30 mL). The resulting mixture was partitioned between $H_2O$ (25 mL) and EtOAc (35 mL). The aqueous layer was extracted with EtOAc (30 mL). The combined organic extracts were dried ($Na_2SO_4$), filtered and concentrated under reduced pressure to provide an off white solid, which was purified by flash chromatography over silica gel (60-100% EtOAc in hexanes) to provided the title compound as a colourless solid (150 mg, 78%): $^1$H NMR (400 MHz, $d_6$-acetone, δ in ppm) 9.47 (s 1H), 7.90 (dm, J=8.8 Hz, 2H), 7.81 (dm, J=8.8 Hz, 2H), 7.49 (d, J=8.6 Hz, 1H), 6.88 (d, J=8.8 Hz, 1H), 5.86 (d, J=8.8 Hz, 1H), 5.04 (dd, J=5.3, 8.6 Hz, 1H), 4.68 (br s, 1H), 4.51 (pentet, J=6.1 Hz, 1H), 2.36 (s, 3H), 2.12 (s, 3H), 1.42 (d, J=6.5 Hz, 3H).

Example 71

N-(4-(5-((1R,2R)-1-(3-Chloro-4-cyano-2-methylphenylamino)-2-hydroxypropyl)-1,3,4-oxadiazol-2-yl)phenyl)butyramide

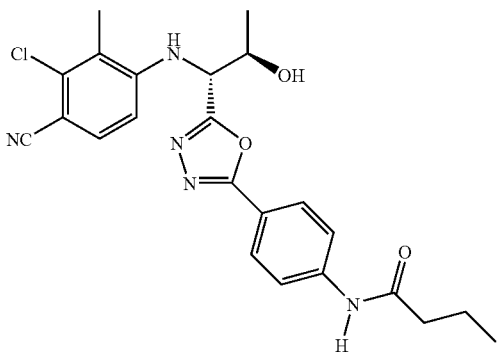

Intermediate 71a

N-(4-(5-((1R,2R)-2-(tert-Butyldimethylsilyloxy)-1-(3-chloro-4-cyano-2-methylphenylamino)propyl)-1,3,4-oxadiazol-2-yl)phenyl)butyramide

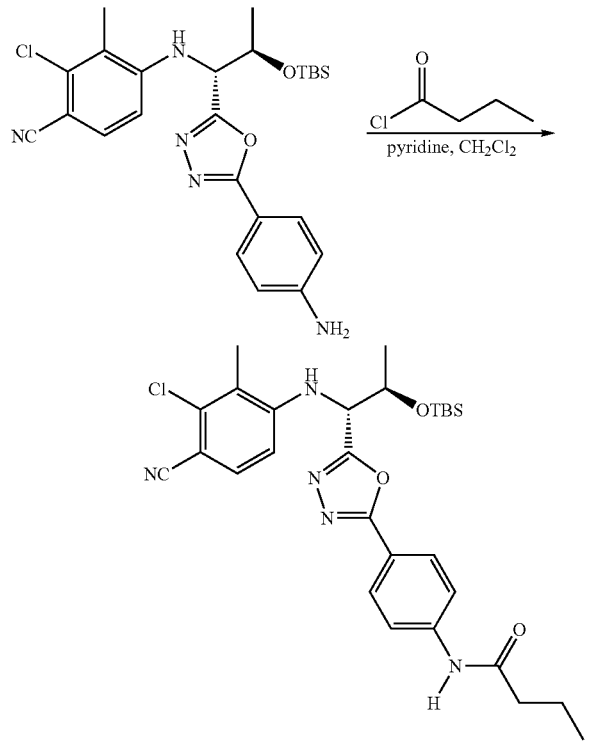

To a solution of 4-((1R,2R)-1-(5-(4-aminophenyl)-1,3,4-oxadiazol-2-yl)-2-(tert-butyldimethylsilyloxy)propylamino)-2-chloro-3-methylbenzonitrile (intermediate 69d) (308 mg, 0.62 mmol) in CH₂Cl₂ (10 mL) and pyridine (1.5 mL) was added butyrylchloride (90 μL, 0.87 mmol) at room temperature. The resultant solution stirred for 90 hours and quenched with 2N aq. HCl (15 mL). The mixture was further partitioned between H₂O (40 mL) and CH₂Cl₂ (35 mL). The aqueous layer was extracted with CH₂Cl₂ (35 mL). The combined organic extracts were washed with sat. aq. NaHCO₃ (2×45 mL), dried (Na₂SO₄), filtered and concentrated under reduced pressure to provide a colourless oil (352 mg, 100%): ¹H NMR (400 MHz, d₆-acetone, δ in ppm) 9.42 (s 1H), 7.93 (dm, J=8.8 Hz, 2H), 7.85 (dm, J=8.8 Hz, 2H), 7.51 (d, J=8.6 Hz, 1H), 6.94 (d, J=8.6 Hz, 1H), 5.74 (d, J=9.2 Hz, 1H), 5.03 (dd, J=6.5, 9.0 Hz, 1H), 4.66 (pentet, J=6.3 Hz, 1H), 2.38 (t, J=7.2 Hz, 2H), 2.35 (s, 3H), 1.70 (sextet, J=7.4 Hz, 2H), 1.44 (d, J=6.1 Hz, 3H), 0.95 (t, J=7.4 Hz, 3H), 0.81 (s, 9H), 0.09 (s, 3H), −0.01 (s, 3H).

Example 71

N-(4-(5-((1R,2R)-1-(3-Chloro-4-cyano-2-methylphenylamino)-2-hydroxypropyl)-1,3,4-oxadiazol-2-yl)phenyl)butyramide

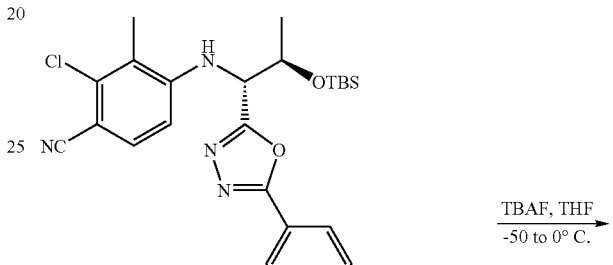

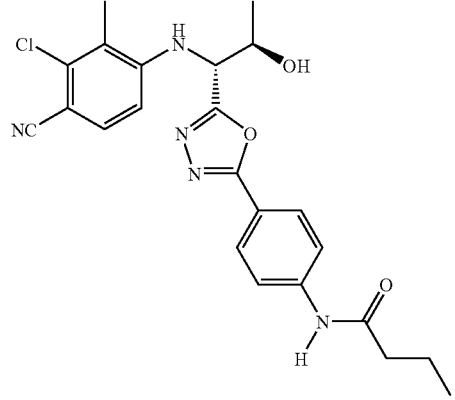

To a pre-cooled (−55° C.) solution of N-(4-(5-((1R,2R)-2-(tert-butyldimethylsilyloxy)-1-(3-chloro-4-cyano-2-methylphenylamino)propyl)-1,3,4-oxadiazol-2-yl)phenyl)butyramide (352 mg, 0.62 mmol) in THF (25 mL) was added TBAF (0.74 mL, 0.74 mmol, 1 M solution in THF) over 5 minutes. Upon complete addition the reaction mixture was allowed to warm to 10° C. over 2.5 h and quenched with sat. aq. NH₄Cl (30 mL). The resulting mixture was partitioned between H₂O (30 mL) and EtOAc (40 mL). The aqueous layer was extracted with EtOAc (35 mL). The combined organic extracts were dried (Na₂SO₄), filtered and concentrated under reduced pressure to provide a colourless oil, which was purified by flash chromatography over silica gel (50-100% EtOAc in hexanes) to provided the title compound as a colourless solid (274 mg, 97%): ¹H NMR (400 MHz, d₆-acetone, δ in ppm) 9.41 (s 1H), 7.91 (dm, J=9.0 Hz, 2H), 7.87 (dm, J=9.0 Hz, 2H), 7.49 (d, J=8.6 Hz, 1H), 6.89 (d, J=8.8 Hz, 1H), 5.86 (d, J=8.8 Hz, 1H), 5.04 (dd, J=5.5, 8.6 Hz, 1H), 4.69 (br s, 1H), 4.52 (pentet, J=5.9 Hz, 1H), 2.38 (t, J=7.2 Hz, 2H), 2.36 (s, 3H), 1.69 (sextet, J=7.2 Hz, 2H), 1.42 (d, J=6.5 Hz, 3H), 0.95 (t, J=7.4 Hz, 3H).

Example 72

Sodium 4-(5-((1R,2S)-1-(3-chloro-4-cyano-2-methylphenylamino)-2-hydroxypropyl)-1,3,4-oxadiazol-2-yl)phenyl sulfate

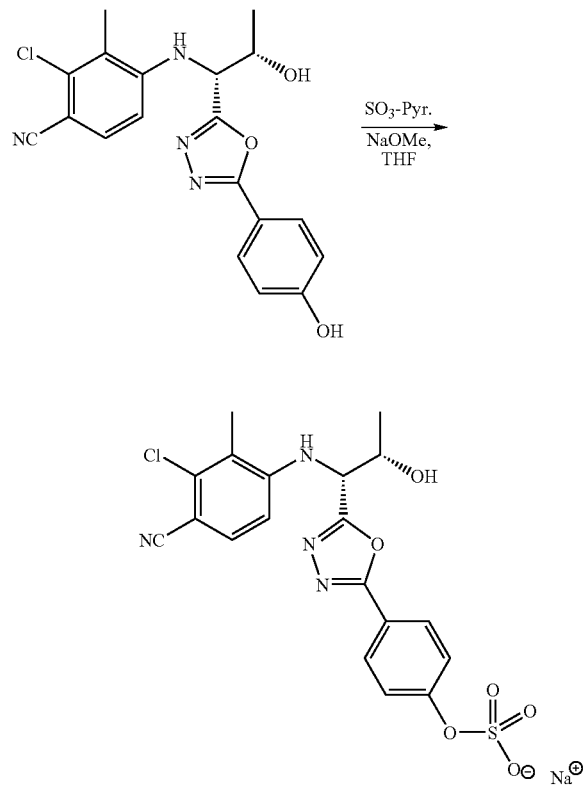

To a solution of 2-chloro-4-((1R,2S)-2-hydroxy-1-(5-(4-hydroxyphenyl)-1,3,4-oxadiazol-2-yl)propylamino)-3-methylbenzonitrile (example 8) (257 mg, 0.67 mmol) in THF (2.0 mL) was added a solution of sodium methoxide (36 mg, 0.67 mmol) in THF (1.5 mL) at room temperature. After 20 minutes sulfur trioxide-pyridine (85 mg, 0.53 mmol) was added and the mixture was stirred for 40 minutes, then partitioned between H₂O (25 mL) and Et₂O (20 mL). The aqueous layer was concentrated under reduced pressure to provide a colourless solid (177 mg, 68%): ¹H NMR (400 MHz, d₆-DMSO, δ in ppm) 7.88 (dm, J=9.0 Hz, 2H), 7.56 (d, J=8.6 Hz, 1H), 7.36 (dm, J=8.8 Hz, 2H), 6.80 (d, J=8.8 Hz, 1H), 5.86 (d, J=8.6 Hz, 1H), 5.49 (d, J=6.1 Hz, 1H), 5.08 (dd, J=4.3, 8.4 Hz, 1H), 4.40 (tq, J=3.9, 5.9 Hz, 1H), 2.33 (s, 3H), 1.25 (d, J=6.3 Hz, 3H).

Example 73

4-(5-((1R,2S)-2-Acetoxy-1-(3-chloro-4-cyano-2-methylphenylamino)propyl)-1,3,4-oxadiazol-2-yl) phenyl acetate

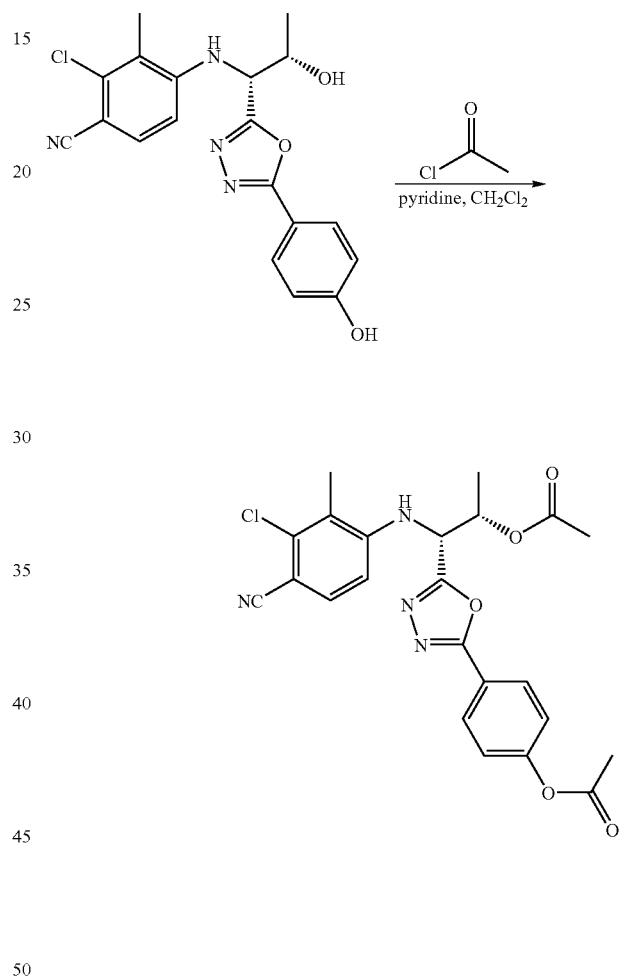

To a solution of 2-chloro-4-((1R,2S)-2-hydroxy-1-(5-(4-hydroxyphenyl)-1,3,4-oxadiazol-2-yl)propylamino)-3-methylbenzonitrile (example 8) (200 mg, 0.52 mmol) in pyridine (1.0 mL) and CH₂Cl₂ (7.0 mL) was added acetyl chloride (0.11 mL, 1.56 mmol). Upon complete addition the reaction mixture was stirred for 23 h, then quenched with 10% aqueous HCl (15 mL). The mixture was partitioned between H₂O (30 mL) and CH₂Cl₂ (40 mL). The aqueous layer was extracted with CH₂Cl₂ (35 mL). The combined organic extracts were washed with NaHCO₃ (40 mL), dried (Na₂SO₄), filtered and concentrated under reduced pressure to provide an off white solid (241 mg, 99%): ¹H NMR (400 MHz, d₆-acetone, δ in ppm) 8.02 (dm, J=8.4 Hz, 2H), 7.38 (d, J=8.6 Hz, 1H), 7.25 (dm, J=8.6 Hz, 2H), 6.72 (d, J=8.8 Hz, 1H), 5.57 (pentet, J=5.6 Hz, 1H), 5.15 (d, J=8.0 Hz, 1H), 5.01 (dd, J=5.9, 8.0 Hz, 1H), 2.33 (s, 3H), 2.31 (s, 3H), 2.11 (s, 3H), 1.37 (d, J=6.5 Hz, 3H).

Example 74

4-(5-((1R,2S)-2-(Butyryloxy)-1-(3-chloro-4-cyano-2-methylphenylamino)propyl)-1,3,4-oxadiazol-2-yl) phenyl butyrate

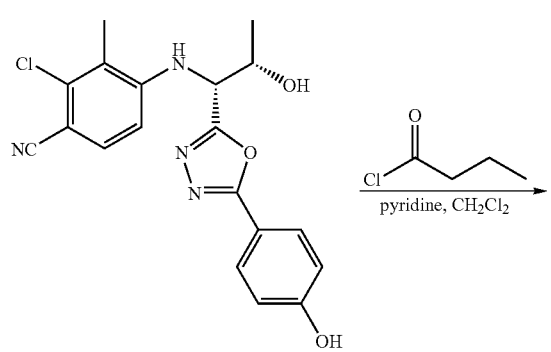

To a solution of 2-chloro-4-((1R,2S)-2-hydroxy-1-(5-(4-hydroxyphenyl)-1,3,4-oxadiazol-2-yl)propylamino)-3-methylbenzonitrile (example 8) (200 mg, 0.52 mmol) in pyridine (1.0 mL) and CH$_2$Cl$_2$ (7.0 mL) was added n-butyryl chloride (0.16 mL, 1.56 mmol). Upon complete addition the reaction mixture was stirred for 23 h, then quenched with 10% aqueous HCl (10 mL). The mixture was partitioned between H$_2$O (25 mL) and CH$_2$Cl$_2$ (30 mL). The aqueous layer was extracted with CH$_2$Cl$_2$ (20 mL). The combined organic extracts were washed with NaHCO$_3$ (30 mL), dried (Na$_2$SO$_4$), filtered and concentrated under reduced pressure to provide an orange viscous oil, which was purified by flash chromatography over silica gel (15-25% EtOAc in hexanes) to provide the title compound as a colourless solid (194 mg, 71%): $^1$H NMR (400 MHz, d$_6$-acetone, δ in ppm) 8.00 (dm, J=8.8 Hz, 2H), 7.36 (d, J=8.6 Hz, 1H), 7.23 (dm, J=8.8 Hz, 2H), 6.72 (d, J=8.8 Hz, 1H), 5.57 (pentet, J=5.9 Hz, 1H), 5.18 (d, J=8.0 Hz, 1H), 5.02 (dd, J=5.7, 8.0 Hz, 1H), 2.55 (t, J=7.4 Hz, 2H), 2.32 (dt, J=2.6, 7.4 Hz, 2H), 2.30 (s, 3H), 1.77 (sextet, J=7.4 Hz, 2H), 1.63 (sextet, J=7.4 Hz, 2H), 1.36 (d, J=6.5 Hz, 3H), 1.03 (t, J=7.4 Hz, 3H), 0.91 (t, J=7.2 Hz, 3H).

Example 75

4-(5-((1R,2S)-2-(Benzoyloxy)-1-(3-chloro-4-cyano-2-methylphenylamino)propyl)-1,3,4-oxadiazol-2-yl) phenyl benzoate

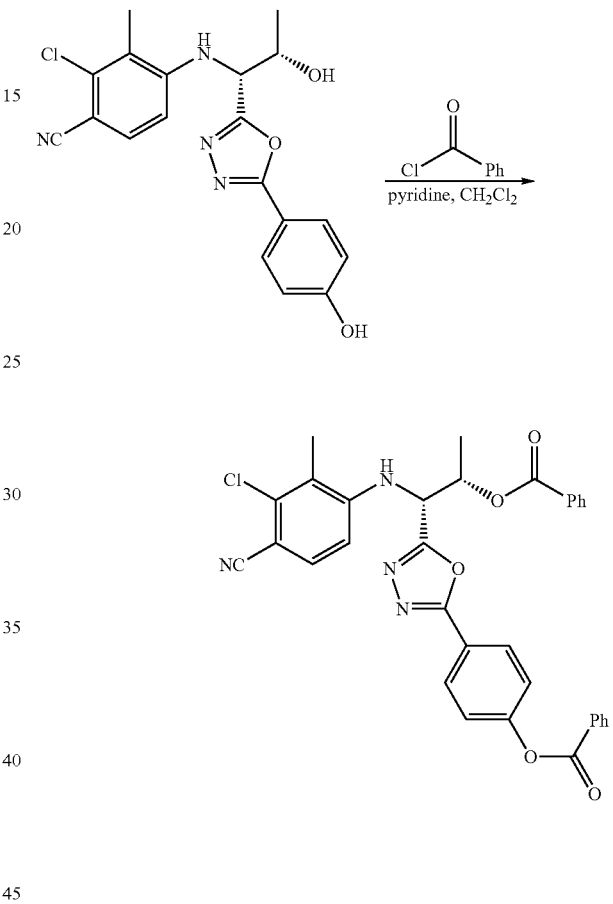

To a solution of 2-chloro-4-((1R,2S)-2-hydroxy-1-(5-(4-hydroxyphenyl)-1,3,4-oxadiazol-2-yl)propylamino)-3-methylbenzonitrile (example 8) (200 mg, 0.52 mmol) in pyridine (1.0 mL) and CH$_2$Cl$_2$ (7.0 mL) was added benzoyl chloride (0.18 mL, 1.56 mmol). Upon complete addition the reaction mixture was stirred for 23 h, then quenched with 10% aqueous HCl (15 mL). The mixture was partitioned between H$_2$O (30 mL) and CH$_2$Cl$_2$ (40 mL). The aqueous layer was extracted with CH$_2$Cl$_2$ (35 mL). The combined organic extracts were washed with NaHCO$_3$ (40 mL), dried (Na$_2$SO$_4$), filtered and concentrated under reduced pressure to provide an off white solid, which was purified by flash chromatography over silica gel (20-40% EtOAc in hexanes) to provide the title compound as a colourless solid (252 mg, 82%): $^1$H NMR (400 MHz, d$_6$-acetone, δ in ppm) 8.21 (d, J=8.0 Hz, 2H), 8.07 (d, J=6.4 Hz, 2H), 8.00 (dm, J=8.4 Hz, 2H), 7.68 (t, J=6.8 Hz, 1H), 7.64 (t, J=8.0 Hz, 1H), 7.54 (t, J=7.8 Hz, 2H), 7.49 (t, J=8.0 Hz, 2H), 7.44 (d, J=8.8 Hz, 1H), 7.35 (dm, J=8.4 Hz, 2H), 6.85 (d, J=8.6 Hz, 1H), 5.82 (pentet, J=6.3 Hz, 1H), 5.37 (d, J=7.6 Hz, 1H), 5.21 (dd, J=5.9, 7.6 Hz, 1H), 2.34 (s, 3H), 1.51 (d, J=6.5 Hz, 3H).

Example 76

(1R,2S)-1-(3-chloro-4-cyano-2-methylphenylamino)-1-(5-phenyl-1,3,4-oxadiazol-2-yl)propan-2-yl acetate

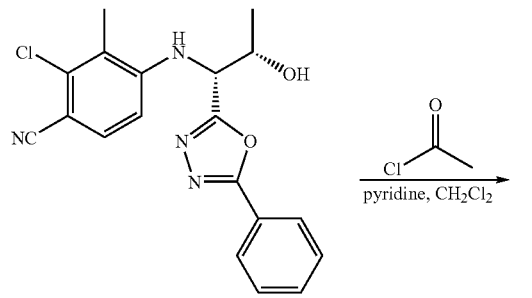

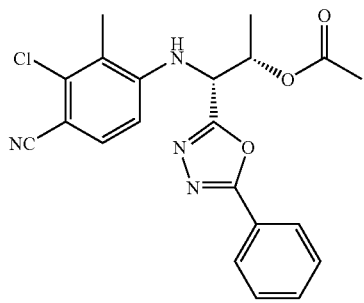

To a solution of 2-chloro-4-((1R,2S)-2-hydroxy-1-(5-phenyl-1,3,4-oxadiazol-2-yl)propylamino)-3-methylbenzonitrile (example 1) (200 mg, 0.54 mmol) in pyridine (1.0 mL) and CH$_2$Cl$_2$ (7.0 mL) was added acetyl chloride (58 µL, 0.81 mmol). Upon complete addition the reaction mixture was stirred for 48 h, then quenched with 10% aqueous HCl (15 mL). The mixture was partitioned between H$_2$O (25 mL) and CH$_2$Cl$_2$ (35 mL). The aqueous layer was extracted with CH$_2$Cl$_2$ (30 mL). The combined organic extracts were washed with NaHCO$_3$ (40 mL), dried (Na$_2$SO$_4$), filtered and concentrated under reduced pressure to provide a yellow oil, which was purified by flash chromatography over silica gel (30-60% EtOAc in hexanes) to provide the title compound as a colourless solid (217 mg, 98%): $^1$H NMR (400 MHz, d$_6$-acetone, δ in ppm) 8.01 (dm, J=8.0 Hz, 2H), 7.60-7.49 (m, 3H), 7.41 (d, J=8.6 Hz, 1H), 6.74 (d, J=8.6 Hz, 1H), 5.58 (pentet, J=6.1 Hz, 1H), 5.16 (d, J=8.0 Hz, 1H), 5.02 (dd, J=5.9, 8.0 Hz, 1H), 2.32 (s, 3H), 2.13 (s, 3H), 1.38 (d, J=6.4 Hz, 3H).

Example 77

N-(4-(5-((1R,2S)-1-(3-Chloro-4-cyano-2-methylphenylamino)-2-hydroxypropyl)-1,3,4-oxadiazol-2-yl)phenyl)benzamide

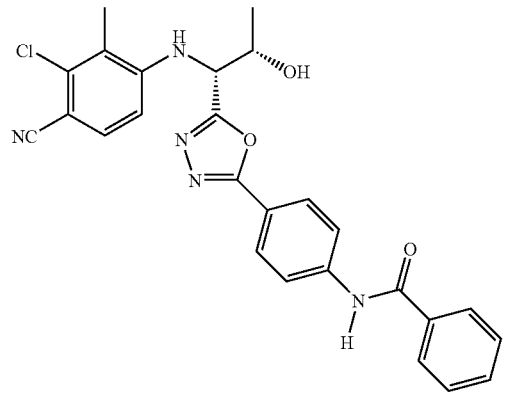

Intermediate 77a

N'-((2R,3R)-2-(3-chloro-4-cyano-2-methylphenylamino)-3-hydroxybutanoyl)-4-nitrobenzo-hydrazide

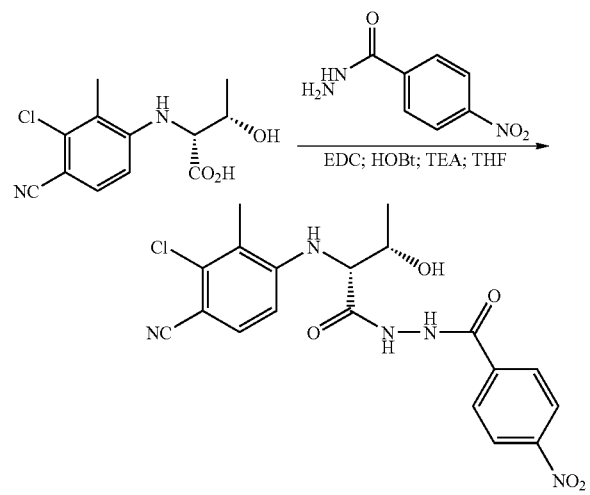

(2R,3R)-2-(3-chloro-4-cyano-2-methylphenylamino)-3-hydroxybutanoic acid (intermediate 1a)(8.3 g, 30.9 mmol), 4-nitrobenzohydrazide (6.16 g, 34.0 mmol) and anhydrous THF (200 mL) were placed in a 500 mL round bottomed flask and the mixture was cooled to −50° C. 1-Hydroxybenzotriazole hydrate (4.2 g, 30.9 mmol) was added to the mixture together with N-(3-Dimethylaminopropyl)-N'-ethylcarbodimide HCl (7.34 g, 38.3 mmol) at −50° C. followed by triethylamine (5.3 mL, 38.3 mmol). The reaction mixture was maintained at −15° C. and stirred for 1 h after which stirring continued overnight while the mixture slowly warmed to room temperature. After 18 h the mixture was filtered under vacuum and the residue washed with THF (50 mL). The THF solution was concentrated to ca. 20 mL, whereupon ethyl acetate (200 mL) was added followed by water (100 mL). The phases were partitioned and the organic phase washed with water (150 mL), brine (150 mL), dried ($Na_2SO_4$) and concentrated to furnish a light yellow solid as the title compound (15.9 g, 80%) that was used without further purification. $^1$H NMR (400 MHz, $d_6$-acetone, δ in ppm) 9.88 (br s, 2H), 8.35 (d, J=6.7 Hz, 2H), 8.16 (d, J=6.7 Hz, 2H), 7.53 (d, J=7.5 Hz, 1H), 6.69 (d, J=7.5 Hz, 1H), 5.56 (d, J=6.6 Hz, 1H), 4.46-4.36 (m, 1H), 4.18-4.10 (m, 1H), 3.26 (s, 3H), 1.37 (d, J=7.4 Hz, 3H).

Intermediate 77b

N'-((2R,3S)-3-(tert-butyldimethylsilyloxy)-2-(3-chloro-4-cyano-2-methylphenylamino)butanoyl)-4-nitrobenzohydrazide

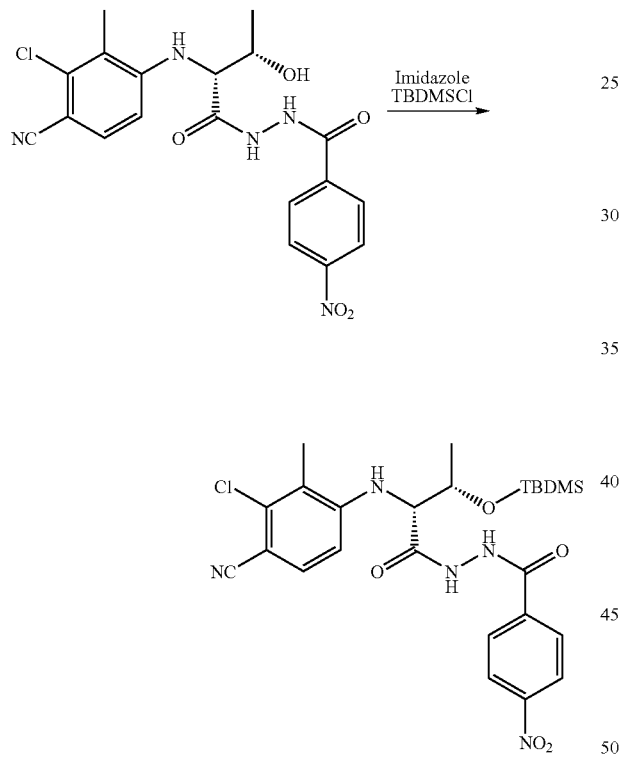

N'-((2R,3R)-2-(3-chloro-4-cyano-2-methylphenylamino)-3-hydroxybutanoyl)-4-nitrobenzo-hydrazide (2.0 g, 4.63 mmol) was added to DMF (100 mL), followed by addition of TBDMS-Cl (1.74 g, 11.6 mmol) and imidazole (1.58 g, 23.2 mmol) at 0° C. The solution was allowed to stir at 0° C. for 30 minutes and then at room temperature for overnight. The reaction was quenched with the addition of 200 mL brine and extract with EtOAc. Purification by flash column chromatography [EtOAc-hexanes (1:1) as eluent] afforded the title compound as a white solid (780 mg, 82%). $^1$H NMR (400 MHz, $d_6$-acetone, δ in ppm) 9.88 (br s, 2H), 8.35 (d, J=6.7 Hz, 2H), 8.16 (d, J=6.7 Hz, 2H), 7.53 (d, J=7.5 Hz, 1H), 6.69 (d, J=7.5 Hz, 1H), 5.56 (d, J=6.6 Hz, 1H), 4.46-4.36 (m, 1H), 4.18-4.10 (m, 1H), 3.26 (s, 3H), 1.37 (d, J=7.4 Hz, 3H), 0.94 (s, 9H), 0.14 (s, 3H), 0.11 (s, 3H).

Intermediate 77c 4-(1R,2S)-2-(tert-butyldimethylsilyloxy)-1-(5-(4-nitrophenyl)-1,3,4-oxadiazol-2-yl)propylamino)-2-chloro-3-methylbenzonitrile

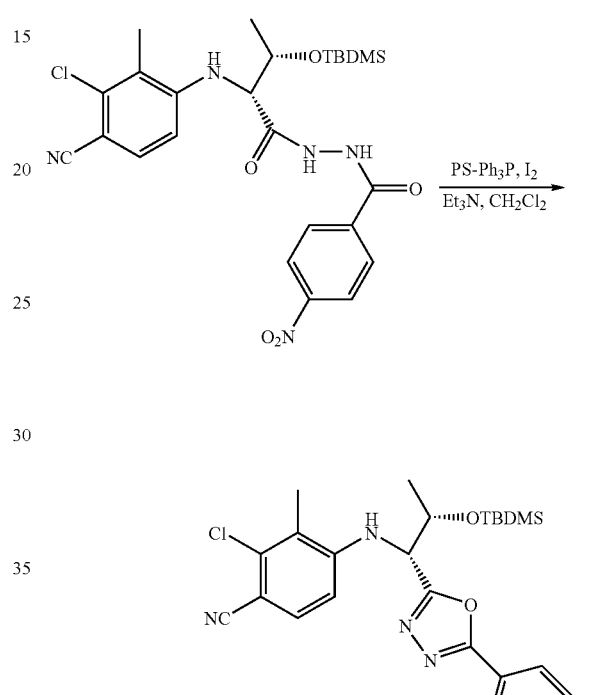

N'-((2R,3S)-3-(tert-butyldimethylsilyloxy)-2-(3-chloro-4-cyano-2-methylphenylamino)butanoyl)-4-nitrobenzohydrazide (1.4 g, 2.56 mmol) was placed in a 100 mL round bottomed flask and $CH_2Cl_2$ (40 mL) was added, followed by $I_2$ (650 mg, 5.12 mmol), $Ph_3P$ (1.34 g, 5.12 mmol), and $Et_3N$ (1.43 mL, 10.24 mmol). The reaction mixture was allowed to stir at room temperature for 20 min, whereupon it was filtered and the filtrate washed with $CH_2Cl_2$ (50 mL). The organic layer was washed with 10% aq. $Na_2S_2O_3$ (100 mL) (×2) and the aqueous layer extracted with $CH_2Cl_2$ (3×100 mL). The combined organic extracts were dried ($Na_2SO_4$), filtered and concentrated to provide a yellow oil. Purification by flash column chromatography [EtOAc-hexanes (1:1.5) as eluent] afforded the title compound as a white solid (750 mg, 72%). $^1$H NMR (400 MHz, $d_6$-acetone, δ in ppm) 8.62 (d, J=8.8 Hz, 2H), 8.47 (d, J=8.8 Hz, 2H), 7.65 (d, J=8.6 Hz, 1H), 7.02 (d, J=8.6 Hz, 1H), 5.72 (d, J=8.9 Hz, 1H), 5.48 (dd, J=1.8, 8.9 Hz, 1H), 5.01-4.92 (m, 1H), 2.59 (s, 3H), 1.66 (d, J=7.4 Hz, 3H), 1.02 (s, 9H), 0.28 (s, 3H), 0.00 (s, 3H).

Intermediate 77d 5-((1R,2S)-1-(5-(4-aminophenyl)-1,3,4-oxadiazol-2-yl)-2-(tert-butyldimethylsilyloxy)propylamino)-2-chloro-4-methylbenzonitrile

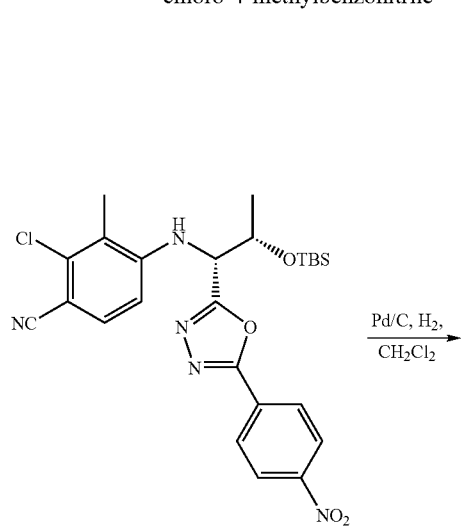

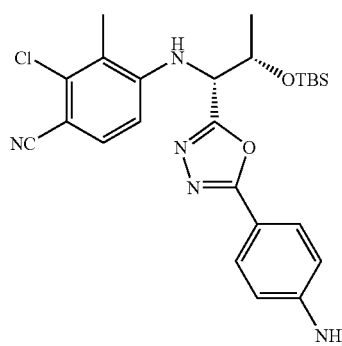

A suspension of 4-(1R,2S)-2-(tert-butyldimethylsilyloxy)-1-(5-(4-nitrophenyl)-1,3,4-oxadiazol-2-yl)propylamino)-2-chloro-3-methylbenzonitrile (650 mg, 1.4 mmol), 10 wt. % Pd on activated carbon (303 mg) in CH$_2$Cl$_2$ (20 mL) was pressurized with 25 psi of H$_2$ and reacted on a Parr shaker for 4.5 h. The reaction was filtered through Celite and rinsed with CH$_2$Cl$_2$ (4×40 mL). The filtrate was concentrated under reduced pressure to provide a dark yellow solid, which was purified by flash chromatography over silica gel (CH$_2$Cl$_2$) to provide the title compound as a yellow solid (580 mg, 83%): $^1$H NMR (400 MHz, d$_6$-acetone, δ in ppm) 7.92 (d, J=8.8 Hz, 2H), 7.52 (d, J=8.6 Hz, 1H), 7.45 (s, 2H), 6.89 (d, J=8.8 Hz, 2H), 6.65 (d, J=8.6 Hz, 1H), 5.57 (d, J=8.9 Hz, 1H), 4.99 (dd, J=1.8, 8.9 Hz, 1H), 4.76-4.68 (m, 1H), 2.56 (s, 3H), 1.58 (d, J=6.3 Hz, 3H), 1.07 (s, 9H), 0.27 (s, 3H), 0.00 (s, 3H).

Intermediate 77e

N-(4-(5-((1R,2S)-2-(tert-butyldimethylsilyloxy)-1-(4-chloro-5-cyano-2-methylphenylamino)propyl)-1,3,4-oxadiazol-2-yl)phenyl)benzamide

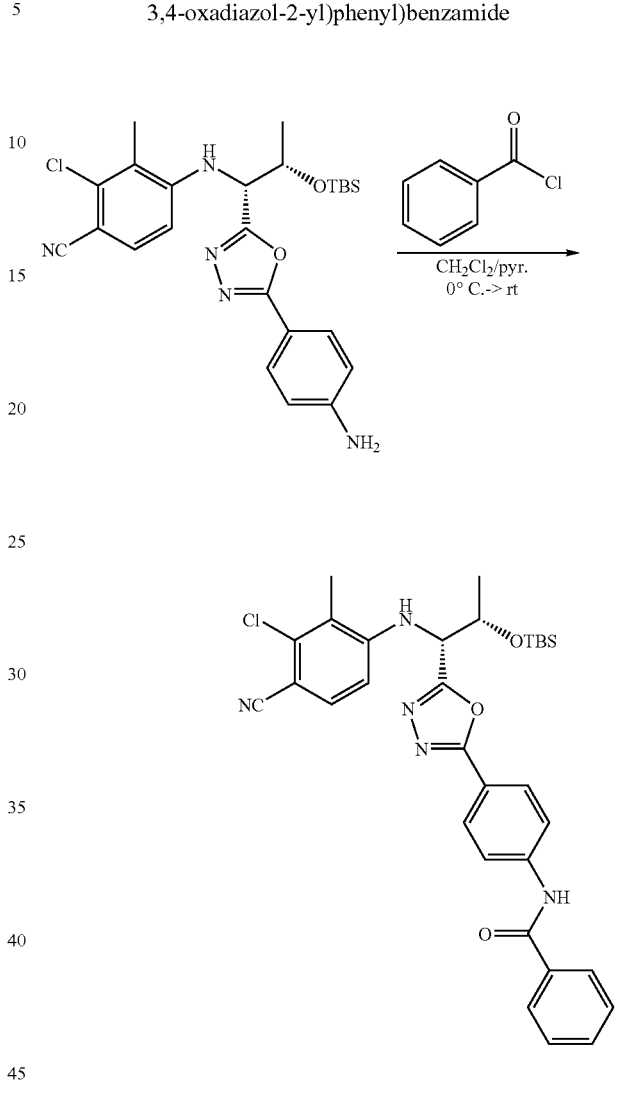

To a pre-cooled (0° C.) solution of 5-((1R,2S)-1-(5-(4-aminophenyl)-1,3,4-oxadiazol-2-yl)-2-(tert-butyldimethylsilyloxy)propylamino)-2-chloro-4-methylbenzonitrile (290 mg, 0.58 mmol) in CH$_2$Cl$_2$ (10.0 mL) and pyridine (1.2 mL) was added, portion wise, acetyl chloride (0.34 mL, 2.9 mmol). Upon complete addition the reaction mixture was warmed slowly to room temperature and stirred for 23 h. The reaction mixture was then cooled to 0° C. and quenched with 10% aq HCl (5 mL) then H$_2$O (15 mL) was added. The solution was extracted with CH$_2$Cl$_2$ (2×40 mL). The combined organic extracts were dried (Na$_2$SO$_4$), filtered and concentrated under reduced pressure to provide an orange oil, which was used without further purification (400 mg). $^1$H NMR (400 MHz, d$_6$-acetone, δ in ppm) 8.36 (d, J=8.4 Hz, 2H), 8.27 (br s, 1H), 8.16 (d, J=8.6 Hz, 2H), 8.08 (d, J=8.2 Hz, 1H), 8.02 (d, J=8.6 Hz, 2H), 7.94-7.83 (m, 3H), 7.53 (d, J=8.2 Hz, 1H), 5.57 (d, J=8.9 Hz, 1H), 4.99 (dd, J=1.8, 8.9 Hz, 1H), 4.76-4.68 (m, 1H), 2.58 (s, 3H), 1.61 (d, J=6.3 Hz, 3H), 1.09 (s, 9H), 0.26 (s, 3H), 0.01 (s, 3H).

Example 77

N-(4-(5-((1R,2S)-1-(3-Chloro-4-cyano-2-methylphenylamino)-2-hydroxypropyl)-1,3,4-oxadiazol-2-yl)phenyl)benzamide

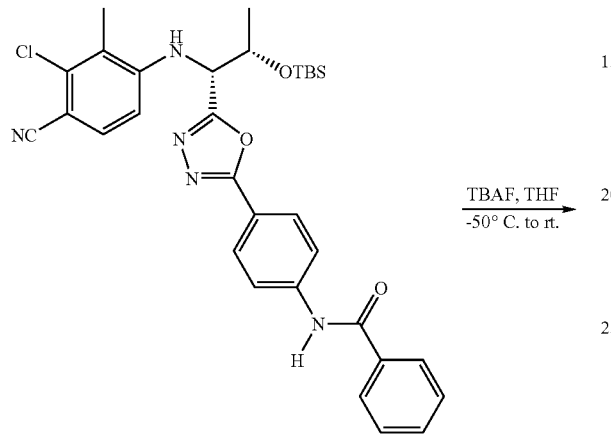

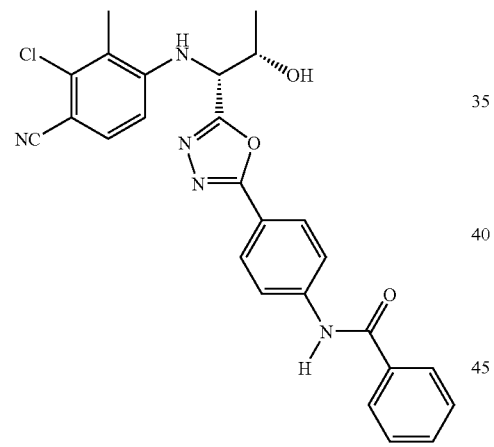

To a pre-cooled (−55° C.) solution of N-(4-(5-((1R,2S)-2-(tert-butyldimethylsilyloxy)-1-(3-chloro-4-cyano-2-methylphenylamino)propyl)-1,3,4-oxadiazol-2-yl)phenyl)benzamide (100 mg, 0.17 mmol) in THF (10 mL) was added TBAF (20 µL, 0.20 mmol, 1 M solution in THF) over 5 minutes. Upon complete addition the reaction mixture, was allowed to warm to room temperature over 1.5 h and stirred for a further 20 minutes before being quenched with sat. aq. NH$_4$Cl (10 mL). The resulting mixture was partitioned between H$_2$O (15 mL) and EtOAc (25 mL). The aqueous layer was extracted with EtOAc (25 mL). The combined organic extracts were dried (Na$_2$SO$_4$), filtered and concentrated under reduced pressure to provide a pale yellow oil, which was purified by flash chromatography over silica gel (60-100% EtOAc in hexanes) to provided the title compound as a colourless solid (9.3 mg, 11%): $^1$H NMR (400 MHz, d$_6$-acetone, δ in ppm) 9.86 (s 1H), 8.09-7.91 (m, 6H), 7.64-7.42 (m, 4H), 6.88 (d, J=8.8 Hz, 1H), 5.69 (d, J=6.6 Hz, 1H), 5.11 (dd, J=3.7, 8.2 Hz, 1H), 4.83 (br s, 1H), 4.62 (dq, J=3.5, 5.9 Hz, 1H), 2.41 (s, 3H), 1.41 (d, J=6.3 Hz, 3H).

Example 78

N-(4-(5-((1R,2S)-1-(3-Chloro-4-cyano-2-methylphenylamino)-2-hydroxypropyl)-1,3,4-oxadiazol-2-yl)phenyl)acetamide

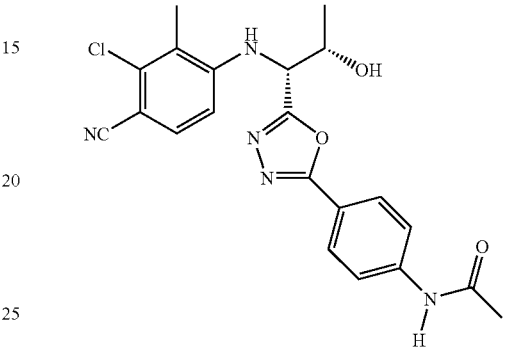

Intermediate 78a

N-(4-(5-((1R,2S)-2-(tert-butyldimethylsilyloxy)-1-(4-chloro-5-cyano-2-methylphenylamino)propyl)-1,3,4-oxadiazol-2-yl)phenyl)acetamide

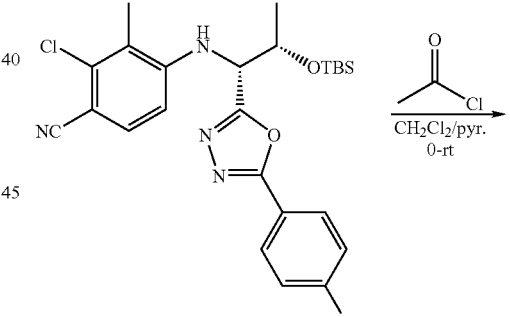

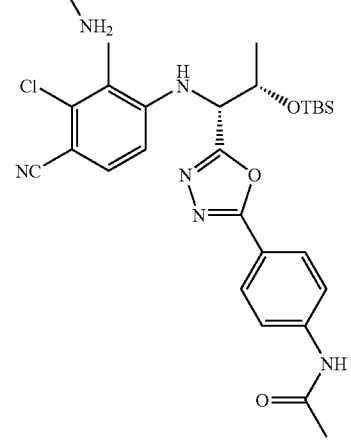

To a pre-cooled (0° C.) solution of 5-((1R,2S)-1-(5-(4-aminophenyl)-1,3,4-oxadiazol-2-yl)-2-(tert-butyldimethylsilyloxy)propylamino)-2-chloro-4-methylbenzonitrile (intermediate 77d) (200 mg, 0.40 mmol) in CH$_2$Cl$_2$ (4.0 mL) and pyridine (1.04 mL) was added, portion wise, acetyl chloride (0.14 mL, 2.0 mmol). Upon complete addition the reaction mixture was warmed slowly to room temperature and stirred for 23 h. The reaction mixture was then cooled to 0° C. and quenched with 10% ap HCl (5 mL) then H$_2$O (15 mL) was added. The solution was extracted with CH$_2$Cl$_2$ (2×30 mL). The combined organic extracts were dried (Na$_2$SO$_4$), filtered and concentrated under reduced pressure to provide an orange oil, which was used without further purification (199 mg, 92%): $^1$H NMR (400 MHz, d$_6$-acetone, δ in ppm) 8.11 (d, J=8.4 Hz, 2H), 7.87 (d, J=8.6 Hz, 2H), 7.80 (br s, 1H), 7.54 (d, J=8.4 Hz, 1H), 7.67 (d, J=8.4 Hz, 1H), 5.57 (d, J=8.9 Hz, 1H), 4.99 (dd, J=1.8, 8.9 Hz, 1H), 4.76-4.68 (m, 1H), 2.58 (s, 3H), 2.44 (s, 3H), 1.62 (d, J=6.3 Hz, 3H), 1.07 (s, 9H), 0.27 (s, 3H), 0.00 (s, 3H).

Example 78

N-(4-(5-((1R,2S)-1-(3-Chloro-4-cyano-2-methylphenylamino)-2-hydroxypropyl)-1,3,4-oxadiazol-2-yl)phenyl)acetamide

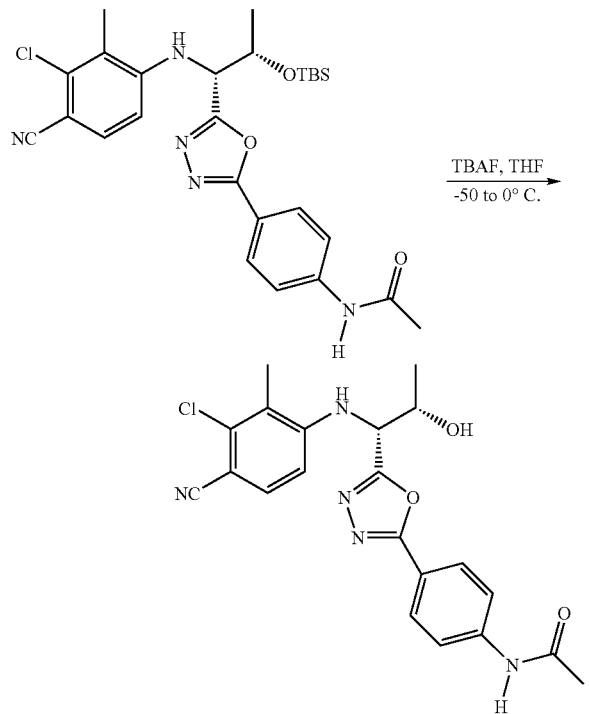

To a pre-cooled (−55° C.) solution of N-(4-(5-((1R,2S)-2-(tert-butyldimethylsilyloxy)-1-(3-chloro-4-cyano-2-methylphenylamino)propyl)-1,3,4-oxadiazol-2-yl)phenyl)acetamide (216 mg, 0.40 mmol) in THF (20 mL) was added TBAF (0.48 mL, 0.48 mmol, 1 M solution in THF) over 5 minutes. Upon complete addition the reaction mixture was allowed to warm to 11° C. over 3 h and quenched with sat. aq. NH$_4$Cl (15 mL). The resulting mixture was partitioned between H$_2$O (25 mL) and EtOAc (40 mL). The aqueous layer was extracted with EtOAc (50 mL). The combined organic extracts were dried (Na$_2$SO$_4$), filtered and concentrated under reduced pressure to provide a colourless oil, which was purified by flash chromatography over silica gel (50-100% EtOAc in hexanes) to provided the title compound as a colourless solid (150 mg, 88%): $^1$H NMR (400 MHz, d$_6$-acetone, δ in ppm) 9.49 (s 1H), 7.90 (dm, J=9.0 Hz, 2H), 7.80 (dm, J=9.0 Hz, 2H), 7.47 (d, J=8.8 Hz, 1H), 6.85 (d, J=8.6 Hz, 1H), 5.66 (d, J=8.4 Hz, 1H), 5.07 (dd, J=3.7, 8.4 Hz, 1H), 4.84 (br s, 1H), 4.61 (dq, J=3.5, 5.9 Hz, 1H), 2.39 (s, 3H), 2.12 (s, 3H), 1.40 (d, J=6.3 Hz, 3H).

Example 79

(R)-2-chloro-4-(1-(5-(4-cyanophenyl)-1,3,4-oxadiazol-2-yl)-3-hydroxypropylamino)-3-methylbenzonitrile

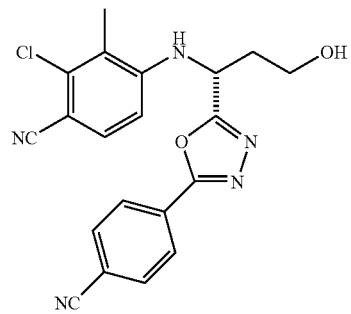

Intermediate 79a (R)-2-(3-chloro-4-cyano-2-methylphenylamino)-4-hydroxybutanoic acid

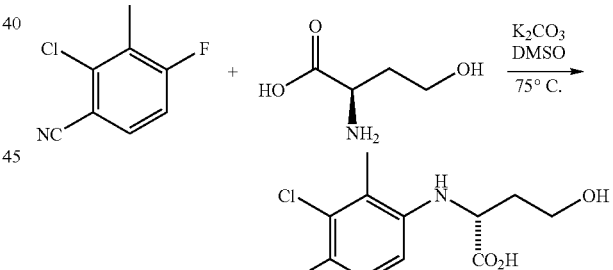

To a suspension of D-Homoserine (2.5 g, 20.99 mmol) and K$_2$CO$_3$ (5.8 g, 41.98 mmol) in DMSO (30 mL) was added 2-chloro-3-methyl-4-fluorobenzonitrile (3.56 g, 20.99 mmol) at room temperature. The reaction mixture was heated to 80° C. and stirred for 17 h. The reaction mixture was allowed to cool to room temperature and quenched with H$_2$O (200 mL) and extracted with EtOAc (3×200 mL). The aqueous layer was then acidified with solid citric acid and extracted with EtOAc (2×100 mL). The organic extracts were combined, washed with H$_2$O (3×100 mL), dried (Na$_2$SO$_4$), filtered and concentrated under reduced pressure to provided the title compound as a beige solid (3.39 g, 60%): $^1$H NMR (400 MHz, d$_6$-acetone, δ in ppm) 7.49 (d, J=9 Hz, 1H), 6.62 (d, J=9 Hz, 1H), 6.06 (br d, J=9 Hz, 1H), 4.49-4.41 (m, 1H), 3.83-3.80 (m, 2H), 2.29 (s, 3H), 2.27-2.20 (m, 1H) and 2.18-2.09 (m, 1H).

Intermediate 79b (R)-4-(tert-butyldimethylsilyloxy)-2-(3-chloro-4-cyano-2-methylphenylamino)butanoic acid

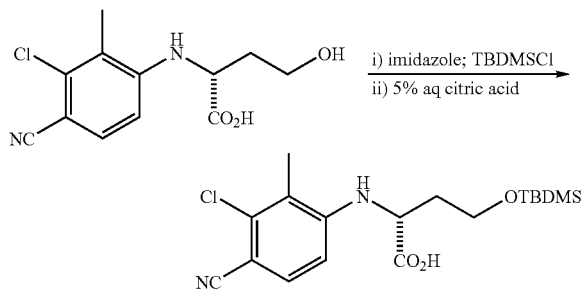

To a 25 mL round-bottomed flask equipped with a magnetic stir bar and a septum was added (R)-2-(3-chloro-4-cyano-2-methylphenylamino)-4-hydroxybutanoic acid (1.49 g, 5.55 mmol). This was dissolved in dry DMF (68 mL) under an atmosphere of nitrogen. This mixture was cooled to 0° C. followed by addition of imidazole (3.02 g, 44.36 mmol) and TBDMSCl (4.18 g, 27.75 mmol). The reaction was allowed to slowly warm to room temperature overnight quenched by slow addition of aqueous ammonium chloride (sat) (60 mL). The solution was extracted with EtOAc (3×100 mL). The combined organic extracts were washed with (5%) aqueous citric acid (100 mL) (×2), water (80 mL) then dried over $Na_2SO_4$, filtered, and concentrated under reduced pressure to reveal a yellow oil (4.2 g). This material was used directly in the next step.

Intermediate 79c (R)—N'-(4-(tert-butyldimethylsilyloxy)-2-(3-chloro-4-cyano-2-methylphenylamino)butanoyl)-4-cyanobenzohydrazide

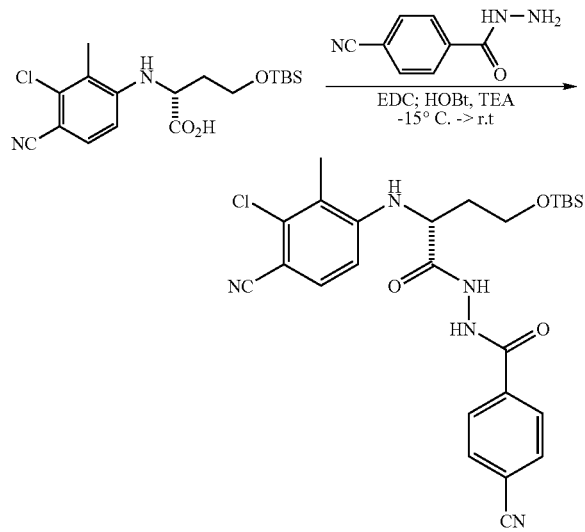

(R)-4-(tert-butyldimethylsilyloxy)-2-(3-chloro-4-cyano-2-methylphenylamino)butanoic acid (840 mg, 2.19 mmol) and 4-cyanobenzohydrazide (329 mg, 2.41 mmol) were mixed together in THF (100 ml) and cooled to −15° C. under $N_2$ atmosphere. To the pre-cooled reaction mixture were added hydroxybenzotriazole (HOBT) (296 mg, 2.19 mmol), TEA (0.458 mL, 3.29 mmol) followed by N-(3-Dimethylaminopropyl)-N'-ethylcarbodiimide hydrochloride (EDCI) (630 mg, 3.29 mmol). The reaction mixture was allowed to stir at −20° C. for 20 min and then at room temperature overnight. After the reaction was complete based on TLC, the urea was filtered off and the solution was washed with water, 5% citric acid followed by 5% $NaHCO_3$ to provide the crude product as a yellow solid (0.95 g). Purification by flash column chromatography [EtOAc-hexanes (1:1) as eluent] afforded the title compound as a white crystalline solid (605 mg, 53%). $^1H$ NMR (400 MHz, Acetone-$d_6$, δ in ppm) 9.78 (br s, 2H), 8.03 (d, J=9 Hz, 2H), 7.87 (d, J=9 Hz, 2H), 7.48 (d, J=9 Hz, 1H), 6.63 (d, J=9 Hz, 1H), 5.87 (d, J=9 Hz, 1H), 4.40-4.34 (m, 1H), 4.03-3.82 (m, 2H), 2.31 (s, 3H), 2.29-2.04 (m, 2H), 0.81 (s, 9H), 0.1 (s, 3H) and 0.00 (s, 3H).

Intermediate 79d (R)-4-(3-(tert-butyldimethylsilyloxy)-1-(5-(4-cyanophenyl)-1,3,4-oxadiazol-2-yl)propylamino)-2-chloro-3-methylbenzonitrile

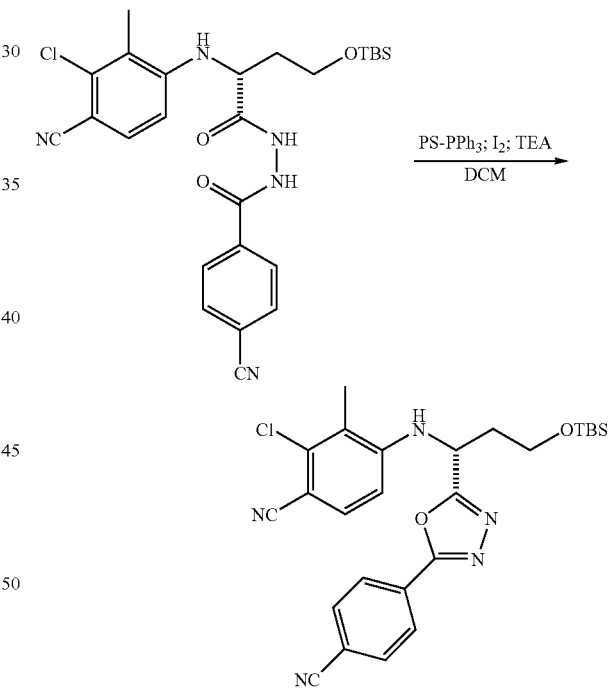

To a 25 mL round bottom flask equipped with a magnetic stir bar and septum was added triphenylphosphine (polymer bound, 3.0 mmol/g loading) (1 g, 3 mmol) under an atmosphere of nitrogen. To this was added methylene chloride (60 mL) followed by addition of solid iodine (688 mg, 2.71 mmol). This was allowed to stir at room temperature for a period of 10 min followed by slow addition of triethylamine (1 mL, 7.24 mmol). (R)—N'-(4-(tert-butyldimethylsilyloxy)-2-(3-chloro-4-cyano-2-methylphenylamino)butanoyl)-4-cyanobenzohydrazide (950 mg, 1.81 mmol) was taken up in methylene chloride (15 mL) and slowly added to the stirred reaction mixture. After a period of 30 min, the solid polymer was filtered out and washed with additional methylene chloride (50 mL). The organic filtrate was then washed with 10% sodium thiosulfate/water (2×25 mL), brine (1×30 mL) and dried (Na$_2$SO$_4$). The solution was then filtered and concentrated under reduced to reveal a brown solid (1.03 g). Purification by flash column chromatography [EtOAc-hexanes (1:2) as eluent] afforded the title compound as a white crystalline solid (900 mg, 98%). $^1$H NMR (400 MHz, Acetone-d$_6$, δ in ppm) 8.19 (d, J=9 Hz, 2H), 8.00 (d, J=9 Hz, 2H), 7.53 (d, J=9 Hz, 1H), 6.98 (d, J=9 Hz, 1H), 6.05 (d, J=9 Hz, 1H), 5.4 (m, 1H), 4.00-3.95 (m, 1H), 3.94-3.89 (m, 1H), 2.57-2.40 (m, 2H), 2.38 (s, 3H), 0.88 (s, 9H), 0.04 (s, 3H) and 0.00 (s, 3H).

Example 79

(R)-2-chloro-4-(1-(5-(4-cyanophenyl)-1,3,4-oxadiazol-2-yl)-3-hydroxypropylamino)-3-methylbenzonitrile

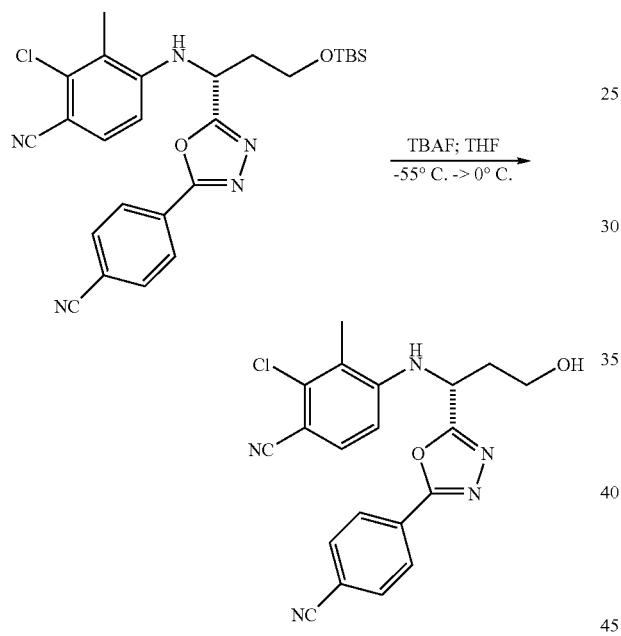

To a 25 mL round bottom flask equipped with a magnetic stirrer and a septum was added (R)-4-(3-(tert-butyldimethylsilyloxy)-1-(5-(4-cyanophenyl)-1,3,4-oxadiazol-2-yl)propylamino)-2-chloro-3-methylbenzonitrile (900 mg, 177 mmol), which was then dissolved in anhydrous THF (50 mL) under an atmosphere of nitrogen and cooled to −40° C. To this was added the tetrabutylammonium fluoride as a 1M solution in THF (2.13 mL, 2.13 mmol) producing an instant color change to yellow. The mixture was then allowed to warm to −20° C. over a period of 2 h, at which point TLC analysis suggested the reaction was complete. The solvent was then removed under reduced pressure to yield a dark brown residue. This residue was taken up in EtOAc (40 mL) and washed with water (2×25 mL), brine (1×25 mL) and dried over Na$_2$SO$_4$. The solution was then filtered and concentrated under reduced pressure using rotary evaporation to reveal a yellow solid (1.08 g). Purification by flash column chromatography [EtOAc-hexanes (1:1) as eluent] afforded the title compound as a white crystalline solid (0.605 mg, 87%): $^1$H NMR (400 MHz, Acetone-d$_6$, δ in ppm) 8.21 (d, J=9 Hz, 2H), 7.99 (d, J=9 Hz, 2H), 7.48 (d, J=9 Hz, 1H), 6.92 (d, J=9 Hz, 1H), 6.41 (d, J=9 Hz, 1H), 5.4 (m, 1H), 4.28-4.26 (m, 1H), 3.97-3.77 (m, 1H), 2.58-2.38 (m, 2H), 2.37.

Example 80

2-chloro-4-((1R,2S)-1-(5-(4-cyanophenyl)-1,3,4-oxadiazol-2-yl)-2-hydroxypropylamino)-3-vinylbenzonitrile

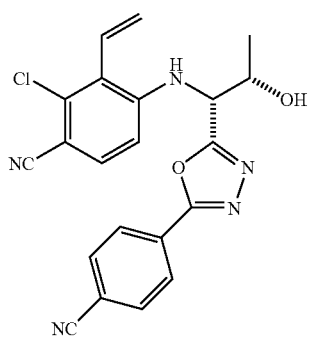

Intermediate 80a 2-chloro-4-fluoro-3-(2-hydroxyethyl)benzonitrile

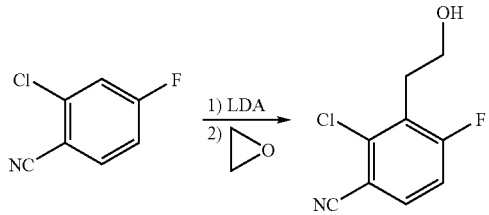

To a solution of 2-chloro-4-fluorobenzonitrile (20.0 g, 128.6 mmol) in THF (200 mL) was added LDA (28% wt in THF, 71.0 mL, 142.0 mmol) at −78° C. After addition, the mixture was stirred at the same temperature for 5 h, then ethylene oxide (9.7 ml, 194.2 mmol) was added. The reaction mixture was allowed to warm to R. T. gradually and stirred overnight. The reaction was quenched by adding saturated aqueous NH$_4$Cl solution and extracted with EtOAc (400 mL). The EtOAc extracts were washed with water, brine and dried over Na$_2$SO$_4$. After the solvent was removed, the residue was purified by SiO$_2$ column to give 2-chloro-4-fluoro-3-(2-hydroxyethyl)benzonitrile (17.0 g, 66%). $^1$H NMR (400 MHz, CDCl$_3$, δ in ppm) 7.58 (dd, J=5.5, 8.6 Hz, 1H), 7.10 (t, J=8.6 Hz, 1H), 3.88 (m, 2H), 3.13 (t, J=6.8 Hz, 2H).

Intermediate 80b 3-(2-bromoethyl)-2-chloro-4-fluorobenzonitrile

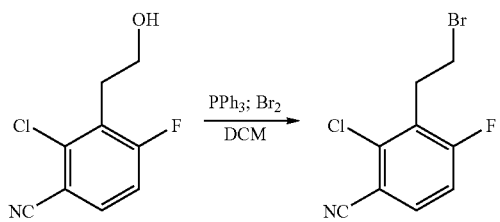

To a 25 mL round bottomed flask equipped with a magnetic stirrer was added triphenylphosphine (1.57 g, 6 mmol) and methylene chloride (8 mL). Upon cooling the mixture to −10° C., bromine (0.28 mL, 5.5 mmol) was added dropwise. After 10 min, 2-chloro-4-fluoro-3-(2-hydroxyethyl)benzonitrile (1 g, 5 mmol) in methylene chloride (6 mL) was added and stirring was continued for 20 min while the internal reaction temperature was allowed to warm to 15° C. The mixture was then diluted with hexane (30 mL) and purified via a silica plug [hexane-Et$_2$O (20:1) as eluent]. The combined filtrates were concentrated to furnish the title compound (1.26 g, 96%): $^1$H NMR (400 MHz, Acetone-d$_6$, δ in ppm) 7.92 (dd, J=6 and 9 Hz, 1H), 7.42 (t, J=9 Hz, 1H), 3.70 (t, J=7 Hz, 2H), 3.13 (dt, J=2 and 7 Hz, 2H).

Intermediate 80c 2-(3-Chloro-4-cyano-2-vinyl-phenylamino)-3-hydroxy-butyric acid

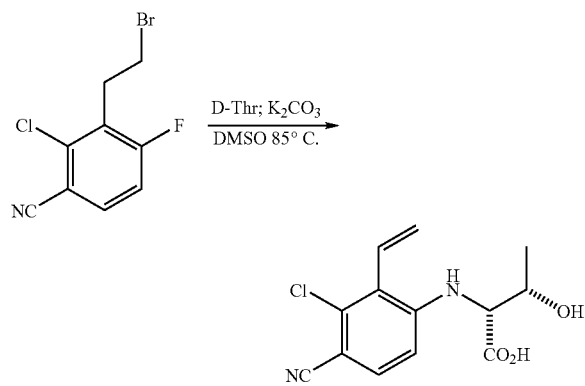

To a suspension of D-Threonine (0.299 g, 2.51 mmol) and K$_2$CO$_3$ (1.21 g, 8.72 mmol) in DMSO (24 mL) was added 3-(2-Bromo-ethyl)-2-chloro-4-fluoro-benzonitrile (572 mg, 2.18 mmol) at room temperature. The reaction mixture was heated to 85° C. and stirred for 18 h. The reaction mixture was allowed to cool to room temperature and quenched with H$_2$O (20 mL) and extracted with EtOAc (3×60 mL). The aqueous layer was then acidified with solid citric acid and extracted with EtOAc (2×80 mL). The later organic extracts were combined, washed with H$_2$O (3×30 mL), dried (Na$_2$SO$_4$), filtered and concentrated under reduced pressure to provided the title compound as a pale yellow solid (594 mg, 97%): $^1$H NMR (400 MHz, d$_6$-acetone, δ in ppm) 7.48 (d, J=9 Hz, 1H), 6.74 (d, J=9 Hz, 1H), 6.63 (dd, J=12 and 18 Hz, 1H), 5.97 (d, J=9 Hz, 1H), 5.88 (dd, J=2 and 12 Hz, 1H), 5.78 (dd, J=2 and 18 Hz, 1H), 4.51-4.42 (m, 2H), 4.23-4.21 (m, 1H), and 1.24 (d, J=7 Hz, 3H).

Intermediate 80d

4-Cyano-benzoic acid N'-[2-(3-chloro-4-cyano-2-vinyl-phenylamino)-3-hydroxy-butyryl]-hydrazide

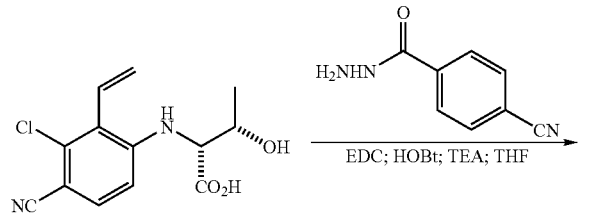

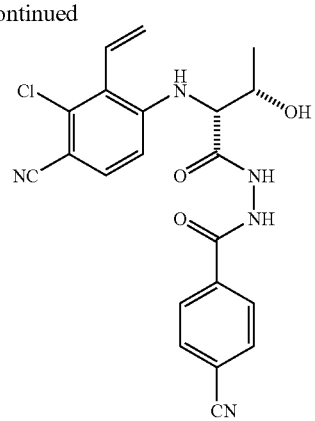

2-(3-Chloro-4-cyano-2-vinyl-phenylamino)-3-hydroxy-butyric acid (690 mg, 3.8 mmol) and 4-cyanobenzohydrazide (673 mg, 4.18 mmol) were mixed together in THF (100 ml) and cooled to −15° C. under N$_2$ atmosphere. To the pre-cooled reaction mixture were added hydroxybenzotriazole (HOBT) (514 mg, 3.8 mmol), TEA (0.8 mL, 5.7 mmol) followed by N-(3-Dimethylaminopropyl)-N'-ethylcarbodiimide hydrochloride (EDCI) (1.09 g, 5.7 mmol). The reaction mixture was allowed to stir at −20° C. for 20 min and then at room temperature overnight. After the reaction was complete based on TLC, the urea was filtered off and the solution was washed with 5% citric acid (2×60 mL), 5% NaHCO$_3$ (2×60 mL) followed by water (60 mL) and then dried (Na$_2$SO$_4$) to provide the crude product as a yellow solid (0.79 g, 49%): $^1$H NMR (400 MHz, d$_6$-acetone, δ in ppm) 9.92 (br s, 1H), 9.49 (br s, 1H), 7.99 (d, J=9 Hz, 2H), 7.81 (d, J=9 Hz, 2H), 7.42 (d, J=9 Hz, 1H), 6.61 (d, J=9 Hz, 1H), 6.53 (dd, J=12 and 18 Hz), 5.99 (d, J=9 Hz, 1H), 5.73 (dd, J=2 and 12 Hz, 2H), 5.64 (dd, J=2 and 18 Hz), 4.29-4.22 (m, 1H), 4.01-3.99 (m, 1H) and 1.20 (d, J=7 Hz, 3H).

Example 80

2-chloro-4-((1R,2S)-1-(5-(4-cyanophenyl)-1,3,4-oxadiazol-2-yl)-2-hydroxypropylamino)-3-vinylbenzonitrile

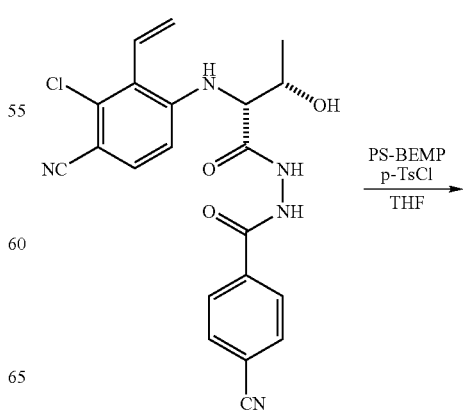

-continued

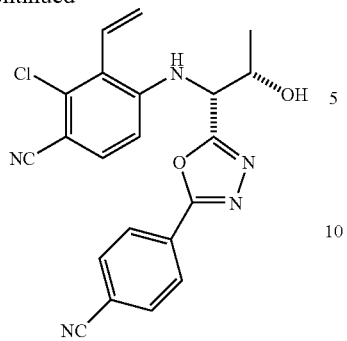

To a solution of N'-((2R,3S)-2-(3-chloro-4-cyano-2-vinylphenylamino)-3-hydroxybutanoyl)-4-cyanobenzohydrazide (0.79 g, 1.86 mmol) in anhydrous THF (200 mL) at room temperature was added 2-tert-butylamino-2-diethylamino-1,3-dimethyl perhydro-1,3,2-diazaphosphorine on polystyrene (3 mmol base/g) (2.54 g, 5.59 mmol) followed by para-toluene sulfonyl chloride (p-TSCl) (355 mg, 1.86 mmol) and the mixture was stirred for 1 h. The mixture was filtered under suction, the residue then washed with acetone (300 mL) followed by methanol (300 mL) and then concentrated to furnish a yellow oil (0.92 g). Purification by flash column chromatography [EtOAc-hexanes (3:2) as eluent] afforded the title compound as a white crystalline solid (86 mg, 11%). $^1$H NMR (400 MHz, $d_6$-acetone, δ in ppm) 8.20 (d, J=9 Hz, 2H), 7.99 (d, J=9 Hz, 2H), 7.56 (d, J=9 Hz, 1H), 6.90 (d, J=9 Hz, 1H), 6.83 (dd, J=12 and 18 Hz), 6.22 (d, J=9 Hz, 1H), 5.94 (dd, J=2 and 12 Hz) 5.84 (dd, J=2 and 18 Hz), 5.19 (d, J=9 Hz, 1H), 4.68-4.60 (m, 1H) and 1.20 (d, J=7 Hz, 3H).

Example 81

2-chloro-4-((1R,2S)-1-(5-(3-fluorophenyl)-1,3,4-oxadiazol-2-yl)-2-hydroxypropylamino)-3-methyl-benzonitrile

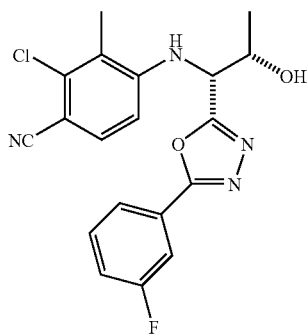

Intermediate 81a

N'-((2R,3S)-2-(3-chloro-4-cyano-2-methylphenylamino)-3-hydroxybutanoyl)-3-fluorobenzohydrazide

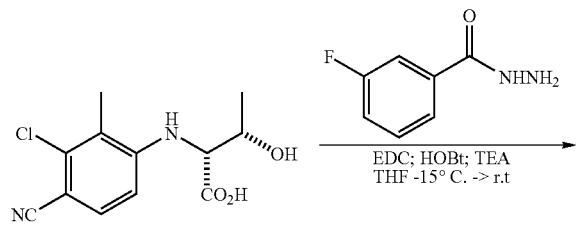

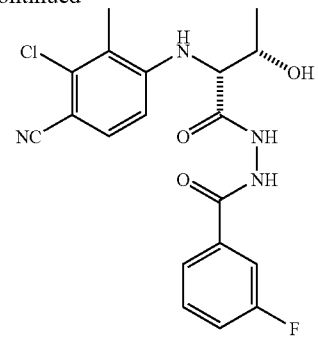

(2R,3S)-2-(3-chloro-4-cyano-2-methylphenylamino)-3-hydroxybutanoic acid (intermediate 1a) (2 g, 7.44 mmol) and 3-Fluorobenzohydrazide (1.26 g, 8.19 mmol) were mixed together in THF (100 ml) and cooled to −15° C. under $N_2$ atmosphere. To the pre-cooled reaction mixture were added hydroxybenzotriazole (HOBT) (1.0 g, 7.44 mmol), TEA (1.56 mL, 11.16 mmol) followed by N-(3-Dimethylaminopropyl)-N'-ethylcarbodiimide hydrochloride (EDCI) (2.14 g, 11.16 mmol). The reaction mixture was allowed to stir at −20° C. for 20 min and then at room temperature overnight. After the reaction was complete based on TLC, the urea was filtered off and the solution was washed with 5% citric acid (2×80 mL), 5% NaHCO$_3$ (2×80 mL) followed by water (80 mL) and then dried (Na$_2$SO$_4$) to provide the crude product as a yellow solid (2.75 g, 91%): $^1$H NMR (400 MHz, $d_6$-acetone, δ in ppm) 9.84 (br s, 2H), 7.79-7.76 (m, 1H), 7.67-7.63 (m, 1H), 7.58-7.51 (m, 2H), 7.41-7.35 (m, 1H), 6.68 (d, J=9 Hz, 1H), 5.55 (d, J=9 Hz, 1H), 4.79 (br s, 1H), 4.42-4.36 (m, 1H), 4.14-4.10 (m, 1H), 2.36 (s, 3H) and 1.36 (d, J=6.5 Hz).

Example 81

2-chloro-4-((1R,2S)-1-(5-(3-fluorophenyl)-1,3,4-oxadiazol-2-yl)-2-hydroxypropylamino)-3-methyl-benzonitrile

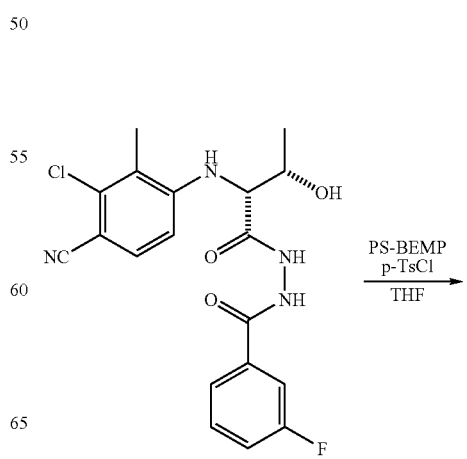

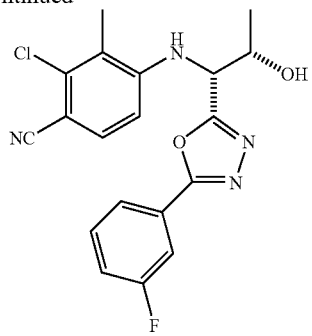

To a solution of N'-((2R,3S)-2-(3-chloro-4-cyano-2-methylphenylamino)-3-hydroxybutanoyl)-3-fluorobenzohydrazide (1 g, 2.47 mmol) in anhydrous THF (15 mL) at room temperature was added 2-tert-butylamino-2-diethylamino-1,3-dimethyl perhydro-1,3,2-diazaphosphorine on polystyrene (3 mmol base/g) (3.37 g, 7.41 mmol) followed by para-toluene sulfonyl chloride (p-TSCl) (471 mg, 2.47 mmol) and the mixture was stirred for 1 h. The mixture was filtered under suction, the residue then washed with acetone (300 mL) followed by methanol (300 mL) and then concentrated to furnish a yellow oil (0.968 g). Purification by flash column chromatography [EtOAc-hexanes (1:1) as eluent] afforded the title compound as a white crystalline solid (101 mg, 10%). $^1$H NMR (400 MHz, d$_6$-acetone, δ in ppm) 7.86-7.83 (m, 1H), 7.75-7.71 (m, 1H), 7.67-7.61 (m, 2H), 7.49 (d, J=9 Hz, 1H), 7.43-7.37 (m, 1H), 6.87 (d, J=9 Hz, 1H), 6.69 (d, J=9 Hz, 1H), 5.13 (m, 1H), 4.82 (br s, 1H), 4.67-4.59 (m, 1H), 2.41 (s, 3H) and 1.41 (d, J=6.5 Hz).

Example 82

(1R,2S)-1-(3-chloro-4-cyano-2-methylphenylamino)-1-(5-phenyl-1,3,4-oxadiazol-2-yl)propan-2-yl butyrate

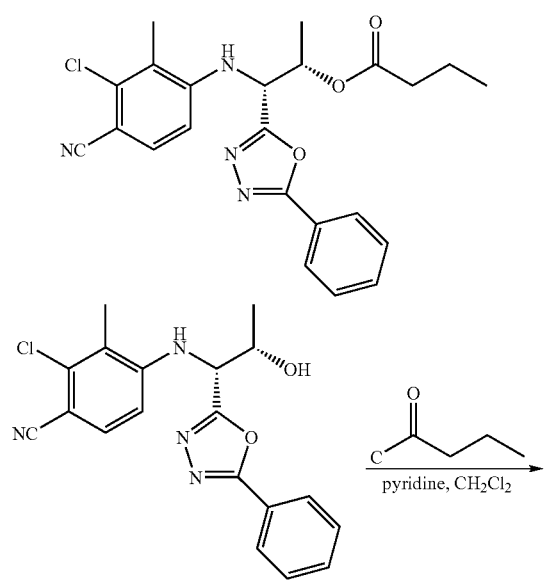

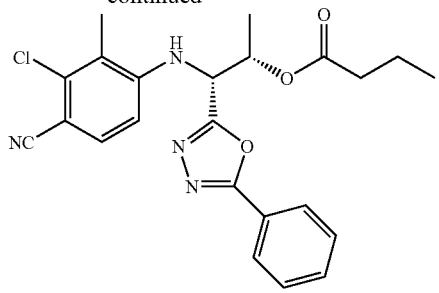

To a solution of 2-chloro-4-((1R,2S)-2-hydroxy-1-(5-phenyl-1,3,4-oxadiazol-2-yl)propylamino)-3-methylbenzonitrile (200 mg, 0.54 mmol) in pyridine (1.0 mL) and CH$_2$Cl$_2$ (7.0 mL) was added n-butyryl chloride (84 μL, 0.81 mmol). Upon complete addition the reaction mixture was stirred for 60 h, then quenched with 10% aqueous HCl (10 mL). The mixture was partitioned between H$_2$O (25 mL) and CH$_2$Cl$_2$ (30 mL). The aqueous layer was extracted with CH$_2$Cl$_2$ (25 mL). The combined organic extracts were washed with NaHCO$_3$ (30 mL), dried (Na$_2$SO$_4$), filtered and concentrated under reduced pressure to provide an orange viscous oil, which was purified by flash chromatography over silica gel (15-30% EtOAc in hexanes) to provide the title compound as a colourless solid (231 mg, 97%): $^1$H NMR (400 MHz, CDCl$_3$, δ in ppm) 7.99 (td, J=1.4, 8.8 Hz, 2H), 7.57-7.47 (m, 3H), 7.38 (d, J=8.6 Hz, 2H), 6.73 (d, J=8.6 Hz, 1H), 5.59 (pentet, J=6.5 Hz, 1H), 5.19 (d, J=8.0 Hz, 1H), 5.03 (dd, J=5.9, 7.8 Hz, 1H), 2.34 (dt, J=2.3, 7.6 Hz, 2H), 2.31 (s, 3H), 1.64 (sextet, J=7.4 Hz, 2H), 1.37 (d, J=6.5 Hz, 3H), 0.92 (t, J=7.4 Hz, 3H).

Example 83

(1R,2S)-1-(3-chloro-4-cyano-2-methylphenylamino)-1-(5-phenyl-1,3,4-oxadiazol-2-yl)propan-2-yl benzoate

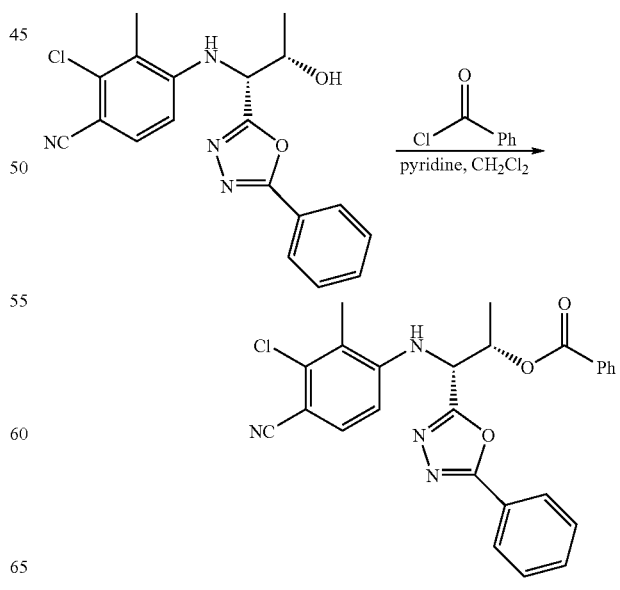

To a solution of 2-chloro-4-((1R,2S)-2-hydroxy-1-(5-phenyl-1,3,4-oxadiazol-2-yl)propylamino)-3-methylbenzonitrile (200 mg, 0.54 mmol) in pyridine (1.0 mL) and $CH_2Cl_2$ (7.0 mL) was added benzoyl chloride (94 μL, 0.81 mmol). Upon complete addition the reaction mixture was stirred for 60 h, then quenched with 10% aqueous HCl (15 mL). The mixture was partitioned between $H_2O$ (35 mL) and $CH_2Cl_2$ (40 mL). The aqueous layer was extracted with $CH_2Cl_2$ (35 mL). The combined organic extracts were washed with $NaHCO_3$ (35 mL), dried ($Na_2SO_4$), filtered and concentrated under reduced pressure to provide an off white solid, which was purified by flash chromatography over silica gel (20-40% EtOAc in hexanes) to provide the title compound as a colourless solid (225 mg, 88%): $^1$H NMR (400 MHz, $CDCl_3$, δ in ppm) 8.05 (dm, J=7.2 Hz, 2H), 7.91 (dm, J=7.2 Hz, 2H), 7.62 (tt, J=1.2, 7.4 Hz, 1H), 7.55-7.41 (m, 5H), 7.39 (d, J=8.6 Hz, 1H), 6.84 (d, J=8.8 Hz, 1H), 5.81 (pentet, J=6.3 Hz, 1H), 5.38 (d, J=7.6 Hz, 1H), 5.21 (dd, J=5.9, 7.4 Hz, 1H), 2.31 (s, 3H), 1.50 (d, J=6.5 Hz, 3H).

The binding data shown in table 1 (below) is from the result of a single or multiple determinations based on the same compound. Where multiple data points have been taken, the value reported is the average of the multiple determinations.

TABLE 1

Compound AR-Binding Affinity

| Compound | Binding $IC_{50}$ (nM) |
|---|---|
| Example 1 | 3 |
| Example 2 | 5 |
| Example 3 | 6 |
| Example 4 | 11 |
| Example 5 | 50 |
| Example 6 | 16 |
| Example 7 | 0.4 |
| Example 8 | 15 |
| Example 9 | 10 |
| Example 10 | 15 |
| Example 11 | 12 |
| Example 12 | 300 |
| Example 13 | 5 |
| Example 14 | 17 |
| Example 15 | 0.5 |
| Example 16 | 35 |
| Example 17 | 10 |
| Example 18 | 60 |
| Example 19 | 19 |
| Example 20 | 15 |
| Example 21 | 3 |
| Example 22 | 2 |
| Example 23 | 0.7 |
| Example 24 | 200 |
| Example 25 | 258 |
| Example 26 | 10 |
| Example 27 | 10 |
| Example 28 | 16 |
| Example 29 | 0.03 |
| Example 30 | 0.3 |
| Example 31 | 5.9 |
| Example 32 | 2 |
| Example 33 | 15 |
| Example 34 | 4 |
| Example 35 | 0.2 |
| Example 36 | 12 |
| Example 37 | 0.2 |
| Example 38 | 60 |
| Example 39 | 0.1 |
| Example 40 | 0.2 |
| Example 41 | 0.02 |
| Example 42 | 9 |
| Example 43 | 3 |
| Example 44 | 5 |
| Example 45 | 470 |
| Example 46 | 6 |
| Example 47 | 1 |
| Example 48 | >1000 |
| Example 49 | 2 |
| Example 50 | 5 |
| Example 51 | 600 |
| Example 52 | 9 |
| Example 53 | 1 |
| Example 54 | 1 |
| Example 55 | 11 |
| Example 56 | 10 |
| Example 57 | 11 |
| Example 58 | 10 |
| Example 59 | >1000 |
| Example 60 | 8 |
| Example 61 | 1 |
| Example 62 | 15 |
| Example 63 | 1 |
| Example 64 | 1 |
| Example 65 | 1 |
| Example 66 | 430 |
| Example 67 | 246 |
| Example 68 | 12 |
| Example 69 | >1000 |
| Example 70 | 4 |
| Example 71 | 280 |
| Example 72 | 780 |
| Example 73 | na |
| Example 74 | na |
| Example 75 | na |
| Example 76 | na |
| Example 77 | 1000 |
| Example 78 | 1 |
| Example 79 | 2 |
| Example 80 | 1 |
| Example 81 | 2 |
| Example 82 | na |
| Example 83 | na |

In Vivo Activity—Rat Herschberger Assay

In vivo utility of the compounds of this invention may be demonstrated through use of various in vivo animal models including the Herschberger assay. Selected data from examples 1 and 3 are shown in Table 2 below:

TABLE 2

Rat Herschberger Assay

| Example | Dose | Prostate | Seminal vesicle | LABC |
|---|---|---|---|---|
| 1 | 10 mg/kg (po) | 46% | 69% | 85% |
| 3 | 10 mg/kg (po) | 43% | 37% | 99% |

Prostate, seminal vesicle and levator ani bulbus cavernosus (LABC) are all represented as % relative to sham. After sacrifice, organ weights of young, orchidectomized rats treated with compound for 4 days are compared to sham operated animals. Preferred compounds of this invention demonstrate increased levator ani stimulation relative to prostate and/or seminal vesicles.

While this invention has been particularly shown and described with references to example embodiments thereof, it will be understood by those skilled in the art that various changes in form and details may be made therein without departing from the scope of the invention encompassed by the appended claims.

What is claimed is:

1. A compound selected from the following:

2-chloro-4-((1R,2S)-1-(5-(4-cyanophenyl)-1,3,4-oxadiazol-2-yl)-2-hydroxypropylamino)-3-methylbenzonitrile;

2-chloro-4-((1R,2S)-2-hydroxy-1-(5-phenyl-1,3,4-oxadiazol-2-yl)propylamino)-3-methylbenzonitrile;

2-chloro-4-((1R,2R)-2-hydroxy-1-(5-phenyl-1,3,4-oxadiazol-2-yl)propylamino)-3-methylbenzonitrile;

2-chloro-4-((1R,2S)-1-(5-(4-chlorophenyl)-1,3,4-oxadiazol-2-yl)-2-hydroxypropylamino)-3-methylbenzonitrile;

2-chloro-4-((1R,2S)-2-hydroxy-1-(5-(4-hydroxyphenyl)-1,3,4-oxadiazol-2-yl)propylamino)-3-methylbenzonitrile;

2-Chloro-4-((1R,2S)-1-(5-(4-fluorophenyl)-1,3,4-oxadiazol-2-yl)-2-hydroxypropylamino)-3-methylbenzonitrile;

(R)-2-chloro-4-(1-(5-(4-chlorophenyl)-1,3,4-oxadiazol-2-yl)-2-hydroxy-2-methylpropylamino)-3-methylbenzonitrile;

2-chloro-4-((1R,2R)-2-hydroxy-1-(5-(4-hydroxyphenyl)-1,3,4-oxadiazol-2-yl)propylamino)-3-methylbenzonitrile;

2-Chloro-4-((1R,2R)-1-(5-(3,4-dichlorophenyl)-1,3,4-oxadiazol-2-yl)-2-hydroxypropylamino)-3-methylbenzonitrile;

2-Chloro-4-((1R,2S)-1-(5-(3,4-dichlorophenyl)-1,3,4-oxadiazol-2-yl)-2-hydroxypropylamino)-3-methylbenzonitrile;

2-chloro-4-((1R,2R)-1-(5-(4-cyanophenyl)-1,3,4-oxadiazol-2-yl)-2-hydroxypropylamino)-3-methylbenzonitrile;

2,3-Dichloro-4-((1R,2S)-1-(5-(4-chlorophenyl)-1,3,4-oxadiazol-2-yl)-2-hydroxypropylamino)benzonitrile;

4-((1R,2S)-1-(5-(4-Cyanophenyl)-1,3,4-oxadiazol-2-yl)-2-hydroxypropylamino)-3-methyl-2-(trifluoromethyl)benzonitrile;

4-((1R,2R)-1-(5-(4-Cyanophenyl)-1,3,4-oxadiazol-2-yl)-2-hydroxypropylamino)-3-methyl-2-(trifluoromethyl)benzonitrile;

2-Chloro-4-((1R,2R)-1-(5-(4-cyanophenyl)-1,3,4-oxadiazol-2-yl)-2-hydroxypropylamino)-3-ethylbenzonitrile;

2-Chloro-4-((1R,2S)-1-(5-(4-cyanophenyl)-1,3,4-oxadiazol-2-yl)-2-hydroxypropylamino)-3-ethylbenzonitrile; and 4-((1R,2R)-1-(5-(4-cyanophenyl)-1,3,4-oxadiazol-2-yl)-2-hydroxypropylamino)benzo[b]thiophene-7-carbonitrile; or a pharmaceutically acceptable salt thereof.

2. A pharmaceutical composition comprising a compound according to claim 1, and at least one pharmaceutically acceptable excipient.

3. A method of modulating an androgen receptor in a cell, comprising the administration of a compound according to claim 1, or a pharmaceutically acceptable salt thereof.

4. A method of identifying a compound capable of modulating an androgen receptor comprising contacting a cell expressing an androgen receptor with a compound according to claim 1, or a pharmaceutically acceptable salt thereof, and monitoring the effect of the compound on the cell.

* * * * *